United States Patent
Klenner et al.

(10) Patent No.: US 10,478,580 B2
(45) Date of Patent: Nov. 19, 2019

(54) NASAL CANNULA ASSEMBLIES AND RELATED PARTS

(71) Applicant: Fisher & Paykel Healthcare Limited, Auckland (NZ)

(72) Inventors: Jason Allan Klenner, Auckland (NZ); Milanjot Singh Assi, Auckland (NZ); Mark Thomas O'Connor, Auckland (NZ); Callum James Thomas Spence, Auckland (NZ); Caroline Geraldine Hopkins, Auckland (NZ); Neil Gray Duthie, Auckland (NZ); Craig Karl White, Auckland (NZ); Alicia Jerram Hunter Evans, Auckland (NZ); Brent Ian Laing, Auckland (NZ); Sooji Hope Clarkson, Auckland (NZ); Laurence Gulliver, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 459 days.

(21) Appl. No.: 14/776,932

(22) PCT Filed: Mar. 14, 2014

(86) PCT No.: PCT/NZ2014/000040
§ 371 (c)(1),
(2) Date: Sep. 15, 2015

(87) PCT Pub. No.: WO2014/142681
PCT Pub. Date: Sep. 18, 2014

(65) Prior Publication Data
US 2016/0030696 A1    Feb. 4, 2016

Related U.S. Application Data

(60) Provisional application No. 61/799,583, filed on Mar. 15, 2013, provisional application No. 61/815,671, (Continued)

(51) Int. Cl.
*A61M 16/06* (2006.01)
*A61M 16/00* (2006.01)
(Continued)

(52) U.S. Cl.
CPC .... *A61M 16/0677* (2014.02); *A61M 16/0003* (2014.02); *A61M 16/0066* (2013.01);
(Continued)

(58) Field of Classification Search
CPC .......... A61M 16/0666; A61M 16/0672; A61M 16/0677; A61M 2210/0618
See application file for complete search history.

(56) References Cited

U.S. PATENT DOCUMENTS 4,106,505 A * 8/1978 Salter ................ A61M 16/0666
128/207.18
4,248,218 A * 2/1981 Fischer ............... A61M 16/009
128/204.18
(Continued)

FOREIGN PATENT DOCUMENTS

CN           1213277 A      4/1999
CN         102003774 A      4/2011
(Continued)

OTHER PUBLICATIONS

First Office Action and Search Report for Chinese App No. 201480015555.1, dated Oct. 10, 2016 in 10 pages.
(Continued)

*Primary Examiner* — Michael J Tsai
(74) *Attorney, Agent, or Firm* — Knobbe, Martens, Olson & Bear, LLP

(57) ABSTRACT

Nasal cannula assemblies for providing respiratory therapy to patients are provided. A nasal cannula assembly can (Continued)

include a cannula, an optional manifold, a gas supply tube, and a securement mechanism. Securement mechanisms can include headgear straps, cheek pads, or an adhesive nose strip. A nasal cannula assembly can also include a lanyard, lanyard clip, and/or lanyard connector to help support the weight of a main gas delivery conduit.

17 Claims, 135 Drawing Sheets

Related U.S. Application Data filed on Apr. 24, 2013, provisional application No. 61/829,103, filed on May 30, 2013, provisional application No. 61/880,541, filed on Sep. 20, 2013, provisional application No. 61/881,316, filed on Sep. 23, 2013, provisional application No. 61/881,693, filed on Sep. 24, 2013, provisional application No. 61/916,686, filed on Dec. 16, 2013.

(51) Int. Cl.
*A61M 16/08* (2006.01)
*A61M 16/10* (2006.01)
*A61M 16/16* (2006.01)

(52) U.S. Cl.
CPC .... *A61M 16/0622* (2014.02); *A61M 16/0672* (2014.02); *A61M 16/0683* (2013.01); *A61M 16/0858* (2014.02); *A61M 16/0875* (2013.01); *A61M 16/1095* (2014.02); *A61M 16/16* (2013.01); *A61M 2205/3368* (2013.01); *A61M 2207/00* (2013.01)

(56) References Cited

U.S. PATENT DOCUMENTS

| | | | | |
|---|---|---|---|---|
| 4,782,832 | A * | 11/1988 | Trimble | A61M 16/0666 128/204.18 |
| 6,431,172 | B1 * | 8/2002 | Bordewick | A61M 16/0666 128/206.11 |
| 2004/0261797 | A1 * | 12/2004 | White | A61M 16/0666 128/206.11 |
| 2005/0011524 | A1 * | 1/2005 | Thomlinson | A61M 16/0666 128/207.18 |
| 2006/0124131 | A1 | 6/2006 | Chandran et al. | |
| 2010/0192957 | A1 | 8/2010 | Hobson et al. | |
| 2012/0132209 | A1 | 5/2012 | Rummery et al. | |
| 2012/0266890 | A1 | 10/2012 | Baecke et al. | |
| 2012/0318270 | A1 | 12/2012 | McAuley et al. | |

FOREIGN PATENT DOCUMENTS

| | | |
|---|---|---|
| CN | 102014999 A | 4/2011 |
| CN | 202538113 A | 4/2011 |
| CN | 102762250 | 10/2012 |
| CN | 102665810 A | 11/2012 |
| WO | WO 2007/125487 A1 | 11/2007 |
| WO | WO 2009/064202 | 5/2009 |
| WO | WO 2009/109005 A1 | 9/2009 |
| WO | WO 2009/151344 | 12/2009 |
| WO | WO 2010/023590 | 3/2010 |
| WO | WO 2011/062510 A1 | 5/2011 |
| WO | WO 2011/110961 A1 | 9/2011 |
| WO | WO 2012/040791 A1 | 4/2012 |

OTHER PUBLICATIONS

International Search Report, PCT/NZ2014/000040; dated Jun. 25, 2014; 9 pages.
Japanese Office Action with English Translation, dated Jan. 9, 2018, 8 pages.
China Office Action; dated Feb. 23, 2018; 5 pages.
China Office Action; dated Aug. 11, 2017; 9 pages.
Australian Examination Report; dated Mar. 5, 2018; 4 pages.
Australian Examination Report; dated Sep. 11, 2018; 4 pages.
European Examination Report; dated Oct. 12, 2018; 4 pages.

* cited by examiner

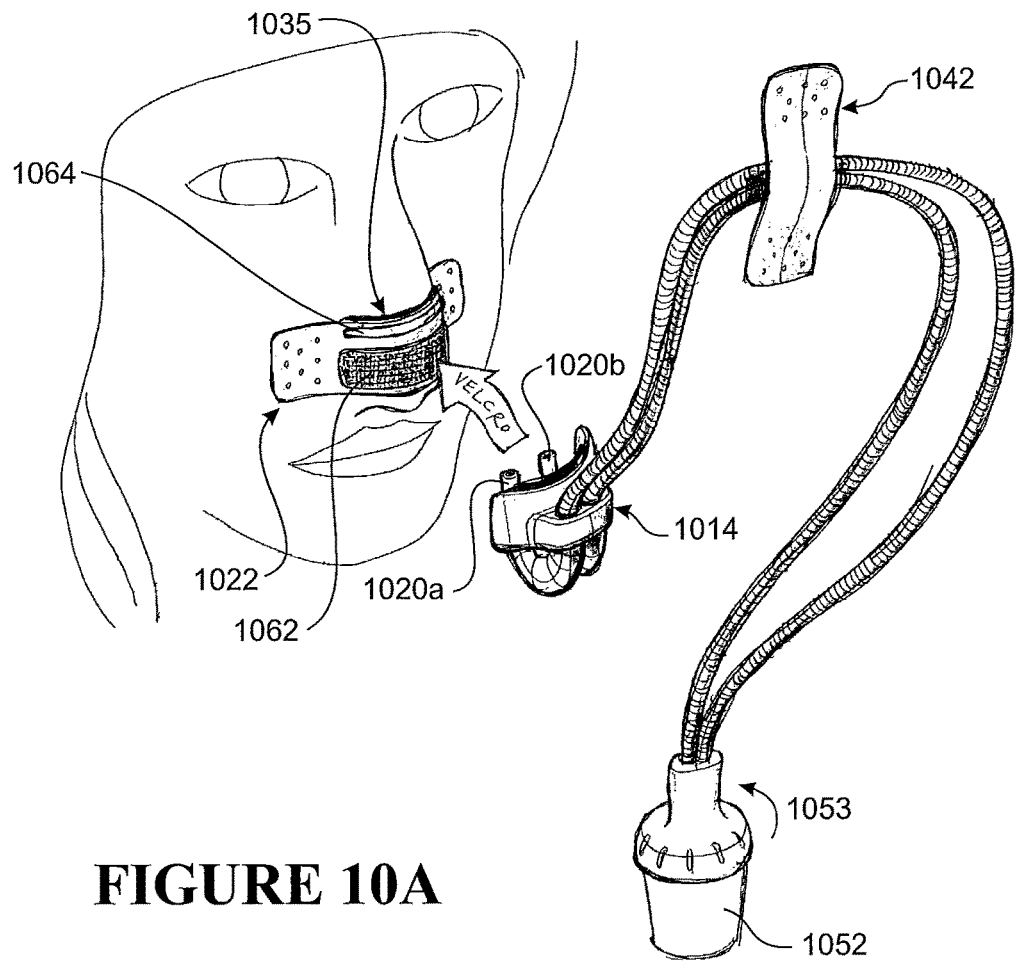
FIGURE 10A
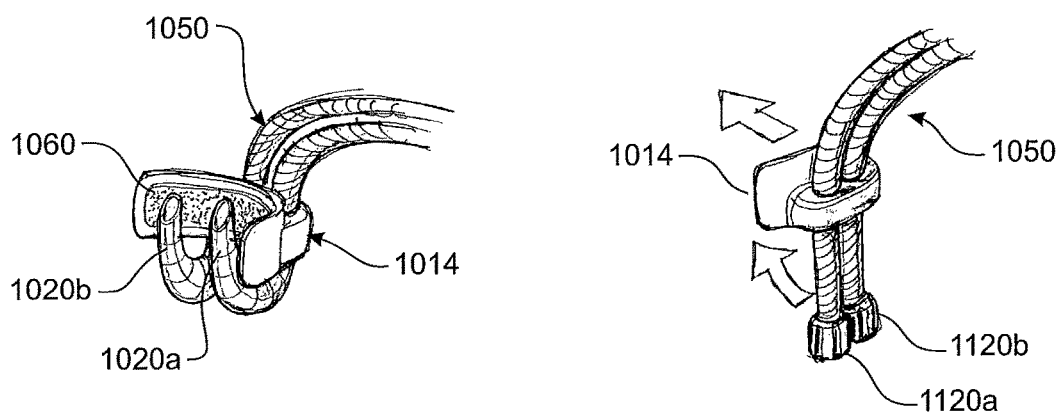
FIGURE 10B  FIGURE 11

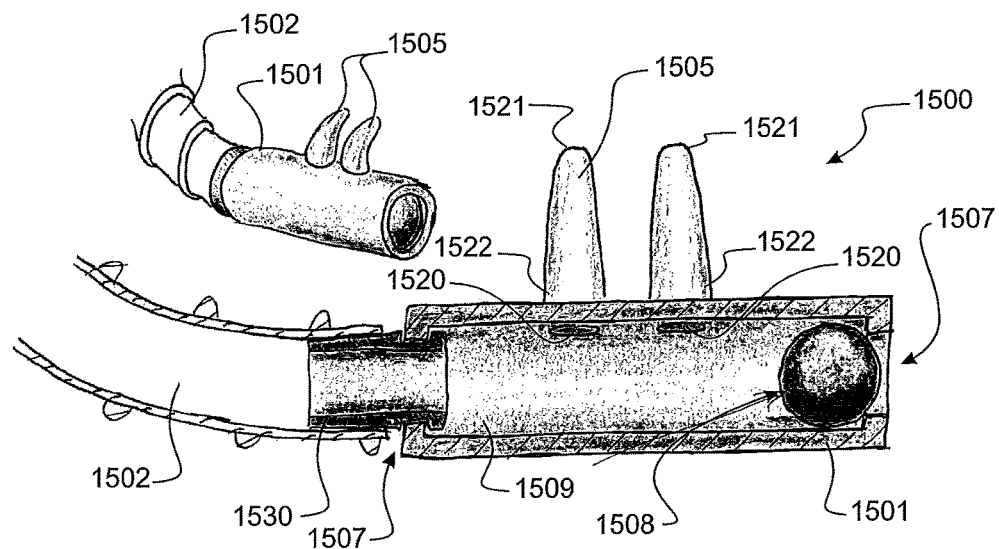
FIGURE 15A
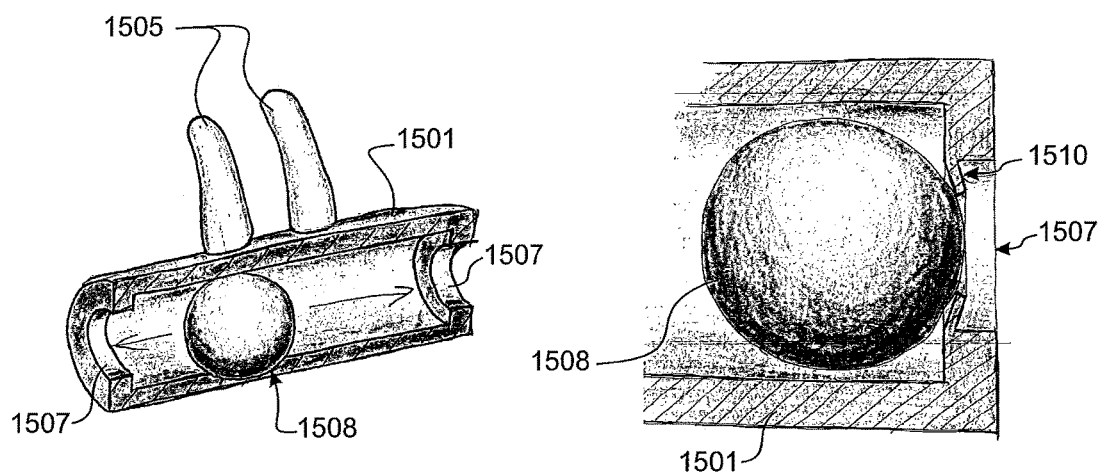
FIGURE 15B
FIGURE 15C
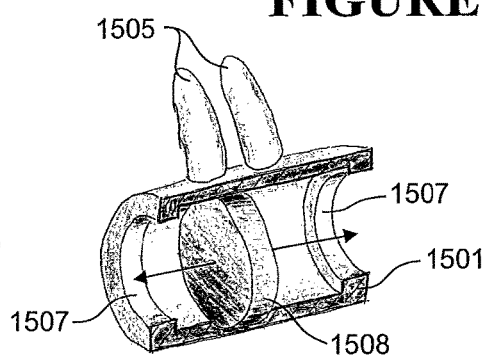
FIGURE 15D

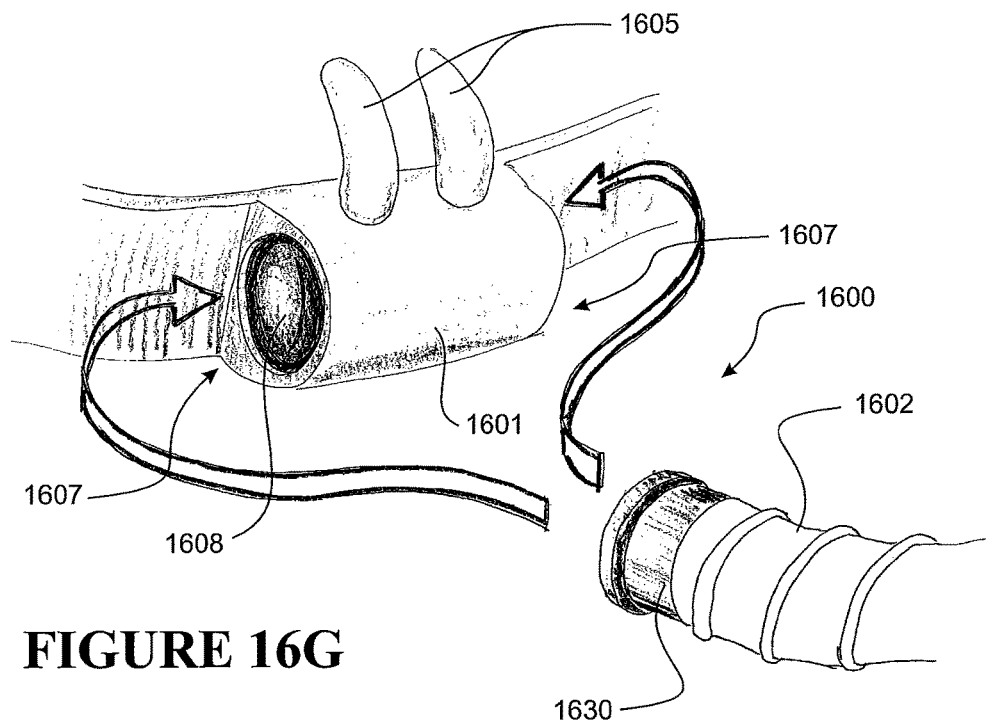
FIGURE 16G
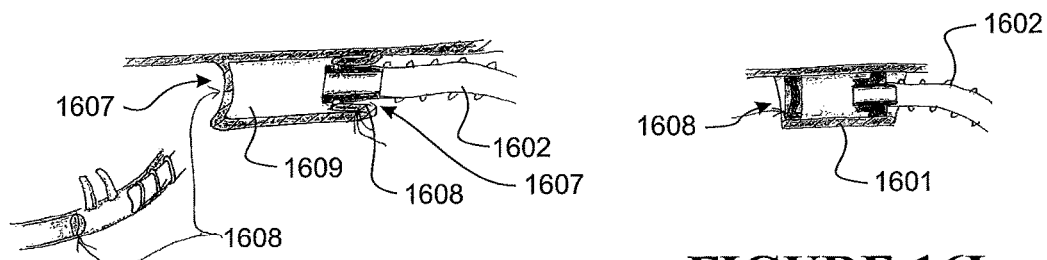
FIGURE 16H
FIGURE 16I
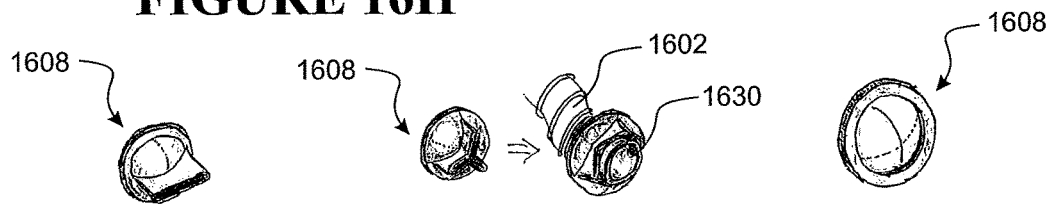
FIGURE 16J    FIGURE 16K    FIGURE 16L

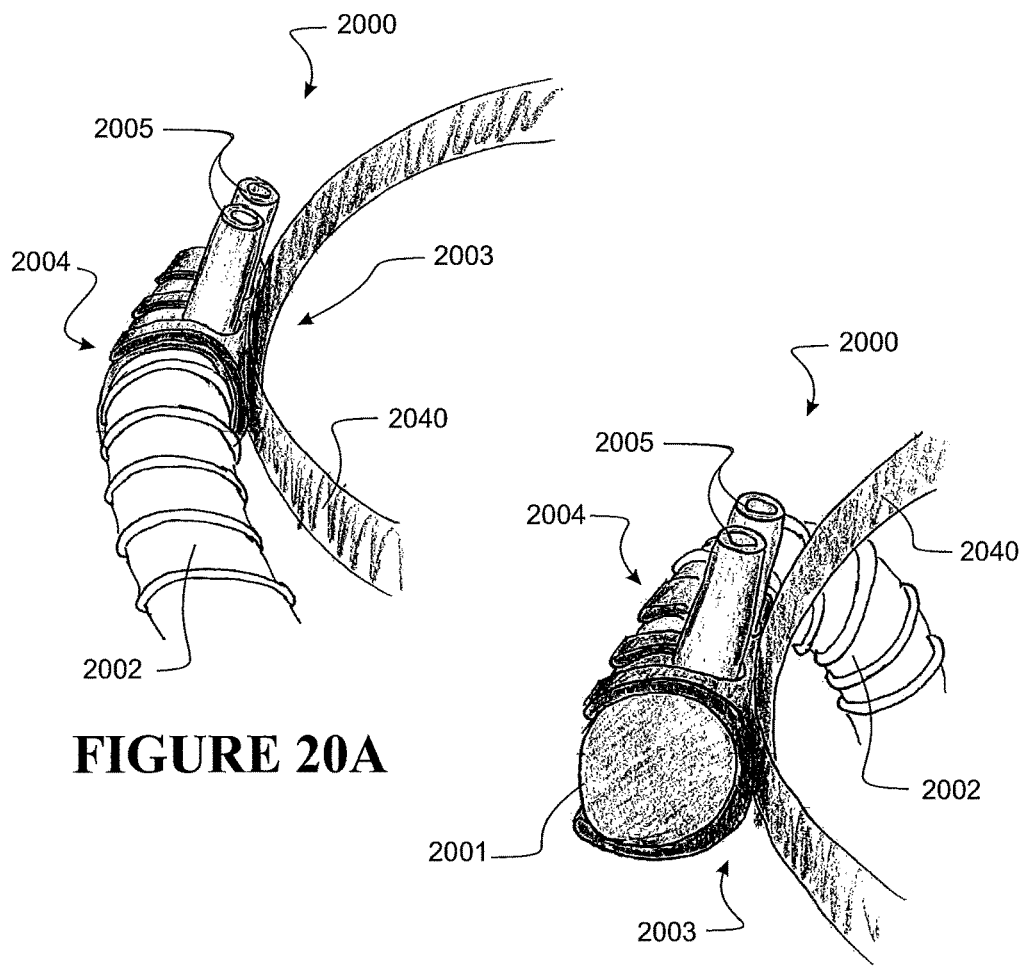
FIGURE 20A
FIGURE 20B
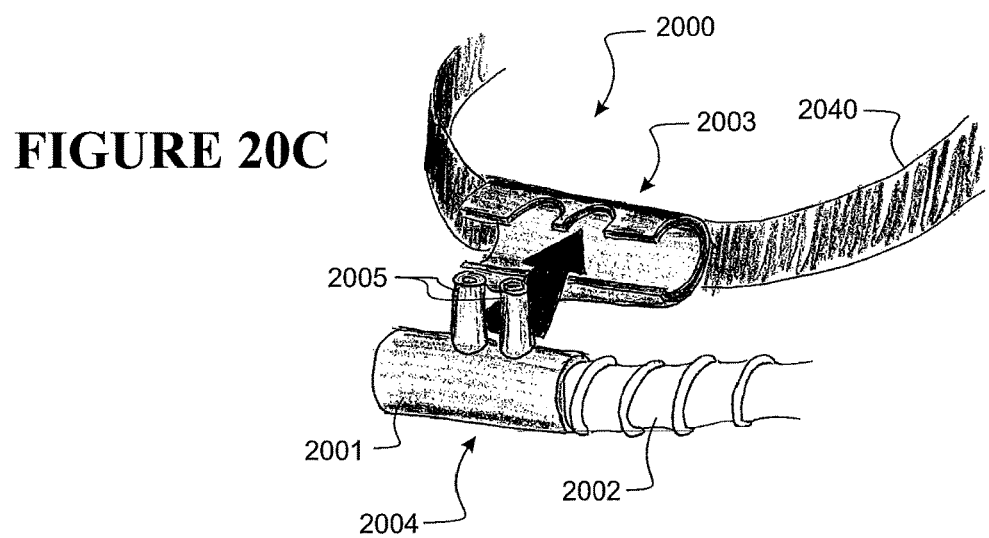
FIGURE 20C

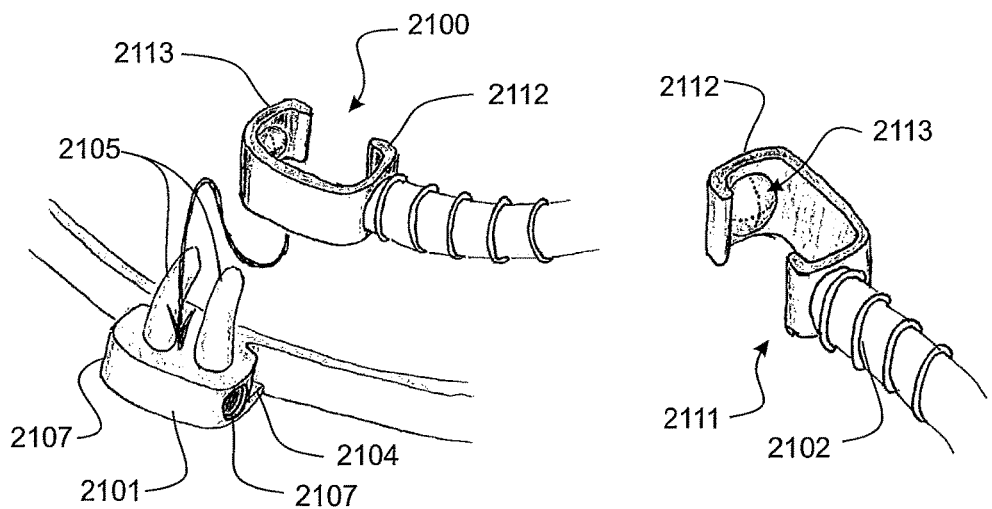
FIGURE 21A    FIGURE 21B
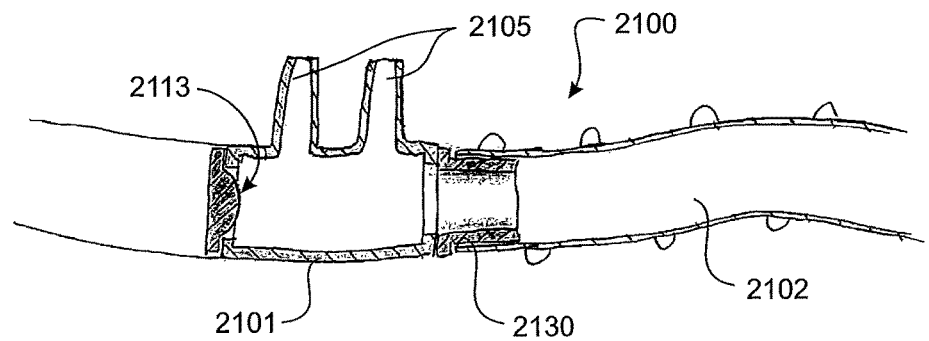
FIGURE 21C
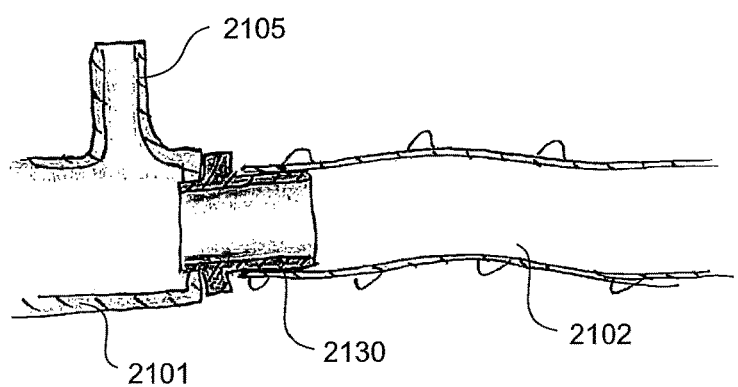
FIGURE 21D

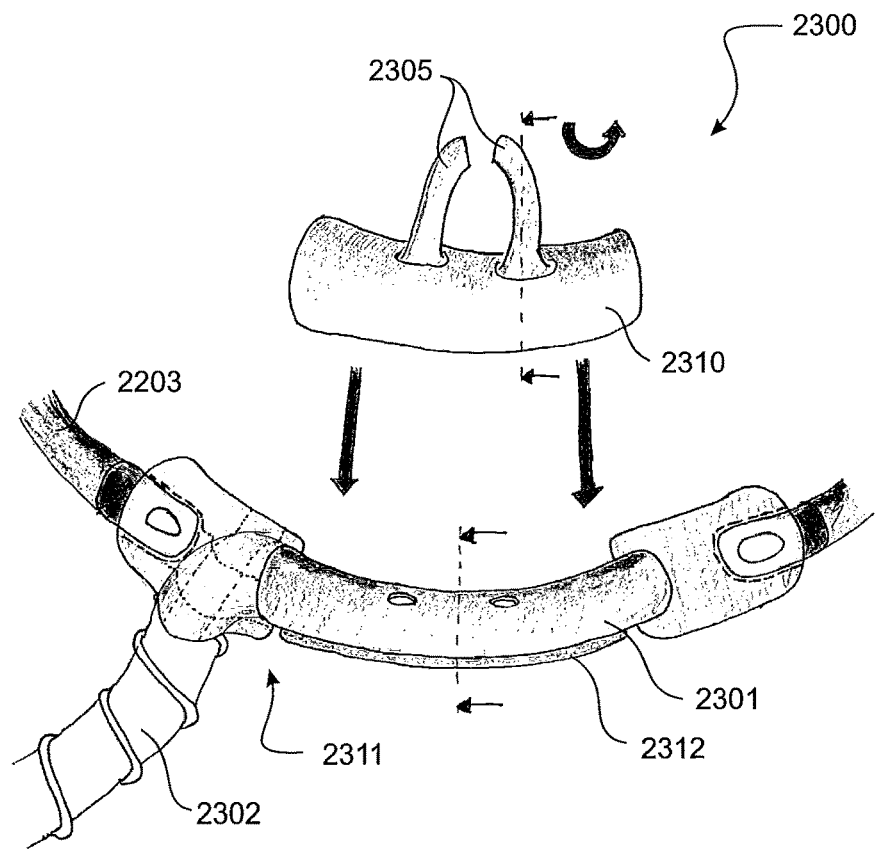
FIGURE 23A
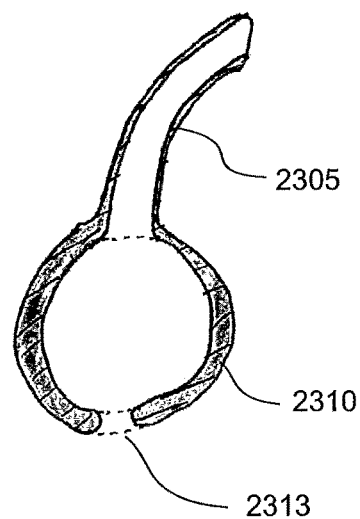 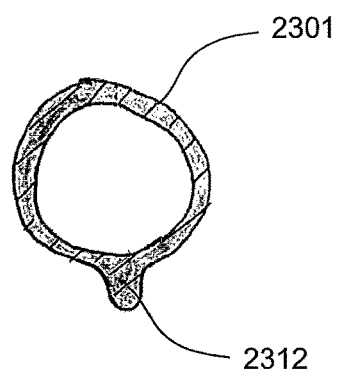
FIGURE 23B FIGURE 23C

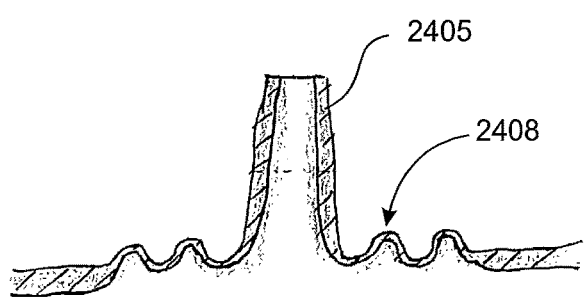
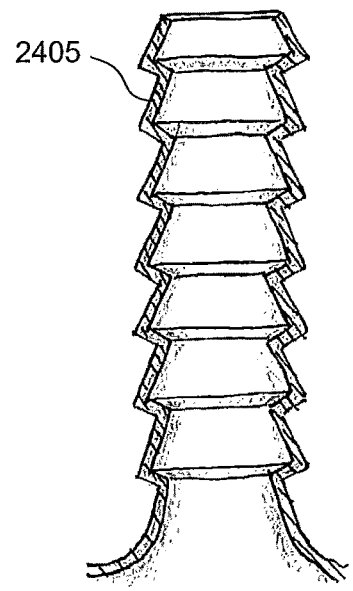
FIGURE 24C
FIGURE 24D
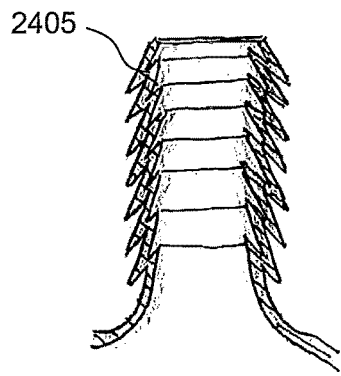
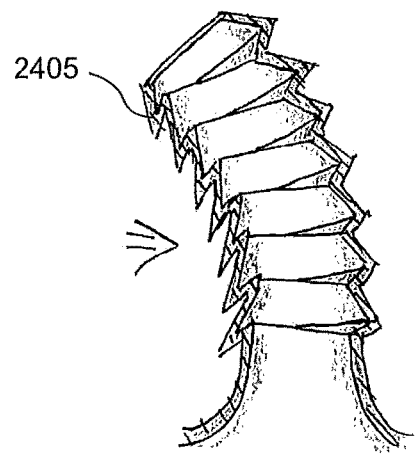
FIGURE 24E
FIGURE 24F

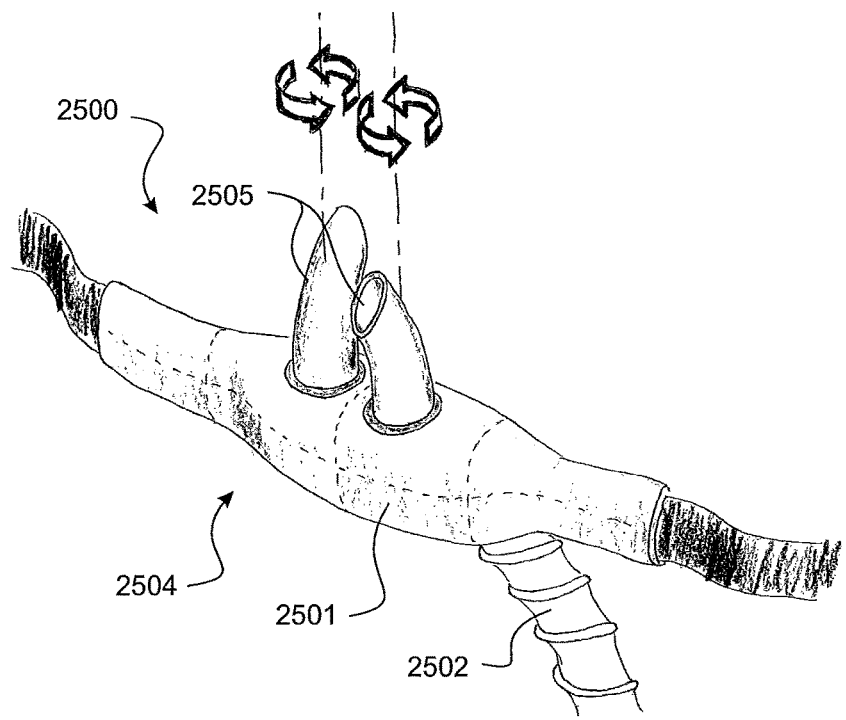
FIGURE 25A
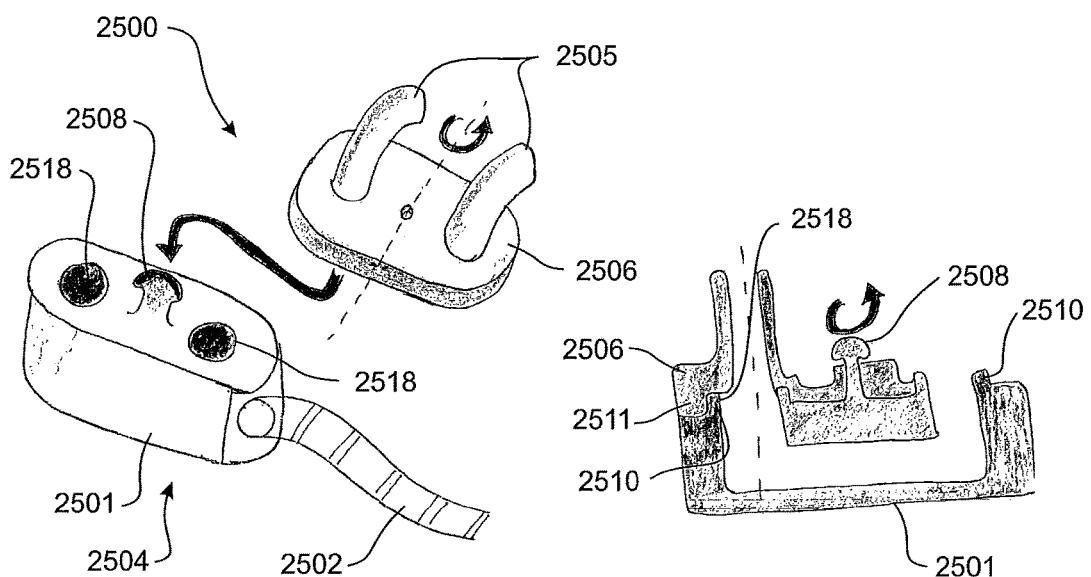
FIGURE 25B     FIGURE 25C

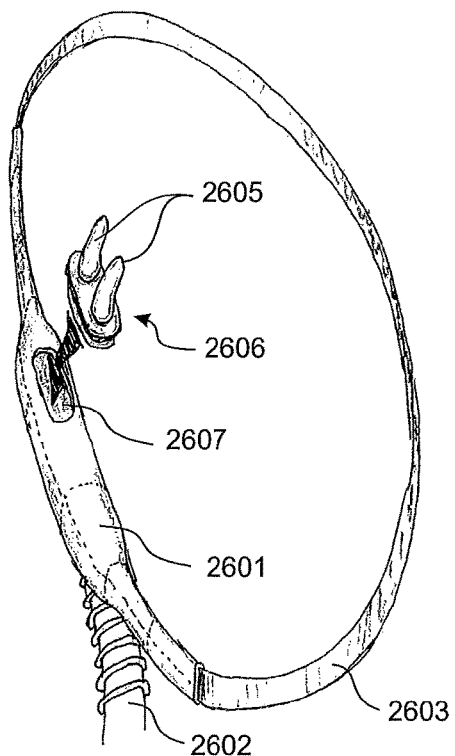
FIGURE 26C
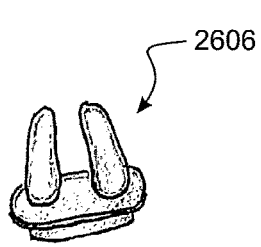 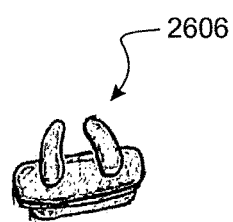 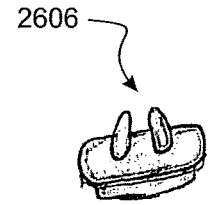
FIGURE 26D  FIGURE 26E  FIGURE 26F small     medium     large

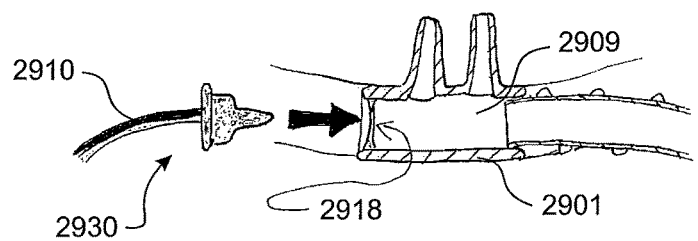
FIGURE 29D
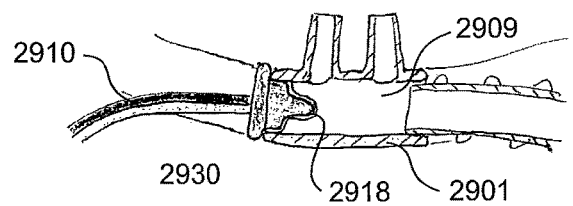
FIGURE 29E
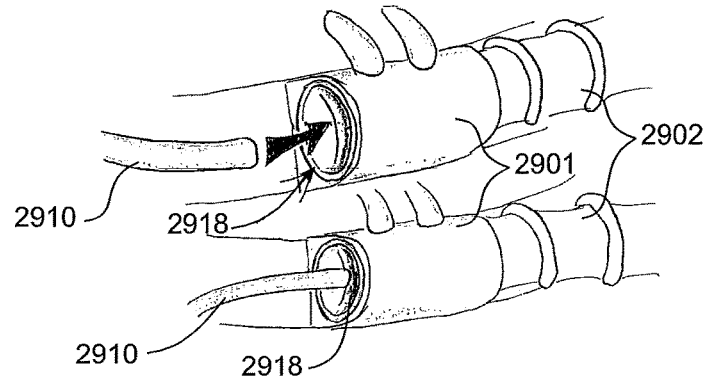
FIGURE 29F
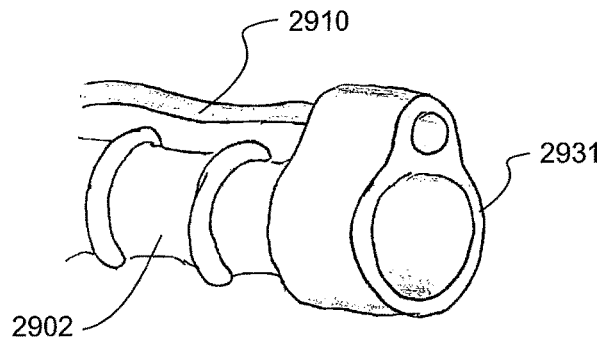

FIGURE 30G
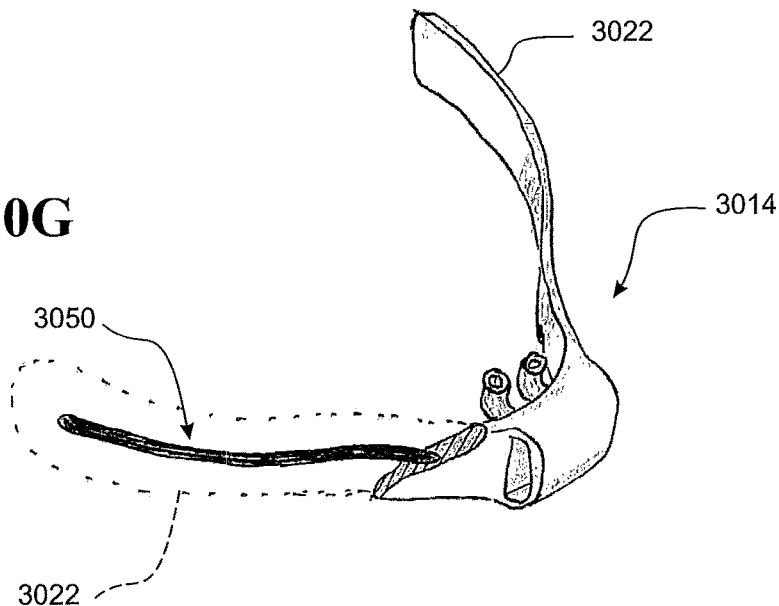
FIGURE 30H
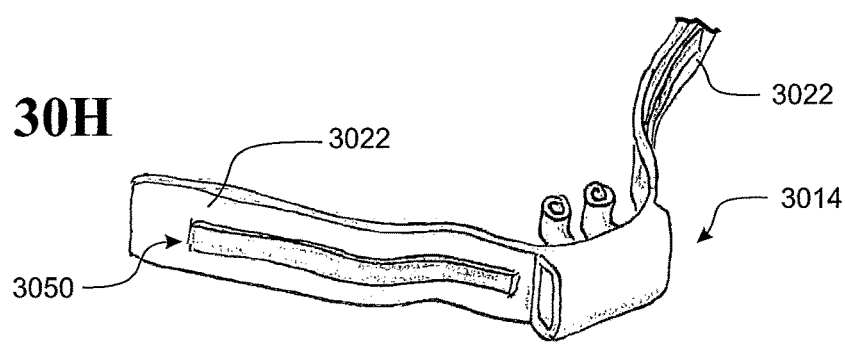
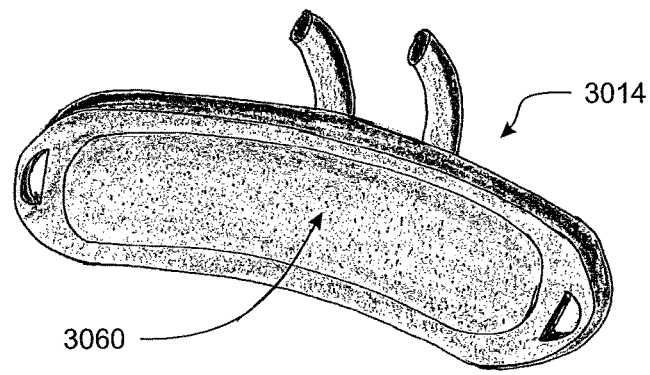
FIGURE 30I

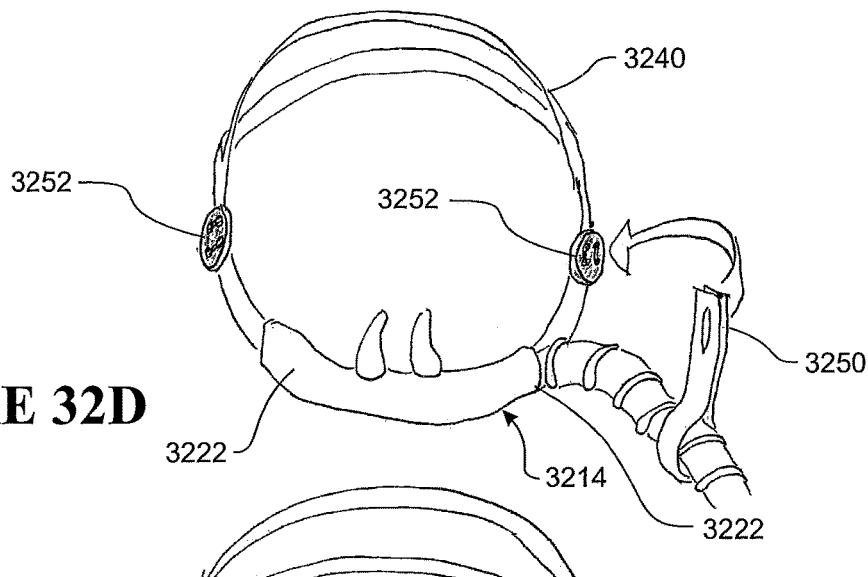
FIGURE 32D
FIGURE 32E
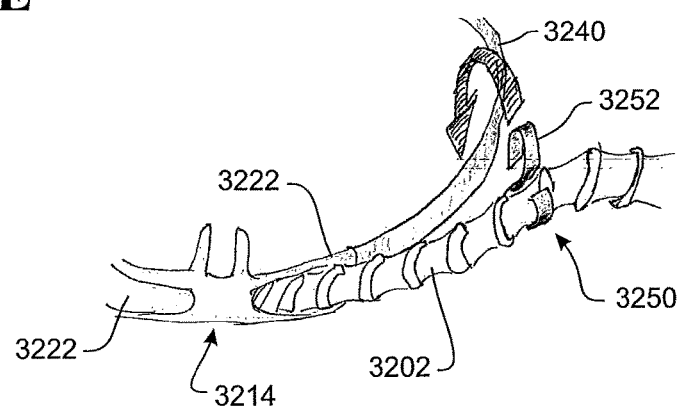
FIGURE 32F

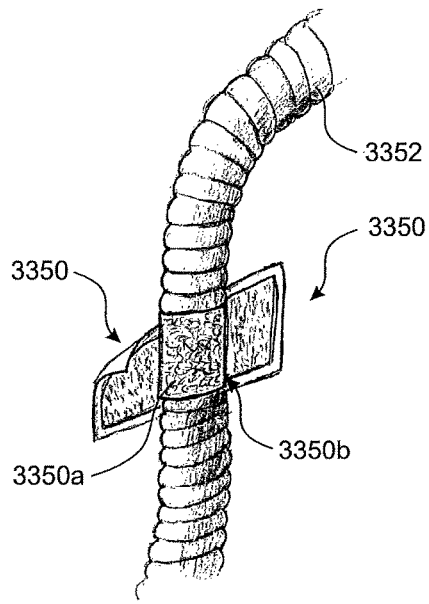
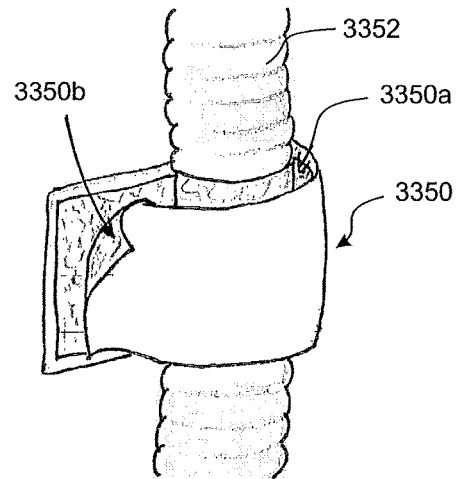
FIGURE 33N    FIGURE 33O
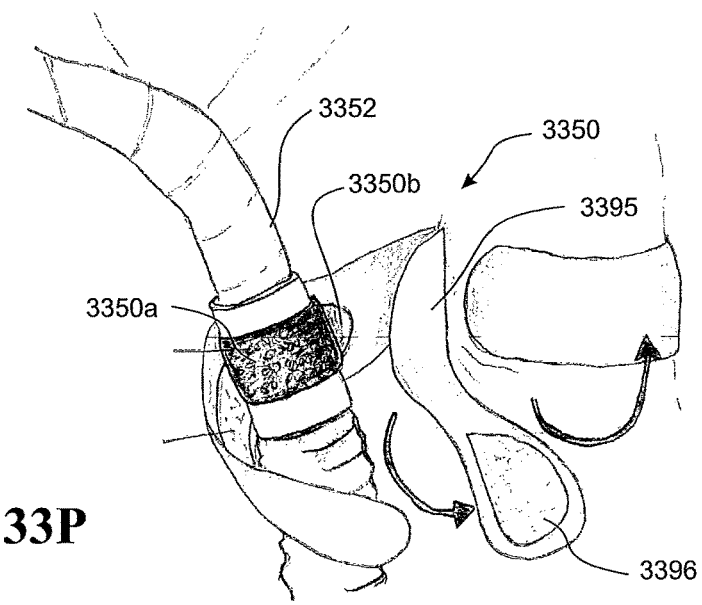
FIGURE 33P

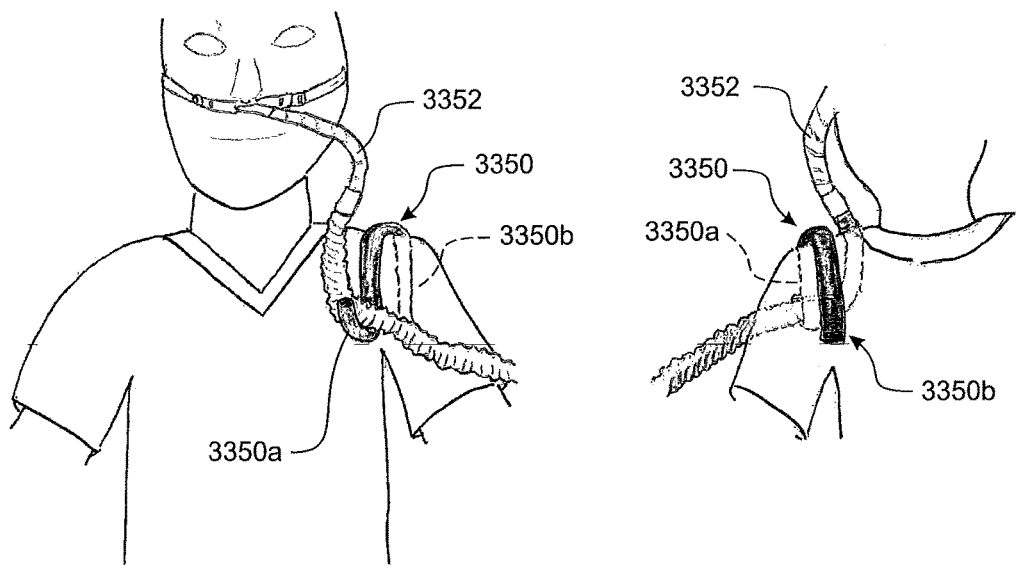
FIGURE 33Q FIGURE 33R
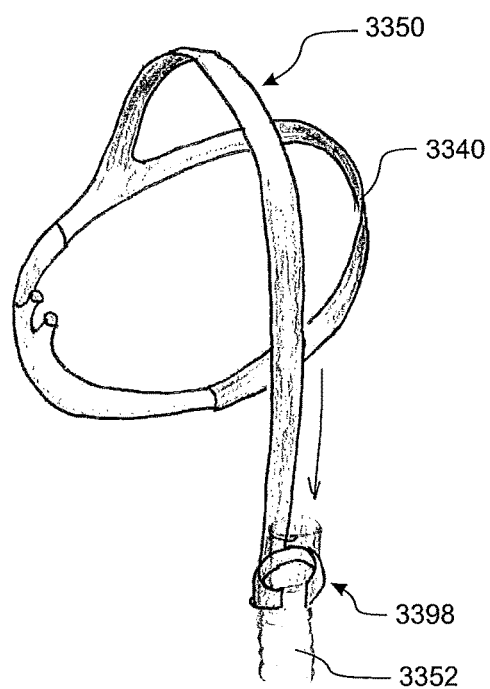
FIGURE 33S

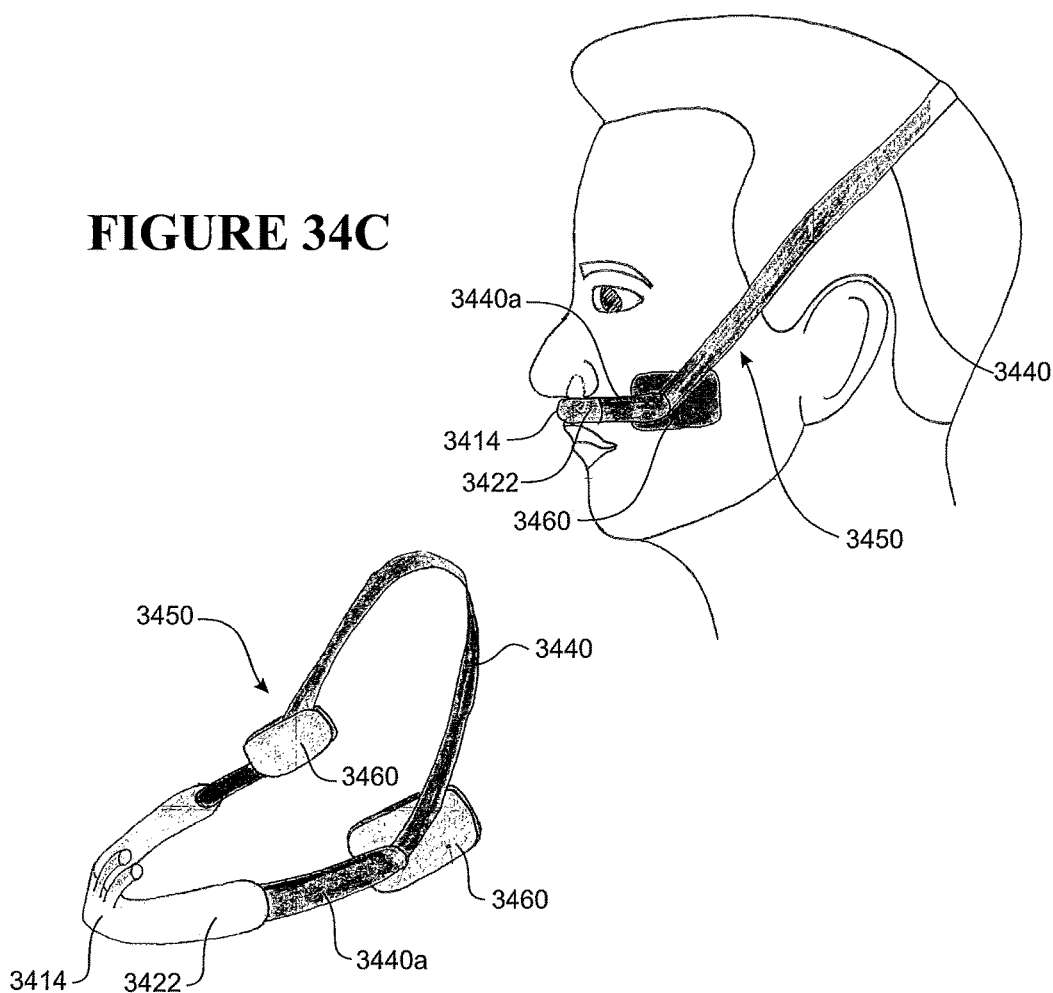
FIGURE 34C
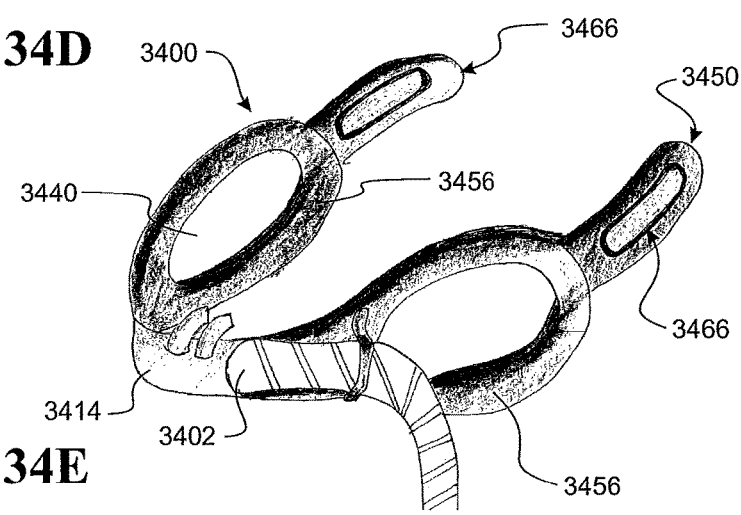
FIGURE 34D
FIGURE 34E

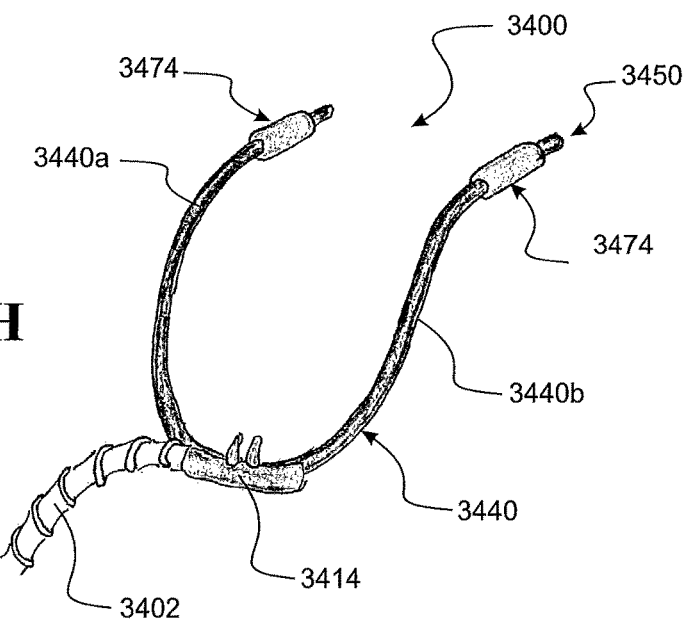
FIGURE 34H
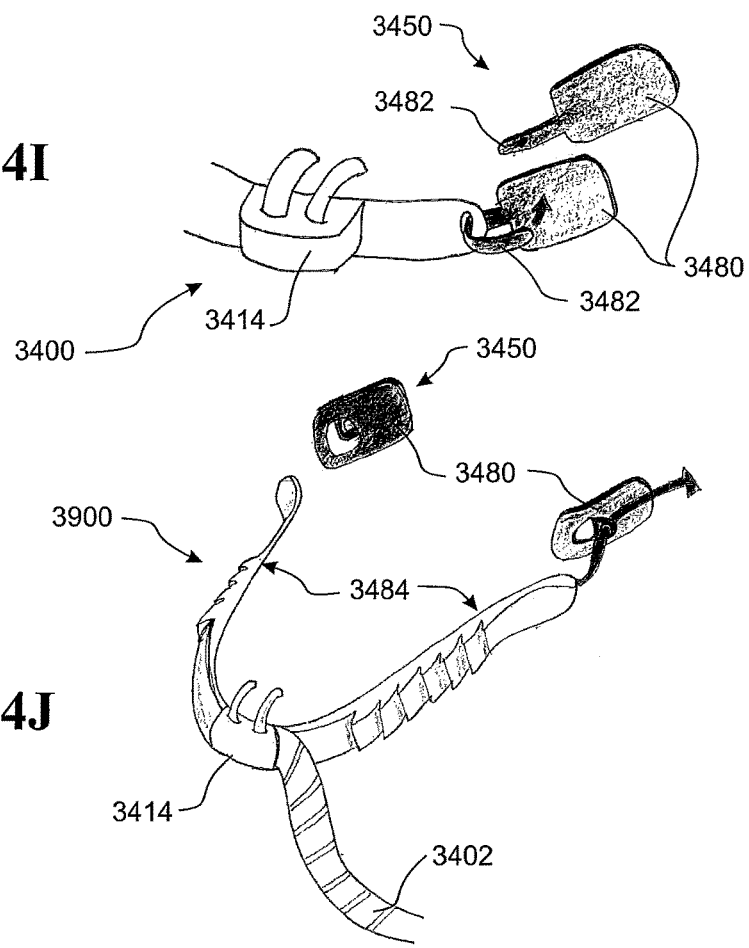
FIGURE 34I
FIGURE 34J

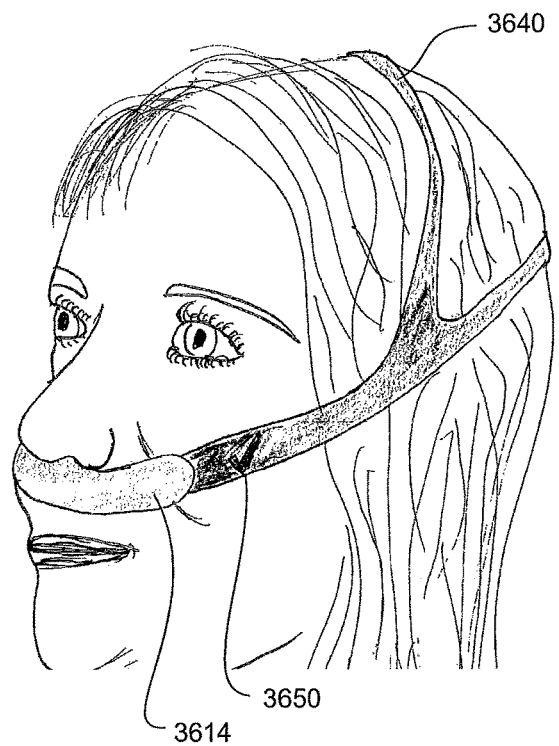
FIGURE 36A
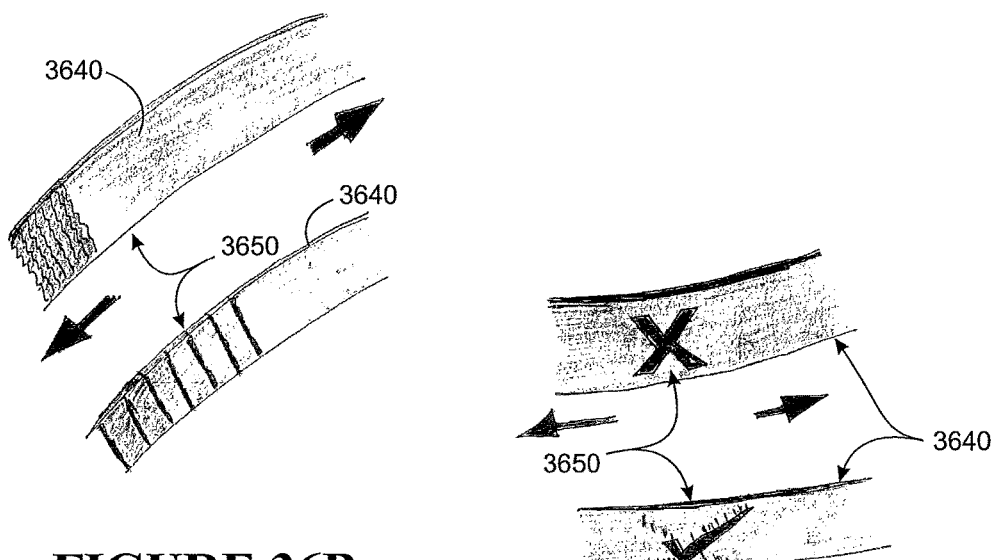
FIGURE 36B
FIGURE 36C

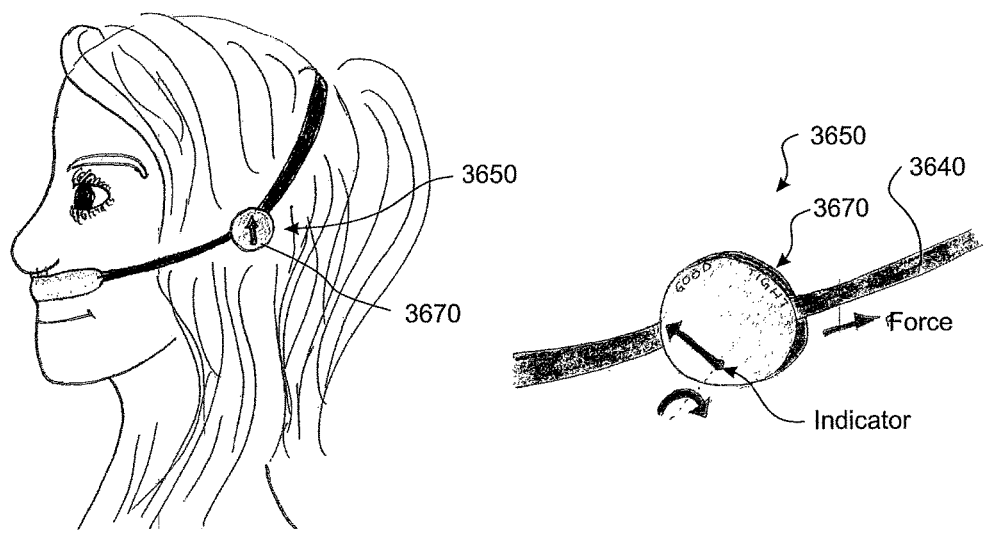
FIGURE 36H  FIGURE 36I
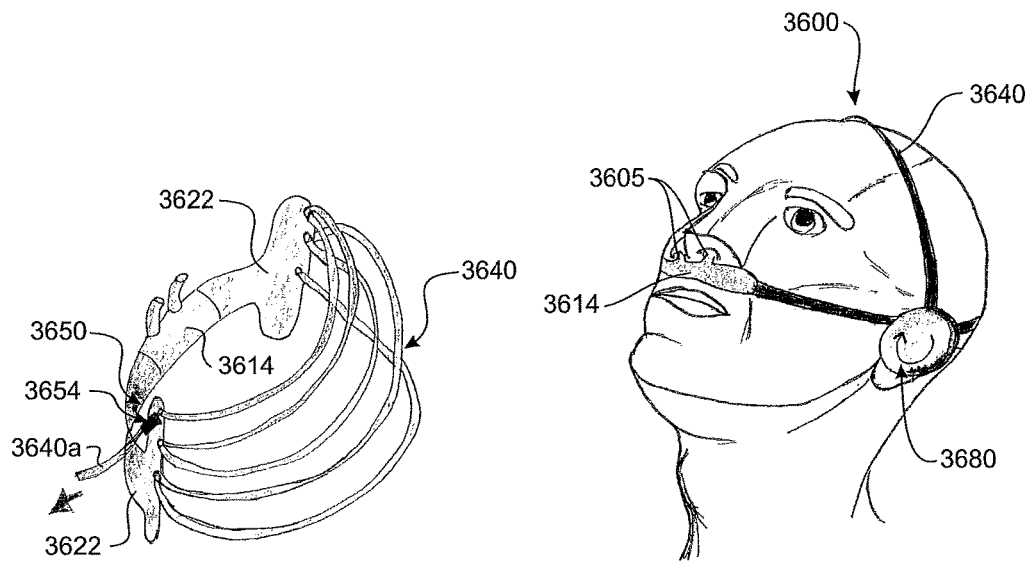
FIGURE 36J  FIGURE 36K

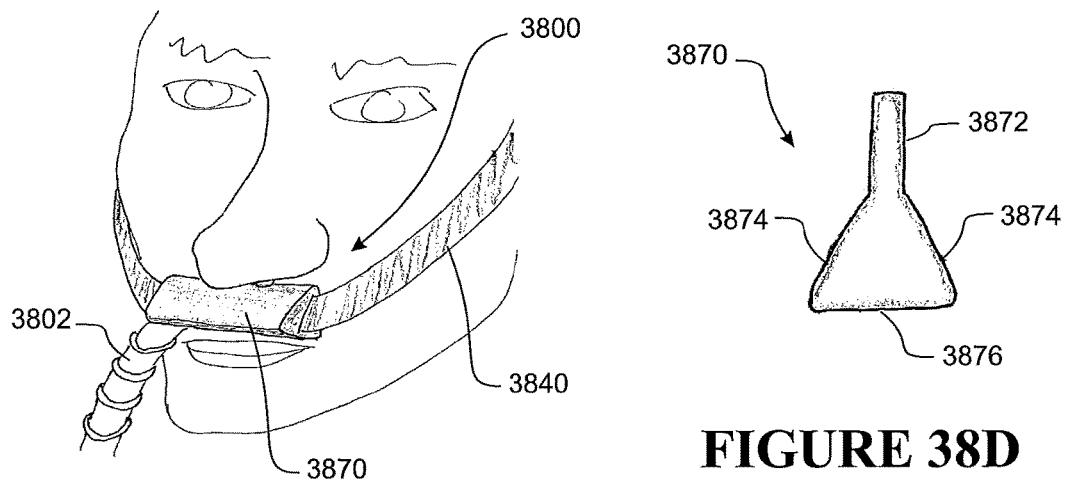
FIGURE 38C
FIGURE 38D
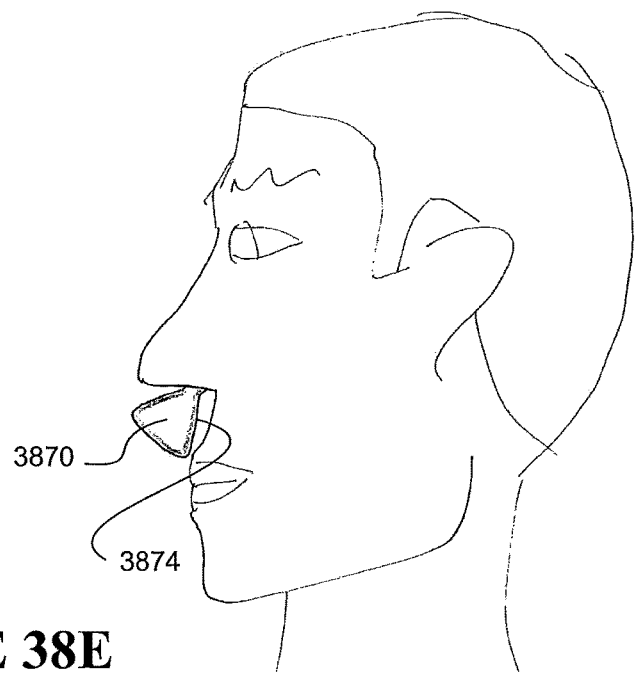
FIGURE 38E

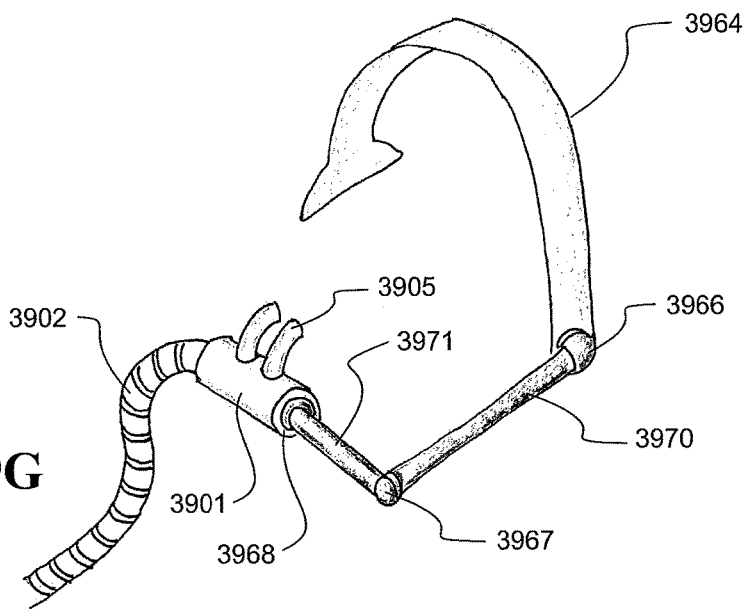
FIGURE 39G
FIGURE 39H
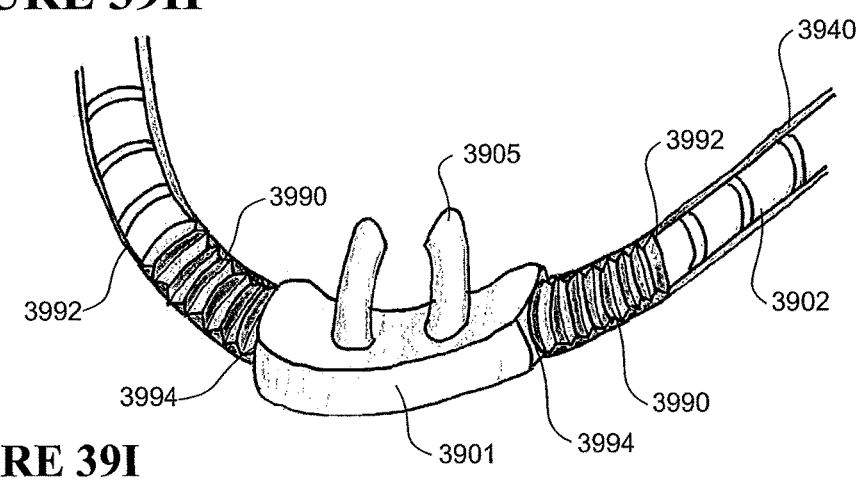
FIGURE 39I

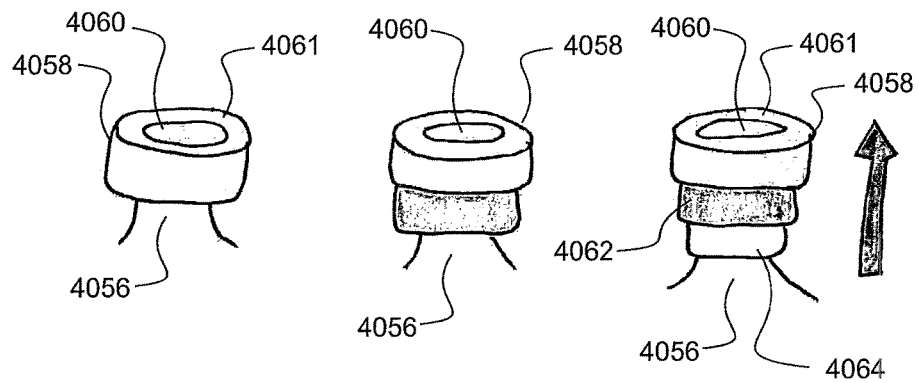
FIGURE 40E
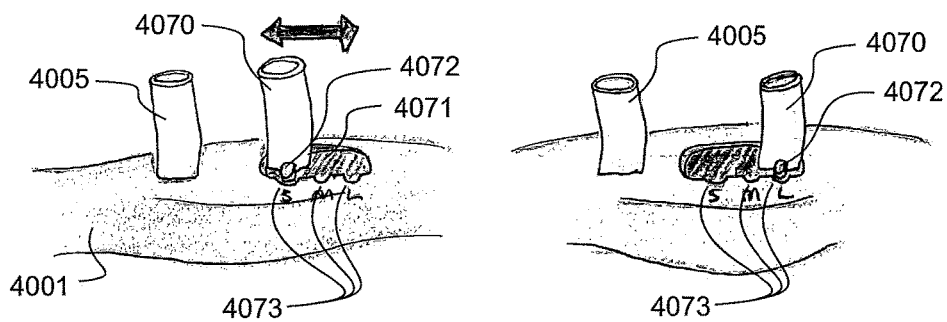
FIGURE 40F
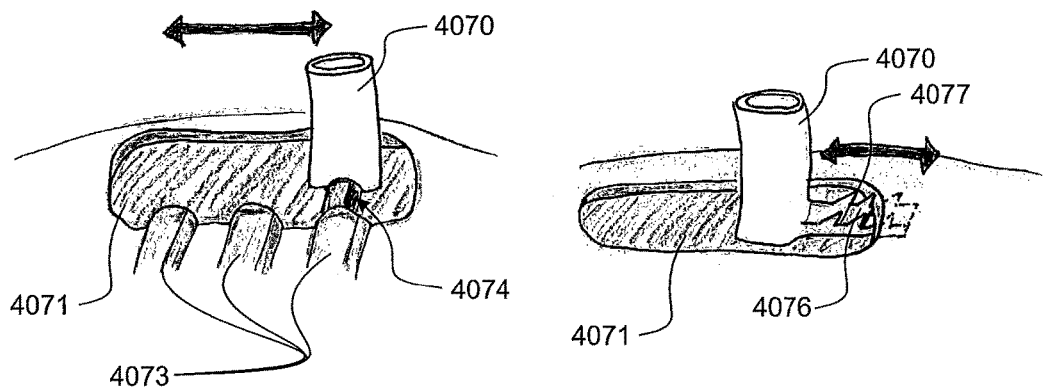
FIGURE 40G      FIGURE 40H

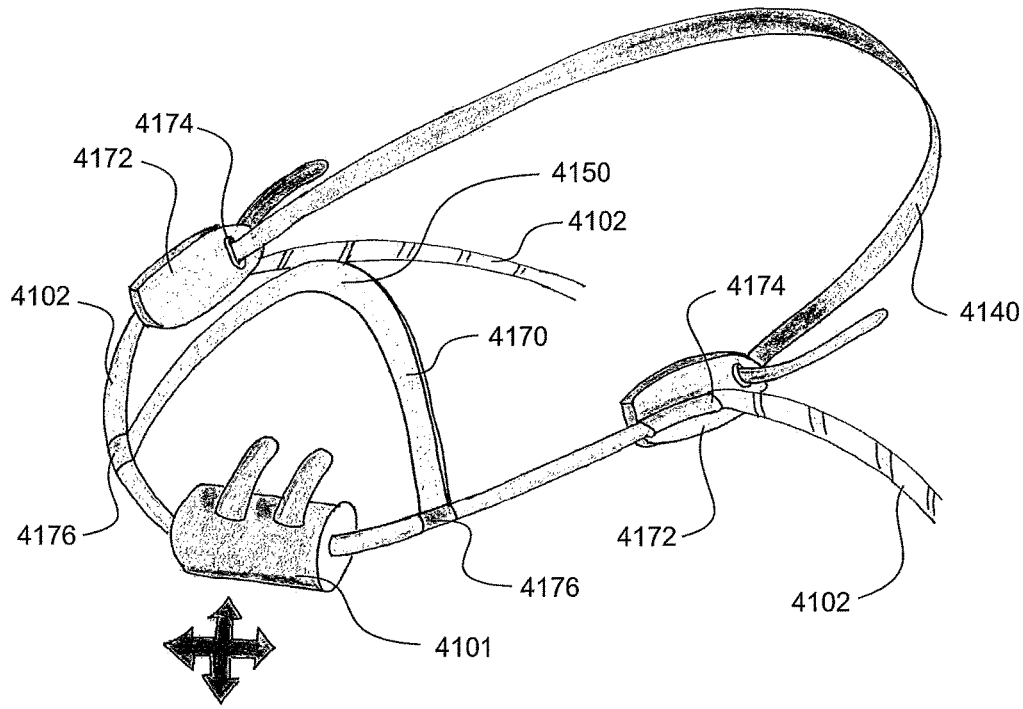
FIGURE 41D
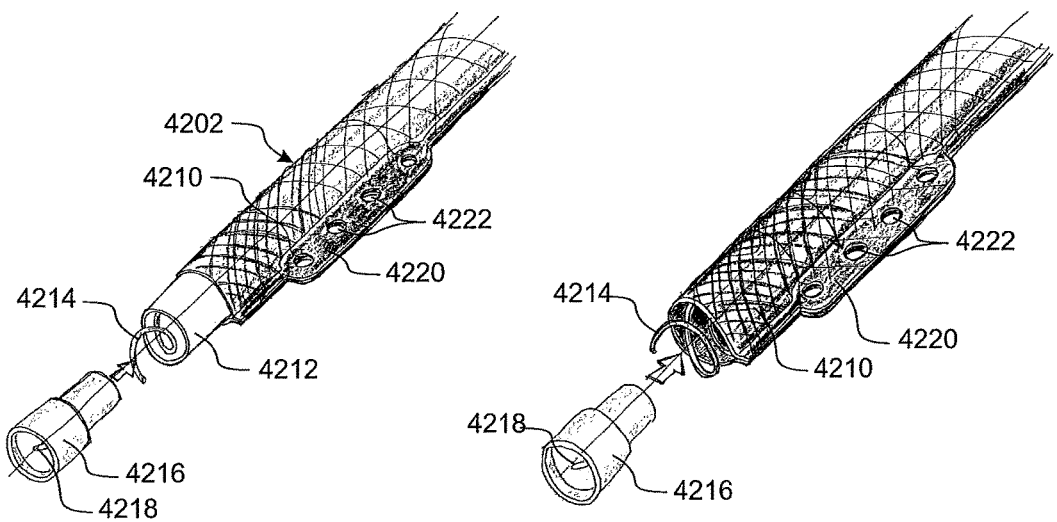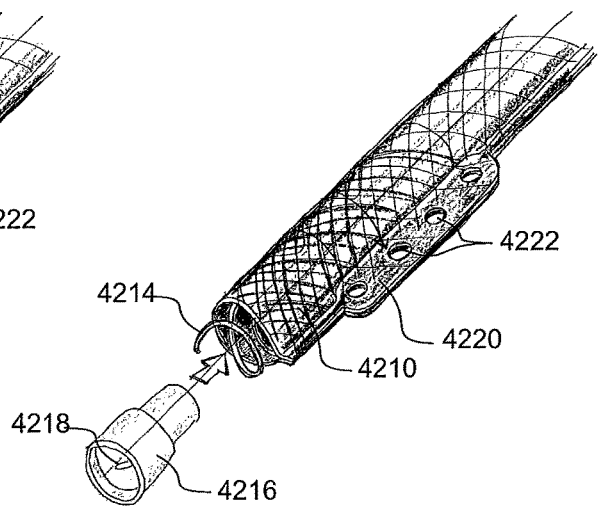
FIGURE 42A  FIGURE 42B

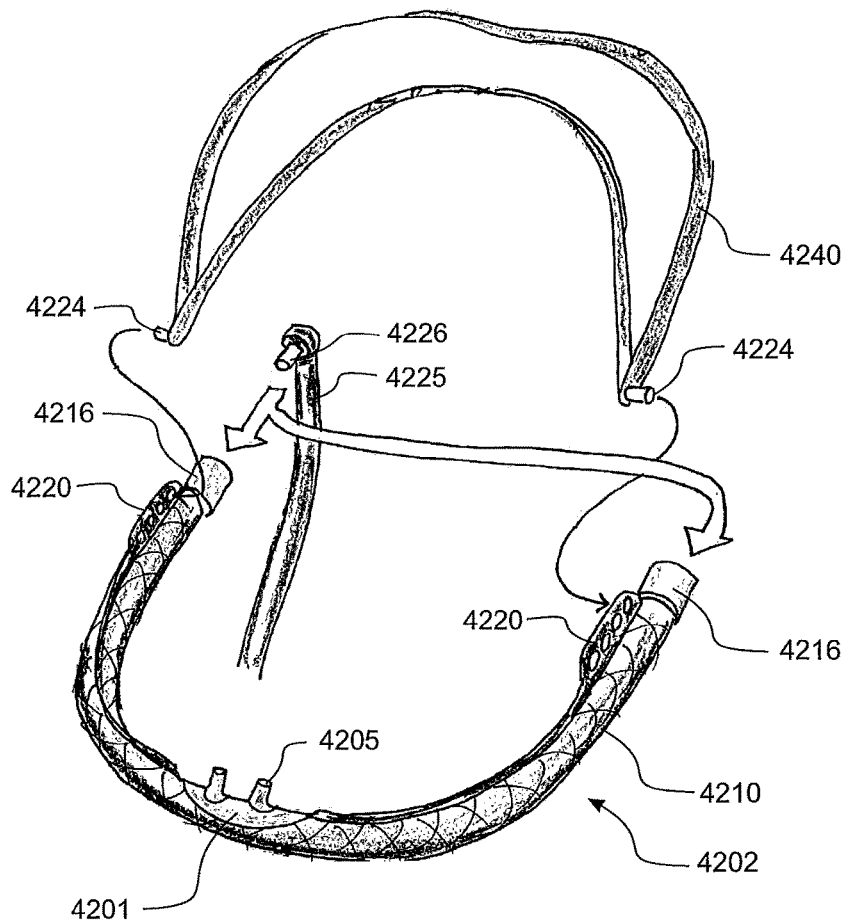
FIGURE 42C
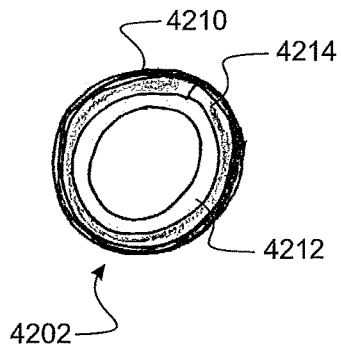 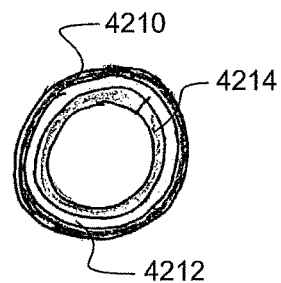 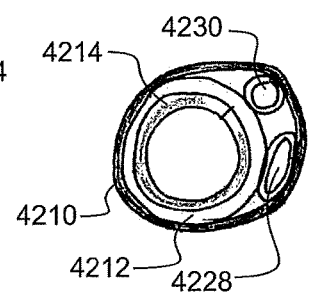
FIGURE 42D  FIGURE 42E  FIGURE 42F

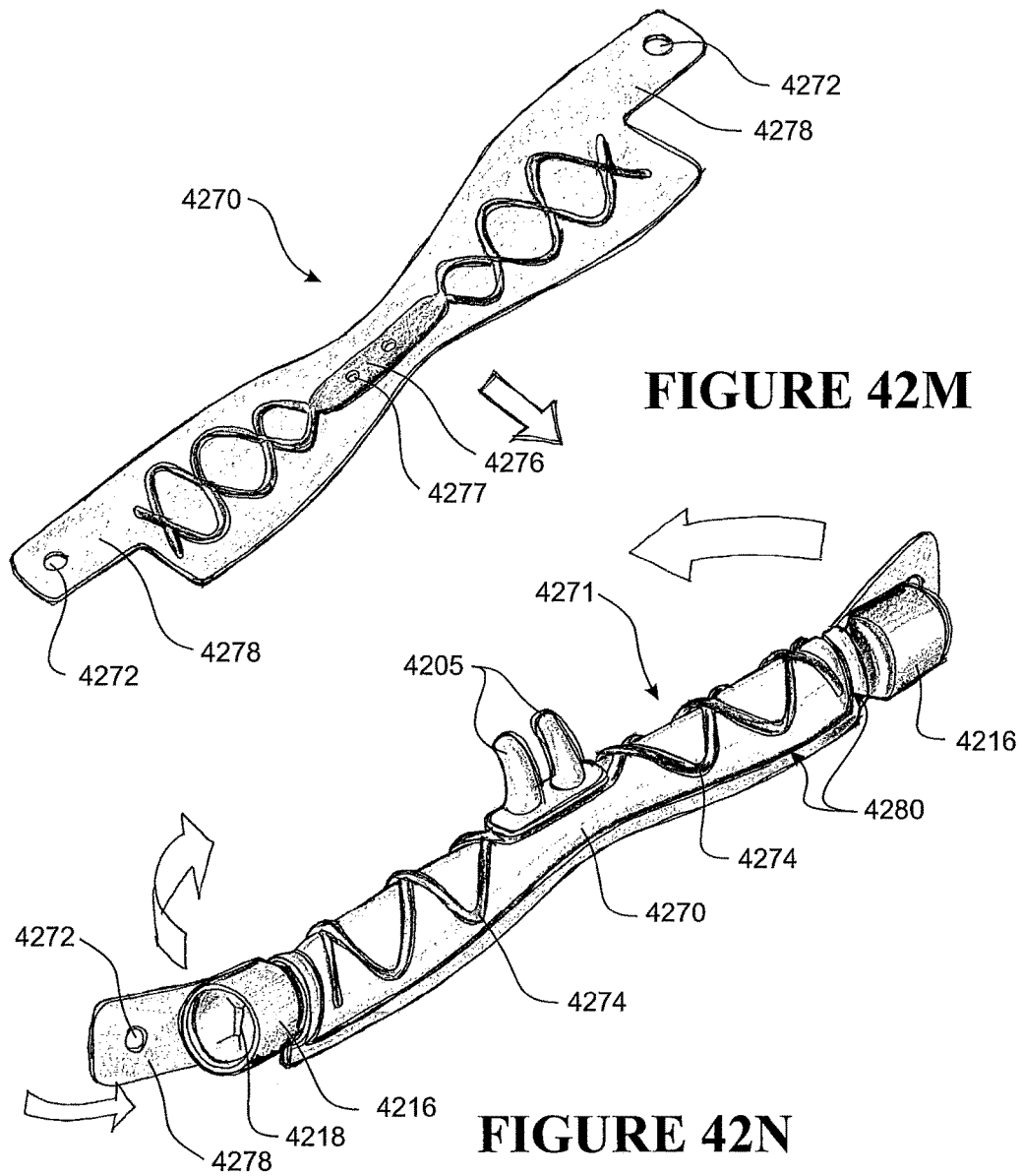
FIGURE 42M
FIGURE 42N
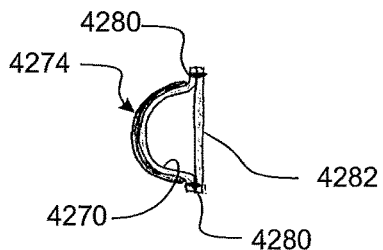
FIGURE 42O

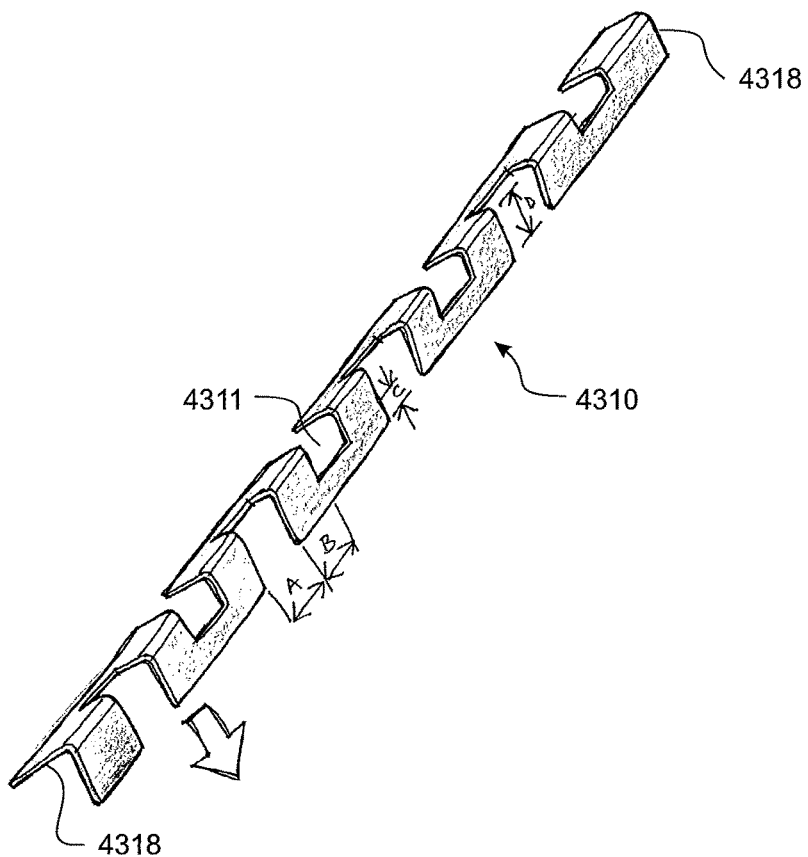
FIGURE 43A
FIGURE 43B
FIGURE 43C

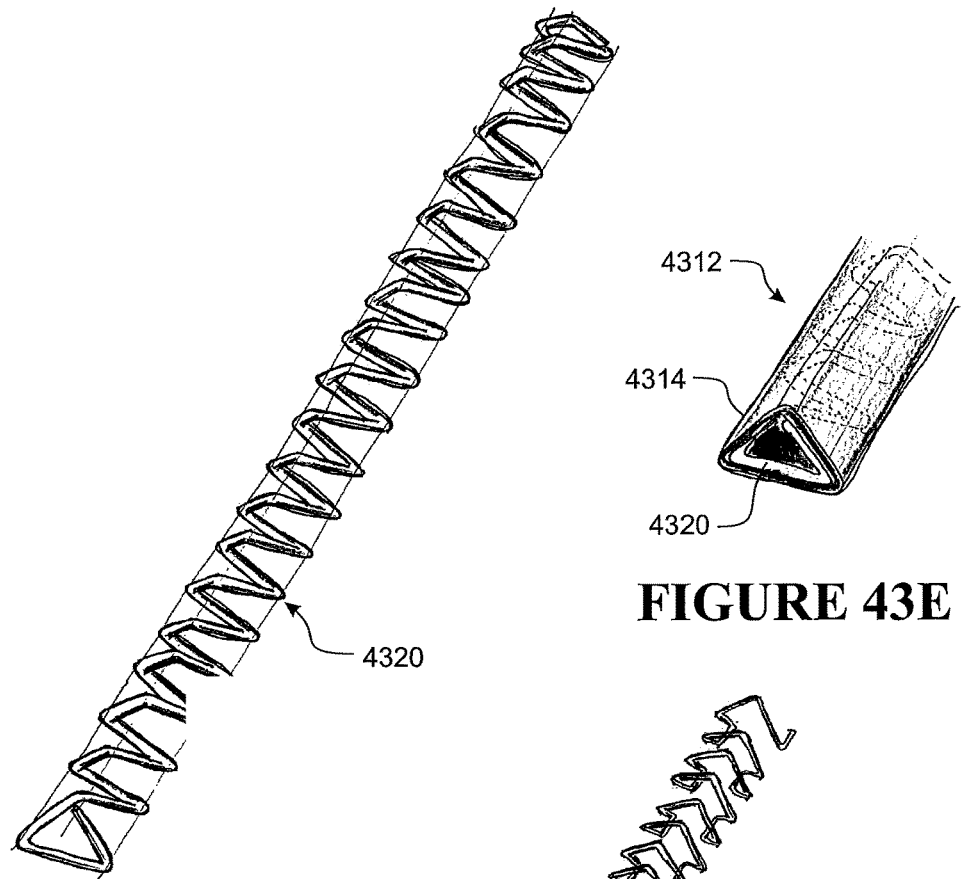
FIGURE 43E
FIGURE 43D
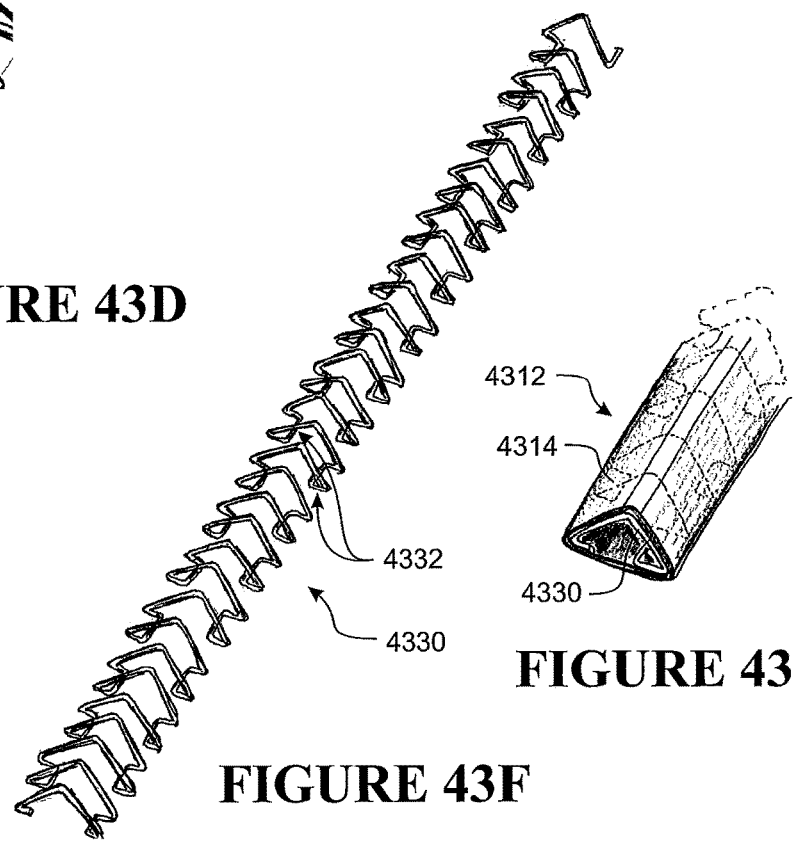
FIGURE 43G
FIGURE 43F

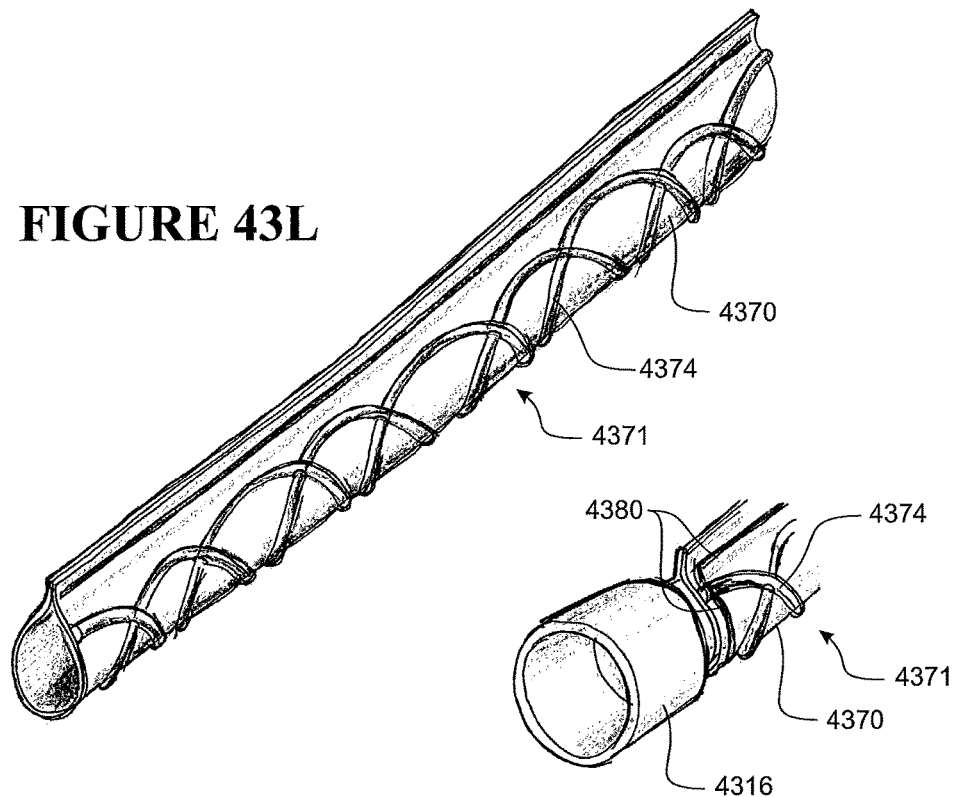
FIGURE 43L
FIGURE 43M
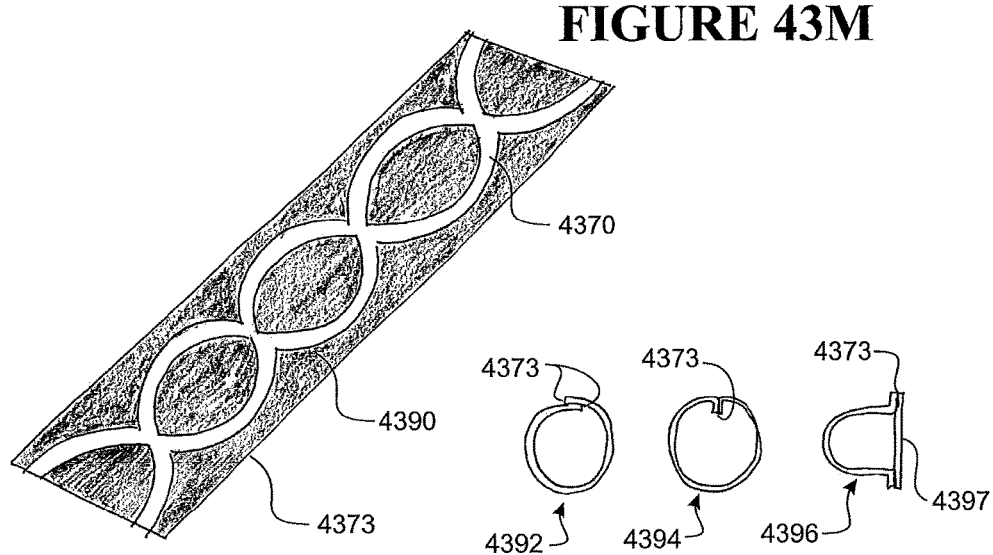
FIGURE 43N
FIGURE 43O

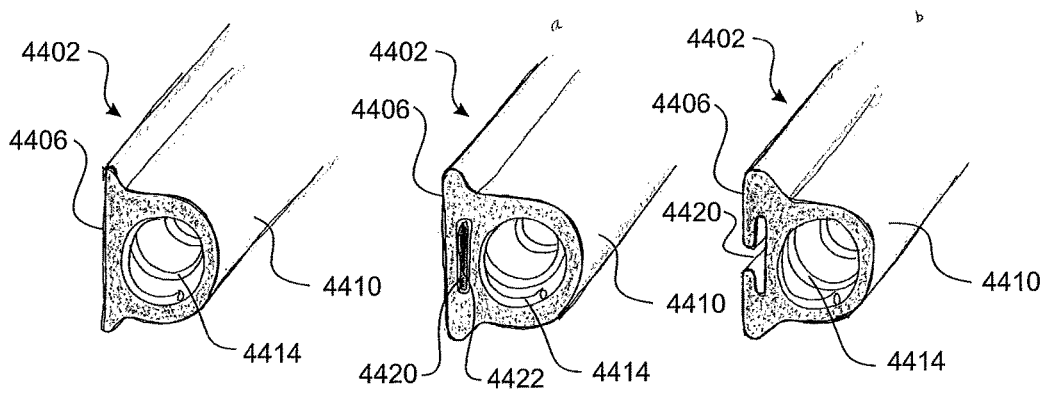
FIGURE 44A  FIGURE 44B  FIGURE 44C
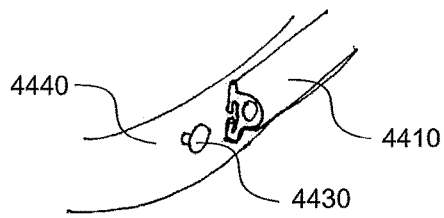
FIGURE 44D
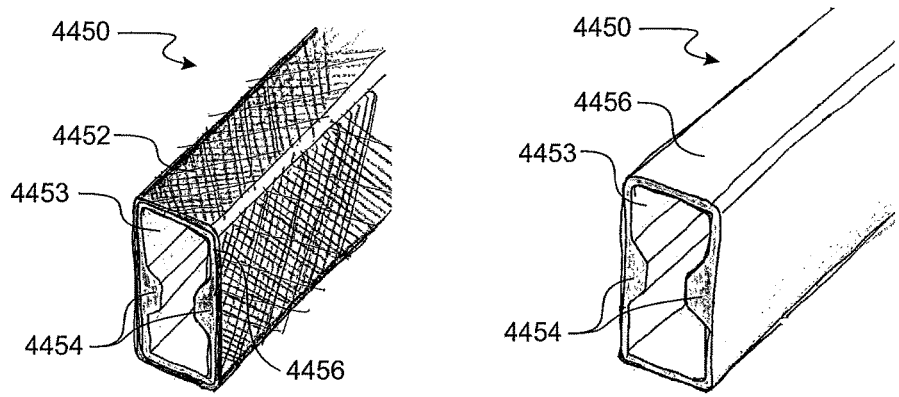
FIGURE 44E  FIGURE 44F
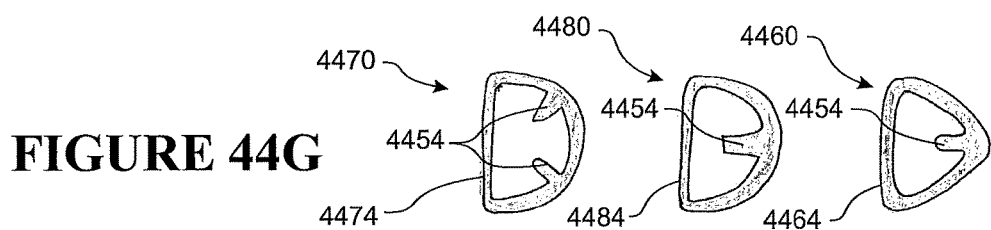
FIGURE 44G

FIGURE 45F
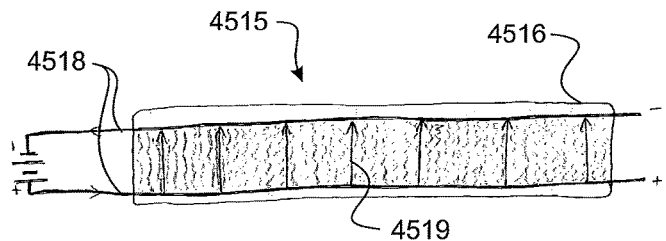
FIGURE 45G
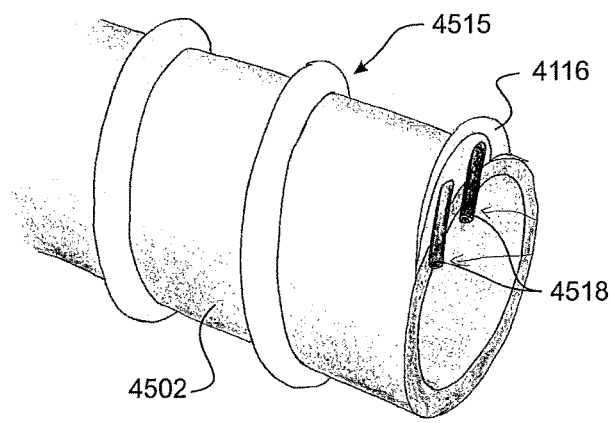
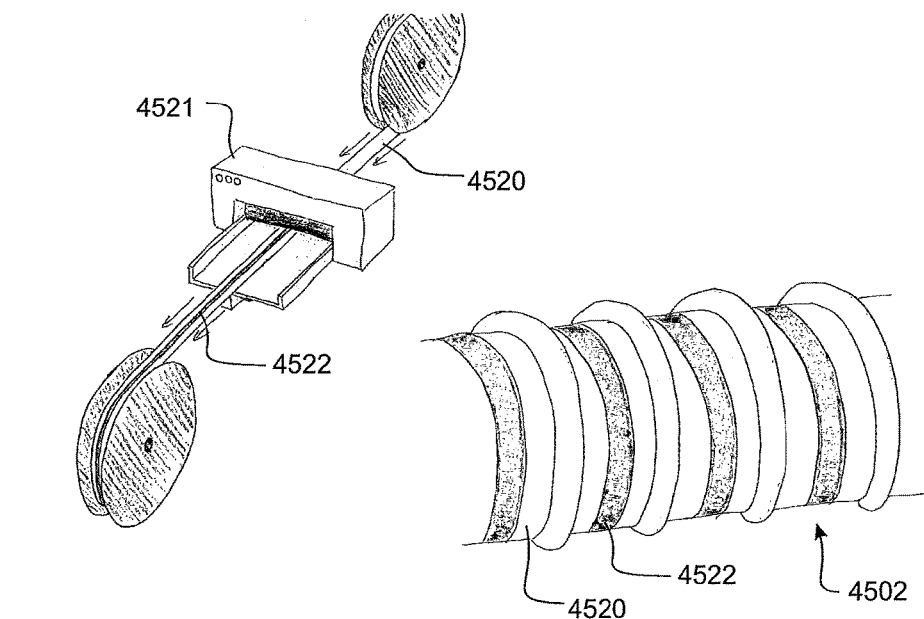
FIGURE 45H
FIGURE 45I

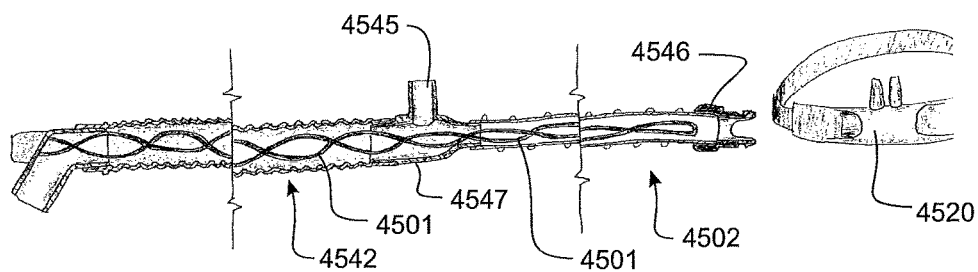
FIGURE 45M
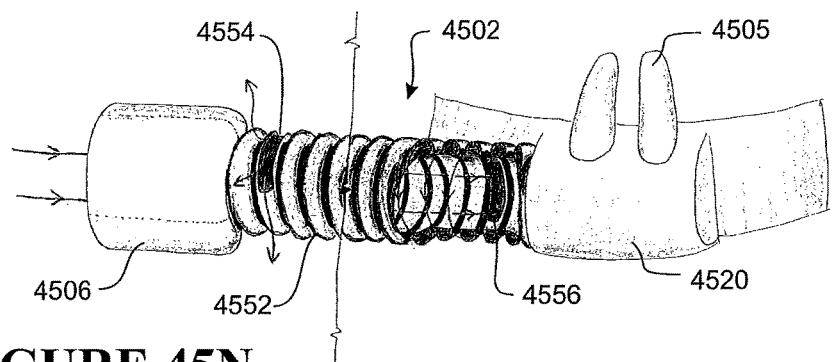
FIGURE 45N
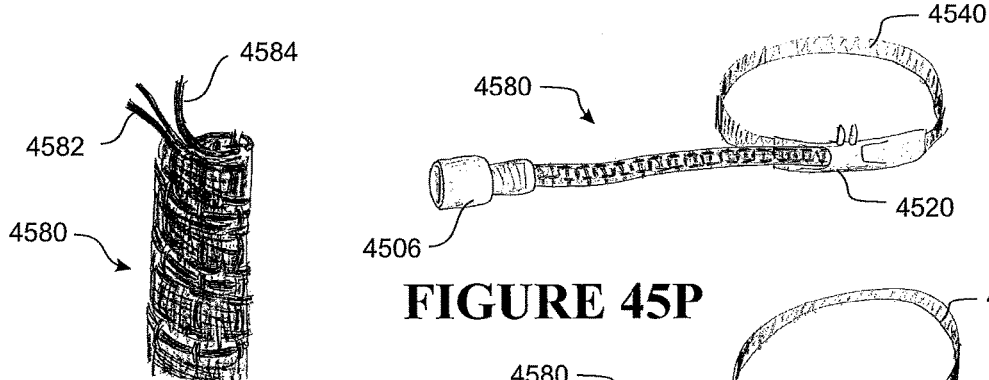
FIGURE 45O
FIGURE 45P
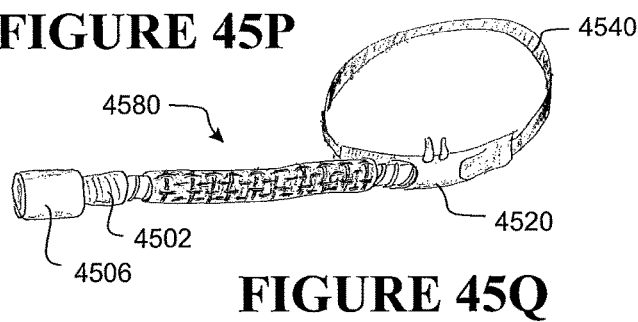
FIGURE 45Q

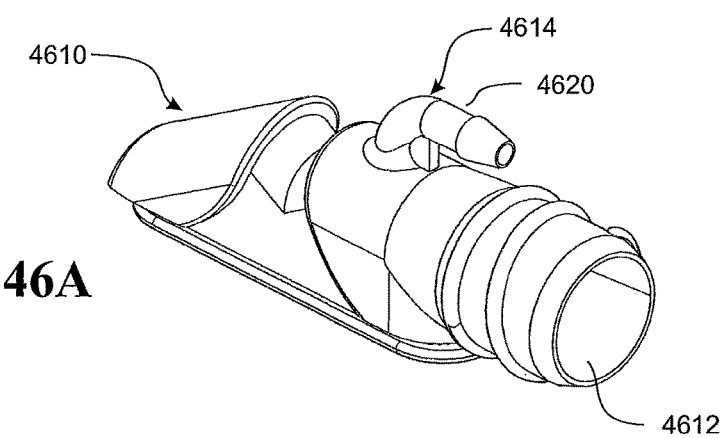
FIGURE 46A
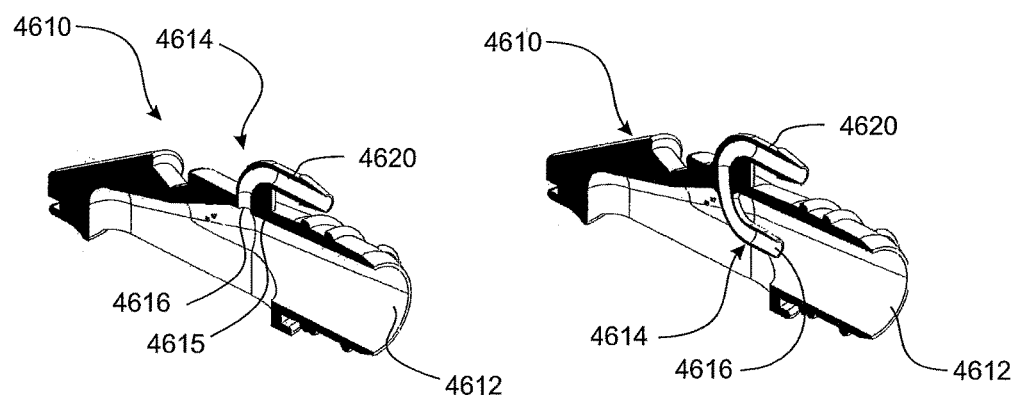
FIGURE 46B  FIGURE 46C
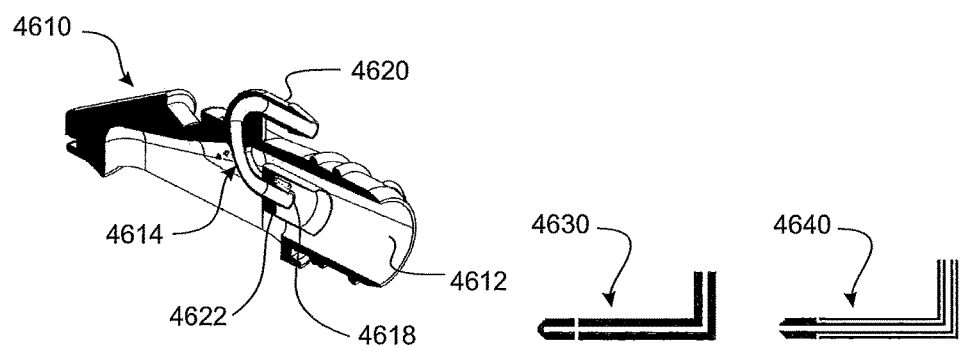
FIGURE 46D  FIGURE 46E

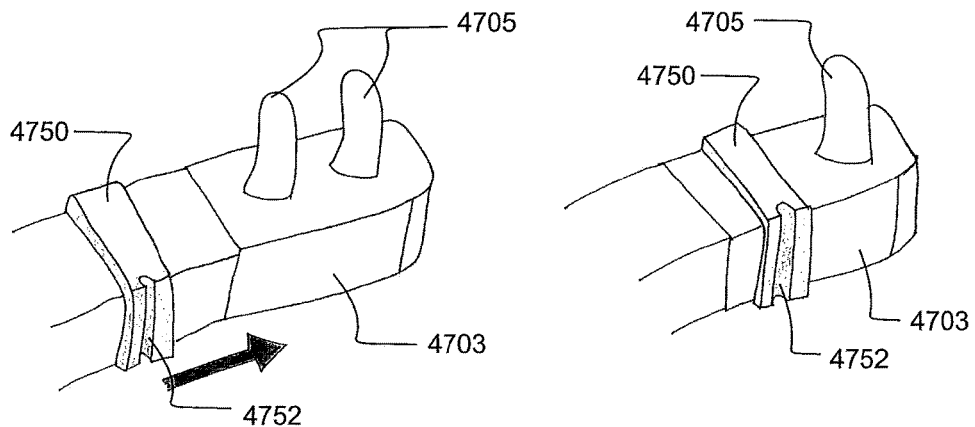
FIGURE 47L
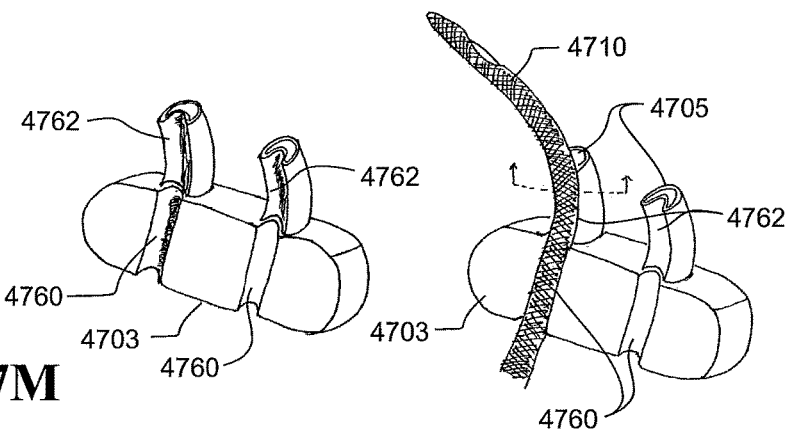
FIGURE 47M
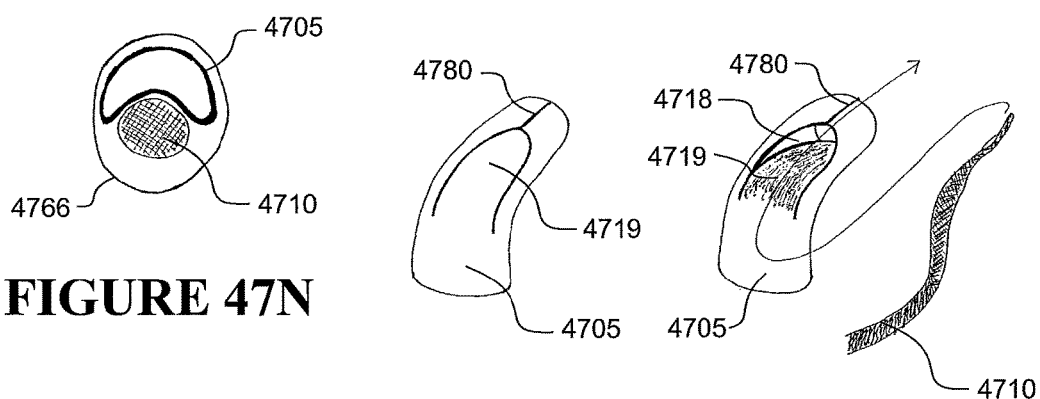
FIGURE 47N
FIGURE 47O

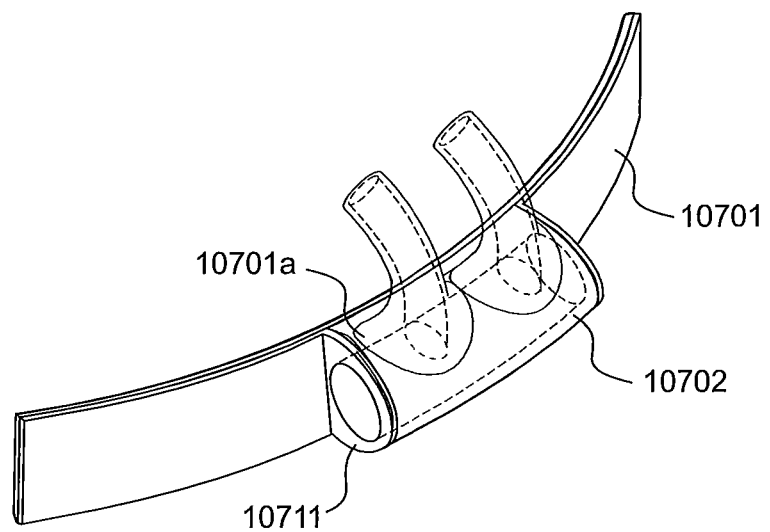
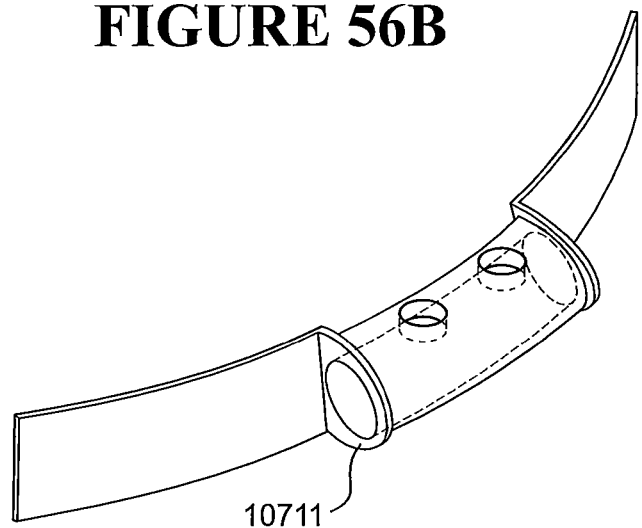
FIGURE 56B
FIGURE 56C

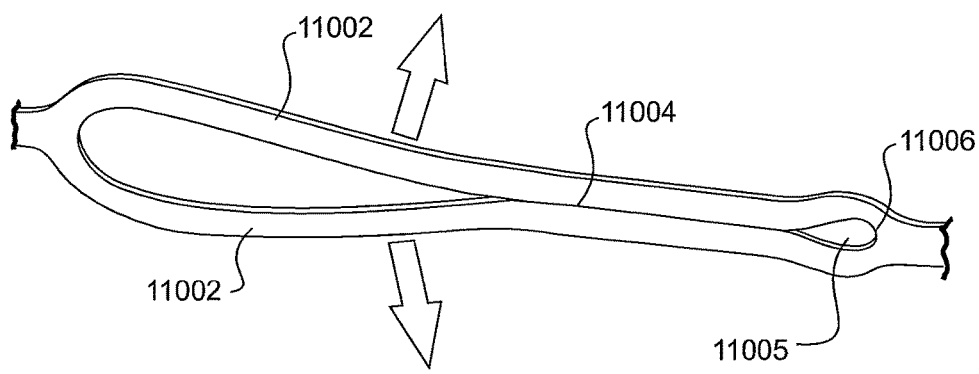
FIGURE 58D
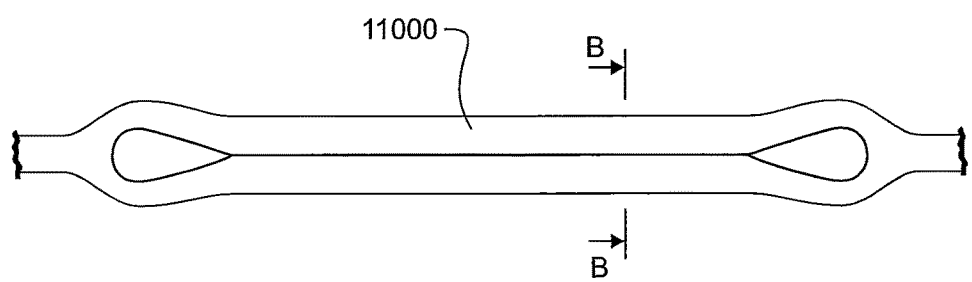
FIGURE 58E
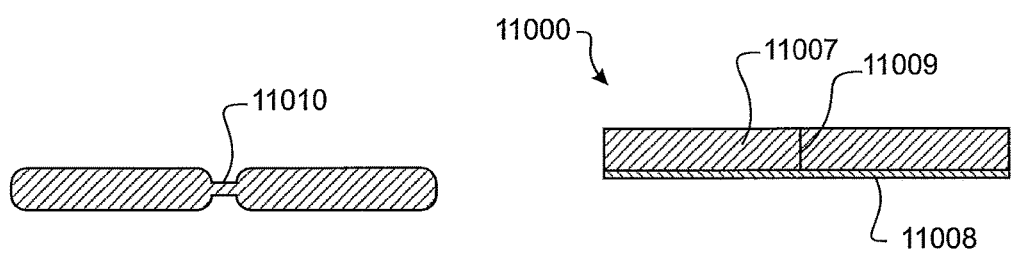
FIGURE 58F      FIGURE 58G

NASAL CANNULA ASSEMBLIES AND RELATED PARTS

FIELD OF THE INVENTION

The present disclosure relates to devices and systems for providing gases to patients for respiratory therapy. More specifically, the present disclosure relates to nasal cannula interfaces for providing gases to patients via the nasal passages.

BACKGROUND OF THE INVENTION

Medical professionals may wish to provide patients with respiratory assistance in the form of supplemental oxygen or airflow for many reasons in ICU (intensive care unit), other hospital, or home environments. Different types of interfaces for supplying gases to patients are available. For example, various nasal masks, full face masks, oral interfaces, nasal pillows, and nasal cannula interfaces exist. Nasal cannula interfaces typically include two nasal prongs that are placed in the patient's nostrils to deliver gases to the patient.

Nasal cannula assemblies generally consist of entry tubing, either symmetric or single sided that lies across the upper lip. Protruding from this tubing are open ended prongs which extend into the nares of the patient to deliver oxygen. Nasal cannula have the advantage of being more comfortable and acceptable than a face mask to most patients. A single flow entry nasal cannula has the advantage of being unobtrusive, and may be more relevant to delivering humidity than a dual flow entry style of nasal cannula, due to the advantage of flow rates and surface area for heat loss. A single flow entry however is provided at one side of the cannula, the left or the right side. If the tube is on the left side for example, the user has difficulty in use if the flow source is on the opposite or right side of the user requiring longer lengths of tubing and causing the tube to cross the body.

When providing humidified gases to a patient it is common to use a heated breathing circuit (tubing). This circuit is heavy and can drag and pull on the patient interface. It is common to use a short flexible tube between the heated circuit and patient interface to reduce any torque or twisting. In order to stop the weight pulling on the patient interface, circuit hangers are occasionally used. This is a large extendable metal arm to take the weight. It also has been known in the art to clip part of the tubing to the patient's clothes or bedclothes. Both of these solutions have been found to be quite unsuitable for mobile patients especially when sleeping and turning in bed.

With patient interfaces such as nasal cannula the stability of the nasal prongs on the face is very important, as movement of the prongs within the nares can cause severe irritation. Current methods employed to retain a single entry nasal cannula on the face use a simple elastic band of material around the back of the patients head. This is prone to rotating the nasal cannula relative to the patient's head especially when turning ones head on a pillow. This rotation causes the prongs move within the nares, irritating this sensitive area.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved nasal cannula assembly or patient interface headgear, or to at least provide the public with a useful choice.

SUMMARY OF THE INVENTION

The nasal cannula interfaces described herein can advantageously be used to deliver gases to patients over a wide range of concentrations and flow rates. The nasal cannula interfaces described herein also include various features designed to improve patient comfort, safety, ease of use, and/or efficiency, reduce costs, and/or provide other benefits.

In some embodiments, a nasal cannula system includes a cannula and a manifold. The cannula includes a central body portion, first and second side portions that extend in opposite lateral directions from the central body portion and contact a cheek of a user when the system is in use, and first and second nasal prongs extending from the central body portion. The central body portion includes a patient facing side and at least one retention strap that cooperate to define a cavity. The first and second nasal prongs communicate with the cavity. The manifold receives a supply of gas from a gas source and includes a gas inlet and a gas outlet. The manifold is receivable within the cavity of the cannula such that the gas outlet is aligned with the first and second nasal prongs. The at least one retention strap defines first and second lateral edges, and the first and second nasal prongs are located between the first and second lateral edges.

In some embodiments, a nasal cannula system includes a cannula and a supply tube. The cannula includes a central body portion, first and second side portions that extend in opposite lateral directions from the central body portion and contact a cheek of a user when the system is in use, and first and second nasal prongs extending from the central body portion. The cannula defines a cavity having an inlet at a first end and a second end communicating with first and second gas paths. The first and second gas paths communicate with the first and second nasal prongs, respectively. The inlet is located at one of the first and second side portions, and the first and second gas paths extend in a lateral direction toward the first and second nasal prongs. The supply tube has a first end connectable to a supply of gas from a gas source and a second end coupled to the inlet of the cavity of the cannula.

In some embodiments, a nasal cannula system includes a cannula, a manifold, and a supply tube. The cannula includes a central body portion, first and second side portions that extend in opposite lateral directions from the central body portion, and first and second nasal prongs extending from the central body portion. The central body portion defines a cavity and a forward-facing inlet to the cavity. The first and second nasal prongs communicate with the cavity. The manifold receives a supply of gas from a gas source and includes a gas inlet and a gas outlet. The manifold is connectable with the cannula such that the gas outlet is aligned with the forward-facing inlet of the cannula and the gas inlet faces a lateral direction. The supply tube is connected to the gas inlet of the manifold and positioned forward of the forward-facing inlet of the cannula.

In some embodiments, a nasal cannula patient interface includes first and second nasal prongs, each including an inlet end and an outlet end, and at least one support portion configured to rest upon the nose of a patient at a point at or above the tip of the nose. In use, no portion of the patient interface contacts an upper lip of the patient to provide any substantial support to the patient interface.

In some embodiments, a nasal cannula system comprises a cannula having a central body portion, a first nasal prong and a second nasal prong extending from the central body portion. The cannula defines a cavity in communication with the first and second nasal prongs. An integrated head strap includes a first section and a second section, wherein the first and second sections extend in opposite lateral directions from the central body portion. The first section defines a rear portion of the head strap. An adjustable coupling arrangement permits coupling of the first and section sections in an adjustable manner such that a circumference of the head strap is adjustable. A supply tube has a first end connectable to a supply of gas from a gas source and a second end coupled to the cavity of the cannula.

In some embodiments, a nasal cannula system includes a cannula comprising a central body portion, a first nasal prong and a second nasal prong extending from the central body portion. The cannula defines a cavity in communication with the first and second nasal prongs. The cannula defines a lateral slot. A head gear strap extends through the lateral slot of the cannula. A supply tube has a first end connectable to a supply of gas from a gas source and a second end coupled to the cavity of the cannula.

In some embodiments, a nasal cannula system comprises a cannula comprising a central body portion, a first nasal prong and a second nasal prong extending from the central body portion. The cannula defines a cavity in communication with the first and second nasal prongs. The cannula defines a first opening at a first location of the cavity and a second opening at a second location of the cavity spaced from the first location. A valve body is movable within the cavity. A supply tube has a first end connectable to either one of the first opening or the second opening of the cannula and a second end connectable to a supply of gas from a gas source. When the first end of the supply tube is connected to the first opening of the cannula, the valve body moves in response to a flow of gas in the cavity from the gas source to block the second opening such that the flow of gas is directed to the first and second nasal prongs and, when the first end of the supply tube is connected to the second opening of the cannula, the valve body moves in response to the flow of gas in the cavity from the gas source to block the first opening such that the flow of gas is directed to the first and second nasal prongs.

In some embodiments, a nasal cannula system comprises a cannula comprising a central body portion, a first nasal prong and a second nasal prong extending from the central body portion. The cannula defines a cavity in communication with the first and second nasal prongs. The cannula defines a first opening at a first location of the cavity and a second opening at a second location of the cavity spaced from the first location. The cannula comprises a first valve that selectively closes the first opening and a second valve that selectively closes the second opening. A supply tube has a first end connectable to either one of the first opening or the second opening of the cannula and a second end connectable to a supply of gas from a gas source. When the first end of the supply tube is connected to the first opening of the cannula, the second valve blocks the second opening such that a flow of gas from the gas source is directed to the first and second nasal prongs and, when the first end of the supply tube is connected to the second opening of the cannula, the first valve blocks the first opening such that the flow of gas is directed to the first and second nasal prongs.

In some embodiments, a nasal cannula system comprises a cannula comprising a central body portion, a first nasal prong and a second nasal prong extending from the central body portion. The cannula defines a cavity in communication with the first and second nasal prongs. The cannula defines a first opening at a first end of the cavity and a second opening at a second end of the cavity. A supply tube has a first end comprising a first insert and a second end comprising a second insert. Each of the first insert and the second insert is positionable within the cavity to seal the first opening and the second opening and deliver a flow of gas from the gas source to the first and second nasal prongs. When the first end of the supply tube is connected to the cannula, the second end is connectable to the gas source and, when the second end of the supply tube is connected to the cannula, the first end is connectable to the gas source.

In some embodiments, a nasal cannula system comprises a cannula comprising a central body portion, a first nasal prong and a second nasal prong extending from the central body portion. The cannula defines a cavity in communication with the first and second nasal prongs. A supply tube has a first end coupled to the cavity of the cannula and a second end connectable to a supply of gas from a gas source. The first end of the supply tube defines a connection axis relative to the cannula. The supply tube comprises a flexible portion at or adjacent the first end that can be bent at least about 90 degrees to either the left or right side without significant occlusion of an internal passage of the supply tube.

In some embodiments, a nasal cannula system comprises a cannula comprising a cavity and a first nasal prong and a second nasal prong in communication with the cavity. A supply tube receives a flow of gas from a gas source. The supply tube is connected to the cannula to supply the flow of gas to the cavity of the cannula. A clip removably receives the cannula. A retention arrangement secures the clip to the head of a patient. The cannula is positionable within the clip in a first orientation such that the supply tube extends in a first direction from the clip, and the cannula is positionable within the clip in a second orientation such that the supply tube extends in a second direction from the clip.

In some embodiments, a nasal cannula system comprises a cannula comprising a first nasal prong and a second nasal prong. The cannula defines a cavity in communication with the first and second nasal prongs. The cannula defines a first opening at a first location of the cavity and a second opening at a second location of the cavity spaced from the first location. A supply tube assembly comprises a clip that can be releasably coupled to the cannula in either of a first orientation and a second orientation. The supply tube assembly further comprises a supply tube connectable to a supply of gas from a gas source. The clip supports the supply tube and comprises a sealing portion. When the clip is connected to the cannula in the first orientation, the supply tube is connected to the first opening of the cannula and extends in a first direction from the cannula and the sealing portion at least substantially seals the second opening and, when the clip is connected to the cannula in the second orientation, the supply tube is connected to the second opening of the cannula and extends in a second direction from the cannula and the sealing portion at least substantially seals the first opening.

In some embodiments, a nasal cannula system comprises a cannula clip comprising a first nasal prong and a second nasal prong. The cannula defines a cavity in communication with the first and second nasal prongs. A supply tube assembly comprises a manifold having at least one manifold opening and a supply tube connectable to a supply of gas from a gas source. The cannula clip is capable of being releasably coupled to the manifold in either of a first orientation and a second orientation in which the manifold is received within the cavity of the cannula clip and the first and second prongs are aligned with the at least one manifold opening such that a flow of gas is provided to the first and second prongs. When the cannula clip is connected to the manifold in the first orientation, the supply tube extends in a first direction relative to the first and second prongs and, when the cannula clip is connected to the manifold in the second orientation, the supply tube extends in a second direction relative to the first and second prongs.

In some embodiments, a nasal cannula system comprises a cannula comprising a main body defining a cavity and a first nasal prong and a second nasal prong extending from the main body and in communication with the cavity. A supply tube is coupled to the cannula and is in communication with the cavity. The supply tube is connectable to a supply of gas from a gas source to deliver a flow of gas to the cavity and the first and second nasal prongs. The first and second nasal prongs are tiltable relative to the main body of the cannula between at least a first position in which the first and second nasal prongs are tilted in a first direction relative to the main body and a second position in which the first and second nasal prongs are tilted in a second direction relative to the main body. A first surface of the main body defines a patient-facing surface of the cannula in the first position and a second surface of the main body defines the patient-facing surface of the cannula in the second position to effectively switch the side from which the supply tube extends from the cannula between the first and second positions.

In some embodiments, a nasal cannula system comprises a cannula defining a cavity and comprising a first nasal prong and a second nasal prong extending from the cannula and in communication with the cavity. A supply tube is coupled to the cannula and is in communication with the cavity. The supply tube is connectable to a supply of gas from a gas source to deliver a flow of gas to the cavity and the first and second nasal prongs. The first and second nasal prongs are directionally-oriented relative to the cannula and are movable between at least a first position in which the first and second nasal prongs are oriented such that openings of the prongs generally face in a first direction relative to the cannula and a second position in which the first and second nasal prongs are oriented such that the openings of the prongs generally face in a second direction relative to the cannula. A first surface of the cannula defines a patient-facing surface in the first position and a second surface of the cannula defines the patient-facing surface in the second position to effectively switch the side from which the supply tube extends from the cannula between the first and second positions.

In some embodiments, a nasal cannula system comprises a cannula defining a patient-facing surface and a cavity and comprising a first nasal prong and a second nasal prong extending from the cannula and in communication with the cavity. A manifold supports the cannula for rotation about at least one axis between at least a first position and a second position opposite the first position. A supply tube is coupled to the manifold and in communication with the cavity. The supply tube is connectable to a supply of gas from a gas source to deliver a flow of gas to the cavity and the first and second nasal prongs. When the cannula is in the first position, the supply tube is positioned on a first side of the first and second nasal prongs and, when the cannula is in the second position, the supply tube is positioned on a second side of the first and second nasal prongs to effectively switch the side from which the supply tube extends from the cannula between the first and second positions.

In some embodiments, a nasal cannula system comprises a cannula defining a cavity and comprising a first nasal prong and a second nasal prong extending from the cannula and in communication with the cavity. A supply tube is coupled to the cannula and is in communication with the cavity. The supply tube is connectable to a supply of gas from a gas source to deliver a flow of gas to the cavity and the first and second nasal prongs. A pressure line is in communication with the cavity and is configured to be connectable to a control unit of the gas source or a display unit to provide a signal to the control unit or display unit indicative of a pressure within the cavity.

In some embodiments, a nasal cannula comprises a cannula body defining a cavity and comprising a first nasal prong and a second nasal prong extending from the cannula and in communication with the cavity. The cannula defines a patient-facing surface having one or more comfort features selected from a plurality of through-holes, a plurality of raised bumps, a plurality of grooves and a gel pad.

In some embodiments, a nasal cannula comprises a cannula body defining a cavity and comprising a first nasal prong and a second nasal prong extending from the cannula and in communication with the cavity. The cannula body comprises a central portion containing the first and second nasal prongs and first and second side portions extending from each side of the central portion. The cannula body defines a patient-facing surface. The central portion is spaced forwardly of adjacent portions of the first and second side portions such that, in use, the patient-facing surface of the central portion is spaced from the upper lip of the patient.

In some embodiments, a supply tube for a nasal cannula comprises a tube body having a first end a second end. The tube body comprises a malleable section that permits the section to be shaped by an external force and that substantially retains the shape after the external force is removed.

In some embodiments, a nasal cannula system comprises a cannula defining a cavity and comprising a first nasal prong and a second nasal prong extending from the cannula and in communication with the cavity. A supply tube is coupled to the cannula and is in communication with the cavity. The supply tube is connectable to a supply of gas from a gas source to deliver a flow of gas to the cavity and the first and second nasal prongs. A support arrangement supports the supply tube at a spaced location from the cannula. The support arrangement comprises a fastener having a first portion coupled to the supply tube and a second portion located at the spaced location.

In some embodiments, a nasal cannula system comprises a cannula defining a cavity and comprising a first nasal prong and a second nasal prong extending from the cannula and in communication with the cavity. A supply tube is coupled to the cannula and is in communication with the cavity. The supply tube is connectable to a supply of gas from a gas source to deliver a flow of gas to the cavity and the first and second nasal prongs. A retention arrangement secures the cannula to the patient. A support arrangement supports the supply tube at a spaced location from the cannula, which is located on the retention arrangement.

In some embodiments, a nasal cannula system comprises a cannula defining a cavity and comprising a first nasal prong and a second nasal prong extending from the cannula and in communication with the cavity. A supply tube is coupled to the cannula and is in communication with the cavity. The supply tube is connectable to a supply of gas from a gas source to deliver a flow of gas to the cavity and the first and second nasal prongs. A support arrangement supports the supply tube at a spaced location from the cannula. The support arrangement comprises a fastener that engages a piece of fabric at the spaced location.

In some embodiments, a nasal cannula system comprises a cannula defining a cavity and comprising a first nasal prong and a second nasal prong extending from the cannula and in communication with the cavity. A supply tube is coupled to the cannula and is in communication with the cavity. The supply tube is connectable to a supply of gas from a gas source to deliver a flow of gas to the cavity and the first and second nasal prongs. A support arrangement supports the supply tube at a spaced location from the cannula. The support arrangement comprises at least one of an armband that engages the supply tube, an adhesive pad comprising a fastener for releasably fastening the supply tube to the adhesive pad, a generally U-shaped support that sits on the patient's shoulder and engages the supply tube, and a headgear strap comprising a strap extending over the top of the patient's head and engages the supply tube.

In some embodiments, a retention arrangement for a nasal cannula assembly comprises a headgear strap comprising a first ear loop and a second ear loop, each of which at least partially surround an ear of the patient. A connection portion connects the retention arrangement to the nasal cannula assembly. A strap portion extends around the back of the patient's head between the first and second ear loops.

In some embodiments, a retention arrangement for a nasal cannula comprises a headgear strap comprising a strap portion. A first pad and a second pad, in use, contact first and second cheeks of the patient. A connection portion connects the retention arrangement to the nasal cannula. The strap portion extends around the patient's head and extends from the first and second pads at an angle relative to the nasal cannula.

In some embodiments, a retention arrangement for a nasal cannula comprises a frame comprising a connection portion that connects the retention arrangement to the nasal cannula. A first ear stem portion and a second ear stem portion extend rearwardly from opposite sides of the connection portion. The ear stem portions are configured to be positioned above the ears of the patient.

In some embodiments, a nasal cannula system comprises a cannula having a central portion defining a cavity and comprising a first nasal prong and a second nasal prong extending from the central portion and in communication with the cavity. A first side portion and a second side portion extend in a lateral direction from opposing sides of the central portion. A supply tube is coupled to the cannula and is in communication with the cavity. The supply tube is connectable to a supply of gas from a gas source to deliver a flow of gas to the cavity and the first and second nasal prongs. A first adhesive pad and a second adhesive pad are configured to be adhesively secured to the face of the patient and connectable to a respective one of the first and second side portions of the cannula through an adjustable fastening arrangement.

In some embodiments, a nasal cannula system comprises a cannula defining a cavity and comprising a first nasal prong and a second nasal prong extending from the cannula and in communication with the cavity. A modular retention arrangement secures the cannula to the patient. The cannula is configured to be used with any one of the retention arrangements selected from a set of adhesive pads that attach to the patient's face, a headgear strap and a halo-style headgear strap that has a strap portion extending over the top of the patient's head.

In some embodiments, a nasal cannula system comprises a cannula defining a cavity and comprising a first nasal prong and a second nasal prong extending from the cannula and in communication with the cavity. A modular retention arrangement secures the cannula to the patient. The retention arrangement comprises a nose strip coupled to the cannula and attachable to the nose of a patient and a headgear strap comprising a clip configured to receive the cannula. The cannula can be secured to the patient using either the nose strip or the headgear strap.

In some embodiments, a retention arrangement for a nasal cannula comprises a headgear strap that is connectable to a nasal cannula and capable of being tensioned around the head of a patient. The headgear strap comprises a tension indicator that provides a first indication when the tension is at an incorrect value and a second indication when the tension is at a correct value.

In some embodiments, a retention arrangement for a nasal cannula comprises a headgear strap that is connectable to a nasal cannula. At least one strap extends around the head of a patient from one side to the other of the cannula. A tension adjuster tensions the headgear strap by varying an effective length of the at least one strap by winding up a portion of the at least one strap.

In some embodiments, a headgear strap for a nasal cannula comprises a first portion that is connectable to a nasal cannula and a second, elastic portion that is positioned at a back of a head of a patient in use. A pad extends at least partially along the second, elastic portion.

In some embodiments, a nasal cannula assembly comprises a cannula defining a cavity and comprising a first nasal prong and a second nasal prong extending from the cannula and in communication with the cavity. A head strap is positioned around the head and above the ears of the patient in use. A first arm is coupled to a first side of the cannula and a second arm is coupled to a second side of the cannula. Upper end portions of each of the first and second arms are attached to the head strap.

In some embodiments, a nasal cannula system comprises a cannula defining an open cavity and comprises a first nasal prong and a second nasal prong extending from the cannula and in communication with the cavity. A manifold is configured to be removably coupled to the cannula and a portion of the manifold received into the cavity of the cannula. The manifold includes first and second holes that align with the first and second nasal prongs when the manifold is coupled to the cannula, and the manifold also includes a side opening configured to be coupled to a tube. An inner surface of the cavity of the cannula includes a first attachment portion and an outer surface of the portion of the manifold includes a second attachment portion. The first and second attachment portions can be configured to engage one another to secure the manifold to the cannula.

In some embodiments of a nasal cannula system, the first and second attachment portions comprise cooperating portions of a hook and loop material fastener. The nasal cannula system can also include an arrangement in which the cavity and the portion of the manifold have corresponding symmetrical shapes so that the portion of the outer surface of the manifold can be positioned within the cavity in multiple orientations. In some embodiments, the cavity and the portion of the manifold are circular or oval shaped. In some embodiments, the first and second attachment portions are substantially planar.

In some embodiments, a nasal cannula assembly comprises a cannula defining a cavity and a first nasal prong and a second nasal prong extending from the cannula and in communication with the cavity. The cannula includes a first outer surface and a second outer surface that are substantially planar and extending along the length of the cannula. The cannula also includes a first end and a second end. A retention arrangement is coupled to the cannula and configured to support the cannula on the face of a patient. A tube can be coupled to the cannula adjacent either the first end or the second end of the cannula and configured to be in communication with the cavity. The cannula has a first position in which the first outer surface contacts the face of the patient and the first and second nasal prongs extend into the nostrils of the patient. The cannula has a second position in which the second outer surface contacts the face of a patient and the first and second nasal prongs extend into the nostrils of the patient.

In some embodiments of a nasal cannula assembly, the cannula has a substantially triangular cross-sectional shape. The nasal cannula assembly can be arranged so that an angle between the first and second nasal prongs and the first outer surface is substantially the same as an angle between the first and second nasal prongs and the second outer surface. In some embodiments, the first and second nasal prongs extend outward from the cannula at a corner of the substantially triangular cross-sectional shape between the first and second outer surfaces.

In some embodiments, a nasal cannula assembly comprises a cannula body defining a cavity and comprises a first nasal prong and a second nasal prong extending from the cannula and in communication with the cavity. The first and second nasal prongs can have a relaxed position in the absence of any substantial external force. An outer portion is configured to be movably coupled to the cannula body and configured to surround at least a portion of the cannula body. The outer portion defines at least one opening through which the first nasal prong extends and the outer portion includes at least one edge defining the at least one opening. The outer portion can move relative to the cannula body and the first and second nasal prongs, and the at least one edge is configured to engage the first and second prongs and deflect the first and second prongs from their relaxed positions.

In some embodiment of a nasal cannula assembly, the cannula body and the outer portion are substantially cylindrical and the outer portion extends around the circumference of the cannula body, and the outer portion can be rotated about the cannula body. Each of the first and second nasal prongs can include a flexible base portion configured to allow the angle at which the prong extends from the cannula body to change. The at least one opening can comprise a first opening and a second opening and the at least one edge can comprise a first edge and a second edge, the first opening defining the first edge and the second opening defining the second edge. The first nasal prong can extend through the first opening and the second nasal prong extends through the second opening. In some embodiments of a nasal cannula assembly, the outer portion includes a slot and the cannula body includes a protrusion that extends into the slot. The protrusion can be configured to move within the slot and the slot can have side walls configured to engage the protrusion and limit the amount of movement of the outer portion relative to the cannula body.

In some embodiments, a nasal cannula system comprises a cannula defining a cavity and comprises at least one nasal prong extending from the cannula and in communication with the cavity. A frame portion is configured to support the cannula and at least one head strap is coupled to the frame portion and positioned around the head of the patient in use. The cannula is slidably supported by the frame portion and can move relative to the frame portion, the cannula including an opening through which the frame portion extends. The cannula system can comprise a tube support member supported by the frame portion or the head strap and the tube support member can be configured to support and selectively release a tube.

In some embodiments of a nasal cannula system, the tube support member is configured to loosely support the tube so that the tube can slide within the support member. The tube support member can comprise a strap configured to wrap around a tube and a clip configured to couple the strap to the head strap or frame portion. The frame portion can have a circular or rounded cross-section and the cannula can move laterally relative to the frame portion and can rotate relative to the frame portion. In some embodiments of a nasal cannula system, the interface between the cannula and the frame portion is a friction fit that allows the cannula to retain its position relative to the frame portion when not being moved by a user. The frame portion can include a plurality of notches configured to interact with the cannula and provide discrete locations along the frame portion at which the cannula can be supported.

In some embodiments, a nasal cannula system comprises a cannula defining a cavity and comprises a first nasal prong and a second nasal prong extending from the cannula and in communication with the cavity. The cannula includes an opening extending through a portion of the cannula and a head strap is positioned around the head of the patient in use. The opening on the cannula is configured to receive the head strap so that the head strap extends through the opening and supports the cannula and the cannula is configured to slide relative to the head strap and change positions along the head strap.

In some embodiments of a nasal cannula system, the cannula comprises a planar outer surface configured to contact the face of a patient when the first and second prongs are inserted into the nostrils of a patient. The head strap can be made of an elastic material and configured to hold the cannula against the face of a patient.

In some embodiments, a nasal cannula system comprises a cannula defining a cavity and comprising at least one nasal prong extending from the cannula and in communication with the cavity. The cannula includes a first slot and a second slot. A first frame portion is configured to be slidably received by the first slot of the cannula and a second frame portion is configured to be slidably received by the second slot. At least one head strap is coupled to the first and second frame portions and positioned around the head of the patient in use. The cannula is slidably supported by the first and second frame portions and can be selectively moved relative to the first and second frame portions.

In some embodiments of a nasal cannula system, the cannula includes a side opening configured to receive a supply tube, and the first and second frame portions are configured to allow a tube to pass between them. A nasal cannula system can also comprise a tube support member supported by the first and second frame portions and configured to slide relative to the first and second frame portions to position the supply tube relative to the first and second frame portions. The first and second frame portions can have circular cross-sections and the first and second slots can be configured to retain the first and second frame portions. In some embodiments of a nasal cannula system, the first frame portion is positioned above the second frame portion and the first and second slots are located on the outer side of the cannula facing away from the patient. The cannula can include a planar surface facing the face of the patient.

In some embodiments, a nasal cannula system comprises a cannula defining a cavity and comprising at least one nasal prong extending from the cannula and in communication with the cavity. The cannula includes a slot and a first frame portion is configured to be slidably received by the slot of the cannula. A second frame portion is fixedly coupled to the cannula. A first dial and a second dial are each coupled to both the first frame portion and the second frame portion. At least one head strap is coupled to the first and second frame portions and positioned around the head of the patient in use. The cannula is slidably supported by the first frame portion and the dials can be configured to rotate to move a section of the second frame portion and the cannula relative to the first frame portion. The first and second frame portions can be wires coated with a soft material. In some embodiments, the second frame portion is located above the first frame portion when the cannula system is worn by a patient.

In some embodiments, a retention arrangement for a nasal cannula comprises a band configured to extend around the head of a patient and a first arm pivotally coupled to the band at a first joint. A second arm is pivotally coupled to the first arm at a second joint and the second arm can be connectable to a nasal cannula at a third joint. The first, second and third joints are configured to allow three dimensional movement and are configured to retain the relative position of the band, first arm, second arm, and cannula unless moved by a user.

In some embodiments of a retention arrangement, the band includes a stabilizing portion that is wider than the band and configured to contact the head of a patient. The third joint can be coupled to the side of a cannula. In some embodiments, the first, second and third joints are ball joints.

In some embodiments, a nasal cannula system comprises a cannula defining a cavity and comprises at least one nasal prong extending from the cannula and in Communication with the cavity. The cannula includes a slot and has a clip portion extending from the cannula. A frame is configured to support the cannula and be coupled to a head strap. The frame includes an opening configured to receive the clip portion of the cannula and the clip portion can be movable within the opening so that the cannula can assume different positions relative to the frame while being supported by the frame.

In some embodiments of a nasal cannula system, the cannula is positioned between the frame and the face of a patient when in use. The frame can include at least one pad member arranged to contact the face of a patient when in use. In some embodiments, the interface between the clip portion and the frame opening allows the cannula to be moved laterally and rotated relative to the frame. A cannula system can also include a head strap coupled to the frame and a tube support member supported by the head strap or frame.

In some embodiments, a nasal cannula system comprises a cannula defining a cavity and comprises at least one nasal prong extending from the cannula and in communication with the cavity. The cannula has a first end portion and a second end portion. A first corrugated tube section is coupled to the first end portion of the cannula and a second corrugated tube section is coupled to the second end portion of the cannula. The position of the cannula relative to a patient's face can be adjusted by expanding and compressing the first and second corrugated tube sections. In some embodiments, the cannula system also comprises a first non-corrugated tube coupled to the first corrugated tube section and a second non-corrugated tube coupled to the second corrugated tube section. The first and second corrugated tube sections can be backed by a head strap.

In some embodiments, a prong arrangement for a nasal cannula comprises a prong comprising a first prong portion comprising a first slot and a second prong portion comprising a first flange. The second prong portion is coupled to the first prong portion and the first flange extends longitudinally within the first slot. The first and second prong portions are configured to extend away from a cannula and define a passageway and the first flange is movable within the first slot so that the first prong portion and second prong portion can be moved toward and away from one another to adjust an outer dimension of the prong.

In some embodiments of a prong arrangement, the first and second prong portions each include a sealing member adjacent the cannula and the sealing members overlap each other and are configured to slide relative to one another. The prong can further comprise a size indicator configured to indicate the relative outer dimensions of the prong. In some embodiments, the prong includes a second slot and a second flange, the second flange extending longitudinally within the second slot. The first slot can comprises two side walls configured to limit the extent to which the first flange can move within the first slot.

In some embodiments, a prong arrangement for a nasal cannula comprises a prong comprising a first collapsible portion configured to be coupled to a cannula. The first collapsible portion includes a first passageway. A second collapsible portion is coupled to the first collapsible portion and has a second passageway. A third collapsible portion is coupled to the second collapsible portion and has a third passageway. The first, second and third collapsible portions are configured to collapse and expand telescopically relative to one another so that the height of the prong can be adjusted.

In some embodiments of a prong arrangement, the third collapsible portion includes a top edge that is configured to form a seal with a patient's nostril. The outer dimensions of the third collapsible portion can be larger than the outer dimensions of the second collapsible portion, and the outer dimensions of the second collapsible portion can be larger than the outer dimensions of the first collapsible portion. The first, second and third passageways can be coaxial.

In some embodiments, a prong arrangement for a nasal cannula comprises a cannula defining a cavity and the cannula includes a slot. A first prong extends from the cannula and is fixed relative to the cannula. A second prong extends from the cannula through the slot and is movable relative to the cannula. The second prong can be moved within the slot in order to adjust a distance between the first prong and the second prong.

In some embodiments of a prong arrangement, the second prong includes a pin and the slot includes multiple notches, and the notches are configured to receive the pin when the second prong is moved to discrete locations within the slot. The second prong can include a rib that extends from the base of the prong and the slot can include multiple grooves configured to receive the rib. In some embodiments, the second prong includes a tab having multiple notches that are configured to engage an edge of the slot so that the second prong can be held in multiple discrete positions relative to the slot.

In some embodiments, a prong for a nasal cannula comprises a film having a substantially cylindrical shape and a plurality of ribs coupled to the film around the circumference of the film. The film and ribs expand outward as gas flow increases through the prong, and the outer diameter of the prong increases to form a seal with a patient's nostril. In some embodiments, the ribs are substantially fixed and do not bend or move relative to one another.

In some embodiments, a nasal cannula system comprises a cannula defining a cavity and comprises at least one nasal prong extending from the cannula and in communication with the cavity. A support member is coupled to the cannula and configured to support the cannula. The support member is configured to extend upward from the cannula and around a patient's nose when in use. The support member contacts a portion above a tip of the patient's nose and the support member comprises a bendable material that can be shaped to correspond to the shape of the face of a patient.

In some embodiments, a nasal cannula system, also includes a head strap configured to wrap around the head of a patient and the head strap is removably coupled at one end to the support member and adjustably coupled to the support member at the other end. In some embodiments, the bendable material is a metal material and is located at the upper portion of the support member. The support member can include an attachment portion having multiple notches and the cannula can include an opening configured to receive the attachment portion. The notches can be configured to interact with the opening to couple the support member to the cannula and allow for adjustment of the support member relative to the cannula. In some embodiments, the cannula includes a first tube extending from one side of the cannula and a second tube extending from the other side of the cannula, and the support member is coupled to the first and second tubes of the cannula. The first tube can be supported by a first padded member and the second tube can be supported by a second padded member, and the first and second padded members can be configured to rest against a patient's face. In some embodiments, a nasal cannula system also includes a head strap coupled to the first and second padded members and configured to extend around the head of a patient. The first tube and the second tube can be removable from the cannula so that the cannula can be removed and rotated relative to the rest of the system.

In some embodiments, a tube arrangement for a nasal cannula system comprises a cannula tube comprising an outer wall and an opening. The tube includes a longitudinal axis and the outer wall comprises a thin material that has been folded or rolled and sealed at an edge.

In some embodiments of a tube arrangement, the outer wall is made of a fabric that provides insulation. Embodiments of a tube arrangement can also include a spring extending within the outer wall. The cannula tube can also be coupled to a connector at its opening and the connector can include a valve. In some embodiments, the cannula tube further comprises an extruded tube extending within the outer wall. The outer wall can include a tab having one or more holes configured to be coupled to a head strap. In some embodiments, the outer wall is made of an insulating material, a spring extends within the outer wall, and a breathing tube extends within the spring.

In some embodiments of a tube arrangement, the outer wall is made of an insulating material, a breathing tube extends within the outer wall, a spring extends within the breathing tube, and at least a pressure line tube extends within the outer wall in addition to the breathing tube. Some embodiments can also include a breathing tube within the outer wall, the breathing tube having a cannula portion from which at least one prong extends, the cannula tube being flexible so that it can curve around the face of a patient. Each end of the cannula tube can include a tab with holes configured to receive a pin located on a head strap. Each end of the cannula tube can include a connector configured to receive an inspiratory tube connector, each connector including a valve. In some embodiments, the outer wall is made of a breathable material.

In some embodiments, a tube arrangement for a nasal cannula system comprises a tube comprising an outer wall and an opening. The tube includes a longitudinal axis and the outer wall comprises a thin material that has been folded or rolled, and the outer wall includes one or more cut portions that extend through the material. In some embodiments, the one or more cut portions comprise a tab that can be pulled away from the tube, and the tab is configured to engage a support device in order to hang the tube.

In some embodiments of a tube arrangement, the tab includes a hole configured to receive a hook or hanger. The cut portions can comprise slots defining a portion of the material that can be pulled away from the tube while remaining connected at two sides, and the pulled away material can form a hook portion that can engage a hanger. In some embodiments, the cut portions can comprise two tabs that can be pulled away from the tube, the ends of the tabs being configured to be coupled together or to another structure. The tube can also comprise an inner tube and a spring within the inner tube.

In some embodiments, a cannula tube arrangement for a nasal cannula system comprises a tube comprising an outer wall and the outer wall comprises a thin film having a first edge and a second edge. The film is folded or rolled and the first and second edges are sealed together. A bead is located on the outer wall and configured to provide structural support to the tube.

In some embodiments of a cannula tube arrangement, the bead includes a cannula portion configured to receive a cannula with prongs, and the cannula portion includes two holes that extend through the film. The tube can include a first end and a second end, and the first end and second end can be coupled to connectors having valves. The first and second ends can each include a tab having a hole configured to be coupled to a head strap. In some embodiments, the first and second edges of the film are heat-sealed to form the tube. The bead can be printed or extruded onto the outer wall. The bead can have a pattern that is configured to create bend areas along the tube length. In some embodiments, the bead is on the inside of the tube. The bead can comprise thermal and structural elements printed on the film. In some embodiments, the first edge overlaps the second edge and the first and second edges can extend into the tube.

In some embodiments, a cannula tube arrangement for a nasal cannula system comprises a tube comprising an outer wall. The outer wall comprises a thin plastic film having a first edge and a second edge. A substantially planar side wall is coupled to the outer wall and a bead is located on the other wall and configured to provide structural support to the tube. The first edge is coupled to the side wall and the second edge is also coupled to the side wall so that a cavity exists between the outer wall and the side wall. In some embodiments, the first edge and second edge are heat-sealed to the side wall, and the side wall is made of a fabric material.

In some embodiments, a cannula tube arrangement comprises a spring having a length and a cross-section having at least one substantially planar side. A tube surrounds the spring and the tube defines a passageway through which gas can pass. At least one nasal prong is coupled to the tube and communicates with the passageway.

In some embodiments of a cannula tube arrangement, the spring has a V-shaped or triangular cross-section. The spring can comprise a thin folded sheet of metal having cut-out portions along the length of the spring. The spring can include a middle section and first and second ends, and the cross-section of the middle section can be smaller than the cross-section at the first and second ends. In some embodiments, the spring is a helical spring having a triangular cross-section. The spring can be a helical wire having bent ends that extend in the direction of a third side. The spring can also have a substantially triangular cross-section with curved sides. In some embodiments, the spring has a cross-section shaped like a half-circle.

In some embodiments, a cannula breathing tube arrangement comprises a tube made at least in part from a foam material. The tube has a length and a substantially planar side extending along the length of the tube and the tube defines a passageway. A spring extends through the passageway of the tube and along the length of the tube, and the spring is configured to impede kinking of the tube.

In some embodiments of a cannula breathing tube arrangement, the tube includes a cavity extending along the length of the tube and a shapeable rod extending through the cavity. In some embodiments, the foam material is a closed cell foam material. The tube can include a slot extending along the length of the tube, the slot being configured to receive a coupling member. In some embodiments, the coupling member is a mushroom head member configured to slide into the slot.

In some embodiments, a cannula tube arrangement comprises a tube having a length and a substantially planar side extending along the length of the tube. The tube defines a passageway and has an inner surface. The tube includes at least one rib located on the inner surface and extending along the length of the tube, and the at least one rib is configured to provide structural support and impede kinking of the tube.

In some embodiments of a cannula tube arrangement, the at least one rib comprises multiple ribs on the inner surface. The tube can comprise a rectangular cross-section and include a fabric material surrounding the tube. In some embodiments, the tube has a substantially triangular cross-section and in other embodiments, the tube has a substantially half-circle cross-section.

In some embodiments, a cannula tube arrangement comprises a cannula tube defining a passageway and having an end. A connector is coupled to the end of the cannula tube and a supply tube is configured to be coupled to the connector of the cannula tube. A wire configured to transfer heat extends out of the supply tube. The cannula tube is configured to receive the wire into the passageway, and the wire is configured to transfer heat into the cannula tube.

In some embodiments of a cannula tube arrangement, the wire is insulated and bendable so that it can conform to the shape of the cannula tube. The wire can be rigid enough to support the cannula tube.

In some embodiments, a cannula and tube arrangement comprises a cannula tube having a length and defining a passageway. A heating element extends along the length of the cannula tube and is configured to transfer heat to gas passing through the cannula tube. A cannula comprising at least one nasal prong and is coupled to the cannula tube.

In some embodiments of a cannula and tube arrangement, the heating element is a coiled wire that extends within the cannula tube. The cannula tube can include an end and an electrical connector coupled to the end of the cannula tube. In some embodiments, the electrical connector is also a tube connector configured to attach a second tube to the cannula tube. The heating element can be surrounded by a thin film. In some embodiments, the heating element comprises two wires coupled to a conductive polymer, and the two wires are configured so that a voltage can be applied through the polymer to generate heat. In some embodiments, the heating element is configured to provide structural support to the cannula tube. In some embodiments, the heating element is wrapped around the outer surface of the cannula tube.

In some embodiments of a cannula tube arrangement, the heating element comprises a film having a conductive strip, the film is wrapped around the cannula tube, and the conductive strip is configured to generate heat when a current is passed therethrough. In some embodiments, the heating element can be made from positive temperature coefficient material configured so that its resistance increases with temperature so that a constant voltage power supply can be used to power the heating element. In some embodiments, the cannula tube is made of a flexible and light material, the cannula tube is coupled to a connector, the connector is coupled to a tube that is less flexible and heavier than the cannula tube, and the heating element extends along substantially the entire length of the cannula tube and the tube. The connector can include an opening configured to receive a temperature sensor and the cannula tube can be configured to be removably attached to the cannula.

In some embodiments, a cannula tube arrangement comprises a cannula tube having a length and defining a first passageway. The cannula tube has an outer surface and a spiral tube is wrapped around the outer surface of the cannula tube. The spiral tube defines a second passageway and has an inner wall adjacent the cannula tube and an outer wall facing away from the cannula tube. A first opening extends through the cannula tube and through the inner wall of the spiral tube so that gas flowing inside the cannula tube can enter the spiral tube through the first opening.

In some embodiments of a cannula tube arrangement, the spiral tube includes a second opening extending through the outer wall of the spiral tube so that gas flowing in the spiral tube can escape into the surrounding environment. In some embodiments, the second opening is positioned at an opposite end of the cannula tube from the first opening.

In some embodiments, a cannula tube arrangement comprises a cannula tube having a length and defining a passageway. The cannula tube has an outer portion and the outer portion comprises a textile material and a heating element knitted or woven into the textile material. The heating element is configured to transfer heat to a gas passing through the passageway.

In some embodiments of a cannula tube arrangement, the heating element is a wire configured to generate heat when electrical current is passed therethrough. In some embodiments, the heating element is made of a semi-rigid material that provides structural support to the cannula tube.

In some embodiments, a manifold for a cannula assembly comprises a manifold body comprising a connector portion having an inlet opening and being configured to receive a tube. The manifold also includes a port configured to assist in measuring the pressure of the gas flow and an outlet portion configured to be in communication with the port and configured to be coupled to a pressure sensor.

In some embodiments of a manifold, the port is a static pressure port positioned on an inner wall of the manifold that is substantially parallel to the bulk flow direction of the gas within the manifold. In some embodiments, the port is a total pressure port that is directed towards the bulk flow direction and is configured to measure a combination of the static and dynamic pressure. In some embodiments, the port includes a shroud and is directed towards the bulk flow direction.

In some embodiments, a nasal cannula assembly comprises a cannula defining a cavity and comprising a first nasal prong and a second nasal prong extending from the cannula and in communication with the cavity. The cannula also includes an opening. A valve is supported within the opening and configured to form a seal when nothing is inserted therethrough. The cannula and valve are configured so that a tube can extend through the valve, into the cavity, and through the second nasal prong.

In some embodiments of a nasal cannula assembly, the valve is a located substantially below the second prong. The valve in can be configured to form a seal around a tube extending therethrough. In some embodiments, the valve is a duck bill valve. Embodiments of a nasal cannula assembly can further comprise a removable cover coupled to the outer surface of the cannula and covering the opening. The cannula can also include two openings and two corresponding valves where each of the valves is configured to receive either a cannula tube or a nasogastric tube. In some embodiments, the cannula includes a first side and a second side, and one of the valves is located on each of the first and second sides. In some embodiments, the second prong is removable from the cannula.

In some embodiments, a nasal cannula assembly comprises a cannula defining a cavity and comprising a first nasal prong extending from the cannula and in communication with the cavity. The cannula includes a first groove and the first prong includes a second groove. The first groove is aligned with the second groove so that a portion of a tube can extend through the first and second grooves and is directed into a nostril of a patient.

In some embodiments of a nasal cannula assembly, the first and second grooves are configured to accommodate a nasogastric tube. The first prong can include an outer surface and the second groove can be located on the outer surface of the first prong and can extend longitudinally relative to the first prong. In some embodiments, the cannula includes a second prong and a third groove, the second prong includes a fourth groove, and the third and fourth grooves are aligned so that a portion of a tube can extend through the third and fourth grooves and is directed into a nostril of a patient.

In some embodiments, a nasal cannula comprises a nasal prong having an outer wall and an end. The outer wall includes a cut portion defining a flap that can be pushed into the prong to form an opening in the outer wall of the prong. The opening is configured to receive a tube so that the tube can extend through the opening and out of the end of the prong.

In some embodiments of a nasal cannula, the outer wall defines a passageway, and the flap is configured to block the passageway when a tube is inserted through the opening. In some embodiments, the flap is configured to align with and form at least a substantial seal with the outer wall when a tube is not inserted through the opening. The prong can also include a slit that extends from the cut portion to the end of the prong, the slit being configured to allow a tube to selectively pass through the slit.

In some embodiments, a nasal cannula assembly comprises a cannula defining a cavity and comprising a first nasal prong extending from the cannula and in communication with the cavity. The cannula includes an opening and a valve supported within the opening. An inner member is supported within the cavity and movable relative to the cannula. The inner member includes a hole configured to receive a tube. The opening is positioned substantially below the first nasal prong and the inner member can be moved so that the hole is aligned with the valve so that a tube can extend through the valve and the hole and into the first prong.

In some embodiments of a nasal cannula assembly, the cannula includes a second opening having a second valve positioned substantially below a second nasal prong, and the inner member includes a second hole that can be aligned with the second valve and second prong. In some embodiments, the inner member is substantially cylindrical and is configured to be coupled to a supply tube. The valve can be configured to form a seal when nothing is extended therethrough.

In some embodiments, nasal cannula assembly comprises a cannula body having a first slot and a second slot. The assembly also includes a first sliding portion having a first prong coupled to a first tube and a second sliding portion having a second prong coupled to a second tube. A portion of the first sliding portion is configured to slide within the first slot and a portion of the second sliding portion is configured to slide within the second slot. The first and second prongs are movable relative to the cannula body so that each of the first and second prongs can be adjusted relative to the cannula body. In some embodiments, the first slot and the second slot extend substantially horizontally and are positioned side by side on the cannula body.

In some embodiments, a nasal cannula assembly comprises a cannula defining a cavity and comprising a first nasal prong extending from the cannula and in communication with the cavity. The assembly also includes a slider member that engages an outer surface of the cannula, and the slider member is configured to move relative to the cannula. The slider member is configured to selectively move along the outer surface of the cannula and over the first nasal prong.

In some embodiments of a nasal cannula assembly, the slider member includes a groove configured to receive a portion of a tube. In some embodiments, the first nasal prong is flexible and can fold under the slider member when the slider member is moved to cover the first nasal prong.

In some embodiments, a nasal cannula assembly comprises a cannula defining a cavity and comprising a single nasal prong extending from the cannula and in communication with the cavity. The assembly also includes a strap configured to support the prong and engage the face of a patient. The strap includes an adhesive material configured to selectively couple the strap to a patient's face. The strap includes an opening through which the prong extends and the strap is configured to extend from under the patient's nose upward along the sides of the patient's nose.

In some embodiments of a nasal cannula assembly, the strap includes at least one slot configured to receive a tube. In some embodiments, the strap includes holes positioned to align with a nostril of a patient when the strap is in use. The prong can include corrugations configured to allow the prong to bend and change shape. In some embodiments, the prong includes a tapered base portion that is configured to form a seal with a patient's nostril. In some embodiments, the cannula is coupled to a tube and the tube includes a support member configured to support the tube and be selectively coupled to the face of a patient. The support member can also include a support portion configured to receive and support a nasogastric or other tube. Embodiments of the cannula assembly can further comprise a cheek pad configured to adhere to a patient's cheek and be selectively coupled to the support member. In some embodiments, the prong includes a tapered base portion that is narrower toward the top and wider toward the bottom, and the prong includes a recess below the tapered portion and the recess is configured to retain the portion of the strap adjacent the opening.

In some embodiments, a nasal cannula assembly comprises a cannula defining a cavity and comprising a single nasal prong extending from the cannula and in communication with the cavity. The assembly also includes a frame having a bridge portion that extends away from the face of a patient and creates a space between the bridge portion and the patient's face. The bridge portion is configured to support the cannula, and the bridge portion including a slot and a portion of the cannula can move within the slot. A tube is coupled to the cannula and extends from a bottom portion of the cannula. The tube is configured to extend from under the cannula and bend upward so that it extends over the frame.

In some embodiments of a nasal cannula assembly, the cannula is supported by the frame and positioned substantially within the space between the bridge portion and the patient's face when the cannula assembly is in use. In some embodiments, the bridge portion of the frame includes cut out portions configured to receive a portion of the tube. In some embodiments, the cannula includes a grip portion that extends through the slot. The frame can include a pad configured to contact the face of a patient when in use. In some embodiments, the frame includes one or more openings configured to receive a head strap. In some embodiments, the bridge portion includes a tubing arm that at least partially defines a tubing recess through which the tube can extend.

In some embodiments, a nasal cannula assembly comprises a cannula frame having an upper extension portion, and the upper extension portion having a single prong and a prong opening in communication with the prong. The assembly also includes a retainer portion coupled to the extension portion and having a retainer opening aligned with the prong opening. The assembly also includes a manifold pivotally coupled to the retainer portion, and the manifold has a manifold opening aligned with the retainer opening and the prong opening. The manifold is configured to pivot relative to the cannula frame about the axis of the manifold opening, and gas can pass through the manifold and into the prong.

In some embodiments of a nasal cannula assembly, the cannula frame includes a lower extension portion and the retainer portion includes a lower portion that engages a bottom portion of the manifold. In some embodiments, the bottom portion of the manifold includes a pin and the lower portion of the retainer portion includes a hinge recess, and the pin is configured to be received within the hinge recess, and the manifold configured to pivot about the pin. In some embodiments, the manifold is configured to rotate about 180 degrees relative to the cannula frame so that tubing coupled to the manifold can exit in an opposite direction.

In some embodiments, a nasal cannula assembly comprises a cannula frame having an upper extension portion. The upper extension portion has a single prong and a prong opening in communication with the prong. The upper extension portion also has a bottom side. The assembly includes a tube rotatably coupled to the bottom side of the upper extension portion and in communication with the prong so that gas can pass from the tube through the prong opening and into the prong. The tube is configured to bend and rotate relative to the cannula frame.

In some embodiments, a nasal cannula assembly comprises a cannula defining a cavity and comprising a single nasal prong extending from the cannula and in communication with the cavity. The assembly comprises a cable configured to slidably support the cannula and a tube coupled to the cannula and configured to provide gas to the cavity. The position of the cannula can be adjusted by sliding the cannula along the cable.

In some embodiments of a nasal cannula assembly, the tube is tapered so that its cross-section is narrower closer to the cannula. Some embodiments further comprise an attachment portion coupled to the cable and configured to receive a portion of the tube. In some embodiments, the tube includes an attachment member that is configured to engage and be coupled to the attachment portion. In some embodiments, the cable can include indent portions configured to retain the cannula in a selected position.

In some embodiments, a nasal cannula assembly comprises a cannula frame having a bridge portion that extends away from the face of a patient and creates a space between the bridge portion and the patient's face. The bridge portion supports a single nasal prong. The assembly includes a first tube coupled to the prong and extending downward from the prong. The cannula frame defines a recess through which a second tube can extend between the bridge portion and a patient's face when in use.

In some embodiments of a nasal cannula assembly, the bridge portion includes a cut-out portion configured to receive a portion of the first tube, causing the tube to bend and extend away from the assembly to the side of a patient. In some embodiments, the cannula frame includes a contact portion that is configured to contact the face of a patient and comprises a soft material.

In some embodiments, a nasal cannula assembly comprises a cannula defining a cavity and comprising a single nasal prong extending from the cannula and in communication with the cavity. The cannula has a cannula opening in communication with the cavity and the opening has an axis. The assembly also includes a manifold pivotally coupled to the cannula and configured to pivot about the axis of the cannula opening. The assembly also includes a tube coupled to the manifold and configured to supply gas to the manifold. The manifold includes a manifold opening aligned with the cannula opening and in communication with the cavity.

In some embodiments of a nasal cannula assembly, the cannula includes frame portions extending outward from the cannula, the frame portions form one or more recesses between the cannula and the face of a patient when in use, and the one or more recesses are configured to receive a second tube. In some embodiments, the cannula includes a soft material on the side of the cannula facing a patient when in use. In some embodiments, the cannula includes a recess on each side of the prong so that a second tube can extend between the manifold and the cannula.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

In some embodiments, a nasal cannula assembly comprises:

a cannula part comprising a pair of tubular nasal prongs for insertion into the nares of a patient, and a manifold in fluid communication with the nasal prongs, the manifold comprising an aperture at left hand end of the manifold and an aperture at the right hand end of the manifold, a connector adapted to receive an end of a gases flow conduit and be removably received in the aperture at left hand end of the manifold and the aperture at the right hand end of the manifold, and a plug adapted to be removably received in the aperture at left hand end of the manifold and the aperture at the right hand end of the manifold, in use the connector or the plug fitted to one of the apertures at the left and right sides of the manifold, and the plug fitted to the other one of the apertures at the left and right sides of the manifold to configure the conduit to extend from either the left side or right side of the nasal cannula assembly.

Preferably the plug and connector are separate parts.

Preferably the plug and connector are coupled or attached together by a lateral member to form a clip, optionally the lateral member is a connecting portion.

Preferably the clip is an integrally formed unitary member.

Preferably the clip and cannula part are complimentary adapted so that in use the lateral member is elastically deflected to fit the clip to the cannula part.

Preferably the clip is fitted to the cannula part by pushing the clip onto the cannula part in a direction perpendicular to a lateral direction of the cannula.

Preferably the cannula part comprises a rigid member for interfacing with the clip and the prongs are formed of a resilient material attached to the rigid member.

Preferably the rigid member and the lateral member are adapted so that the lateral member is flexed to spread the plug and connector apart when attaching the clip to the cannula part.

Preferably the clip is substantially 'C' or 'U' shaped.

Preferably the plug and connector each extend into the aperture at the ends of the manifold.

Preferably the clip provides a positive force against the manifold to grip the manifold between the plug and the connector.

Preferably the cannula part comprises a recessed portion that is sized and shaped to receive the lateral member.

Preferably the cannula part comprising the manifold and nasal prongs is integrally formed.

Preferably the resilient material is over moulded to the rigid member.

Preferably the cannula part comprises side arms and the rigid member extends along the side arms.

Preferably the rigid part comprises through holes in the side arms for the resilient material to extend through by an over moulding process or assembly process.

Preferably the rigid member comprises a recessed portion that is sized and shaped to receive the lateral member.

Preferably the apertures at the ends of the manifold are formed in the rigid member.

Preferably the lateral member is length adjustable.

Preferably the clip comprises a first part and a second part, the first part comprises one of the plug and the connector and the second part comprises the other one of the plug and the connector, the first part comprises a first lateral member and the second part comprises a second lateral member, and the first and second lateral members coupled together in a telescoping arrangement and comprising complementary features to set the lateral distance between the plug and the connector.

Preferably the complementary features comprise a projection on one of the first and second parts and a corresponding aperture in the other one of the first and second parts, the projection being received in the aperture to set the lateral distance between the plug and the connector.

Preferably one of the first and second parts comprises a plurality of corresponding apertures, the projection being received in the one of the plurality of apertures to set the lateral distance between the plug and the connector, the plurality of apertures providing for a range of cannula part sizes.

Preferably the clip is movably attached to the cannula part.

Preferably the clip is rotationally coupled to the cannula part.

Preferably the clip is rotationally coupled to the cannula part on a rotational axis on or parallel to the sagittal plane of the cannula to position the conduit to the left or right side of the nasal cannula assembly.

Preferably the manifold is formed of a relatively rigid material, and the cannula part comprises a resilient material moulded over the manifold, the nasal prongs integrally formed with the resilient material, and the cannula part comprises an axle extending from the manifold, and the clip rotationally mounted on the axle.

Preferably the axle is integrally formed with the manifold.

Preferably the clip comprises a keyway so that the clip can be removably mounted to the cannula part.

Preferably cannula part comprises a flange at the end of the axle to retain the clip on the axle in a direction along the rotational axis.

Preferably ends of the manifold are curved with a centre of curvature on the rotational axis, and the plug and the connector each have a complementary curvature so that the clip can rotate on the rotational axis to position the connector at either end of the manifold.

Preferably the over moulded resilient material covers ends of the manifold to provide a seal with the plug and connector.

In some embodiments a nasal cannula assembly comprises, for example such the assembly when the plug and connector are coupled or attached together by a lateral member to form a clip, the clip is fitted to the cannula part by pushing the clip laterally into the manifold via one of the aperture at the left hand end and the aperture at the right hand end so that the connector is received in one of the aperture at the left hand end and the aperture at the right hand end and the plug is received in the other one of the aperture at the left hand end and the aperture at the right hand end to configure the conduit to extend from either the left side or right side of the nasal cannula assembly.

Preferably the cannula part comprises a rigid member for interfacing with the clip and the prongs are formed of a resilient member attached to the rigid member, and the cannula part and the rigid member each comprise side arms extending laterally from the manifold.

In some embodiments, a nasal cannula assembly comprises:

a cannula part comprising a pair of tubular nasal prongs for insertion into the nares of a patient, a connector adapted to receive an end of a gases flow conduit, a manifold attached to or integrally formed with the connector, the connector providing an inlet to the manifold and the manifold having at least one outlet, the cannula part movably attached to the manifold to be attached to the manifold in two orientations to configure the conduit to extend from either the left side or right side of the nasal cannula assembly.

Preferably the cannula part is rotatable relative to the manifold about a substantially vertical axis.

Preferably the manifold comprise an open top that is the manifold outlet, and the cannula part fits over the open top so that the prongs are in communication with the connector.

Preferably the manifold comprises a lip on a surface of the manifold to which the cannula part connects.

Preferably an axle extends from the manifold or the cannula part and the cannula part rotates relative to the manifold on the axle.

In some embodiments a nasal cannula assembly comprises:

a cannula part comprising a pair of tubular nasal prongs for insertion into the nares of a patient, and a left and a right lateral side arm for attaching headgear, a first conduit for providing as flow of gas to one said nasal prong and a second conduit for providing a flow of gas to the other said nasal prong, a first joint connecting the first conduit to one said nasal prong and a second joint connecting the second conduit to the other said nasal prong, the joints adapted to allow the first and second conduits to be routed to a left side or a right side of the nasal cannula assembly, and a left clip on the left lateral side arm and a right clip on the right lateral side arm, in use, the first conduit being held by the left clip or the right clip to configure the first conduit to extend from either the left side or right side of the nasal cannula assembly, and the second conduit being held by the left clip or the right clip to configure the second conduit to extend from either the left side or right side of the nasal cannula assembly.

Preferably the cannula part is an integrally formed part.

Preferably each joint is a flexible tube adapted to bend at least 90 degrees in any direction without substantial occlusion.

Preferably the flexible tubes comprise circumferentially extending ribs so that bending of the flexible conduit section does not cause the flexible conduit section to collapse.

Preferably each joint is a swivel joint.

Preferably each swivel joint rotates on an axis that is at an angle to an axis of the corresponding nasal prong so that rotation of the swivel joint allows both conduits to be routed to the left side or the right side without overlapping.

Preferably each swivel joint is a swivel elbow.

Preferably each said clip comprises two channels or receptacles each for receiving one of the tubes.

Preferably each flexible tube is integrally formed with a nasal prong.

Preferably each clip is integrally formed with a said side arm.

With respect to the embodiments above, reference to the manifold may be an open cavity formed by the cannula part, such as a cannula body, and in such embodiments the connector forms a component to be engaged with the open cavity, the connector forming a flow path for delivery of gases to the open cavity. Such embodiments may also be referred to below.

In some embodiments a nasal cannula system comprises:

a cannula body defining an open cavity and comprising at least one nasal prong extending from the cannula in communication with the cavity; and a manifold comprising a manifold body capable of accepting a gases supply tube, the manifold body capable of being attached to the cannula in a first position and a second position, wherein the second position is different to the first position;

wherein the ends of the manifold body protrude into the open cavity of the cannula body, and the cannula body comprises a recess for retaining the manifold body.

Preferably wherein the manifold comprises a first side portion and a second side portion, where the first and second side portions extend from the manifold body and are adapted to be attached to headgear.

Preferably the recess of the cannula body retains the first and second side portions of the manifold.

Preferably one end of the manifold comprises a cap comprising a hinged area which divides the cap into inner and outer regions connected by a band, and wherein the hinged area permits relative motion between the inner and outer regions at the band.

In some embodiments a nasal cannula comprises:

a cannula body defining an open cavity and comprising at least one (and preferably a pair of) nasal prong(s) extending from the cannula in fluid communication with the open cavity; and a manifold comprising a manifold body capable of engaging with the cannula for fluid connection with the open cavity, the manifold body orientable in either of a first operational position or a second operational position, wherein the first position and second positions are different to each other, wherein the manifold body is adapted to accept a gases supply conduit at a first end of, or a gases inlet to, the manifold body, the first end adapted to engage with one end of the open cavity for delivery of gases into the open cavity, and a second end of the manifold body adapted to form a seal or connection with an other end of the open cavity, the manifold body forming an enclosure to the open cavity.

Preferably the cannula body comprises at least one recess or at least one surface relief or region of surface relief for retaining the manifold body in an engaged either of the first operational position or the second operational position.

Preferably the first end and the second end of the manifold body are connected to each other, the first end providing for a gases inlet to the open cavity and the second end providing for a plug or cap to substantially enclose the open cavity and provide for a fluid delivery pathway of supplied gases from the first end of the manifold body into the open cavity and to a terminal end of the at least one nasal prong.

Preferably the first and second ends of the manifold body are connected to each other by a connecting portion or connecting portions.

Preferably the connecting portion is one or more of at least one arm or at least one finger or at least one frame member.

Preferably the first and second ends of the manifold body are integrally formed.

Preferably the connecting portion or the cannula body defining at least in part the open cavity, or both, comprise an alignment feature adapted to enable a predetermined geometric orientation of the manifold body relative to the cannula body for engagement therewith.

Preferably the alignment feature may be a region or regions of associated male and female parts or region or regions of associated surface relief.

Preferably the alignment feature is adapted to provide for an audible response to an engagement of the manifold with the cannula body when in an engaged operational first position or an engaged operational second position.

Preferably a connecting portion of the manifold body connecting the first and second ends to each other extends through an internal region of the open cavity, such that, in-situ, the first end of the manifold body is adapted to engage with one end of the open cavity for delivery gases into the open cavity, and the second end of the manifold body is adapted to form a seal or connection with the other end or any remaining portion of the open cavity requiring sealing to enable the delivery of gases to the open cavity.

Preferably the connecting portion extending through the internal region of the open cavity is shaped or configured to engage with, or be received by, an associated surface or region of the cannula body or an associated surface or region of the cannula body defining the open cavity.

Preferably a connecting portion of the manifold body connecting the first and second ends to each other extends about an external surface or exterior region of the cannula body defining at least in part the open cavity, such that, in-situ, the first end of the manifold body is adapted to engage with one end of the open cavity for delivery gases into the open cavity, and the second end of the manifold body is adapted to form a seal or connection with the other end or any remaining portion of the open cavity requiring sealing to enable the delivery of gases to the open cavity.

Preferably the connecting portion extending about the external surface or exterior region of the cannula body is shaped or configured to engage with, or be received by, an associated surface or region of the cannula body or an associated surface or region of the cannula body defining the open cavity.

Preferably a gas supply conduit is positioned or located substantially about a side or region of the cannula body from which the first end of the manifold body is positioned or projects from the cannula body.

Preferably the manifold can be oriented or is orientable with respect to the cannula body, such that a gas supply tube, in-use, is substantially positioned or located to one side of a user.

Preferably a first operational position allows for the first end of the manifold body to be located to either a left-end or a right-end of the cannula body defining the open cavity, and a second operational position allows for the first end of the manifold body to be located to either a respective right-end or a respective left-end of the cannula body defining the open cavity.

Preferably the first operational position or the second operational position enable for connection of a gases supply conduit to the first end of the manifold body from either a left or a right side.

Wherein the cannula body further comprises side arms or side portions extending away from the cannula body defining the open cavity, in-use, each of the side arms or side portions are adapted to extend at least in part along a portion of a user's face.

Preferably the nasal cannula as defined above comprises a first section formed from a first material and a second section formed from a second material, wherein the first section is relatively softer than the second section.

Optionally, the embodiments described above in relation to a first section being formed of a first material and a second section being formed of a second material are reiterated here.

Preferably a terminal end of the side arms adapted to accept connection thereto with a headgear.

Optionally the headgear to be associated with a nasal cannula described herein may be that as defined above in any of the other embodiments as described herein.

In some embodiments, a nasal cannula system comprises a nasal cannula assembly as defined in any one of the above embodiments and a headgear attached to the nasal cannula assembly for attaching the nasal cannula assembly to a patient's head.

In some embodiments there is a system for providing a flow of respiratory gases to a user or patient comprising a blower, a humidifier, the conduit and a nasal cannula system as defined in the embodiments described herein.

In some embodiments a headgear comprises:

a strap, each end of the strap adapted to be attached to a patient interface and extend around a patient's head to hold the patient interface in place on a patients face, wherein at least a portion of the strap is configured to bifurcate into more than one band to extend around the patients head.

Preferably the strap comprises a longitudinal frangible section extending along a portion of the strap to be torn by a user to separate the portion of the strap into more than one band.

Preferably the frangible section comprises a relatively thin section.

Preferably the frangible section is a perforated section.

Preferably the bands are separated by the frangible section.

Preferably the strap comprises a finger hole at the frangible section to assist with separating the bands by tearing the frangible section.

Preferably the strap comprises a hole at an end of the frangible section, the hole comprising a rounded portion defining an end of the frangible section to prevent tearing the strap beyond the frangible section.

Preferably the hole is a finger hole.

Preferably at least the portion of the strap is formed from fabric forming the bands, and the fabric is coated with a polymer with the bands arranged together, the coating providing the frangible section between the bands, the coating adapted to be torn to separate the bands.

Preferably the bands are formed by a longitudinal cut in the fabric along the portion of the strap, the polymer coating bridging the cut to hold the bands together in a non-bifurcating configuration.

Preferably the fabric is a foamed fabric.

Preferably the bands are separated by a removable section of the strap comprising a lift tab, the removable section joined to the bands by the frangible section.

Preferably the headgear comprises a clasp that is slidable along at least the portion of the strap configured to bifurcate.

Preferably to bifurcate the strap to separate the bands the clasp is slidable to an end of the bands, and the clasp is slidable to a midpoint of the bands to hold the bands together as a single strap.

Preferably to bifurcate the strap to separate the bands the clasp is slidable to an end of the bands, and the clasp is slidable to an opposite end of the bands to hold the bands together as a single strap.

Preferably each band comprises a feature that interfaces with a corresponding feature on the clasp to bind the bands together when in a non-bifurcated configuration.

Preferably the bands comprise interlocking teeth that are separated or mated by sliding the clasp along the bands.

Preferably the headgear comprises a web that extends between the bands, in a non-bifurcated configuration the web is bunched up or folded into a non-expanded configuration, and in a bifurcated configuration where the bands are spaced apart the web is expanded or unfolded to cover an area between the spaced apart bands.

Preferably the headgear comprises two clasps, in a non-bifurcated configuration both clasps are slid towards a central position of the strap to hold the bands together, and in a bifurcated configuration each clasp is slid to an end of the bands so that the bands may separate between ends of the bands.

Preferably each clasp and the straps are complementary adapted so that moving each clasp to an end of the bands forces the bands apart to separate the bands into a bifurcated configuration.

Preferably each clasp comprises two spaced apart flanges and three pins extending between the spaced apart flanges, the bands extending between the flanges, one said pin positioned between the bands and the other two pins positioned on outer edges of the bands, and the bands comprises a cross over portion near ends of the bands.

Preferably one or each band may comprise a central tab or stop to limit the amount of travel of the clasps along the bands.

Preferably the portion of the strap configured to bifurcate extends around the back of the patient's head from behind the patient's ears in use.

Preferably ends of the bands are pivotally coupled together.

Preferably the bands in a non-bifurcated configuration are arranged edge-to-edge.

Preferably the bands in a non-bifurcated configuration are arranged side-by-side.

Preferably the bands in the non-bifurcated configuration are held together by one or more of tearable stitching, a clasp or clasps, buttons, clips, hook and loop fasteners or magnets.

In some embodiments, there is a headgear for securing a patient interface to a user's face, the headgear comprising:
a strap, each end of the strap adapted to be attached to a patient interface and extend around a patient's head to hold the patient interface in place on a patients face, wherein the strap comprises a non-stretchable section and a stretchable section, the non-stretchable section adapted to be attached the patient interface and support a gases supply conduit coupled to the patient interface.

Preferably each end of the strap is a non-stretchable section adapted to be attached to the patient interface and the stretchable section is an intermediate section that extends between the non-stretchable sections around the back of the patient's head.

Preferably the non-stretchable section is adapted to be attached to one side of the patient interface and the stretchable section is adapted to be attached to an opposite side of the patient interface.

Preferably the non-stretchable section comprises a feature for securing the conduit.

In some embodiments there is a headgear for securing a patient interface to a user's face comprising:
a strap comprising a first stretchable section adapted to be attached to one side of a patient interface and a second stretchable section adapted to be attached to an opposite side of a patient interface, and a non-stretchable intermediate section extending between each end of the stretchable sections.

Preferably the intermediate portion is an annular portion, ends of the stretchable sections attached to the annular portion.

Preferably the headgear comprises a first non-stretchable sleeve and a second non-stretchable sleeve each extending from the non-stretchable intermediate section, and the first stretchable section extends along an inside of the first non-stretchable sleeve and the second stretchable section extends along an inside of the second non-stretchable sleeve.

Preferably the first and second non-stretchable sleeves extend from the intermediate portion to forward of the patient's ears in use.

Preferably the first and second stretchable sections are not attached to the first and second non-stretchable sleeve along the length of the sleeve from the intermediate portion.

Preferably one or both sleeves is/are adapted to support a gas conduit for providing a gas flow to the patient interface.

Preferably the head gear comprises a lanyard connected to a said sleeve adapted to secure the gas conduit.

Preferably the lanyard is stretchable.

Preferably the non-stretchable intermediate section is bifurcated to comprise two separate bands.

Preferably the non-stretchable section is configured to bifurcate into more than one band to extend around the patients head.

Preferably the headgear comprises a bifurcated section comprising two bands and one said band is the non-stretchable intermediate section.

Preferably the headgear comprises a first non-stretchable 'Y' connector connecting between the first stretchable section and one end of the two bands and a second non-stretchable 'Y' connector connecting between the second stretchable section and an opposite end of the two bands.

Preferably one of the two bands is a stretchable band.

Preferably an upper one of the two bands is the stretchable band and a lower one of the two bands is the non-stretchable band.

Preferably the non-stretchable band is length adjustable.

Preferably at least one of the bands is adjustable in length.

Preferably an upper one of the two bands is adjustable in length.

In some embodiments there is a headgear for a patient interface comprising:
a stretch region, a non-stretch region, wherein said stretch region located sufficiently away from a tube loading region.

In some embodiments, there is a headgear, interface and tube assembly comprising, at least one stretch region, at least one non-stretch region, said stretch region located sufficiently away from a tube loading region, said stretch-region located at the back a user's head in use, wherein the tube is configured to be attached to either side of the interface.

In some embodiments, there is a headgear, interface and tube assembly comprising, at least one stretch region, at least one non-stretch region, said stretch region located sufficiently away from a tube loading region, where the tube loading region is a region that the tube is tethered to the headgear or interface.

In some embodiments there is a nasal cannula for administering a source of gases, such as breathable gases, to a user (e.g. a patient), the nasal cannula comprising:
at least a first section formed from a first material; and
at least a second section formed from a second material;
wherein the first section is relatively softer than the second section.

Preferably the second material is the same as the first material (for example, may be the same material but may be a different grade of such a material having different characteristics, such as a different Shore hardness or other rating).

Preferably the second material is different from the first material (for example, may be a different material having different characteristics, such a different Shore hardness or other ratings).

Preferably the sections are integrally formed with each other.

Preferably the sections are assembled to each other through the use of one or more mechanical fasteners or one or more chemical fastening systems (e.g. such as adhesive or plastic welding or ultrasonic welding of first and second sections, or portions thereof, together).

Preferably the first section provides for a user-friendly or comfort contacting component part of a nasal cannula.

Preferably the second section provides for a structural or support or shape-defining, component part, of a nasal cannula. Alternatively, the second section, in-use, is non-contacting of a user.

Preferably the configuration or shape of the first section is at least in part defined by parts or portions of the second section.

Preferably the first section forms a patient contacting surface, and the second section forms a frame upon which the first section is attached.

Preferably the first section encapsulates at least a part of the second section.

Preferably the second section is at least in part over-moulded by the first section.

Preferably the first section is at least an arm or a pair of arms extending outwards from a central body portion that comprises at least one (or preferably a pair of) nasal prong(s).

Preferably headgear is connectable to one or each arm, the headgear extending substantially about a rear part of a user's head.

Preferably the first section is adapted to receive a manifold connection for delivery of a source of gases to the nasal cannula or a body of the nasal cannula in fluid communication with a delivery system for delivery of gases to the user, such as via at least one nasal prong (or preferably a pair of nasal prongs) to, in-use, the nare or nares of the user.

Preferably the second section is adapted to receive a manifold connection for delivery of a source of gases to the nasal cannula or a body of the nasal cannula in fluid communication with a delivery system for delivery of gases to the user, such as via at least one nasal prong (or preferably a pair of nasal prongs) to, in-use, the nare or nares of the user.

Preferably a manifold is a component of a relatively rigid material, relative to the first material, the manifold connectable with an associated region of the nasal cannula or a body of the nasal cannula.

Preferably the first section comprises one or more surface relief portions, the surface relief portion(s) of the first section engageable with an associated one or more commensurately or complimentarily shaped or configured surface relief portions of the second section.

Preferably the first section comprises at least one raised region receivable by an associated aperture or detent region of the second section.

Preferably the first section comprises raised tabs or mushroom-shaped heads, and the second section comprises associated apertures receivable of the raised tabs or mushroom-shaped heads.

Preferably the first section comprises a cannula body portion defining at least in part an open cavity receivable of a supply of gases directed thereto via a manifold, the open cavity in fluid communication with one or a pair of nasal prongs.

Preferably the first section and second section are commensurately or complimentarily shaped or configured to communally receive a manifold connection for delivery of a source of gases to be delivered to a user.

Preferably the first section is at least in part a nasal cannula body defining an open cavity.

In an alternative, or additionally, the second section at least in part surrounds a nasal cannula body defining an open cavity.

Preferably the second section supports the first section in a predetermined configuration.

Preferably the second section extends substantially about the length of a nasal cannula defined by a first section. Alternatively, the second section extends to a longer length than the nasal cannula defined by a first section. In a further alternative, the second section extends to a shorter length than the nasal cannula defined by a first section.

Preferably a nasal cannula includes a pair of side arms extending outwardly from a cannula body defining at least in part an open cavity receivable of a source of gases, such as via a manifold connection.

Preferably located substantially toward each end of the side arms is a connection system for connecting a headgear, the headgear in-use, to be worn by a user.

Preferably the connection system is a part of the second section.

Preferably the first section provides for a gasket-type seal for a manifold connection or a manifold receivable by at least a part of the first section, such as that defining an open cavity of a cannula body.

Preferably the second section provides for a structure to which a manifold connection may be made, and the first section provides for a sealing, such as a fluid-type seal, of a manifold in making such a manifold connection.

Preferably a nasal cannula comprises a body defining an open cavity engageable by a manifold, a rear portion of said body being, in-use, substantially adjacent to a user's septum region, the rear portion being substantially compliant or deformable in response to a pressure applied by a user to said rear portion.

Preferably the rear portion is a substantially thinned wall section of the body. Wherein the rear portion is defined by a hollow section of the body, with the open cavity being a separate distinct region of the body.

In an alternative, the rear portion defines at least a part of a wall of the open cavity.

Preferably the rear portion is substantially elasticised.

Preferably the rear portion is elastically deformable.

Preferably, the body comprises a hollowed enclosure substantially adjacent to the user's septum region, Preferably, the body comprises a pillow section substantially adjacent to the user's septum region.

Preferably, the pillow section is a hollow region, the hollow region bounded by walls of the body, and separate to an open chamber (such as a plenum chamber), and having a relatively thin wall or elasticised section in the region substantially adjacent to, in use, the user's septum. Alternatively, the pillow section is formed by a rear wall of such an open cavity (or plenum chamber), the rear wall being a relatively thin wall or elasticised section in the region substantially adjacent to, in use, the user's septum.

Preferably, the pillow section is formed of a material capable of deforming under application of a pressure by a user during use.

As noted above, in some configurations or embodiments, the nasal cannula interface may comprise a first section and a second section. The first section may comprise a relatively soft material. The second section may comprise a relatively hard material. Preferably, the first section in use contacts the patient's face, and the second section in use does not contact the patient's face.

The sections may be assembled together by any method of manufacture. In some configurations, the sections could be overmoulded, for example, one on top of the other. In some configurations, the sections could be glued together using an adhesive. In some configurations, the sections could be assembled together using ultrasonic welding. In some configurations, the sections could be assembled together using one or more mechanical or other fasteners or fastening systems.

Preferably a nasal cannula as defined above may be utilised in combination with each of the other details described in this specification to provide for a nasal cannula interface.

In some embodiments a patient interface, such as a nasal cannula, comprises a gases delivery mechanism (such as one or a pair of nasal prongs to engage with the nare or nares of a user's nose), and a body from which the gases delivery mechanism is associated, and extending from the body is a pair of side arms, the body and side arms being connected in a manner such that application of a tension to the side arms directs the gases delivery mechanism to move away from a position otherwise imposing upon a user's nasal spine.

In some embodiments a nasal cannula, comprising a cannula body from which a nasal prong or a pair of nasal prongs extend to engage with the nare(s) of a user, and from which a pair of side arms extends outwardly and to which a headgear system is connectable, the cannula body being substantially conformable to a user's face yet providing sufficient rigidity so that, in-use, a force or a tension applied to outer-more portions of the side arms directs or encourages the nasal prong or nasal prongs to impose less upon a user's nasal spine region.

Preferably a continuous section of material extends along each side arm and connects, or is mechanically coupled, in a region of the nasal prong or nasal prongs.

Preferably the continuous section of material is a material capable of translating an applied force or tension from the side arms to the region of the nasal prong or nasal prongs.

Preferably each of the side arms define a pre-form or shape such that, before application of a force or a tension from a headgear, the side arms curve outwardly away from the face of the user, extending more outwardly so as the side arms extend further away from a gas delivery mechanism of the interface or from a nasal prong or a pair of nasal prongs.

Preferably each of the side arms is substantially in contact with a user's face as the arms extend outwardly away from the gas delivery mechanism or nasal prong or pair of nasal prongs, with each of the side arms becoming less in contact or more distant (or both) from a user's face the further the arms extend from the gas delivery mechanism or nasal prong or pair of nasal prongs.

Preferably, the side arms define a pre-form or shape such that, in-use, application of a force or a tension to the side arms via the headgear encourages (or directs) the side arms to more into a position of greater facial contact with the user's face or cheeks and the body is encouraged (or directed) to move into a position less engaged with, or imposing upon, or further away from, the user's nasal spine region.

Preferably the side arms are configured to, in-use, encourage the translation or location or re-locating or distribution or re-distribution of a force or a tension being applied by a headgear to a nasal cannula, to a user's cheeks and away from the user's nasal spine region or away from the force or tension being applied to the user's nasal spine region.

Preferably each of the side arms are pre-formed or shaped such that, in-use, application of a force or a tension to the side arms, requires the side arms, or at least portions of the side arms, to move closer to a user's face, a hinging or flexing point (or point of flexure) of the side arm upon a user's face being established upon a cheek region, and the nasal prong or nasal prongs or another gases delivery mechanism being encouraged away from imposing upon a user's nasal spine region.

Preferably the hinging or flexing point (or point of flexure) being established in-use, is a region at or about any one or more of the user's left or right (or both): lower outer maxilla, upper outer maxilla, zygomatic arch, maxilla recess (or below the zygomatic arch).

In some embodiments a connector for connecting a breathing tube to a device (such as a humidifier or ventilator or other source of gases), or for connecting to at least another breathing tube, the connector comprising:

an inner body and an outer body, each of the inner body and outer body having a first end and a second end, the first end of the inner and outer bodies for receiving a terminal end of a first breathing tube, and the second end of the inner and outer bodies for connecting to a further component, such as for example: a further breathable tube, or a device (e.g. such as a humidifier, or a ventilator or a source of gases), wherein the first end of the inner body receives and fluidly connects with the terminal end of the first breathing tube, the inner body providing a lumen for fluid connection between the first end and the second end of said inner body, and wherein the inner body is rotatable relative to the outer body.

Preferably the inner body is adapted to swivel relative to the outer body.

Preferably the outer body may comprise one or more surface relief features. More preferably, such surface relief features are provided, in use, as finger grips for a user.

Preferably the second ends of the inner body and/or the outer body are adapted to provide a connection system for connecting with another breathing tube or with a device (e.g. such as a humidifier, or a ventilator or a source of gases).

Preferably the terminal end of the first breathing tube connected to the first end of the inner body may be, in use, longitudinally rotatable with respect to the outer body.

Preferably the inner body is sleeved with respect to the outer body.

Preferably the connector as defined above may be provided as a connector for use with a gas supply tube for a nasal cannula or other patient interface as described in this specification.

Preferably the second end of the outer body is adapted to connect to the further component, the outer body being non-swivelable relative to a connection being made with the further component, for example at a machine end of a breathing circuit.

The various references to tube or conduit in this specification may optionally, but not necessarily, relate to application of such tubes or conduit to those typically understood to as being "breathing tubes", such as those referred to in ISO 5367:2000(E) (Fourth edition, 2000-06-01). It will be appreciated the tubes or conduits of this invention may relate to, or find particular application to, such breathing tubes for use in delivery of gases to a user or a patient.

As used herein the term "and/or" means "and" or "or", or both.

As used herein "(s)" following a noun means the plural and/or singular forms of the noun.

The sagittal plane of a nasal cannula or other patient interface is defined as the sagittal plane of a user that extends through the cannula or patient interface when the cannula or patient interface is positioned on a user's face in use. For example, the sagittal plane of a nasal cannula comprising a nasal prong for each nostril is positioned centrally between the nasal prongs.

The lateral direction with respect to a nasal cannula is the direction extending between left and right hand ends of the cannula. The lateral direction is perpendicular to a direction extending between the front and back of the cannula. The sagittal plane of a cannula is perpendicular to the lateral direction.

The invention involves the foregoing and also envisages constructions of which the following gives examples only.

BRIEF DESCRIPTION OF THE DRAWINGS

These and other features, aspects and advantages of the present disclosure will be described with reference to the following drawings, which are illustrative but should not be limiting of the present disclosure.

FIG. 10A illustrates a side perspective view of an example embodiment of a nasal cannula assembly including a cannula and a nose strip attached to a patient's face;

FIG. 10B illustrates a partial rear perspective view of the nasal cannula assembly of FIG. 10A;

FIG. 11 illustrates an alternative configuration of the nasal cannula assembly of FIGS. 10A and 10B;

FIGS. 15A-G illustrate an example embodiment of a nasal cannula assembly with a shuttle valve.

FIGS. 16G-L illustrate embodiments of a nasal cannula assembly with a manifold having a one way valve formed from a slit valve of various types.

FIGS. 20A-C illustrate an example embodiment of a manifold that snaps into an assembly securing device or clip.

FIGS. 21A-F illustrate example embodiments of a nasal cannula assembly with a removable tubing assembly and manifold.

FIGS. 23A-C illustrate an example embodiment of a nasal cannula assembly with a manifold insert which can be clipped over a tubing assembly.

FIGS. 24A-C illustrate an example embodiment of a nasal cannula assembly having prongs formed with a ripple shape around the base to allow for flexibility of the prongs.

FIGS. 24D-F illustrate an example embodiment of the prongs formed with a corrugated geometry to allow for flexibility of the prongs.

FIG. 25A illustrates an example embodiment of a nasal cannula assembly that includes individually rotatable prongs.

FIGS. 25B-C illustrate an example embodiment of a nasal cannula assembly that includes a pair of prongs mounted on a vertical shaft and rotatable as a unit.

FIGS. 26A-F illustrate an example embodiment of a nasal cannula assembly configured to allow insertion of a removable prong insert in at least two orientations.

FIGS. 29B-L illustrate example embodiments of nasal cannula assemblies having pressure measurement capability.

FIGS. 30A-I illustrate example embodiments of nasal cannula assemblies having features to address, reduce or minimize patient discomfort, especially at or near the upper lip area.

FIGS. 34A-K illustrate example embodiments of headgear arrangements for securing the cannula to the face of a patient.

FIGS. 36A-K illustrate example embodiments of retention arrangements, such as headgear straps, including an indicator of tightness, such as strap tension.

FIGS. 38A-G illustrate example embodiments of an adjustable cannula and prong arrangement for a nasal cannula assembly.

FIGS. 39A-I illustrate example embodiments of a cannula and prong arrangement with adjustable alignment for a nasal cannula assembly.

FIGS. 40A-J illustrate example embodiments of adjustable prong arrangements for a nasal cannula assembly.

FIGS. 41A-D illustrate example embodiments of support arrangements for a nasal cannula assembly.

FIGS. 44A-G illustrate example embodiments of tubing arrangements for a nasal cannula assembly.

FIGS. 46A-E illustrate example embodiments of pressure measurement port arrangements for a nasal cannula assembly.

FIG. 53B is an exploded view.

FIGS. 56A to 56C illustrate a nasal cannula assembly comprising a cannula part and a clip comprising a plug and conduit connector for connecting a gas conduit to the cannula part. The clip is inserted laterally into a manifold of the cannula part.

FIG. 58D illustrates how a bifurcate-able strap comprising a frangible section is separated to form a bifurcated a portion comprising two separate bands.

FIG. 58E illustrates a bifurcate-able strap in a non-bifurcated configuration.

FIG. 58F illustrates a cross section of the strap of FIG. 58E.

FIG. 58G illustrates a cross section of the strap of FIG. 58A.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below. Various features described herein can be used individually or in various combinations and sub-combinations in existing and/or improved respiratory interfaces.

Whether used in a hospital environment or in a home environment, a system for providing a flow of gases to a patient or user may comprise four main pieces of apparatus. Firstly a blower for providing a flow of pressurised gas to the patient. Secondly an active humidifier that controls the temperature of a heater plate heating a body of water to achieve a desired temperature and humidity of the flow of gas. Thirdly a transport conduit from the humidifier to the patient is also required, which may be heated to reduce condensation, or "rain out". Fourthly a patient interface for delivering the pressurized humidified flow of gases to a patient, for example a nasal cannula designed to fit into the nasal cavity of a patient or user. In some situations a flow of pressurized gases may be provided to a patient without humidification, in which case a humidifier is not a necessary apparatus.

Figure 49:
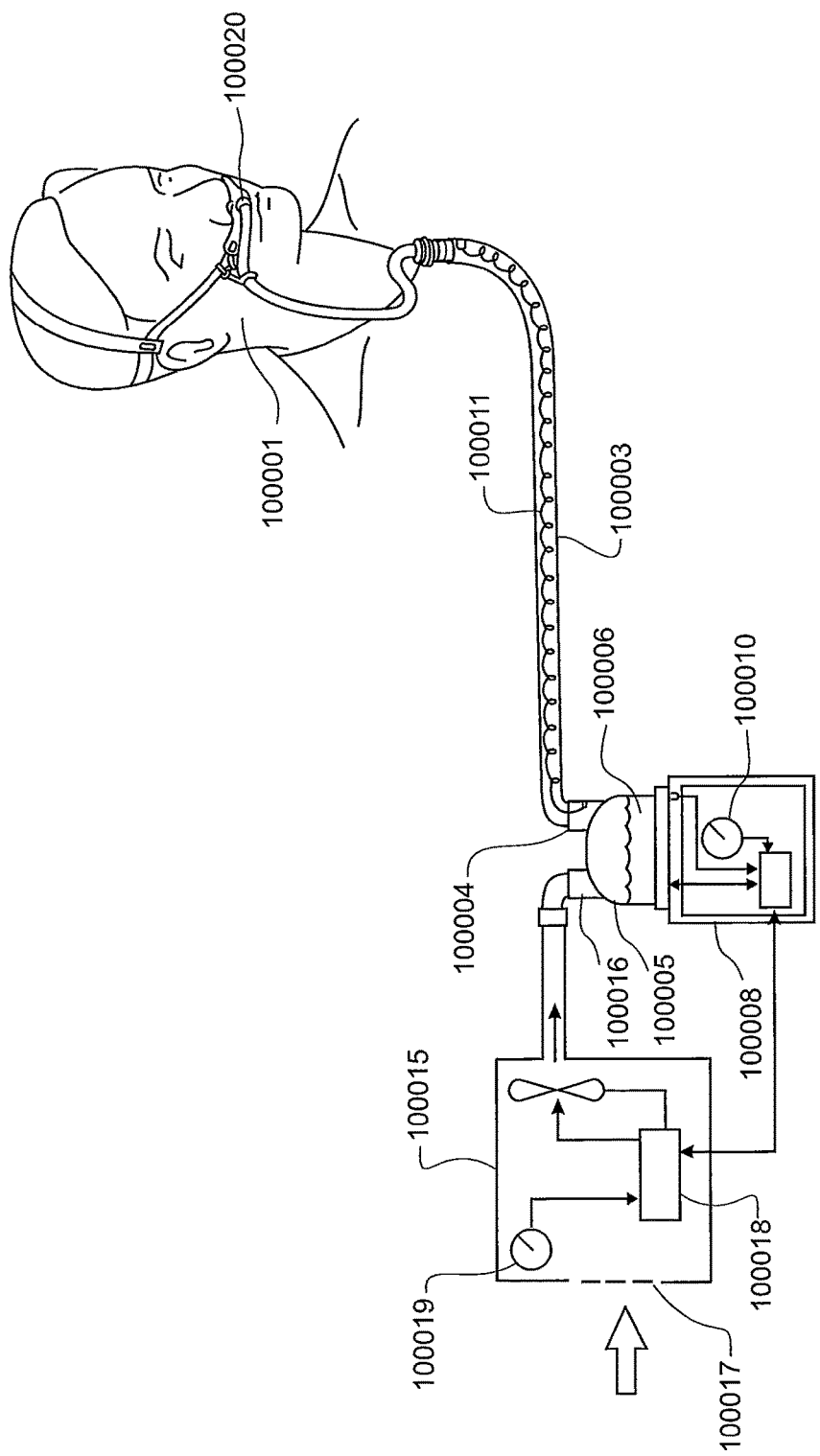
FIG. 49 illustrates a respiratory humidifier system that may be used with a nasal cannula assembly according to one or more embodiments of the present invention.

Referring to FIG. 49 a humidifying circuit as might be used with a patient interface comprising the present invention is shown. A patient 100001 is receiving humidified and pressurised gases through a nasal cannula assembly 10020 connected to a humidified gases transportation pathway or inspiratory conduit 100003 that in turn is connected to a humidifier 100008 (including humidification chamber 100005) that is supplied with gases from a blower 10015 or other appropriate gases supply means. The inspiratory conduit 100003 is connected to the outlet 100004 of a humidification chamber 100005 which contains a volume of water 100006. Humidification chamber 100005 is preferably formed from a plastics material and may have a highly heat conductive base (for example an aluminium base) which is in direct contact with a heater plate 100007 of humidifier 100008. The humidifier 100008 is provided with control means or electronic controller 100009 which may comprise a microprocessor based controller executing computer software commands stored in associated memory. Gases flowing through the inspiratory conduit 100003 are passed to the patient by way of the nasal cannula assembly 100020.

Controller 100009 receives input from sources such as user input means or dial 10010 through which a user of the device may, for example, set a predetermined required value (preset value) of humidity or temperature of the gases supplied to patient 100001. In response to the user set humidity or temperature value input via dial 10010 and other possible inputs such as internal sensors that sense gases flow or temperature, or by parameters calculated in the controller, controller 100009 determines when (or to what level) to energise heater plate 100007 to heat the water 100006 within humidification chamber 10005. As the volume of water 100006 within humidification chamber 100005 is heated, water vapour begins to fill the volume of the chamber above the water's surface and is passed out of the humidification chamber 100005 outlet 100004 with the flow of gases (for example air) provided from a gases supply means or blower 10015 which enters the chamber through inlet 10016. It should be noted that it is possible to obtain the relationship between the humidity of the gases in humidification chamber 100005 and the temperature of the heater plate 100007. Accordingly, it is possible to utilise the heater plate temperature in an algorithm or a look-up table to determine the humidity of the gases.

The blower 10015 may be provided with a variable speed pump or fan 100002 which draws air or other gases through the blower inlet 10017. The speed of variable speed pump or fan 100002 may be controlled by a further control means or electronic controller 10018 (or alternatively the function of this controller 10018 could be carried out by the other controller 100009) in response to inputs from controller 100009 and a user set predetermined required value (preset value) of pressure or fan speed via dial 10019.

A heating element 10011 may be provided within the conduit or tubing 100003 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

Figure 1A:
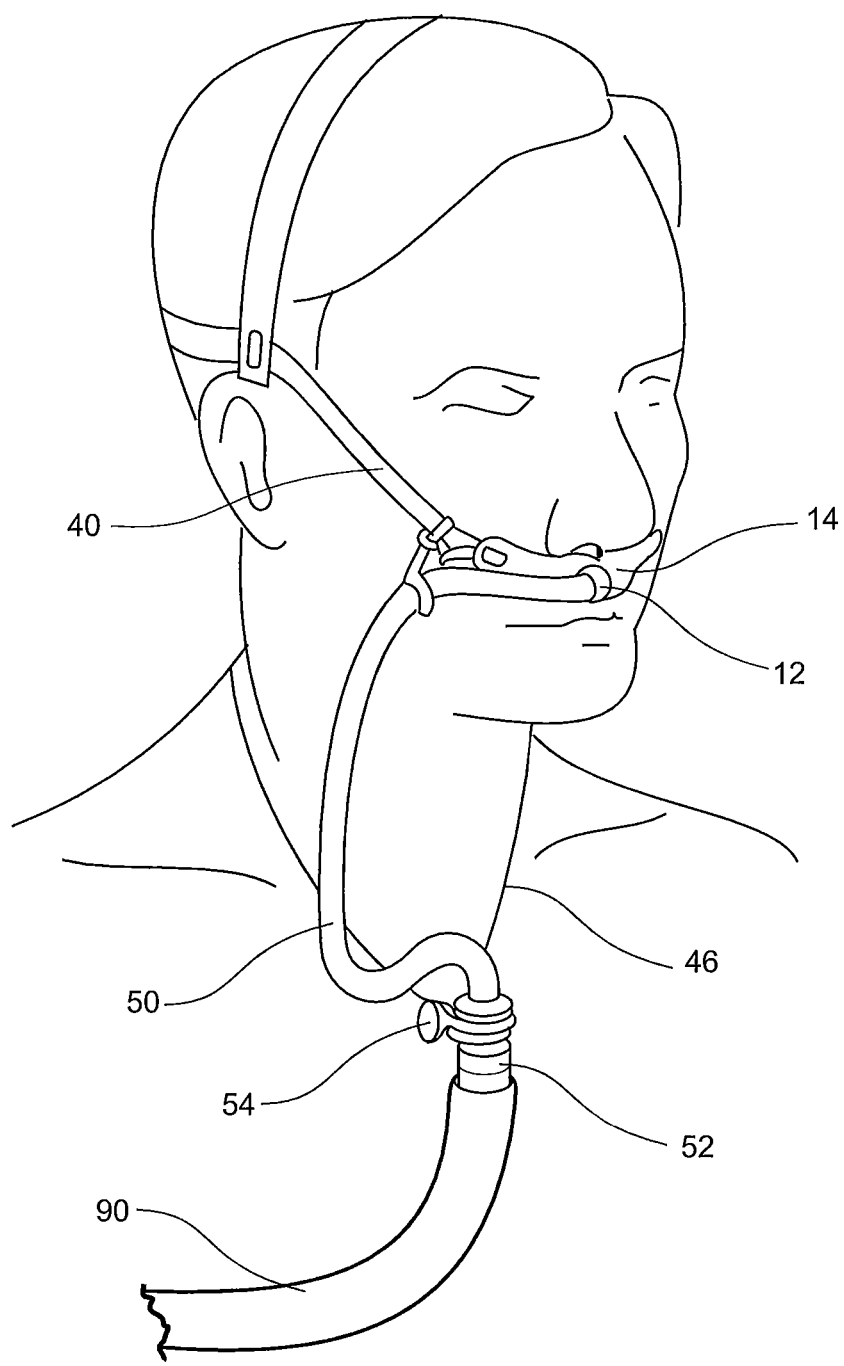
FIG. 1A illustrates an example embodiment of a nasal cannula assembly coupled to a patient.
Figure 1B:
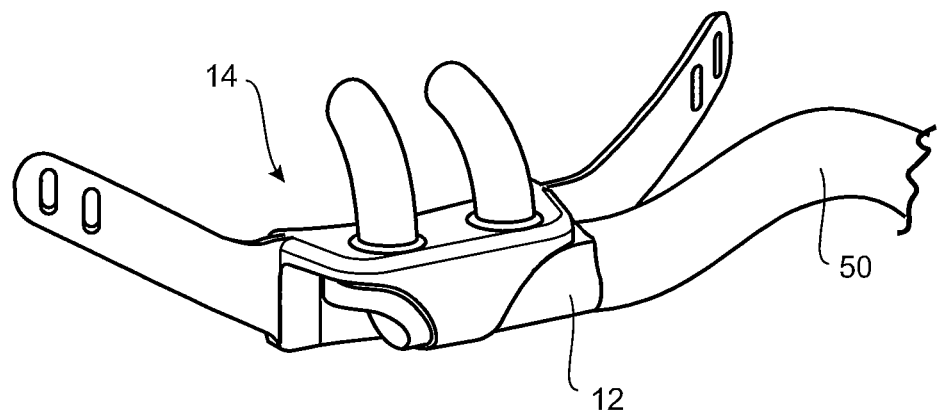
FIG. 1B illustrates a partial front perspective view of the nasal cannula assembly of FIG. 1A.
Figure 1C:
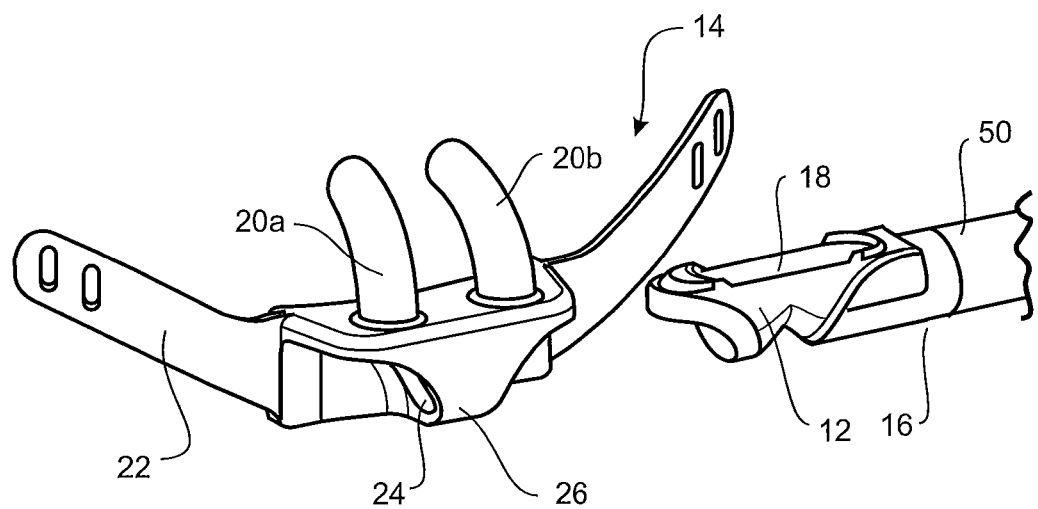
FIG. 1C illustrates an exploded view of the nasal cannula assembly of FIGS. 1A and 1B.

With reference to FIGS. 1A-1C, an example embodiment of a nasal cannula assembly or system includes a manifold 12 and cannula 14. The cannula 14 includes nasal prongs 20a, b, side straps 22, and a tubular aperture 24 defined or encircled by a retention strap 26 and configured to receive the manifold 12. In some embodiments, the manifold is generally tubular and includes a circular inlet 16 and an elongated oval outlet 18. In use, the manifold 12 is coupled to the cannula 14 by inserting the manifold 12 into the aperture 24 so that the manifold outlet 18 is aligned and in fluid communication with the nasal prongs 20a, b. The manifold inlet 16 is configured to be coupled, removably or permanently, to a gas supply tube 50. In use, the gas supply tube 50 is coupled to and in fluid communication with a main delivery conduit 90, which is configured to be connected to and supply gases from a gas source, for example, a ventilator, gas tank, wall outlet, and/or humidifier that heats and/or humidifies gases before they are delivered to a patient. The gas supply tube 50 can be coupled to the main delivery conduit 90 by a connector 52.

The nasal cannula system can further include a securement mechanism to secure the cannula 14 to a user's head in a proper operational position. In the illustrated embodiment, the securement mechanism includes a headgear strap 40. The strap 40 can be coupled to the side straps 22 of the cannula 14. The nasal cannula system can also include a lanyard 46 that in use is placed around the patient's neck. The lanyard 46 can be coupled to the supply tube 50 and/or the connector 52 via a lanyard connector 54, which can also allow for adjustment of a length of the lanyard. The lanyard 46 advantageously helps support the weight of the main delivery conduit 90 to reduce patient discomfort and the potential for dislodgement of the cannula 14. Further details regarding example nasal cannula assemblies or systems can be found in U.S. Publication 2010/0192957, the entirety of which is incorporated by reference herein. Various components and features of such nasal cannula assemblies can be selected and modified to achieve various benefits as described herein.

Figure 2A:
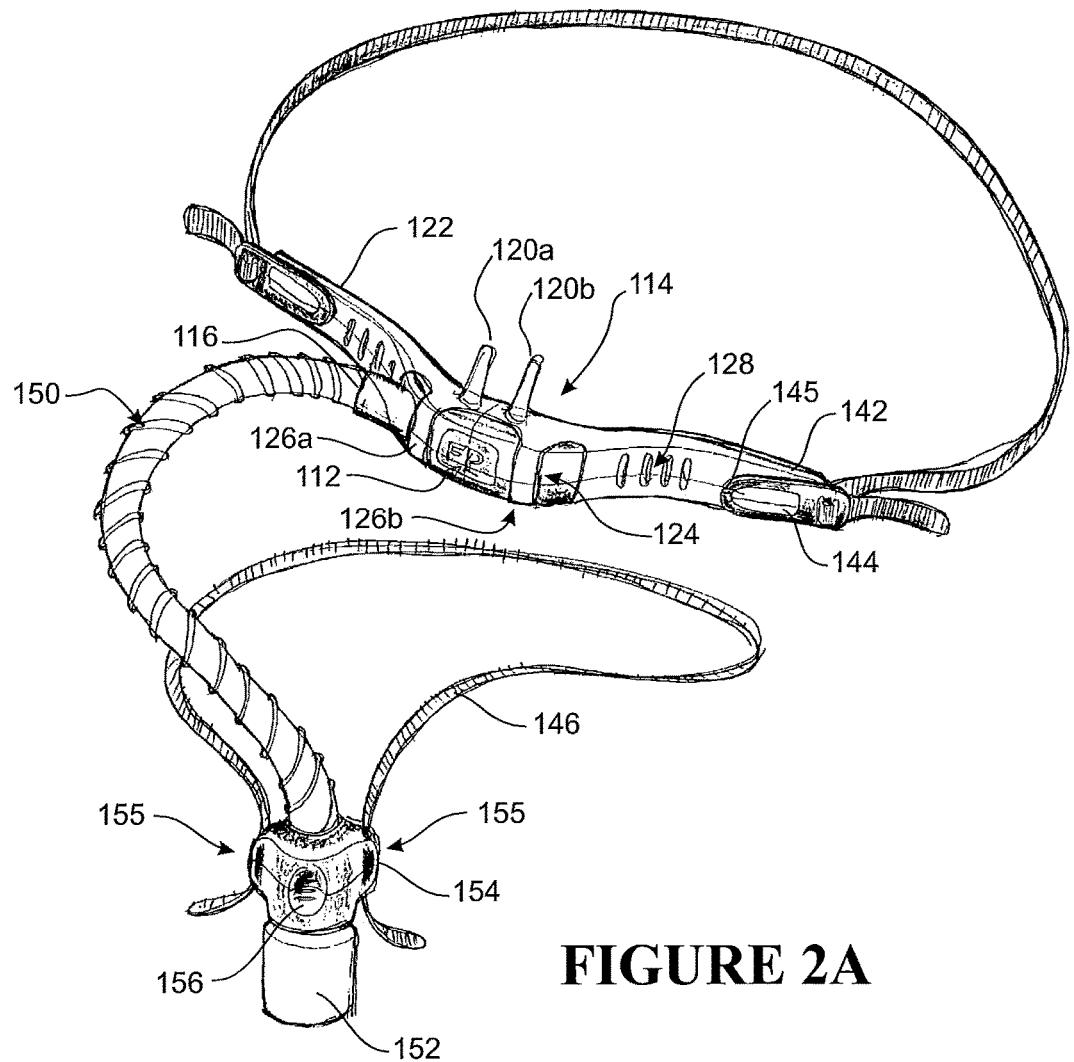
FIG. 2A illustrates a front perspective view of an example embodiment of a nasal cannula assembly including a cannula and manifold.
Figure 2B:
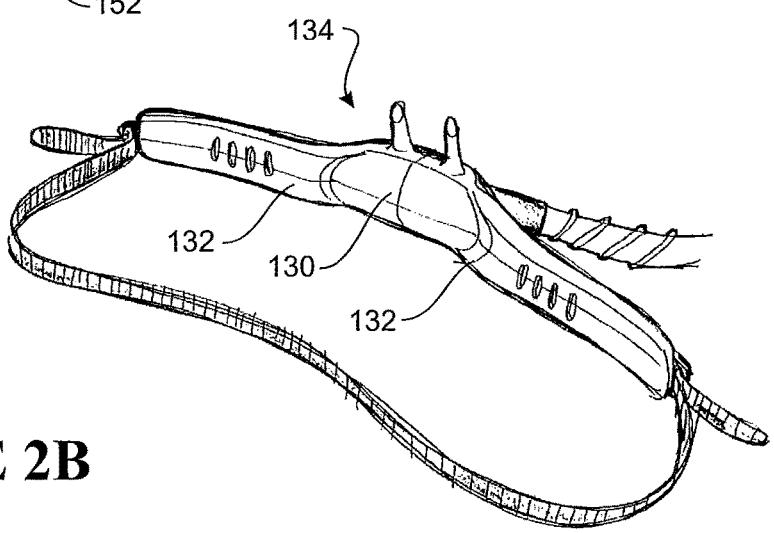
FIG. 2B illustrates a partial rear perspective view of the nasal cannula assembly of FIG. 2A.

With reference to FIGS. 2A and 2B, an embodiment of a nasal cannula assembly or system includes a cannula 114, manifold 112, headgear strap 140, gas supply tube 150, and lanyard 146. The cannula 114 can be formed of a thermoplastic, silicone-like material and includes nasal prongs 120a, b, side straps 122, and two spaced manifold retention portions or straps 126a, b defining/encircling an aperture configured to receive the manifold 112. In some embodiments, the nasal prongs 120a, b, side straps 122, and manifold retention straps 126a, b are integrally formed. The cannula 114 is configured such that the manifold 112 can be inserted into the aperture of the manifold retention straps 126a, b from either side, so that the manifold inlet 116 can be positioned to either side of the cannula 114. The side straps 122 can include flex slots 128 to provide ventilation and allow the cannula 114 to bend or stretch more easily, for example, when adjusting the headgear strap 140 and when adjusting the cannula 114 against the users face to help achieve a more effective and/or comfortable fit. The flex slots 128 can be generally vertical as shown or diagonally slanted. As shown in FIG. 2B, a patient facing and contacting side 130 of the cannula 114 can have a contoured surface to better and more comfortably fit the patient's face, reduce the overall profile of the cannula system, and help align the supply tube 150. For example, transition portions 132 positioned between a central body portion 134 of the cannula 114 and the side straps 122 can curve toward the patient's face to rest against the nasolabial folds. The side straps 122 can taper in thickness toward outer edges of the straps 122 to create a thin profile and help further reduce the cannula system profile.

The headgear strap 140 can be coupled to the side straps 122 via clips or buckles 142. The clips 142 can include an aperture 144 so that an inner edge 145 of the clip 142 on the side nearest the center of the cannula 114 can engage a corresponding undercut on the side strap 122. As shown in FIG. 2B, the clips 142 do not substantially contact the patient's skin, thereby maintaining a smooth and more comfortable patient contacting surface. A side of the clip 142 farthest from the center of the cannula 114 can include a buckle mechanism configured to receive ends of the headgear strap 140 and allow for adjustment of the circumference of the headgear strap 140 to fit the patient's head. In some embodiments, the strap 140 can be flexible (e.g., elastic) to allow the strap 140 to accommodate a wide range of patient head sizes with minimal adjustment required.

In use, the manifold 112 is coupled to the cannula 114 by inserting the manifold 112 into the aperture 124 and stretching the flexible cannula 114 around the manifold 112. As described above, the manifold 112 can be inserted into the aperture 124 of the manifold retention straps 126a, b from either side, so that the manifold inlet 116 and, thus, the supply tube 150 can be positioned to either side of the cannula 114. In some embodiments, the manifold 112 is made of a relatively hard plastic material that can withstand relatively high loading conditions to protect the manifold 112 from being crushed. In addition, the retention straps 126a, b can be spaced apart from one another to provide support to the manifold 112 at spaced apart locations, which can inhibit or resist undesirable movement (e.g., rotation or twisting) of the manifold 112, such as that caused by forces acting on the supply tube 150, for example. In some configurations, the outer lateral edges of the retention straps 126a, b are spaced outwardly of the nasal prongs 120a, b such that the nasal prongs 120a, b are located between the lateral edges of the retention straps 126a, b. In some configurations, the inner edges of the retention straps 126a, b can be substantially aligned with or spaced outwardly from the nasal prongs 120a, b. Although a pair of retention straps 126a, b is illustrated, other suitable retention arrangements or structures are possible, such as a single retention strap, for example. In the illustrated embodiment, the manifold inlet 116 has an inner diameter slightly larger than an outer diameter of the supply tube 150 so that the tube 150 can be coupled to the manifold 112 by inserting an end of the tube 150 into the manifold inlet 116. The supply tube 150 can have a reduced diameter compared to other supply tubes to allow for this coupling. An end of the tube 150 opposite the manifold can include a connector 152 configured to couple the supply tube 150 to the main delivery conduit coupled to the gas source. In the illustrated embodiment, the connector 152 is a 22 mm taper connector.

The cannula system can include a lanyard connector 154, which in the illustrated embodiment is located on the supply tube 150 proximal (nearer to the patient) the connector 152. The lanyard connector 154 can include mechanisms 155 for receiving ends of the lanyard 146 on either side. For example, each side of the lanyard connector 154 can include three or more offset slots or posts through which an end of the lanyard 146 is threaded. The slots or posts can be internal to the lanyard connector 154 or exposed. This configuration advantageously allows one or both ends of the lanyard to be adjusted as needed or desired, and allows the weight of the connector 152 (and the main delivery circuit 90) to be hung or oriented in a vertical orientation or direction. In some embodiments, the lanyard 146 is non-elastic. The lanyard 146 is secured to the lanyard connector 154 via friction between the lanyard 146 and slots or posts. The lanyard 146 can be ribbed to help secure the lanyard 146 to the lanyard connector 154. However, the lanyard 146 and lanyard connector 154 can be designed so that the friction force is overcome and the lanyard 146 releases from the lanyard connector 154 if the connector 154 is pulled too far away from the patient and/or pulled with sufficient force to avoid the lanyard 146 choking or otherwise causing discomfort to the patient. The lanyard connector 154 can include a grip 156 to allow the patient or others to better grasp the lanyard connector 154 for adjustments and/or for easy removal of the connector 152 from the main delivery conduit 90.

Figure 3A:
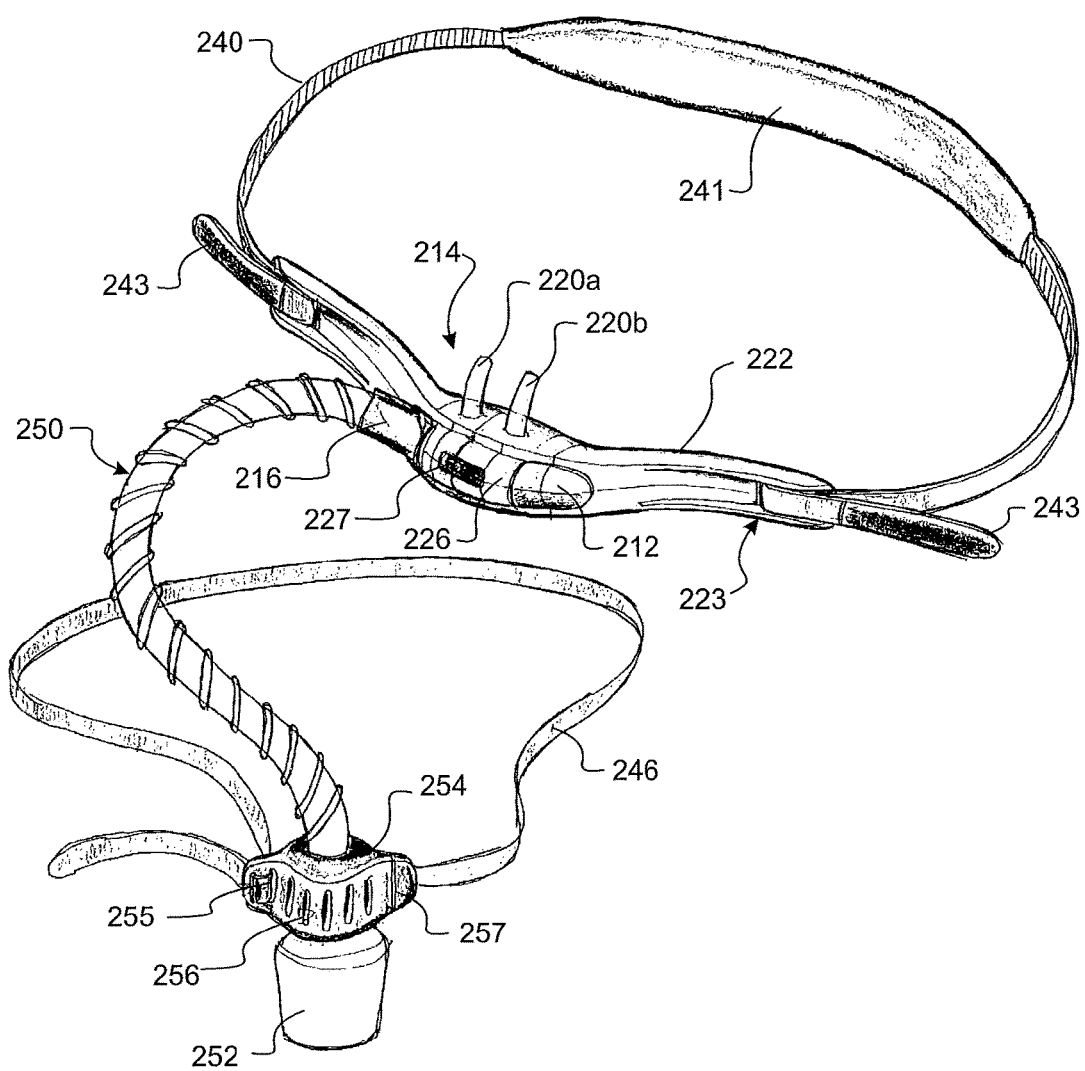
FIG. 3A illustrates a front perspective view of an example embodiment of a nasal cannula assembly including a cannula and manifold.
Figure 3B:
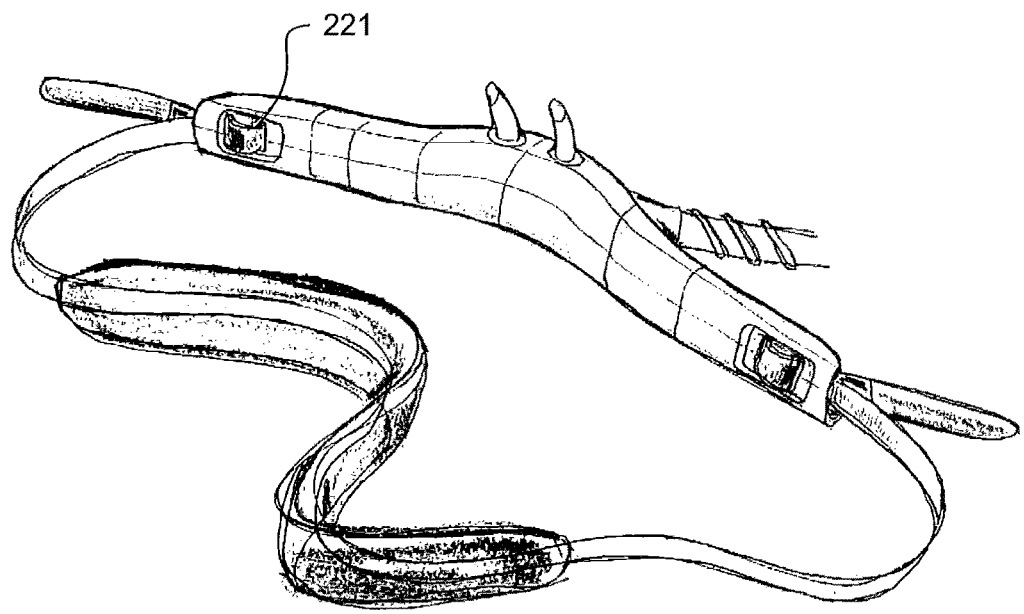
FIG. 3B illustrates a partial rear perspective view of the nasal cannula assembly of FIG. 3A.

With reference to FIGS. 3A and 3B, a nasal cannula assembly or system includes a cannula 214, manifold 212, headgear strap 240, gas supply tube 250, and lanyard 246. The cannula 214 includes nasal prongs 220a, b, side straps 222, and a manifold retention strap 226 defining or encircling an aperture configured to receive the manifold 212. The cannula 214 is configured such that the manifold 212 can be inserted into the aperture of the manifold retention strap 226 from either side, so that the manifold inlet 216 can be positioned to either side of the cannula 214. In the illustrated embodiment, the manifold retention strap 226 is wide compared to the retention strap 26 shown in FIGS. 1A and 1B and straps 126a, b shown in FIG. 2. The retention strap 226 can include a window 227 that allows part of the manifold 212 to be visible, for example, indicating that the manifold 212 is correctly inserted into manifold retention strap 226. The window 227 can display, for example, branding, size, and/or other information printed, stamped, adhered or otherwise presented on the visible portion of the manifold 212.

The cannula 214 is generally soft and flexible for patient comfort. Outer portions 223 of the side straps 222 can be made to have increased strength, for example, by making the outer portions 223 thicker or otherwise reinforcing them, such as via strengthening ribs, which can be positioned at upper and/or lower edges of the side straps 222, for example. The added strength allows the headgear strap 240 to be coupled directly to the outer portions 223 of the side straps 222 without the need for additional clips, buckles, or other attachment mechanisms and allows the cannula 214 and side straps 222 to hold their moulded shape, preventing or inhibiting deformation during tension. The outer portions 223 of the side straps 222 can include two or more slits or apertures through which ends 243 of the strap 240 can be threaded and pulled through a desired length to obtain a headgear strap 240 circumference appropriate to fit the patient. The ends 243 of the headgear strap 240 can be folded back and removably secured to portions of the headgear strap 240 proximate the outer portions 223 of the side straps 222 via a hook and loop type closure. For example, a segment of fabric including hooks can be attached (e.g., sewn, adhered, etc.) to the ends 223 of the headgear strap 240, and a segment of fabric including loops can be attached (e.g., sewn, adhered, etc.) to the portions of the headgear strap 240 proximate the outer portions 223 of the side straps 222. An opposite side of the ends 243 of the strap 240 visible when worn can include branding or other information printed, stamped, adhered, or otherwise attached thereto.

As shown in FIG. 3B, a rear or patient-facing side of the side straps 222 can include recessed areas 221 to accommodate the portions of the headgear strap 240 looped through the side straps 222 so that the strap 240 does not significantly press against the patient's face. A section of the headgear strap 240 configured to be placed against the back of the patient's head in use can include a padded section 241 for patient comfort. The padded section can be inserted between two halves of the headgear strap 240 or placed on top of or around the headgear strap 240.

In use, the manifold 212 is coupled to the cannula 214 by inserting the manifold into the aperture defined by the manifold retention strap 226. The manifold 212 can be inserted into the aperture of the manifold retention strap 226 from either side, so that the manifold inlet 216 can be positioned to either side of the cannula 214. In the illustrated embodiment, the manifold 212 includes a cylindrical inlet 216. The inlet 216 has an inner diameter slightly larger than an outer diameter of the supply tube 250 so that the tube 250 can be coupled to the manifold 212 by inserting an end of the tube 250 into the manifold inlet 216. An end of the tube 250 opposite the manifold 212 can include a connector 252 configured to couple the supply tube 250 to the main delivery conduit coupled to and in fluid communication with the gas source.

The cannula system can further include a lanyard connector 254 located on the supply tube 250 proximal to the connector 252. In some embodiments, the lanyard connector 254 is color coded to indicate size or other information. One side of the lanyard connector 254 can include a mechanism 255 for adjustably receiving one end of the lanyard 246. For example, one side of the lanyard connector 254 can include two slits or apertures through which the end of the lanyard 246 can be threaded. This mechanism 255 allows the lanyard 246 to be easily placed around the patient's neck and coupled to the lanyard connector 254 without having to put the lanyard 246 over the patient's head. The lanyard connector 254 can also include a grip 256 to allow the patient or others to better grasp the lanyard connector 254 for adjustments and/or easy removal the connector 252 from the main delivery conduit 90.

One side of the lanyard connector 254 can include a breakaway clip 257. An end of the lanyard 246 can include molding configured to be inserted into the breakaway clip 257 to secure the lanyard 246 to the lanyard connector 254. The breakaway clip 257 is designed so that if the lanyard 246 applies too great a force to the patient's neck due to, for example, the main delivery conduit, connector 252, supply tube 250, and/or lanyard connector 254 being pulled away from the patient with a force exceeding a certain threshold, the breakaway clip 257 releases the lanyard 246 or detaches from the lanyard connector 254 to avoid patient injury or discomfort. This configuration advantageously allows the weight of the connector 252 (and the main delivery circuit 90) to be hung or oriented in a vertical orientation or direction. In some embodiments, the lanyard 246 is made of an inelastic material to improve the function of the breakaway clip 257 and so that the weight of the main delivery conduit coupled to the connector 252 does not stretch the lanyard 246 and apply additional force to the patient's neck. In some embodiments, the breakaway clip 257 allows the lanyard 246 to be easily looped around the patient's neck then inserted into the breakaway clip 257.

Figure 4:
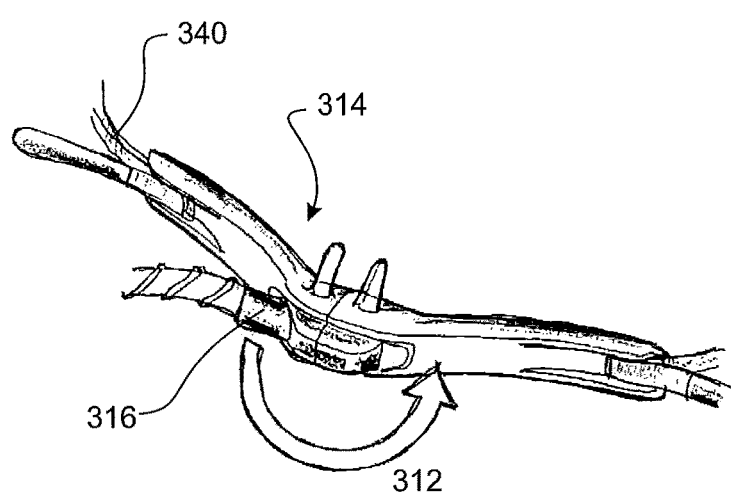
FIG. 4 illustrates a partial front perspective view of an alternative configuration of the nasal cannula assembly of FIGS. 3A and 3B.

FIG. 4 illustrates a cannula system having a cannula 314 and headgear strap 340 similar in some ways to the cannula 214 and headgear strap 240 illustrated in FIGS. 3A and 3B. However, the cannula system of FIG. 4 lacks a manifold retention strap and includes a reversible manifold 312. The manifold 312 can pivot or rotate or be decoupled from the cannula 314 and turned 180° so that the inlet 316 can be located to either side of the cannula 214.

Figure 5A:
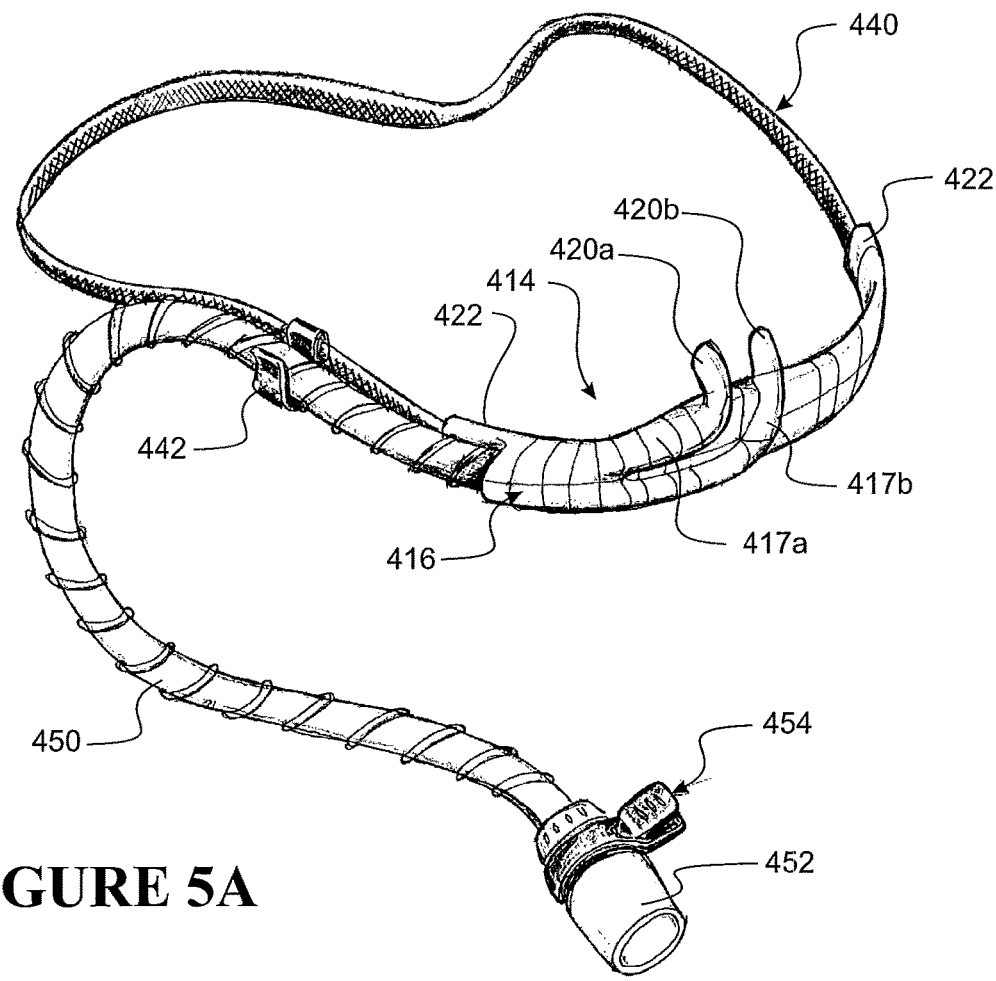
FIG. 5A illustrates a front perspective view of an example embodiment of a nasal cannula assembly including a cannula without a manifold.
Figure 5B:
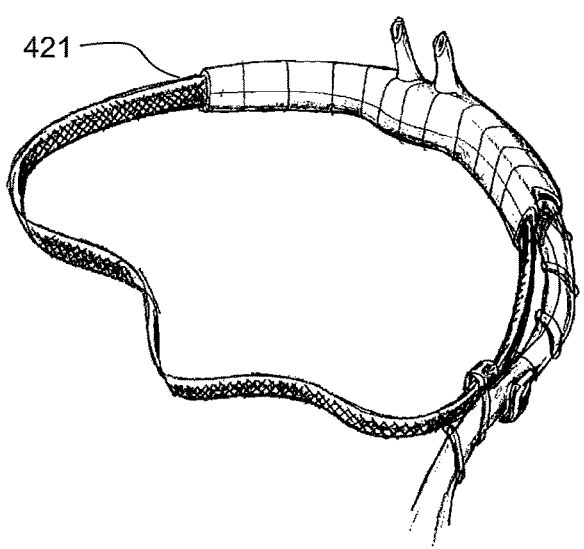
FIG. 5B illustrates a partial rear perspective view of the nasal cannula assembly of FIG. 5A.

An embodiment of a nasal cannula assembly or system as illustrated in FIGS. 5A and 5B includes a cannula 414, headgear strap 440, and gas supply tube 450. The cannula 414 includes nasal prongs 420a, b, side straps 422, and an inlet 416. In the illustrated embodiment, an end of the gas supply tube 450 couples directly to the inlet 416 of the cannula 414. The supply tube 450 can have a reduced diameter so that the end of the supply tube 450 can be received within the inlet 416. The supply tube 450 can be secured to the cannula 414 by stretching the cannula inlet 416 over the end of the supply tube 450, using an adhesive (e.g., glue), mechanical interference features, and/or other means. The cannula 414 further includes two gas paths 417a, b extending from and in fluid communication with the inlet 416, so that a first gas path 417a extends to and is in fluid communication with a first nasal prong 420a, and a second gas path 417b extends to and is in fluid communication with a second nasal prong 420b. The geometry of the gas paths 417a, b can be designed to balance gas flow between the two gas paths 417a, b and nasal prongs 420a, b so that the patient receives balanced flow in both nostrils. The flow path has reduced, minimal or no significantly abrupt transitions or sharp corners, which advantageously reduces or minimizes resistance to flow.

Ends of the side straps 422 can include apertures or slots 421 designed to receive ends of the headgear strap 440. The headgear strap 440 can be formed of a highly elastic material capable of a large degree of stretch to allow the strap 440 to accommodate and fit various patient head sizes, particularly where, as in the illustrated embodiment, the side straps 422 do not include clips or buckles to allow for adjustment of the circumference of the headgear strap 440. For example, the headgear strap 440 can be made of a material having a relatively flat force extension curve so that the strap 440 maintains the same or substantially the same tension over a range of degree of stretch. The ends of the headgear strap 440 can include a rigid material overmolded thereon to help secure the ends of the strap 440 within the apertures 421. The strap 440 can also or alternatively be secured to the cannula 414 with an adhesive (e.g., glue), ultrasonic welding, and/or other means.

The cannula system can include a tube clip 442 coupled (permanently or removably, immovably or movably) to the headgear strap 440. The tube clip 442 can be located on the side of the cannula 414 nearest the inlet 416 and can receive the supply tube 450 to help hold the tube 450 away from the mouth and face of the patient in use. An end of the supply tube 450 opposite the end coupled to the cannula inlet 416 can include a connector 452 configured to couple the supply tube 450 to the main delivery conduit. The cannula system can include a lanyard clip 454 positioned on the supply tube 450 proximal to the connector 452. The lanyard clip 454 can releasably clip to a lanyard worn around the patient's neck in use. Alternatively, the lanyard clip 454 can be directly attached to, for example, the patient's clothing or hospital gown, bed sheets, or another location nearby to help support the weight of the main delivery conduit. The nasal cannula system illustrated in FIGS. 5A and 5B does not include a manifold or clips or buckles for attaching the headgear strap 440 to the cannula 414. This configuration minimizes the parts of the nasal cannula system, which can advantageously help provide easier manufacturing and/or reduce the cost.

Figure 6A:
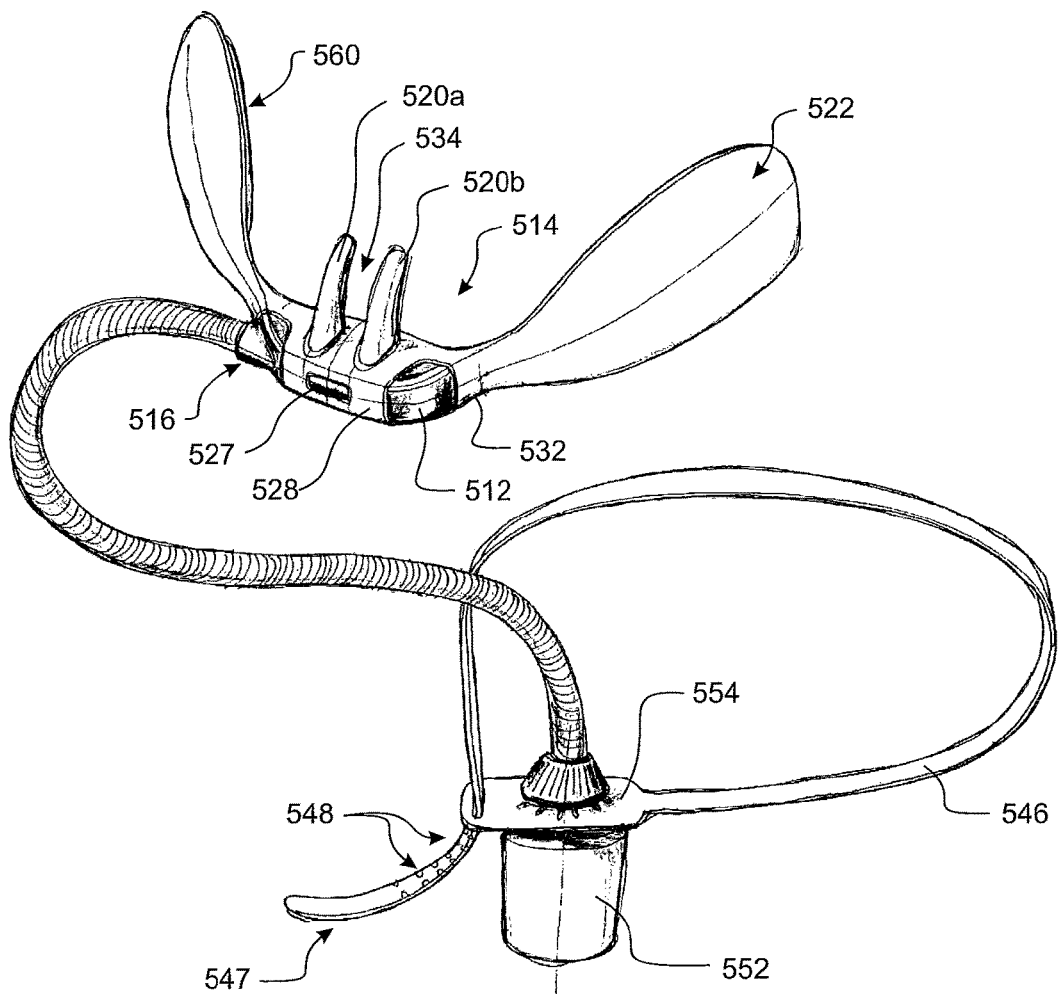
FIG. 6A illustrates a front perspective view of an example embodiment of a nasal cannula assembly including cheek pads.
Figure 6B:
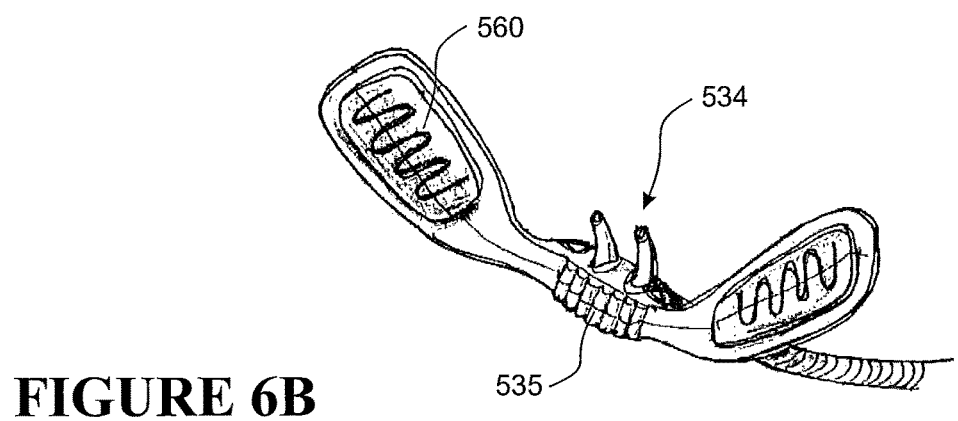
FIG. 6B illustrates a partial rear perspective view of the nasal cannula assembly of FIG. 6A.

Another embodiment of a nasal cannula assembly or system includes a cannula 514, manifold 512, gas supply tube 550, and lanyard 546 as shown in FIGS. 6A and 6B. The cannula 514 includes nasal prongs 520a, b, a manifold retention strap 526, and cheek pads 522. The cheek pads 522 are designed to be positioned on the patient's cheeks and/or upper cheeks in use. The cannula 514 includes thin flex areas 532 located at transition regions between a central body portion 534 of the cannula 514 and the cheek pads 522. The thin flex areas 532 have a reduced cross-sectional thickness to allow the cheek pads 522 to move and be adjusted relative to the central body portion 534 more easily to improve the fit, positioning, and comfort of the cannula 514 on the patient's face. A rear or patient contacting side of the central body portion 534 can include soft and/or thin wall cushion details 535. The cushion details 535 can include, for example, a ribbed, rippled, folded or other surface designed to space the central body portion 534 of the cannula 514 away from the patient's face slightly. This advantageously allows for airflow between the central body portion 534 and the patient's face and provides a collapsible region to help absorb forces pressing the cannula 514 into the patient's face.

Rear surfaces of the cheek pads 522 include attachment pads 560 integrally formed with the cheek pads 522 or sewn, adhered, or otherwise attached thereto. The attachment pads 560 can include a releasable and reattachable adhesive to attach the cheek pads 522 to the patient's face. Alternatively, the attachment pads 560 can include one portion of a hook and loop fastener, for example, a fabric segment including the hooks. Patches containing the other portion of the fastener, for example the loops, can be attached to the patient's face at desired locations on the cheeks and/or upper cheeks to allow the attachment pads 560 to be releasably attached to the patient's face.

The manifold 512 includes an inlet 516 designed to receive the gas supply tube 550 and an outlet designed to be aligned and in fluid communication with the nasal prongs 520a, b in use. The manifold 512 is coupled to the cannula 514 by sliding the manifold 512 into an aperture defined by the manifold retention strap 526 so that the outlet aligns with the nasal prongs 520a, b and stretching the cannula 514 around edges of the manifold 512. The manifold 512 can be inserted into the aperture of the manifold retention strap 526 from either side, so that the manifold inlet 516 can be positioned to either side of the cannula 514. The retention strap 526 can include a window 527 that allows part of the manifold 512 to be visible, for example, indicating that the manifold 512 is correctly inserted into manifold retention strap 526. The window 527 can display, for example, branding, size, and/or other information printed, stamped, adhered or otherwise presented on the visible portion of the manifold 512.

In the illustrated embodiment, the supply tube 550 is a small diameter spiral tube. Other types of gas supply conduits are also possible. An end of the supply tube 550 opposite the end coupled to the manifold 512 can include a connector 552 configured to be connected to the main delivery conduit. The cannula system can include a lanyard retention connector 554 located on the connector 552 or on the supply tube 550 proximal to the connector 552. One end of the lanyard 546 can be integrally formed with or coupled to one side of the lanyard retention connector 554. An opposite side of the lanyard retention connector 554 can include a slot designed to receive a free end 547 of the lanyard 546. The free end 547 of the lanyard 546 can include a series of protrusions or notches 548. The protrusions 548 can be pulled through the slot of the lanyard retention connector 554 to adjust the circumference of the lanyard 546 but resist sliding through the slot when not being adjusted to help secure the lanyard 546 at the desired circumference. The lanyard 546 can be made of a stamped fabric, for example, white non-woven laminated polyethylene, which can advantageously help reduce the cost of the cannula system.

Figure 7A:
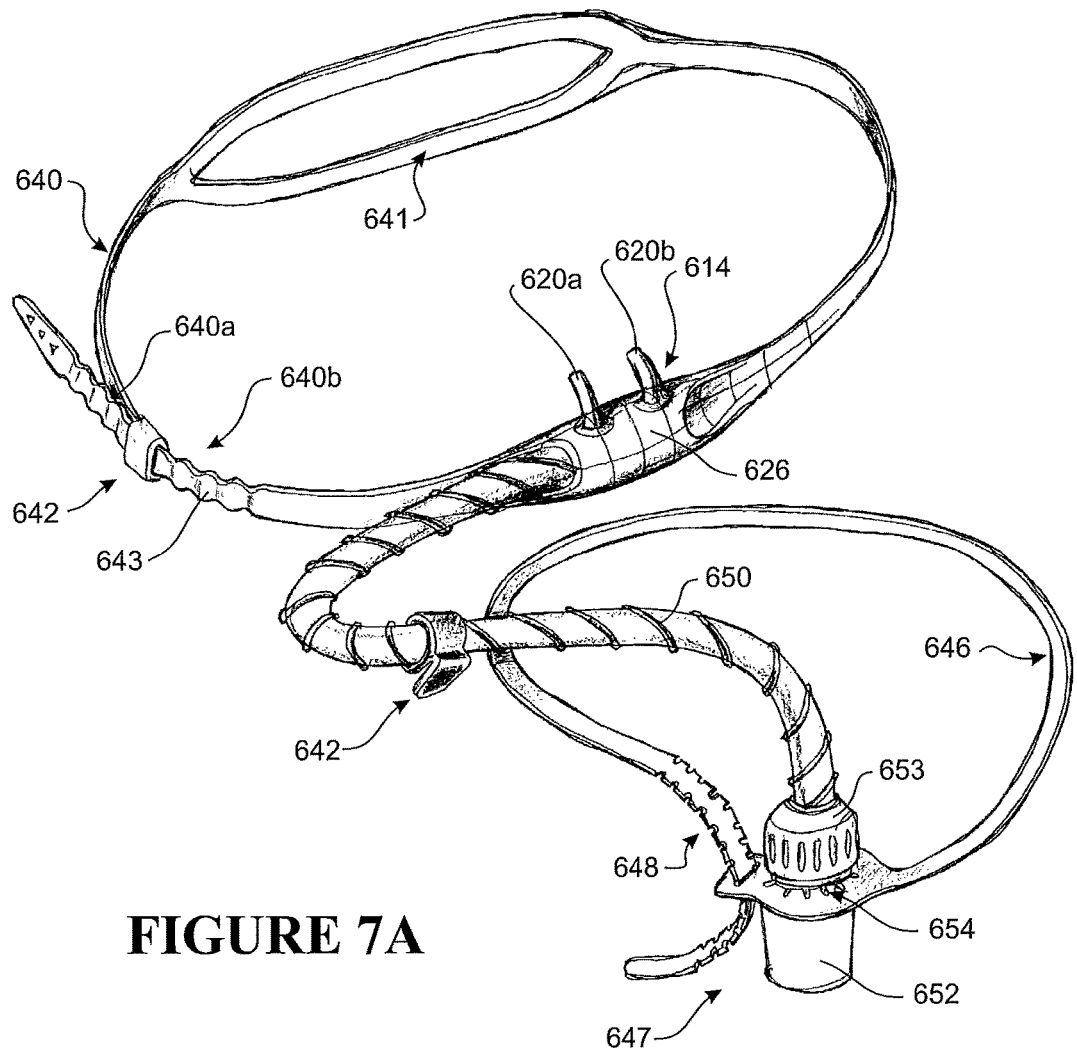
FIG. 7A illustrates a front perspective view of an example embodiment of a nasal cannula assembly including a cannula with an integrated head strap.
Figure 7B:
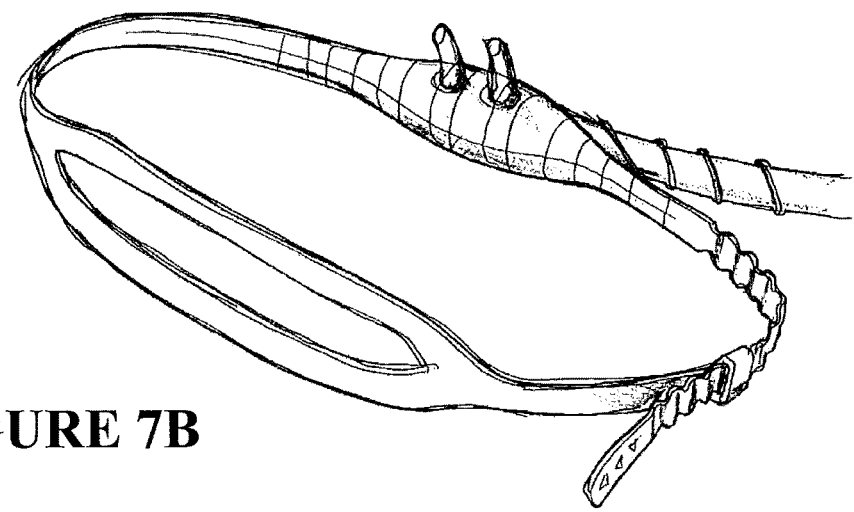
FIG. 7B illustrates a partial rear perspective view of the nasal cannula assembly of FIG. 7A.

An example embodiment of a cannula system as shown in FIGS. 7A-7B includes a cannula 614, gas supply tube 650, and lanyard 646. The cannula 614 includes nasal prongs 620a, b, a retention strap 626, and an integrated headgear strap 640. In some embodiments, the headgear strap 640 can include a break on one side so that the headgear strap 640 includes a first section 640a and a second section 640b. The free end of one section (first section 640a in the illustrated embodiment) can include a slot 642 configured to receive the free end of the other section (second section 640b in the illustrated embodiment). A segment of the strap 640 near the free end of the second section 640b can include teeth 643 configured to engage sides of the slot 642 to help inhibit the second section 640b from being pulled out of the slot 642. A rear portion 641 of the headgear strap 640, which is part of the first section 640a in the illustrated embodiment, can separate into a double strap configuration to aid stability of headgear strap 640 on the patient's head and/or help distribute forces on the patient's head and improve patient comfort.

In the illustrated embodiment, an end of the gas supply tube 650 is coupled directly to the cannula 614. The supply tube 650 can have a reduced diameter so that the end of the supply tube 650 can be received within an aperture defined by the retention strap 626. The supply tube 650 can be secured to the cannula 614 by stretching the manifold retention strap 626 over the end of the supply tube 650, using an adhesive (e.g., glue), mechanical interference feature, and/or other means. The cannula system can include a tube clip 642 coupled (permanently or removably, immovably or movably) to the supply tube 650. The tube clip 642 can include a hook configured to be placed on the headgear strap 640 to help hold the tube 650 away from the mouth and face of the patient in use.

An end of the supply tube 650 opposite the end coupled to the cannula 614 can include a connector 652 configured to be connected to the main delivery conduit. The cannula system can further include a lanyard retention connector 654. The connector 652 can include a lower portion and an upper portion 653 including grip features. In some embodiments, the connector 652 includes a reduced diameter section between the upper and lower portions to receive the lanyard retention connector 654. Alternatively, the upper and lower portions can be separate pieces. In use, the lanyard retention connector 654 is pressed over a portion of the connector 652 and held in place between the upper and lower portions or in the reduced diameter section.

In the illustrated embodiment, the lanyard 646 is integrally formed with one side of the lanyard retention connector 654. Alternatively, the lanyard 646 can be coupled to the lanyard retention connector 654. An opposite side of the lanyard retention connector 654 can include a slot designed to receive a free end 647 of the lanyard 646. The free end 647 of the lanyard 646 can include a series of notches 648 along the sides. In use, the lanyard 646 is wrapped around the patient's neck and the free end 647 of the lanyard is threaded through the slot of the lanyard retention connector 654 to achieve the desired circumference of the lanyard 646. The notches 648 allow the free end 647 of the lanyard 646 to be pulled through the slot of the lanyard retention connector 654 to adjust the circumference of the lanyard 646 but resist sliding through the slot when not being adjusted to help secure the lanyard 646 at the desired circumference. The lanyard 646 can be made of a stamped fabric, for example, white non-woven laminated polyethylene, which can advantageously help reduce the cost of the cannula system.

Figure 7C:
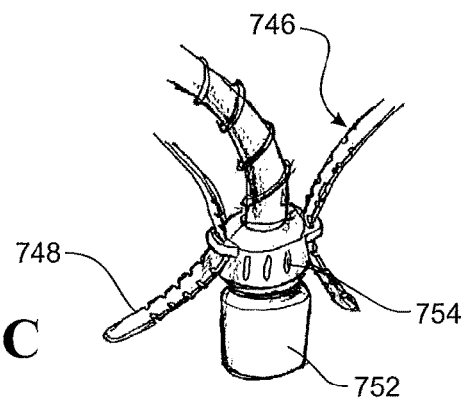
FIG. 7C illustrates an example embodiment of a lanyard connector for a nasal cannula assembly.

In an alternative embodiment, shown in FIG. 7C, the cannula system can include a connector 752, a lanyard connector 754 positioned on the supply tube 650 proximal to the connector 752, and a separate lanyard 746. The lanyard connector 754 includes two slots to receive the ends of the lanyard 746. Both ends of the lanyard 746 can include a series of notches 748 similar to the notches 648 described herein to allow for adjustment of one or both ends of the lanyard 746. This configuration advantageously allows the weight of the connector 752 (and the main delivery circuit 90) to be hung or oriented in a vertical orientation or direction.

Figure 8A:
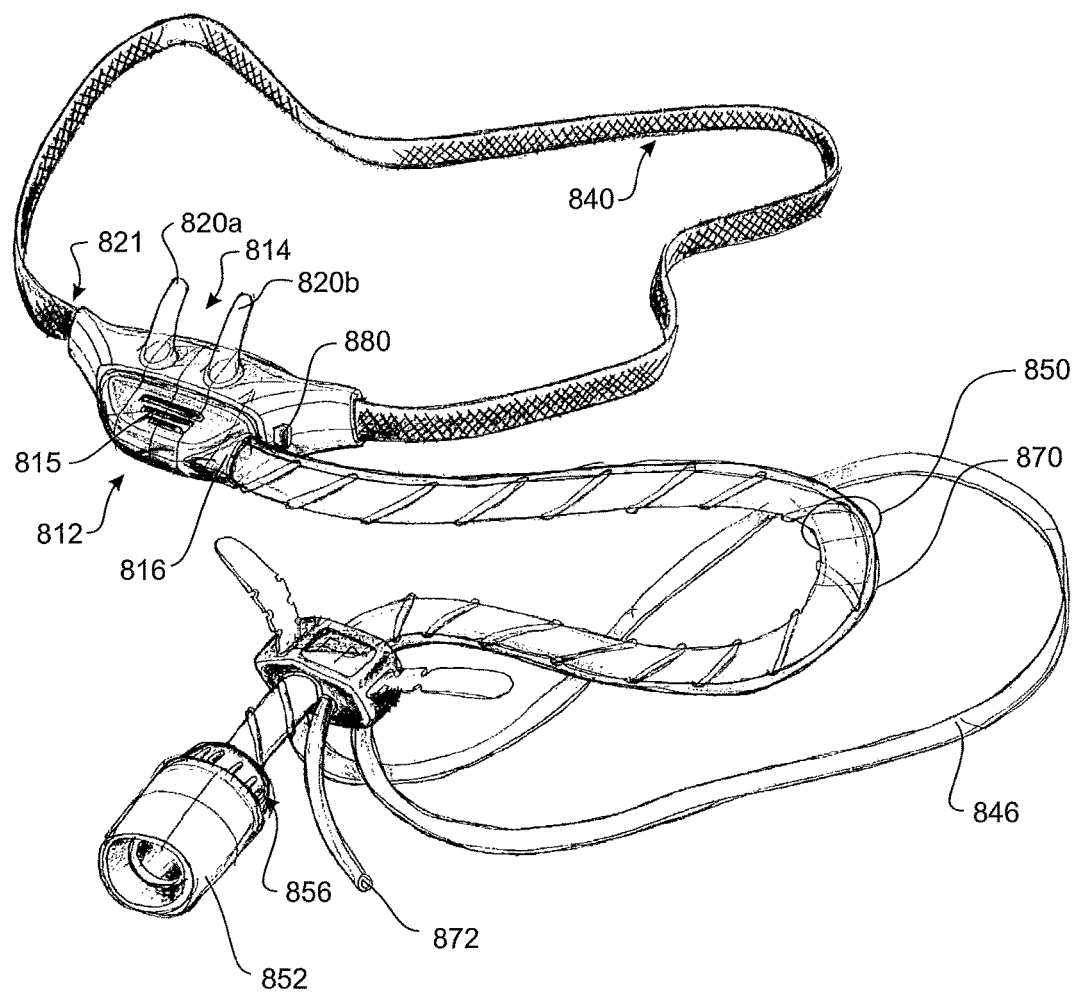
FIG. 8A illustrates a front perspective view of an example embodiment of a nasal cannula assembly including a cannula and manifold.
Figure 8B:
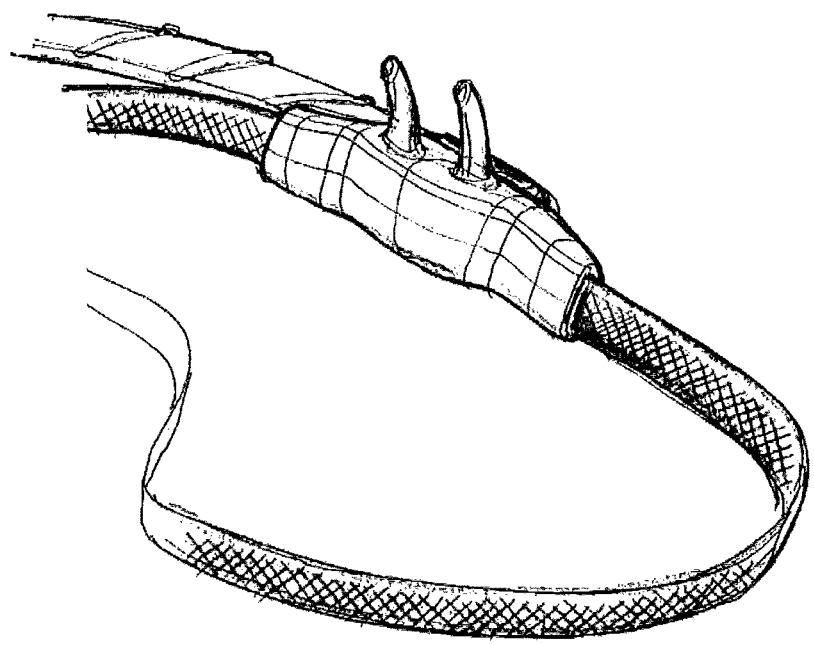
FIG. 8B illustrates a partial rear perspective view of the nasal cannula assembly of FIG. 8A.
Figure 8C:
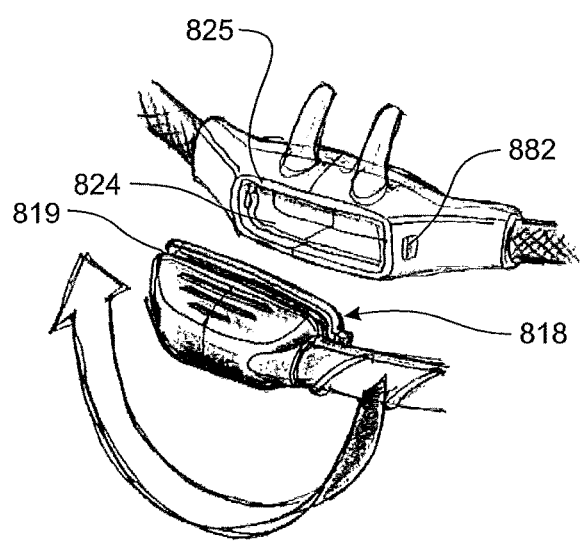
FIG. 8C illustrates an exploded view of the nasal cannula assembly of FIGS. 8A and 8B.

In some embodiments, for example as shown in FIGS. 8A-8C, a cannula system includes a cannula 814, manifold 812, headgear strap 840, gas supply tube 850, and lanyard 846. The cannula 814 includes nasal prongs 820a, b, and an inlet 824. As shown in FIG. 8C, a flange 825 encircles a perimeter of the inlet 824. The manifold 812 includes an inlet 816 configured to receive the supply tube 850 and an outlet 818. The outlet 818 of the manifold 812 includes a recess 819 configured to receive the flange 825 of the cannula 814. In some embodiments, the manifold 812 and cannula 814 can be designed to have a reduced size to advantageously reduce the profile of the cannula system on the patient's face, which can improve patient comfort and reduce the chance of obstructing the face or mouth in some circumstances.

In use, the manifold 812 is coupled to the cannula 814 by inserting one side of the manifold 812 into the cannula 814 inlet 824 so that the flange 825 of the cannula 814 sits in the recess 819 of the manifold 812 and stretching the cannula 814 around the manifold 812 outlet 818 so that the flange 824 sits in the recess 819 around the entire perimeters of the cannula 814 outlet 824 and manifold 812 outlet 818. The flange 824 and corresponding recess 819 advantageously help secure the connection between the cannula 814 and manifold 812 and can also help prevent air leaks at the connection. The manifold 812 can further include a tab 880 designed to fit into a corresponding recess or aperture 882 on the cannula 814 to help further secure the manifold 812 to the cannula 814 and indicate that the manifold 812 is correctly inserted into the cannula 814. As shown in FIG. 8C, the manifold 812 is reversible, i.e., the manifold 812 can be coupled to the cannula 814 so that the manifold inlet 816 extends to either side of the cannula 814. The manifold 812 can include a grip 815 to advantageously assist a user in grasping the manifold 812 to couple and/or remove the manifold 812 to and/or from the cannula 814.

In the illustrated embodiment, the headgear strap 840 is coupled directly to the cannula 814, and the cannula system does not include clips, buckles, or other mechanisms that allow for adjustment of the circumference of the strap 840. Sides of the cannula 814 can include apertures or slots 821 designed to receive ends of the headgear strap 840. The ends of the strap 840 can be secured to the cannula 814 with an adhesive (e.g., glue), ultrasonic welding, and/or other means. The headgear strap 840 can be formed of a highly elastic material capable of a large degree of stretch to allow the strap 840 to accommodate and fit various patient head sizes. For example, the headgear strap 840 can be made of a material having a relatively flat force extension curve so that the strap 840 maintains the same or substantially the same tension over a range of degree of stretch. A pitch of threads of the headgear strap 840 material can be changed to adjust the tightness of the strap 840.

The gas supply tube 850 can be coupled to the manifold 812 inlet 816 at one end and a connector 852 configured to couple the supply tube 850 to the main delivery conduit at an opposite end. The gas supply tube 850 can have a reduced diameter so that the end of the tube 850 can be inserted into the manifold inlet 816. In some embodiments, the connector 852 can include grip details 856 to help the user grasp the connector 852 more easily to adjust various components of the cannula system. In some embodiments, the gas supply tube 850 can include a pressure line 870. The pressure line 870 can be configured to convey pressure feedback from the end of the supply tube 850 coupled to the manifold 812 to a pressure sensor and/or controller. The pressure line 870 can be integral with or coupled to the supply tube 850. In some embodiments, the pressure line 870 lies within the main flow path of the supply tube 850. In other embodiments, the pressure line 870 lies adjacent the main flow path of the supply tube 850. For example, in some embodiments, the supply tube 850 can be a spiral bubble tube, and the pressure line 870 can lie in the hollow spiral of the spiral bubble supply tube 850.

The cannula system can further include a lanyard connector 854 located on the supply tube 850 proximal to the connector 852. In some embodiments, the lanyard connector 854 is fixed relative to the tube 850. In other embodiments, the lanyard connector 854 is slidable relative to the tube 850. The lanyard connector 854 can include apertures or slots on either side to receive ends of the lanyard 846. In the illustrated embodiment, the lanyard connector 854 also acts as a point of separation of the pressure line 870 from the supply tube 850. In use, the lanyard 846 is wrapped around the patient's neck and the ends of the lanyard 846 are threaded through the apertures or slots of the lanyard connector 854 to achieve the desired circumference of the lanyard 846. Ends of the lanyard 846 can include notches 848 along the sides. The notches 848 allow the lanyard 846 to be pulled through the slots of the lanyard connector 854 to adjust the circumference of the lanyard 846 but resist sliding through the slots when not being adjusted to help secure the lanyard 846 at the desired circumference. This configuration advantageously allows the weight of the connector 852 (and the main delivery circuit 90 illustrated in FIG. 1A) to be hung or oriented in a vertical orientation or direction. The lanyard 846 can be made of a stamped fabric, for example, white non-woven laminated polyethylene, which can advantageously help reduce the cost of the cannula system.

Figure 9B:
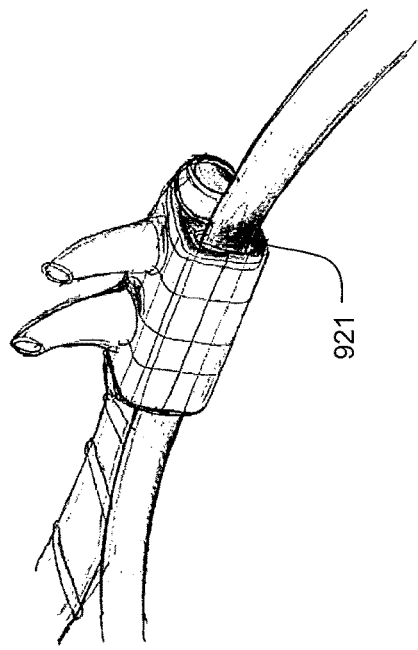
FIG. 9B illustrates a partial rear perspective view of the nasal cannula assembly of FIG. 9A.
Figure 9C:
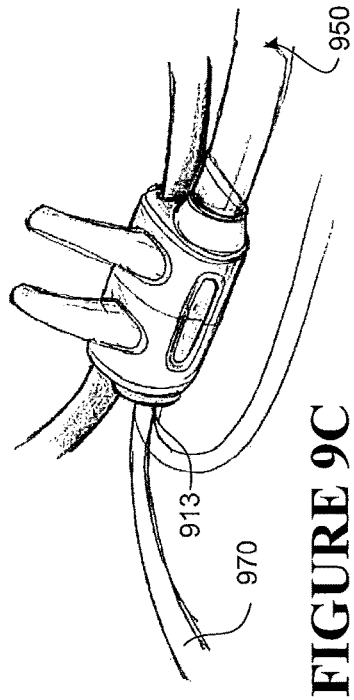
FIG. 9C illustrates a variation of the nasal cannula assembly of FIGS. 9A and 9B.
Figure 9A:
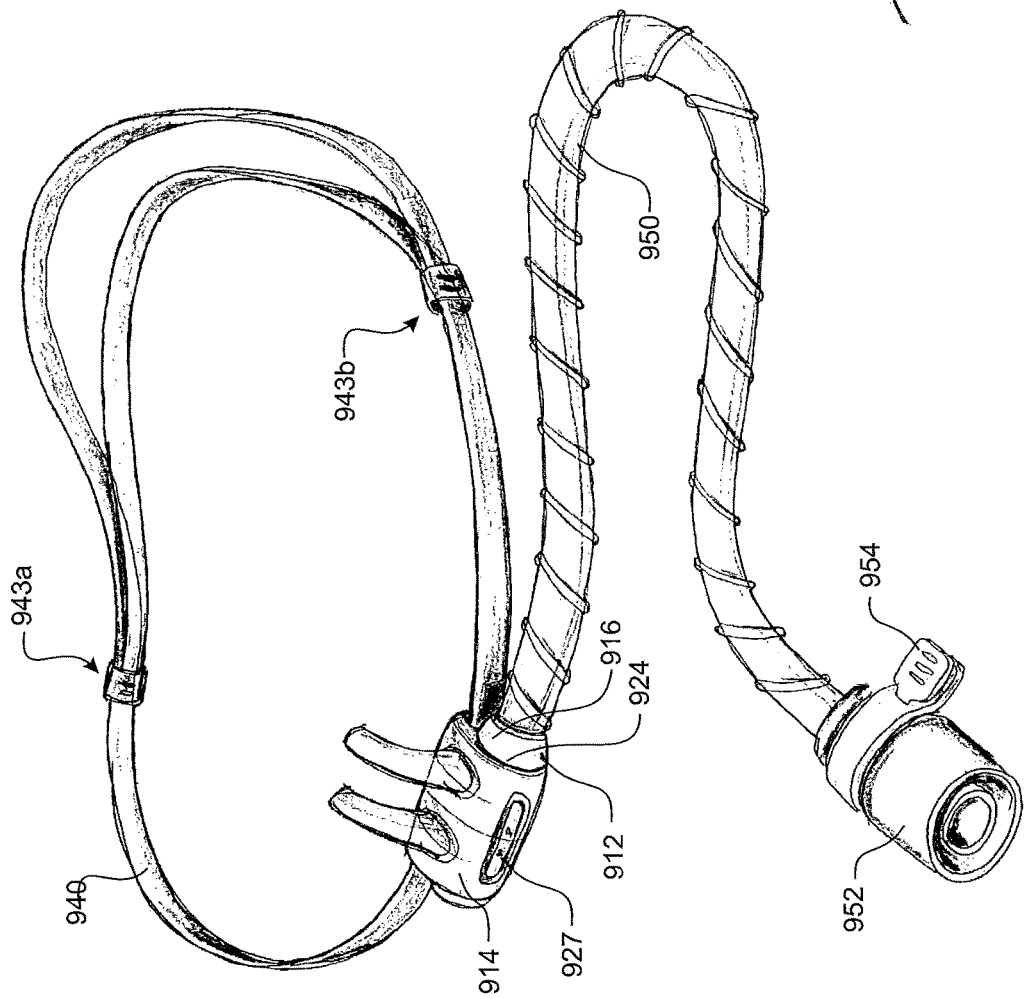
FIG. 9A illustrates a front perspective view of an example embodiment of a nasal cannula assembly including a cannula and manifold.

An example embodiment of a cannula system as illustrated in FIGS. 9A and 9B includes a cannula 914, manifold 912, headgear strap 940, and gas supply tube 950. As shown, the cannula 914 can include a manifold aperture 924 configured to receive the manifold 912 and a headgear strap aperture 921 configured to receive the headgear strap 940. The manifold 912 can be inserted into the aperture of the cannula 914 from either side, so that the manifold inlet 916 can be positioned to either side of the cannula 914. In the illustrated embodiment, the manifold 912 is generally cylindrical, and the manifold aperture 924 is therefore also generally cylindrical. The manifold 912 can be substantially hollow to allow for gas flow. The cannula 914 can include a window 927 that allows part of the manifold 912 to be visible, for example, indicating that the manifold 912 is correctly inserted into cannula 914. The window 927 can display, for example, branding, size, or other information printed, stamped, adhered or otherwise presented on the visible portion of the manifold 912.

One end of the cylindrical manifold 912 is open and forms an inlet 916 configured to receive one end of the gas supply tube 950. An opposite end of the manifold 912 is closed, as shown in FIG. 9B. In some embodiments, the closed end of the manifold 912 includes a removable cap. In some such embodiments, a solid cap can be interchangeable with a cap 913 that can include a pressure line 970, for example as shown in FIG. 9C. As explained above, the manifold 912 can be inserted into the aperture of the cannula 914 from either side, so that the manifold inlet 916 can be positioned to either side of the cannula 914. The cap 913 therefore can also be located on either side of the cannula 914.

In the illustrated embodiment, the headgear strap 940 is threaded through the headgear strap aperture 921 of the cannula 914. In some embodiments, the headgear strap 940 is secured to the cannula 914 with an adhesive (e.g., glue), ultrasonic welding, or another mechanism. In some embodiments however, the cannula 914 and headgear strap 940 are slidable relative to each other. The headgear strap 940 can be a single length of strap. One end of the length of strap can be secured to clasp 943a, and an opposite end of the length of strap can be secured to clasp 943b. The clasps 943a, b are coupled to and slidable on the strap 940 to allow for adjustment of the circumference of the strap 940 to fit the patient's head. In some embodiments, the headgear strap 940 is made of a non-stretch material.

The cannula system can include a connector 952 on the supply tube 950 at an end opposite the manifold 912. The connector 952 can be configured to couple the supply tube 950 to the main supply conduit. The cannula system can further include a lanyard clip 954 encircling a proximal portion of the connector 952 or encircling the supply tube 950 proximal to the connector 952. The lanyard clip 954 can releasably receive a lanyard. Alternatively, the lanyard clip 954 can be directly clipped to, for example, the patient's clothing or gown, the bedding, or a lanyard placed around the patient's neck to help support the weight of the main supply conduit coupled to connector 952.

An example embodiment of a cannula system as shown in FIGS. 10A and 10B includes a cannula 1014, nose strip 1022, supply tube 1050, and nasal prongs 1020a, b. The cannula 1014 is shaped and sized to be positioned on top of the patient's nose. For example, a portion of the cannula 1014 can have a curved profile designed to follow the curvature of the nose. The cannula 1014 can be secured to the patient's nose via the nose strip 1022. In some embodiments, the nose strip 1022 resembles an adhesive bandage. A central portion of the nose strip 1022 can include a comfort pad 1035 configured to rest against the patient's nose and provide added cushioning in use. Adhesive portions of the nose strip 1022 extend from the central portion to adhere to portions of the patient's cheeks. A side of the nose strip 1022 facing away from the patient's face includes an attachment pad 1062 coupled (e.g., sewn, adhered, or otherwise attached) thereto. A patient facing side of the cannula 1014 includes a corresponding attachment pad 1060. For example, in some embodiments, the attachment pads 1060, 1062 are the components of a hook-and-loop fastener, e.g., Velcro. The attachment pads 1060, 1062 therefore allow the cannula 1014 to be releasably attached to the nose strip 1022.

In some embodiments, the nose strip 1022 includes a strip 1064 designed to help hold the patient's nasal passages open. In some embodiments, the strip 1064 can be made of a flexible, spring-like metal that is biased toward a substantially straight state. When the nose strip 1022 is placed across the curved nasal bridge, the strip 1064 attempts to straighten, thereby gently lifting the sides of the patient's nose to open the nasal passages. In some embodiments, the strip 1064 can be made of a shape memory material such as nitinol, and heat from the patient's face causes the strip 1064 to attempt to return to a straighter state. The strip 1064 can be located on either side of the nose strip 1022, i.e., on the side facing away from the patient or the side facing the patient, e.g., between the nose strip 1022 and comfort pad 1035. In some embodiments, the nose strip 1022 can also act as a blackhead removing strip. The patient contacting side of the nose strip 1022 can include bonding agents capable of bonding to dirt and/or other impurities in the patient's pores so that they are removed with the nose strip 1022 when it is removed.

In the illustrated embodiment, the supply tube 1050 is a dual-tube including two small-diameter tubes extending between a main delivery conduit connector 1052 and nasal prongs 1020a, b. The cannula system can include an adapter 1053 designed to receive the small-diameter supply tubes 1050 and couple to the main delivery conduit connector 1052. The adapter 1053 can be integrally formed with, attached to, or proximal to the connector 1052. Each of the supply tubes 1050 can be integrally formed with or coupled to one of the nasal prongs 1020a, b. In some alternative embodiments, the supply tube 1050 can include a single tube over part or all of its length. The single tube can separate at the nasal prongs 1020a, b or can separate into two tubes distal to the nasal prongs 1020a, b. As shown in FIGS. 10A and 10B, the two supply tubes 1050 pass downward into a portion of the cannula 1014. The nasal prongs 1020a, b extend downward from the supply tubes 1050 and cannula 1014, then turn approximately 180° to extend upward on the patient contacting side of the cannula 1014. In the illustrated embodiment, the nasal prongs 1020a, b are molded or formed to retain their shape and orientation. In some embodiments, the nasal prongs 1020a, b can include a wire made of a shape memory material, for example, nitinol. Gas flow through the nasal prongs 1020a, b or heat radiating from the patient's face can cause the wire to assume and/or maintain the formed shape. The nasal prongs 1020a, b extend upwardly into the patient's nostrils when the cannula 1014 is coupled to the nose strip 1022.

In some alternative embodiments, for example as shown in FIG. 11, the cannula system can include nasal pillows 1120a, b instead of nasal prongs. As shown, the supply tubes 1050 pass downward through a portion of the cannula 1014 and hang freely. The nasal pillows 1120a, b are coupled to the free ends of the supply tubes 1050. In some embodiments, the nasal pillows 1120a, b can be self-inflating pillows. In use, the nasal pillows 1120a, b are turned upward and inserted into the patient's nostrils and the cannula 1014 is coupled to the nasal strip 1022.

The cannula system can further include a cheek pad 1042. The cheek pad 1042 can include an adhesive strip that can be used to secure a portion of the supply tubes 1050 to the patient's cheek. The cheek pad 1042 can advantageously help hold the supply tubes 1050 away from the patient's mouth and help support some of the weight of the supply tubes 1050. The cheek pad 1042 can include branding or other information printed or otherwise displayed thereon. In some embodiments, the supply tubes 1050 include an anti-kink spring, which can advantageously help allow the tubes 1050 to be manipulated, for example when positioning the cannula 1014 or cheek pad 1042 on the patient, without interrupting the gas supply.

Figure 12A:
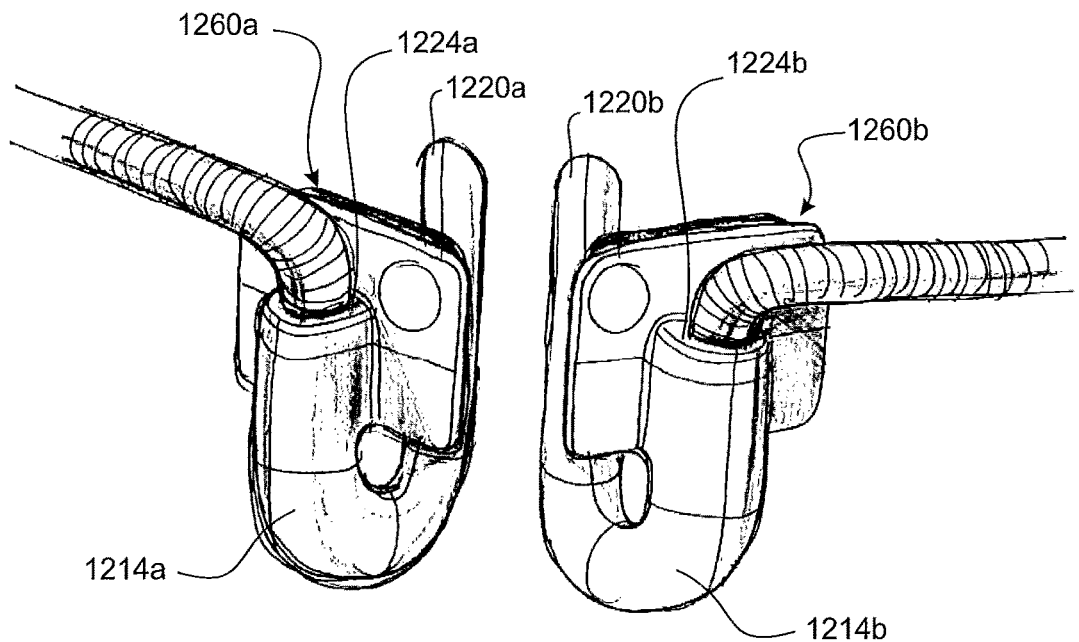
FIG. 12A illustrates a partial front perspective view of an example embodiment of a nasal cannula assembly including two cannulas.
Figure 12B:
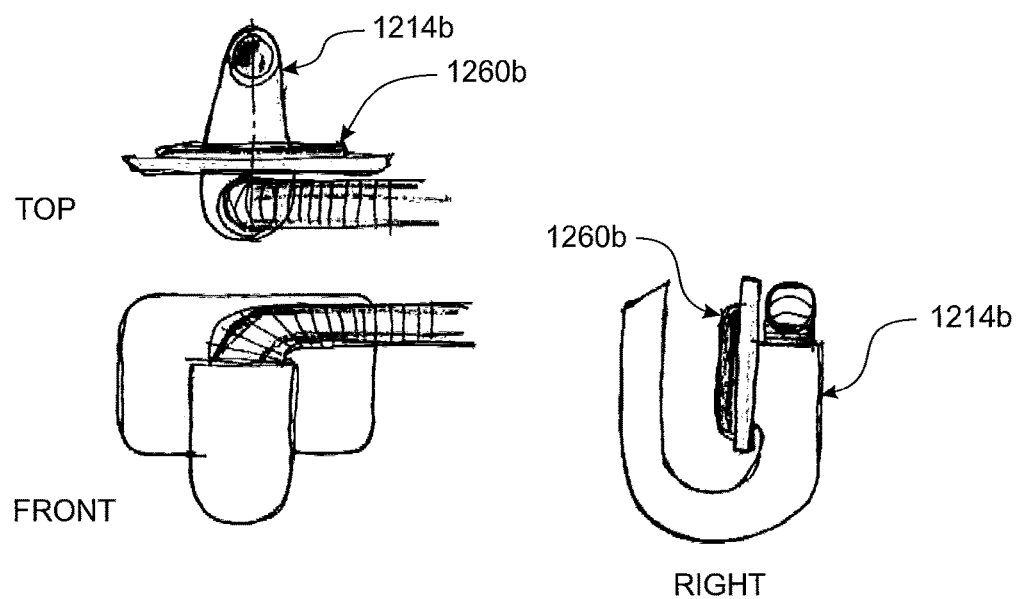
FIG. 12B illustrates top, front, and side views of one of the cannulas of FIG. 12A.
Figure 12C:
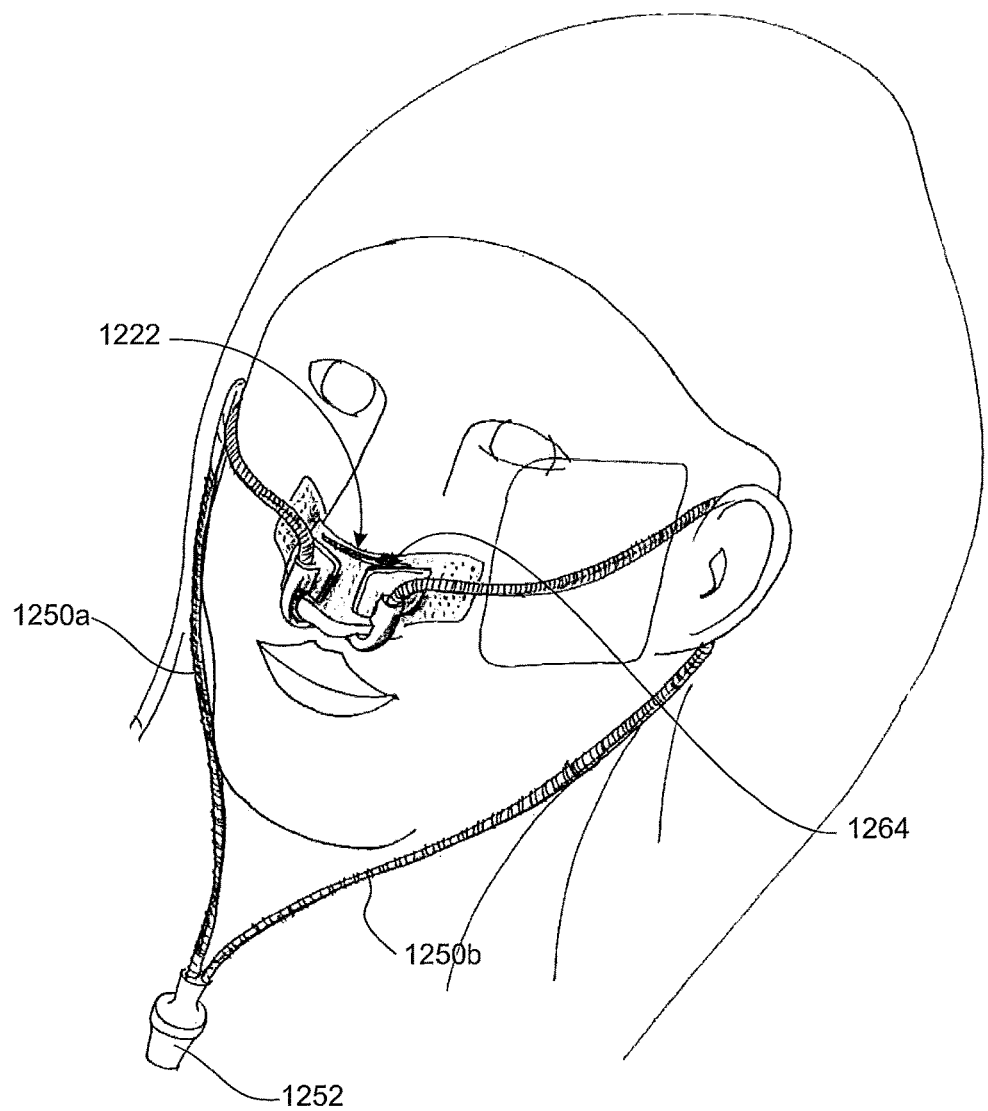
FIG. 12C illustrates a front perspective view of the nasal cannula assembly of FIG. 12A coupled to a patient.

An example embodiment of a cannula system can include two cannulas 1220a, b, nose strip 1222, and supply tubes 1250a, b, as shown in FIGS. 12A-12C. The nose strip 1222 can be similar to nose strip 1022 shown in FIGS. 10A and 10B and described in the accompanying text. In the embodiment of FIGS. 12A-12C, however, the cannula is separated into a right cannula 1214a and a left cannula 1214b. In some embodiments, the cannulas 1214a, b are symmetrical rather than right and left biased. Right cannula 1214a includes an integral nasal prong 1220a, and left cannula 1214b includes an integral nasal prong 1220b. A patient facing surface of each cannula 1214a, b includes an attachment pad 1260a, b to removably attach the cannulas 1214a, b, to the attachment pad of the nose strip 1222. In some embodiments, nose strip 1222 includes a strip 1264 to help hold the patient's nasal passages open as described with respect to FIGS. 10A and 10B.

The supply tube includes small diameter right 1250a and left 1250b supply tubes extending from a main delivery conduit connector 1252 to the right 1214a and left 1214b cannulas. The supply tubes 1250a, b are received into inlets 1224a, b of the cannulas 1214a, b. As shown, the supply tubes 1250a, b can be looped around the patient's ears to help hold the tubes 1250a, b away from the patient's mouth and support some of the weight of the tubes 1250a, b. The tubes 1250a, b can include spring winding to help provide kink-resistance and strength. In some embodiments, only one of the cannulas 1214a, b can be used at a given time for a certain patient as needed or desired.

Figure 13A:
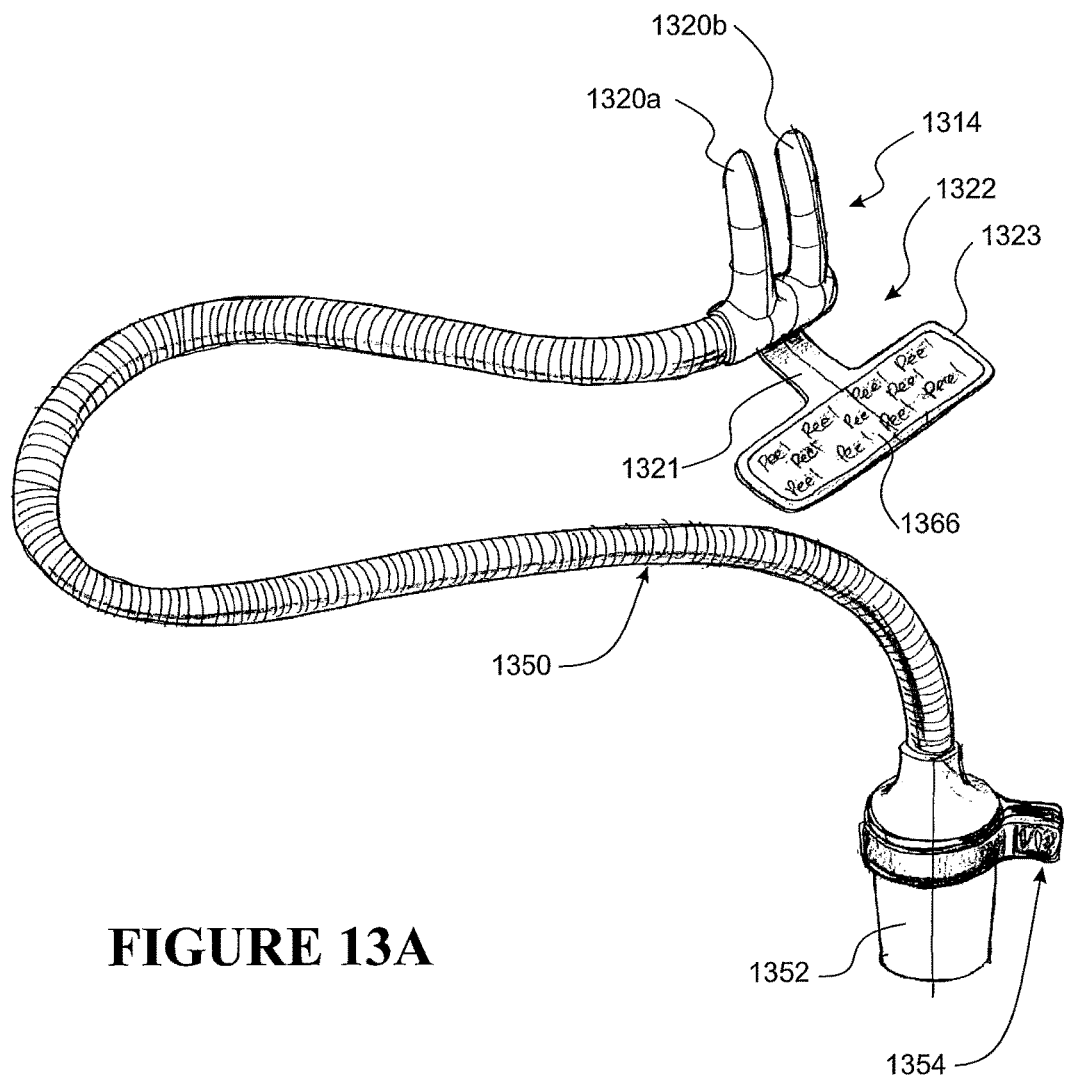
FIG. 13A illustrates a front perspective view of an example embodiment of a nasal cannula assembly including a cannula and retainer.
Figure 13B:
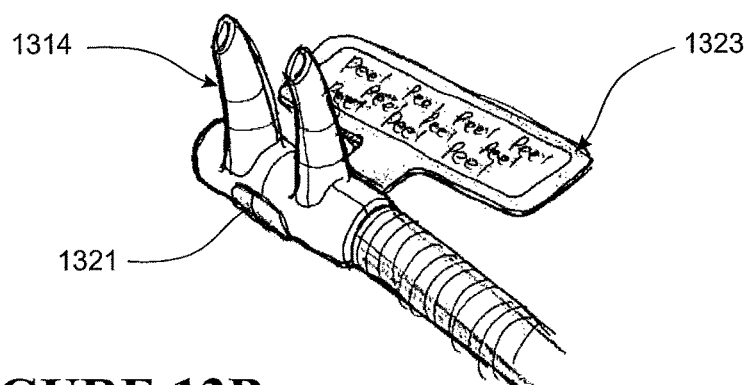
FIG. 13B illustrates a partial side perspective view of the nasal cannula assembly of FIG. 13A.
Figure 13C:
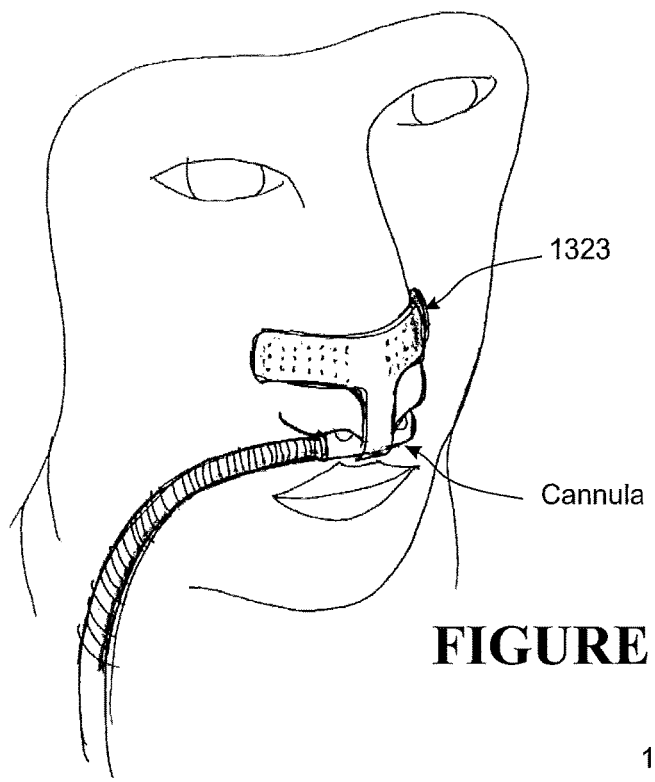
FIG. 13C illustrates a partial front perspective view of the nasal cannula assembly of FIGS. 13A and 13B coupled to a patient.

An example embodiment of a cannula system as shown in FIGS. 13A-13C can include a cannula 1314, retainer 1322, and supply tube 1350. The cannula 1314 can have a minimal size and profile. In the illustrated embodiment, the cannula 1314 includes a generally cylindrical body having an inlet 1324 and integrally formed nasal prongs 1320a, b. The retainer 1322 includes a cannula engaging portion 1321 and a nasal strip portion 1323. In some embodiments, the cannula engaging portion 1321 is attached to the cylindrical body of the cannula 1314 with an adhesive, e.g., glue. In some embodiments, the cannula engaging portion 1321 is moulded as part of the cannula 1314. In some embodiments, the cannula engaging portion 1321 has a formed shape configured to snap or clip onto the cannula 1314. The nasal strip portion 1323 is designed to be adhered across the patient's nose to help secure the cannula 1314 to the patient. A patient facing side of the nasal strip portion 1323 can include an adhesive strip covered by a protective backing 1366 for storage. The protective backing is peeled off to expose the adhesive strip when needed to secure the cannula 1314 to the patient. The retainer 1322 can be removed and replaced as needed during the duration of therapy. In embodiments in which the cannula engaging portion 1321 is moulded as part of the cannula 1314, the adhesive strip can be removed and/or replaced as needed.

In some embodiments, the supply tube 1350 is a small diameter spring tubing. The supply tube 1350 can be coupled to a main delivery conduit connector 1352 at one end and the cannula 1314 inlet 1324 at an opposite end. The supply tube 1350 diameter can be sized so that the supply tube 1350 can be inserted into the cannula inlet 1324 and the cannula 1314 stretched or otherwise formed or positioned around the tube 1350 to secure the tube 1350 to the cannula 1314. The cannula system can also include a lanyard clip 1354 positioned on the connector 1352 or on the supply tube 1350 proximal to the connector 1352. The lanyard clip 1354 can releasably receive a lanyard placed around the patient's neck. Alternatively, the lanyard clip 1354 can be attached to, for example, the patient's clothing or hospital gown, bed sheets, or another location nearby to help support the weight of the main delivery conduit.

Figure 14A:
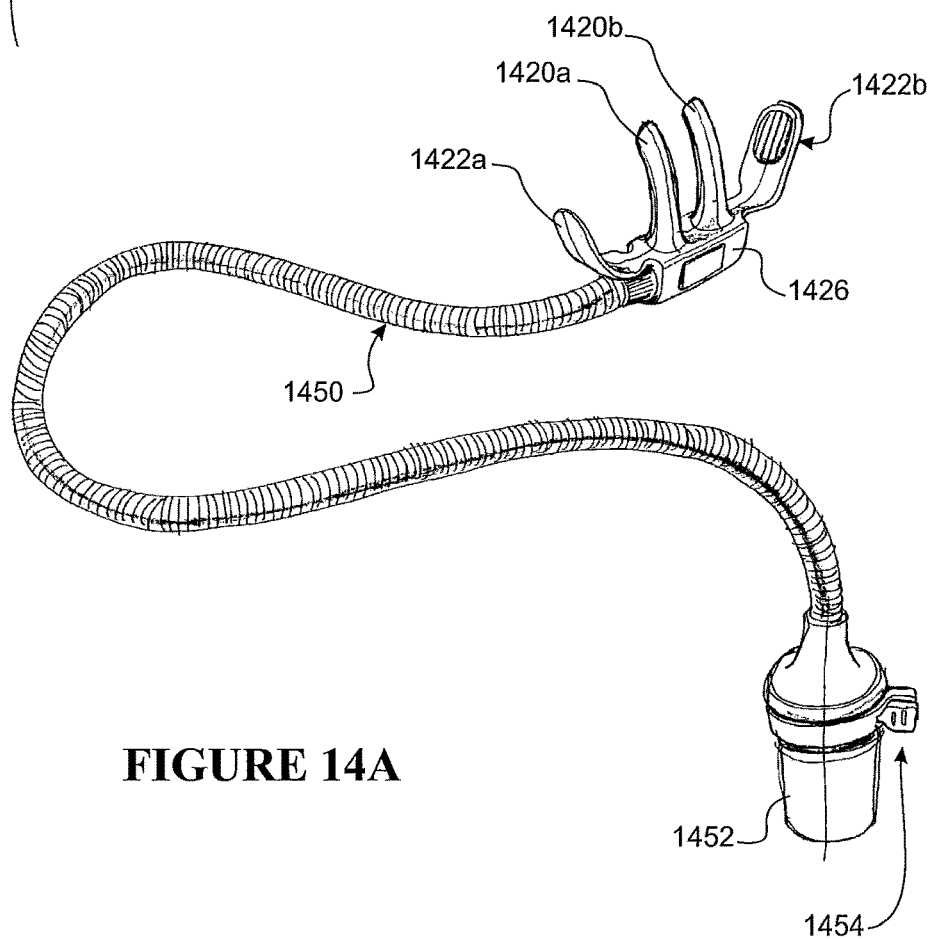
FIG. 14A illustrates a front perspective view of a nasal cannula assembly including a manifold and a cannula having nasal flaps.
Figure 14B:
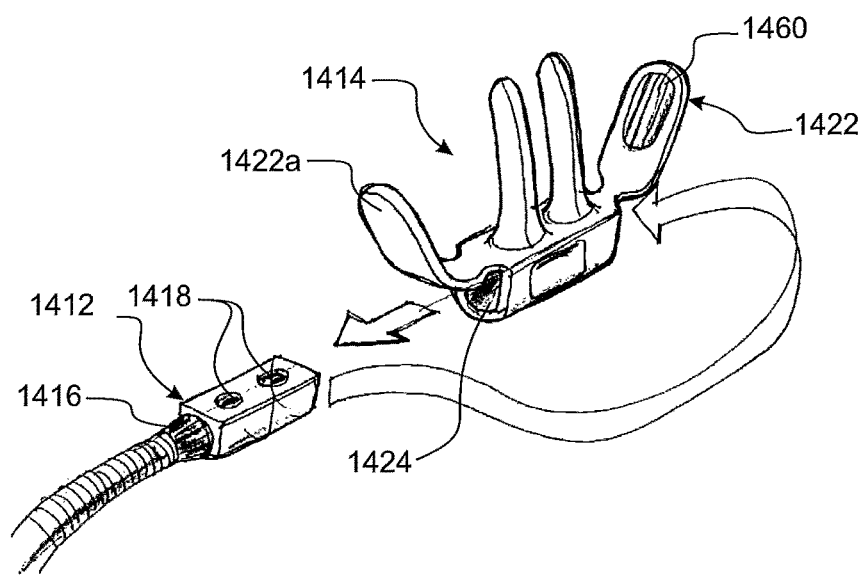
FIG. 14B illustrates an exploded view of the nasal cannula assembly of FIG. 14A.
Figure 14C:
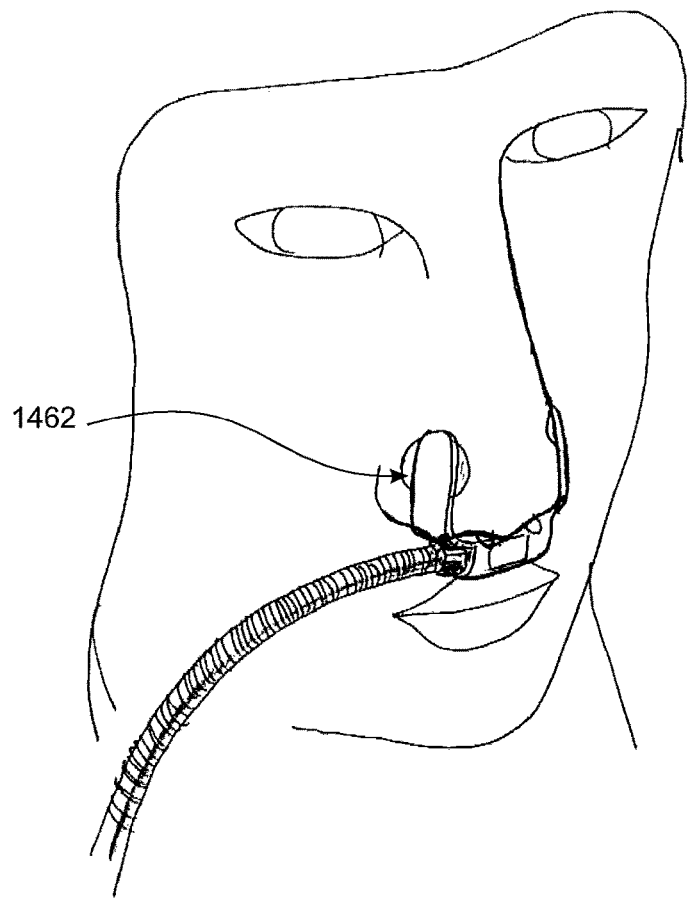
FIG. 14C illustrates the nasal cannula assembly of FIGS. 14A and 14B coupled to a patient.

An example embodiment of a cannula system as shown in FIGS. 14A-14C includes a cannula 1414, manifold 1412, and gas supply tube 1450. The cannula 1414 includes nasal prongs 1420a, b, nose flaps 1422a, b, and a manifold retention strap 1426 defining/encircling an aperture 1424 configured to receive the manifold 1412. In use, the manifold 1412 is coupled to the cannula 1414 by inserting the manifold 1412 into the aperture 1424 and stretching the manifold retention strap 1426 around the manifold 1412. In the illustrated embodiment, the manifold includes an inlet or collar 1416 and two outlets 1418. In use, the outlets 1418 are aligned and in fluid communication with the nasal prongs 1420a, b.

The nose flaps 1422a, b extend from the sides of the cannula 1414 and are configured to fold over the sides of the patient's nostrils. The nose flaps 1422a, b can include a thin section near the manifold retention strap 1426, allowing the nose flaps 1422a, b to bend easily and conform to the geometry of the nose. In some embodiments, each nose flap 1422a, b includes an attachment pad 1460, which can be one part of a hook-and-loop fastener. The attachment pads 1460 can be removably coupled to corresponding attachment pads 1462, which can be the other part of the hook-and-loop fastener, on the user's nose. The attachment pads 1462 can be attached to the outsides of the patient's nostrils with an adhesive. In some embodiments, the attachments pads 1460 of the nose flaps 1422a, b can be adhesive patches that are adhered directly to the user's nose. In some embodiments, the nose flaps 1422a, b can comprise a malleable material that can hold its shape once deformed such that the nose flaps 1422a, b and remain substantially in place once folded. In such an arrangement, the attachment pads 1460 can be grip pads comprising a grip material to grip the skin of the patient and inhibit undesired movement of the cannula 1414.

In some embodiments, the supply tube 1450 is a small-diameter spring tube. The supply tube 1450 can be coupled to a main delivery conduit connector 1452 at one end and the manifold inlet or collar 1416 at an opposite end. In some embodiments, the supply tube 1450 is permanently attached to the collar 1416 and/or the collar 1416 is permanently attached to the manifold 1412. Alternatively, the supply tube 1450 can be removably coupled to the collar 1416 and/or the collar 1416 can be removably coupled to the manifold 1412. As shown in FIG. 14B, the manifold 1412 can be inserted into the aperture 1424 of the cannula 1414 from either side so that the supply tube 1450 can extend from either side of the cannula 1414. The cannula system can further include a lanyard clip 1454 positioned on the connector 1452 or on the supply tube 1450 proximal to the connector 1452. The lanyard clip 1454 can be releasably coupled to a lanyard placed around the patient's neck or can be attached to, for example, the patient's clothing or hospital gown, bed sheets, or another location nearby to help support the weight of the main delivery conduit.

FIGS. 15-18 illustrate embodiments of a nasal cannula assembly including a cannula, which preferably includes a pair of nasal prongs. The cannula can be integrated with a supply conduit or tubing or can connect to a separate supply conduit or tubing, such as through any of the manifold arrangements disclosed herein. In some configurations, the cannula has a tubular shape with a first end, a second end, and a body extending between the first and second ends and is coupled to a supply tube at one of the ends. Accordingly, the cannula body can define a hollow "manifold" volume that is at least partially defined by the manifold in other embodiments disclosed herein. Additionally, in some embodiments, the cannula can contain one or more prong exit holes in the middle of the cannula body which can be arranged to allow exit of gas to a pair of nasal prongs. In some embodiments, the cannula can be a hollow volume cannula containing at least one inlet that can be positioned and shaped to be attached to a supply tubing or conduit. In certain embodiments, the cannula can contain an inlet at each end of the cannula. The cannula can be configured to be connected to or integrated within an assembly securing device, for example a headgear strap. The cannula can be configured to be integrally connected or permanently connected to a supply tube or conduit, such as through any of the manifold arrangements described herein or through a connector. In some embodiments, the cannula can be integrated or unitary with a tube creating a cannula/tube assembly or structure. In certain embodiments, the cannula can be flexible to allow bending or manipulation of the cannula. In other embodiments, the manifold can be relatively stiff or rigid. Any of the cannula embodiments discussed herein can comprise attached or clip-on or slide-on prongs and/or fixed or tilted/adjustable prongs as described herein.

In some embodiments, the cannula can have tubing exit holes at each end of a first end and a second end of the cannula. In some embodiments, the first end or the second end can be configured to be connected to the supply conduit or tubing that connects to the humidifier, circuit, or other gas or flow supply apparatus. The end not connected to the tubing can be selectively blocked. For example, the selective side switching of the device can occur through a system where when the first end is connected to the tubing allowing air to enter the manifold space of the cannula, the second end is blocked, and when the second end is connected to the tubing allowing air to enter the manifold space of the cannula, the first end is blocked. FIGS. 15-18 illustrate embodiments of the selective side switching in the manifold.

FIGS. 15A-D illustrate embodiments of a nasal cannula assembly incorporating a shuttle valve that selectively occludes one end of the cannula or manifold (hereinafter referred to as the "manifold"). In some embodiments, the manifold 1501 can have an opening, port or inlet 1507 or, preferably, openings 1507 on each side of the manifold 1501. In particular, a first opening 1507 can be positioned at a first end and a second opening 1507 can be positioned at a second end of the manifold 1501. In certain embodiments, a lightweight shuttle object or valve body 1508, for example a ball or disk, can move (e.g., slide or roll) freely inside the manifold volume or hollow cavity 1509. Preferably, the shuttle object 1508 has a larger diameter than the prongs 1505 and the openings 1507 to prevent the shuttle object 1508 from exiting the hollow cavity 1509.

In some embodiments, a supply tube 1502 can be connected to one of the openings or inlets 1507. The supply tube 1502 can supply resulting positive pressure from the flow of air or gas from the humidifier or other apparatus into the hollow cavity 1509. The resulting positive pressure from the flow of air or gas pushes the shuttle object 1508 along the hollow cavity 1509 until it blocks off the opposite opening 1507. The blocking of the opposite opening 1507 can prevent the air from travelling through that opening 1507 while still allowing the air to flow through the prongs 1505. In some embodiments, the supply tube 1502 can be attached to one opening 1507 of the manifold 1501 and the opposite opening 1507 is blocked by the shuttle object 1508. For example, to switch sides of the supply tube 1502 relative to the manifold 1501, the supply tube 1502 can be removed from one opening 1507 and put into the opposite opening 1507 and the shuttle object 1508 will swap sides automatically. In some embodiments, the opening 1507 can have a localized thin wall section 1510, preferably defining an annular shape surrounding the opening 1507. The localized thin wall section 1510 can deform relative to at least a surrounding portion of the manifold 1501 to aid in sealing the hollow cavity 1509 at that end when the shuttle object 1508 is pushed to that side. In certain embodiments, the shuttle object 1508 can be made of a relatively soft material, for example material used to make compressible earplugs (e.g., compressible PVC foam), to further assist in sealing of the hollow cavity 1509.

In some embodiments of the nasal cannula assembly 1500, the manifold 1501 has at least one prong 1505 and, preferably, a pair of prongs 1505. Preferably, the nasal cannula assembly 1500 contains prongs 1505 positioned on or configured to be positioned on the manifold 1501. In certain embodiments, the prongs 1505 on the manifold 1501 can be flexible or rotatable to allow use of the nasal cannula assembly 1500 in either direction. The prongs 1505 illustrated in FIG. 15 comprise a distal end 1521 and a proximal end 1522. The distal end 1521 of each prong 1505 is configured to be placed within the nose of the user when in use. The proximal end 1522 of each prong 1505 is configured to be attached to or to be flush with the manifold 1501 and prong exit holes 1520 in the manifold 1501 that communicate with the interior spaces of the prongs 1505. In some embodiments, the prongs 1505 are twin nasal prongs and are located in the middle of body of the manifold 1501.

The supply tube 1502 can be coupled to the manifold 1501 by any suitable arrangement. For example, the supply tube 1502 can include a connector 1530 coupled to the end of the supply tube 1502 and configured to be coupled to the manifold 1501. The connector 1530 can have a snap-fit arrangement with the openings 1507 of the manifold 1501. In some configurations, the connector 1530 can comprise a groove that is engaged by either one of the openings 1507 of the manifold 1501 and the thin wall section 1510 can facilitate the seal between the manifold 1501 and the connector 1530.

Figure 15E:
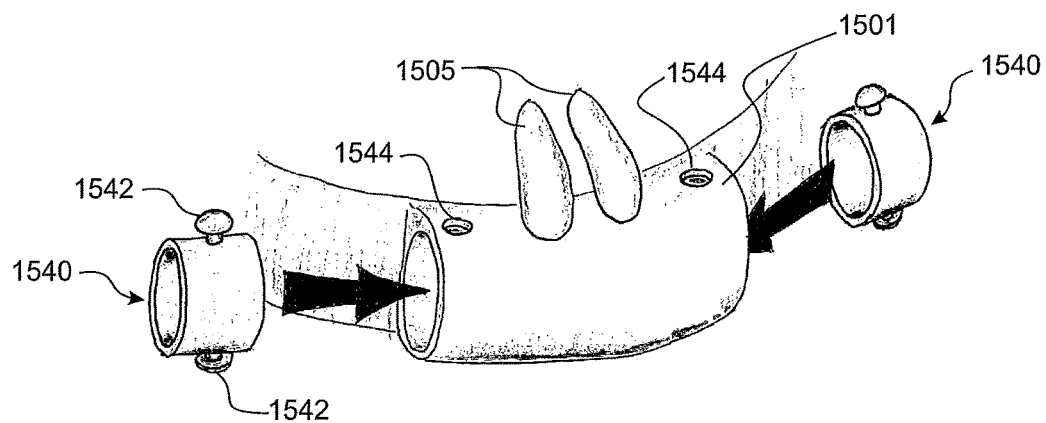
Figure 15F:
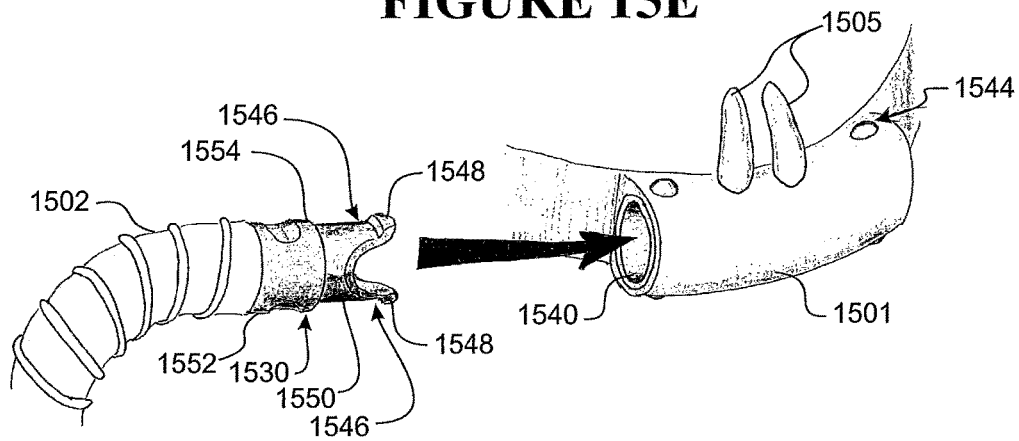
Figure 15G:
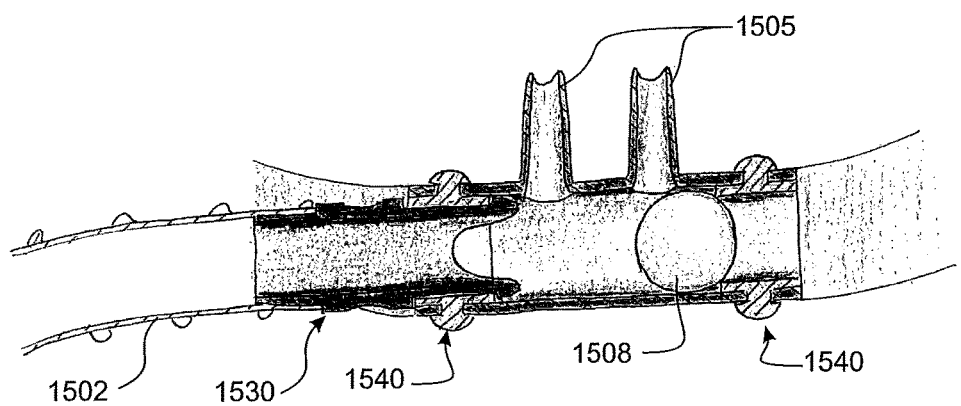

FIGS. 15E-G illustrate an alternative coupling arrangement between the supply tube 1502 and the manifold 1501, which incorporates an insert 1540 that facilitates the connection between the supply tube 1502 and the manifold 1501. In some configurations, the manifold 1501 is constructed from a soft and/or stretchable material, which can increase comfort for the user. The insert 1540 can be constructed from a relatively stiff material, which preferably has greater stiffness than the material of the manifold 1501 such that the insert 1540 can be positioned within one or both openings 1507 of the manifold 1501 with a relatively tight fit therebetween. In some configurations, the manifold 1501 and the insert 1540 can create at least a substantial seal therebetween at least at the expected working pressures of the nasal cannula system 1500. The insert 1540 can include one or more interference features that secure the insert 1540 relative to the manifold 1501 via complementary interference features of the manifold 1501. For example, the insert 1540 can include at least one protrusion, and preferably a pair of opposed protrusions 1542, that engage recesses or openings 1544 of the manifold 1501. In the illustrated arrangement, the protrusions 1542 are button-head or mushroom-head protrusions having an enlarged head portion distal of a shaft portion relative to the body of the insert 1540. The openings 1544 can engage the shaft portion of the protrusions 1542 when the inserts 1540 are assembled to the manifold 1501. The soft and/or stretchable material of the manifold 1501 can assist in assembling of the inserts 1540 into the manifold 1501 and passing of the protrusions 1542 through the openings 1544.

The connector 1530 can be shaped or otherwise configured to engage the insert 1540 to securely connect the supply tube 1502 to the manifold 1501. In the illustrated arrangement, the connector 1530 comprises at least one interlocking member, such as a resilient arm portion 1546. Preferably, the connector 1530 comprises a pair of resilient arm portions 1546. Each arm portion 1546 includes an engagement protrusion 1548 that engages a portion (e.g., an end surface) of the insert 1540. The illustrated connector 1530 includes a cylindrical base portion 1550 between a flange 1552 and the arm portions 1546. The flange 1552 has an enlarged diameter or circumferential dimension relative to the base portion 1550 to define a shoulder 1554 that can abut the end surface of the insert 1540 opposite the end surface engaged by the protrusions 1548. Thus, a linear distance between the shoulder 1554 and the protrusion 1548 can be approximately equal to a length of the insert 1540. In some configurations, the arm portions 1546 can flex toward a central axis of the connector 1530 to facilitate passage of the arm portions 1546 through the interior space of the insert 1540. Preferably, a length of the manifold 1501 and a length of the inserts 1540 are configured such that neither the inserts 1540 nor the shuttle object 1508 block the prongs 1505.

FIGS. 16A-F illustrate embodiments of a nasal cannula assembly with a manifold having a one way valve at each end. Similar to the embodiment discussed in FIG. 15, FIGS. 16A-F illustrate a nasal cannula assembly 1600 having a manifold 1601 with nasal prongs 1605 in a central portion, a hollow cavity 1609, and inlets or openings 1607 on each side of the manifold 1601. A supply tube 1602 can be attached to either opening 1607 of the manifold 1601. However, instead of or in addition to a shuttle object (e.g., valve body 1508) to seal the hollow cavity 1609 at one opening 1607, a one way valve 1608 is used. In some embodiments, the one way valve 1608 is positioned at one opening 1607 of the hollow cavity 1609 of the manifold 1601 and the supply tube 1602 is positioned within the opening 1607 by being pushed through the one-way valve 1608 or positioned up against the one-way valve 1608. In certain embodiments, the opposite one way valve 1608 will remain sealed and therefore the flow of air or gas from the supply tube 1602 will be directed toward the nasal prongs 1605. In some embodiments, the one way valve 1608 can be molded into the manifold 1601. In other embodiments, the one way valve 1608 can be assembled as inserts configured to be inserted into the manifold 1601. In certain embodiments, the one way valve 1608 can also function as a pressure pop-off safety valve to release any excess pressure.

Figure 16A:
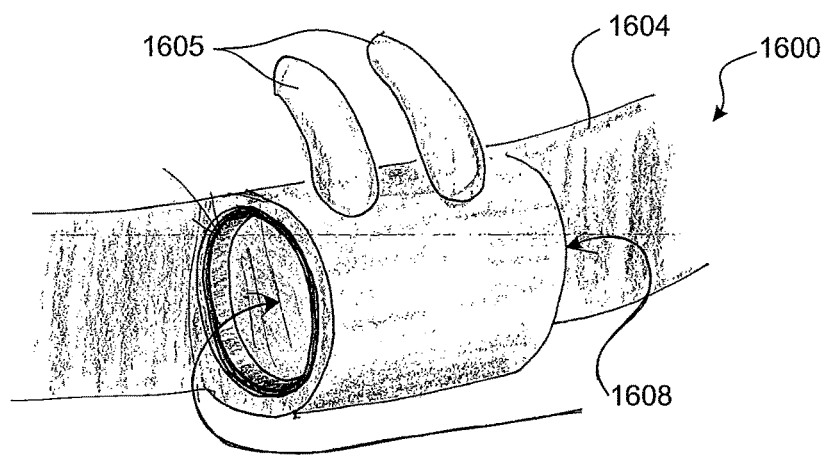
FIGS. 16A-F illustrate example embodiments of a nasal cannula assembly with a manifold having a one way valve formed from an exhalation style valve with a loosely hinged flap.
Figure 16B:
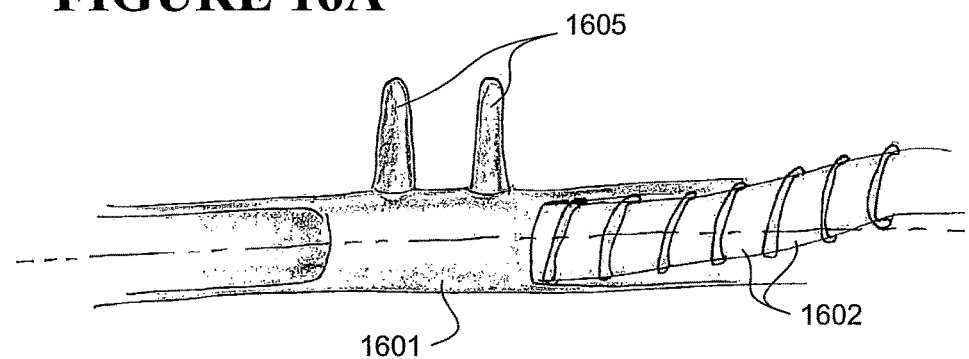
Figure 16C:
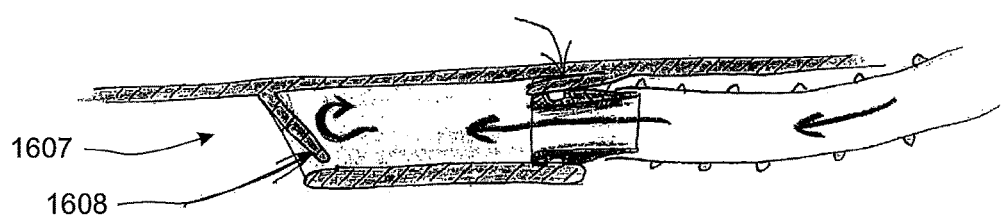
Figure 16D:
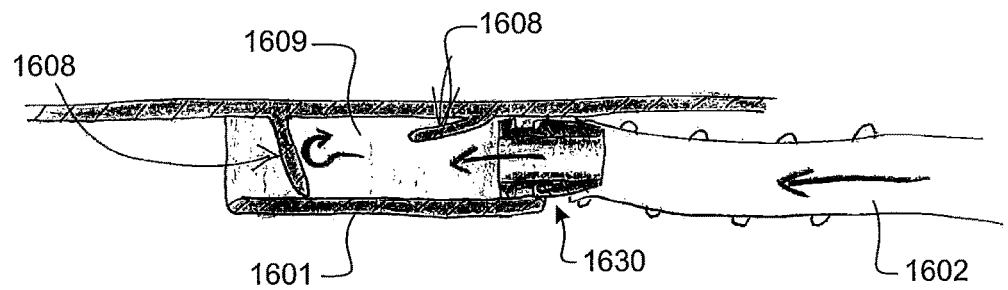
Figure 16E:
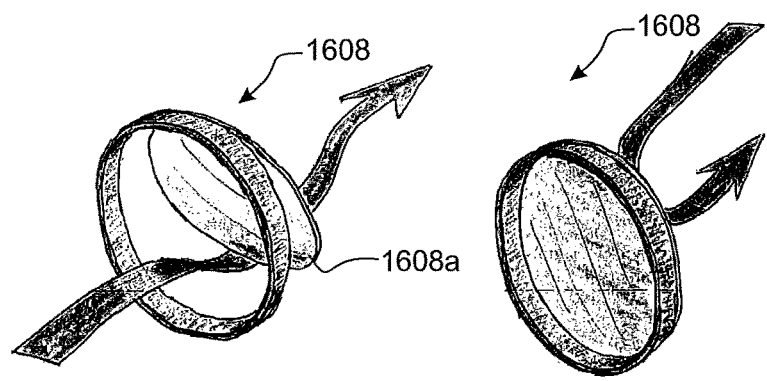
Figure 16F:
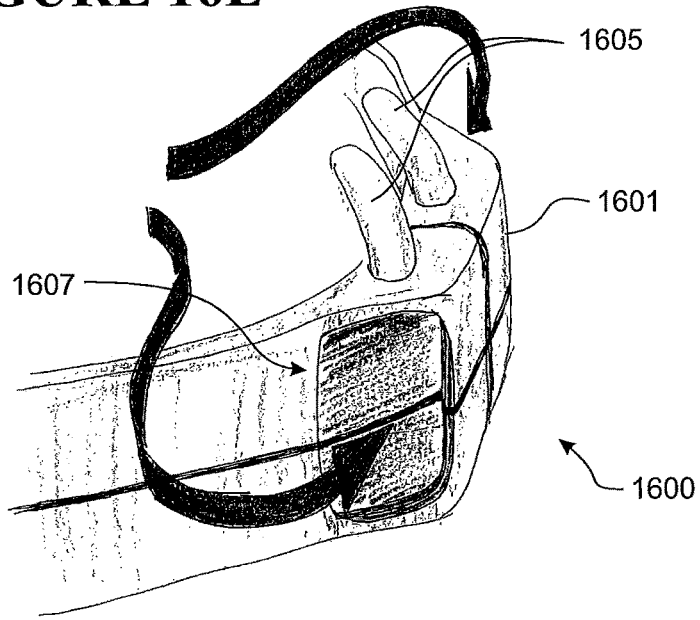

FIGS. 16A-F illustrate embodiments of a nasal cannula assembly 1600 with the manifold 1601 having a one way valve 1608 formed from an exhalation style valve with a loosely hinged flap 1608*a* (FIG. 16E). In some embodiments, the supply tube 1602 can be inserted through the one-way valve 1608 as illustrated in FIG. 16C, thereby holding the flap opens with the supply tube 1602. In some embodiments, the supply tube 1602 is placed up against the one way valve 1608 and the valve 1608 is held open by the air flow from the supply tube 1602 as illustrated in FIG. 16D. The supply tube 1602 can be connected to the manifold 1601 directly or through any suitable connector, such as any of the connectors disclosed herein. The valve 1608 can have any suitable shape, such as circular (FIGS. 16A-E) or rectangular (FIG. 16F).

FIGS. 16G-L illustrate embodiments of a nasal cannula assembly 1600 with a manifold 1601 having a one way valve 1608 formed from a slit valve of various shapes. Preferably, the one way valve 1608 comprises a stretchable material. In some embodiments, the one way valve 1608 can be a slit valve (FIGS. 16G and 16H), which in particular can be a duck-billed valve (FIGS. 16I and 16J), a joker or tricuspid valve (FIG. 16K), a slit-dome valve (FIG. 16L), and/or any other slit valve known in the art. The supply tube 1602 can be connected to the manifold 1601 by any suitable arrangement, either directly or via a connector 1630.

Figure 17A:
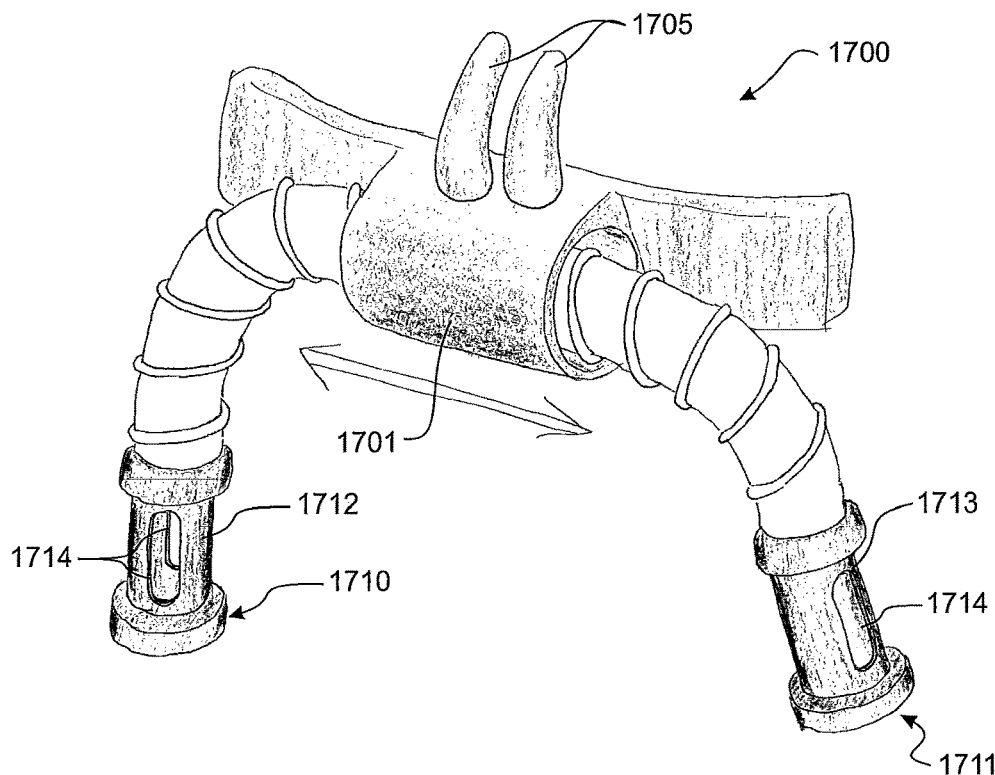
FIGS. 17A and 17B illustrate an example embodiment of a nasal cannula assembly with a tube threaded through the manifold to allow for selective side switching of the tube exit side.

FIG. 17 illustrates an embodiment of a nasal cannula assembly 1700 with a supply tube 1702 threaded through the manifold 1701 to allow for selective side switching of the exit side of the supply tube 1702 relative to the manifold 1701. In some embodiments, the supply tube 1702 can have a first end 1710 and a second end 1711. The first end 1710 and the second end 1711 can have a respective manifold insert 1712, 1713 attached thereto. The manifold inserts 1712, 1713 can each have one or more manifold insert openings 1714 (e.g., a pair of openings 1714 on opposing sides of the inserts 1712, 1713) extending along a length of the manifold insert 1712, 1713. In addition, each insert 1712, 1713 can include a pair of spaced-apart flanges 1716 positioned on opposite sides of the openings 1714 and configured to create at least a substantial seal with the manifold 1701. A recess 1718 is defined between the flanges 1716 such that air or gas communication between the openings 1714 and the nasal prongs 1705 is assured despite the location of the openings 1714.

Figure 17B:
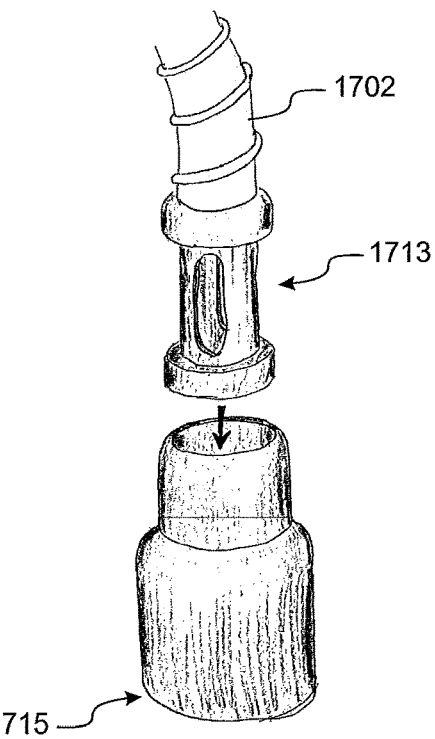

In certain embodiments, the tube exit side can be selectively chosen by pushing or pulling the supply tube 1702 one way or the other to whichever side is desired. In some embodiments, when the supply tube 1702 is pulled or pushed to one side, the manifold insert 1712, 1713 on the opposite side seals against the manifold 1701 and the manifold insert 1712, 1713 on the side pulled through can be connected to the gas or air supply circuit. For example, if the supply tube 1702 is pulled through the manifold 1701 and the manifold insert 1712 is sealed against the manifold 1701, the opposite end manifold insert 1713 would be connected to the gas or air supply circuit (FIG. 17B). Alternatively, if the tube 1702 is pulled through the manifold 1701 and the manifold insert 1713 is sealed against the manifold 1701, the opposite end manifold insert 1712 would be connected to the gas or air supply circuit. In some embodiments, to connect the supply tube 1702 to the circuit may require a connector or adapter 1715 so that the appropriate fitting can be achieved for connection to the humidifier or other gas or air supply. Additionally, in other embodiments, a proprietary connection is used to connect the supply tube to the gas or air supply circuit, thereby eliminating the need for an adapter or connector 1715. In some embodiments, the manifold insert opening 1714 can be lined up with the nasal prongs 1705 on the manifold when the manifold insert 1712, 1713 is positioned inside the manifold 1701. Additionally, in some embodiments, the manifold insert 1712, 1713 can be held in position with a locking mechanism once the supply tube 1702 is pulled through to the desired side of the manifold 1701. In some embodiments, the locking mechanism can include a twist lock, press fit, screw, or any other locking mechanism known in the art.

Figure 18A:
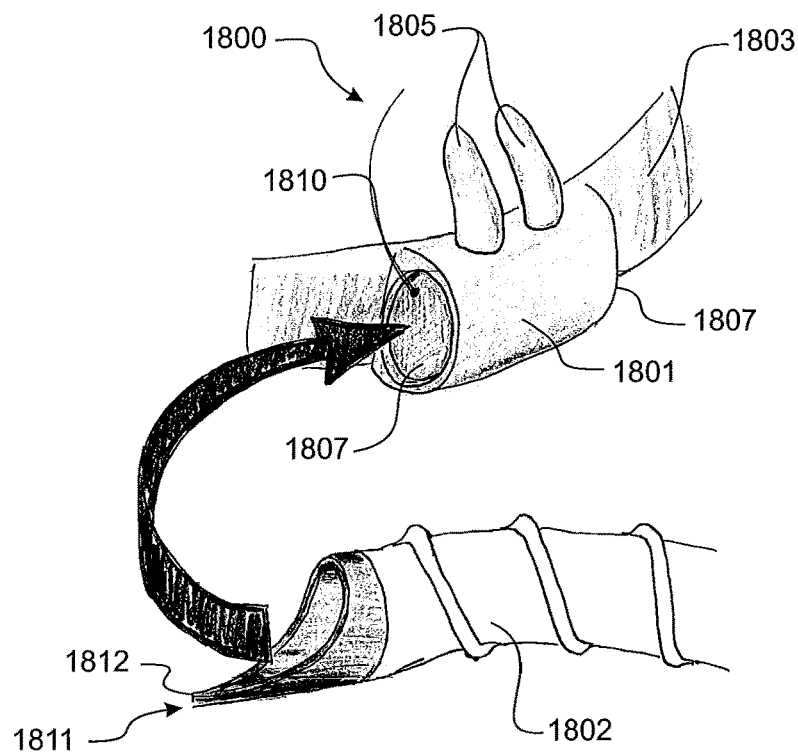
FIGS. 18A and 18B illustrate an example embodiment of a nasal cannula assembly with each tubing exit hole sealed by a thin membrane that is pierced by a sharpened end of the supply tube.
Figure 18B:
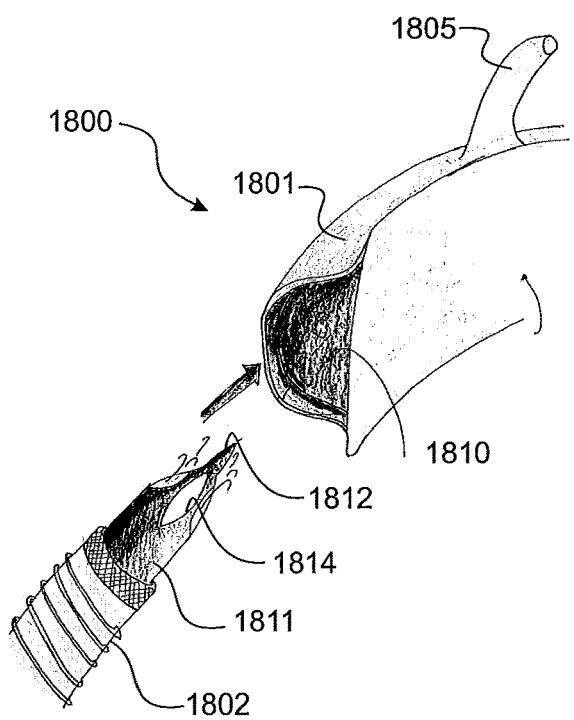

FIGS. 18A and 18B illustrate embodiments of a nasal cannula assembly with each tubing exit hole sealed by a thin membrane or other member that can be pierced. Similar to the embodiment described with reference to FIGS. 15A-G, FIGS. 18A and 18 illustrate nasal cannula assemblies 1800 having a manifold 1801 with nasal prongs 1805 in a central portion, a hollow cavity (not shown) and openings 1807 on each side of the manifold 1801. A supply tube 1802 can be attached to either opening 1807 of the manifold 1801. In some embodiments, the openings 1807 of the manifold 1801 are sealed by a thin membrane 1810. The thin membrane 1810 can be a film, pierceable membrane, or other pierceable material known in the art. In some embodiments, the connector or end portion 1811 of the supply tube 1802 comprises a piercing portion, such as a sharpened point 1812 that is capable of piercing the membrane 1810 at whichever opening 1807 of the manifold 1801 the supply tube 1802 is inserted. The sharpened point 1812 can be located in any suitable location, such as at or near a circumferential edge (FIG. 18A) or at or near a center (FIG. 18B). When the sharpened point 1812 is at or near the center, the end portion 1811 can define one or more openings 1814 to permit air or gas to pass through the end portion 1811. In certain embodiments, the user can choose the side in which the supply tube 1802 is positioned and can puncture the membrane 1810 on that opening 1807 with the end portion 1811 of the supply tube 1802. In some embodiments, the membrane 1810 is a single-use arrangement such that, once the membrane 1810 is pierced on one side, the membrane 1810 cannot be re-sealed. However, in some embodiments, the membrane 1810 can be replaceable or resealable. In some embodiments, the end portion 1811 can contain one or more barbs to assist in piercing the membrane 1810 and/or securing the end portion 1811 within the manifold 1801. In some embodiments, the barbs or sharp section can be removed before the supply tube 1802 is inserted and the supply tube 1802 can be press fit into the opening 1807 of the manifold 1801. In some embodiments, the barbs or end portion 1811 can remain on the supply tube 1802 and can assist in securing the supply tube 1802 within the manifold 1801. In some embodiments, the end portion 1811 can have a cover to prevent injury to a user or damage to the end portion 1811 when not in use and ensure the end portion remains clean and sterile before use.

Figure 19:
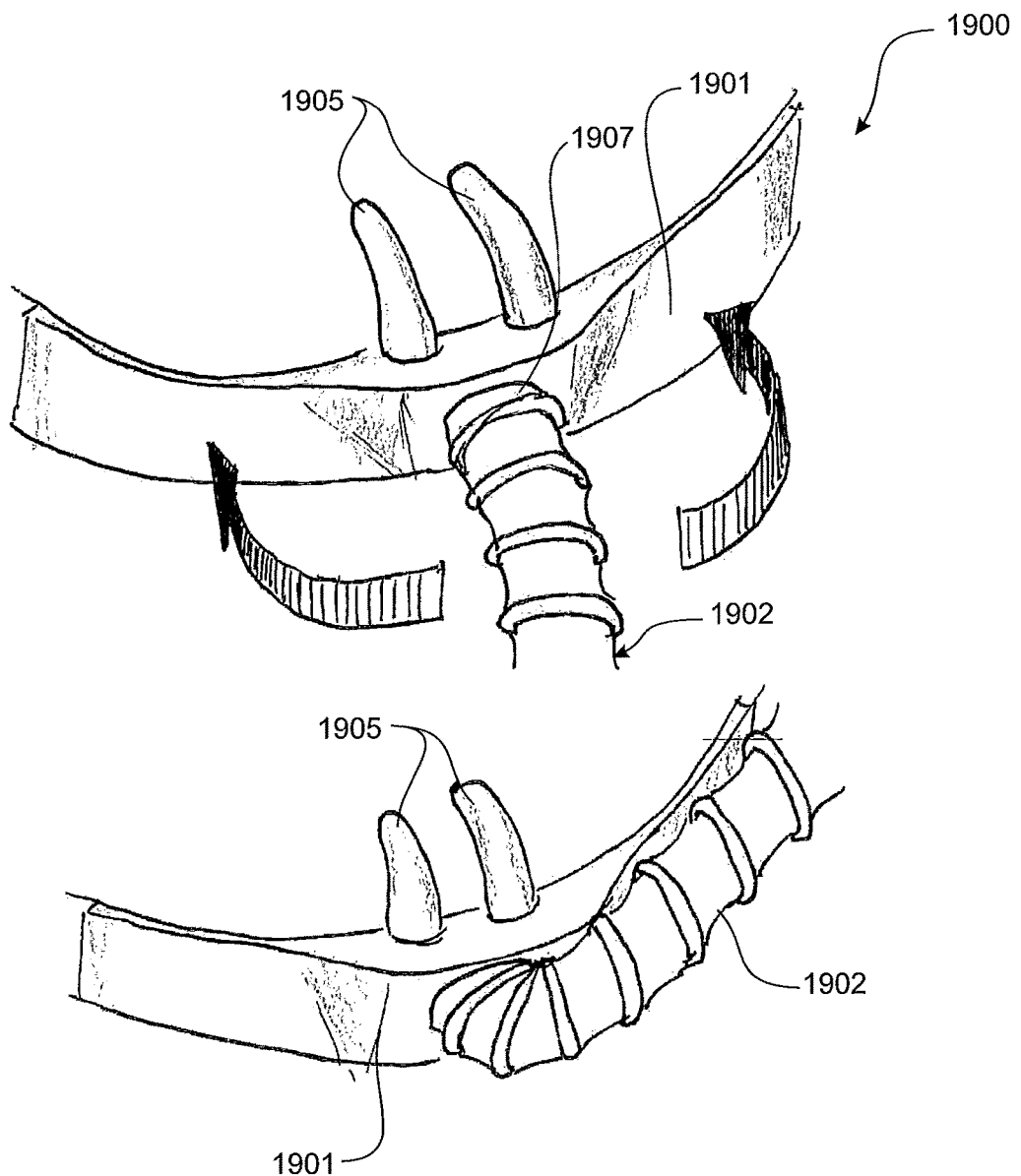
FIG. 19 illustrate an example embodiment of a manifold with a flexible tube exiting the front tubing exit hole of the manifold.

In some embodiments, the selective side switching of the manifold and prongs relative to the supply tube can be accomplished by manipulation of the supply tube. FIG. 19 illustrate embodiments of a manifold 1901 with a flexible supply tube 1902 exiting an opening 1907 of the manifold 1901. In the illustrated arrangement, because the flexible supply tube 1902 is used for selective side switching, only one opening 1907 is provided. However, in other arrangements, two or more openings 1907 can be provided. In some embodiments, the supply tube 1902 attached to and/or exiting the manifold 1901 can be a highly flexible tube. The highly flexible tube can allow for the supply tube 1902 to be routed to either side of the face and away from the mouth. In some embodiments, a highly flexible tubing is used that can be bent around a zero radius without substantial kinking or at least without fully occluding the internal passage of the tube. Preferably, bending of the highly flexible tube does not cause substantial occlusion of the internal passage of the tube. In some embodiments, the highly flexible supply tube 1902 can exit from the front of the manifold 1901 and routed to either side of the patient without disassembling the nasal cannula assembly 1900 and/or without moving any of the nasal cannula assembly parts. In certain embodiments, the flexible supply tube 1902 can exit from the front of the manifold 1901 from the opening 1907 and can be bent at least about 90 degrees to either the left or right side of the face.

Further, in some embodiments, the manifold can be configured to be inserted into an assembly securing device in either direction allowing for the nasal cannula assembly to be used interchangeably with the tube coming from either the right side of the patient or the left side of the patient. FIGS. 20A-C illustrate an embodiment of a nasal cannula assembly 2000 including a manifold 2001 that snaps into a manifold securing device or clip 2003. In some embodiments, the manifold 2001 can interchangeably switch sides on which the supply tube 2002 is positioned by allowing the manifold 2001 to be inserted into the clip 2003 in at least two different orientations. In some embodiments, the manifold 2001 and supply tube 2002 can be integrated into one manifold/tubing assembly 2004. For example, to change the direction from which the supply tube 2002 extends relative to the nose of the patient, the manifold/tubing assembly 2004 can be unclipped from the clip 2003, flipped around 180 degrees and then clipped back in. Two available orientations of the supply tube 2002 are illustrated in FIGS. 20A and 20B, respectively. The clip 2003 can be coupled to a retention arrangement, such as any suitable type of headgear strap 2040, including those disclosed herein or other suitable arrangements.

Additionally, in some embodiments, the manifold can be configured for use with a clip-on supply tube. For example, FIGS. 21A-D illustrate a nasal cannula assembly 2100 with a separable supply tube assembly 2102 and manifold 2101. In some embodiments, the nasal cannula assembly 2100 can comprise a manifold 2101 that includes prongs 2105 and two openings 2107 at each end of the manifold 2101. In some embodiments, the manifold 2101 can be connected to a supply tube assembly 2111. In some embodiments, the supply tube assembly 2111 can include a supply tube 2102 and a manifold receiving structure 2112. The manifold receiving structure 2112 can be assembled to the supply tube 2102 at the time of manufacture or can be connectable to the supply tube 2102 prior to use. In certain embodiments, the manifold receiving structure 2112 can be a 'C' shaped manifold receiving structure or clip 2112 as illustrated in FIG. 21A-D or the manifold receiving structure 2112 can have any shape that allows for complimentary coupling to the manifold 2101. In some embodiments, the manifold 2101 has a complimentary shape or matching shape to receive the manifold receiving structure 2112 which can either be slid onto, clipped onto, or otherwise attached through any means known in the field to the manifold 2101 with the supply tube 2102 positioned facing either way as desired. In certain embodiments, the manifold receiving structure 2112 can have location, and/or sealing details 2113 incorporated on the inside of, or elsewhere on, the manifold receiving structure 2112 to ensure a secure connection and/or a proper seal with the manifold 2101. In some configurations, the sealing detail 2113 is a protrusion, such as a spherical protrusion. The sealing detail 2113 preferably seals one of the openings 2107 and the end portion 2130 of the supply tube 2102, which can be defined by the manifold receiving structure 2112 or can be a separate component, engages the other opening 2107. The end portion 2130 can rest against and be flush with an outer surface of the manifold 2101 that surrounds the opening 2107 (FIG. 21C) or can extend into the opening 2107 (FIG. 21D).

Figure 21E:
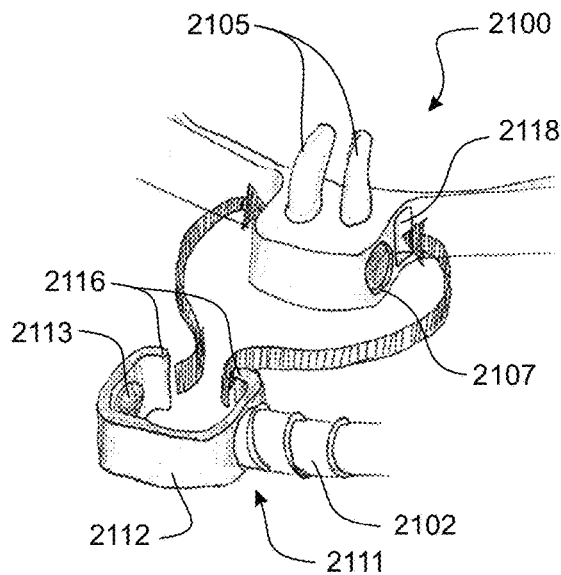
Figure 21F:
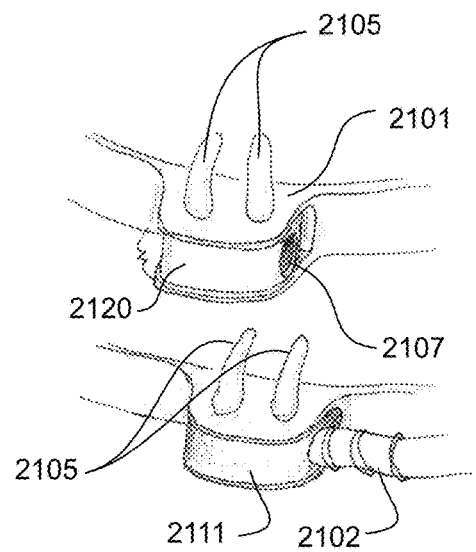

In some embodiments, one or more stops 2104 can be molded into, or otherwise secured to, the manifold 2101 to inhibit or prevent downward movement of the manifold receiving structure 2112 when pulled during use. For example, as shown in FIG. 21A, a pair of stops 2104, each defining a stop surface, can be formed on each side of the manifold 2101. In some embodiments, the manifold receiving structure 2112 can be slid upwardly relative to the manifold 2101 for removal and flipping of the tubing side. In some configurations, as shown in FIG. 21E, portions of the manifold receiving structure 2112, such as end portions 2116, can engage complementary portions, such as recesses 2118, of the manifold 2101 to assist in securing the manifold receiving structure 2112 to the manifold 2101. As shown in FIG. 21F, the manifold 2101 can include a recessed portion 2120 that is sized and shaped to receive the manifold receiving structure 2112. The recessed portion 2120 can be located on the forward and lateral portions of the manifold 2101 and can have a depth suitable to accommodate an entirety of the thickness of the manifold receiving structure 2112, such that an outward-facing surface of the manifold receiving structure 2112 is flush with or recessed within the outer surface of the manifold 2101. Such an arrangement assists in securing the manifold receiving structure 2112 to the manifold 2101 and/or can inform the user how to correctly locate and secure the manifold receiving structure 2112 to the manifold 2101. The recessed portion 2120 can be utilized separately or in combination with the recesses 2118.

Figure 21G:
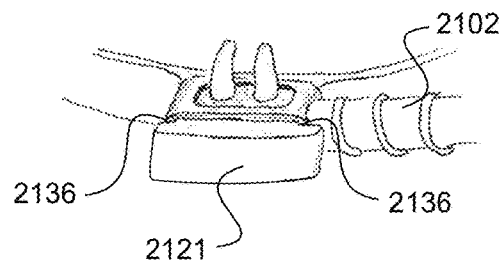
FIGS. 21G and 21H illustrate an example embodiment of a nasal cannula assembly with a manifold receiving structure, separate nasal prong insert and a manifold.
Figure 21H:
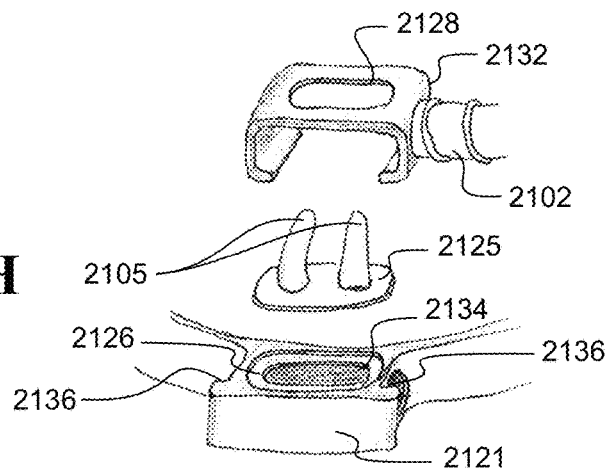
Figure 22A:
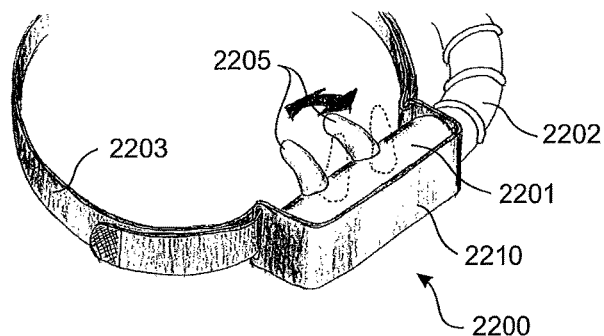
FIGS. 22A-D illustrate an example embodiment of a nasal cannula assembly with a manifold insert and a manifold receiving structure.
Figure 22B:
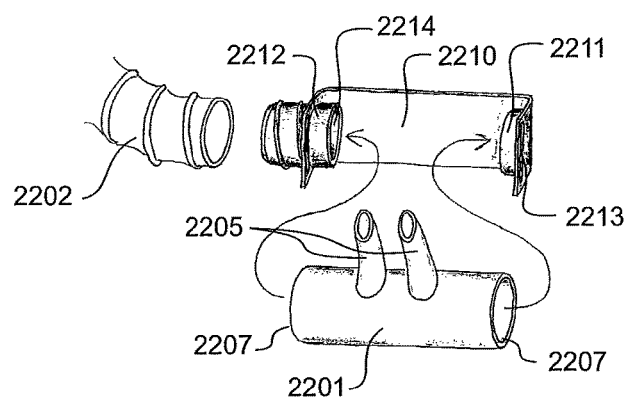
Figure 22C:
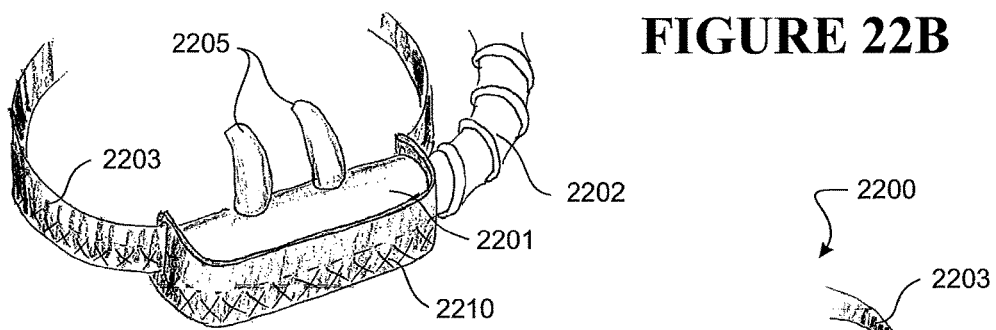
Figure 22D:
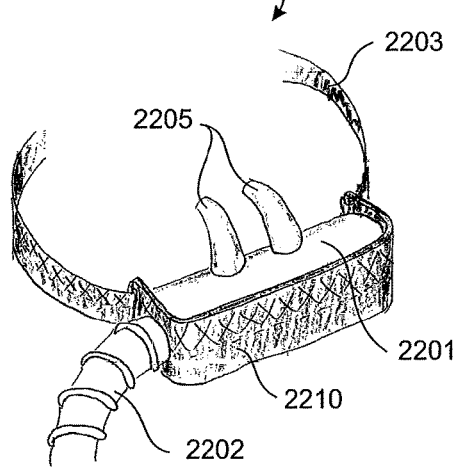

FIGS. 21G and 21H illustrate an embodiment of a nasal cannula assembly 2100 having a manifold receiving structure 2132, a separate nasal prong insert 2125 and a manifold 2121. In some embodiments, the manifold 2121 can have no prongs and an opening 2126 in the manifold 2121 to communicate with the prong insert 2125. The prong insert 2125 can be formed with prongs 2105 of different sizes so that the appropriate sized prongs 2105 can be selected for different nose sizes and ensure correct prong sizing for the patient. In some embodiments, the manifold 2121 and the prong insert 2125 can be connected with a manifold receiving structure 2132, such as a C-shaped clip, for example. In some embodiments, the manifold receiving structure 2132 can be used to hold the prong insert 2125 in place and will complimentarily fit the manifold 2121. Thus, the manifold receiving structure 2132 can include one or more openings 2128 that accommodates the prongs 2105. The manifold 2121 can include a recess 2134 surrounding the opening 2126 and that accommodates a base of the prong insert 2125. The manifold 2121 can also include recessed portions 2136 on lateral sides thereof configured to accommodate the manifold receiving structure 2132 and assist in securing the manifold receiving structure 2132 to the manifold 2121. Although in the illustrated arrangement the opening 2126 is positioned on an upper surface of the manifold 2121, the opening 2126 could be positioned on other portions (e.g., a forward surface) of the manifold 2121 in addition or in the alternative.

FIGS. 22A-D illustrate an embodiment of a nasal cannula assembly 2200 having a manifold insert 2201 and a manifold receiving structure 2210. In some embodiments, the manifold insert 2201 can include prongs 2205 and an opening 2207 on each end of the manifold insert 2201. The manifold insert 2201 can be made of a soft or flexible material. The prongs 2205 on the manifold insert 2201 can be flexible or stiff. In some embodiments, the manifold insert 2201 can be inserted into a manifold receiving structure 2210. In some embodiments, the manifold receiving structure 2210 can be attached to or integrated with an assembly securing device 2203, such as a headgear strap. The manifold receiving structure 2210 has one closed end 2213 and one open end 2214. In some embodiments, the manifold receiving structure 2210 can be attached to a supply tube 2202 on the open end 2214 side of the manifold receiving structure 2210 allowing for the passage of air or gas. In some embodiments, the manifold insert 2201 can be clipped or slid into the manifold receiving structure 2210. In some embodiments, the manifold receiving structure 2210 can have a round or spherical boss or protrusion 2211 at one end 2213 of the manifold receiving structure 2210 which can provide an effective radial seal with one opening 2207 of the manifold insert 2201 and assist in holding the manifold insert 2201 in place. The other end 2212 can include a connector 2214 that can be unitary with or separate from the supply tube 2202 and engage the other opening 2207 of the manifold insert 2201. In some embodiments, once the manifold insert 2201 is placed within the manifold receiving structure 2210, the manifold insert 2201 and/or the prongs 2205 can be turned or tilted to the correct comfort configuration for the user. For example, in some embodiments, to flip the tubing side, the manifold insert 2201 is removed and the remainder of the nasal cannula assembly, including the manifold receiving structure 2210, the assembly securing device 2203, and/or the supply tube 2202, is flipped around so that the supply tube 2202 faces the desired direction, and then the manifold insert 2201 with prongs 2205 are re-assembled to point back toward the nose of the patient.

FIGS. 23A-C illustrate an embodiment of a nasal cannula assembly with a manifold receiving structure or cannula that can be clipped over a supply tubing assembly, which includes a manifold. In some embodiments, the nasal cannula assembly 2300 includes a supply tube assembly 2311, which comprises a manifold 2301 and a supply tube 2302. The nasal cannula assembly 2300 also includes a manifold receiving structure or cannula 2310, which comprises a pair of prongs 2305. The supply tube 2302 connects the manifold 2301 to an air or gas supply circuit. In some embodiments, the manifold receiving structure 2310 can be a generally tubular member with an opening or slot 2313 extending partially or completely along its length to form a 'C' shaped section which can be clipped over the manifold 2301. In some embodiments, the manifold 2301 can have a ledge or rib 2312 that is complementary with the opening or slot 2313 of the 'C' shaped manifold receiving structure 2310 such that the rib 2312 can be received in the slot 2313. Advantageously, such an arrangement assists in securing or locking the manifold receiving structure 2310 in place on the manifold 2301. In some embodiments, the supply tube assembly 2311 can be attached to or integrated within an assembly securing device 2303, such as a headgear strap. For example, in some embodiments, to reverse the direction of the supply tube 2302, the manifold receiving structure 2310 is removed or unclipped from the manifold 2301, flipped around and reconnected so that the supply tube 2302 faces the desired direction.

FIGS. 24A-F illustrate embodiments of flexible, tilting or directionally-adjustable prongs and embodiments of a nasal cannula assembly 2400 having such flexible, tilting or adjustable prongs 2405. With such prongs 2405, the exit side of the supply tube 2402 can be changed by simply adjusting the direction of the prongs 2405 and rotating the manifold/tubing assembly 2404 by 180 degrees on the patients face.

Figure 24A:
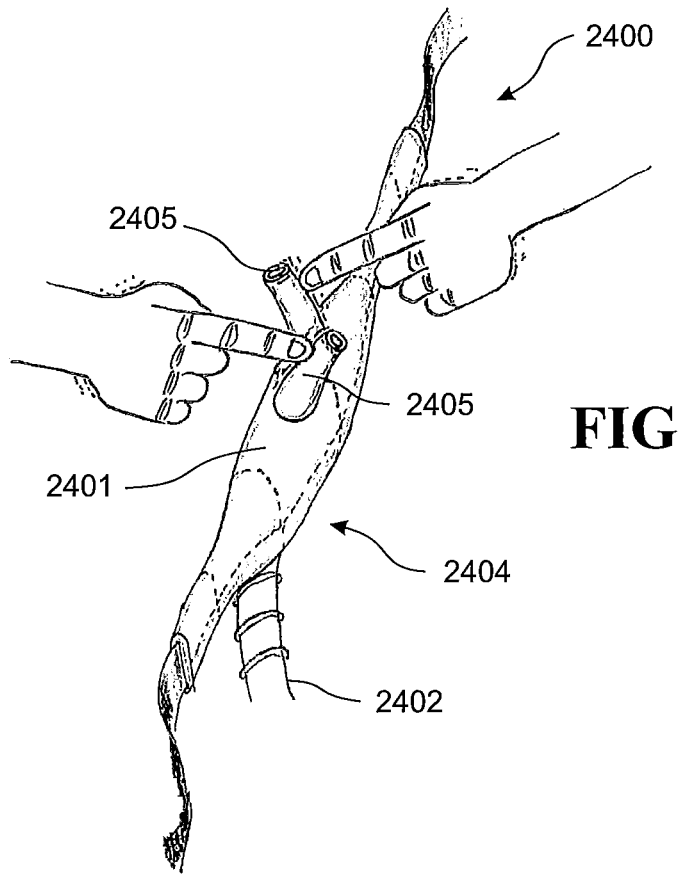
Figure 24B:
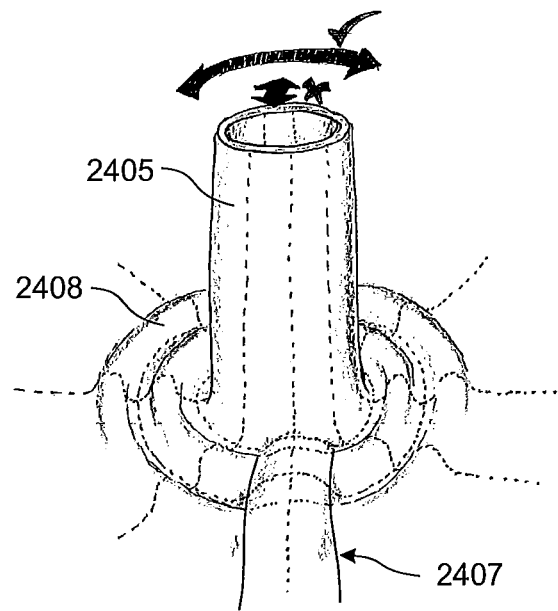
Figures 26A, 26B:
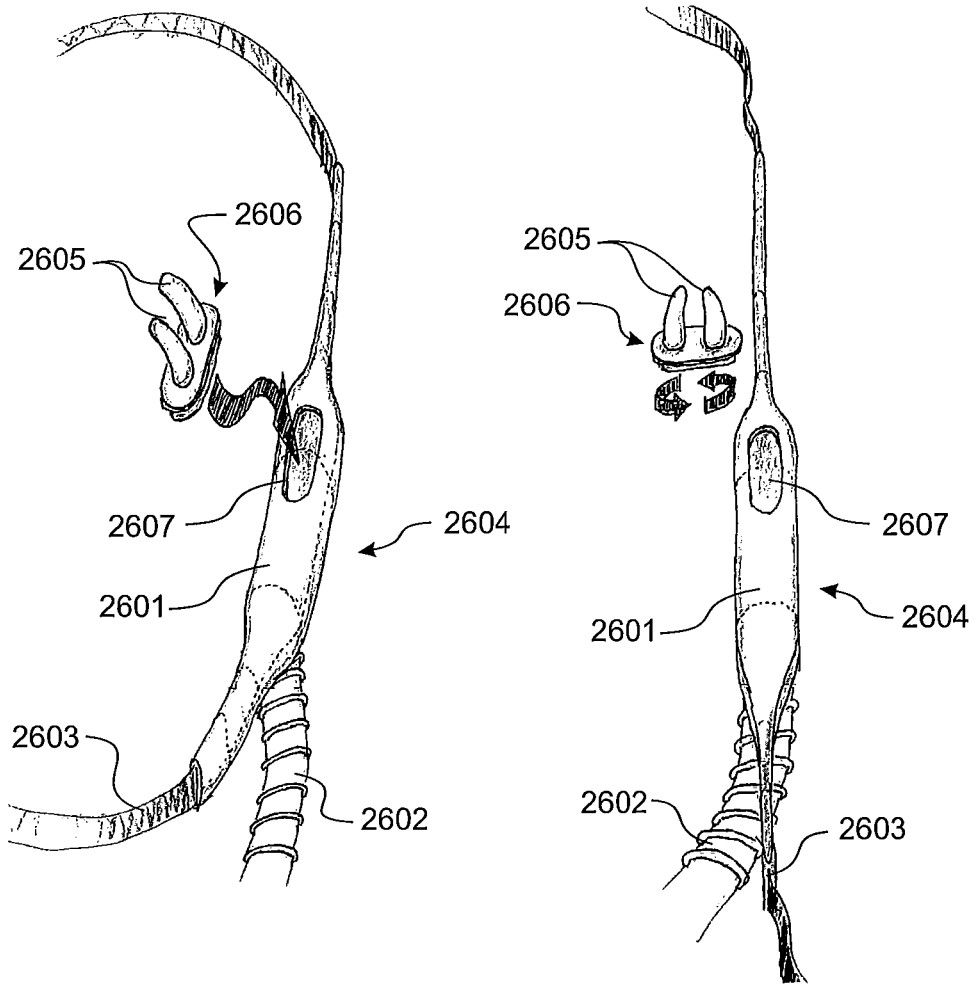

With reference to FIGS. 24A-C, in certain embodiments, the prongs 2405 can be flexed to the side of the manifold 2401 desired for use. In particular, the prongs 2405 can be formed with a ripple shape around the base of the prong 2405. FIGS. 24B and 24C illustrate an embodiment of a prong 2405 formed with a ripple shape 2408 around the base to allow for flexibility of the prong 2405. In some embodiments, the ripple shape 2408 comprises at least one and, preferably, multiple ripples. In the illustrated arrangement, two ripples are provided; however, in other embodiments, three or more ripples can be provided. The ripples are illustrated as being annular in shape and having a semi-circular cross-section. The ripples can have a reduced wall thickness relative to a portion of the manifold 2401 adjacent the ripples or can have the same or a similar wall thickness. The ripple shape 2408 allows the prong 2405 to be shaped in whichever direction is desired for use. In some embodiments, the prongs 2405 could have a ripple shape 2408 around the base which allows them to tilt in any direction. In certain embodiments, the prong 2405 can have a thickened section(s) or stiffening rib(s) 2407 to make the prong favor certain tilting directions, thereby allowing the prong 2405 to bend in a first direction but inhibiting or preventing the prong 2405 from bending in a second direction, which may be substantially perpendicular to the first direction. In the illustrated arrangement, two stiffening ribs 2407 are provided on each side of each prong 2405 and extend in a substantially radial direction relative to the prong 2405.

FIGS. 24D-F illustrate an embodiment of prongs 2405 comprising a collapsible corrugated concertina section, which can define a portion or a substantial entirety of a length of the prongs 2405. Preferably, the formation of the prongs 2405 with such geometry allows the prongs 2405 to be bent in any direction and hold that shape. In some embodiments, the prong 2405 can be compressed and extended to vary a length of the prong 2405, as illustrated in FIGS. 24D and 24E. In some embodiments, the prong 2405 can be expanded from the compressed shape and bent to the desired direction or shape, as illustrated in FIG. 24F. For example, in certain embodiments, the prongs 2405 are packaged in the compressed form and are then expanded and bent as configured by a caregiver or the user to the appropriate direction and shape.

In some embodiments, the nasal cannula assembly can contain rotating prongs. FIGS. 25A-C illustrate embodiments of a nasal cannula assembly 2500 with rotating prongs. In some embodiments, the nasal cannula assembly 2500 can be flipped to change the side of the supply tube 2502, and then the prongs 2505 can be rotated to face the appropriate orientation toward the nose of the patient. FIG. 25A illustrates an embodiment of a nasal cannula assembly 2500 that includes individually rotatable prongs 2505. In some embodiments, the prongs can rotate freely in a clockwise or counter clockwise direction relative to the manifold 2505. In some embodiments, the prongs 2505 can rotate to a limited degree when the manifold 2501 and prongs 2505 are constructed as a unit.

FIGS. 25B and 25C illustrate an embodiment of a nasal cannula assembly 2500 that comprises a prong insert 2506 having a pair of prongs 2505. Preferably, the prong insert 2506 is rotatable relative to the manifold 2501. The illustrated prong insert 2506 is mounted on and rotatable about a vertical shaft 2508 such that the prongs 2505 rotate together. In some embodiments, the prong insert 2506 is a separate component from the manifold/tubing assembly 2504 and the removable prong insert 2506 can allow for the use of different sizes of prongs 2505 for different nose sizes while using a single size manifold 2501. Additionally, in some embodiments, the manifold 2501 can have a lip 2510 on a surface of the manifold 2501 to which the prong insert 2506 connects. The prong insert 2506 can have a mating section 2511 that is complementary to the lip 2510. In some embodiments that contain a lip 2510 on the manifold 2501, the prong insert 2506 can be lifted from the surface of the manifold 2501 and rotated about the vertical shaft 2508 so that the prongs 2505 can be repositioned to the appropriate direction. The prong insert 2506 can be rotatable about a vertical, central axis of the manifold 2501 or an axis that is centrally located relative to openings 2518 in the manifold 2501 that communicate with the nasal prongs 2505, as shown in FIG. 25B, such that the prongs 2505 switch openings 2518 between the two orientations.

In some embodiments, the manifold can have a prong exit hole in the midsection of the manifold configured to receive an insert or clip-on attachment including the prongs. FIGS. 26A-F illustrate an embodiment of a nasal cannula assembly 2600 configured to allow insertion of a removable prong insert 2606. In some embodiments, the prong insert 2606 can be pushed into an opening 2607 in the hollow manifold 2601. This allows the prongs 2605 to be configured in the appropriate direction for use by the patient in the same manifold 2601 and/or manifold/tube assembly 2604. The manifold 2601 and/or manifold/tube assembly 2604 can be connected to an assembly securing device 2603, such as a headgear strap. For example, in some embodiments, the supply tube 2602 and manifold 2601 are assembled with the securing device 2603 and the nasal prongs 2605 are carried by the removable nasal prong insert 2606. The manifold/tube assembly 2604 and the assembly securing device 2603 can be symmetrical so it can be assembled to the face in one direction (e.g., FIG. 26B) or an opposite direction (e.g., FIG. 26C). In some embodiments, the assembly securing device 2603 and the manifold/tube assembly 2604 can be flipped around to suit whichever direction the supply tube 2602 is desired to be positioned. For example, in certain embodiments, to switch the side the supply tube 2602 is positioned, the nasal prong insert 2606 is removed and the remainder of the manifold/tube assembly 2604 is flipped around so that the supply tube 2602 faces the desired direction, and the nasal prong insert 2606 is then reinserted into the receiving opening 2607 of the manifold/tube assembly 2604 in the proper orientation to point toward the nose of the patient. Further, the nasal prong insert 2606 can be of different sizes (FIGS. 26D-F) and the different size inserts can be interchanged on the same assembly 2604 for use and adaptation for different patient nose sizes and to ensure correct prong sizing for the patient.

In some embodiments, a nasal cannula assembly can comprise a manifold, supply tube and a cannula that is removable from the manifold and/or adjustable about at least one axis relative to the manifold. The cannula can be adjustable about two axes relative to the manifold and can be available in different prong sizes to allow the assembly to fit a variety of patients. In particular, with reference to FIGS. 27A-D, a nasal cannula assembly 2700 includes a pivoting cannula 2714, which preferably incorporates a pair of nasal prongs 2705. The cannula 2714 is pivotally coupled to a moulding (head strap moulding) or manifold 2701, which can include side portions 2722 that extend in opposing lateral directions from the cannula 2714. A suitable retention assembly (not shown), such as a headgear strap, can secure the manifold 2701 and cannula 2714 to the patient. In some arrangements, the headgear strap is an elastic, high-stretch strap, which can assist in or improve the seal between the manifold 2701 and the cannula 2714. The headgear strap can be unitary with, integral with, or separate from the manifold/moulding 2701.

Preferably, the manifold 2701 defines a conduit or passage 2709 that allows air or gas to pass from a supply tube 2702 to the cannula 2714. The passage 2709 can be defined by a molding from which the manifold 2701 and side straps 2722 are constructed (e.g., a single integrated structure) or can be defined by a separate member. The supply tube 2702 can be coupled to the manifold 2701 by any suitable arrangement, such as a jaw expander arrangement or any other arrangement disclosed herein. A clip 2742 can secure the supply tube 2702 to the side strap 2722. An end of the supply tube 2722 opposite the manifold 2701 can include a connector 2752, which permits coupling of the supply tube 2722 to an air or gas source.

In some embodiments, the cannula 2714 can be rotated relative to the manifold 2701 about an axis that extends in a generally fore-aft direction or a generally horizontal axis that lies in the sagittal plane. Preferably, the cannula 2714 can be rotated at least 180 degrees such that the prongs 2705 can be rotated from the top (the orientation of FIG. 27A) to the bottom, which provides an effective change of the supply tube 2702 exit side. In some embodiments, the cannula 2714 is coupled to the manifold 2701 by a ball-and-socket joint 2726 such that the cannula 2714 is also rotatable about an axis that extends in a generally lateral direction or a generally horizontal axis that lies in the frontal plane. Such an arrangement not only provides a simple change of the supply tube 2702 exit side, but also allows adjustment of the nasal prong 2705 orientation relative to the manifold 2701 to increase patient comfort and/or fit a wider variety of patients.

Figure 27A:
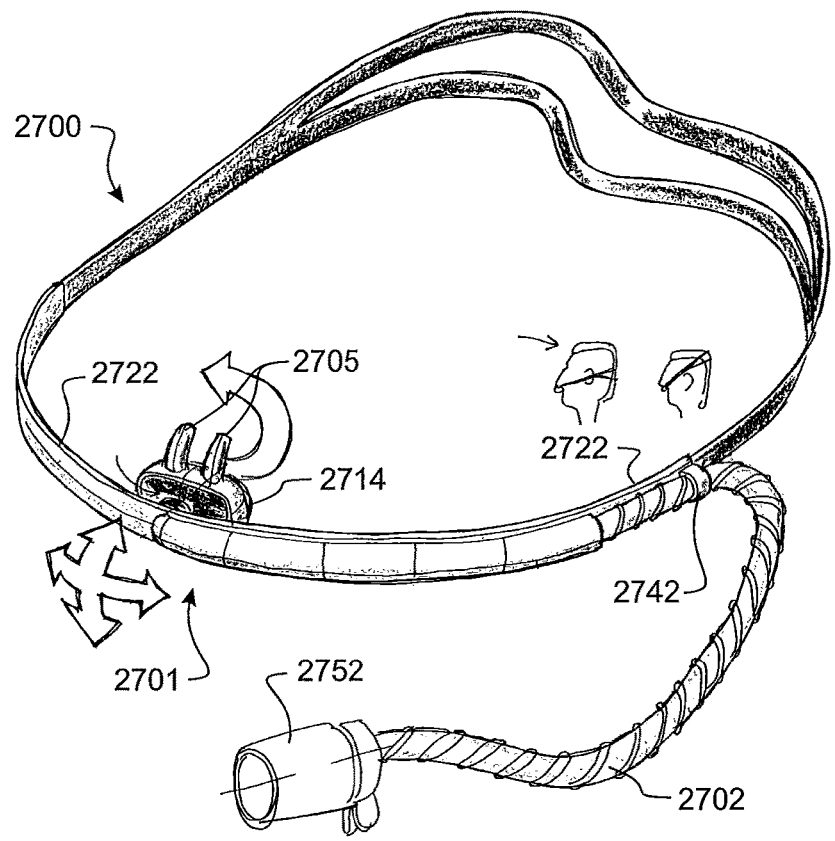
FIGS. 27A-D illustrate example embodiments of a nasal cannula assembly that includes a manifold that is rotatable about an axis extending in a generally fore-aft direction.
Figure 27B:
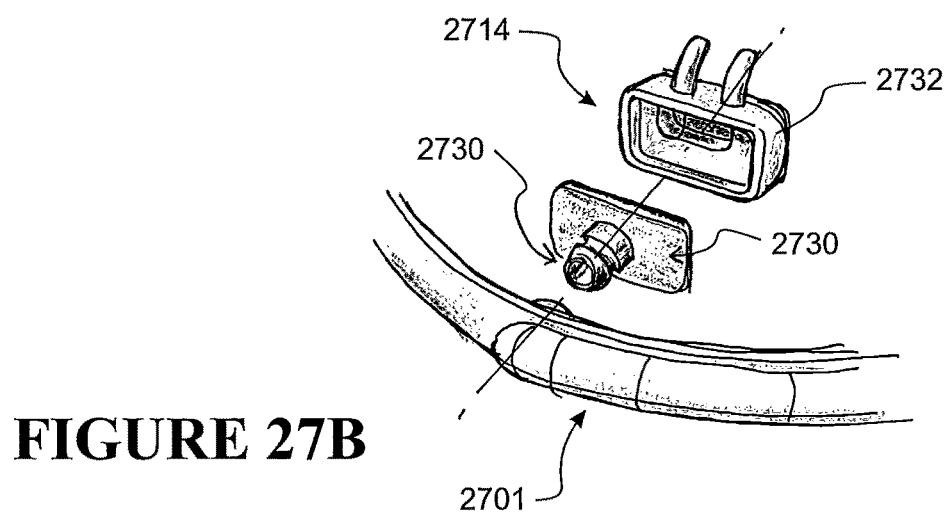
Figure 27C:
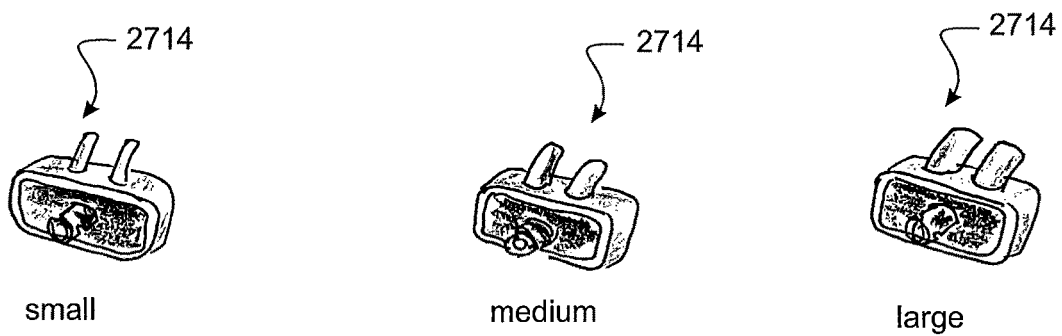

In some embodiments, a size of the prongs 2705 is adjustable. For example, as shown in FIGS. 27B and 27C, the ball joint portion 2730 can be separable from a prong portion 2732 of the cannula 2714. Several prong portions 2732 can be included in a kit or can be otherwise made available that provide several different sizes of nasal prongs 2705. For example, three different prong portions 2732 are shown in FIG. 27C, which include three differently-sized prongs 2705. An appropriate or desired one of the available prong portions 2732 can be coupled to the ball joint portion 2730, such as via a snap-fit or other suitable arrangement. Alternatively, two or more complete cannulas 2714 can be provided, each with different size prongs 2705. Accordingly, with such an arrangement, the cannula 2714 could be constructed as a single piece.

Figure 27D:
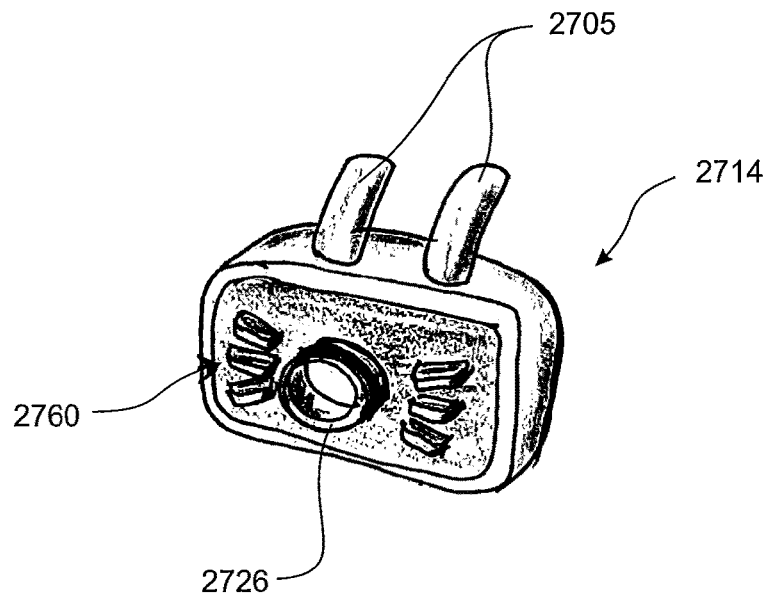

However, it is not necessary that the cannula 2714 be rotatable in multiple axes, or even rotatable through an arc. Instead, the cannula 2714 can have discrete adjustment positions relative to the manifold 2701. Preferably, at least the position shown in FIG. 27A and the 180 degree rotation of the cannula 2714 are provide such that the exit side of the supply tube 2702 can be switched. If desired, other discrete position options can be provided. The cannula 2714 and manifold 2701 could include interference surface features to assist in securing the cannula 2714 in a desired position relative to the manifold 2701. For example, as shown in FIG. 27D, the cannula 2714 could include one or more teeth 2760 or other protrusions that engage corresponding recesses of the manifold 2701. In the illustrated arrangement, the cannula 2714 includes multiple teeth 2760 on each lateral side of the ball joint 2726, which can extend in a radial direction relative to the ball joint 2726. Other suitable arrangements can also be employed.

Figure 28A:
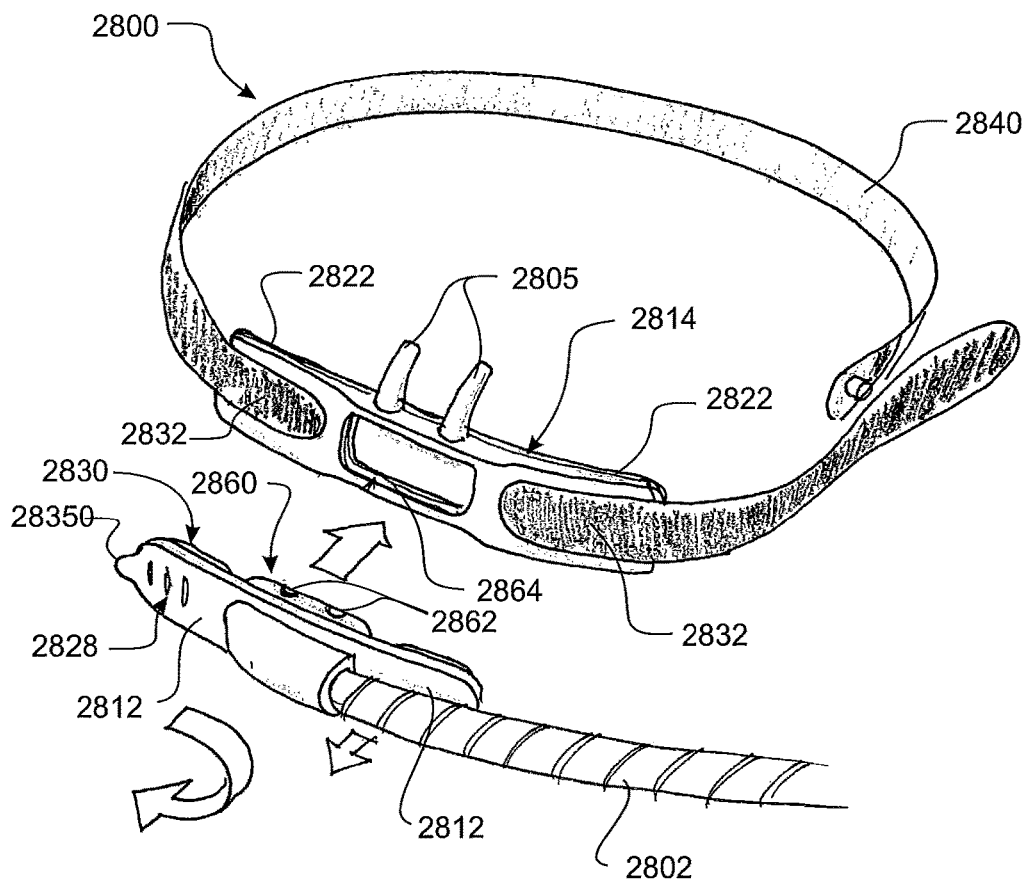
FIGS. 28A and 28B illustrate example embodiments of a nasal cannula assembly that includes a manifold and supply tube that can be coupled to the cannula in at least two orientations.

In some embodiments, as shown in FIG. 28A, a nasal cannula assembly 2800 includes a manifold 2801 that is capable of being coupled to a cannula 2814 in at least two orientations to allow a simple switching of the exit side of the supply tube 2802. The cannula 2814 can include a central portion that includes prongs 2805 and side portions 2822 on each lateral side of the central portion. The manifold 2801 can include side portions 2812 that overlap with the side portions 2822 of the cannula 2814. The side portions 2812 and 2822 can facilitate a secure connection between the manifold 2801 and the cannula 2814. For example, the side portions 2812 or 2822 of one or both of the manifold 2801 and the cannula 2814 can include couplers or coupling mechanisms that couple or assist in coupling the manifold 2801 and the cannula 2814. In the illustrated arrangement, the side portions 2812 include a first component 2830 of a coupler (e.g., a hook and loop fastener) and the side portions 2822 of the cannula 2814 includes a second component 2832 of a coupler (e.g., a hook and loop fastener). One or both of the side portions 2812 of the manifold 2801 include a tab 2850 that provides a finger grip surface to facilitate removal of the manifold 2801 from the cannula 2814. In addition, one or both of the side portions 2812 can include flex slots 2828 to facilitate flexing of the side portions 2812, which can assist in removal of the manifold 2801 from the cannula 1814 and can also facilitate the manifold 2801 conform to the shape of the cannula 2814.

The manifold 2801 and the cannula 2814 can include cooperating structures that create a seal between the two components. For example, the manifold 2801 can include a protruding portion 2860 that defines a cavity in communication with the supply tube 2802 and includes at least one and preferably a pair of openings 2862 that allow air or gas communication with the prongs 2805 when the manifold 2801 is assembled to the cannula 2814. The protruding portion 2860 engages an opening 2864 of the cannula 2814 and, preferably, defines at least a substantial seal therewith. The seal can be created by contact or engagement (e.g., a lip and groove) between the protruding portion 2860 and the opening 2864 or a separate sealing member (e.g., a perimeter seal or O-ring) can be used.

A securement device, such as a headgear strap 2840 can be used to secure the cannula 2814 and, thus, the manifold 2801 to a patient. In some embodiments, the headgear strap 2840 is a non-stretch strap that is coupled to the side portions 2822 of the cannula 2814. The ends of the headgear strap 2840 can be heat-welded to the side portions 2822 and can include the second components 2832 of the coupler between the manifold 2801 and the cannula 2814. The headgear strap 2840 can include a suitable adjuster 2842 that permits a circumference of the strap 2840 to be adjusted. In other arrangements, a stretchable headgear strap 2840 can be used.

Figure 28B:
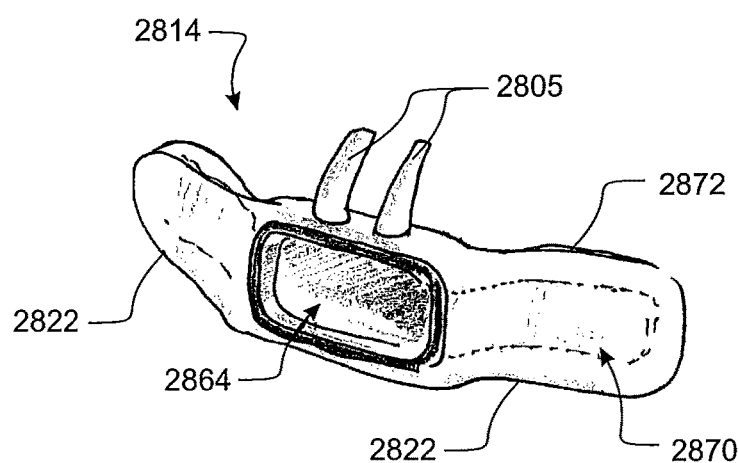

With reference to FIG. 28B, the cannula 2814 can be of a composite construction and include a frame member 2870 constructed from a relatively rigid material and a body 2872 constructed from a relatively soft material. For example, the frame 2870 can be a rigid plastic or a metal material, which may be deformable and substantially hold its shape once deformed. The frame 2870 can be external of the body 2872 or the body 2872 can be molded over the frame 2870. Preferably, the frame 2870 is located in the side portions 2822 of the cannula 2814 and can be formed to bridge the central portion containing the prongs 2805 away from the nose to reduce the pressure just below the nose and spread the pressure applied to the patient over the side portions 2822 for increased comfort. The frame 2870 can also surround or partially or completely define the opening 2864 instead of or in addition to extending into the side portions 2822.

Figure 29A:
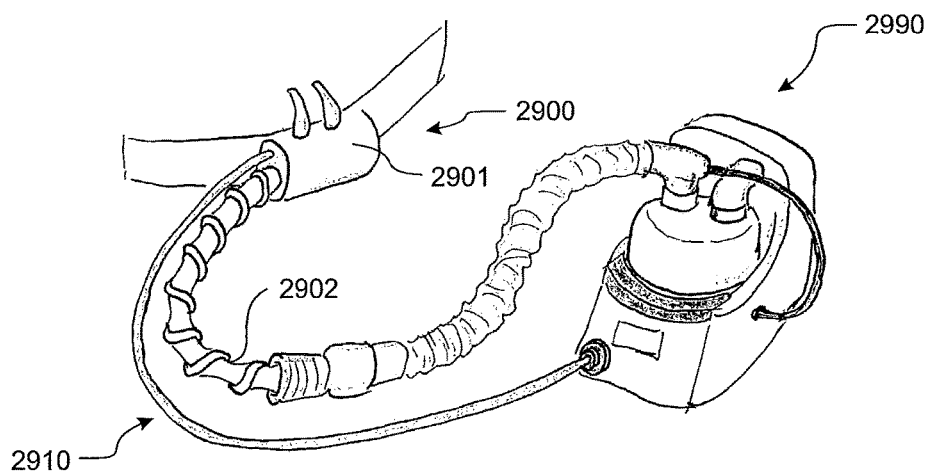
FIG. 29A illustrates an example embodiment of a respiratory assistance system with a nasal cannula assembly having pressure measurement capability.

With reference to FIG. 29A, in some embodiments of a respiratory assistance system utilizing a nasal cannula system 2900 it is desirable to be able to measure the pressure in the flow path near the patient (e.g., at or near the cannula or manifold 2901) for at least one or both of 1) monitoring of the pressure delivered to the patient and 2) pressure feedback control of a blower flow source (e.g., blower and humidifier 2990). FIG. 29A illustrates a basic arrangement for providing pressure feedback control. In particular, a pressure line 2910 connects the manifold 2901 (or manifold/cannula assembly—hereinafter "manifold") to a flow source control system, which can be a part of the blower/humidifier 2990. With such an arrangement, the flow source 2990 can utilize the information regarding the pressure at or near the manifold 2901 provided by the pressure line 2910 in the operation of the flow source 2990, such as to adjust the supplied pressure to achieve a desired delivered pressure at the patient. Advantageously, this arrangement can compensate for factors that may cause the delivered pressure to be different than expected, such as supply tube 2902 length, cross-sectional area or other geometry, for example. If only pressure monitoring was required or desired, the pressure line 2910 could be connected to a pressure gauge or readout instead.

Figure 29B:
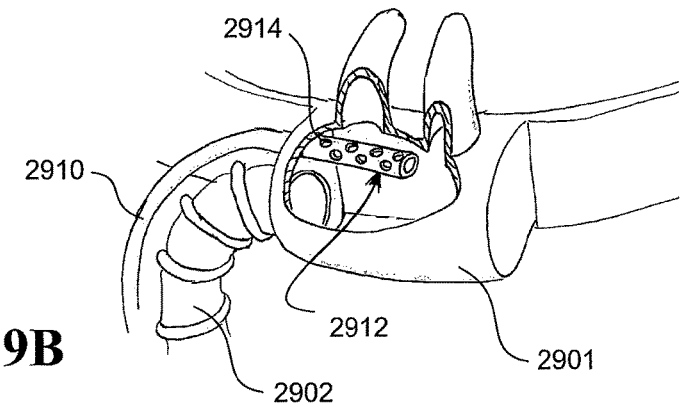

With reference to FIG. 29B, the pressure line 2910 can be passed through a wall of the manifold 2901 and terminated within a manifold space of the manifold 2901. In the illustrated arrangement, a terminal end 2912 of the pressure line 2910 is perforated with a number of holes 2914 so that if some of the holes 2914 are blocked with condensation, there are other holes 2914 still functioning such that the pressure within the manifold 2901 can be communicated to the pressure source 2990. The terminal end 2912 of the pressure line 2910 can be positioned anywhere within the manifold 2901, such as between the supply tube 2902 and the prongs 2905 along a flow path of the supplied air or gas, for example but without limitation.

Figure 29C:
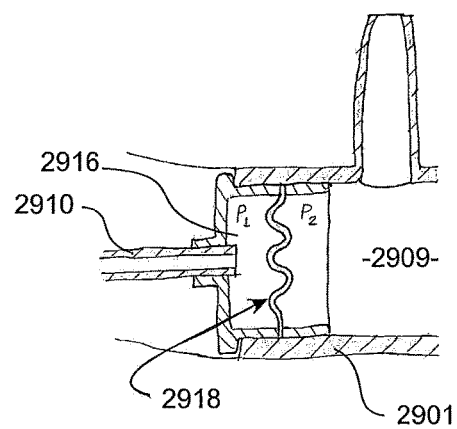

With reference to FIG. 29C, the pressure line 2910 can permit direct or indirect communication between the manifold 2901 and the pressure source 2990. The arrangement of FIG. 29C separates the manifold chamber 2909 of the manifold 2901 from a pressure chamber 2916 that is in direct communication or is directly sensed by the pressure line 2910. For example, a thin flexible diaphragm seal 2918 (or other movable membrane or member, such as a floating or sliding piston) separates the manifold chamber 2909 from the pressure chamber 2916, which prevents condensate from entering the pressure line 2910 and keeps the pressure line 2910 clean.

With reference to FIG. 29D, the pressure line 2910 can comprise a pressure sensor 2930, which can sense pressure within the manifold chamber 2909. The pressure sensor 2930 can be located within the manifold 2901, such as being configured as a plug that engages and/or closes one end of the manifold 2901. In some embodiments, a separator, such as a wall or membrane 2918 is positioned between the pressure sensor 2930 and the manifold chamber 2909. The membrane 2918 can be of any suitable type, such as an ultra-thin silicone membrane. The pressure sensor 2930 can be of any suitable type, such as an electrical pressure sensor. The pressure sensor 2930 can be pushed up against the membrane 2918, which can conform to the shape of the pressure sensor 2930, to measure the pressure without directly contacting the flow of air or gas, thus avoiding condensate accumulating on the pressure sensor 2930. In addition, with such an arrangement, the membrane 2918 can be constructed to close and seal the end of the manifold 2901 such that the nasal cannula assembly 2900 can be used with or without the pressure sensor 2930.

With reference to FIG. 29E, the membrane 2918 can be a self-sealing slit valve through which the pressure line 2910 and/or the pressure sensor 2930 could be inserted, if desired. Advantageously, self-sealing slit valve 2918 can close in the absence of the pressure line 2910 and/or pressure sensor 2930 such that there would be no substantial leaking if it was removed. Therefore, the nasal cannula assembly 2900 could function with or without the pressure line 2910 and/or pressure sensor 2930.

With reference to FIG. 29F, the pressure line 2910 and the supply tube 2902 can be integrated into one connector 2931 that is connectable to the manifold 2901 to permit connection of both the pressure line 2910 and the supply tube 2902 at one time. Advantageously, such an arrangement simplifies set up of the nasal cannula assembly 2900 by avoiding the need to connect multiple tubes or components to the manifold 2901.

Figure 29G:
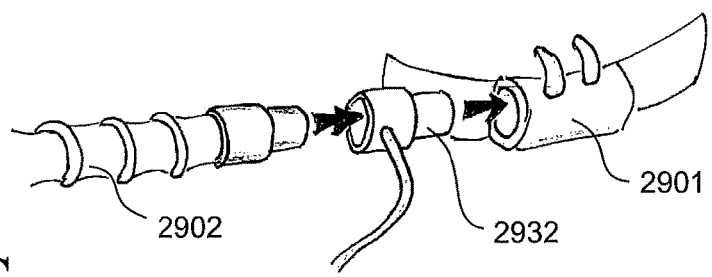
Figure 29H:
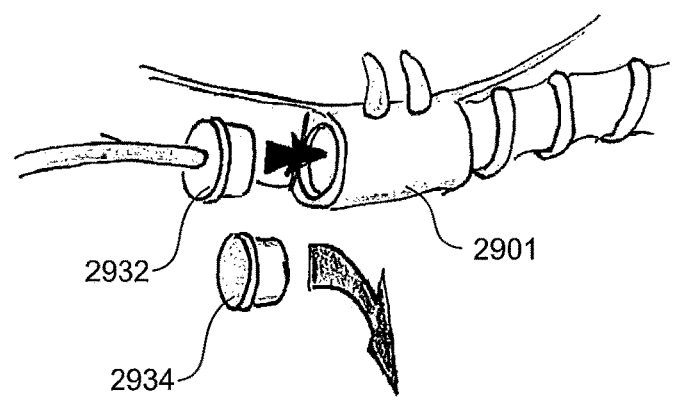

With reference to FIG. 29G, the pressure line 2910 can be connected as an optional accessory in series with the supply tube 2902. The pressure line 2910 can include a plug portion 2932 that connects to the manifold 2901 and the supply tube 2902 can connect to the plug portion 2932. Alternatively, with reference to FIG. 29H, the pressure line 2910 can be connected as an optional accessory separately from the supply tube 2902, such as on an opposite side of the manifold 2901 from the supply tube 2902. The pressure line 2910 can have a plug portion 2932 that replaces a plug 2934 of the manifold 2901.

Figure 29I:
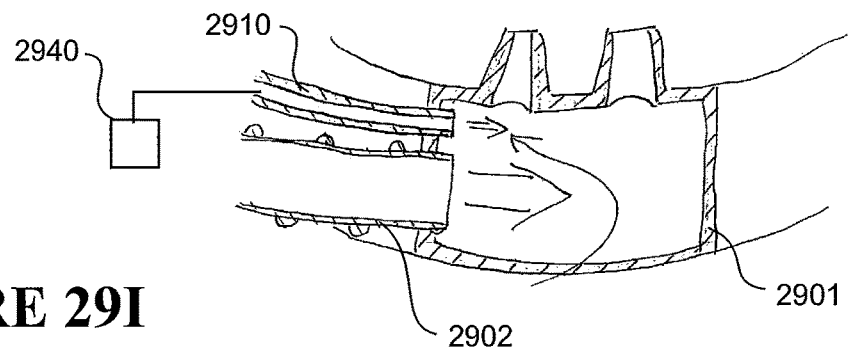

With reference to FIG. 29I, a small blower 2940 or other source of air or gas flow can be connected to the pressure line 2910 to apply a small flow of air or gas through the pressure line 2910 preferably sufficient to expel some or all of any condensate which accumulated inside the pressure line 2910. The flow of air through the pressure line 2910 can be provided intermittently or continually and can be considered by the control system in the calculation of the pressure within the manifold 2901.

Figure 29J:
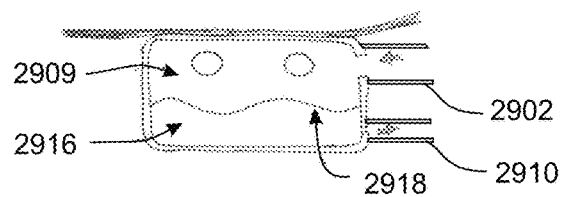

With reference to FIG. 29J, a thin flexible diaphragm seal 2918 (or other movable barrier) can separate the manifold chamber 2909 from the pressure measurement chamber 2916 to inhibit or prevent condensate from entering the pressure line 2910 and keep the pressure line 2910 clean. If the pressure measurement feature is not utilized and, thus, the pressure line 2910 is not needed, an opening or port 2942 of the manifold 2901 that receives the pressure line 2910 can be left open and can function as a vent to the pressure measurement chamber 2916. Alternatively, the port 2942 can be closed if desired, such as be a suitable plug.

Figure 29K:
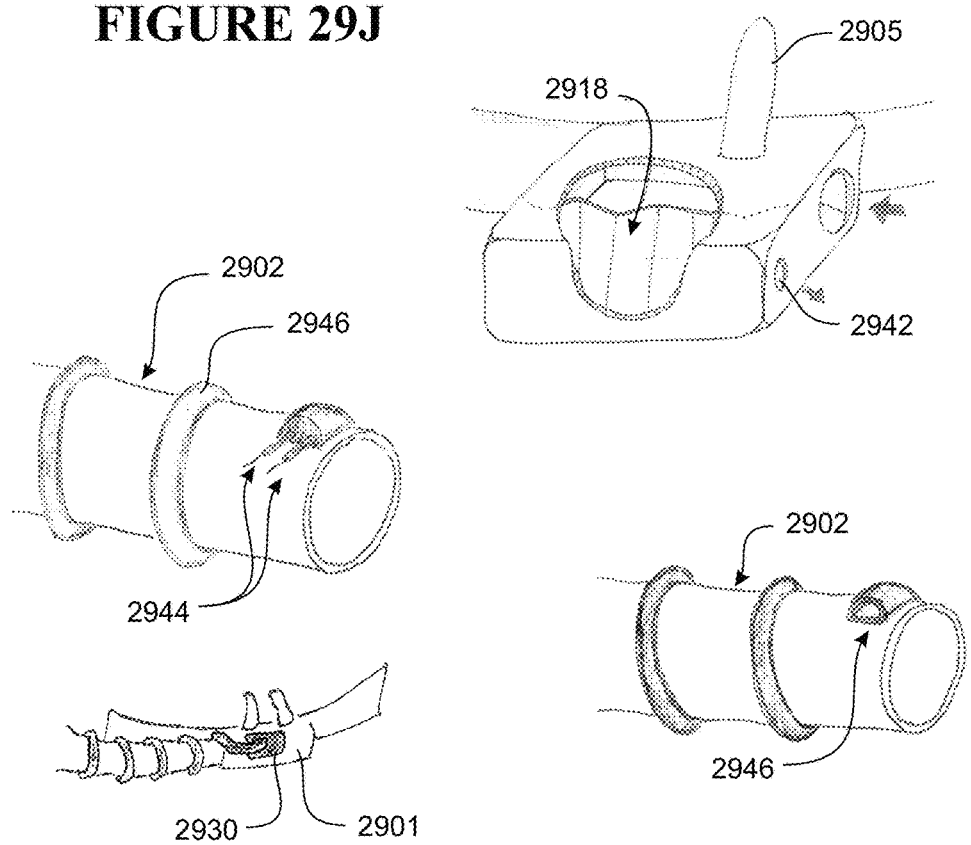

In some embodiments, with reference to FIG. 29K, for example, electrical wiring 2944 is incorporated into the spiral bead 2946 of the supply tube 2902. The electrical wiring 2944 can connect to an electrical pressure sensor 2930 mounted in the manifold 2901. The wiring 2944 (or additional wiring) could also be used to heat the supply tube 2902. In some arrangements, the wiring 2944 can switch between measuring pressure & temperature readings, and heating.

Figure 29L:
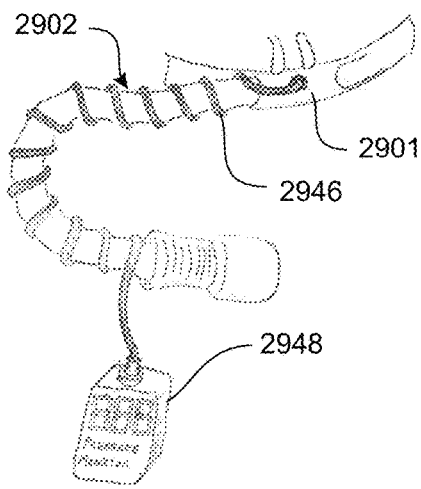

With reference to FIG. 29L, the spiral reinforcement 2946 of the supply tube 2902 can be made hollow or otherwise contain a passage to act as a pressure line (similar to pressure lines 2910 disclosed herein). With such an arrangement, no additional pressure line (e.g., 2910) would need to be used. The spiral reinforcement 2946 could connect at one end to the chamber of the manifold 2901 and at the other end to the operating system of an air or gas source, or a pressure monitor or gauge 2948.

In some embodiments, the nasal cannula assembly includes features that improve patient comfort. Discomfort can exist for some patients using some nasal cannula assemblies. For example, two types of discomfort include: 1. a hot, damp, clammy feel of the cannula/manifold in contact with the skin on the upper lip, which may be caused by moisture originating from perspiration and the circulation of warm humidified gases in this area, and 2. pain and numbness associated with the pressure applied to the upper lip by the cannula/manifold. Some embodiments of a nasal cannula assembly 3000 address one or both of these types of discomfort to at least some degree.

Figure 30A:
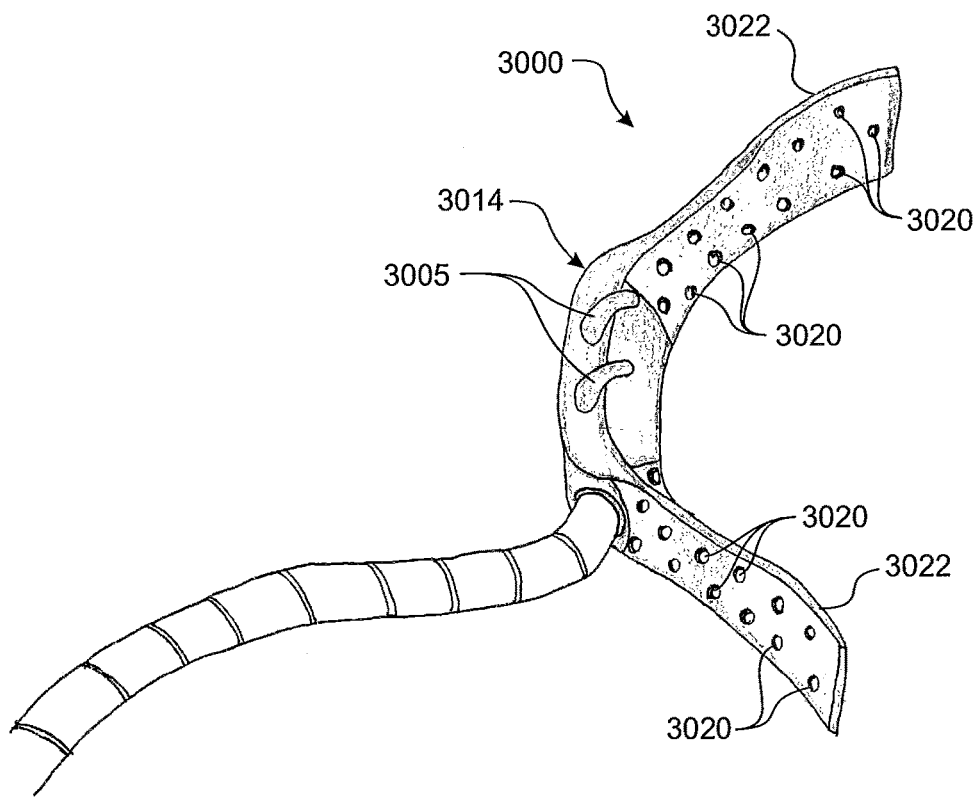

With reference to FIG. 30A, holes, recesses or depressions 3020 of any desired shape can be cut into or otherwise formed in the cannula or manifold (hereinafter "cannula") material, which allow fresh air to reach the skin helping to keep the area cool and reducing the build-up of moisture. In some embodiments, the holes, recesses or depressions 3020 are cut into or formed in areas that do not cause leakage of the therapy air flow from the cannula 3014. For example, the holes, recesses or depression 3020 are provided in the side portions 3022 of the cannula 3014 and not in the central portion that contains the prongs 3005. In the illustrated arrangement, holes 3020 that pass completely through the side portions 3022 of the cannula 3014 are provided. The holes, recesses or depressions 3020 can also improve flexibility of the cannula 3014, allowing it to conform more easily to the shape of the patient's lip and distribute pressure more evenly for improved comfort.

Figure 30B:
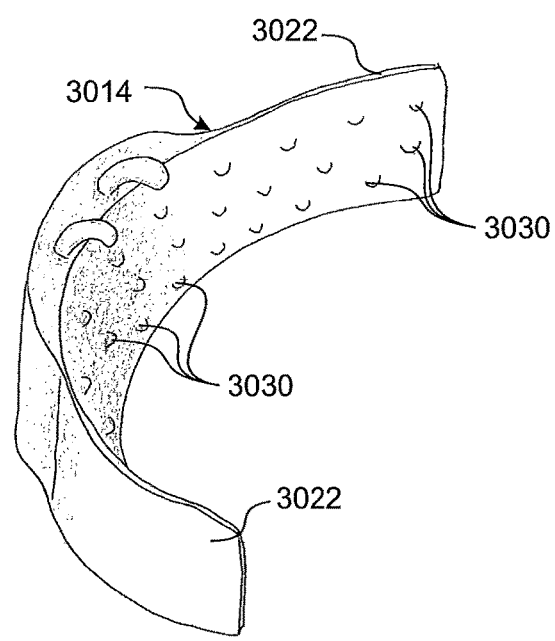

With reference to FIG. 30B, the cannula 3014 could also include small raised bumps or protrusions 3030 on the rear or patient-facing surface of the cannula 3014. The bumps 3030 hold some or all of the remaining rear or patient-facing surface of the cannula 3014 away from the lip of the patient, allowing fresh air to reach the skin, helping keep the area cool and reducing moisture build-up. The bumps 3030 can be provided over an entirety of the rear surface, as shown, or over only a portion of the rear surface, such as the side portions 3022 similar to the cannula 3014 of FIG. 30A, for example.

Figure 30C:
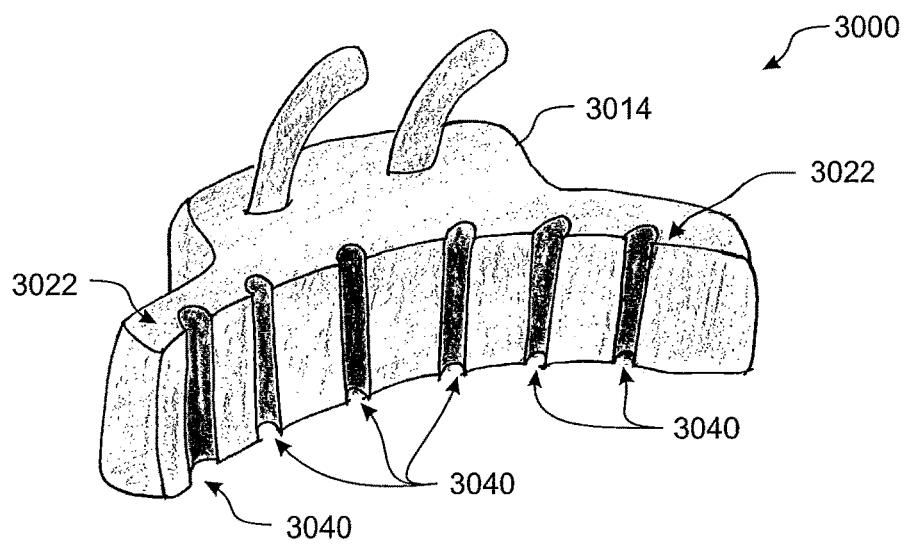
Figure 30D:
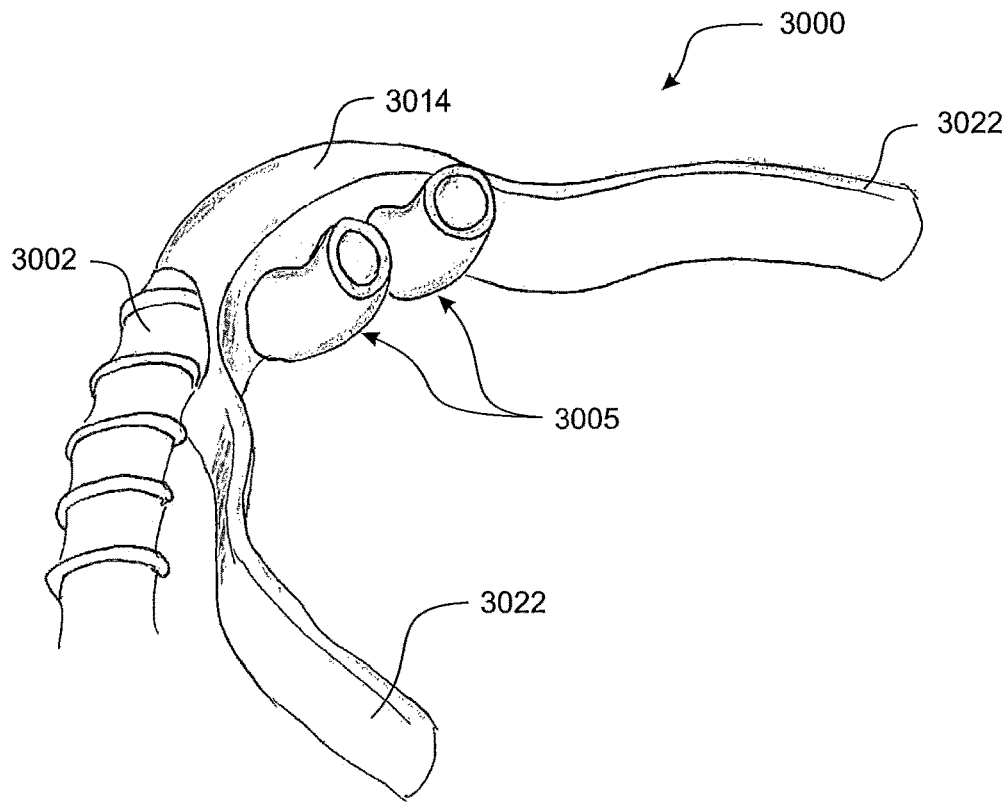
Figure 30E:
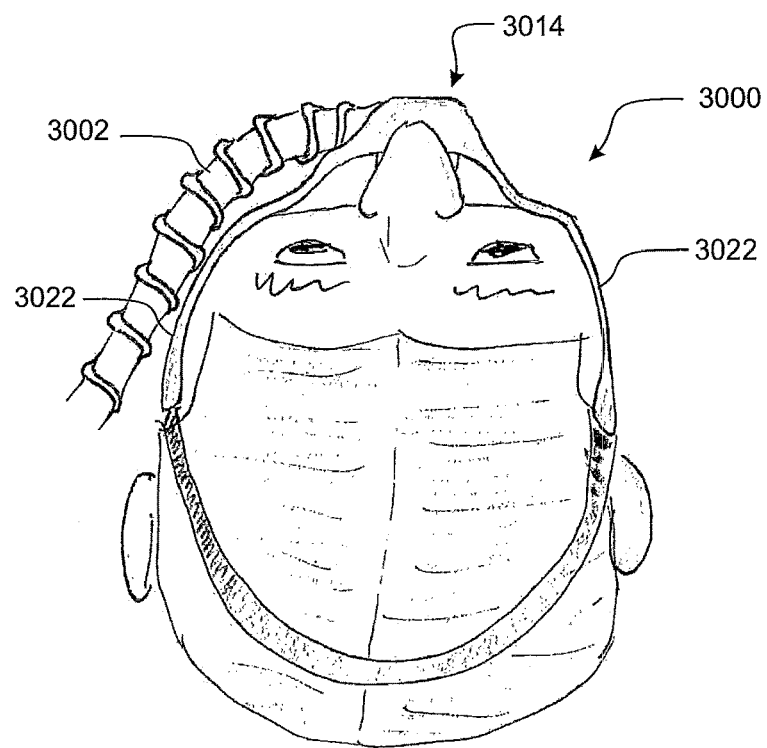
Figure 30F:
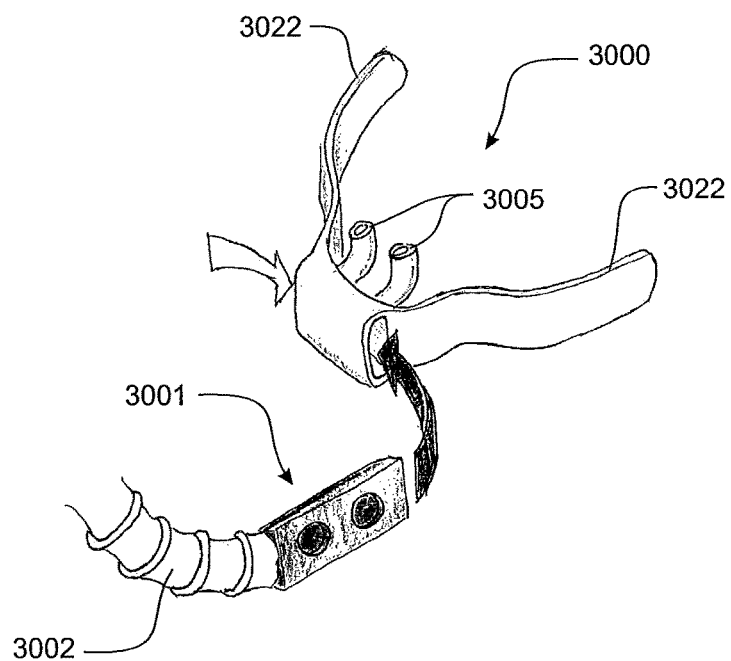

With reference to FIG. 30C, grooves 3040 can be cut into or otherwise formed in the rear surface of the cannula 3014. The grooves 3040 allow fresh air to reach the skin, helping keep the area cool and reducing moisture build-up. In some embodiments, the grooves 3040 extend in a generally vertical direction or perpendicular to the lateral direction of the cannula 3014. In addition, the grooves 3040 can extend partially through the cannula 3014 such that one end is closed or can extend completely through the cannula 3014 such that both ends are open, as shown in FIG. 30C. The grooves 3040 can also improve flexibility of some portions (e.g., side portions 3022) or all of the cannula 3014, allowing it to conform more easily to the shape of the patient's lip and distribute pressure more evenly for improved comfort.

With reference to FIGS. 30D-H, in some embodiments, the cannula 3014 can include a cannula lip bridge arrangement in which the cannula 3014 is shaped so that it curves away from the face at the upper lip, reducing pressure or completely avoiding any contact with the upper lip thereby resulting in improved circulation of fresh air in the area, and reduced (e.g., little or none at all) pressure on the lip. The pressure is instead is applied by the side portions 3022 and absorbed by the cheeks, which are less sensitive to pressure. In some arrangements, the prongs 3005 are reverse mounted horizontally on the inside of the cannula 3014 and are curved up into the nares. This design has the additional benefit of allowing clearance for a moustache.

Preferably, such embodiments of the cannula 3014 have some rigidity, which can be accomplished by any suitable construction or arrangement, such as using a stiffer material for the cannula 3014 (FIGS. 30D-F), reinforcing ribs, or a structural member such as an internal (FIG. 30G) or external (FIG. 30H) wire or strip 3050, which could be malleable for adjustment to suit individual patients. The cannula 3014 can be of any suitable arrangement, such as having and integrated or directly-connected supply tube 3002 or by utilizing a manifold 3001 connected to the supply tube 3002 and received within the cannula 3014, for example.

With reference to FIG. 30I, in some embodiments, a comfort pad or insert 3060, such as a gel pad or other type of pad can be provided on the rear or patient-facing surface of the cannula 3014. At least the rear surface of the cannula 3014 in contact with the patient's upper lip can be made of a soft gel material or can include a soft gel pad 3060 that, in some arrangements, moulds to the shape of an individual patient's lip to create a relatively large contact surface area to evenly distribute pressure across the skin. The pad 3060 can deform as the headgear strap or other retention mechanism (not shown) is tightened to accommodate a patient's facial geometry and prevent the occurrence of localized areas of pressure. The pad 3060 preferably occupies a substantial portion, such as substantially an entirety, of the rear surface. The pad 3060 could be scented to make the odor of the cannula 3014 more pleasing.

In some embodiments of a nasal cannula assembly, the supply tube can be manually shaped or positioned and remain in that shape or position or substantially in that shape or position. One of the major benefits of some nasal cannula assemblies, such as the Optiflow® nasal cannula assemblies sold by Fisher & Paykel Healthcare Ltd., is to be able to eat, drink and talk while on therapy. In some cases, the shape or position of the supply tube exiting the cannula can inhibit these activities. Thus, in some embodiments, it may be desirable to be able to shape or position the supply tube as desired. Any suitable arrangement or technique can be used to allow shaping or positioning of the tubing, such as those described herein with reference to FIGS. 31A-F.

Figure 31A:
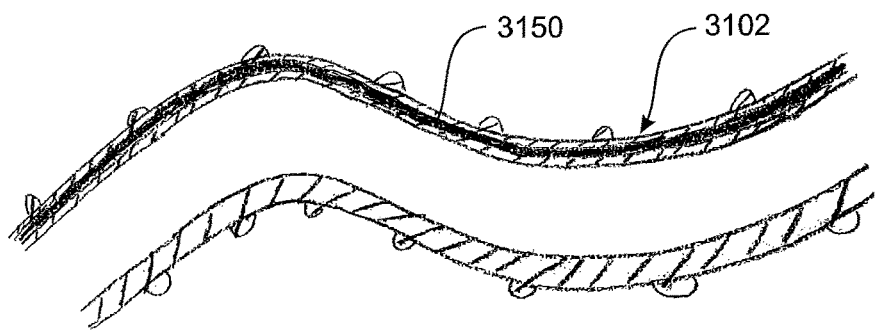
FIGS. 31A-F illustrate example embodiments of adjustable or formable supply tubes for nasal cannula assemblies.
Figure 31B:
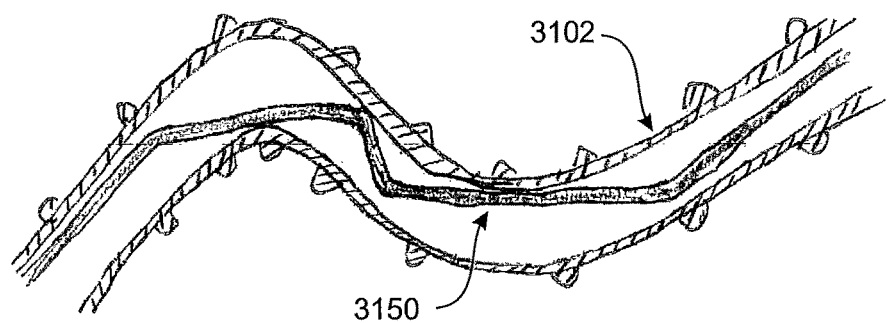
Figure 31C:
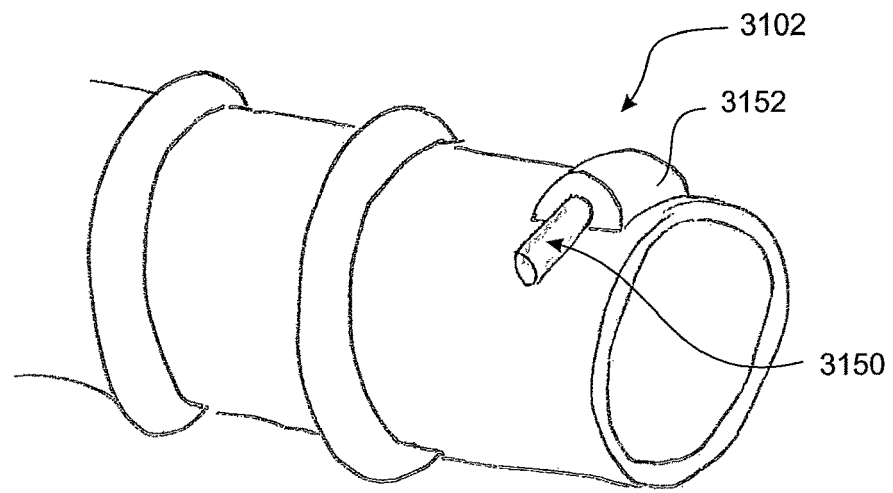

With reference to FIGS. 31A and 31B, the supply tube 3102 can comprise an internal axial malleable wire or strip 3150. The supply tube 3102 can be assembled or formed with the internal axial malleable wire or strip 3150 that can be deformed into a variety of shapes. Preferably, the stiffness of the wire is significantly greater than the stiffness of the supply tube 3102, such that the shape is retained or substantially retained after forming. The wire or strip 3150 may be contained within, formed within or otherwise coupled to the supply tube 3102 in any suitable manner. For example, as shown in FIG. 31A, the wire or strip 3150 can be embedded into the wall of the supply tube 3102 external of a supply passage of the supply tube 3012. Alternatively, as shown in FIG. 31B, the wire or strip 3150 can be provided within the supply passage or bore of the supply tube 3102. In such an arrangement, it may be desirable to construct the wire or strip 3150 from, or coat the wire or strip 3150 with, a suitable (e.g., inert) material to tolerate or be suitable for contact with the supplied air or gas. With reference to FIG. 31C, the wire or strip 3150 may be a malleable spiral wound wire or strip wound around the circumference of the supply tube 3102, such as in a helical manner. The wire or strip 3150 can be covered or contained within another material (e.g., plastic) to form a bead 3152. The bead 3152 could give the tube structure (e.g., a reinforcement bead) as well as being shapeable or formable and retaining, or at least substantially retaining, the adjusted shape or form of the supply tube 3102. Advantageously, with such an arrangement, the bead spiral 3152 wound around the outside of the supply tube 3102 keeps it out of the air or gas path.

Figure 31D:
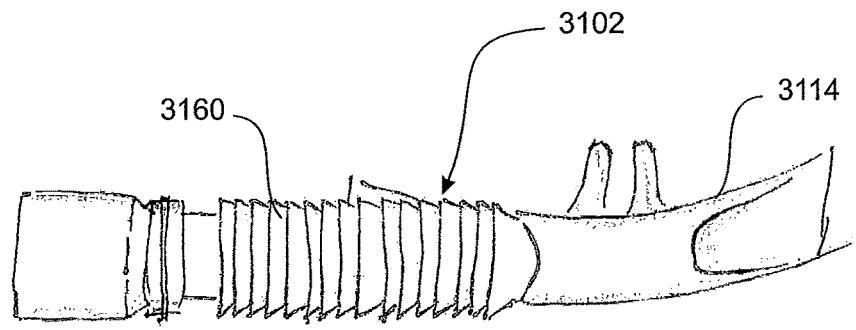
Figure 31E:
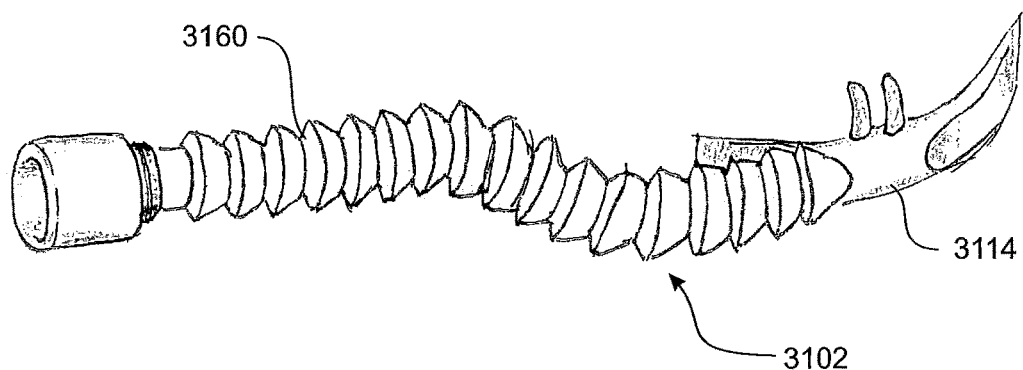
Figure 31F:
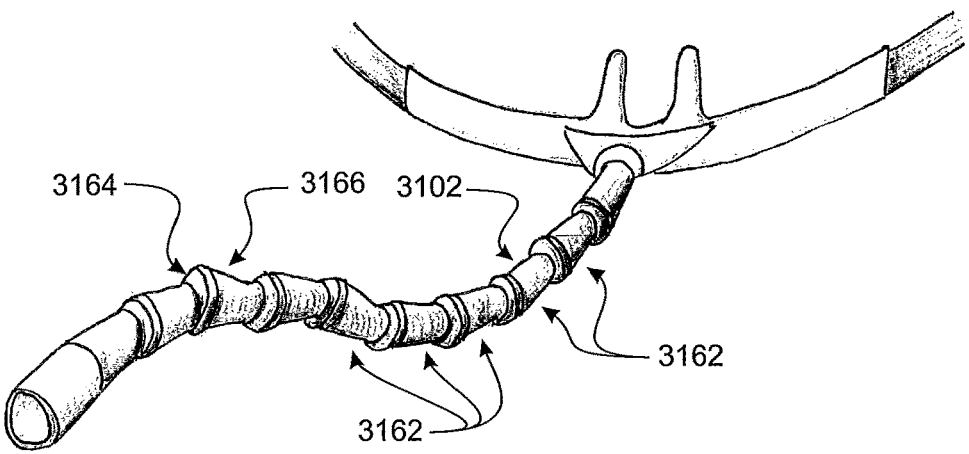

With reference to FIGS. 31D and 31E, the supply tube 3102 can be in the form of a collapsing corrugated tube having a section or a substantial entirety of collapsing corrugations 3160 that could be used to set one or both of the length and position of the supply tube 3102, as desired. The corrugations 3160 can be manufactured such that when the supply tube 3102 is compressed in a length or axial direction, the corrugations 3160 would each fold into themselves. FIG. 31D illustrates the supply tube 3102 in a axially compressed orientation and FIG. 31E illustrates the supply tube 3102 in an axially uncompressed or elongated position. The supply tube 3102 can be coupled to the cannula 3114 by any suitable arrangement, such as directly or via a suitable connector. With reference to FIG. 31F, alternatively, the supply tube 3102 can include a section or a substantial entirety that is constructed as a ball-and-socket chain. In particular, at least a section of the supply tube 3102 is constructed from a plurality of individual segments or members 3162 or similar that together form a sealed or substantially sealed, yet positionable or formable tube. Preferably, one end of each segment 3162 comprises a ball end 3164 and the other end comprises a socket 3166. Accordingly, a plurality of segments 3162 can be assembled with the ball end 3164 of one segment 3162 positioned within the socket 3166 of the adjacent segment 3162. In some arrangements, the fit of the ball end 3164 into the socket 3166 can be such that each segment 3162 can rotate or move relative to an adjacent segment 3152, yet provide enough frictional force to seal or substantially seal and remain in position or substantially within position once adjusted. If desired, an additional structure or arrangement can be used to hold the segments 3162 in an assembled state or assist in holding or sealing the segments 3162, such as a sleeve that extends over the segments 3162. Advantageously, these and similar embodiments can allow the supply tube 3102 to be positioned out of the patient's way to reduce or minimize disruption to eating, drinking and talking while on the therapy.

In some existing nasal cannula assemblies, the supply tube hangs down from its attachment point to the cannula or manifold, which is often just above the corner of the mouth. Such an arrangement can cause, among other issues, the supply tube to hang very close to the mouth, which can be a nuisance to the patient, as it interferes with eating, drinking and talking. In addition, the weight of the supply tube hanging down so close to the nose tends to drag one side of the cannula or manifold down, pulling it out of the nose. This is especially true in high flow therapies, which require a relatively large supply tube that cannot be comfortably routed behind the patient's ears, as is the case with smaller low-flow systems. Accordingly, some embodiments route the supply tube to exit the nasal cannula assembly further away from the nose and/or mouth of the patient, to partially or completely address the two issues described above.

Figure 32A:
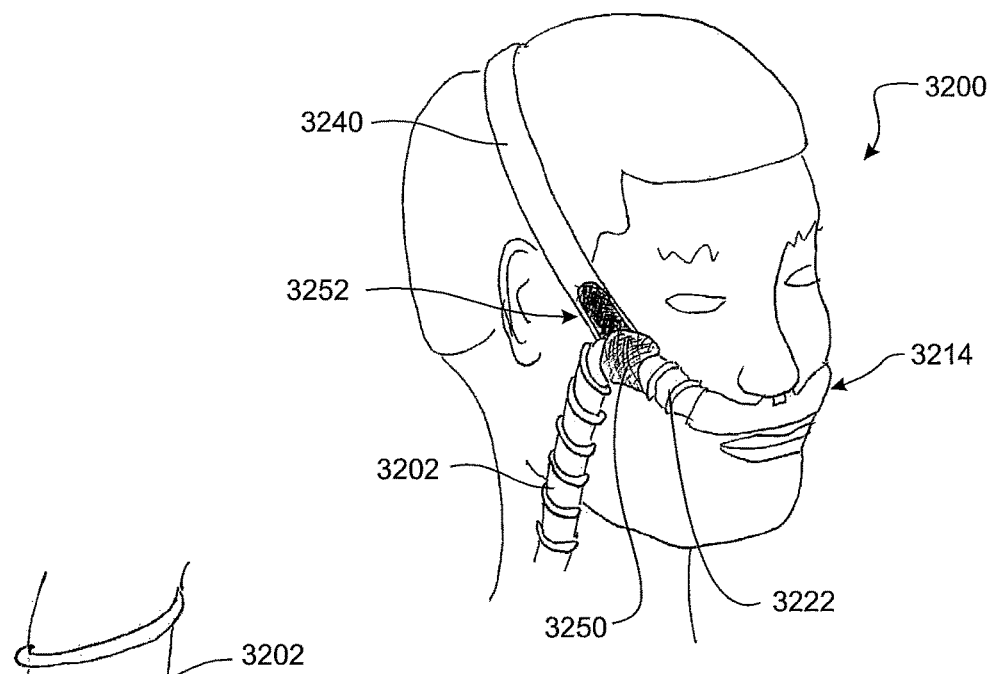
FIGS. 32A-N illustrate example embodiments of nasal cannula assemblies having arrangements and features to manage the positioning of the supply tube.
Figure 32B:
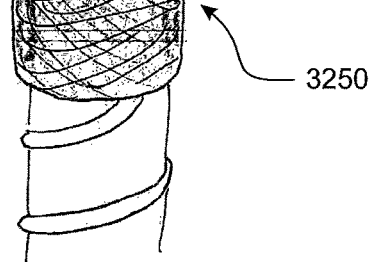
Figure 32C:
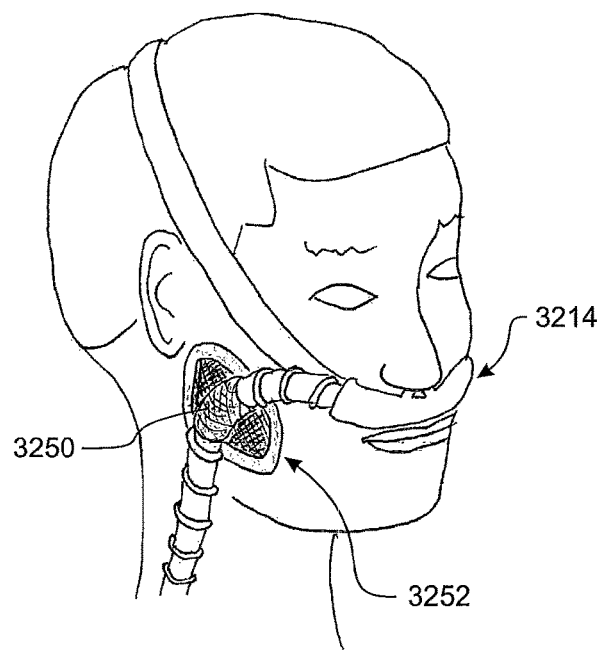

With reference to FIGS. 32A-C, one portion 3250 of a coupler, such as hook-and-loop fastener, is provided on the supply tube 3202 of a nasal cannula assembly 3200. For example, the portion 3250 can be a sheath of hook-and-loop material. The sheath 3250 can be coupled to the supply tube 3202 by any suitable arrangement, and may be removable or a non-removable from the supply tube 3202. In the illustrated embodiment, the sheath 3250 is permanently attached to the supply tube 3202. The sheath 3250 can be movable along the supply tube 3202 or can be provided at a fixed location on the supply tube 3202, preferably at a spaced location from the manifold or cannula 3214 (hereinafter "cannula"). The sheath 3250 can be secured to the other portion 3252 of the hook-and-loop fastener or other coupler, which can be appropriately positioned to align with the sheath 3250 and, preferably, space the vertical hanging portion of the supply tube 3202 away from the patient's nose or mouth. Preferably, the other portion 3252 of the coupler is a pad of the other portion of the hook-and-loop fastener relative to the sheath 3250. In one arrangement, as illustrated in FIG. 32A, the pad 3252 is provided on each side of a headgear strap 3240 or other retention mechanism of the nasal cannula assembly 3200. Thus, the supply tube 3202 can be routed to either side of the patient's face, as desired, and supported to hang down at a spaced location from the patient's nose and/or mouth. In another arrangement, as illustrated in FIG. 32C, the pad 3252 is an adhesive pad positioned on the patient's face, preferably at a location spaced from the nose and/or mouth, such as the cheek, for example. In such an arrangement, the pad 3252 can be applied only to the desired side of the face for the desired routing of the supply tube 3202.

In addition or in the alternative, other suitable mechanisms for similarly securing the supply tube 3202 can be used. FIGS. 32D-F illustrate several mechanical fastening mechanisms for securing the supply tube 3202 such that the downward hanging portion is spaced from the patient's nose and/or mouth. Preferably, a first portion 3250 of a mechanical fastener is positioned on the supply tube 3202, in a permanent or removable and fixed or movable fashion. A second portion 3252 of a mechanical fastener is positioned on a portion of the nasal cannula assembly 3200, such as the headgear strap 3240 (or, in another arrangement, side portions 3222 of the cannula 3214). Accordingly, in a manner similar to the arrangements of FIGS. 32A-C, the first portion 3250 can be coupled to the second portion 3252 of the mechanical fastener such that the supply tube 3202 can be supported away from the patient's nose or mouth. In FIG. 32D, the mechanical fastener is a button and button loop. In FIG. 32E, the mechanical fastener is a popper dome or other snap-fit arrangement. In FIG. 32F, the mechanical fastener is a hook, which can engage the supply tube 3202 and the headgear strap 3240. Thus, in such an arrangement, the first portion 3250 and the second portion 3252 of the mechanical fastener are formed by a single component. Thus, the portions 3250 and 3252 can be permanently coupled to one another and removable from one or both of the supply tube 3202 and the headgear strap 3240 or other portion of the nasal cannula assembly 3200.

Figure 32G:
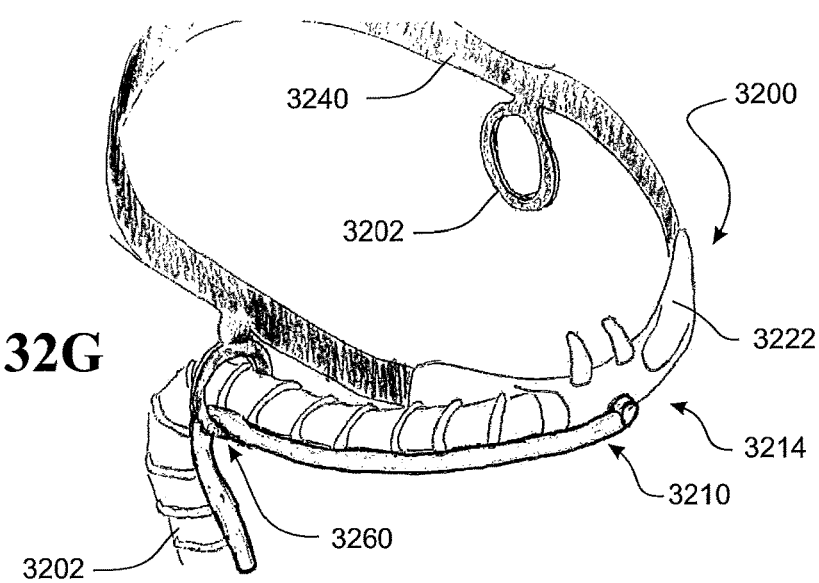
Figure 32H:
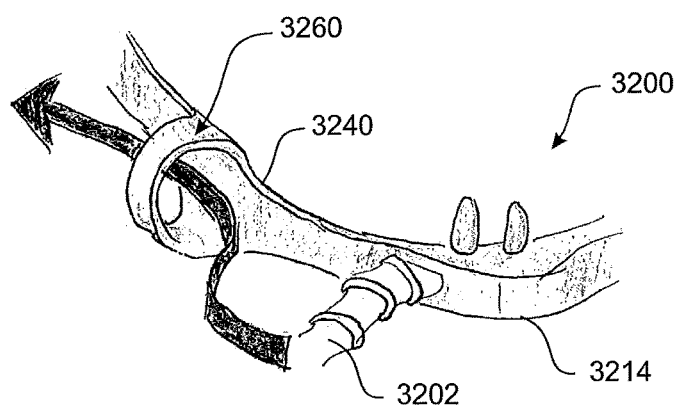
Figure 32I:
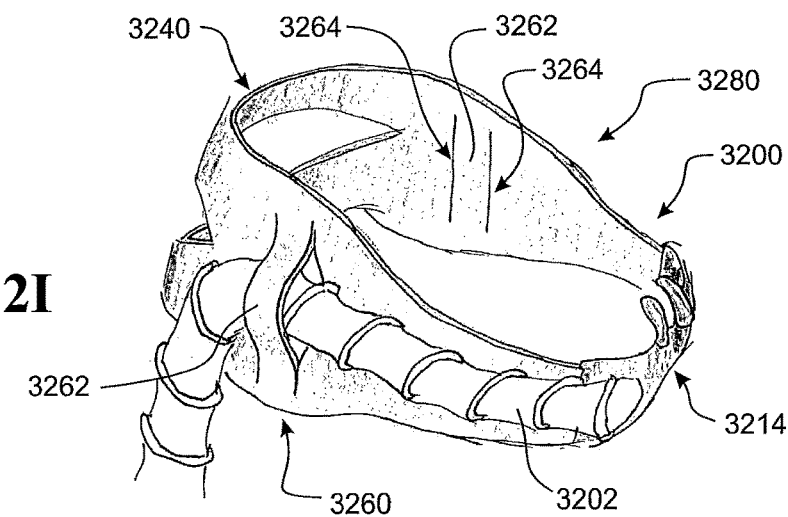

In some embodiments, the supply tube 3202 can be secured by a permanent securing device provided on a portion of the nasal cannula assembly 3200, such as the headgear strap 3240 or a side portion 3222 of the cannula 3214—especially on cannula designs having extended or large side portions 3222. For example, the securing device can be a permanent loop 3260 on the headgear strap 3240. Preferably, a permanent loop 3260 is present on each side of the headgear strap 3240 to permit routing of the supply tube 3202 to either side. The supply tube 3202 can be threaded through either loop 3260 to provide support and positioning of the supply tube 3202. The loop 3260 can be injection molded or die cut, for example, or formed by any other suitable process. FIG. 32G illustrates a loop 3260 that is a hoop or ring positioned generally in the plane of the headgear strap 3240. The illustrated loop 3260 extends below the headgear strap 3240; however, it could also be provided above the headgear strap 3240. Preferably, the loop 3260 can rotate relative to the headgear strap 3240 to better accommodate the supply tube 3202 and any other component, such as a pressure measurement tube 3210, for example. The headgear strap 3240 could include a portion that spaces the loop 3260 away from the circumferential portion of the headgear strap 3240 to facilitate rotation of the loop 3260. FIG. 32H illustrates a molded-in loop 3260 that is positioned beside the headgear strap 3240. FIG. 32I illustrates a loop 3260 that is formed by a section 3262 of the headgear strap 3240 that is defined by a pair of spaced-apart slits 3264, which allows the section 3262 to be pulled away from adjacent portions of the headgear strap 3240 to form a passage therewith. The slits 3264 can be substantially parallel with one another and oriented in a substantially vertical direction or along an axial direction of the perimeter defined by the headgear strap 3240, as illustrated. However, in other arrangements, the slits 3264 can be non-parallel and oriented in other directions.

Figure 32J:
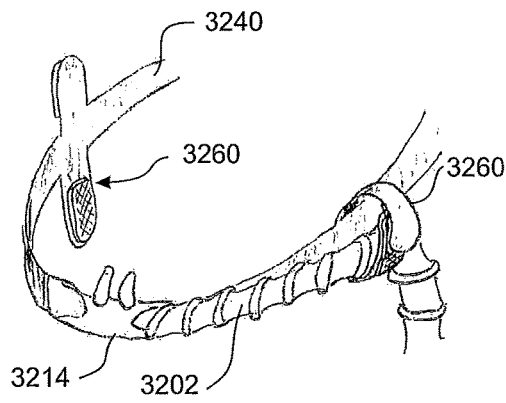
Figure 32K:
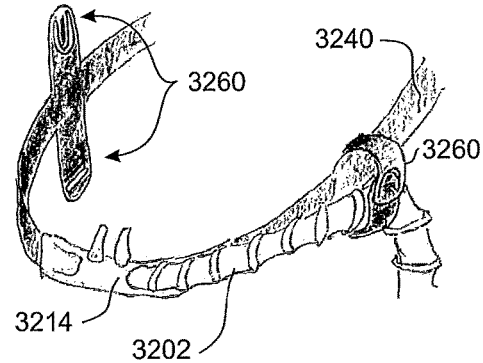
Figure 32L:
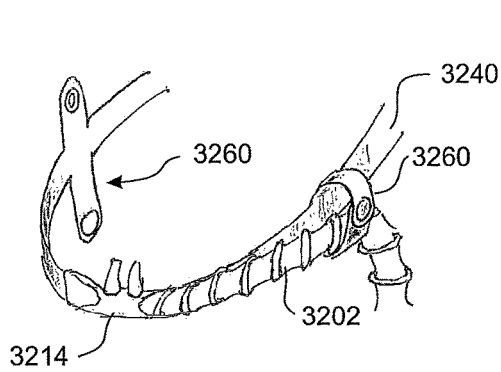
Figure 32M:
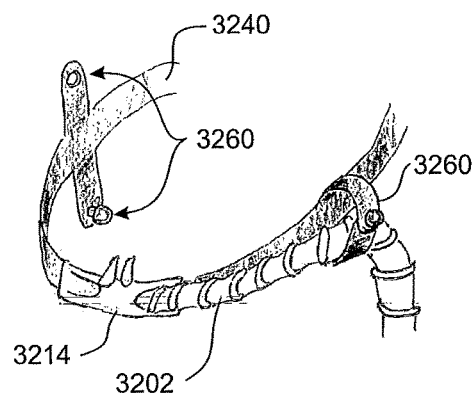
Figure 32N:
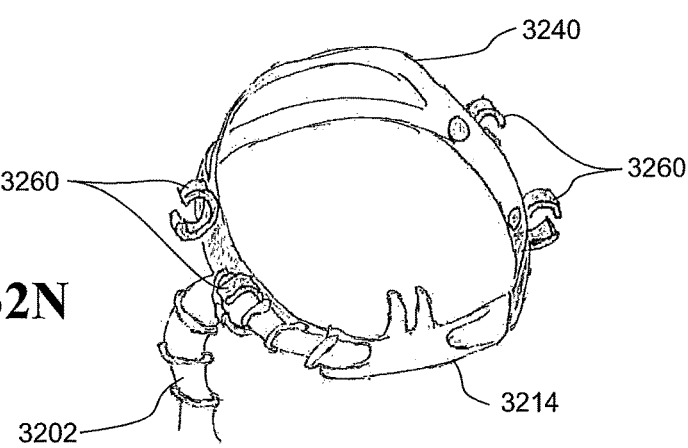

In some embodiments, the loop 3260 can be a breakable loop to facilitate positioning of the supply tube 3202 within the loop 3260. Preferably, at least one breakable loop 3260 is present on each side of the cannula assembly 3200, such as on the headgear strap 3240. The supply tube 3202 can be clipped into either loop 3260. The loop 3260 could be breakable via any suitable arrangement, such as hook-and-loop fastener (FIG. 32J), die cut or otherwise formed tab-and-slot arrangement (FIG. 32K), popper domes or other snap-fit arrangement (FIG. 32L), injection-molded or otherwise formed mushroom-head-and-recess arrangement (FIG. 32M), or push-in clips (FIG. 32N), for example. The loop 3260 can be broken at any location, such as in a central portion of the loop 3260 or at the headgear strap 3240. Preferably, any of these arrangements for managing the supply tube 3202 can be used or modified to managing a pressure line 3210 in addition to or in the alternative to the supply tube 3202.

The circuit delivering air or gas to the patient interface (e.g., cannula or manifold) is reasonably long to reach between the flow source and the patient. The mass of this long circuit, without some circuit supporting device causes the load to be transferred directly to the patient interface. The load of the circuit can cause the cannula to move and be pulled from the patient's nares thereby interrupting therapy. It also can be uncomfortable for the patient to support the load of the circuit directly on the face. The circuit includes the supply tube described herein (e.g., supply tube 50 of FIG. 1) and can also include other conduits (e.g., main delivery conduit of FIG. 1 and/or pressure line 872 of FIG. 8A). To address this issue, several techniques or arrangements can be used to support at least a portion of the load or mass of the circuit, as described in connection with FIGS. 33A-S.

Figure 33A:
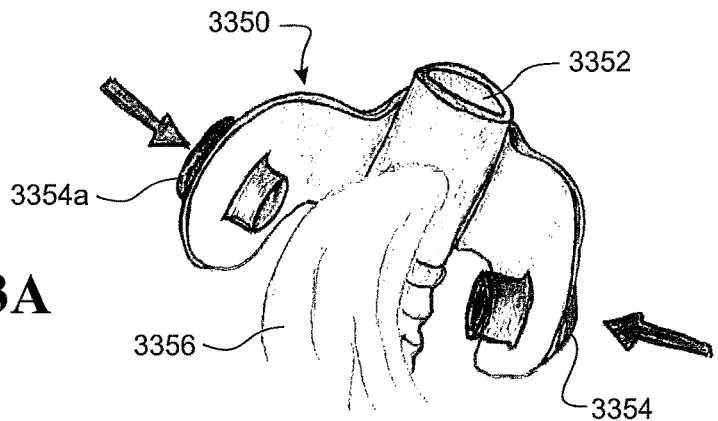
FIGS. 33A-S illustrate example embodiments of arrangements for providing support to the supply tube.
Figure 33B:
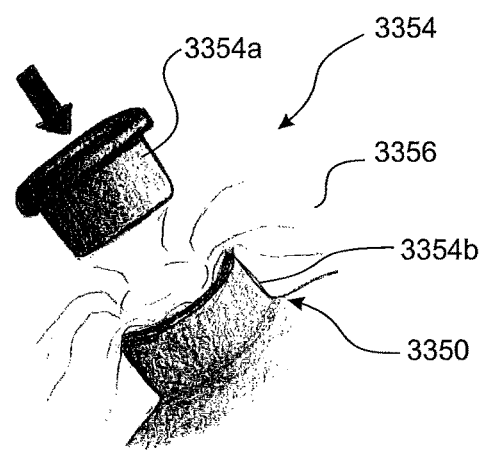

FIGS. 33A-H illustrate support devices 3350 that can be coupled to a portion of the circuit, generally 3352, to the patient's clothing, bed sheets or other fabric or thin material and use that to support at least a portion of the load or mass of the circuit 3352. FIGS. 33A and 33B illustrate a support device 3350 affixed to the circuit 3352 by any suitable arrangement and comprising a two-part dome 3354 that sandwiches the bedding/clothing 3356 between the parts 3354*a, b* when assembled, such as via a snap-fit arrangement.

Figure 33C:
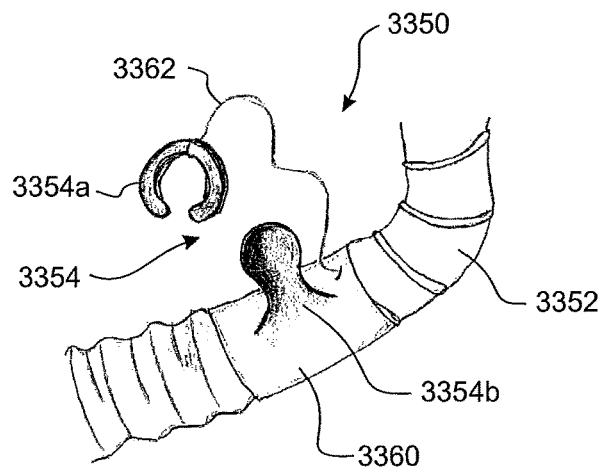
Figure 33D:
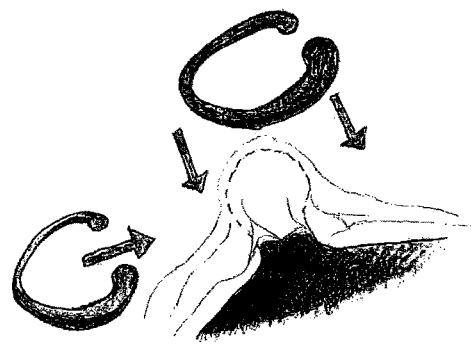
Figure 33E:
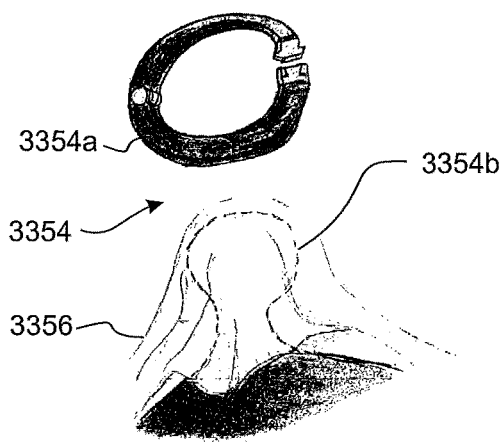
Figure 33F:
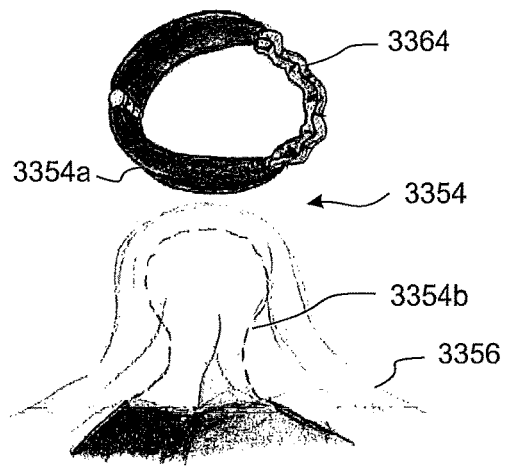

With reference to FIGS. 33C-F, the support device 3350 can comprise a clip-and-post (e.g., mushroom head) arrangement 3354 that sandwiches the bedding/clothing 3356 between the clip 3354*a* and post or mushroom head 3354*b* when the clip 3354*a* is assembled to the post or mushroom head 3354*b*. Either portion of the support device 3350 can be affixed to the circuit 3352 by any suitable arrangement. In the illustrated arrangement, the post or mushroom head 3354*b* is secured to the circuit 3352 by a sleeve 3360. If desired, the clip 3354*a* can be coupled to the sleeve 3360 by a tether 3362. The clip 3354*a* can be of any suitable arrangement to be capable of secure engagement and disengagement with the post or mushroom head 3354*b* with clothing, sheeting or other fabric or material 3356 therebetween. For example, FIG. 33C illustrates a simple C-shaped resilient clip 3354*a*. FIG. 33D illustrates a clip 3354*a* that is capable of being engaged to the post or mushroom head 3354*b* in a radial or axial direction relative to the post or mushroom head 3354*b*. FIG. 33E illustrates a hinged clip 3354*a*, which can have a snap-fit arrangement or other mechanism to couple the unhinged ends of the clip 3354*a*. FIG. 33F illustrates a clip 3354*a* having an elastic retention portion 3364. The clip 3354*a* is illustrated as a hinged clip, but could also be unhinged. Alternatively, the clip 3354*a* could be entirely replaced with an elastic member.

Figure 33G:
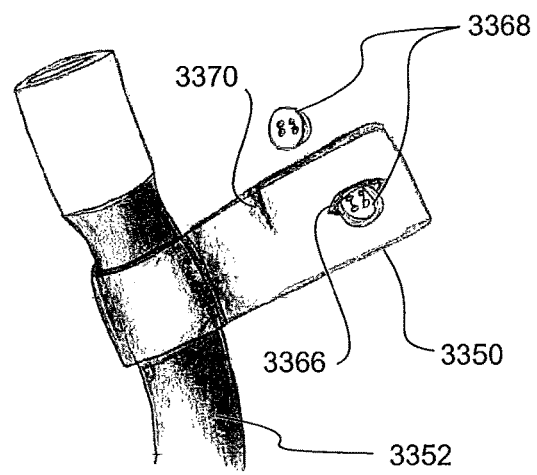

In some embodiments, with reference to FIG. 33G, the support device can comprise a tag 3350 that is coupled to the circuit 3352 and includes a button hole feature 3366 that can be attached to an existing button 3368 of a patient's shirt or other article of clothing. Alternatively, a specific garment or other piece of material could be provided with a specific button 3368 to engage the button hole feature 3366. The tag 3350 could feature a tear-away feature (e.g., a slit, score line or weakened portion) 3370 that would tear before the patient's shirt or other article supporting the button 3368.

Figure 33H:
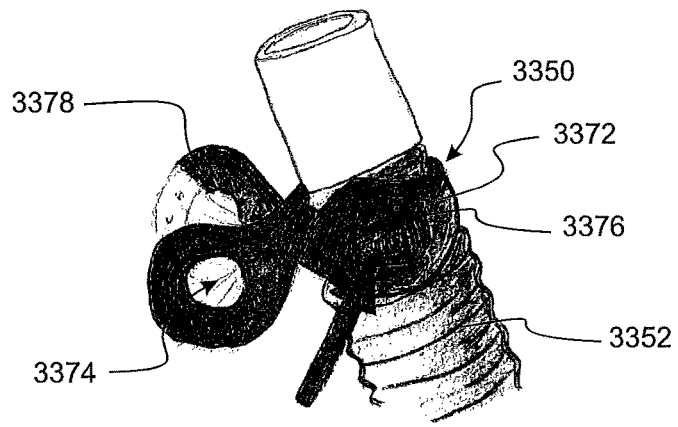

With reference to FIG. 33H, the support device can comprise a clip 3350 having a portion 3372 that surrounds the circuit 3352 and a portion 3374 that can grip bedding, clothing or other fabric or thin material. In the illustrated arrangement, the clip 3350 has two arms that cross one another and are movable relative to one another between an open position and a closed position. The portion 3372 is defined by the portion of the arms that extend between the intersection or connection to one another and the point at which they cross one another. The portion 3374 is defined by the end portions of the arms. The clip 3350 can include finger grip portions 3376 that facilitate squeezing of the clip 3350 to move the clip to the open position. In addition, the clip 3350 can include retention, grip or friction-enhancing features or traction elements 3378 (e.g., knobs or protrusions) that assist in inhibiting the bedding, clothing or other material from being released from in between the arms of the clip 3350 when in the closed position.

Figure 33I:
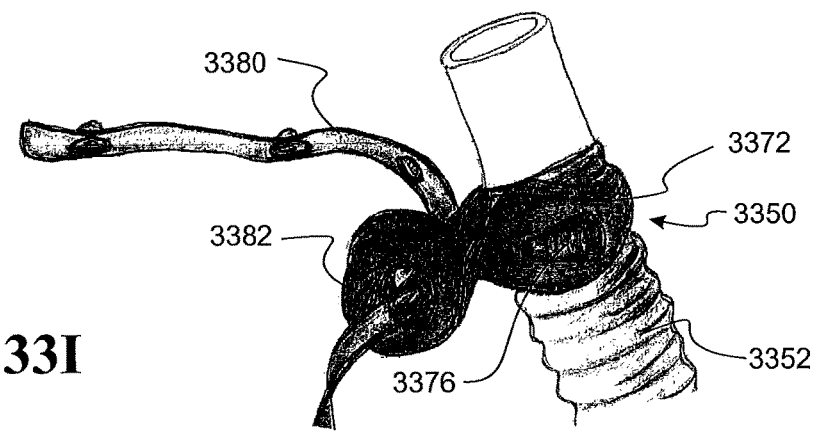

In other arrangements, the support device can comprise a lanyard 3380 that can be placed around the patient's neck or another body part or object and used to support at least a portion of the circuit 3352. With reference to FIG. 33I, the lanyard 3380 can be used in combination with the clip 3350 of FIG. 33H. For example, the clip 3350 can be a dual use clip that has at least one opening or hole 3382, such as in the centers of the arms within the portion 3374 so it can also be used to thread the lanyard 3380 and/or another supporting device through it. The lanyard 3380 can be used instead of or in combination with clipping the patient's clothing, bedding or another piece of material.

Figure 33J:
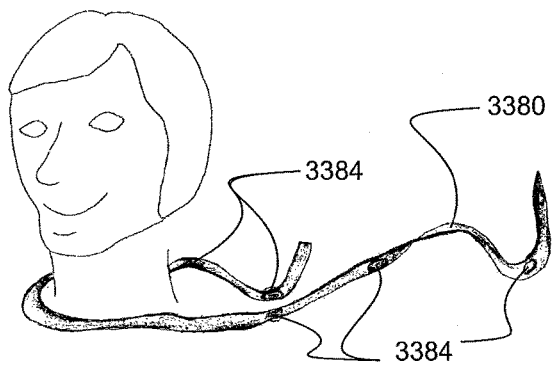

The lanyard 3380 can be of any suitable construction. For example, with reference to FIG. 33J, the lanyard 3380 can include a series of snaps, hook-and-loop fasteners or other fasteners 3384 that could be used to adjust the length of the lanyard 3380. In addition, the fasteners 3384 could act as a breakaway feature to avoid or minimize discomfort or injury to the patient should the lanyard 3380 get caught on something.

Figure 33K:
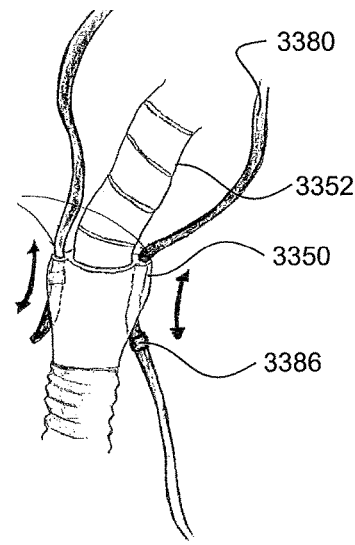

With reference to FIG. 33K, the lanyard 3380 could be centered about the circuit 3352 with attachment points on opposing sides of the circuit 3352. The ends of the lanyard 3380 can be received within a support device 3350, which can surround the circuit 3352. Preferably, the ends of the lanyard 3380 pass through the support device 3350 in a substantially axial direction relative to the circuit 3352, which assists in holding the support device 3350 upright with the axis of the circuit 3352 generally in a vertical orientation or generally aligned with the patient's body and reduce or prevent awkward side angles when hanging from the patient's neck. In the illustrated arrangement, the support device 3350 is a connector between the supply tube and the main delivery conduit. Sliders or other retention devices 3386 on the lanyard could be used for adjustment and to allow asymmetric positioning.

Figure 33L:
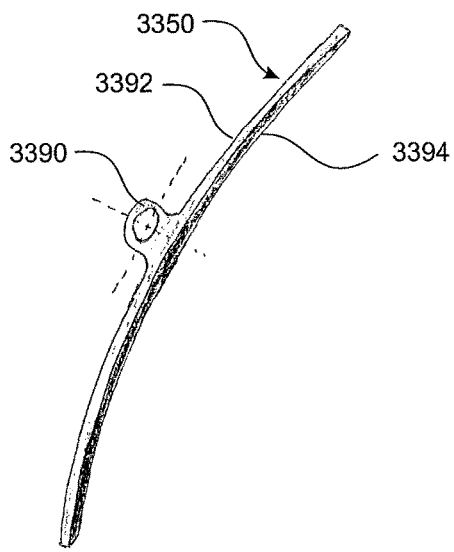
Figure 33M:
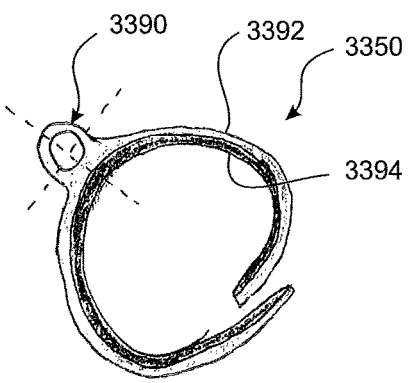

With reference to FIGS. 33L and 33M, the support device can comprise a band 3350 that can engage the circuit and also be attached to the body of the patient or equipment near the patient. The band 3350 can be permanently connected to the circuit or can be removable from the circuit. In one arrangement, the band 3350 is a fabric coated thin metal, plastic or combination thereof band that is fixed to the circuit, such as with a loop 3390 that surrounds the circuit. The band 3350 can be deformable such that it can be secured to the patients arm, bed frame or other object. The band 3350 can have a first layer 3392 that defines the loop 3390 and a second layer 3394 that comprises a deformable material such that the band 3350 can be deformed and substantially hold its shape. In another arrangement, the second layer 3394 comprises a bi-stable spring or similar element that can be straightened and hold its shape, but once bending of the spring or other element is initiated, it tends to collapse into a loop or roll. Such an arrangement can be opened to allow fitment and then collapsed about the patient's arm, a bed frame or another suitable object and, once fitted, can provide enough retention force to hold the circuit.

With reference to FIGS. 33N-P, the support device can comprise a fastener 3350 having a first portion 3350a affixed to the circuit 3352 and a second portion 3350b that can be affixed to another object, such as a bed frame or other equipment. The portions 3350a and 3350b can be coupled to support the circuit 3352. In the arrangement of FIG. 33N, one portion 3350a of a hook-and-loop fastener 3350 is affixed to the circuit 3352, such as by surrounding the circuit 3352, and the other portion 3350b of the hook-and-loop fastener 3350 is affixed (e.g., via adhesive) to an object, such as a bed frame or other equipment. The two portions 3350a and 3350b can be coupled to one another to provide support to the circuit 3352. In the arrangement of FIG. 33O, the portion 3350b includes a non-adhesive section that can loop over the circuit 3352 and then be connected to the adhesive section to provide a more secure support. In an alternative arrangement, the portion 3350a on the circuit 3352 can be omitted. In the arrangement of FIG. 33P, the portion 3350b can be formed into or provided on an armband 3395 that can be wrapped around the patient's arm (or another object). The armband 3395 could be an endless loop or, as illustrated, can be breakable or separable and selectively fixed in a loop by a suitable fastener 3396 (e.g., hook-and-loop fastener).

With reference to FIGS. 33Q and 33R, the support device 3350 can be or comprise an over the shoulder support that would loop over the patient's shoulder to support the circuit 3352. One portion 3350a of the support 3350 can comprise a flexible or formable generally U-shaped section defining an opening that can receive and engage the circuit 3352. Another portion 3350b of the support 3350 can comprise a flexible or formable generally U-shaped portion that can receive and engage the patient's shoulder or upper arm.

With reference to FIG. 33S, the support device 3350 can be a portion of or be supported by the headgear strap 3340 or other cannula-supporting device or arrangement. With such an arrangement, the headgear strap 3340 can be utilized to support at least a portion of the weight of the circuit 3352. For example, the support device portion 3350 of the headgear strap 3340 can extend directly over and rest upon the top of the patient's head and then continue down to a clip 3398 or similar to engage the circuit 3352 such that the support device portion 3350 of the headgear strap 3340 assists in supporting the weight of the circuit 3352.

Some embodiments involve retention assemblies for use with or integrated with the nasal cannula assemblies. In many existing systems, the cannula is retained on the face using a single elastic head strap or held onto the face by looping the supply tube(s) over the ears. In some such designs, the cannula is not secured to the patient's face in an ideal manner and may allow shifting or movement from the desired position. Many factors can cause the cannula to be moved from its ideal positioning, some of which include the weight of the air or gas supply circuit may cause the cannula to hang in that direction, the cannula will slide as the patient moves around during sleep, and the small surface area of single elastic head straps may not be sufficient to secure the cannula. Over time the head strap may slide down the patient's head, further reducing the security of the head strap on the face. Thus, with some existing systems, the cannula can easily become unsecure, especially over long periods of time. Furthermore, cannula assemblies that rely on the ears to hang the supply tube(s) usually have the supply tube(s) taped to the patients face as a secondary means of securement. This technique is time consuming and does not allow for easy readjustment.

Figure 34A:
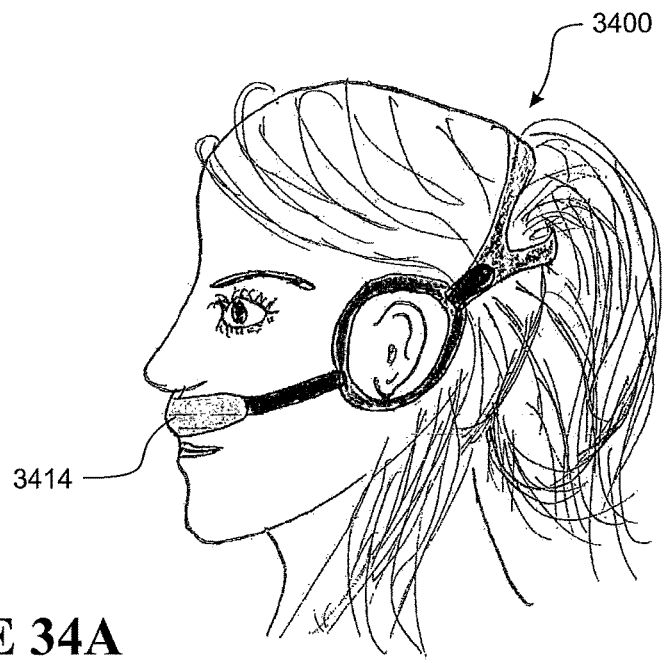
Figure 34B:
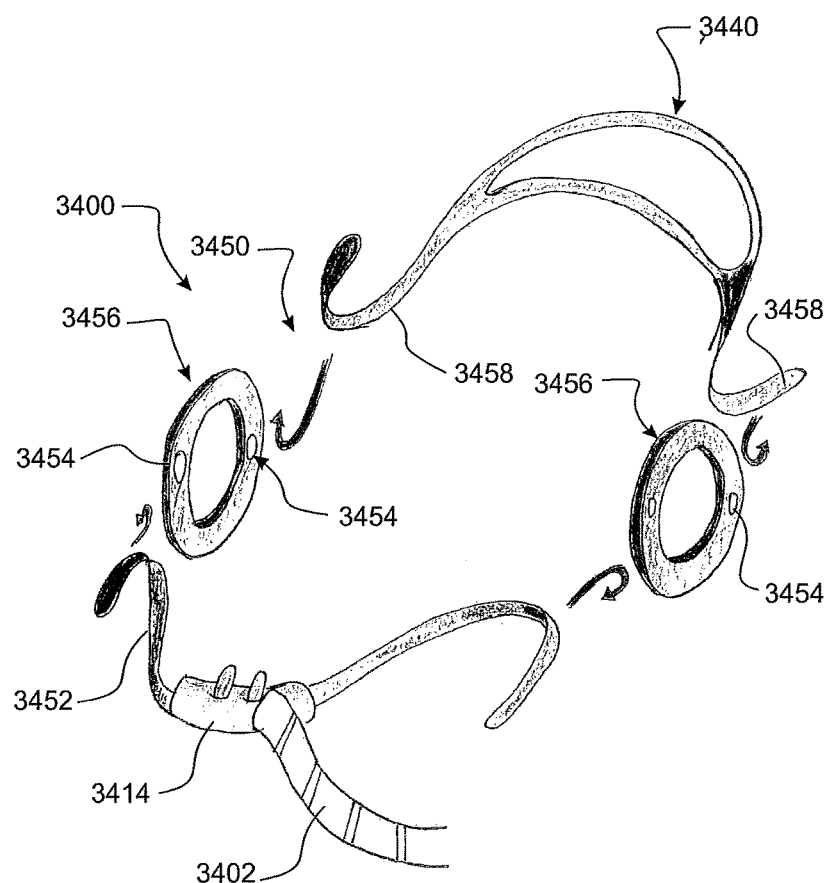

With reference to FIGS. 34A and 34B, a nasal cannula assembly 3400 includes a cannula 3414 and a retention arrangement 3450, which can be separate components or assemblies or can be integrated with one another. In the illustrated arrangement, hook-and-loop strips 3452 extend respectively from left and right sides of the cannula 3414. These hook-and-loop strips 3452 can be threaded thorough openings or slots 3454 located in annular or circular ear pads 3456. The ear pads 3456 may be made of any suitable material, which preferably provides a soft comfortable feel to the patient while being strong enough to cope with the force applied when the headgear strap 3440 is tightened. The shape of the ear pads 3456 can be annular (e.g., circular) or any other geometry which allows for an anatomical fit and, in at least some configurations, partially or completely surrounds a patient's ears.

The ear pads 3456 are then connected to the headgear strap 3440. The headgear strap 3440 also can have hook-and-loop strips 3458 coupled thereto or integrated therewith, which can be threading through additional openings 3454 of the ear pads 3456. The headgear strap 3440 can be of any suitable arrangement, such as a bi-varicated style strap and preferably is made from or incorporates a non-stretch material. In some configurations, the cannula assembly 3400 is supplied with one or more of the components pre-assembled. For example, three out of the four hook-and-loop strips 3452, 3458 threaded through the slots 3454 in the ear pads 3456. In such an arrangement, the patient or a caregiver would put on the cannula assembly 3400 by strapping it around the head ensuring that the ears are inside the hole of the ear pads 3456. The patient or a caregiver would then thread the open hook-and-loop strip (or strips, in other arrangements) through the ear pads 3456 and tighten until comfortable.

Advantageously, with such an arrangement, the cannula 3414 will be more secure on the patient's head than existing arrangements. For example, the patient's ears will inhibit or prevent the ear pads 3456 from sliding out of position and hence inhibit or prevent the cannula 3414 dislodging from its intended position. This is especially beneficial to a patient who is asleep, as natural body movements during sleep will not affect the delivery of therapy through the cannula 3414. The foam (or other material) ear pads 3456 may also provide more comfort to the patient as they act as cushions during the event a patient is sleeping on his or her side. The bi-varicated strap 3440 will also contribute to the improved security of the cannula 3414 by increasing the area over which the cannula 3414 is attached to the head. The increased surface area will inhibit or prevent the headgear strap 3440 from sliding down and reducing the security of the cannula 3414 on the face.

With reference to FIGS. 34C and 34D, a cannula retention arrangement 3450 incorporates friction pads 3460 into the headgear strap 3440. The friction pads 3460 preferably are positioned to sit on the patient's cheeks, or on portions of the face near the cheeks, and direct a line of action or force from the headgear strap 3440 away from the ears. In some arrangements, the friction pads 3460 are made from, or include, a soft material that allows for a comfortable fit on the face while providing enough friction to allow the headgear strap 3440 to change direction relative to a lateral direction or relative to lateral side portions 3422 of the cannula 3414 or lateral portions 3440*a* of the headgear strap 3440. The friction pads 3460 preferably are of a thickness that allows the cannula 3414 to bridge slightly from the skin of the patient, creating less pressure on the skin. Such pads 3460 would have the added benefit of preventing the cannula 3414 from moving on the face as a larger frictional force would need to be overcome for movement to begin. The pads 3460 can be affixed to the headgear strap 3440, if desired, by any suitable arrangement, such as sewing, adhesives, for example.

Advantageously, such an arrangement for attaching the cannula 3414 to the head of the patient is more secure than many existing techniques and arrangements. For example, the friction pads inhibit or prevent the cannula 3414 from easily moving on the face, as is experienced by many existing arrangements. Furthermore, by elevating the cannula 3414 from the skin with the aid of the thickness of friction pads 3460 will reduce the pressure felt by the patient on the upper lip, thereby making the cannula 3414 more comfortable to wear. Comfort can also be increased by using the friction pads 3460 to spread the force of the headgear strap 3440 over a larger area on the face, which will inhibit or prevent localized pressure marks on the skin. By directing the line of action of the headgear strap 3440 away from the ears, a more comfortable position of the headgear strap 3440 can be achieved because the ears will not be compressed by the force of the headgear strap 3440 going over them.

With reference to FIG. 34E, a cannula assembly 3400 includes a cannula 3414, a supply tube 3402 and a retention arrangement 3450. The retention arrangement 3450 straps onto the head using the ears as anchor points during the setup process. Preferably, the headgear strap 3440 is divided into two portions 3440*a* and 3440*b*, which are connectable to one another by a suitable fastening arrangement, such as a hook-and-loop fastener 3466, for example. Preferably, the fastening arrangement 3466 is adjustable, such that the circumferential length of the headgear strap 3440 can be adjusted. Preferably, each portion 3440*a*, 3440*b* of the headgear strap 3440 includes an ear loop 3456 that includes an opening that can be placed over the ear of a patient. In use, the cannula assembly 3400 is applied to the patient by first hanging the assembly 3400 on the ears via the ear loops 3456 and positioning the prongs 3405 of the cannula 3414 in the correct position. Once the cannula 3414 is in place, the fastener arrangement 3466 can be used to couple the two portions 3440*a*, 3440*b* of the headgear strap 3440. Preferably, the fastener arrangement 3466 permits the circumference of the headgear strap 3440 to be adjusted to a suitable tightness such that the headgear strap 3440 supports the cannula 3414 without substantially relying on engagement of the ear loops 3456 with the ears of the patient. In some arrangements, once the headgear strap 3440 is adjusted (e.g., tightened), the ear loops 3456 do not contact and/or apply any significant force to the ears of the patient. Preferably, the headgear strap 3440 (which can include the ear loops 3456) is made from or incorporates a material which stretches slightly to provide a relatively constant force on the face when the headgear strap 3440 is adjusted, such as by fastening the fastener arrangement 3466. In some arrangements, the loop section of the hook-and-loop fastener 3466 is positioned closer to the head than the hook portion in order to prevent the hook material sticking to or grabbing the hair of the patient. In some arrangements, the material used to make the headgear strap 3440 is thick enough to allow the cannula 3414 to hang on the ears of the patient when put through the ear holes 3456.

Advantageously, such an arrangement for attaching the cannula 3414 is more secure than many existing techniques and arrangements. For example, the ears will inhibit or prevent the headgear strap 3440 from moving out of position and inhibit or prevent the cannula 3440 dislodging from its desired position. This is especially beneficial to a patient who is asleep, as natural body movements during sleep will not affect the delivery of therapy through the cannula 3414. The ear loops 3456 allow for easier application of the cannula assembly 3400 and the cannula 3414 can be positioned without the headgear strap 3440 being secured by hanging it from the patient's ears. The caregiver or patient can move the cannula 3414 around until the correct positioning achieved and then easily secure the headgear strap 3440 using the fastening mechanism 3466. Advantageously, the headgear strap 3440 will inhibit or prevent the cannula 3414 from sliding down as a larger surface area of the strap 3440 is in contact with the head and the ear loops 3456 will act as an anchor point should the headgear strap 3440 be moved down by an external force.

Figure 34F:
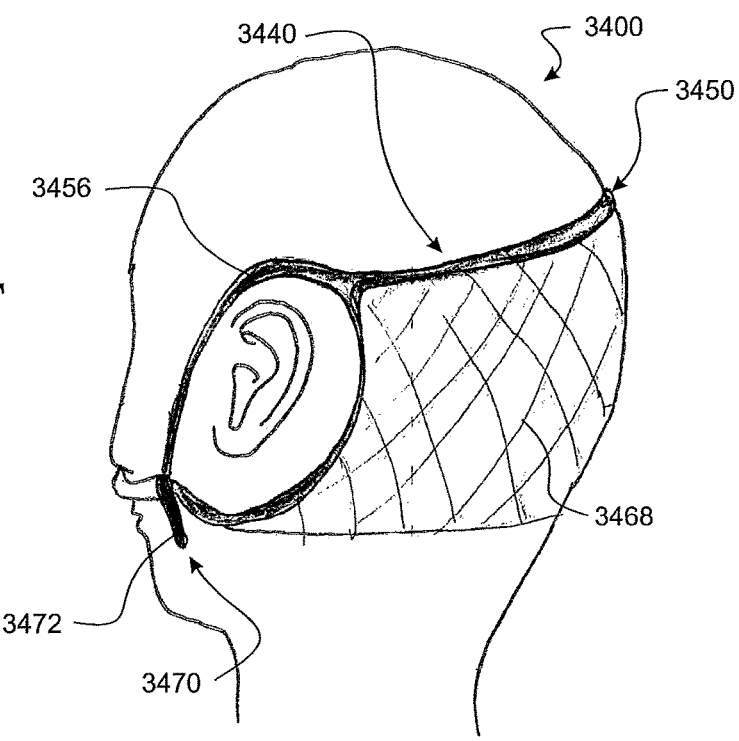

With reference to FIG. 34F, a cannula assembly 3400 includes a retention arrangement 3450, which comprises a headgear strap frame 3440 and a flexible mesh portion 3468 supported by the frame 3440. In some arrangements, at least a portion of the frame 3440 can be constructed from a substantially non-stretchable material or can otherwise be constructed to be substantially non-stretchable. The mesh portion 3468 can be in the form of a net and preferably is constructed from an at least somewhat stretchable material. Such an arrangement creates a hybrid stretch/non-stretch headgear that can be applied by sliding it over the head and positioning until the ears are within openings of ear loops 3456 of the frame 3440. The ear loops 3456 can partially or completely surround the ears of the patient. The frame 3440 can be adjusted using an adjustment mechanism 3470, which can include an adjustment tab 3472 that is utilized to shorten a circumferential length of the mesh portion 3468 of the retention arrangement 3450. In such an arrangement, a portion of the ear loops 3456 to which the mesh portion 3468 is attached (e.g., a rearward portion) can be constructed from a stretchable material or can at least be flexible relative to other portions of the frame 3440 to facilitate adjustment of the mesh portion 3468. In an alternative arrangement, the frame 3440 could also be made from an at least somewhat stretchable material. In such an arrangement, the adjustment mechanism 3470 could be optionally omitted because the stretch would allow for the retention arrangement 3450 to fit a multiple of patient sizes.

In at least some configurations, the flexible mesh portion 3468 conforms to the patient's head shape and increases the friction and surface area between the retention arrangement 3450 and patient. As a result, a much more secure fit is provided. This arrangement for securing the cannula 3414 is much more secure compared to many existing methods and arrangements. The large area in contact with the head will provide friction which will resist movement of the cannula during normal activity or motion during sleep. In addition, by spreading the force over a large area, the illustrated arrangement tends to reduce localized pressure on the back of the head as is experienced by many current methods and arrangements.

Figure 34G:
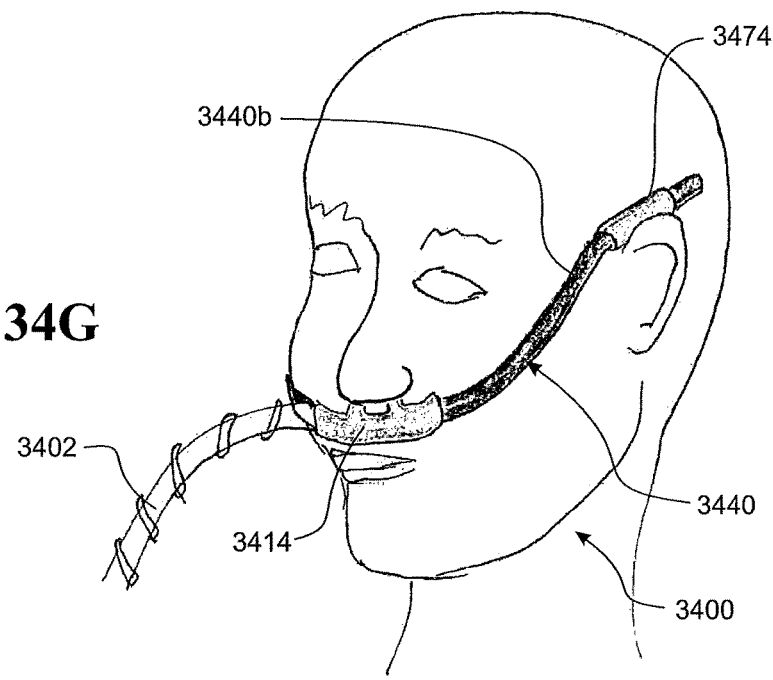

With reference to FIGS. 34G and 34H, a cannula assembly 3400 includes a cannula 3414, a supply tube 3402 and a retention arrangement 3450. In the illustrated arrangement, the cannula 3414 is mounted to a generally U-shaped frame 3440 that is configured to fit the face of a patient in a manner similar to an eyeglass. Thus, preferably, the frame 3440 supports the cannula 3414 and includes rearwardly-extending ear stem portions 3440a, 3440b that extend along the sides of the patient's head, preferably extending at least to the patient's ears. The frame 3440 preferably has substantial rigidity to hold its shape, but has enough flexibility to allow the movement of the ear stem portions 3440a, 3440b apart from one another such that the frame 3440 is suitable for a range of head sizes. In a preferred arrangement, the ends of the ear stem portions 3440a, 3440b (or portions above the ears) are generally straight and the frame 3440 relies on the resiliency of the frame 3440 to secure the frame 3440 to the patient's face. Such an arrangement can fit a wider variety of face sizes. However, in an alternative arrangement, the frame 3440 can include portions that wrap at least partially around (e.g., behind) the ears. Optional pads 3474 can be provided where the frame 3440 contacts the head (e.g., above the ears). Advantageously, the cannula assembly 3400 is easily applied and removed with one hand, such as in a manner similar to a pair of glasses. Furthermore, because there is no strap applying a force behind the head, there will be less of an opposing force on the upper lip to cause discomfort.

With reference to FIGS. 34I and 34J, a cannula assembly 3400 includes a cannula 3414, a supply tube 3402 and a retention arrangement 3450. In the illustrated arrangement, a pair of adhesive pads 3480 is mounted on the patient with one pad 3480 applied to each cheek. The cannula 3414 is attached to the adhesive pads 3480 by any suitable arrangement. In the illustrated arrangements, the cannula 3414 is attached to the pads 3480 by an adjustable and removable system, so that the position and force of the cannula 3414 on the face can be adjusted or fine-tuned after the adhesive of the pads 3480 has set. Advantageously, with such an arrangement, the cannula 3414 can be removed temporarily without removing the adhesive pads 3480. The adjustable systems can be of any suitable arrangement, such as utilizing a hook-and-loop fastener 3482 (FIG. 34I) or other reusable fastener that allows the pad 3480 to be adjustably coupled to the cannula 3414. With reference to FIG. 34J, a ratchet-type adjustable fastener 3484 can be used to secure the pads 3480 to the cannula 3414 in an adjustable manner. The ratchet-type adjustable fastener 3484 can be integrated with the pads 3480 and/or cannula 3414, as illustrated, or can be a separate assembly or separate components that are coupled to the pads 3480 and/or cannula 3414. Advantageously, the use of adhesive pads 3480 means there is no strap applying a force behind the head, so there will be less of an opposing force on the upper lip to cause discomfort.

Figure 34K:
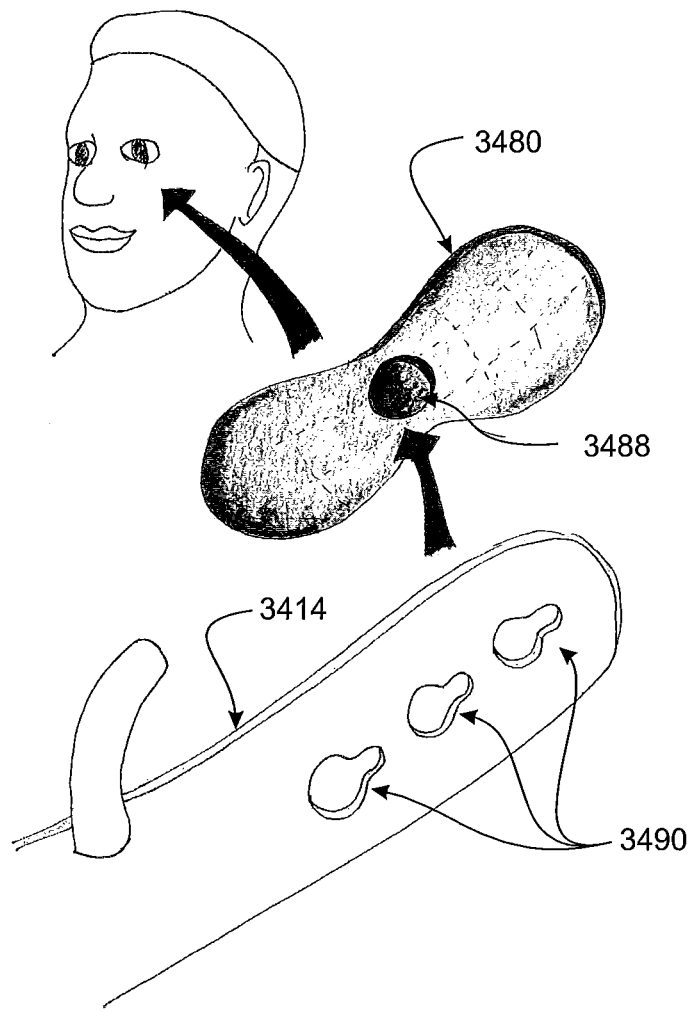

With reference to FIG. 34K, an alternative adjustable fastener 3486 is illustrated for coupling the cannula 3414 to the pads 3480 in an adjustable manner. However, in other arrangements, the fastener 3486 can have a single position relative to the cannula 3414 and any adjustment can be addressed by placement of the pads 3480 on the patient. Preferably, the pads 3480 include a post or knob 3488 that clip into openings or notches 3490 on the cannula 3414. This arrangement could also be reversed. The knobs 3488 may be of any shape as long as the notches 3490 in the cannula 3414 are of a complimentary design. The shape of these pads 3480 can be of any suitable arrangement such that they conform to the facial geometry. The illustrated pads 3480 are generally hourglass-shaped. However, other suitable shapes can also be used. The notches 3490 in the cannula 3414 allow for adjustment on the face. To increase the force of retention, notches 3490 closer to the prongs 3405 can be clipped into the knob 3488 on the adhesive pads 3480. Any suitable number of notches 3490 can be provided to allow a range of adjustment forces and/or fit a range of head sizes.

Advantageously, such an arrangement removes or reduces localized pressure that often present with the use of a tightened strap. In addition, it also reduces or prevents marking on the skin from a headgear strap being worn for long periods of time. It is also easier to apply and remove the cannula 3414 because no headgear strap needs to be passed over the head. This is especially beneficial for a patient who is lying on their back.

Figure 35A:
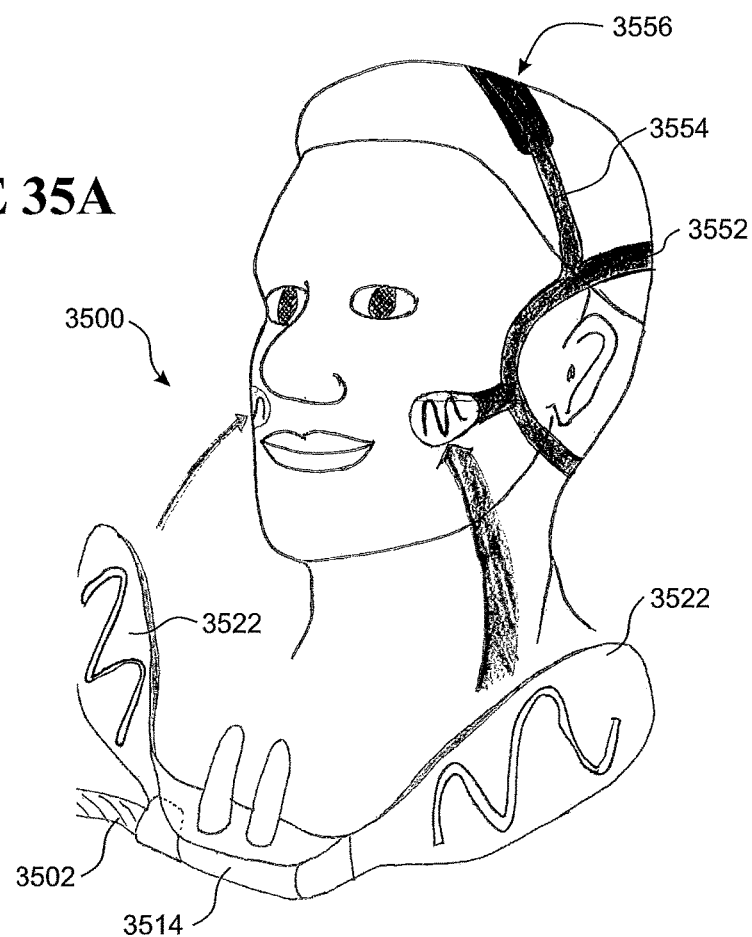
FIGS. 35A-G illustrate example embodiments of retention arrangements for nasal cannula assemblies.

With reference to FIGS. 35A-D, in some embodiments, the nasal cannula assembly is a modular system that provides several different retention arrangements. Cannulas are used on patients in a range of different environments, from an intensive care unit (ICU), to a standard hospital ward, and to the home. In view of these different environments of use, a modular system in which the patient/caregiver may choose the form of retention used may be desirable. In some embodiments, a cannula assembly 3500 includes a cannula 3514, a supply tube 3502 and a retention arrangement 3550. The cannula 3514 comprises side portions 3522 of any suitable shape. In the illustrated arrangement, the side portions 3522 comprise enlarged, generally ovalized pads. The side portions 3522 can permit the cannula 3514 to be coupled to several types of retention arrangements 3550 by any suitable fastener, such as a hook-and-loop fastener, for example. In one arrangement, as shown in FIG. 35A, the cannula 3514 can be coupled to a halo-type headgear strap assembly 3540, which includes at least one strap 3552 extending around the side of the patient's head and a second strap 3554 that extends over the top of the patient's head. In some arrangements, as illustrated, the headgear strap assembly 3540 can include a pair of straps 3552 extending around the side of the head and may position one strap 3552 above the ear and the other strap 3552 below the ear. If desired, a pad can be provided on one or more of the straps 3552, 3554. The straps 3552, 3554 can include a suitable fastener, such as a hook-and-loop fastener 3556, for example, to permit the headgear strap assembly 3540 to be applied, removed or adjusted. The halo-type headgear strap assembly 3540 can include end portions that utilize the complementary portion of the fastener of the side portions 3522. This form of retention can be desirable for patients who are not compliant to the therapy. This larger, complex headgear can inhibit or prevent the cannula 3514 from moving on the face and further make it difficult to remove the cannula 3514 by pulling on it.

Figure 35B:
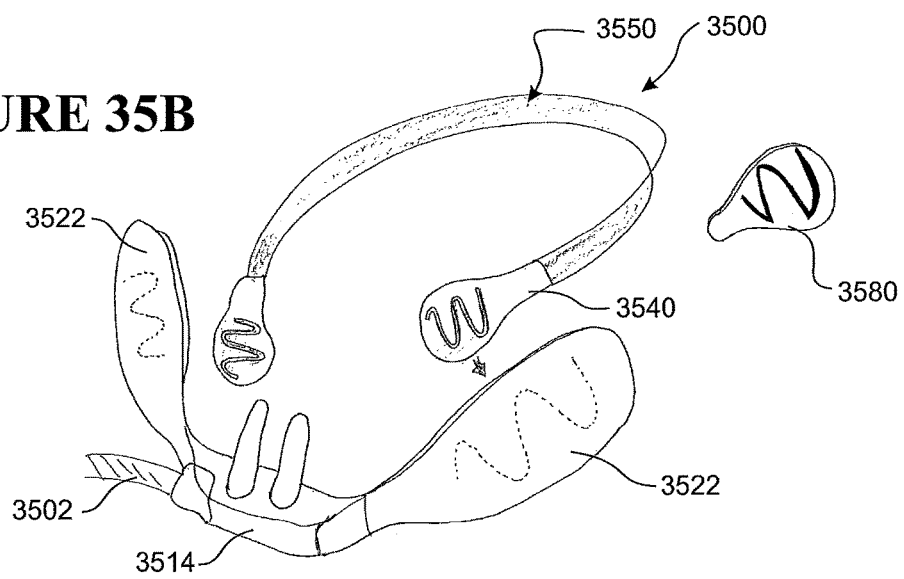

In other arrangements, as shown in FIG. 35B, the side portions 3522 allow the cannula 3514 to be coupled to either a headgear strap 3540 or a set of adhesive pads 3580, which can be the same as or similar to any other straps or pads disclosed herein, or can be of any other suitable arrangement. The headgear strap 3540 can include end portions that utilize the complementary portion of the fastener of the side portions 3522 and may be used for patients who do not want pads 3580 stuck to the cheeks or for those taking the therapy intermittently on a regular basis. The headgear strap 3540 can be a single size or adjustable. The adhesive pads 3580 can also utilize the complementary portion of the fastener of the side portions 3522 and can have a shape that is complementary to or compatible with the side portions 3522. This type of retention can be desirable for patients who are compliant or are on the therapy for an extended time.

Figure 35C:
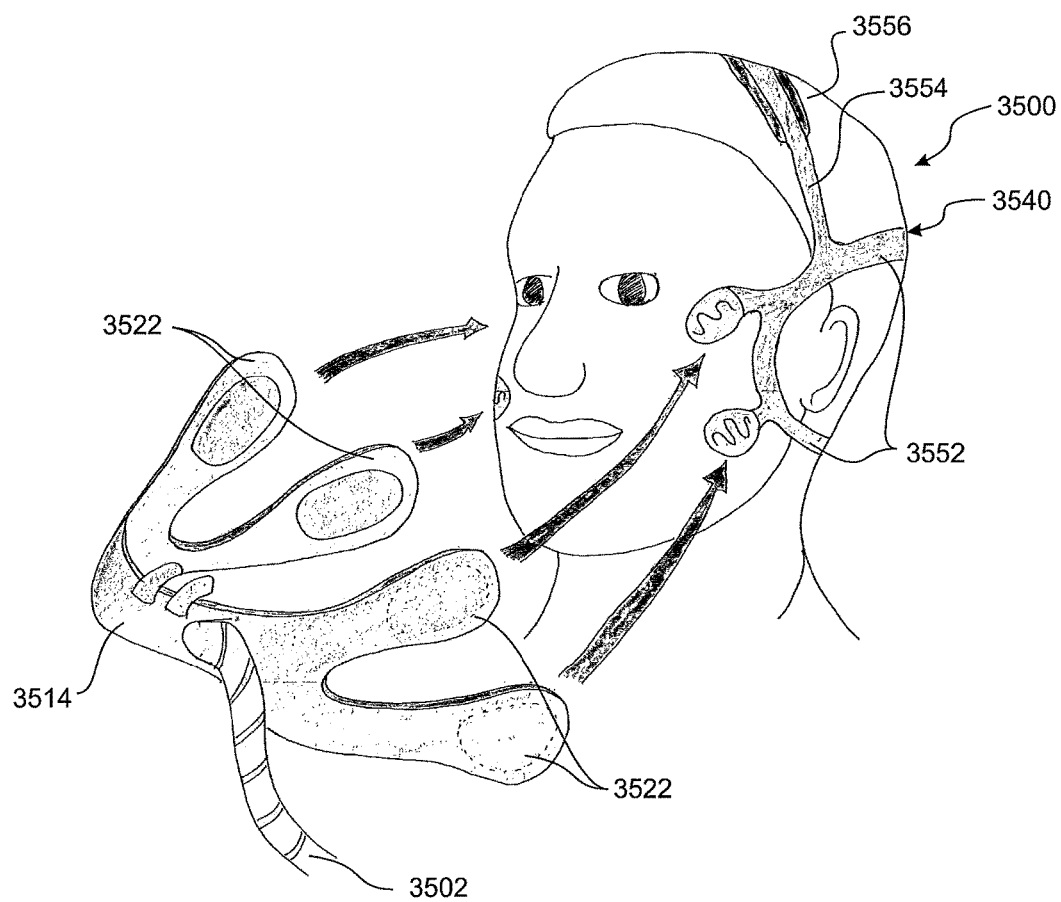
Figure 35D:
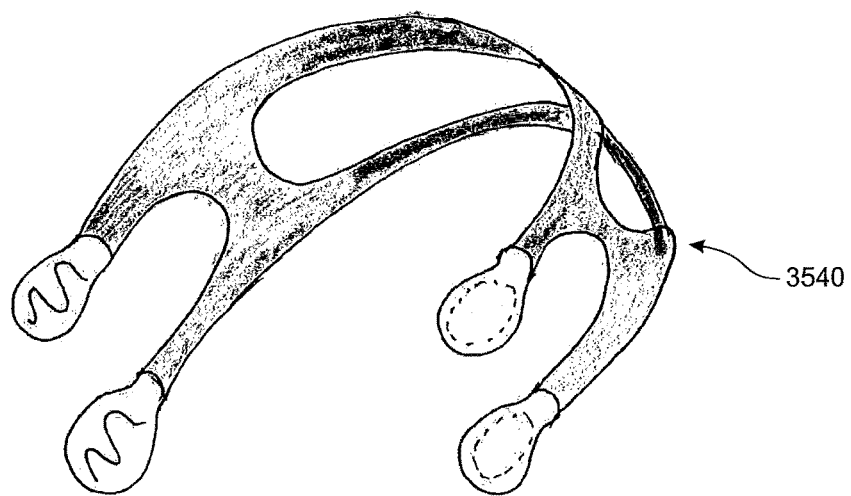

With reference to FIGS. 35C and D, each side of the retention arrangement 3550 and each of the side portions 3522 of the cannula 3514 can include more than one pad, such as two pads (a bivaricated arrangement), for example. Such an arrangement includes a total of four hook-and-loop (or other) fastener locations, which can reduce the load experienced by each fastener and can spread the load over a larger area of the patient's head for increased comfort. In addition, the spaced locations to which retention force is applied to the cannula 3514 can result in greater stability of the cannula 3514 on the patient's face. In the illustrated arrangement of FIG. 35C, the cannula 3514 is coupled to a halo-type headgear strap 3540, similar to the strap 3540 of FIG. 35A. As illustrated in FIG. 35D, a non-halo-type headgear strap 3540 can be employed, which can include two straps, or other numbers of straps, such as one or more than two straps, for example. This style of retention arrangement 3550 can also be applied to the face using adhesive pads or other suitable retention arrangements.

With many existing systems, if a patient inadvertently removes the cannula, the head strap is tightened further or the cannula is taped onto the face. The arrangements of FIGS. 35A-D provides the caregiver or patient the flexibility of choosing which form of retention is desired, needed or best suited to the specific situation. By using a desirable level of retention, comfort for the patient can be increased as the method for securing the cannula on a non-compliant patient will not need to be used on a compliant patient. Another benefit of the illustrated modular system is that it allows for users to choose which method of retention is more comfortable to them. This gives the patient/user more in control of the therapy and can result in greater patient/user satisfaction and compliance.

Figure 35E:
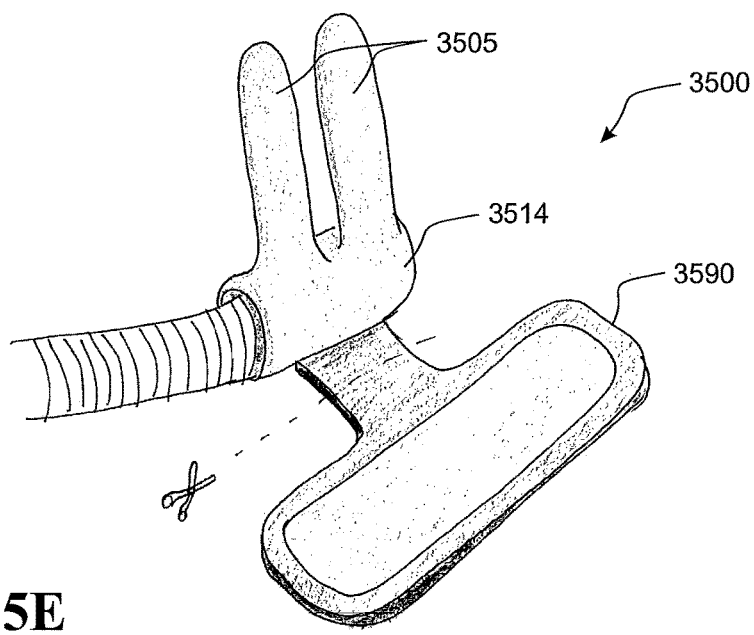
Figure 35F:
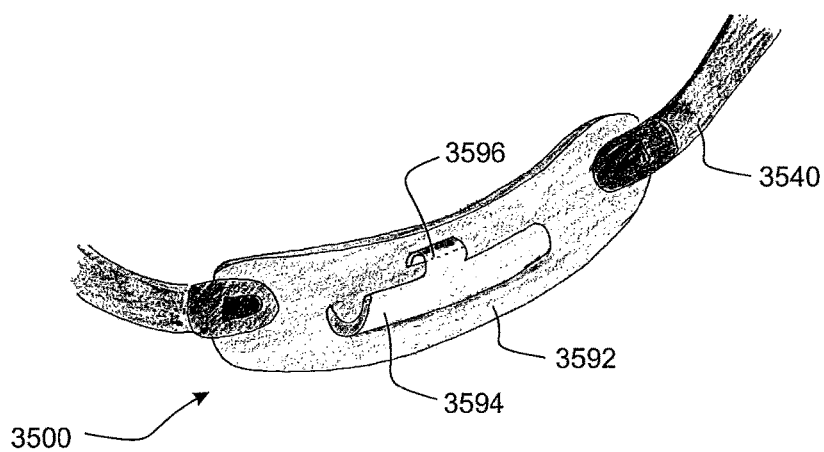
Figure 35G:
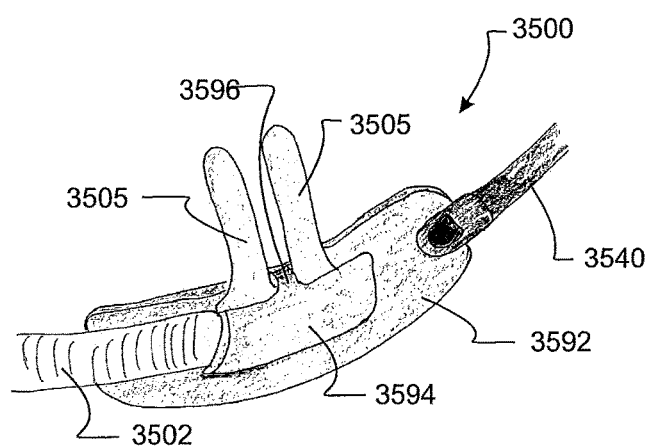

With reference to FIGS. 35E-G, another modular retention arrangement 3550 is illustrated. The illustrated retention arrangement 3550 comprises a light weight and relatively small cannula 3514, which can stick on the patient's nose via an adhesive pad or strip 3590. A supply tube 3502 is coupled to the cannula 3514 by any suitable arrangement, such as any of the coupling arrangements disclosed herein, for example. In the illustrated arrangement, the adhesive strip 3590 is affixed to, integral with or unitary with the cannula 3514 and configured to extend to the top portion of the patient's nose, preferably at or above the tip of the nose, when the prongs 3505 are positioned into the patient's nares.

The adhesive strip 3590 can be adhered to the patient's nose to retain the cannula 3514 in place. Alternatively, the strip 3590 could be adhered to the patient indirectly, such as using a fastener (e.g., hook-and-loop fastener) that couples the strip 3590 to a separate adhesive pad. This retention arrangement 3550 can be desirable for patients who are compliant and aware of the therapy they are on.

For patients who are not compliant, or in other suitable situations, the adhesive pad or strip 3590 can be removed (e.g., cut off) and the cannula 3514 can be inserted into a cannula holder 3592 that cooperates with a headgear strap 3540. The whole assembly can now be used as a standard cannula. The cannula holder 3592 can be of any suitable arrangement to hold the cannula 3514, when desired. For example, the cannula holder 3592 can include any type of snap-fit arrangement, which can include a support portion 3594 (e.g., a semi-cylindrical or other shape tray) and a retention portion 3596 (e.g., a clip). The headgear strap 3540 can be non-adjustable, adjustable or can be of any suitable arrangement, such as the same or similar to any of the straps disclosed herein.

With reference to FIGS. 36A-K, in some embodiments, the cannula retention arrangement 3650 is configured to facilitate achieving a desirable tightness or retention force, which may be a value within (preferably, a relatively narrow) range. In many existing arrangements of cannula secured by a headgear strap, the tightness (tension) of the strap and resulting retention force applied to the cannula can be very dependent on the particular user and, therefore, can vary widely. If the cannula is applied too tightly, marks will be left on the skin due to the headgear strap and the headgear strap can apply uncomfortable pressure to the patient's face. On the other hand, if the headgear strap is not sufficiently tight, it will slip over time and cause the cannula to move from its original or ideal position. This may result in discomfort for the patient. The embodiments of FIGS. 36A-K preferably address these issues to at least some degree. At least some of the embodiments illustrated in FIGS. 35A-G incorporate a tightness indicator, which provides the patient or caregiver with user feedback regarding the tightness of or tension within the headgear strap 3540. Such arrangements can provide, for example, either a qualitative or a quantitative of headgear strap tightness.

For example, with reference to FIGS. 36A-C, a cannula assembly 3600 includes a cannula 3614 and a retention arrangement, such as a headgear strap 3640, which secures the cannula 3614 to the patient. Preferably, the headgear strap 3640 includes a tightness indicator 3650, which provides the user (e.g., a patient or caregiver) with feedback regarding the tightness of the headgear strap 3640. For example, the tightness indicator 3650 may provide a first indication (which may be the absence of an indication) when the headgear strap 3640 is at an incorrect tightness value, which may be outside of a desired tightness range to either side (too tight or too loose). If desired, the first indication could indicate whether the actual tightness is above or below the desired or correct tightness value or range. The tightness indicator 3650 may provide a second indication when the headgear strap 3640 is at a correct or desired tightness value, which may be within a range of correct or desired tightness.

In the illustrated arrangement, the material used to make or otherwise provide on, the headgear strap 3640 is layered with at least two colors. While the strap 3640 remains in its relaxed position only one color will show (first indication) and as the strap 3640 stretches other color(s) incorporated into the strap 3640 begin to show (second indication). The point or range at which the change in color occurs is calibrated to correspond to a certain tensile force in the strap 3640. As a result, such an arrangement will allow the user to know when a certain tightness of a strap 3640 has been achieved. The strap 3640 can be adjustable by any suitable arrangement, such as any of those disclosed herein, which can facilitate the user achieving a desired tightness via adjustment of the strap 3640. Alternatively, the strap 3640 can be non-adjustable, in which case the tightness indicator 3650 can allow the user to determine if the strap 3640 provides a correct fit, and may facilitate selecting a size of strap 3640 from two or more available sizes.

The feedback or tightness indication provided may be simple, such as the use of a strap 3640 that changes color (FIG. 36B) or have symbols which appear as the strap 3640 achieves the correct or desired tightness. In some arrangements, only a section of the strap 3640 changes color, while in other arrangements the whole strap 3640 may change color. The user may also be warned when the strap 3640 is too tight in a similar manner. Such an arrangement provides a mechanism for easily determining whether correct tightness on a headgear strap 3640 has been achieved. Advantageously, it will inhibit or prevent the user from inadvertently over tightening and causing discomfort by displaying when correct fit has been achieved. In some arrangements, the headgear strap 3640 does not prevent the user from tightening the strap 3640 above the desired or indicated tension level should the user prefer such a level of tightness.

With reference to FIGS. 36D-G, the headgear strap 3640 includes a tightness indicator 3650, which provides the user with feedback regarding the tightness of the headgear strap 3640 by indicating movement of one portion 3640a of the headgear strap 3640 relative to another portion 3640b of the headgear strap 3640. For example, with reference to FIGS. 36D and 36E, the headgear strap 3640 includes a spring 3652 or other biasing member or arrangement inside the first portion 3640a (inner strap), which is fixed to the remaining second portion 3640b (outer strap) of the headgear strap 3640. The spring 3652 applies a force (either by compression or extension) tending to overlap the portions 3640a, 3640b thereby reducing a circumference of the strap 3640. The tightness indicator 3650 includes a window 3654 on a portion of the outer strap 3640b that, when an appropriate tightness has been achieved, allows a marker or indication 3656 (e.g., a green marking or band) carried by the inner strap 3640a or spring 3652 to be seen. As the strap 3640 is tightened, the tightness indicator 3650 changes color (e.g., displays the green band) to indicate that the correct or desired tension has been achieved. The two portions 3640a, 3640b can be secured to one another by any suitable fastener, such as a hook-and-loop fastener 3658, for example.

Figure 36D:
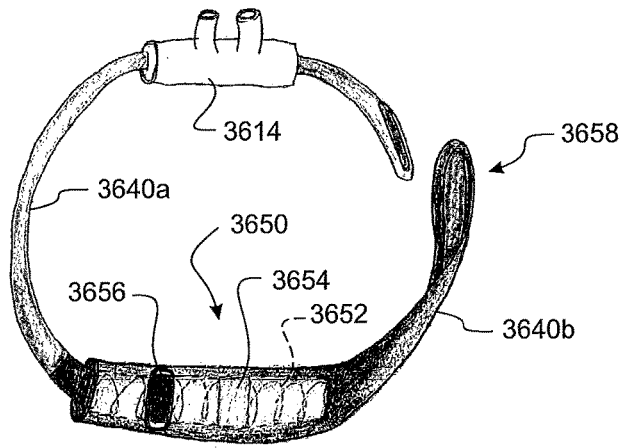
Figure 36E:
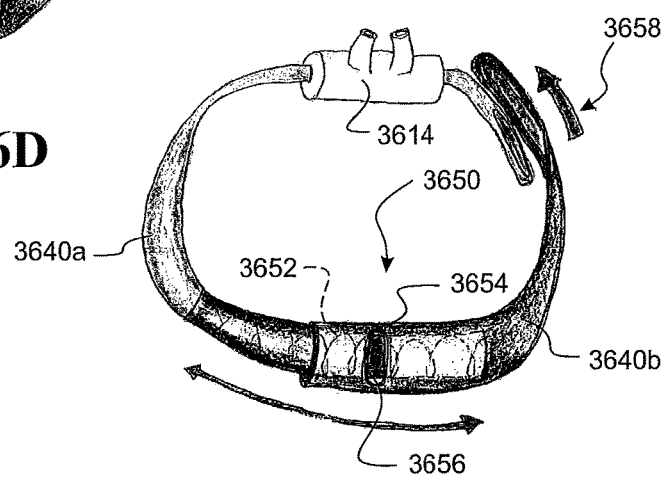
Figure 36F:
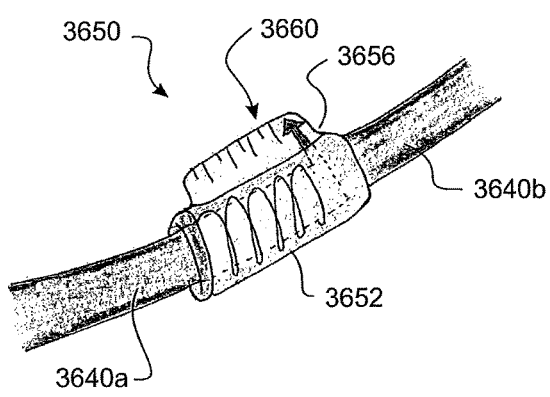
Figure 36G:
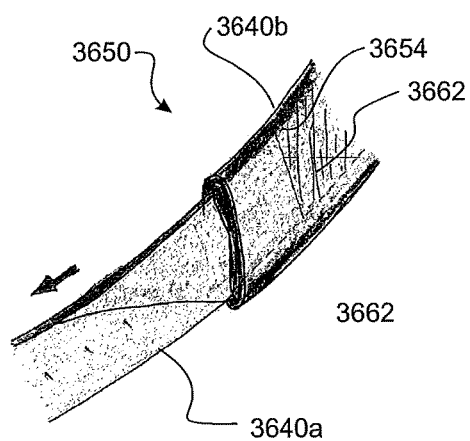

With reference to FIG. 36F, instead of a simple binary indicator, the strap 3640 could provide an indication of tightness over a range. For example, this can be achieved by replacing the window 3654 or providing on the window 3654 a gauge or scale 3660 and utilizing the indication 3656 (e.g., an arrow or thin line) to provide a quantitative display of strap 3640 tightness on the scale 3660. In yet another alternative arrangement, with reference to FIG. 36G, the spring 3652 can be replaced with an elastic region 3662 coupled to or integrated with the inner strap 3640a. As the strap 3640 is tightened, a graduated colored indicator provides tightness information, such as through a window 3654 in the outer strap 3640b. The graduated color changing on the elastic system allows for a region over which ideal fit is achieved as opposed to a single point. The colored indicator could be replaced by numbers, words, symbols, etc.

Advantageously, the arrangements of FIGS. 36D-G a mechanism for easily and quickly determining if a desired or correct tightness of the head strap 3640 has been achieved. Such arrangements can inhibit or prevent the user from inadvertently over tightening and causing discomfort by displaying when correct fit has been achieved. The non-stretch portions of the headgear strap 3640 can be padded to increase comfort to the user. One benefit of having a quantitative display is that it provides repeatability by allowing a user to adjust to a value which is comfortable and secure and note the adjustment value. When the headgear strap 3640 is taken off and then put back on, the user can easily adjust the tightness of the headgear strap 3640 to the desired value using the tightness indicator 3650.

FIGS. 36H and 36I illustrate another headgear strap 3640 including a tightness indicator 3650 that provides an indication of how much force is being applied by the headgear strap 3640 to a patient. Preferably, the tightness indicator 3650 comprises a gauge 3670 (e.g., similar in appearance to a pressure gauge) that can be circular in shape in at least some arrangements. However, other shapes could also be used. However, a generally circular shape can be desirable to provide functional aspects to the strap 3640 in addition to tightness indication. For example, the gauge 3670 could have padding on the underneath surface that contacts the skin. The gauge 3670 may also act to distribute pressure caused by the headgear strap 3640 over a larger surface area and/or to change a direction of the strap 3640. The gauge 3670 preferably operates in a manner similar to the indicators 3650 disclosed herein in that tension applied to the strap 3640 transmitted to and displayed by the gauge 3670. The strap 3640 can be adjustable or non-adjustable, as described herein. The gauge 3670 can provide a binary indication of sufficient tightness or can provide qualitative information as to the actual tightness within a range, as illustrated in FIG. 36I. As with the prior indicators 3650, the gauge 3670 (which can have a dial indicator-type display) provides a means of reading a tightness value. This allows the cannula assembly to be taken off and, when put back on, be easily and quickly adjusted to the desired value. The padded gauge 3670 can provide the added benefit of sitting on or near the cheeks of the patient to distribute any pressure over a larger area, thus increasing comfort. If desired, a gauge 3670 can be provided on each side of the strap 3640 or a pad similar to the gauge 3670 can be provided on the side opposite the gauge 3670. If two gauges are provided, each can indicate the tension of the strap 3640 or each can indicate the tension in a dedicated portion of the strap 3640 (e.g., upper and lower or left and right).

With reference to FIG. 36J, in some embodiments, a very long and stretchy single length headgear strap 3640 can be utilized. Advantageously the long, elastic headgear strap 3640 provides a relatively flat force vs. extension curve, which makes the strap 3640 less likely to be over-tightened. In some arrangements, the headgear strap 3640 extends around the patient's head from one side to the other of the cannula 3614 at least twice and, preferably, more than twice. For example, the strap 3640 can extend around the patient's head from one side of the cannula 3614 to the other between about three to about ten times. The increased length of the strap 3640 assists in flattening the force vs. extension curve. The headgear strap 3640 can be threaded back and forth between the left and right side of the cannula 3614 (e.g., from one side portion 3622 to the other side portion 3622).

In some arrangements or for some applications, the strap 3640 can be non-adjustable. However, in other arrangements, the strap 3640 is adjustable. For example, in the illustrated arrangement, one end 3640a of the headgear strap 3640 can be pulled to adjust a length of the strap 3640 extending between the sides of the cannula 3614 in order to tighten the strap 3614. The strap 3640 can extend through a viewing window 3654 (e.g., moulded in the cannula 3614) and be colored to illustrate the tightness achieved when pulled through the viewing window. One or more colors, symbols or other indications may be used. In some arrangements, the tightness indicator 3650 is able to show qualitatively what tightness has been achieved by the color of the headgear strap 3640 displayed through the viewing window 3654. Advantageously, the multiple strands of the headgear strap 3640 extending from one side to the other of the cannula 3614 provide a larger surface area over which the strap 3640 attaches to the head. The illustrated arrangement provides a means of easily determining if the correct or desired tightness of the headgear strap 3640 has been achieved. The long elastic headgear strap 3640 can render the strap 3640 less likely to exhibit a sudden increase in tightness upon adjustment. This represents an improvement many existing straps, which exhibit a large increase in force for small change in length. In addition, the larger surface area and/or greater vertical distance over which the strap 3640 makes contact with the head improves stability of the cannula 3614 on the face.

With reference to FIG. 36K, the headgear strap 3640 can comprise a torque driver or reel arrangement 3680, which is used to tighten the headgear strap 3640 or any individual portions or straps thereof, such as by winding portion(s) of the strap 3640 onto a reel member in response to rotation of a portion of the torque driver or reel arrangement 3680 by a user. The torque driver or reel arrangement 3680 can be a unidirectional, in which the headgear strap 3640 can only be tightened, or can be a bidirectional in which the headgear strap 3640 can be loosened and re-tightened. If desired, the torque driver or reel arrangement 3680 can have an upper torque limit that only permits the strap 3640 to be tightened up to a certain tightness or tension level. For example, a clutch mechanism could be used to inhibit or prevent over-tightening.

In use, the patient or caregiver can place the cannula assembly 3600 over the head and position the prongs 3605 of the cannula 3614 in the nares. The strap 3640 can be placed appropriately around the head and the dial of the torque driver or reel arrangement 3680 can be rotated to tighten the headgear strap 3640. In some arrangements, the torque driver or reel arrangement 3680 can be calibrated to a set tightness. Once this has been achieved, the torque driver or reel arrangement 3680 will not allow the headgear strap 3640 to be tightened further. The torque driver or reel arrangement 3680 may be padded to increase comfort for the patient when lying on the side. The padding would also increase friction, allowing the cannula 3614 to sit on the face with more stability without over-tightening. If desired, a torque driver or reel arrangement 3680 can be provided on each side of the headgear strap 3640. Advantageously, with such an arrangement, the possibility of a user over-tightening the headgear strap 3640 is reduced or eliminated. The tightness level at which the dial will not tighten further can be a tightness predetermined to provide ample security for retaining the cannula 3614 in place, while maintaining a reasonably high comfort level. In some arrangements, a headgear strap or retention arrangement can include a torque driver or reel arrangement 3680 and a tightness indicator, such as any of those illustrated in FIGS. 35A-G, for example. In particular, a headgear strap could include a torque driver or reel arrangement 3680 and a tightness indicator in the form of a gauge 3670, such as those illustrated in FIGS. 36H and 36I. For example, the torque driver or reel arrangement 3680 could be positioned on one side of the headgear strap or retention arrangement and the gauge 3670 could be positioned on the other side, such as near or covering each ear of the patient, for example.

With reference to FIGS. 37A-E, further embodiments of a retention arrangement 3750 are illustrated, either alone or with a cannula assembly 3700. Tight headgear adjustments and unintended movement of the cannula can apply uncomfortable pressure to the patient's face during use. In some applications or for some patients, methods of attachment that either adhere to the patient's cheeks or rely on facial features (e.g., ears) to support the weight of the cannula can also cause discomfort. Furthermore, positioning the cannula to suit an individual's facial geometry or body position, in some situations, can be difficult and incorrect positioning can result in prong misalignment and discomfort. In at least some embodiments, the retention arrangements 3750 securely support the cannula in a comfortable manner.

Figure 37A:
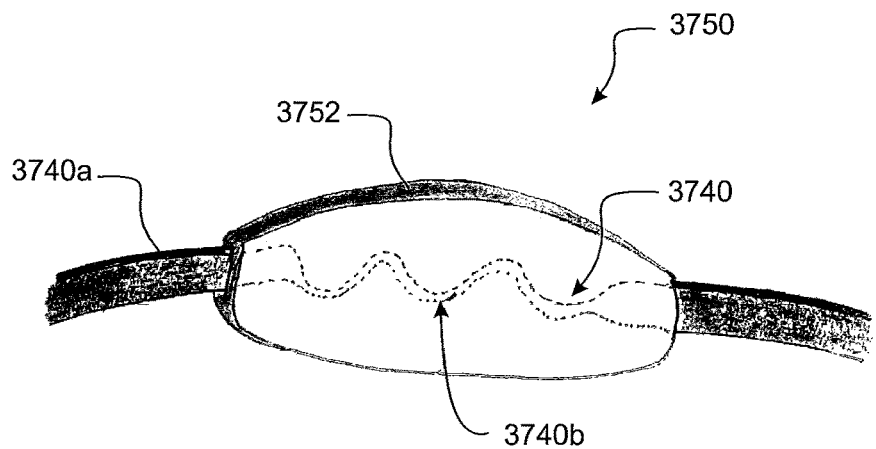
FIG. 37A illustrates an example embodiment of a headgear strap having a strap pad.
Figure 37B:
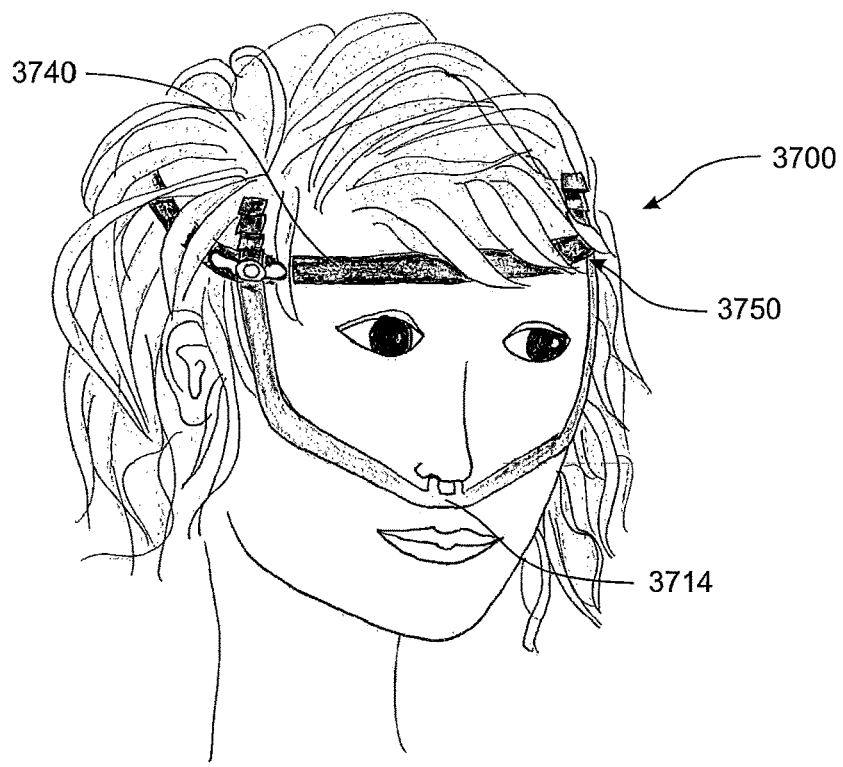
FIGS. 37B-E illustrate example embodiments of an adjustable headgear strap arrangement for a nasal cannula assembly.
Figure 37C:
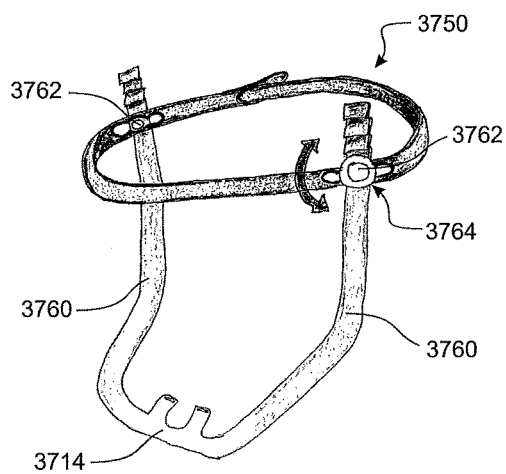
Figure 37D:
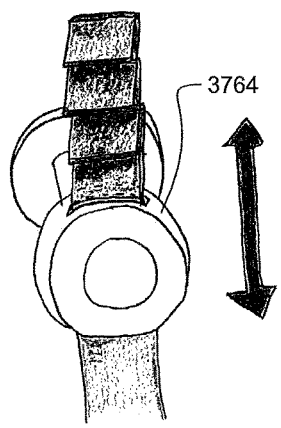
Figure 37E:
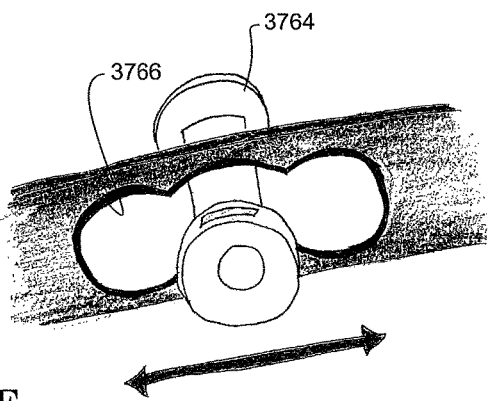

FIG. 37A illustrates an embodiment of an improved retention arrangement 3750 that comprises a headgear strap 3740. The illustrated headgear strap 3740 includes a pad 3752 that is affixed to the strap 3740. In some arrangements, the pad 3752 surrounds the strap 3740 and can be moved along the length of the strap 3740 to a desired location, such as a rearward portion of the strap 3740 that is opposite the cannula (not shown) when the cannula assembly 3700 is assembled or in use. The strap 3740 can have a first portion 3740a and a second portion 3740b. The first portion 3740a can be made from a substantially non-stretchable material or can otherwise be constructed to have limited stretch characteristics. The first portion 3740a can be or include the end portions that connect to the cannula (not shown). Preferably, the second portion 3740b comprises a rear portion of the headgear strap 3740 and can be made from an elastic material or otherwise be constructed to have significant stretch characteristics, or at least significantly greater stretch characteristics than the first portion 3740a. The pad 3752 can be a wide, cushioned pad and can cover the second portion 3740b. That is, the pad 3752 can have a length that is greater than a length of the second portion 3740b in either or both of a relaxed orientation and a stretched orientation. The pad 3752 can also have a height that is significantly greater than a height of the strap 3740. Thus configured, the pad 3752 can distribute pressure over a wider area of the patient's head, while the elastic region or second portion 3740b of the strap 3740 can provide a force on the face when stretched. Preferably, the large surface area of the pad 3752 will also provide substantial stability due to increased friction, thus reducing the chance of the cannula moving from its ideal or preferred position. The non-stretch end portions or first portion 3740a of the headgear strap 3740 can connect to one or both of the elastic region or second portion 3740b of the strap 3740 and the pad 3752. The pad 3752 can be fixed in place relative to the strap 3740 or, in some arrangements, the pad 3752 can slide along the strap 3740 to the desired location and may also act as protection against nearby objects, such as hard bed frames, other equipment, etc. Alternatively, the pad 3752 can be made from an elastic material or otherwise constructed to exhibit stretch characteristics. In such an arrangement, the elastic region or second portion of the headgear strap 3740 can be included or omitted. If desired, a pad 3752 could be used with a substantially or entirely non-stretch strap, which has no elastic region. In such an arrangement, the pad 3752 may still improve comfort and stability, as described above.

With reference to FIGS. 37B-E, a nasal cannula assembly 3700 includes a cannula 3714 and a retention arrangement 3750. Preferably, the retention arrangement 3750 contacts the patient only at an upper region of the head or at a position above a line extending around the head and generally passing through the patient's eyebrows. Such an arrangement supports the cannula 3714 substantially entirely with the upper region of the head for improved comfort. In the illustrated arrangement, the weight of the cannula 3714 is supported by a strap 3740 that encircles the upper head region. Two arms 3760 are supported by or hang from the strap 3740 down either side of the patient's face. The cannula 3714 is attached to the arms 3760 or can be integrally or unitarily formed with the arms 3760. Advantageously, with such an arrangement, no weight is supported by the patient's cheeks or ears, or any region below the strap 3740, thus inhibiting or preventing uncomfortable pressure from being applied to sensitive areas of the patient's head and face.

In some embodiments, the arms 3760 and/or cannula 3714 can be adjusted, such as moved and/or rotated on or relative to the strap 3740 about a hinge point or axis 3762 on either side of the head. Preferably, the arms 3760 and/or cannula 3714 are adjustable relative to the strap 3740. For example, the position of the cannula 3714 can be adjusted by shifting the arms 3760 up and down relative to the strap 3740. In the illustrated arrangement, a retention element or hub 3764 is supported by the strap 3740 and adjustably supports the arms 3760, such as via a ratchet assembly or other suitable adjustment mechanism. In some arrangements, the arms 3760 are adjustable around the circumference of the strap 3740. For example, the arms 3760 can be infinitely adjustable relative to the strap 3740, such as by utilizing a clamp mechanism integrated or separate from the hubs 3764. As illustrated, the hubs 3764 and, thus, the arms 3760 are adjustable to one of a discrete number of adjustment positions, such as via slots 3766 that receive the hubs 3764 and define two or more (e.g., three, four, five or more) discrete adjustment positions. Alternatively, the slots 3766 could permit free movement of the hubs 3764 such that the arms 3760 can float relative to the strap 3740 within a path defined by the slots 3766. If desired, the arms 3760 could be biased toward a relaxed position relative to the strap 3740 (e.g., center of the slots 3766) and can be free to move against the biasing force of a biasing member (e.g., spring). The strap 3740 can be made of or contain an elastic material (e.g., a one-size strap) or can have some form of size adjustment. Advantageously, the illustrated retention arrangement 3750 does not rely on the ears to support the cannula weight, thereby reducing or preventing pressure points. Because existing single headgear straps often sit below the widest point of the head, a tight fit is often required to ensure the strap does not slip down. By having the strap 3740 sit above the widest point of the head, the strap 3740 will not have to be as tight and will be more secure. The illustrated arrangement also allows for at least three modes of cannula position adjustment. In other arrangements, the retention arrangement 3750 may provide for non-discrete adjustment positions between the arms 3760 and the strap 3740. For example, the arms 3760 could be coupled to the strap 3740 via a hook-and-loop fastener, or other similar fastening mechanism, to possibly permit a greater number of and/or more finite adjustment positions relative to the illustrated embodiment.

With reference to FIGS. 38A-G, in some embodiments, the nasal cannula assembly 3800 is configured to facilitate selective switching of the exit side of the supply tube 3802 relative to the cannula 3801. As described above, an advantage of such systems is that patients are able to eat, drink, and talk while receiving the therapy, since the therapy is delivered via the nose and not the mouth. It is therefore very desirable for the tubing 3802 to exit away from the face without having to cross back over the face which would likely obstruct the mouth or field of view, etc. At a hospital bedside, the humidifier is generally set up permanently on either the right or left side of the bed. Therefore these sideward directions are the most desirable for the interface tubing to extend away from the patient.

Figure 38A:
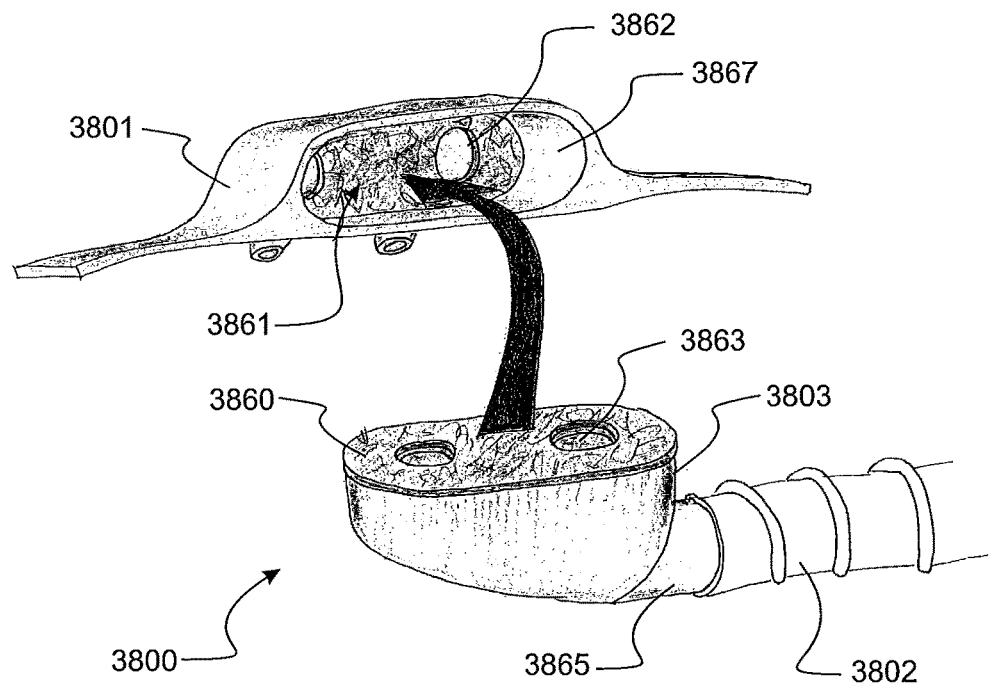
Figure 38B:
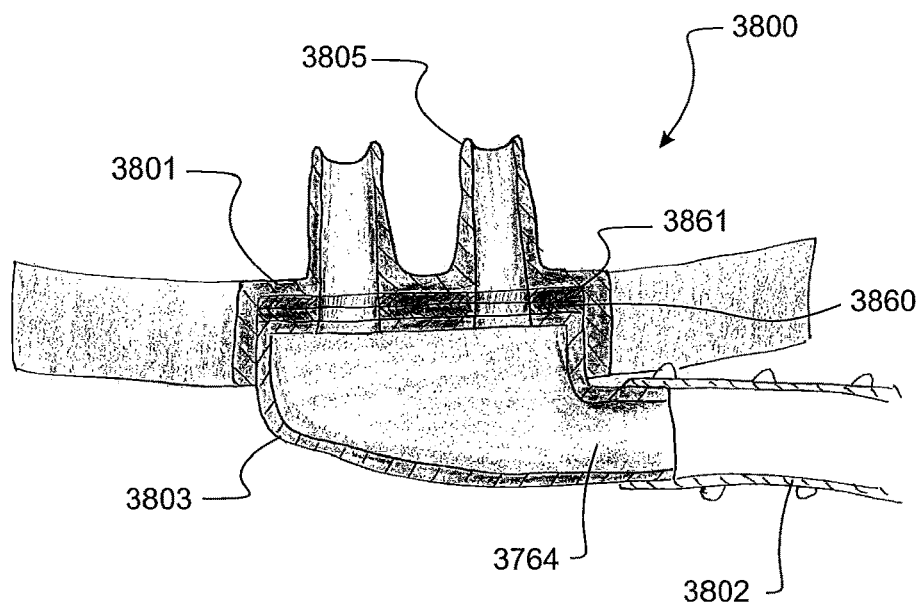

FIGS. 38A and 38B illustrate an embodiment of a nasal cannula assembly 3800 with a supply tube 3802 coupled to a manifold 3803 to allow for selective changing of the exit side of the supply tube 3802. The assembly can also include suitable headgear straps 3840 (FIG. 38C), including those disclosed herein or other suitable arrangements. In some embodiments, the prongs 3805 are mounted on a swivel so that the entire head strap and tubing assembly can be flipped over to direct the tubing 3802 to the other side, as described above. As illustrated, other embodiments can include attachment portions on both the cannula 3801 and manifold 3803 that are configured to hold the cannula 3801 and manifold 3803 together. The attachment portion 3860 on the manifold 3803 can engage with the second attachment portion 3861 on the cannula 3801 to couple the manifold 3803 to the cannula 3801. Preferably, the attachment portions 3860 and 3861 have similar sizes and shapes and each include openings 3862 and 3863 corresponding to the prongs 3805. The attachment portions can comprise a hook and loop fastener material or they can comprise other suitable attachment materials. The manifold 3803 includes an inlet 3865 that opens to the side and can be coupled to the supply tube 3802. These embodiments can be beneficial because one can easily separate the manifold 3803 from the cannula 3801 and then reconnect the two parts after rotating the manifold 3803 so that the tube 3802 extends in the opposite direction.

In some embodiments, the cannula 3801 includes a recess 3867 into which a portion of the manifold 3803 can fit. The recess 3867 can have a shape and size that correspond to the outer shape and size of the manifold 3803. Preferably, the shape of the recess 3867 and the outer shape of the manifold are symmetric so they can be easily disassembled and fit back together after being rotated 180 degrees relative to one another. As illustrated, the shape of the recess 3867 and the outer shape of the manifold 3803 can be circular or oval. The manifold 3803 and the recess 3867 can each have a substantially planar surface or surfaces that correspond and can engage each other. When the manifold 3803 is inserted into the recess 3867 of the cannula 3801, the planar surfaces of the manifold 3803 and recess 3867 can contact one another and form a seal around the prong openings 3862. The planar portions can include a type of sealant or coupling material. Preferably, the coupling material is hook and loop fastener material or some other suitable adhesive or coupling material. A coupling material can be easily uncoupled and re-coupled, while maintaining its security. Preferably, the hook and loop fastener material or locking material is die-cut and precisely shaped and positioned to retain the manifold 3803 to the cannula 3801. Alternatively, the cannula recess 3867 and the manifold 3803 can include a locking mechanism that holds the manifold 3803 within the recess 3867 and that is configured to allow a user to selectively remove and re-couple the manifold 3803 to the cannula 3801 (e.g., a snap-fit connection). Both the cannula 3801 and the manifold 3803 can be made of a pliable, soft or semi-rigid material to increase comfort for a patient. In some embodiments, the cannula 3801 and manifold 3803 can also contact each other directly for sealing, such as along at least a portion of the surface(s) defining the recess 3867 and the corresponding surface(s) of the manifold 3803.

FIGS. 38C-E illustrate embodiments of a cannula assembly 3800 that include a cannula 3870 and a retention arrangement, such as a headgear strap 3840, which secures the cannula 3870 to the patient. Preferably, the cannula 3870 includes a side entry for the tubing 3802. Preferably, the cannula 3870 includes prongs 3872 that extend upward from the top of the cannula 3870 in a substantially straight manner. The cannula 3870 can have angled side portions or walls 3874 that are configured to rest against a patient's face. Preferably, the cannula 3870 also includes a base 3876 that can be flat or curved. In some embodiments, the sidewalls or facets 3874 are inclined relative to the base 3874 and prongs 3872 such that the prongs 3872 (which extend in a substantially straight direction) point in the same direction into the nose, regardless of which tube direction is chosen when the cannula 3870 is held to the face. Preferably, the angles between each side wall 3874 and the base are substantially the same, and/or the angles between each side wall 3874 and the prongs 3872 are substantially the same. When the cannula 3870 is held against a patient's face and the prongs 3872 are inserted into a patient's nose, one of the sidewalls 3872 rests against the face and the prongs extend into the nose at an angle relative to the plane where the sidewall 3874 contacts the face. When the cannula 3870 is removed and rotated so that the tube 3802 exits on the opposite side, the other side wall 3874 contacts the face and the prongs 3872 extend into the nose at substantially the same angle relative to the plane where the sidewall 3874 contacts the face. These embodiments can be beneficial because one can remove the cannula and headgear assembly and replace it again with the tubing exit on the opposite side, without disassembling any part of the cannula assembly 3800. This allows the cannula assembly 3800 to remain sealed and reduces the chance of leaking.

Figure 38F:
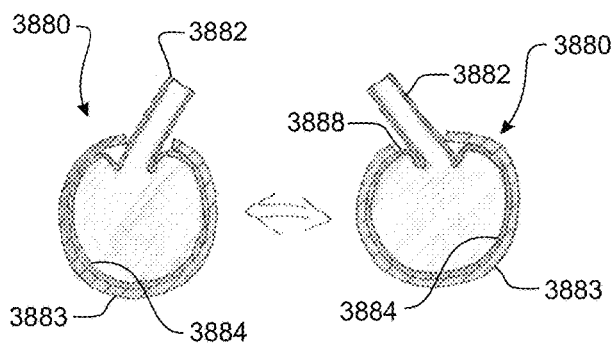
Figure 38G:
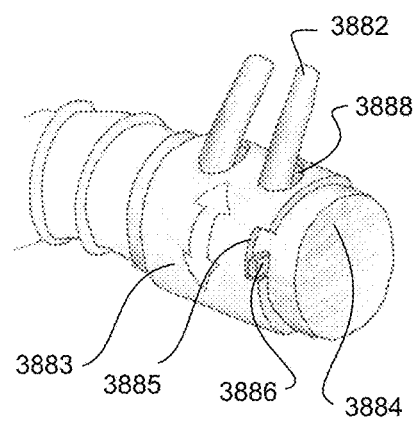

FIGS. 38F and 38G illustrate embodiments of a cannula assembly 3880 that includes an inner cannula portion 3884 with prongs 3882. The assembly also includes an outer portion 3883 that at least partially surrounds the inner portion 3884. The assembly 3880 also includes a side entry into the inner cannula portion 3884 to which the supply tube 3802 can be coupled. Preferably, the prongs 3882 are coupled to the inner portion 3884 and are configured to bend or flex relative to the inner portion 3884. The outer portion 3883 can be rotated relative to the inner portion 3884. The outer portion 3883 includes one or more (e.g., two) openings 3888 through which the prongs 3882 can extend. Preferably, the openings 3888 are larger than the outer circumference or perimeter of the prongs 3882 and the openings 3888 can be circular or oval shaped, or otherwise shaped such that a space exists between the outer surfaces of the prongs 3883 and the surfaces of the openings 3888 in at least a circumferential direction or direction of rotation of the outer portion 3883. Alternatively, the openings 3888 can be slots that extend in a radial direction around the circumference of the outer portion 3883. Preferably, the outer portion 3883 rotates relative to the inner portion 3884 so that the outer portion 3883 causes the prongs 3882 to deflect in a desired direction relative to the cannula 3880 or inner portion 3884. By rotating the outer portion 3883, portions of outer portion 3883 adjacent the openings 3888 contact the flexible base of the prongs 3882 and the prongs 3882 can be tilted one way or the other depending on which direction the outer portion 3883 is rotated. Therefore the prongs 3882 can be directed to extend into the nose, regardless of which tube direction is chosen when coupling the cannula 3880 to the face. This can be especially beneficial in assemblies designed for high flow style tubes which are larger than smaller conventional nasal tubes. It is also beneficial because one can remove the assembly and switch the exit side of the tube 3802 without disassembling any parts of the cannula assembly and the cannula can remain sealed so as to reduce the risk of leaking.

In some embodiments, the cannula assembly 3880 can also include an adjustment limit arrangement, such as a pin 3886 and a slot 3885. Preferably, the pin is coupled to the inner portion 3884 and the slot is located on the outer portion 3883; however, this arrangement could also be reversed. The slot 3885 can extend radially along the circumference of the outer portion 3883 and is sized and shaped to receive the pin 3886 which protrudes from the outer surface of the inner portion 3884. The pin 3886 can move within the slot 3885 as the outer portion 3883 rotates relative to the inner portion 3884, and the edges of the slot 3885 or stop surfaces can stop the outer portion 3883 from rotating past certain points relative to the inner portion 3884.

FIGS. 39A-I illustrate embodiments of a nasal cannula assembly with cannula alignment mechanisms. In some cannula products it is only possible to alter the prong angle and cannula position by adjusting the head strap. In some assemblies, the amount of adjustment achievable is limited and it is difficult to do accurately. Differing facial geometries between patients can cause discomfort due to misaligned prongs as well as reduced therapy if air is allowed to leak outside of the nose. At least some of the disclosed embodiments are designed to be secure around the back of the head and to resist displacement caused by normal patient movement. Some of the embodiments described below isolate the retention of the headgear from the adjustment of the cannula position and allow the cannula to move side to side and/or the angle of the prongs to be fine-tuned for each individual patient. Having the cannula isolated from the headgear can also be beneficial in cases where the cannula has become misaligned and in which it is inconvenient to adjust the positioning of the cannula using the headgear. For example, when the patient is unconscious or the headgear adjustment mechanism is difficult to access. Some of these embodiments isolate the head strap portions from the movement and positioning of the cannula. Some of these embodiments also or alternatively permit customized prong angle adjustment, as well as lateral cannula positioning without causing the headgear or head straps to become unstable, dislodged or the system to appear un-centered on the face.

Figure 39A:
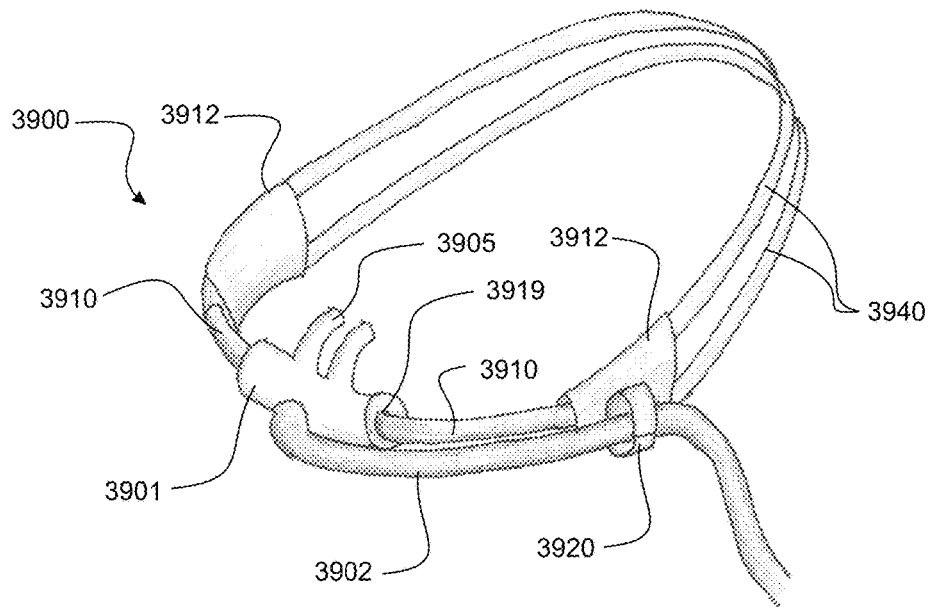

For example, FIG. 39A illustrates a cannula assembly 3900 that includes a cannula 3901, a supply tube 3902, and prongs 3905. The assembly 3900 also includes a retention arrangement, such as head straps 3940 and attachment portions 3912. In some embodiments, the assembly 3900 includes a frame portion 3910 that extends between and, preferably, is coupled to the attachment portions 3912. The cannula 3901 can be slidably coupled to the frame portion 3910 so that the cannula 3901 can slide along the frame portion 3910 and change position along the frame portion 3910. Preferably, the cannula 3901 can also rotate or swivel relative to the frame portion 3910 so that the prongs 3905 can tilt in different directions relative to the frame portion 3910. Preferably the frame portion 3910 is rigid or semi-rigid such that it is flexible enough to bend and can conform to a patient's face while still retaining its form to support the cannula 3901. The frame portion 3910 can be made of plastic or some other suitable semi-rigid or flexible material. The cannula 3901 includes an opening 3919 through which the frame portion 3910 passes. This frame portion 3910 can be circular in cross section and the opening 3919 is shaped and sized to correspond to the shape and size of the frame portion 3910. Such a configuration allows the cannula 3901 to both rotate relative to the frame portion 3910 and slide side-to-side relative to the face or a patient. In some arrangements, the cannula 3901 has a relatively tight fit with the frame portion 3910 such that, once positioned, the cannula 3901 maintains its position on the frame portion 3910. In other arrangements, the cannula 3901 can have a relatively loose, floating fit on the frame portion 3910 such that cannula 3901 moves as necessary along with movement of the patient.

The ends of the frame portion 3910 can be directly or indirectly supported by the attachment portions 3912 and the attachment portions 3912 can include soft face pads that keep the frame portion from contacting or applying too much pressure to a patient's face. In certain embodiments, a tube support 3920 is coupled to the assembly 3900 and is configured to support the tube 3902. Preferably, the tube support 3920 is coupled to the attachment portion 3812 and is a removable strap that supports the tube 3902 from the cannula to the head straps 3940. Preferably, the tube support 3920 can be easily undone or removed to release the tube 3920. The tube support 3920 is also preferably configured to hold the tube 3902 in a relatively loose manner so that the tube 3902 can move or slide within the tube support 3920 as the position of the cannula 3901 is changed on the frame portion 3910. For example, the tube support 3920 can be a strap or tab that loosely supports the tube 3902 and can easily be undone or released. Preferably, the assembly 3900 includes a tube support 3920 on each of the attachment portions 3912 or on each side of the head straps 3940 or frame portion 3910. Other suitable tube supports (e.g., a clip or any suitable fastener) could also be used.

Figure 39B:
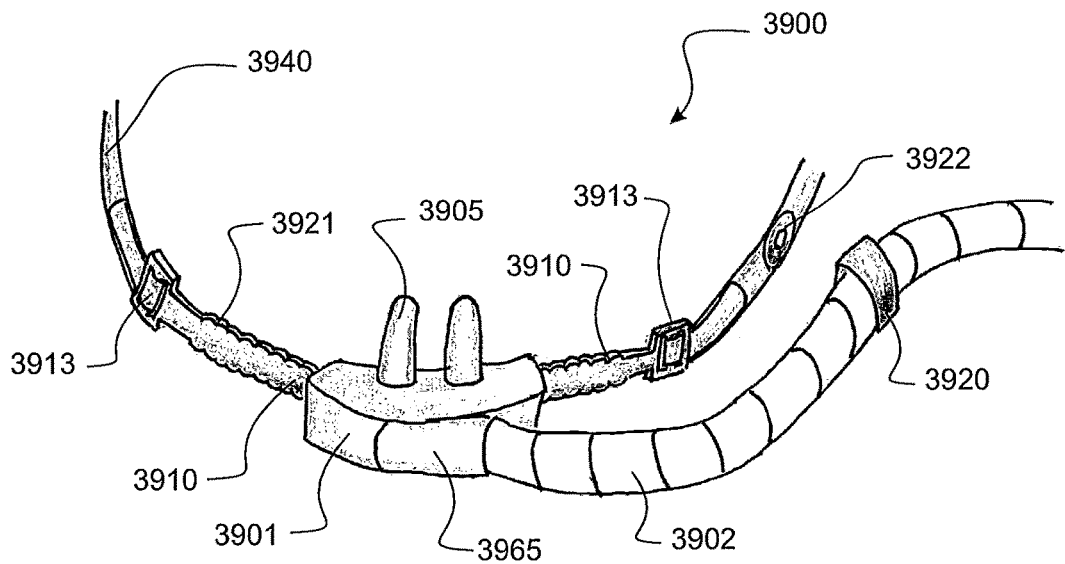

FIG. 39B illustrates a cannula assembly 3900 embodiment in which a frame portion 3910 supports the cannula 3901 and the frame portion 3910 includes detents, such as notches or protrusions 3921, along the length of the frame portion 3910. The notches 3921 can be configured to allow movement and a change of position of the cannula 3901 along the frame portion 3910, while at the same time retaining the cannula 3901 in its selected position. The frame portion 3910 can also be circular and/or configured to allow rotation of the cannula 3901 relative to the frame member 3910. For example, the notched frame portion 3910 can be a flat strip that allows side to side movement of the cannula 3901 or it could have a notched circular cross section that allows both side to side and rotational movement of the cannula 3901 relative to the frame portion 3910. Preferably, the assembly also includes head strap adjustment portions 3913 located at each end of the frame portion 3910. The head strap adjustment portions 3913 can be configured to allow adjustment of the head strap(s) 3940 in any suitable manner, including those discussed in the previous embodiments. The cannula 3901 can also include a side port 3965 that is configured to receive the supply tube 3902 and direct the tube 3902 to one side of the patient. In some embodiments, the head straps 3940 or frame portion 3910 support a tube support portion 3920. Preferably, the tube support portion 3920 is a strap or clip that is removable from the head strap 3940 or frame portion 3910. A dome clip 3922 or other type of clip or locking structure or material can be used to removably couple the tube support 3920 to the head strap 3940 or frame portion 3910.

Figure 39C:
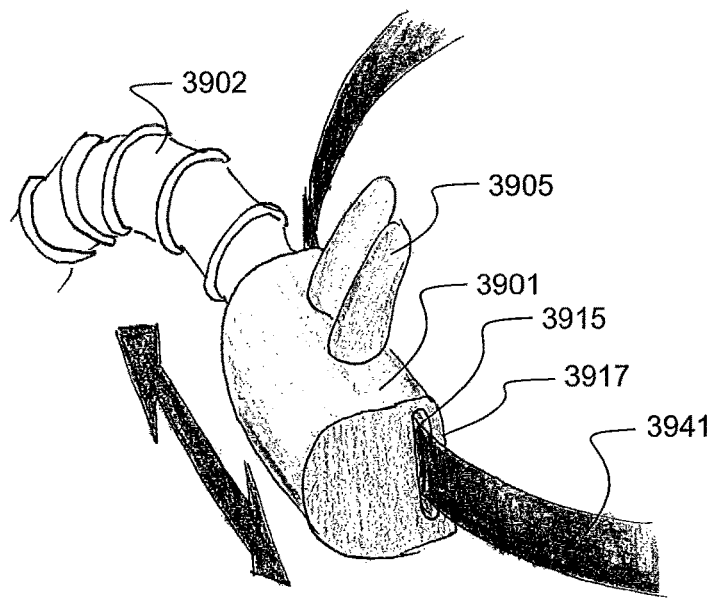

FIG. 39C illustrates a cannula assembly in which the cannula 3901 is supported by a strap or flexible member 3941. The cannula 3901 includes prongs 3905 and an opening 3915 that is configured to receive the strap 3941. Preferably, the flexible member or strap 3941 is worn directly on the face of a patient and is configured to hold the cannula 3901 against the surface of the face. The strap 3941 can pass through the opening 3915 in the cannula 3901 and can be coupled to head straps 3940, or can extend around the head of the patient. Preferably, the strap 3941 is configured to provide a retention force to hold the cannula 3901 to the face, but it also can isolate movements in the head strap 3940 from the prongs 3905. The cannula 3901 can slide or move along the strap 3941 and can change positions relative to a patient's face and the strap 3941. A supply tube 3902 is functionally coupled to the cannula 3901 and, preferably, exits out of one side of the cannula 3901.

Figure 39D:
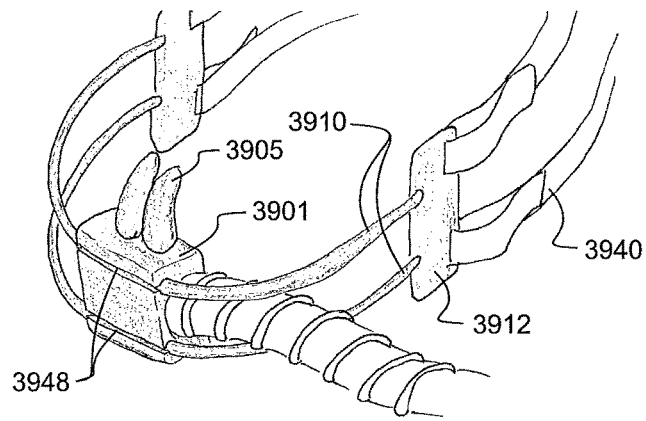
Figure 39E:
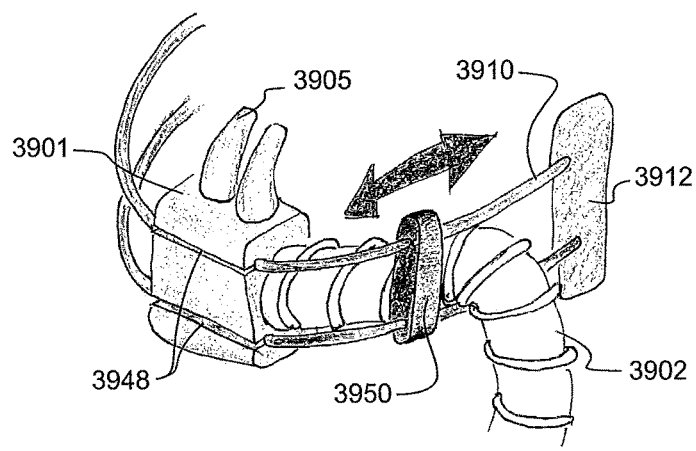

FIG. 39D-E illustrate another embodiment of a cannula assembly in which the cannula 3901 includes two openings or slots 3948 and the cannula 3901 can change position relative to two frame portions 3910. The supply tube 3902 extends from the side of the cannula 3901 and preferably between the two frame portions 3910. The frame portions 3910 are supported by attachment portions 3912 that can be coupled to head straps 3940. Preferably, the openings or slots 3948 extend along the length of the cannula 3901 in a lateral direction and are open in the lengthwise direction so that the frame portions 3948 can be inserted or clipped into the slots 3948. The inner portion of the slots 3948 can be sized and shaped to correspond to the size and shape of the frame portions 3910, and the outer portion of the slots can be sized and shaped such that the slot retains the frame portion 3910 within the inner portion of the slot. In other embodiments, clips could be used to retain the cannula 3901 on the frame portions 3910. The cannula 3901 can be removably coupled onto the frame portions 3910 which allows one to swap in different sizes or configurations of a cannula 3901 into a single head strap/headgear assembly. Two supporting frame portions 3910 can increase the stability of the cannula on the face of a patient while still retaining the ability of the cannula 3901 to move side to side relative to the frame portions 3910. A tube support 3950 can also be incorporated into the assembly as illustrated. The tube support 3950 can be coupled to the frame portions 3910 and can be movable along the frame portions 3910 to a desired position to retain the tube 3902 between the tube support 3950 and an end of the frame portions 3910 (or the attachment portion 3912) in a lateral direction and between the frame portions 3910 in a vertical direction. Thus, the tube support 3950 can be configured to allow a user to control where the tube 3902 exits the cannula assembly between the frame portions 3010.

Figure 39F:
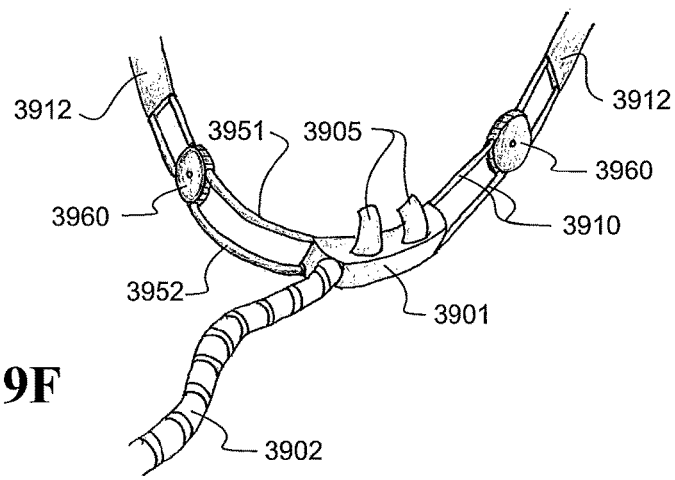

FIG. 39F illustrates an embodiment of a cannula assembly which includes a double wire assembly. In some embodiments, the frame members 3910 are wires that support the cannula 3901 and are coupled to attachment portions 3912 or the head strap(s) 3940 (not shown in FIG. 39F). The cannula 3901 includes a supply opening on the side from which the supply tube 3902 exits. Preferably, the top wire 3951 is fixedly coupled to the cannula 3901 and the bottom portion of the cannula 3901 includes an opening or slot 3948 configured to slidably receive the bottom wire 3952. The assembly can also include dials 3960 that are configured to move at least one of the wires. Preferably, rotating the dials 3960 causes the top wire 3951 and the cannula 3901 to move with respect to the rest of the assembly. The bottom wire 3952 does not move and the cannula 3901 can slide along the bottom wire 3952. Alternatively, the wires supporting the cannula 3901 could both be free to pass through openings in the cannula 3901. The wires 3910 could be coated with a soft TPE or a similar material to increase the softness and comfort for the patient. Alternatively, the dials 3960 could be configured to adjust the length of the head strap(s) 3940 directly or by adjusting (e.g., taking up or letting out) a length of the wires 3910 extending between the dials 3960, thereby effectively adjusting a length of the head strap(s) 3940. Also, the natural flex in the wires 3910 can allow the prongs 3905 to move with movement of the patient's nose or for adjustment.

FIG. 39G illustrates another embodiment of a cannula headgear assembly that includes a band 3964 that is configured to fit over a patient's head and supports an arm assembly and the cannula 3901. A first arm 3970 is coupled to the band 3964 at a first joint 3966. A second arm 3971 is coupled to the first arm 3970 at a second joint 3967 and the second arm 3971 is coupled to the cannula 3901 at a third joint 3968. In some embodiments, the assembly includes only one arm and in other embodiments the assembly includes three or more arms coupled at joints. The cannula 3901 includes prongs 3905 and a supply tube 3902 is coupled to the cannula 3901, preferably at the side opposite the third joint 3968. Preferably, each of the joints 3966, 3967 and 3968 are configured to allow multi-axis movement between the coupled portions. For example, the cannula 3901 can pivot in multiple directions about the third joint 3968. Each of the joints can be ball joints. In some embodiments, the joints are configured to have at least some resistance to pivoting. These joints can provide the ability to adjust the cannula as desired but retain the cannula in position once adjusted. Preferably, the resistance in the joints is enough to hold the relative position of the arms and cannula 3901 when they are not being acted upon by a user, but not too much resistance so that the arms and cannula 3901 can be moved and pivoted when moved by a user. In some embodiments, the tubing 3902 can be routed through one or more of the arms and, thus, the arm(s) can function as a tube support to route the tube 3902 in a lateral direction away from the user's mouth. Alternatively, one or more of the arms can define a portion of the gas conduit between the cannula 3901 and the supply tube 3902. Preferably, the band 3964 is configured to fit snugly on a patients head and in some embodiments the band 3964 is adjustable to fit different head sizes and shapes. In some embodiments, the head band 3964 includes a stabilizing portion 3965 on the side opposite the side supporting the first arm 3970. The band 3964 can fit over the top of a patient's head or around the back portion of the patient's head. In some embodiments, the arms are flexible rods that attach together with ball joints or similar joints.

FIG. 39H illustrates a cannula assembly having a rigid or semi-rigid frame portion 3982 that supports the cannula 3901. The cannula 3901 can be secured to the frame portion 3982 in various ways. For example, the cannula 3901 can include a clip or attachment member 3984 that is configured to engage the frame portion 3982 and couple the cannula 3901 and prongs 3905 to the frame portion 3982. In some embodiments, the frame portion 3982 includes an opening 3983 or slot that is configured to receive a portion of the cannula 3901. For example, the opening 3983 in the frame portion 3982 can receive the clip 3984 of the cannula 3901 and engagement of the clip 3984 and the opening 3983 can couple the cannula 3901 to the frame portion 3982. As illustrated, the cannula 3901 can clip into the frame portion 3982 with a curved hook 3984 which allows the prongs 3905 to both rotate and, if the opening 3983 is longer than the hook 3984, move side to side relative to the frame portion 3982. With such a clip configuration, the cannula 3901 can easily be coupled to and removed from the frame portion 3982 and different cannula 3901 can be used with the same assembly. In some embodiments, different cannula 3901 and prongs 3905, having various shapes and sizes, can be selectively coupled to the frame portion 3982 and used by a patient. For example, larger cannula and prongs can be coupled to the frame portion 3982 for patients with larger dimensions and a cannula having the supply tube 3920 exiting on one side can be replaced on the frame portion 3982 by a different cannula 3901 that has the tube 3920 exiting on the opposite side. The clip or attachment member 3984 and the corresponding portion (e.g. opening 3983) on the frame portion 3982 that receives the attachment member 3984 can also be configured to allow the cannula 3901 and/or prongs 3905 to be adjusted up or down, or side to side relative to the frame portion 3982 and/or a patient's face. Preferably, the position of the cannula 3901 on the frame portion 3982 can be adjusted to change the angle of the prongs 3905 or to rotate the cannula 3901. Thus, one can change the position and characteristics of the cannula 3901 and prongs 3905 without moving or removing the head straps 3940 or entire head gear assembly. In some arrangements, the cannula 3901 may be only loosely coupled to the frame portion 3982 until the assembly is placed onto the patient. Once in position on the patient, the cannula 3901 is trapped between the patient and the frame portion 3982.

As described in the previous embodiments, the supply tube 3902 can exit the cannula 3901 from a side of the cannula 3901, and the frame portion 3982 can be coupled to head strap(s) 3940. Preferably, the frame portion 3982 includes pads or softer portions 3980 on the side of the frame portion 3982 closest to the patient's face. The pads 3980 can be coupled to the frame portion 3982 and can provide padding between the frame portion 3982 and the face of a patient and/or space the frame portion 3982 away from the patient's face. Embodiments of the assembly can also include a tube retention mechanism or tube support 3920 similar to those described in previous embodiments. For example, the tube support 3920 can be a loop or strap that couples the tube 3902 to the head strap 3940 or the frame portion 3982.

FIG. 39I illustrates a nasal cannula assembly comprising corrugated portions of tubing 3990 coupled to one or both sides of the cannula 3901. In some embodiments, the cannula 3901 is supported by collapsible corrugated portions of tubing 3990 and its position and orientation can be adjusted by adjusting the corrugated tubing portions 3990. The cannula 3901 can include prongs 3905 and can include one or more inlet openings 3994 configured to receive an end of the corrugated portions of tubing 3990. The corrugated portions of tubing 3990 can be configured to allow adjustment of the cannula position, as well as deliver a gas to the cannula 3901. The corrugations 3990 allow the cannula 3901 to be moved both side to side (laterally) and up and down relative to a patient's face. For example, in order to move the cannula 3901 to one side, the corrugated portions 3990 on that side can be compressed or collapsed and the corrugated portions 3990 on the opposite side can be expanded. By expanding and compressing the corrugated portions 3990, the tightness of the fit of the assembly on the patient's head can remain the same, while the position of the cannula 3901 is adjusted. Alternatively, the corrugated portions 3990 can be some other material other than tubing that is able to selectively expand and contract while supporting the cannula 3901. Preferably, one end of the corrugated portions 3990 is coupled to a fixed portion 3992 that is not corrugated and not movable relative to a head strap 3940. Preferably, the fixed portions 3992 are also tubing 3902 that delivers gas to the corrugated portions. In some embodiments, the fixed portions 3992 and/or the tubing 3902 are backed by a head strap 3940. In these configurations, the adjustment of the cannula 3901 and prong 3905 positioning is isolated from the head strap 3940 and the rest of the assembly.

With reference to FIGS. 40A-J, in some embodiments, the cannula and prong arrangement is configured to facilitate adjustment of the prong size and/or spacing. Individual patients often require different cannula prong sizes and spacing, depending on the shape and size of the patient's nose. Smaller prongs are desirable to optimize comfort in the nares and minimize visual impact, while larger prongs minimize the resistance to flow to facilitate the delivery of the desired flow rate. Larger prongs can also help to prevent the prongs from falling out of the nose. Achieving an acceptable size and spacing of the prongs can be very desirable in properly treating a patient. Prong sizing can include consideration of prong diameter, prong height, septal spacing between the prongs, etc. Some cannula arrangements provide a range of cannula structures in varying sizes and the prong sizing for each model is fixed. It is desirable to have customizable cannula prongs where one or more of the above characteristics can be adjusted for individual patients. The embodiments of FIGS. 40A-J preferably address at least some of these issues.

For example, with reference to FIGS. 40A-D, a cannula prong assembly includes prongs 4005 having two prong portions or sides 4040 and 4042 that can move relative to one another. Preferably, the prongs 4005 each include a first prong portion 4040 that is slidably coupled to a second prong portion 4042 and the two prong portions can move fore-and-aft with respect to one another or toward and away from one another. The prong portions 4040 and 4042 can be generally U-shaped or semi-circular in cross-section or from an end view with their open sides facing one another. Preferably, the prong portions 4040 and 4042 define a passageway 4047 between them through which gas can pass, the passageway 4047 being the open area between the prong portions 4040 and 4042. In some embodiments, as the prong portions 4040 and 4042 are moved closer together, the cross-sectional area of the passageway 4047 becomes smaller as the overall cross-section of the prong 4005 becomes smaller. As the prong portions 4040 and 4042 move further apart from each other, the cross-section of the passageway 4047 and the overall cross-section of the prong 4005 increase in size. Thus, the two side portions 4040 and 4042 of a prong 4005 can be pulled further apart or pushed closer together, to change the prong inner dimensions and outer dimensions. The pulled apart and extended prong cross-section shape can be more elliptical than the closed or compressed cross-section. The cross-section of the prong 4005 can also be shaped as a semi-circle with one side having a flat section.

Preferably, the prong portions 4040 and 4042 slide back and forth within a slot or opening 4045 in the cannula or manifold 4001. A section of material or base 4046 can extend from each prong portion to fill any open gaps in the slot 4045, and the material 4046 can be configured to maintain a seal between the prong 4005 and the cannula 4001 even when the prong portions 4040 and 4042 are moved relative to the cannula 4001. The sections of material 4046 can extend from the prong 4005 and into the manifold or cannula 4001, or they can extend from the prongs 4005 along the outside of the cannula 4001. The sections of material 4046 can slide over each other as the prong portions 4040 and 4042 move relative to one another ensuring a continuous seal as the dimensions of the prong 4005 change. In some embodiments, the entire prong 4005 can be rotated or moved within the slot 4045 to customize and adjust the position and angle of the prong 4005 relative to a patient. Such adjustment can be more easily accomplished with the prong portions 4040 and 4042 not fully separated or pulled apart from one another. Alternatively, the fully open position of the prong 4005 can be limited to a size smaller than the slot 4045 such that positional or angular adjustment of the prong 4005 is still possible in the fully open position.

In the illustrated arrangements, the second prong portion 4042 includes at least one recess or slot 4049. Preferably, the slot 4049 is defined between a first flange 4050 and a second flange 4051. The first prong portion 4040 includes hook portion or engagement flange 4048 that extends longitudinally within the slot 4049 and can move laterally within the slot 4049. Preferably, the engagement flange 4048 engages or contacts the second prong portion 4042 within the slot 4049 and creates at least a substantial seal with the second prong portion 4042. Also, the first flange 4050 can engage the inner surface of the first prong portion 4040 to form a seal between the two portions.

As the prong portions 4040 and 4042 are pulled away from each other, the engagement flange 4048 moves within the slot 4049 toward the first flange 4050. Preferably, the first flange 4050 acts as a stop so that when the engagement flange 4048 contacts the first flange 4050, it cannot move past the first flange 4050 and the first prong portion 4040 is impeded from moving any further away from the second prong portion 4042. Similarly, the second flange 4051 can be configured so that when the prong portions 4040 and 4042 are pushed together, the engagement flange 4048 contacts the second flange 4051. Preferably, the second flange 4051 can stop the engagement flange 4048 from moving any further or past the second flange 4051, which impedes the prong portions from moving any closer together. In this manner, the slot 4049 and flanges 4050, 4051 can define the range of relative movement between the prong portions 4040 and 4042. In some embodiments, the prong 4005 includes two slots 4049 and two corresponding engagement flanges 4048, which can be positioned on opposite sides (e.g., lateral sides) of the prong 4005. In other embodiments, the prong 4005 includes more than two slots 4049 and corresponding engagement flanges 4048. Certain embodiments can also include a size indicator 4054 that shows a user the extent to which the prong portions 4040 and 4042 are compressed together or moved apart. The size indicator can include size designations for the outer dimensions for the prong 2005, such as "S" for small, "M" for medium, and "L" for large. As illustrated, the size indicator 4054 can be located within the slot 4049 or adjacent the slot 4049 and flanges 4048, 4050 and 4051. As illustrated, the size indicator 4054 can be configured so that the largest revealed letter visible on the outside of the prong 4005 indicates the current size.

FIG. 40E illustrates an embodiment of a prong assembly having multiple collapsible portions 4058, 4062, and 4064 that allow for the prong assembly 4056 to have a variable height. Preferably, the collapsible portions 4058, 4062 and 4064 are coaxial and are coupled together and configured to move in a telescopic manner relative to one another. Different sizes and quantities of collapsible portions can provide many varying sizes and smaller increment for sizes. For example, the prong assembly 4056 can include only two collapsible portions, or it can include four or more collapsible portions depending on the different sizes and options desired. Preferably, the collapsible portions 4058, 4062 and 4064 are pulled telescopically outward to increase the height of the prong assembly 4056 and can be pushed back together in order to decrease the height. A friction fit between the collapsible portions can be used to ensure the selected prong height is maintained, and to allow fine, incremental adjustment within the discrete collapsible portions. Preferably, the smallest portion 4064 is at the base of the prong 4056 so that a seal over the top edge of the prong is created by the largest top portion 4058. The top portion 4058 is preferably selected to correspond to the size of the patient's nasal anatomy. This would also help to prevent contaminates entering between the collapsible portions. Preferably, the top portion 4058 includes a sealing top edge 4061 and an opening 4060.

FIGS. 40F-H illustrate various embodiments of cannula prong assemblies that allow for selective spacing of the prongs relative to one another. In some embodiments, the assembly includes two prongs 4005 and one of the prongs 4005 is fixed relative to the cannula 4001, and the other prong 4070 is able to move laterally within the cannula or manifold 4001. In other embodiments, both prongs 4005 and 4070 are configured to move and be adjustable relative to the cannula 4001. Preferably, a portion of the adjustable prong 4070 is within the cannula 4001 and is configured to maintain a seal between the cannula 4001 and the prong 4070 as the prong 4070 moves within a slot or opening 4071 in the cannula 4001. For example, in the embodiment of FIG. 40F, the cannula 4001 includes a slot 4071 through which the adjustable prong 4070 extends and the prong 4070 can be moved laterally to different positions within the slot 4071. The illustrated arrangements include a number of discrete adjustment positions; however, in other arrangements, infinite adjustability within the adjustment range may be provided. Preferably, the slot 4071 includes a plurality of detents or notches 4073 displaced laterally along the slot 4071. The adjustable prong 4070 can include a pin or protrusion 4072 that is configured to engage the notches 4073 in the slot 4071. The pin 4072 can be configured to fit at least partially within each of the notches 4073 to retain the adjustable prong 4070 in a selected position. A user can move the adjustable prong 4070 to a desired position relative to the other prong 4005, and the pin 4072 engages a notch 4073 to retain the prong 4070 in that position. Sliding the adjustable prong 4070 so that the pin 4072 aligns with and fits into one the various notches 4073 allows a user to select discrete, secure septal spacing. As illustrated, the cannula 4001 can include size indicators that label the different notches 4073 or distances from the fixed prong 4005.

FIG. 40G illustrates another embodiment of a cannula prong assembly that allows selective septal or prong spacing. For example, the adjustable prong 4070 includes a rib 4074 that extends from the base or the prong 4070 and is configured to engage multiple grooves 4075 along the manifold slot 4071. Similar to the previous embodiments, sliding the adjustable prong 4070 so that the rib 4074 engages one of the various grooves 4073 allows a user to select discrete, secure septal spacing. In the illustrated arrangement, the grooves 4073 are inward-facing; however, the grooves 4073 could also be outwardly-facing. Points along the slot 4071 can be labeled to give an indication of the chosen septal spacing. FIG. 40H illustrates an additional embodiment comprising a ratchet assembly in which the adjustable prong 4070 includes a tab 4076 adjacent the base of the prong 4070. Preferably the tab 4076 includes notches or protrusions 4077 that are configured to engage the edge of the slot 4071 (or another suitable engagement surface) in the manifold 4001. Preferably, the notches 4077 can be configured so that they can be moved past the edge of the slot 4071 and positioned so that one of the notches 4077 engages the edge of the slot 4071 and retains the adjustable prong 4070 in the selected position.

Figure 40A:
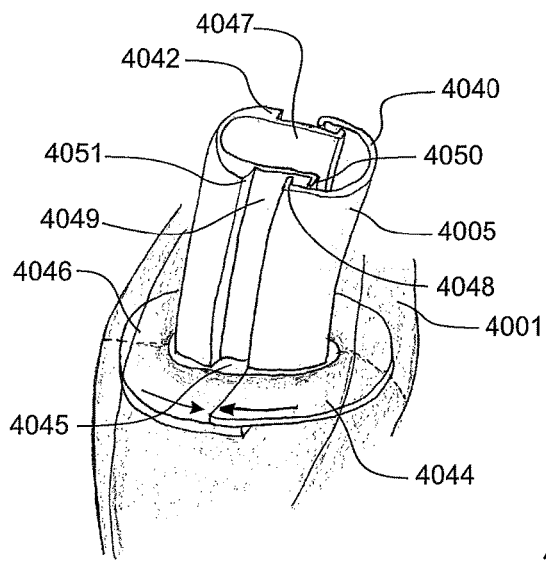
Figure 40B:
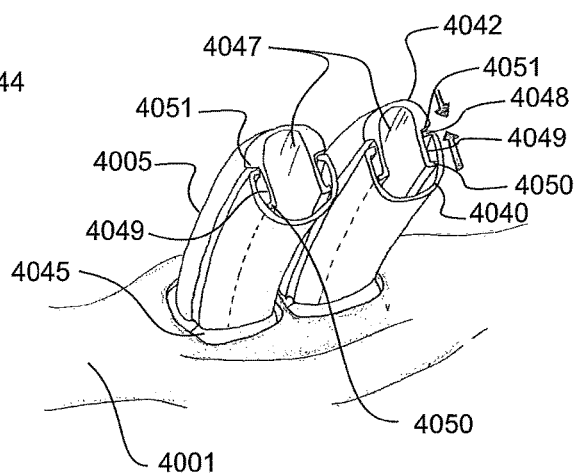
Figure 40C:
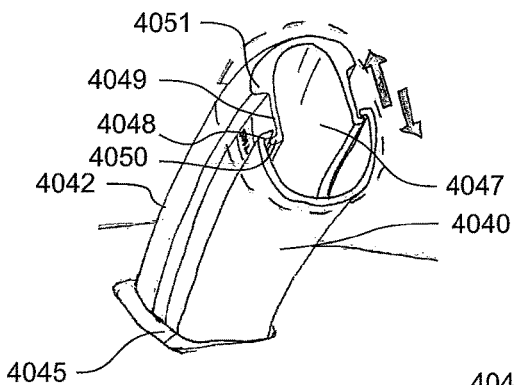
Figure 40D:
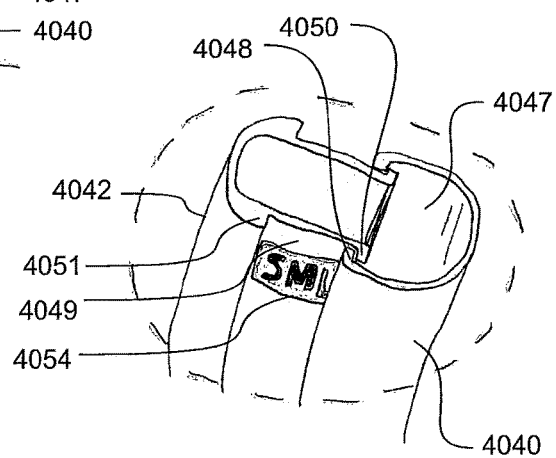
Figure 40I:
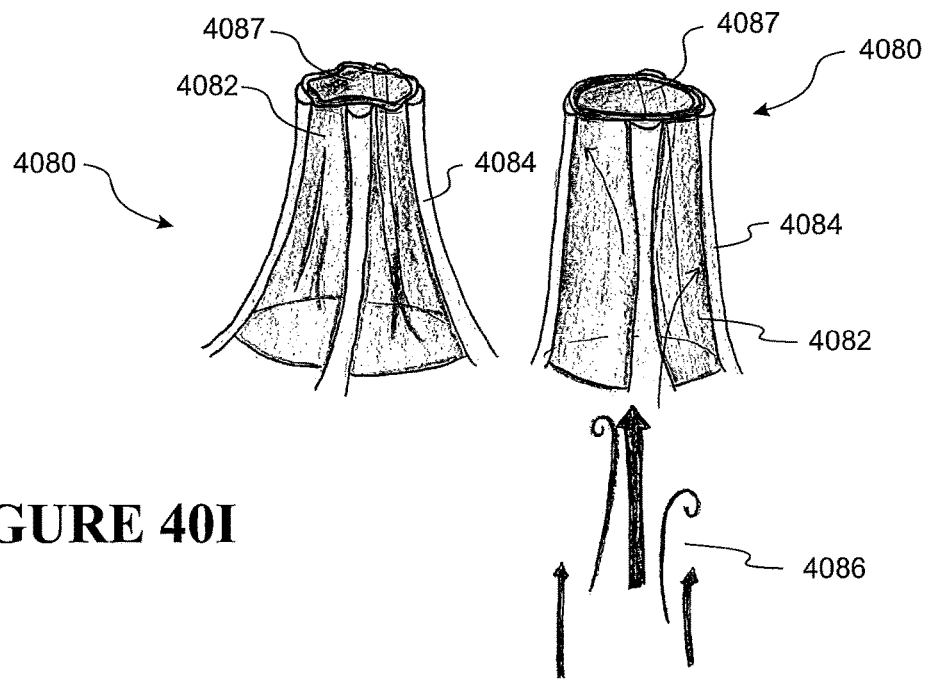
Figure 40J:
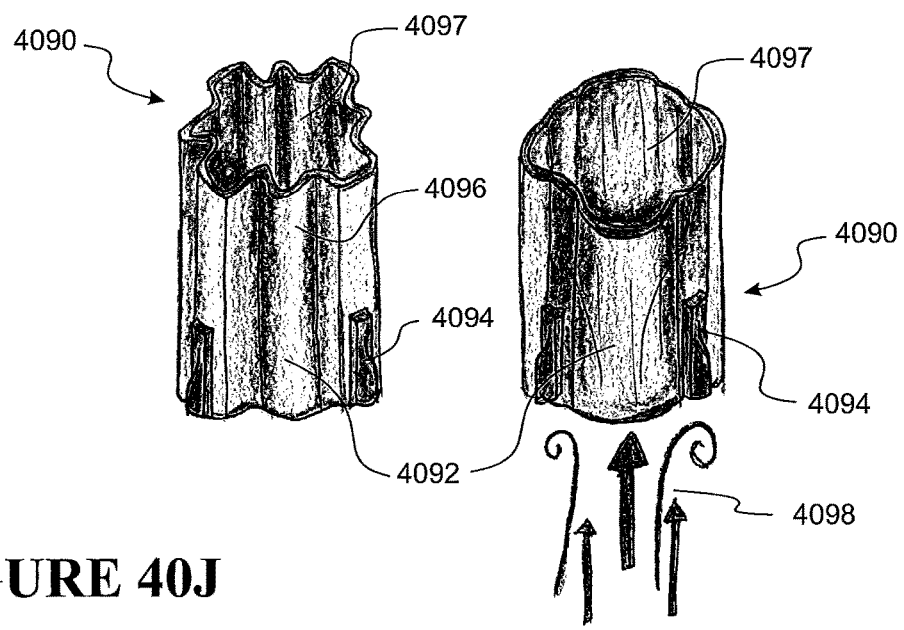

FIGS. 40I and 40J illustrate embodiments of prongs that are made at least partially from a thin film material and are able to expand in response to high air flow or pressure. As illustrated, the prong 4080 is preferably made of a thin film material 4082 outer and has several ribs or other elongate supports 4084 made of a more rigid material and, preferably, extending generally in an axial direction of the prong 4080. Under low or no gas flow, the prong 4080 rests in its natural state and has a smaller diameter. In this state, the film 4082 is at least partially collapsed between the ribs 4084 and the ribs 4084 can be angled toward the center of the opening 4087. As the gas flow increases through the prong 4080, the higher pressure forces the film 4082 to expand outwards and the ribs 4084 are pushed open and away from one another. This increases the diameter of the prong 4080 and the diameter of the prong opening 4087. As the prong 4080 and prong opening 4087 expand, they can form a seal with a patient's nasal anatomy. By using different film materials in these arrangements, one can have some control over the resistance to gas flow, with variable flow rates.

FIG. 40J illustrates an embodiment of a prong 4090 that includes a thin film material 4092 and elongate supports or ribs 4094. Preferably, the ribs 4094 are fixed and do not bend or move relative to one another. In some embodiments, the ribs 4094 are fixed in an upright position and arranged around a circumference of the smallest desired prong diameter. In the absence of air or gas flow, the ribs 4094 remain in an upright position and the film 4092 collapses in between the ribs 4094 and forms folds 4096. As larger gas flow passes through the prong 4090, the film expands outward between the ribs 4094. Thus, the higher gas flow can cause the outer diameter of the prong 4090 and opening 4097 to increase and form a seal with the nasal anatomy of a patient. In this arrangement, preferably, the ribs 4094 do not extend the entire length of the prong 4090. Preferably, the ribs 4094 extend from at or near a base of the prong 4090 along a partial length of the prong 4090, such as up to about one-third to about one-half of a length of the prong 4090 or anywhere within this range. In some arrangements, however, the prongs 4090 can extend a greater portion or an entirety of a length of the prong 4090.

Advantageously, at least some of these thin film prong embodiments require no nurse intervention to choose the prong sizing for the patient, which also prevents poor sizing selection, and increases application efficiency. The prong can be configured to maintain the smallest possible size for prescribed flow rate, thus ensuring maximum possible comfort. These embodiments can be combined with any of the cannula assemblies or configurations described herein. Furthermore, the supports or ribs 4084 or 4094 can be internal, external or positioned within the wall of the prongs 4080, 4090.

The embodiments discussed above allow for customization any or all of the septal spacing, prong diameter and/or prong height. This can help with patients who are 'between sizes,' and allows nurses to use their judgment for fitting an individual patient. Customizable prongs are also advantageous because fewer sizes of cannula can be manufactured, and confusion over choosing between sizes is reduced. Such adjustable prongs can also mitigate the need for training and user instructions on how to select sizes, and potentially reduce waste. These features can also allow the comfort and fit of the cannula to be adjusted as the patient's position and comfort levels change. Each of these embodiments could be used in combination with one or more of the others to provide more than one mode of customization for a single cannula.

With reference to FIGS. 41A-D, in some embodiments, a cannula retention arrangement is configured to improve the retention and security of a cannula on a patient by including a strap or support that is generally U-shaped or has a generally U-shaped portion that fits over and/or around the nose of a patient. Such a support or strap over the patient's nose can provide additional (or substantially all) support for the cannula and can impede unwanted movement of the cannula relative to the patient's face. In some embodiments, the assembly includes a cannula 4101 supported by a support member 4150. For example, the support member 4150 can be coupled to the cannula or manifold 4101 at one or more sides of the cannula 4101, and it can be configured to extend upward relative to a patient's face and over and/or around a patient's nose. Preferably, the support member 4150 is sized and shaped so that its upper portion can rest on a portion of the patient's nose, and preferably the bridge of the nose. The support member 4150 can include softer or more flexible portions, especially the upper portions near or that contact the nose. As described above with respect to other embodiments, the cannula and/or manifold can be removed and adjusted so that the supply tube 4102 can exit the cannula 4101 from a side. The support member 4150 is preferably made from a flexible or semi-rigid material and can be injection molded, stamped or formed by any other suitable process. The support member 4150 can be integral with the top portion of the cannula 4101, or it can be a separate piece that is coupled to the cannula 4101. The support member 4150 can also include a strip 4158 that is configured to bend or conform to the shape of the nose. Preferably, the strip 4158 can retain its shape and is coupled to the support member 4150 so that a portion of the support member 4150 also retains the shape of the strip 4158. Preferably, the strip 4158 can conform to the nose in a way that impedes slipping or falling of the support 4150 from the nose. Preferably, the strip 4158 is made from metal or some other bendable material that maintains its position after being bent or manipulated.

As illustrated, the assembly 4100 includes a head strap 4140 that can be coupled to the support member 4150. In these embodiments, the head strap 4140 can be coupled to the support member 4150 in various different ways. For example, the head strap 4140 can extend through an opening 4153 in the support member 4150 and the end of the head strap 4140 can be fastened back onto a portion of the head strap 4140. The head strap 4140 can include a fastening member 4152 such as a hook and loop material, or any other suitable fastening member or material. The fastening member 4152 can extend along a length of the head strap 4140 in order to allow for adjustment or tightening and loosening of the head strap 4140. The support member 4150 can also include a clip or fastening device 4156 that corresponds to a fastening portion 4154 on the head strap. Preferably, one side of the head strap 4140 is coupled to the support member 4150 with the adjustable fastening member 4152, and the other side is coupled using a clip or snap-fit button device 4156. This allows for adjustability and easy detachment of the head strap 4140 during treatment or the removal process.

Figure 41A:
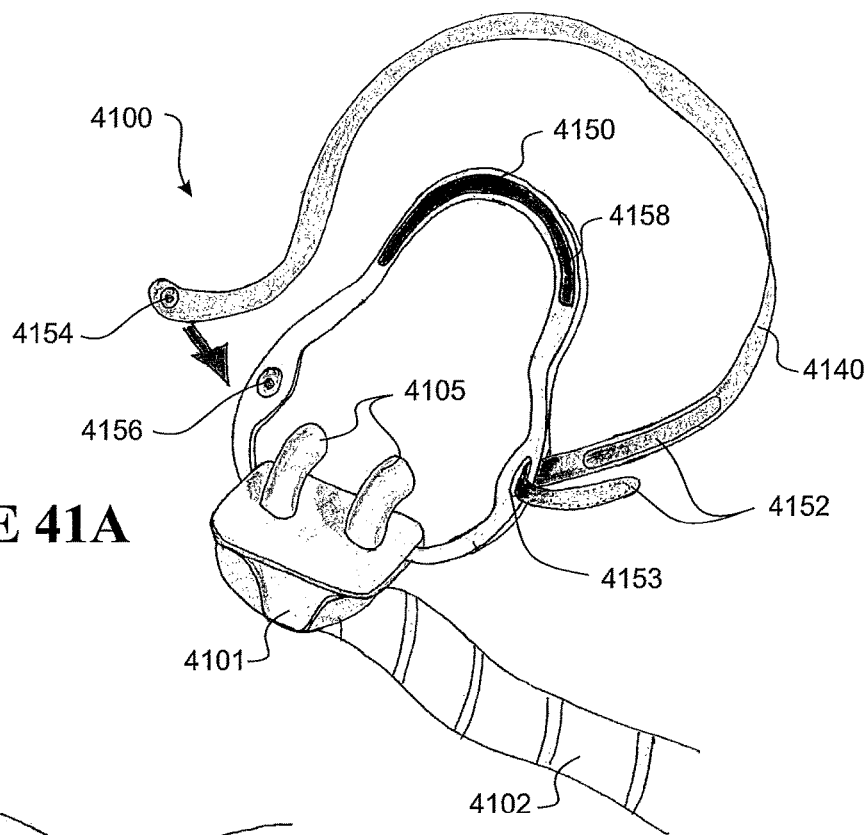
Figure 41B:
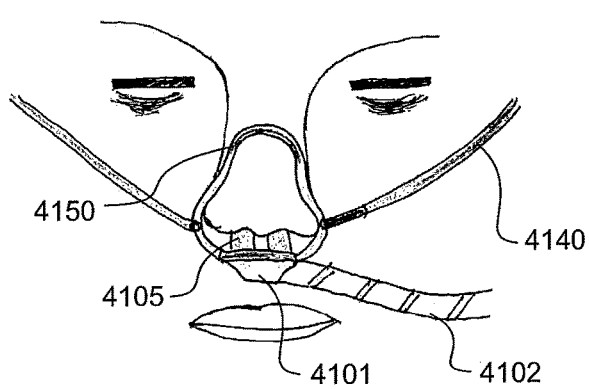
Figure 41C:
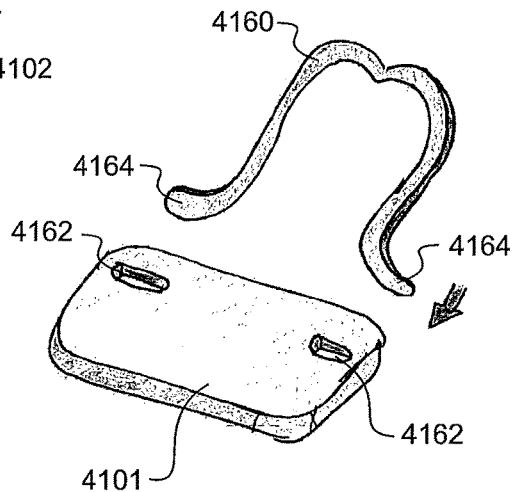

FIG. 41C illustrates an embodiment in which the support member comprises a metal strip 4160 that is coupled to the cannula 4101. Preferably, the metal strip 4160 can be bent and shaped to correspond to the shape of the nose by pressing it into position over the nose. This embodiment can also allow the height of the metal strip 4160 to be adjusted using notches 4164 (or other similar adjustment means) on the metal strip 4160. Such height adjustment can allow for the assembly 4100 and nose strip 4160 to accommodate a wider range of patient nose sizes, and can provide better security and comfort for the patient. The metal strip 4160 can include notches 4164 that can clip into or engage the cannula 4101. The cannula 4101 can include holes or openings 4162 configured to engage the notches 4164. The metal strip 4160 can include multiple notches 4164 on each side to provide height adjustment for the strip 4160.

FIG. 41D illustrates an embodiment of a cannula assembly with a support member 4150 configured to support the supply tubing 4102 and the cannula 4101. The support member 4150 is configured to rest on or around the nose, similar to those support members described in the previous embodiments. The support member 4150 can be made from fabric or a more rigid material like plastic or metal. Preferably, the cannula 4101 has tubes 4102 exiting from both sides, and tubes 4102 can be rigid or semi-rigid. In some embodiments, the support member 4150 is coupled to the supply tubes 4102, and the tubes 4102 are coupled to attachment portions 4172. The attachment portions 4172 can also be coupled to an adjustable head strap 4140. Preferably, the attachment portions 4172 comprise padded portions (not shown) that contact the face of a patient and can be configured to cling to the face and distribute force over a larger area to relieve uncomfortable or painful pressure. The attachment portions 4174 or padded portions can include openings 4174 through which the ends of the head strap 4140 can extend, and which provide adjustment for the head straps 4140. The padded attachment portions 4172 can also be configured to provide bridging of the tubes 4102 and/or the cannula 4101 away from the patient's upper lip and face, such that there is only contact between or substantial pressure exerted on the patient's face where the padded portions 4172 sit. Also, the cannula 4101 and prongs 4105 can be designed to be removed so that cannulas of different sizes and exit sides may be used.

Some cannula systems utilize a heated tubing circuit which can be connected to the humidification chamber. The heated circuit inhibits or prevents condensate formation due to a drop in temperature along the circuit. Some cannula assemblies connected to the end of these circuits are not actively heated and hence are susceptible to temperature losses and condensation formation. One way of reducing temperature drop in one or more of the disclosed embodiments is to insulate the tubing between the circuit and prongs.

Figure 42G:
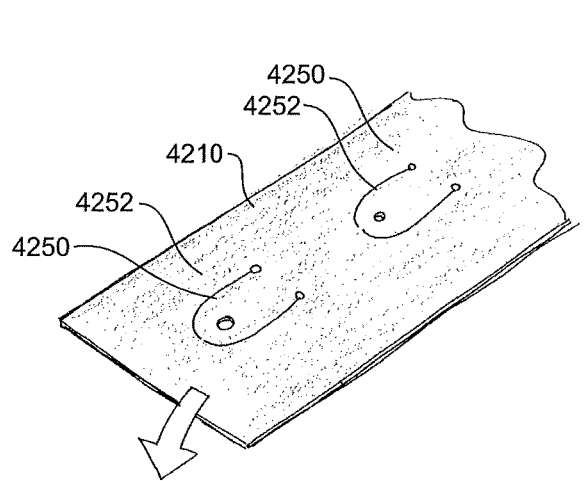
FIGS. 42A-O illustrate example embodiments of insulation and tubing arrangements for a nasal cannula assembly.
Figure 42H:
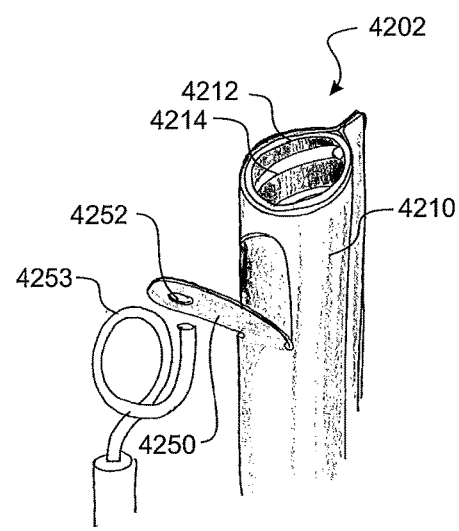

With reference to FIGS. 42A-O, in some embodiments, the tubing is insulated between a heated circuit and the prongs of the cannula. For example, a cannula tube 4202 can include a first (e.g., extruded) tube 4212 and can be wrapped in a fabric or insulating material 4210. The fabric or insulating material 4210 provides insulation for the tube 4212 and any gas that is passing through the tube 4212. In some embodiments, the fabric or insulating material 4210 can be formed into a sleeve around the tube 4212 and can be heat sealed or joined using other suitable processes along its edges or seems. The cannula tube 4202 can also include a coiled member or spring 4214 that extends within the tube 4212 or insulation sleeve 4210. The spring 4214 is preferably a coil spring and is configured to prevent kinks from forming in the tube 4212 when it is bent or deformed. Other suitable mechanisms to avoid occlusion during bending of the tube 4212 can also be used. The outer insulation material 4210 can be made from a breathable material or a non-breathable material. If the insulation material 4210 is a non-breathable material, then it can be directly wrapped around a spring and sealed along an edge to provide a tube and allow the tube 4212 to be omitted.

Some embodiments of the cannula tube 4202 include cannula connector portions 4216 that are coupled to the end of the tube 4202, such as with the tube 4212. Preferably, the connector portions 4216 are configured to be coupled to the cannula tube 4202 by a friction fit, or the connector portion 4216 can also be heat sealed to the tube 4212 and/or insulation material 4210. In some embodiments, the connector portion 4216 includes a valve 4218 and, therefore, the connector portion 4216 provides an airtight or substantially airtight seal with the cannula tube 4202. Preferably, the valve 4218 is a one-way valve that only allows gas flow in one direction. The cannula tube 4202 can also include a tab 4220 coupled to or extending from the outer surface of the tube 4202. Preferably, the tab 4220 includes multiple holes 4222 configured to engage a portion of the head strap 4240 and allow adjustment of the head strap 4240 relative to the cannula tube 4202. For example, the head strap 4240 can include pins or protrusions 4224 that are sized and shaped to extend into and engage any desired one of the holes 4222. The holes 4222 can be positioned on the cannula tube 4202 in a line or row so that the tightness of the head strap 4240 can be adjusted by coupling the pin 4224 to a hole 4222 closer to or further from the cannula 4201 and prongs 4205.

In some embodiments, insulating material 4210 is configured to provide insulation and reduce the temperature drop between a circuit attachment point and the prongs 4205. By reducing temperature drop, the likelihood of condensation forming is greatly reduced. These cannula tube configurations can be used as part of the cannula body 4201 with the prongs 4205 coupled to or inserted into the cannula tube 4202 or insulation material 4210. In some embodiments, the cannula tube 4202 can form part of the structure of the cannula 4201, or it can be integral with the cannula 4201. This arrangement allows the gas to flow through the cannula tube 4202 and into the prongs 4205 which are coupled to or integral with the cannula tube 4202. For example, the arrangement illustrated in FIG. 42C includes an insulated cannula tube 4202 that includes a cannula portion 4201 defined by the walls of the tube 4202. The prongs 4205 can extend directly from the tube 4202 and can be coupled to the inner tube 4212. Preferably, the cannula tube 4202 includes connector portions 4216 that are configured to receive an inspiratory tube 4225 with a corresponding connector 4226. Such an inspiratory tube 4225 can be coupled to either end of the cannula tube 4202, or alternatively in both ends. In these configurations, the exit side of the supply tube 4225 can be changed by simply coupling the supply tube 4225 to the other side of the cannula tube 4202.

As illustrated in FIGS. 42D-F, the cannula tubes 4202 can have various different arrangements, including the following. A cannula tube 4202 can include a tube 4212 on the inside, a spring 4214 wrapped around the tube 4212, and an insulating material or sleeve 4210 wrapped around the spring 4214 and tube 4212. In another embodiment, the spring 4214 can extend along the inner surface of the tube 4212 and the insulation material or sleeve 4210 can be wrapped around the tube 4212. In another embodiment, the insulation material or sleeve 4210 is also wrapped around a pressure line tube 4230 and/or other lines 4228, such as a communication line, etc.

With reference to FIGS. 42G-L, in some embodiments, a cannula tube or inspiratory breathing tube can include a material surrounding the tube that provides features for tube management and/or insulation. The material does not need to be insulation material and can be any breathable or non-breathable material. The features can include tabs, hooks, holes, ties, etc. for hanging and holding the tube. For example, in one embodiment, the insulation material 4210 includes cuts in the material 4210 that form a tab 4250. Preferably, the tabs 4250 are die-cut and include a hole 4252 configured to receive a hook or wire 4253, or any other object that might support the tube 4202. When the insulation material 4210 is wrapped around the tube 4212 and/or spring 4214, the tab 4250 can be pulled outward from the tube 4202 and can be used to engage a hook or other hanging device 4253 to support the tube 4202. Preferably, the tabs 4250 can separate from the insulation material 4210 at multiple edges and include at least one edge that remains coupled to the material 4210. The features can also be folded back in line with the surface of the insulation material 4210 when not being used. Preferably, the tube 4212 is a non-breathable tube wrapped in a fabric sleeve 4210 that includes the die-cut details configured to assist in hanging the tube 4202 and tube management, while also providing insulation.

Figure 42I:
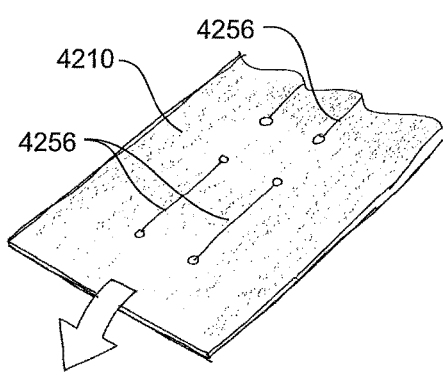
Figure 42J:
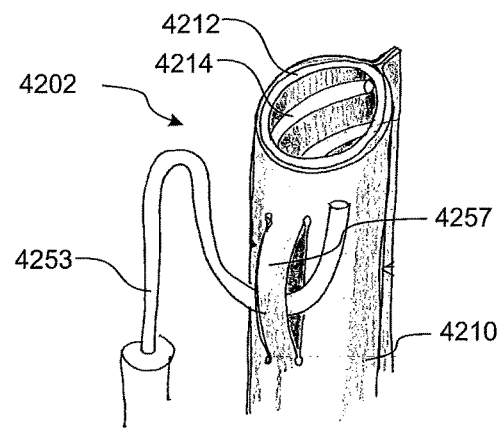
Figure 42K:
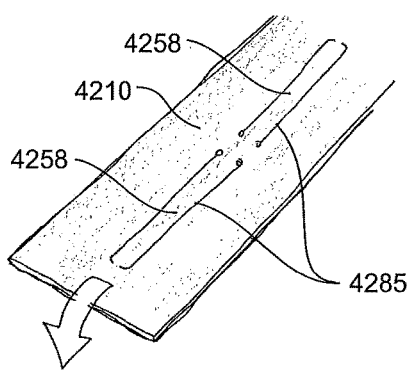
Figure 42L:
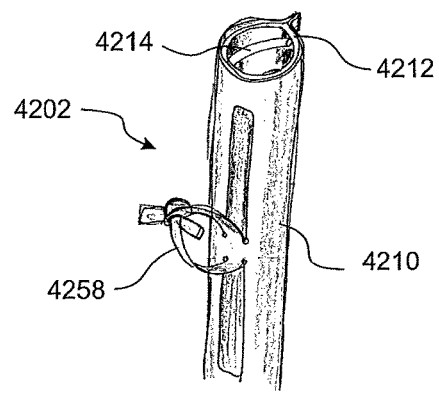

In other embodiments, shown in FIGS. 42I and 42J, the features cut into the insulation material 4210 can be slots 4256 cut into the material and configured to provide a portion of the material 4257 that can be pulled away from the material 4210 to form an opening or hook 4257. Preferably, the insulation material includes two parallel slots 4256 and the material between those slots 4256 can be pulled away from the tube 4202 forming an opening through which a hook 4253 or other hanging device can extend to support the tube 4202. In another embodiment, shown in FIGS. 42K and 42L, the insulation material 4210 includes two tabs 4258 that can be pulled away from the tube 4202 and the ends thereof tied together or coupled to another object such as a bed, ventilator or a hanging device. The tabs 4258 can be defined by cuts or slots 4285. Preferably, each of the die-cut details can be folded back in line with the surface of the insulation material 4210 when features are not being used.

With reference to FIGS. 42M-O, embodiments of the cannula assembly include a cannula portion comprising a thin sheet or film 4270 that can be made from plastic, non-breathable fabric, or a similar material. The film 4270 can be rolled or folded to form a tube-like structure 4271 with an opening at each end. In some embodiments, the tube and cannula are formed out of a thin, breathable or non-breathable film 4270 and the film 4270 includes a bead 4274 that provides some structural support to the tube and cannula assembly. Preferably, the bead 4274 on the film 4270 can provide support that impedes kinking of the tube 4271 or cannula assembly and may be configured to allow the cannula tube 4271 to deform easily in one direction and not as easily in the another direction. The pattern or design of the bead 4274 can be configured to provide specific or intentional bend areas, and the bead 4274 can be extruded, printed or otherwise applied onto the film 4270. The bead 4274 can also be on either side of the film 4270, such that it ends up on either the inside or outside of the tube 4271. Preferably, the film 4270 is wider towards the outer edges and narrower at the center area corresponding to the prongs 4205. The bead 4274 can extend substantially across the film 4270 in both directions. Preferably, the film 4270 is rolled or folded into a tube shape and sealed at the edges to form a cannula tube structure 4271 that contains holes 4277 corresponding to the prongs 4205. For example, the edges can be heat sealed. The prongs 4277 can be coupled or heat sealed to the film 4270 or bead 4276. The film 4270 can also include a cannula portion of the bead 4276 which includes the holes 4277.

In some embodiments of the cannula assembly, the film 4270 includes tabs 4278 at each end of the film 4270, and the tabs 4278 include openings 4272 or other fastening devices that are configured to be coupled to a head strap or other retention device. The cannula tube 4271 can also include connector portions 4216 coupled to each end of the cannula tube 4271. Preferably, the connector portions 4216 are heat sealed to the cannula tube 4271 and include one-way valves 4218, as described in previous embodiments. Preferably, the connector portions 4216 are configured to receive a supply tube. This allows changing of the supply tube exit side by connecting a supply tube to the connector portion 4216 on the desired side of the cannula tube 4271. As illustrated in FIG. 42O, other embodiments include a material portion 4282 made from fabric or some other suitable material. This material portion 4282 can be configured to face the patient and be substantially planar or flat in a vertical direction. The cannula tube 4271 can also include a film portion 4270 that is rolled or rounded and its edges 4280 are sealed to the material portion 4282. The film portion 4270 can include a bead 4274 that provides structure to the film 4270. Preferably, embodiments of the cannula tube 4271 can bend or comply to fit the patient's face.

Figures 43H, 43I, 43J:
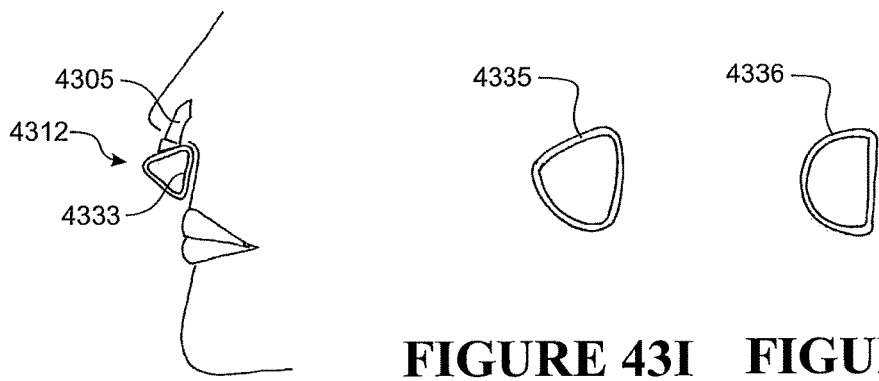
FIGS. 43A-O illustrate example embodiments of tubing arrangements for a nasal cannula assembly.
Figure 43K:
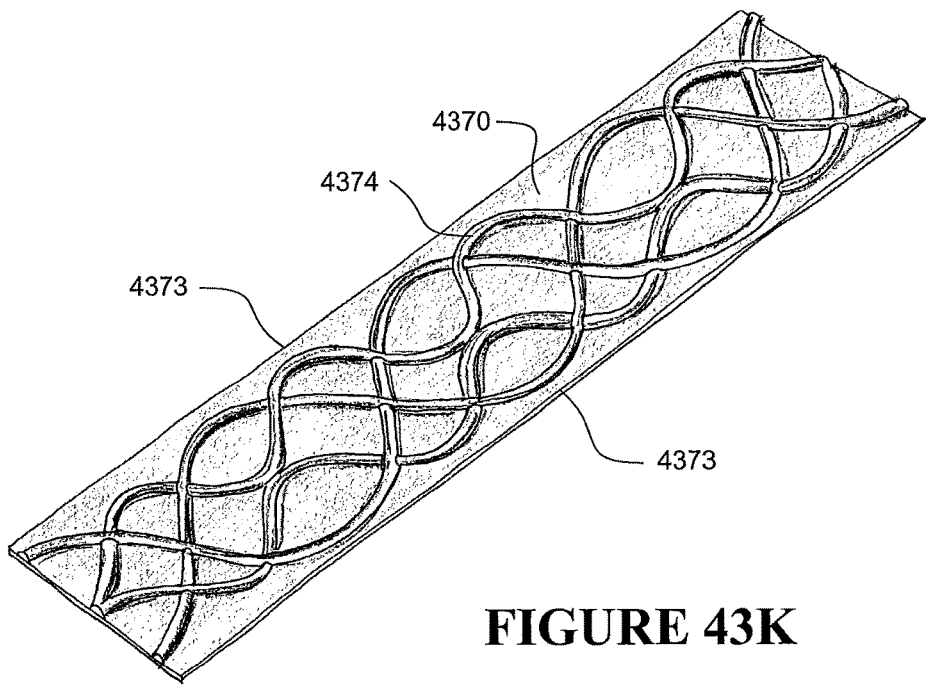

With reference to FIGS. 43A-J, some embodiments of the cannula tubing include tubing that is not circular in its cross-section. In some embodiments, the tube is wrapped or extruded over a section of spring or other structure that has a non-circular cross-section. One benefit of having a non-circular tube cross-section is that it allows the tube to sit flat on the contact area of a patient's skin. These embodiments illustrate techniques for producing tubes with a triangular cross-section, but any shape cross-section could be used that has a substantially planar side portion. In some embodiments, such as shown in FIGS. 43A and 43B, die cutting is used to produce a thin folded sheet of spring metal that has a V-shaped cross-section. Preferably, the folded spring 4310 is configured to fit within a tube 4314 and provide structural support that impedes or prevent kinking of the tube 4312. The folded spring 4310 can also include cutouts 4311 along the length of the spring 4310 and have dimensions A, B, C and D, as illustrated. These dimensions can be modified to provide high flex areas and low flex areas. A thin film of breathable or non-breathable material 4314 can be wrapped around or extruded on the outside of the spring 4310 to form a closed tube. Preferably, the resulting tube 4312 includes substantially planar sides that can rest flat against the skin of a patient. The prongs 4305 can be coupled to one of the planar sides of the tube 4312. In some embodiments, the folded spring 4310 can be configured so that middle portion of the spring 4310 in between the ends 4318 has a smaller cross-section than the outer portions near the ends 4318. This allows for the tube 4312 to be a tapered cannula tube, as illustrated in FIG. 43C, with the narrow portion at the cannula and adjacent the prongs 4305.

In other embodiments, the tube 4312 can include a generally helical spring 4320 that has, for example, a non-circular or a triangular outer shape or cross-section. The tube portion 4314 can be extruded or wrapped over the helical spring 4320 and the resulting tube 4312 can have a triangular cross section. In another embodiment, the spring can be a two-sided wire 4330 with bent ends 4332. This configuration can involve bending a flat wire section 4330 into a triangular cross section. This can be achieved by pressing a straight wire section over a mould to produce a wire frame. The wire 4330 can have bent ends 4332 that extend in the direction of a third side and provide support for a third side. A thin film of breathable or non-breathable material 4314 can be extruded on the outside of the wire 4330 to form a closed tube. The geometry of the folding of the wire 4330 can be changed along the length of the tube 4312 to provide high and low flex areas. The wire 4330 can also be applied over the outside of a tube 4314 to provide a support for the tube 4314 or a type of exo-skeleton. Preferably, the triangular cross-section of the tube 4312 provides substantially planar side portions 4333 that fit to the face of a patient better than a round profile tube. Preferably, the flat side portion 4333 of the tube 4312 can rest against the substantially flat skin portion of the patient under the nose and the prongs 4305 are directed upward into the nose of the patient. In other embodiments, the cross section of the spring and tube 4312 can be a "soft" triangle that has slightly curved side portions or a half circle cross-section that includes one substantially planar side portion, among other suitable cross-section shapes that include substantially planar side portions.

FIGS. 43K-O illustrate other embodiments of a tube 4371 comprising a thin sheet or film 4370 and a bead 4374 configured to provide structural support. For example, the thin film 4370 is made of plastic or fabric and can be rolled or folded to form a tube 4371. The film 4370 can be breathable or non-breathable. The film 4370 includes a bead 4374 that is extruded, printed or otherwise applied onto the film 4370 and is configured to provide structural support to the tube 4371. Preferably, the bead 4374 on the film 4370 provides an anti-kink structure that can be arranged in such a way as to allow for deformation easily in one direction while maintaining rigidity in another. The film 4370 also includes edges or edge portions 4373 that can be sealed together to form the tube 4371. Preferably, the edges are heat sealed. Preferably, the pattern of the bead 4374 can be configured to provide specific bend areas along the tube 4371. Each end of the tube 4371 can be coupled to a connector portion 4316 that can be coupled to a different tube or supply tube. In another embodiment, a thermal reflecting material 4390 may be printed on or attached to film 4370 and function as a support and insulation. Other embodiments have different configurations for coupling the edges 4373 of the film 4370 to form the tube 4371. For example, a first cross section 4392 includes a film 4370 and the edges 4373 of the film are overlapped so that one is on top of the other and the edges 4373 are seals together. In a second cross-section 4394, the edges 4373 are folded toward the center of the tube 4371 and sealed together so that the ends of the edges 4373 are within the tube 4371. In a third cross-section 4396, the edges 4373 are bent outward and coupled and sealed to a second film or material 4397 and the second film or material 4397 can be substantially planar.

With reference to FIGS. 44A-D, some embodiments of cannula breathing tubes include foam tubing having different shapes. Preferably, the tubes are formed from closed cell foam. The use of closed cell foam or other insulating foams can provide excellent insulating properties and reduce the temperature drop between the circuit and the prongs on the cannula, thus reducing the formation of condensate. The tubes are preferably extruded with a spring core. The spring 4414 can be configured to prevent or impede kinking of the tube 4402. Preferably, some embodiments include a flat side portion 4406 which is configured to rest comfortably against a patient's face. For example, as shown in FIG. 44A, a tube 4402 can include a foam outer portion 4410 that has a generally circular cross-section. The foam outer portion 4410 can also include a substantially planar portion or surface 4406. Preferably, a spring 4414 extends within the inner portion of the tube 4402 and provides structural support to the tube 4402 and can also prevent or lessen the likelihood of the tube kinking. Preferably, the foam outer portion 4410 is made from closed cell foam and the spring 4414 is a coil or spiral spring. In another embodiment, as shown in FIG. 44B, the tube 4402 includes a slot 4420 extending lengthwise through a portion of the outer foam portion 4410. Preferably, the slot 4420 is adjacent the substantially planar side portion 4406. Preferably, the slot 4420 contains a malleable rod or member 4422 that is embedded in the foam tube 4402. The rod 4422 allows the tube 4402 to be bent into various shapes and positions and can be configured to hold the tube 4402 in the selected position. For example, the tube 4402 may be bent in such a way as to keep it away from a patient's mouth. The tube 4402 can also be bent so that it conforms to the shape or features of a patient's face. In another embodiment, as shown in FIGS. 44C and 44D, the tube 4402 includes an open slot 4420 adjacent the substantially planar side portion 4406. The open slot 4420 can be configured to receive a pin or mushroom shaped member 4430 located on a head strap 4440 or other retention member. Preferably, the open slot 4420 can receive the pin 4430 and the pin 4430 can slide within the open slot 4420 and allows for adjustment of the head strap 4440 relative to the tube 4410.

With reference to FIGS. 44E-G, in some embodiments, the tube 4450 includes internal ribs 4454 that provide support and are configured to prevent or lessen the likelihood of the tube 4450 kinking. If a tube 4450 is kinked or folded, it could block the pathway of the gas and failed to deliver sufficient gas to the patient. For example, the tube 4450 can be extruded to have a non-circular cross-section and preferably includes one or more ribs 4454 on the inner surface 4453 of the tube portion 4456. The ribs 4454 can extend length wise through a portion or entirety of the tube 4450 and can have sides with edges or can be rounded. The tube 4450 can include an outer layer or sleeve 4452 made from a fabric material or other suitable insulating material, as shown in FIG. 44E. Alternatively, the tube 4450 can omit this layer, as shown in FIG. 44F. Preferably, the tube 4450 contains at least one substantially planar external surface 4464 which is configured to rest comfortably on a patient's face. In some embodiments, the cross section of the tube 4450 is rectangular with ribs 4454 extending along the sides of the inner wall surfaces 4453. The ribs 4454 can eliminate the need for a spring or other member to provide structure and prevent kinking. In other embodiments, as shown in FIG. 44G, the cross section of the tube 4460 is substantially triangular and includes a rib 4454 on the inner wall surface 4453 at one or more corners of the triangular cross-section. The tube 4460 also includes substantially planar side portions. In other embodiments, the tube 4470 includes a semi-circular shape having a substantially planar side portion 4474 and multiple ribs 4454 extending inward from the curved portion of the cross section. In another embodiment, the semi-circular tube 4480 includes a single rib 4454 extending inward from the inner wall surface of the curved portion.

Figure 45A:
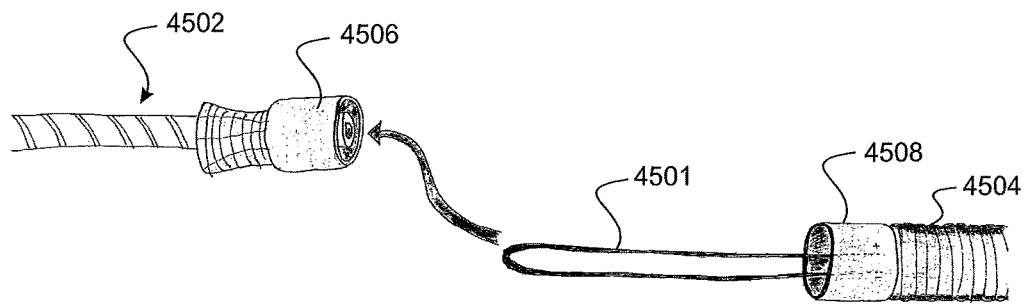
FIGS. 45A-Q illustrate example embodiments of temperature regulation arrangements for a nasal cannula assembly.
Figure 45B:
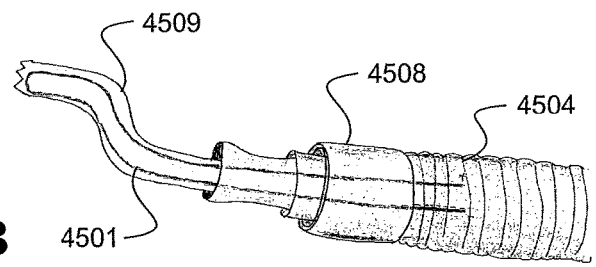

With reference to FIGS. 45A-Q, in some embodiments, cannula or supply tubes can include one or more wires or other heating elements that provide heat to the tube and/or gas passing through the tube. In some situations, it is desirable to minimize the temperature drop through a cannula tube system because any temperature drop may result in condensation and a reduction in the humidity of the gas delivered to the patient. The heat lost to the environment from the cannula system can be at least partially offset by adding heat energy, thus minimizing the temperature drop. For example, a heating element (e.g., wire 4501) can extend within a heated supply tube or circuit 4504, and the wire 4501 can extend out of the end 4508 of the supply tube 4504 or tube circuit. Preferably, the wire 4501 is configured to extend or thread into the cannula tube 4502 through a connector 4506. The wire 4501 can be configured to heat the cannula tubing 4502 and/or the gas passing through the tubing 4502. The tube 4502 can be breathable or non-breathable. Preferably, the wire 4501 is configured to be malleable yet rigid enough so that it can be conformed to a shape and hold that shape to improve routing of the tubing 4502 away from the mouth or face of the patient. In some embodiments, the wire 4501 is rigid enough to hold the weight of the tube 4502 so that it can hold the tube 4502 away from the mouth or face of the patient. Both the cannula tube 4502 and the heated tube 4504 can include connectors 4508 and 4506 that are configured to be coupled together. These connectors are preferably 22 mm tapered connectors. The heated wire 4501 can also be at least partially contained within a film or tube 4509 within the tubing 4502 and/or 4504, if desired.

Figure 45C:
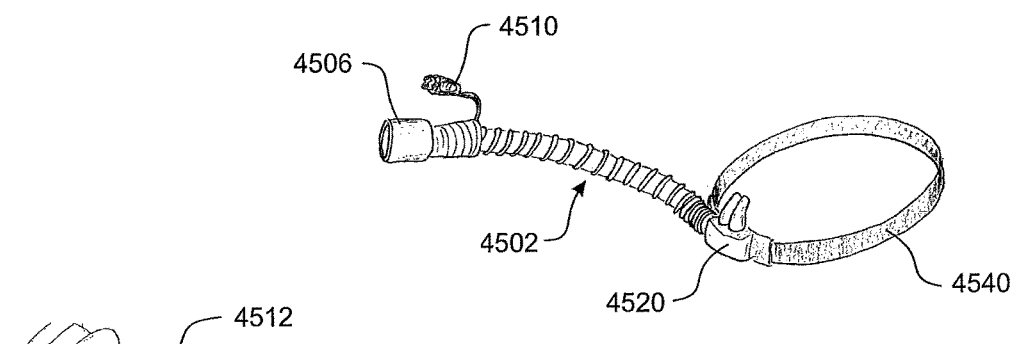
Figure 45D:
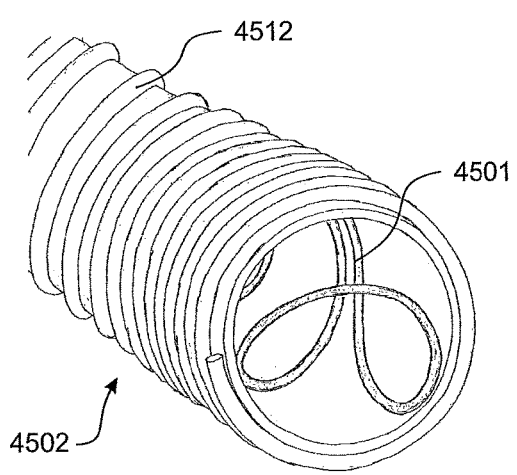
Figure 45E:
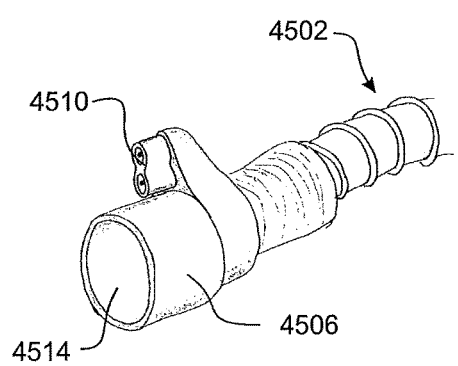

In some embodiments, as shown in FIG. 45D, the interface cannula tubing 4502 can include a heating element or wire 4501, similar to those used in breathing circuits. Preferably, the heating wire 4501 is coiled and extends within the tube 4502. One end the tube 4502 includes a connector 4506 and an electrical connection 4510 configured to receive electrical power, as shown in FIG. 45C. The connector 4506 can also be a dual connector having both an opening or flowpath 4514 and an electrical connection 4510, as shown in FIG. 45E. Preferably, the other end of the tube 4502 is coupled to a cannula 4520 that includes prongs 4505 and is coupled to a head strap 4540 or other retention arrangement.

In some embodiments, as illustrated in FIGS. 45F and 45G, the tube 4502 includes a heating element 4515 coupled to the outside, inside or within a wall of the tube 4502. The heating element 4515 can include two wires 4518 in electrical contact with (e.g., in or on) an electrically conductive polymer 4516. A voltage can be applied across the wires 4518 and through the polymer 4516 to generate heat. The heat can be generated as current 4519 flows through the polymer and can be transferred to the tube 4502 and/or gas flowing through the tube. In some embodiments, the element 4515 can be an internal heater wire as discussed in the previous embodiments, or can be a structural component of the tubing 4502, such as a reinforcement rib. Advantageously, in such an arrangement, because the electrical circuit is completed by the polymer 4516, the element 4515 can be cut to any length and can still be functional, and there is no need to join the wires 4518 at the cut end.

As illustrated in FIGS. 45H and 45I, some embodiments of tubing can include a film 4520 that includes a conductive material and is made into or applied onto a spiral tube 4502. Preferably, a conductive strip 4522 is printed or applied to the film 4520 by a printer 4521. The spiral tube 4502 can include conductive spirals formed by the conductive strip 4522 (e.g., applied in a helical manner between the reinforcement ribs) and when a current is passed through the conductive strip 4522, heat is generated and transferred to the tube 4502. In some embodiments, the spiral film 4520 can be wrapped around a tube or it can form the tube itself.

The conductive strip can be very low profile so the effect of it on the size and mechanical properties of the tubing 4502 is minimal.

Figure 45J:
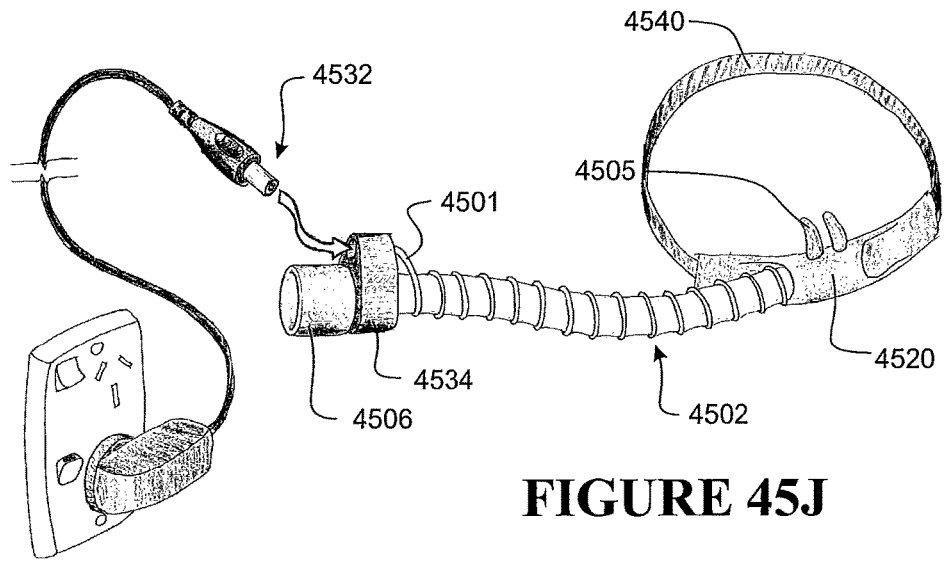
Figure 45K:
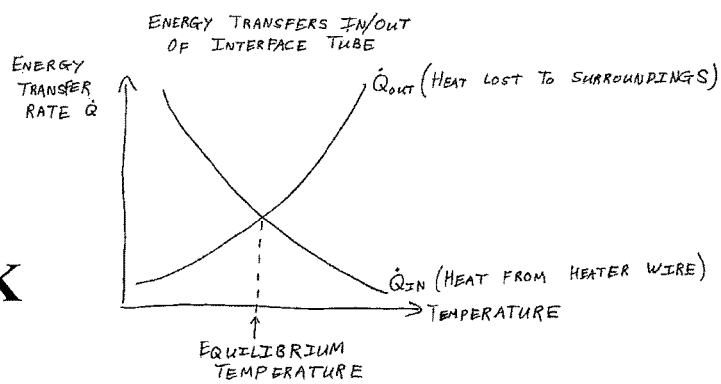

In some embodiments, with reference to FIGS. 45J and 45K, the tube assembly 4502 includes a heating element 4501 made from a material having a positive temperature coefficient (PTC) of resistance. Preferably, the element 4501 is coupled to an interface 4534 which is connected to a basic constant voltage power supply 4532. The basic power supply can be a basic AC/DC adapter 4530 and, in at least some arrangements, no control system is required. The PTC material element 4502 can be configured to act as a temperature control system. Preferably, as the temperature of the material rises, the resistance of the material can increase and the rate of heating input is reduced until an equilibrium temperature is reached at which the rate of heating input is equal to rate of heat lost to the surroundings. This is further illustrated in FIG. 45K, where Qout is the heat lost to the surroundings and Qin is the heat from the heated wire or element 4501. The heated wire or element 4501 can be either internal or external to the tube 4502. The power source is preferably a constant voltage source, such as 12 volts. In these configurations, the PTC element or wire 4501 can be configured so that with a constant voltage, the wire 4501 and/or tube 4502 maintains a constant desired temperature to heat the gas passing through the tube 4502.

Figure 45L:
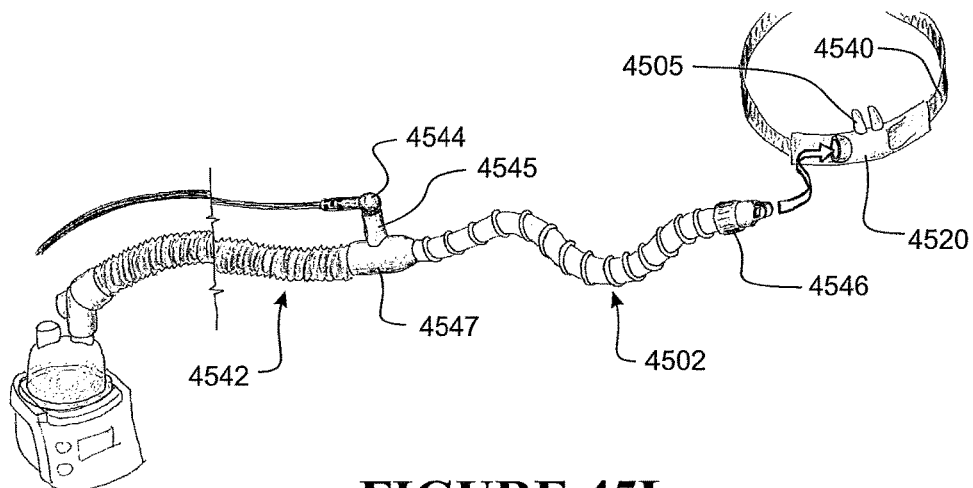

With reference to FIGS. 45L and 45M, the breathing circuit can comprise two types of tubing, one being robust and inexpensive to manufacture and the other being a lightweight and flexible. For example, the main segment of tubing 4542 can be strong, stiff, and inexpensive, while the patient-end segment of tubing 4502 can be a lightweight, very flexible tube. Preferably, a heating element 4501 extends through a substantial entirety or the full length of the tubing circuit through both tube segments 4542 and 4502. For example, the cannula 4520 and head strap 4540 can be separate pieces from the end segment 4502, and the cannula 4520 includes an opening that is configured to receive a connector 4546 at the end of the patient-end tube segment 4502. Preferably, the connector 4546 is a "click" or snap-fit connector that is configured to easily click into the opening on the cannula 4520 and can be easily removed from the cannula 4520. Preferably, the two segments are coupled together at a tubing connector 4547. The heated wire 4501 can be configured to pass through the main segment 4542, the tubing connector 4547 and the patient-end segment 4502. Preferably, the heated wire 4501 extends toward or to a location adjacent the end segment connector 4546 so that there are no substantial unheated segments of the tube 4542 and 4502. In some embodiments, the tubing connector 4547 includes an opening or port 4545 that is configured to receive a temperature sensor 4544. Preferably, the heated wire 4501 extends past the location of the opening 4545 and temperature sensor 4544.

With reference to FIG. 45N, some tube embodiments include one or more outer lumens that extend axially or spirally around the tube. A small amount of the gas or therapy passing through the tube 4502 can enter into the hollow lumen 4552 and can exit from the lumen 4552 into the outer environment. For example, the tube 4502 can be a hollow tube such as a spiral bubble tube and the lumen 4552 can be a spiral lumen. Preferably, the lumen 4552 and tube 4502 include a bleed hole at either the distal or proximal end portion. The bleed hole 4556 can be configured to allow a small portion of the warm therapy or gas to enter and move through the lumen 4552, creating a warmed insulating layer around the tube that minimizes temperature drop in the main gas flow. Preferably, the gas in the lumen 4552 can exit the lumen 4552 through an exit hole 4554 at the opposite end of the tube 4502. Although illustrated with the bleed hole 4556 nearer to the cannula 4520 than the exit hole 4554, in some configurations, this arrangement could be reversed. In some embodiments, the outer surface of the lumen 4552 forms the inner surface of the tube 4502, and in other embodiments, the lumen 4552 is wrapped around the tube.

With reference to FIGS. 45O-Q, some embodiments of a tube 4580 can include textile portions that are knitted or woven with fibers 4582. Electrically conductive wire or material 4584 can also be knitted or incorporated into the knitted portions. The wire or conductive material 4584 can be configured to generate heat when current is passed through it. Preferably, the wire or conductive material 4584 is configured to provide heat to the woven textile portion. The wire 4584 can also be configured to provide structural support for the tube 4580. The woven tube 4580 can also include multiple wires 4584 or portions of conductive material. Is some embodiments, the entire tube is made from the woven textile material (FIG. 45D), and in other embodiments, the woven textile material is configured to be a sheath or covering for the tube 4502 (FIG. 45Q).

With reference to FIGS. 46A-E, and as described with reference to FIGS. 29A-L, some cannula assembly embodiments are configured to measure the pressure in the flow path. As discussed above with respect to previous embodiments, it can be desirable to be able to measure the pressure in the flow path near the patient (e.g., at or near the cannula or manifold) for at least one or both of 1) monitoring of the pressure delivered to the patient and 2) pressure feedback control of a blower flow source (e.g., blower and humidifier). In some embodiments, the cannula or manifold 4610 includes an inlet opening 4612 and a pressure monitoring port 4614 configured to assist in measuring the pressure of the flow path entering the manifold 4610. The manifold 4610 can also include an inlet portion 4616 within the manifold 4610 and an outlet portion 4620 of the port 4614 that extends outside of the manifold 4610 and can be coupled to a pressure sensor. In some embodiments, as shown in FIG. 46B, the port 4614 is a static pressure port positioned on a wall 4615 of the cannula manifold 4610 that is parallel to the bulk flow direction. In other embodiments, as shown in FIG. 46C, the port 4616 is a total pressure port that is directed towards the bulk flow direction and can measure a combination of the static and dynamic pressure. In other embodiments, as shown in FIG. 46D, the port 4618 includes a shroud 4622 and is directed towards the bulk flow direction. This type of port 4618 is less sensitive to flow turbulence and disturbances from any bends or irregularities in the upstream tubing. Some embodiments can also include a static source port 4630 or a pitot-static tube 4640, as illustrated in FIG. 46E.

Figure 47A:
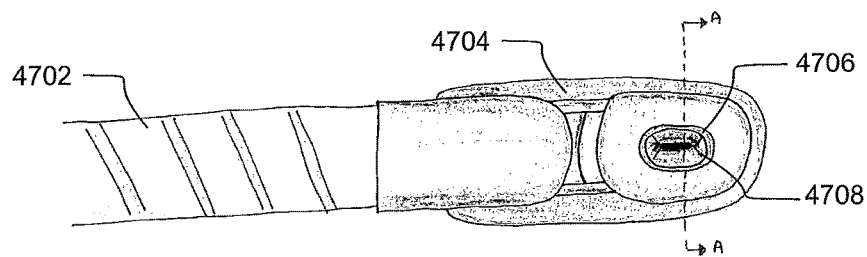
FIGS. 47A-O illustrate example embodiments of nasal cannula arrangements configured to accommodate a nasogastric (NG) or nasojejunal (NJ) tube.
Figure 47B:
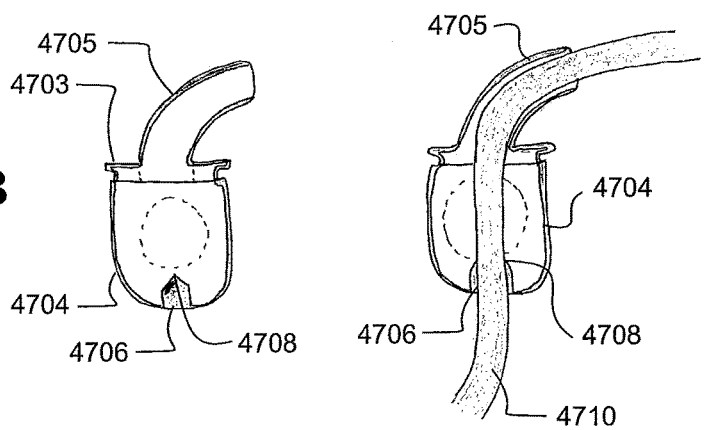
Figure 47C:
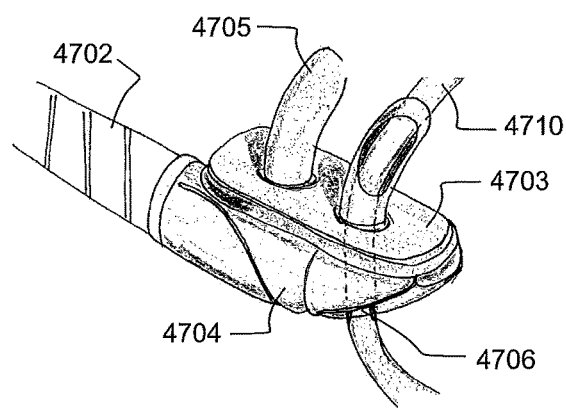
Figure 47D:
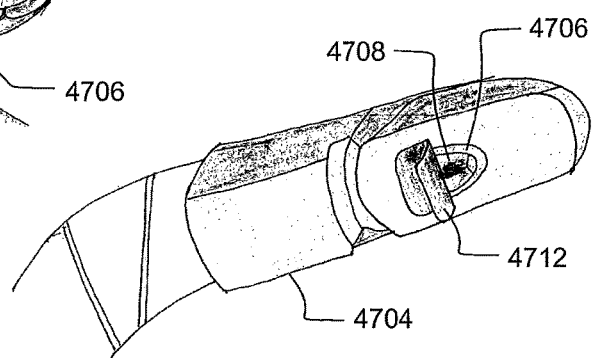

With respect to FIGS. 47A-N, some cannula embodiments are configured to accommodate (e.g., receive or support) feed tubes. In certain situations, a Nasogastric (NG) or Nasojejunal (NJ) (collectively "NG/NJ") tube is used to feed patients undergoing nasal high flow therapy or other therapy requiring nasal prongs. These tubes are inserted into the digestive system through the patient's nose. Currently the method of securing these tubes is to use tape to stick the tube to the patient's face. It is desirable to have prongs or cannulas that allow for NG/NJ tubes to be easily accommodated into the nostrils of a patient. In some embodiments, a cannula assembly includes a manifold 4704 that can be coupled to a supply tube 4702. Preferably, the manifold 4704 includes an opening 4706 and, in some configurations, the opening includes a valve 4708. Preferably, the valve 4708 is configured to form an air-tight or substantially air-tight seal in the absence of something inserted through the valve 4708 and, in at least some configurations, may also provide an air-tight or substantially air-tight seal with an NG/NJ tube passing through the valve 4708. In some embodiments, the valve 4708 is a duck bill valve and the manifold 4704 can include more than one opening 4706 and valve 4708. In one embodiment, the manifold 4704 includes two openings 4706 and two valves 4708, one opening 4706 and one valve 4708 corresponding to each of the prongs 4705. Preferably, a NG/NJ tube 4710 can pass through the opening 4706 and valve 4708, and can extend up through the cannula 4703 and prong 4705 and into the nostril of a patient. The valve 4708 can form a seal around the inserted NG/NJ tube 4710 so that little to no air or gas leaks out of the manifold 4704 through the opening 4706. The manifold 4704 can also include a covering portion, such as an adhesive cover or label 4712, that can be configured to attach to the manifold 4704 and cover the opening 4706 and valve 4708 unless and until the opening 4706 is to be used. Preferably, the covering portion 4712 can be removed or folded back to expose the opening 4706 when a tube 4710 is to be inserted. The covering portion 4712 can be configured to prevent debris from entering the opening 4706 or microbe build-up from forming on the valve 4708. Preferably, the covering portion 4712 can be re-attached to the manifold 4704 to cover the opening 4706 after a NG/NJ tube 4710 can been removed from the manifold 4704. In some embodiments, the valve 4708 can be located under either prong 4705 or in other embodiments valves 4708 can be located under both prongs. In some embodiments, the manifold can provide nasal gas treatment through one prong 4705 while at the same time providing nutrition through an NG/NJ tube 4710.

Figure 47E:
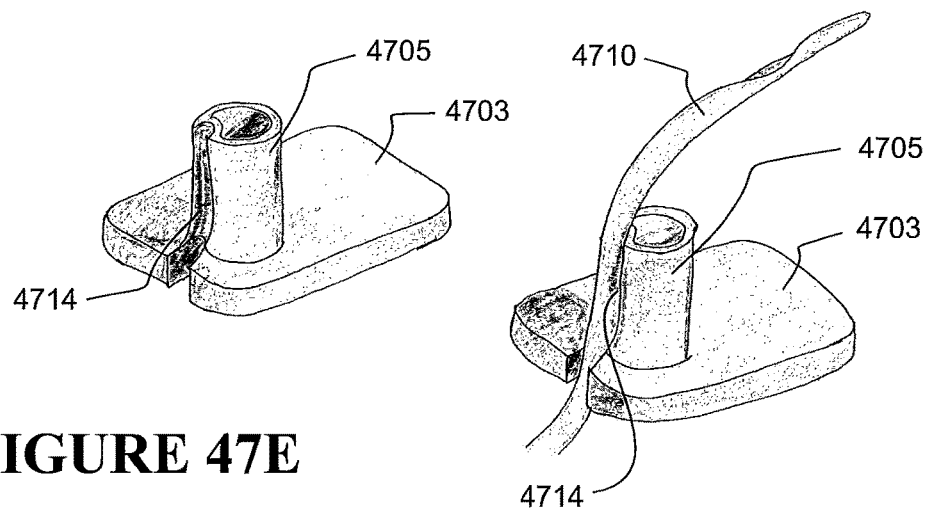

In some embodiments, the cannula 4703 can include a groove 4714 that extends through the cannula 4703 and/or along the prong 4705. For example, as illustrated in FIG. 47E, the cannula 4703 includes a groove 4714 in the side of the cannula 4703, and the groove 4714 runs upward along the outside of the prong 4705. Preferably, the groove 4714 is only on the outer surface of and does not enter the airway of the prong 4705, and the prong 4705 retains its generally tubular shape. The groove 4714 can be sized and shaped to receive at least a portion of a NG or NJ tube 4710 so that the tube 4710 can pass through or run along the groove 4714 and into the nostril of a patient. The groove 4714 can be molded into the cannula 4703 and prong 4705 or can be achieved by any other viable means. The shape of the prongs 4705 may be straight (as shown) or curved. If curved prongs are used, the groove 4714 can follow the curvature of the prongs. Preferably, the groove 4714 can be configured so that the NG/NJ tube can clip into the groove 4714 or have a friction fit with the groove 4714 so that there is no need for taping the tube to the patient.

Figure 47F:
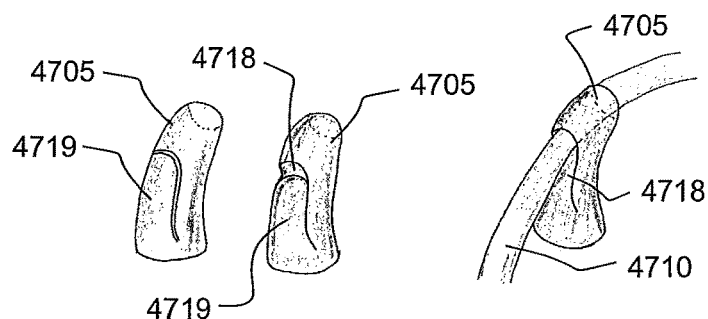

With reference to FIG. 47F, some embodiments include a prong having a slot 4718. The slot 4718 can be open or can be closed by a flap 4719. The flap 4719 can be molded or cut out of the side of the prong 4705. Preferably, the flap 4719 is located at the proximal side of the prong 4705, and the flap 4719 can also be located near the base of the prong 4705. The flap 4719 can be configured to be displaced so that the slot 4718 of the prong 4705 can receive a NG/NJ tube 4710. Preferably, the flap 4719 is configured so that when no NG/NJ tube is being used the flap 4719 forms a seal with the prong 4705 and gas does not leak out of the prong 4705. A NG/NJ tube can be inserted into the prong 4705 through the slot 4718 exposed by the displaced flap 4719, and the flap 4719 can open or bend inward into the prong 4705. With the tube inserted, the flap 4719 can be configured to seal off the prong 4705 so that minimal or no gas leaks out of the cannula 4703 through the prong 4705. A flap 4719 can be included on one of the prongs 4705 or both. In other embodiments, the slot 4718 can be formed by a slit or cut in the prong wall that is configured to receive an NG/NJ tube and form a seal around the tube. With reference to FIG. 47O, the prong 4705 can also include a slit or cut 4780 adjacent the slit or cut that forms the flap 4719. Preferably, the slit 4780 extends from the slit or cut that forms the flap 4719 toward or to the end of the prong 4705. Preferably, the slit 4780 is configured to allow the NG/NJ tube 4710 to selectively pass through the slit 4780 and into or out of the slot 4718 of the prong 4705. This allows the NG/NJ tube 4710 to remain in place while the cannula 4703 is removed from or attached to the patient.

Figure 47G:
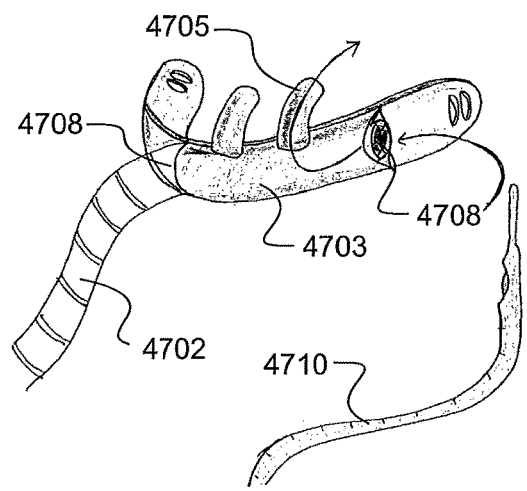
Figure 47H:
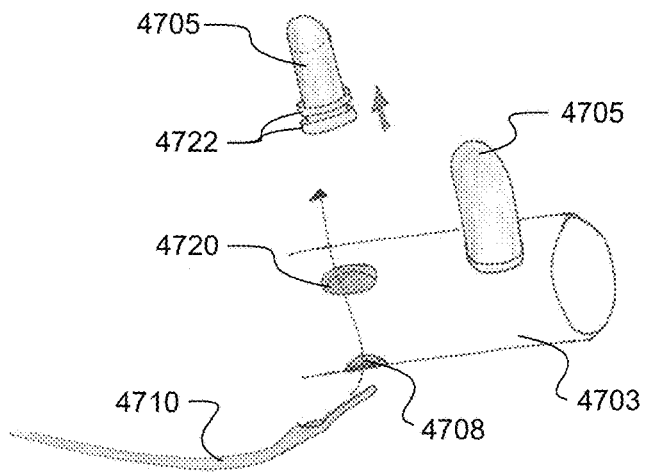

In some embodiments, the cannula 4703 includes a valve 4708 on each side or end of the cannula 4703. For example, the cannula 4703 can include two valves 4708 and one valve 4708 can be located on each of the sides, as illustrated in FIG. 47G. Preferably, the valves 4708 are configured to be one-way valves that only allow gas or airflow to pass through in one direction. Preferably, the valves 4708 inhibit or prevent gas or air from exiting the cannula 4703 through the valves 4708. In some embodiments, the cannula tubing 4702 can be connected to one of the valves 4708 and the valve 4708 on the other side can be used to insert a NG/NJ tube 4710 into the patient's nose through the prong 4705. Preferably, a NG/NJ tube 4710 can pass through the valve 4708, through the cannula 4703 and out of the prong 4705. The valve 4708 can be configured to provide a substantial or complete seal around the NG/NJ tube 4710 so that air or gas does not leak out of the cannula 4703. Preferably, the cannula tube 4702 can be coupled to either of the valves 4708 and the NG/NJ tube 4710 can be passed through either of the valves 4708 to allow for a tube exit direction on either side of the patient. If an NG/NJ tube 4710 is not passed through the valve 4708, the valve 4708 can receive a pressure line or other pressure measurement device.

In certain embodiments, the cannula 4703 can include rotatable prongs 4705 that are configured to be removable to allow the insertion of a NG/NJ tube. The cannula 4703 can include an opening 4720 configured to receive and selectively retain a removable prong 4705. Preferably, the prong 4705 includes ribs 4722 defining a recess therebetween or other suitable features that are configured to engage the opening 4720 of the cannula 4703 and hold the prong 4705 in place relative to the cannula 4703. The cannula 4703 can also include an opening and valve 4708 on the bottom portion of the cannula 4703 at a location that is generally below the prong opening 4720. Preferably, the valve 4708 is a one-way valve or a duck bill valve configured to prevent gas from leaking out of the cannula 4703. A NG/NJ tube 4710 can be inserted through the valve 4708 and the valve 4708 can be configured to form a seal around the NG/NJ tube 4710. The prong 4705 can be removed to allow the NG/NJ tube 4710 to pass through the opening 4720 and into a patient's nose. In some embodiments, the opening 4720 also includes a valve or seal that is configured to form a seal around the NG/NJ tube 4710 so that gas does not leak out of the opening 4720 when the NG/NJ tube 4710 is inserted. With the insertion of the NG/NJ tube 4710 through the cannula 4703, gas therapy can be delivered through only one prong 4705 and nutrition can be simultaneously supplied to the patient. Alternative methods to close the opening 4720 when it is not used can also be employed. For example, a removable plug could be used or the removable prong 4705 could incorporate such a plug, among other possible arrangements.

Figure 47I:
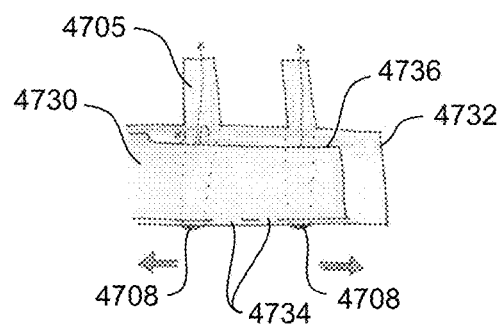
Figure 47J:
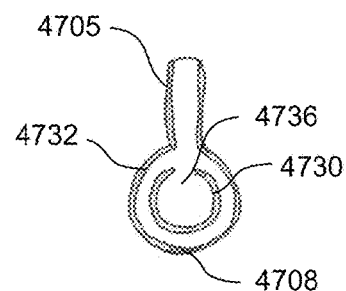

With reference to FIGS. 47I and 47J, some embodiments of a cannula assembly include an inner portion 4730 that can be moved relative to an outer portion or sleeve 4732. The inner portion 4730 can be coupled to the cannula tubing 4702 and configured to receive gas flow therefrom. The outer portion 4732 can extend around the inner portion 4730 can include prongs 4705. Preferably, both the inner portion 4730 and the outer portion 4732 are generally cylindrical and the inner portion 4730 fits within the outer portion 4732. In some embodiments, the inner portion 4730 includes a slot 4736 at or near its upper surface that can be positioned adjacent the prongs 4705 of the outer portion 4732 so that gas can flow out of the slot 4736 and through the prongs 4705. The inner portion 4730 can also include one or more gaps or openings 4734 configured to allow a NG/NJ tube 4710 to pass therethrough. Preferably, the outer portion 4732 also includes one or more openings or valves 4708 located at the bottom of the outer portion 4732 opposite the prongs 4705. Preferably, the valves 4708 can be one-way valves or duck bill valves that are configured to form a seal around the NG/NJ tube 4710. In some embodiments, a user can move the inner portion 4730 relative to the outer portion 4732 (e.g., in an axial direction) so that one of the openings 4734 on the inner portion 4730 is aligned with a valve 4708 on the outer portion 4732. Preferably, an NG/NJ tube 4710 can pass through the aligned valve 4708 and opening 4734, and can also pass through the slot 4736 and the prong 4705. Preferably, the inner portion 4730 is coupled to and sealed with the cannula tube 4702 so it is the outer portion 4732 that is moved to align the valve 4708 with the opening 4734 of the inner portion 4730. Preferably, the inner portion 4730 includes multiple gaps or openings 4734 and one of those openings 4734 and the outer portion 4732 includes two valves 4708 corresponding to the two prongs 4705, and the outer portion 4732 can be moved to align an opening 4734 aligns with either one of the valves 4708. Thus, a user can choose which valve 4708 and prong 4705 through which the NG/NJ tube is inserted.

Figure 47K:
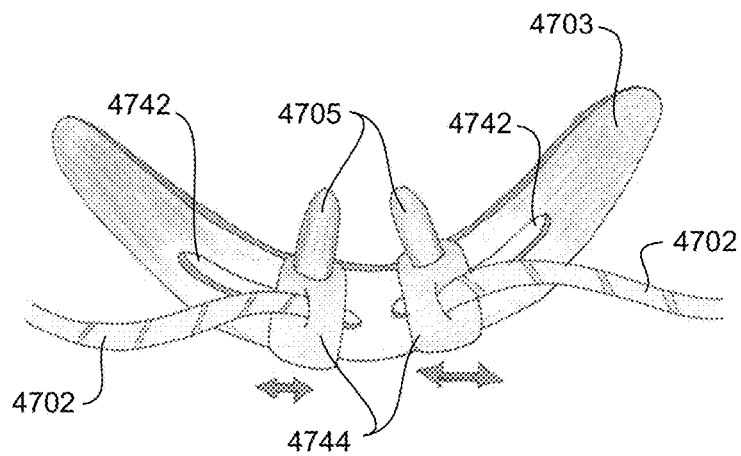

In some embodiments, as shown in FIG. 47K, the cannula assembly includes a cannula body 4703 having slots 4742 in which individual prongs 4705 can move and be adjusted. For example, the assembly can include two individual prongs 7405 that are each coupled to a base or sliding portion 4744. The prong 4705 and/or sliding portion 4744 can be coupled to supply tubing 4702 so that air or gas can flow from the tubing 4702 and through the prong 4705. Preferably, the tubing 4702 is small diameter tubing to facilitate adjustment of the prongs 4705. A portion of the sliding portion 4744 can be configured to engage the slot 4742 so that the sliding portion 4744 can slide along the slot 4742 and remain coupled to the cannula body 4703. This allows the prongs 4705 to be individually adjusted and moved relative to the cannula 4703.

Preferably, the slots 4742 are molded into or cut out of the cannula body 4703 and can be configured to hold the sliding portion 4744 in a selected position while allowing movement of the sliding portion 4744 when moved by a user. The slot 4742 can include notches or grooves to hold the sliding portion 4744 in place and/or the slot 4742 can be sized and shaped to apply frictional force to the sliding portion 4744 to hold it in place. In some embodiments, when one of the prongs 4703 is slid away from the nose, the assembly can be configured to stop air or gas flow from that prong 4705 (e.g., via a valve) so as to prevent humidified air being blown on the patient's face. During treatment in which a NG/NJ tube is to be required, one of the prongs 4705 can be moved to the side of the nose and the NG/NJ tube 4710 can be inserted into the empty nostril. Therapy can be delivered through only one nostril. When no NG/NJ tube 4710 is being used, the prongs 4705 can be placed into the nostrils similar to a conventional cannula.

With reference to FIG. 47L, some embodiments of the cannula include a slider portion 4750 that is configured to move over a prong 4705. For example, a cannula 4703 can include two prongs 4705 extending from the top surface and a slider portion 4750 coupled to the cannula 4703 and configured to move relative to the cannula 4703. Preferably, the slider portion 4750 extends around the cannula 4703 and is adjacent the cannula tubing 4702. The slider portion 4750 can be configured to move over and cover one or more of the prongs 4705. Alternatively, the slider portion 4750 may be positioned at a center portion of the cannula 4703 in between the two prongs 4705. In some embodiments, the slider portion 4750 includes a groove 4752 configured to receive or engage a NG/NJ tube 4710. Preferably, the NG/NJ tube can click into the groove 4752 or form a friction fit with the groove 4752. When a NG/NJ tube is required, the slider portion 4750 can be moved to cover one of the prongs 4705 and a NG/NJ tube 4710 can be inserted into the groove 4752 and directed into the nostril of a patient. This can be done as the other nostril is receiving treatment from the other prong 4705. Preferably, the prong 4705 is configured so that it folds or flattens when covered by the slider portion 4750. For example, the prong 4750 can be made of a soft or flexible material such as a polymer or soft plastic. The prong 4750 can also form a seal with the cannula 4703 when it is flattened or folded so that no gas leaks from the cannula 4703 through that prong 4705.

In some embodiments, the outer portion of the cannula 4703 is configured to receive or guide a NG or NJ tube 4710 into the nostril of a patient. Preferably, the cannula 4703 and prong 4705 include a groove that is configured to allow a nostril to receive both treatment from the prong and the NG/NJ tube simultaneously. For example, as shown in FIGS. 47M and 47N, the cannula 4703 can include a groove that extends along the outer surface of the cannula body 4703 and the prong 4762. Preferably, a first groove portion 4760 extends vertically along the outer surface of the cannula 4760 on the side of the cannula 4703 that faces the patient's face when the cannula 4703 is in use. A corresponding second groove portion 4762 can extend longitudinally along the outer surface of the prong 4705. The groove portions 4760 and 4762 can be configured to receive a NG/NJ tube 4710 so that the tube 4710 is held at least partially within the grooves 4760 and 4762 and extends along the grooves 4760 and 4762 and into the patient's nostril. Preferably, the cannula 4703 includes two first groove portions 4760 and two second groove portions 4762 so that each prong 4705 can receive and direct a NG/NJ tube 4710 into a corresponding nostril. In some embodiments, the cross-section of the grooves 4762, 4760 is circular or semi-circular to correspond to the shape of the NG/NJ tube 4710. The cross-section of the prong 4705 can also be generally circular with a moon-shaped recess to define the groove portion 4762. As illustrated in FIG. 47N, both the prong 4705 and the NG/NJ tube 4710 can fit within the nostril 4766 to deliver treatment. In some embodiments, the groove portions 4760 and 4762 can be curved or configured in different directions so that the NG/NJ tube 4710 enters or exits the cannula 4703 at specific desired locations, e.g. from the side. These configurations allow for simultaneous treatment from the cannula 4703 and the NG/NJ tube 4710 and, in some cases, without the use of tape or any other attachment mechanism for the NG/NJ tube 4710.

Figure 48A:
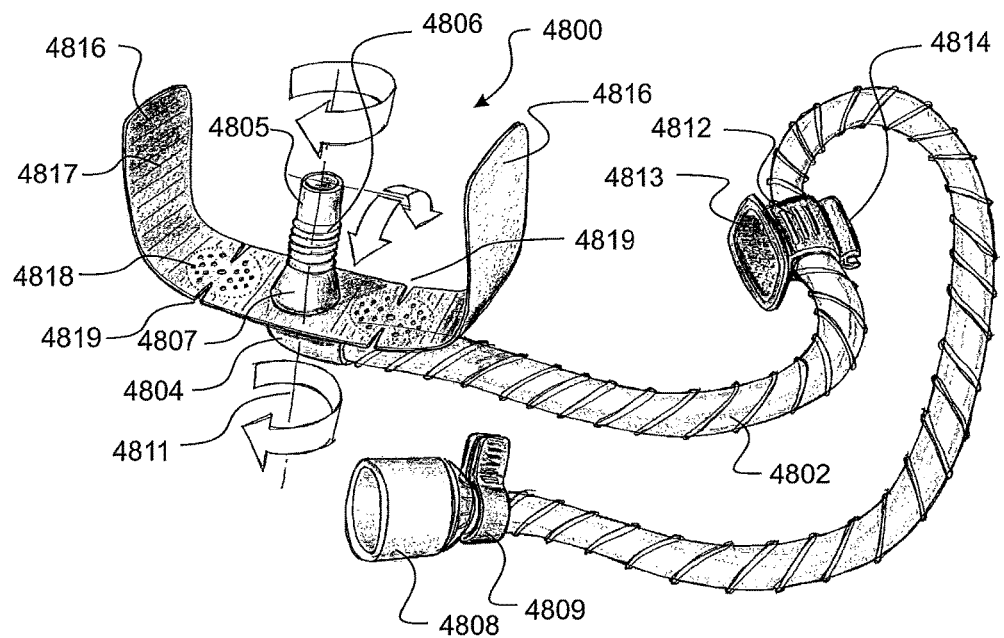
FIGS. 48A-S illustrate example embodiments of single prong arrangements for a nasal cannula assembly.
Figure 48B:
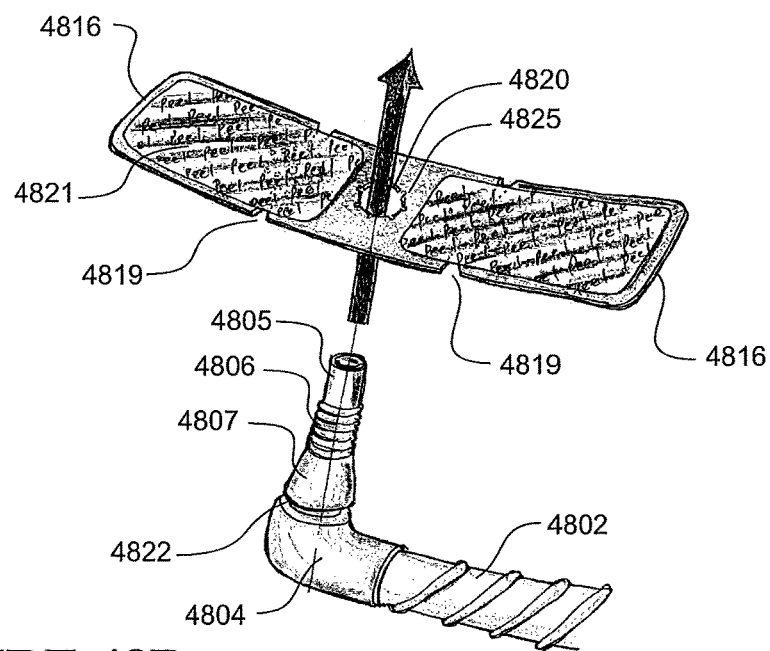
Figure 48C:
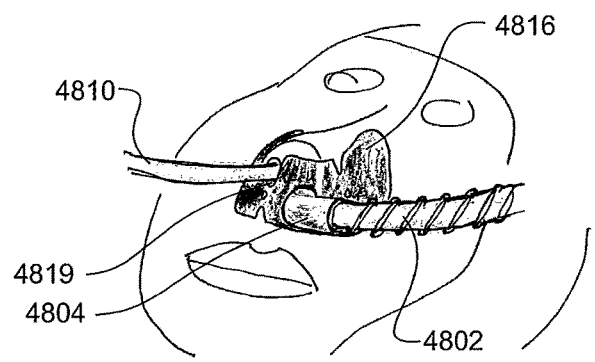
Figure 48D:
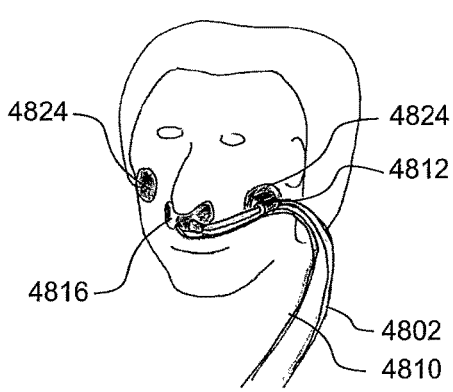
Figure 48E:
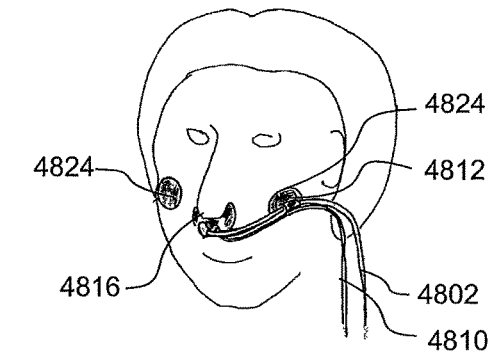
Figure 48F:
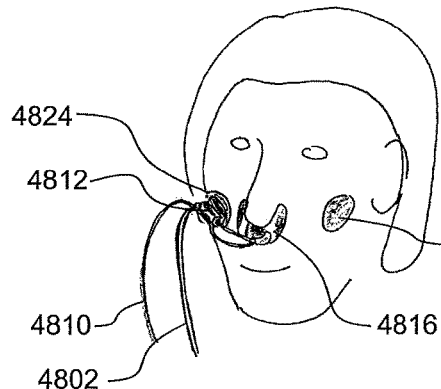
Figure 48G:
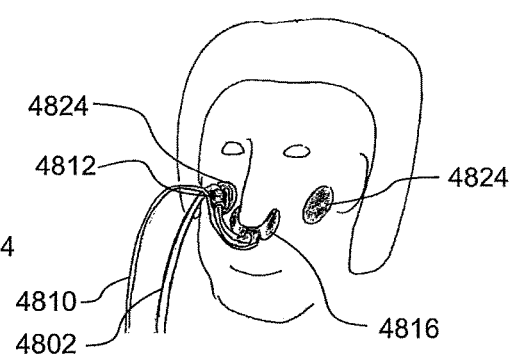
Figure 48H:
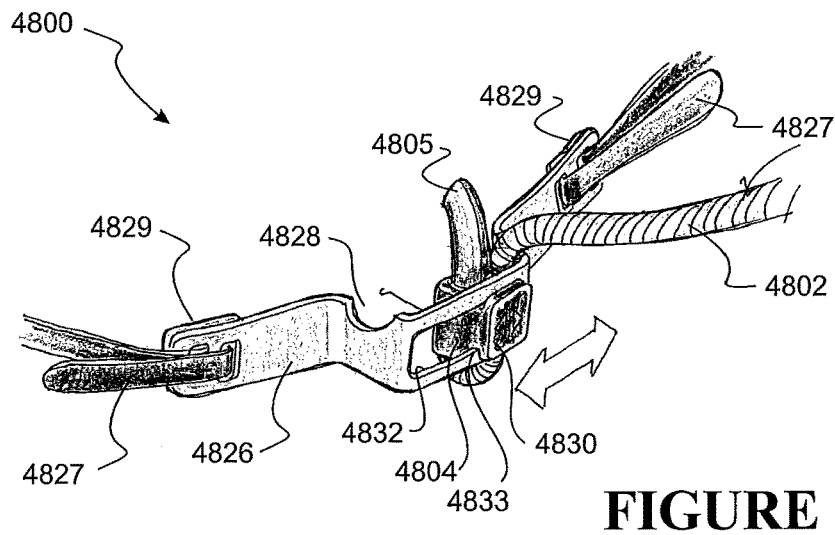
Figure 48I:
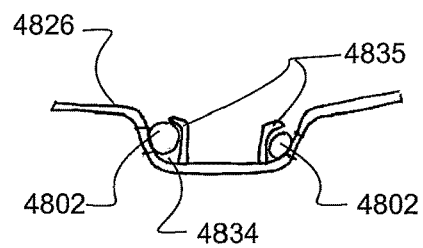
Figure 48J:
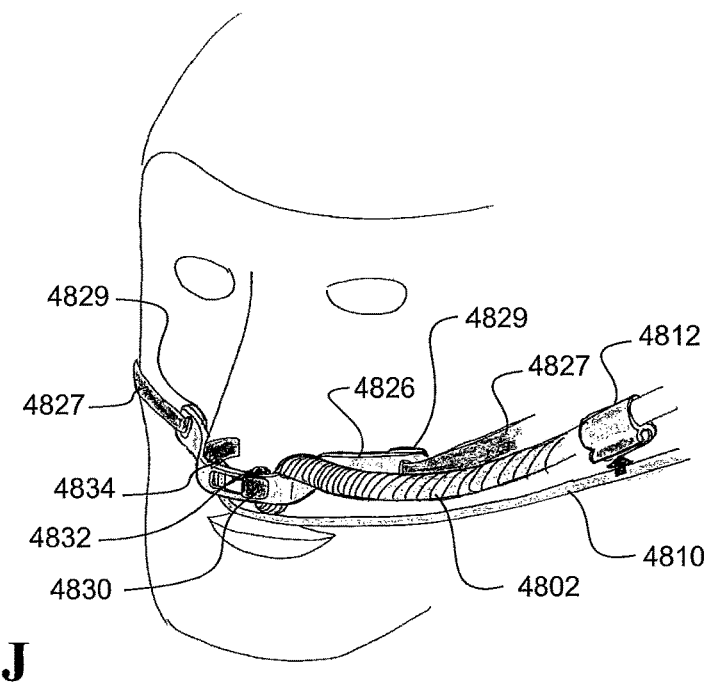
Figure 48K:
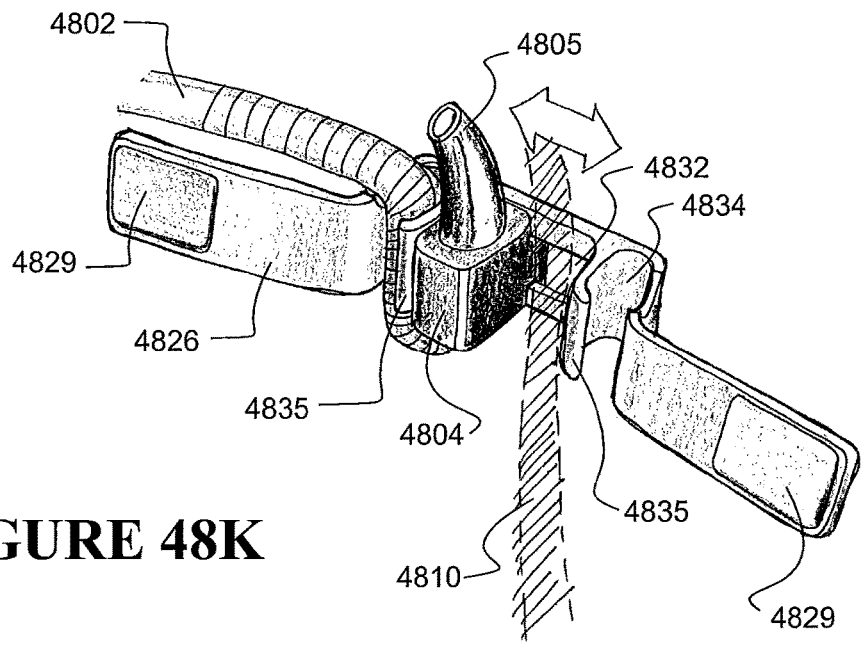
Figure 48L:
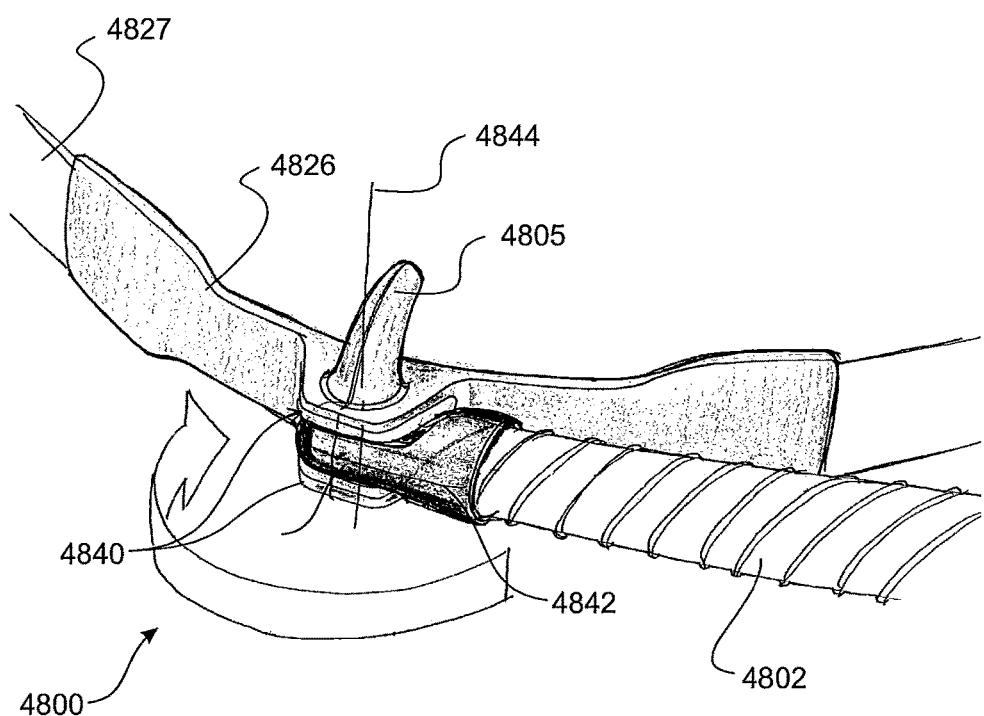
Figure 48M:
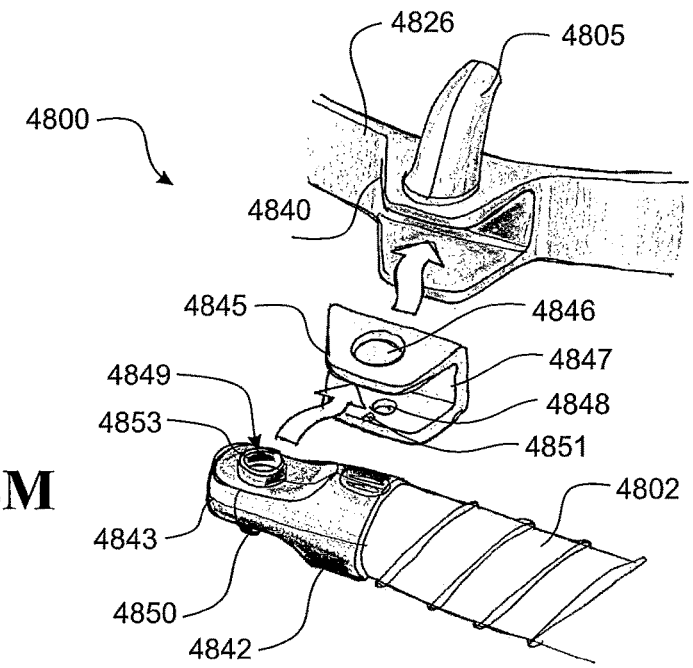
Figure 48N:
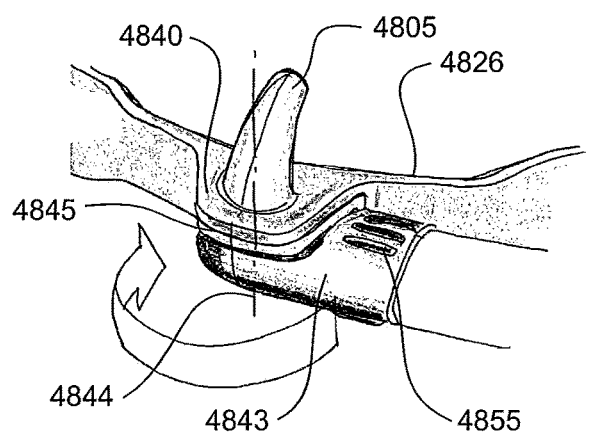
Figure 48O:
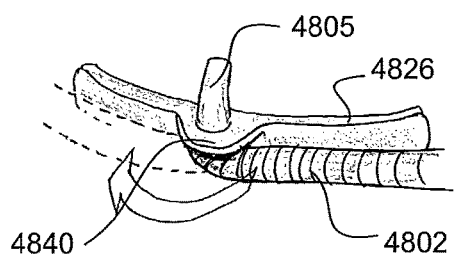
Figure 48P:
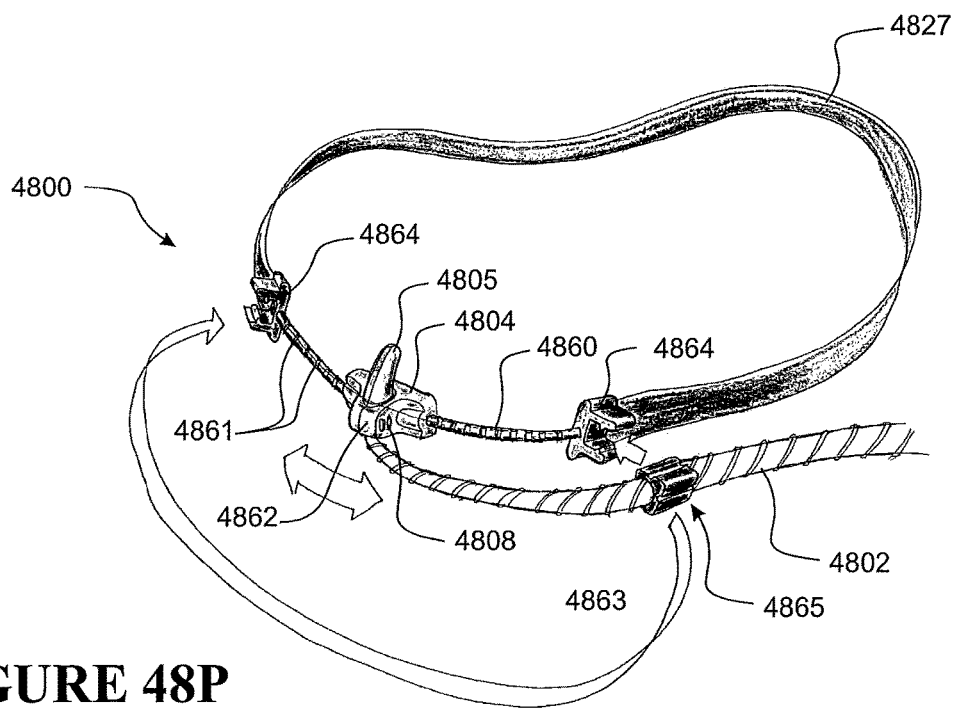
Figure 48Q:
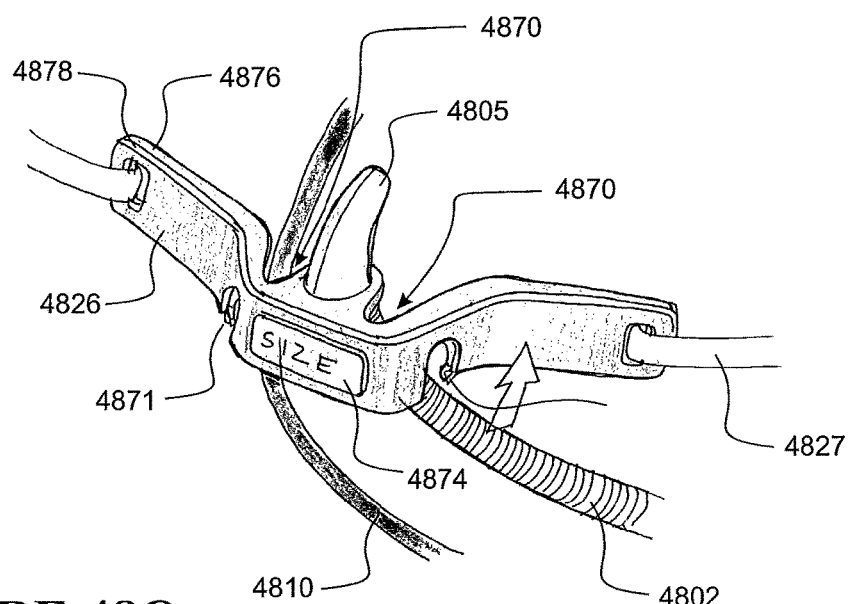
Figure 48R:
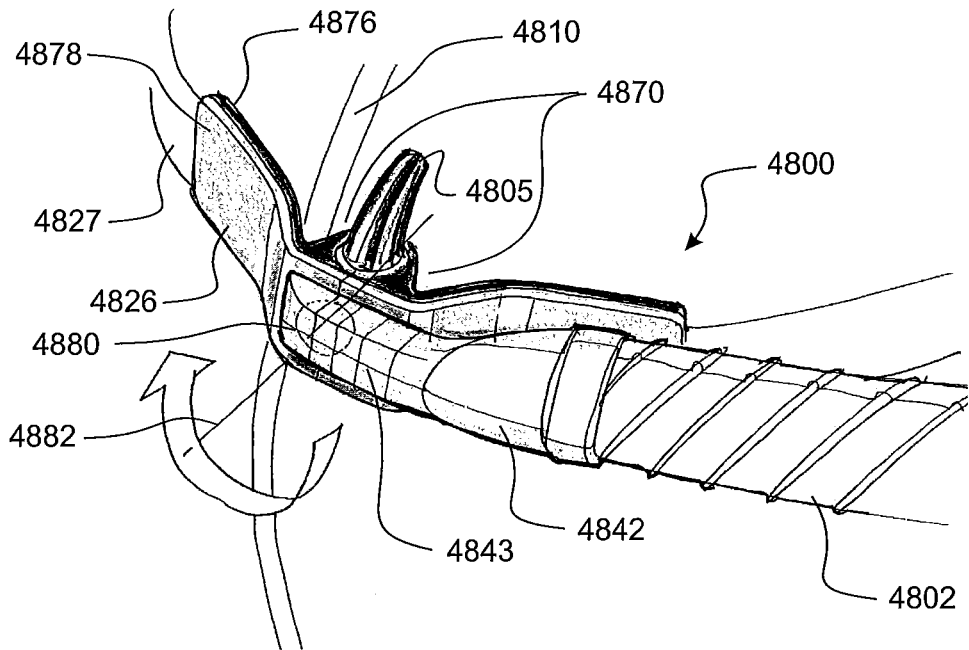
Figure 48S:
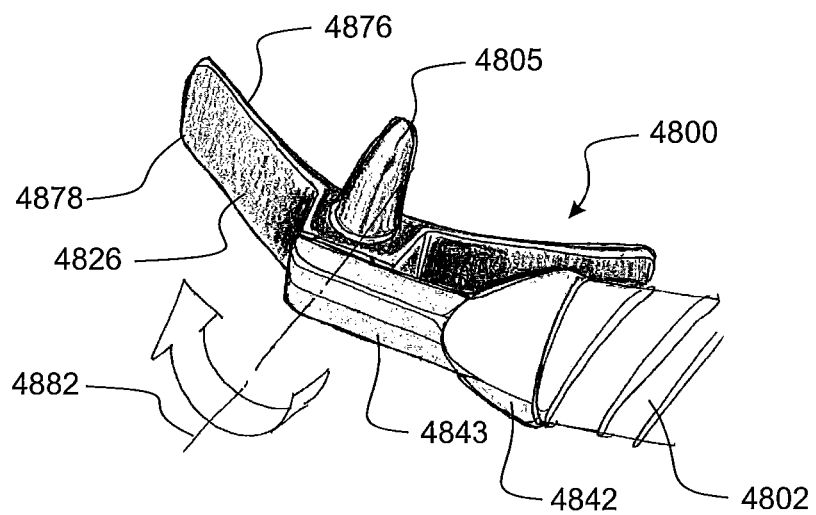

With reference to FIGS. 48A-S, embodiments of a cannula retention assembly are illustrated. As described above, in some circumstances, it is beneficial for the cannula assembly 4800 to include a single nasal prong 4805 and/or a configuration that allows use of the cannula simultaneously with an NG/NJ tube. It is also beneficial to provide a configuration that facilitates or allows for nasopharyngeal deadspace washout. Inserting a NG/NJ tube into a patient's nose while the patient is receiving treatment from a cannula device can be difficult and can also be uncomfortable for a patient. In at least some embodiments, the cannula assembly 4800 includes a single prong 4805 and is configured to allow convenient simultaneous use of a NG/NJ tube. Embodiments having a single prong can also reduce nostril overcrowding when used in conjunction with NG/NJ or other tubes.

FIG. 48A illustrates an embodiment of an improved cannula assembly 4800 that comprises a cannula 4804 with a single prong 4805. The illustrated cannula assembly 4800 includes a retainer strap 4816 and a cannula tube 4802. In some embodiments, the retainer strap 4816 includes an adhesive 4817 and is configured to be adhered or coupled to the face or nose of a patient. In other embodiments, a head strap or hanging strap or any other suitable support mechanism can be used to support the cannula assembly and couple it to a patient. Preferably, the retainer strap 4816 includes two end portions that extend away from the cannula 4804 and the cannula 4804 and prong 4805 can be coupled to the retainer strap 4816 at a generally central location on the strap 4816. In some embodiments, the retainer strap 4816 includes holes or perforations 4818 on either side of the prong 4805. The holes or perforations 4818 can be configured to cover the second nostril of a patient and can be sized and shaped to maintain patient airway pressure in the second nostril. Preferably, the holes or perforations 4818 are located on both sides of the prong 4805 and the prong 4805 can be located in either the left or right nostril of a patient. The prong 4805 can also be configured to rotate relative to the retainer strap 4816 and about the prong axis 4811 so that the exit side of the cannula tubing 4802 can be easily changed. Preferably, the retainer strap 4816 is disposable and can be removed from the cannula assembly 4800 and replaced with a new retainer strap 4816. In some embodiments, the retainer strap 4816 can also include one or more slots 4819 that are configured to receive a NG/NJ tube. Preferably, the slots 4819 are configured to retain an inserted NG/NJ tube in place and hold it relative to a patient's face. The slots 4819 can be triangular-shaped and can extend inward from the outer edge of the retainer strap 4816. In other embodiments, the slots 4819 can extend longitudinally along the retainer strap 4816. In some embodiments, the slots 4819 are circular openings or valves that are configured to receive a NG/NJ tube. Preferably, the slots 4819 are located adjacent the holes or perforations 4818 and are located on both sides of the prong 4805.

In the illustrated embodiment, the prong 4805 is a single nasal prong that can be inserted into either the left or right nostril. In some embodiments, the prong 4805 includes corrugations 4806 that are configured to allow the prong 4805 to bend and adjust to conform to a nasal passage. The corrugations 4806 can extend circumferentially around the central portion of the prong 4805. Preferably, the prong 4805 also includes a tapered portion 4807 at or near the base of the prong 4805. The tapered portion 4807 can be configured to provide a seal with the opening of a nostril when the prong 4805 is inserted into a nostril. The tapered portion 4807 can also be configured to widen at the bottom so that it assists in holding or coupling the retainer strap 4816. Preferably, the prong 4805 is sized and shaped to form a seal in the nostril of a patient, and the holes or perforations 4818 allow exhalation from the other nostril to facilitate nasopharyngeal deadspace washout.

In some embodiments, the cannula tube 4802 includes a connector 4808 and a connector clip 4809 configured to hold the cannula tube 4802 at a certain location and support the weight of a tubing circuit (not shown). Preferably, the connector clip 4809 extends around a portion of the cannula tube 4802 and is configured to clip or hang on a support or hanger. In some embodiments, the cannula assembly 4800 also includes a tube attachment member 4812. The tube attachment member 4812 can be configured to wrap at least partially around a portion of the cannula tube 4802 and can support the tube 4802. Preferably, the tube attachment member 4812 includes an attachment portion 4813 configured to be coupled to or hanged from a support or the patient's face. Preferably, the attachment portion 4813 includes a hook and loop or Velcro material that can be coupled to corresponding material on or near the patient. In some embodiments, the attachment portion 4813 is configured to be attached and coupled to a pad 4824 that is adhered to the face of a patient and the attachment member 4812 is configured to support the tube 4802 and hold it closely to the pad 4824 on the face of the patient. The attachment portion 4813 can also include other suitable means for adhering or coupling the attachment member 4812 and cannula tube 4802 to a patient's face. Such an attachment member 4812 allows for easy and convenient changing of the cannula tube exit side relative to the patient. In some embodiments, the attachment member 4812 also includes a tube support 4814 that is configured to engage and support a secondary tube. This allows for better and more convenient positioning and management of the tubes, and allows for relative tube and patient position adjustment. Preferably, the tube support 4814 is sized and shaped to receive a NG/NJ tube and retain it close to the cannula tube 4802. The tube support 4814 can be sized and shaped to form a friction fit with a NG/NJ tube and can hold at least a portion of the NG/NJ tube within a groove. In other arrangements, the tube support 4814 can support other types of tubes or lines, such as a pressure measurement line, for example.

As illustrated in FIG. 48B, embodiments of the cannula assembly 4800 can include a retainer strap 4816 that has a hole or opening 4820 configured to receive the prong 4805. Preferably the retainer strap 4816 can be coupled to the cannula 4804 by pushing the prong 4805 through the opening 4820 until the opening 4820 passes over the tapered portion 4807 of the prong 4805. In some embodiments, the prong 4805 or cannula 4804 can include a recess 4822 adjacent the tapered portion 4807. Preferably, the recess 4822 is configured to receive the edges of the opening 4820 as the retainer strap 4816 is pushed onto the prong 4805 and past the tapered portion 4807. The recess 4822 can also be configured to retain the edges of the opening 4820 so that the retainer strap 4816 is coupled to the prong 4805 and cannula 4804. Preferably, the retainer strap 4816 can be removed by pulling the retainer strap 4816 away from the cannula 4804 so that the opening 4820 moves back over the tapered portion 4807 and the prong 4805 moves out of the opening 4820. In some embodiments, the retainer strap 4816 is disposable and easily replaceable by pushing a new one over the prong 4805. The retainer strap 4816 can be replaced during therapy or as required. Preferably, the opening 4820 can include one or more notches 4825 along the edge of the opening 4820, and the notches 4825 can be configured to allow the opening 4820 to expand and facilitate moving the opening 4820 over the prong 4805. In some embodiments, the retainer strap 4816 includes a peelable covering 4821 covering the adhesive material 4817 and protecting it until the retainer strap 4816 is to be adhered to a patient's face. Preferably, the covering 4821 covers at least a portion of the slots 4819 and holes 4818 in the retainer strap 4816.

With reference to FIGS. 48C-G, embodiments of the cannula assembly 4800 can be functionally coupled to a patient's face in numerous arrangements depending on the desires of the patient or healthcare provider. Preferably, the cannula 4804 and prong 4805 can be inserted into either one of the patient's nostrils and a NG/NJ tube can pass through a slot 4819 in the retainer strap 4816 and into the other nostril of the patient. Preferably, the retainer strap can curve upward and adhere to the sides and top of a patient's nose. In some embodiments, the slot 4819 or the portion of the retainer strap 4816 forming the slot 4819 forms a seal around the inserted NG/NJ tube 4810, and the holes 4818 in the strap 4816 adjacent the NG/NJ tube 4810 allow the patient to exhale through the retainer strap 4816 covering the nostril. The holes 4818 can also be configured to maintain airway pressure by restricting flow. In one arrangement, the patient has one pad 4824 on or near each cheek. The pads 4824 are configured to attach to and support the attachment member 4812. In one arrangement, shown in FIG. 48D, the attachment member 4812 supporting the cannula tube 4802 and NG/NJ tube 4810 is attached to the left cheek, and the retainer strap 4816 secures the prong 4805 in the left nostril and the NG/NJ tube 4810 in the right nostril. In another arrangement, shown in FIG. 48E, the attachment member 4812 is supported by a pad 4824 on the patient's left cheek, and the retainer strap 4816 secures the prong 4805 in the right nostril and the NG/NJ tube 4810 in the left nostril. In another arrangement, shown in FIG. 48F, the attachment member 4812 is supported by a pad 4824 on the patient's right side, and the retainer strap 4816 secures the prong 4805 in the left nostril and the NG/NJ tube 4810 in the right nostril. In yet another arrangement, shown in FIG. 48G, the attachment member 4812 is supported by a pad 4824 on the patient's right cheek, and the retainer strap 4816 secures the prong 4805 in the right nostril and the NG/NJ tube 4810 in the left nostril. These configurations of the cannula assembly 4800 allow for improved flexibility and easier adjusting of the tube positions and changing positions of the tubes and cannula relative to the patient's nostrils and face.

With reference to FIGS. 48I-K, some embodiments of a cannula assembly 4800 include a frame 4826 that supports the cannula 4804 and allows the position of the cannula 4804 to be adjusted relative to the frame 4826. In some arrangements, single prong cannulas have the benefit of requiring only a very small manifold. The tube diameter entering the manifold can also be much smaller compared to two prong cannula designs. In some embodiments, the frame 4826 can be configured to support and manage the direction of the cannula tube 4802. It can be advantageous for the cannula tube 4802 to exit the cannula 4804 in a downward direction from the bottom of the cannula 4804 because the tube 4802 can exit to the right or the left with minimal bending of the tube 4802. Preferably, in configurations where the cannula tube 4802 exits downward from the cannula 4804, the frame 4826 is configured to cause the cannula tube 4802 to bend and exit the cannula assembly 4800 in a desired direction. As illustrated, a prong 4805 of the cannula 4804 can extend upwardly relative to the frame 4826.

In some embodiments, the frame 4826 is rigid or semi-rigid and is shaped to bridge or extend away from the face at its central portion so that there is space between the nasal/nostril entry area and the frame 4826. Preferably, this space between the central portion of the frame 4826 and the patient's face is configured to accommodate the cannula 4804, cannula tube 4802, and a NG/NJ tube. In some embodiments, the frame 4826 includes soft pads 4829 at each end of the frame 4826 that can be configured to contact the patient's face and distance the rest of the frame 4826 from the face. The soft pads 4829 can be configured to provide comfort to the patient and can inhibit or prevent the cannula 4804 from slipping or sliding on the patient's face. The soft pads 4829 can include a soft padding material that provides friction or adhesion between the pads 4829 and the patient's face. The frame 4826 can also include a slot 4832 through which a portion of the cannula 4804 can extend. Preferably, the cannula 4804 includes a grip portion 4830 that extends through the slot 4832 and facilitates adjustment of the position of the cannula 4804 relative to the frame 4826. The grip portion 4830 can be integral with the cannula 4804 and can include one or more grooves 4833 configured to engage the edges of the slot 4832 so that the cannula 4804 is coupled to the frame 4826, but can also slide relative to the frame 4826 as the grip portion 4830 moves within the slot 4832. Advantageously, the cannula 4804 and prong 4805 can slide along the slot 4832 to align the prong 4805 with the left or right nostril of a patient. The frame 4826 can also include cut-out portions 4828 that are configured to assist in guiding cannula tube 4802 over and away from the frame 4826. Preferably, the frame 4826 includes cut-out portions 4828 on both sides of the frame 4826 that are positioned to facilitate the cannula tube 4802 exiting to the right or the left side. The cannula assembly 4800 can also include an attachment member 4812 configured to support a NG/NJ tube 4810 (or other tubes or lines) and hold it close to the cannula tube 4802, as discussed in the previous embodiments.

As shown in the illustrated arrangements, the small diameter cannula tube 4802 can exit from the bottom of the cannula 4804 and bend back upwards beside the cannula 4804 and over the top of the frame 4826. Preferably, the cannula tube 4802 passes over the top of the frame 4826 at a cut-out portion 4828 and the cannula tube 4802 exits to either the right or left side of the patient. In some embodiments, the frame 4826 also includes tubing recesses 4834 at or adjacent to the lateral ends of the slot 4832 that are sized and shaped to receive a portion of the cannula tube 4802. Preferably, the tubing recesses 4834 are defined, at least in part, by arm portions 4835 that extend from the frame 4826 and are configured to retain a portion of the cannula tube 4802 within the tubing recess 4834. In some embodiments, and as illustrated in FIG. 48K, the cannula tube 4802 can extend downward from the cannula 4804, then bends upward and extends through the tubing recess 4834 and is selectively retained within the tubing recess 4834 by the arm portion 4835. Adjacent to the cannula 4804 and on the opposite side of the cannula tube 4802 there is space between the frame 4826 or tubing arm 4835 and the face for a NG/NJ tube to pass through and into a patient's other nostril. Preferably, the shape of the frame 4826 allows the NG/NJ tube to exit the nostril between the cannula 4804 and the frame 4826 or the recess arm 4835, without interference from the frame 4826 or cannula 4804. The single prong arrangement allows the NG/NJ tube a designated nostril and the NG/NJ tube nostril can also be the expiratory gas nostril to provide nasopharyngeal deadspace washout. Advantageously, the NG/NJ tube 4810 passes between the patient's face and the frame 4826 so that the cannula assembly 4800 and frame 4826 can be removed and adjusted without compromising the NG/NJ tube position. The frame 4826 can also protect the NG/NJ tube from being accidentally bumped or displaced.

With reference to FIGS. 48L-O, some embodiments of a cannula assembly include a pivoting manifold that is configured to rotate relative to the cannula assembly so that the exit side of the cannula tube 4802 is easily adjusted or changed. Preferably, the manifold can be pivoted and the tube exit side changed without having to remove the prong 4805 or cannula from the patient. In some embodiments, the cannula assembly also includes a single prong configuration so that there is space on either side of the prong for a NG/NJ tube. For example, some embodiments of a cannula assembly 4800 include a cannula frame 4826 having a single prong 4805. The cannula frame 4826 can include extension portions 4840 that are configured to extend outward away from the face of a patient and can support the prong 4805. Preferably, a portion of a manifold 4843 fits within the space between the extension portions 4840 and is rotatably coupled to the frame 4826. The manifold 4843 can include a tube connector portion 4842 that is configured to receive the end of a cannula tube 4802. In such embodiments, the manifold 4843 and the cannula tube 4802 can be rotated relative to the cannula frame 4826 and prong 4805 in order to change the exit side of the cannula tube 4802. Preferably, the extension portions 4840 and the prong 4805 are sized and shaped so that a NG/NJ tube 4810 can pass on either side of the prong 4805 and into the other nostril.

In some embodiments, the cannula assembly 4800 includes a retainer portion 4845 that is inserted into the space between the extension portions 4840. The retainer portion 4845 can be a separate piece, or it can also be integral or molded into the cannula frame 4826. In some embodiments, the retainer portion 4845 can be over-molded with the frame 4826. Preferably, the retainer portion 4845 includes an opening 4846 at the top surface that corresponds to the passageway of the prong 4805. The retainer portion 4845 can also include a hinge recess 4848 at or near the lower portion of the retainer portion 4845. The retainer portion 4845 can also include a protrusion 4851 that is configured to engage a portion of the manifold 4843. In some embodiments, a portion of the manifold 4843 is sized and shaped to be received within the retainer portion 4845. Preferably, the manifold 4843 includes a manifold opening 4853 with a flange 4849 surrounding the opening 4853. The manifold opening 4853 can be configured to correspond to the opening 4846 on the retainer portion 4845 and the passageway of the prong 4805 when the manifold 4843 is coupled to the frame 4826. The flange 4849 can be sized and shaped to engage the opening 4846 on the retainer portion 4845, and this engagement can allow pivoting or rotation of the manifold 4843 relative to the retainer portion 4845. In some embodiments, the manifold 4843 also includes a pin 4850 that is configured to engage the hinge recess 4848 on the retainer portion 4845. Preferably, the engagement between the pin 4850 and the hinge recess 4848 also allows the manifold 4843 to pivot or rotate relative to the frame 4826, and the manifold 4843 can rotate about a rotational axis 4844 that passes through the center of the opening 4846 and manifold opening 4853. Preferably, the manifold 4843 also includes a connector portion 4842 that can be coupled to the cannula tube 4802. In some embodiments, the manifold 4843 also includes at least one recess or notch (not shown) that corresponds to the protrusion 4851 on the retainer portion 4845. Preferably, the notch is on the bottom side on the manifold 4843 and is configured to receive the protrusion 4851 when the manifold is rotated to a certain position, and the protrusion 4851 engages the notch to assist in retaining the manifold 4843 in its position. In some embodiments, the protrusion 4851 engages a notch when the manifold 4843 is rotated to the right side of the patient, and the protrusion 4851 engages another notch when it is rotated to the left side of the patient.

In some embodiments, as illustrated in FIG. 48N, the cannula frame 4826 can include a single extension portion 4840 that supports the prong 4805. As illustrated, the retainer portion 4845 can be supported by the extension portion 4840 and the top of the manifold 4843 can be coupled to the retainer portion 4845. In this embodiment, the interaction between the opening 4846 on the retainer portion 4845 and the flange 4849 on the manifold 4843 can provide a pivot about which the manifold can rotate relative to the retainer portion 4845 and frame 4826. Preferably, only the top portion of the manifold 4843 is coupled to and contacting the retainer portion 4845 and the manifold 4843 can rotate about the rotational axis 4844. In some embodiments, the manifold 4843 or tube connector portion 4842 includes a grip portion 4855 configured to assist a user in gripping and moving the manifold 4843. In some embodiments, the retainer portion 4845 comprises a rigid material and the extension portion 4840 comprises a soft or bendable material. Therefore, in such arrangements, the retainer portion 4845 may provide some degree of support or resistance to deformation of the extension portion 4848.

As illustrated in FIG. 48O, other embodiments of the cannula assembly 4800 include a cannula tube 4802 that is directly coupled to the extension portion 4840 supporting the prong 4805. In these embodiments, the cannula tube 4802 is flexible and can be bent to extend in a desired exit direction. For example, the cannula tube 4802 can extend downward from the cannula extension portion 4840 and can bend in order to extend to the patient's left or right side. Preferably, the assembly does not include a manifold and the cannula tube 4802 enters the prong 4805 directly. In some embodiments, the cannula tube 4802 can be tapered so that it is narrower and more flexible near the end of the cannula tube 4802 that is coupled to the cannula frame 4826. Preferably, the cannula tube 4802 can be bent toward one side of the patient or the other side, without having to remove or adjust the position of the prong 4805 or cannula frame 4826.

With reference to FIG. 48P, some embodiments of a cannula assembly 4800 can include a cable portion 4860 supporting the cannula 4804. These embodiments can allow the cannula 4804 to be slid or moved along the cable portion 4860 away from the patient's nostril to provide a break from the therapy without having to remove the cannula assembly 4800. Preferably, the cable portion 4860 extends through a portion of the cannula 4804 and the cannula 4804 can be moved along the cable portion 4860. The cable portion 4860 can include indent portions 4861 configured to retain the cannula 4804 in a selected position. The cannula 4804 can slide along the cable portion 4860 to the left or to the right of the patient to allow positioning and adjustment of the cannula. Preferably, the cannula 4804 includes only a single prong 4805 and the cannula tube 4802 enters the cannula 4804 on its bottom surface below the prong 4805. The shape of the cannula 4804 can be configured to be narrow adjacent to the prong 4805 so that a NG/NJ tube 4810 can pass on either side of the prong 4805 and into the empty nostril of a patient. The cannula 4804 can also include grip portions 4868 that are configured to assist a user in gripping and moving the cannula 4804. In some embodiments, the cannula assembly 4800 also includes one or more attachment portions 4864 coupled to the cable portion 4860 and/or head strap 4827. The attachment portions 4864 can be configured to receive and retain a portion of the cannula tube 4802. Preferably, the cannula tube 4802 includes a support member 4865 that is configured to engage the attachment portion 4864 and be at least partially retained within the attachment portion 4864. The attachment portions 4864 can be located to the sides of the cannula 4804 and adjacent the sides of the patient's face so that they can support the cannula tube 4802 as it exits to one side or the other of the patient. In some embodiments, the cannula tube 4802 can be a tapered cannula tube 4863 that has a smaller cross-section at the end coupled to the cannula 4804. The end of the tapered cannula tube 4863 can have a diameter that is only half the diameter of the tube 4802 far from the end. For example, the diameter of the cannula tube 4802 near the cannula 4804 can be approximately 2-7 mm and the diameter of the tube 4802 far from the cannula 4804 can be approximately 5-15 mm. The tapered cannula tube 4863 can provide a small bend radius near the base of the cannula 4804 so that the bend in tubing is not too large or uncomfortable for the patient, as it is generally near the mouth of the patient. In some embodiments, the support member 4865 can be configured to join a constant diameter cannula tube 4802 with the tapered cannula tube 4863.

With reference to FIG. 48Q, some embodiments of a single prong cannula include a cannula frame 4826 with cut-out portions 4871 configured to allow the cannula tube 4802 to exit towards either the right or left side of the patient. Preferably, the central portion 4872 of the cannula frame 4826 extends away from the face of the patient and includes recesses 4870 between the frame 4826 and the patient's face through which a NG/NJ tube can pass. Preferably, a NG/NJ tube can extend from below the frame 4826 upward through the recess 4870 and into a patient's nostril. This arrangement allows the cannula assembly 4800 to be removed from the patient without disturbing or compromising the NG/NG tube position. Preferably, the central portion 4872 of the frame 4826 does not contact the patient's face and can minimize pressure-related discomfort. In some embodiments, the central portion 4872 of the frame 4826 also includes an indicator portion visible from the front of the frame 4872, and the indicator portion can indicate the size or other characteristics of the cannula frame 4826 or assembly. Preferably, the cannula frame 4826 includes an inner portion 4876 that is made from a soft material such as silicone that provides cushioning against a patient's face. The cannula frame 4826 can also include an outer portion 4878 that is made from a rigid or semi-rigid material such as plastic or metal. The cannula frame 4826 can also include cut-out portions 4871 on each side of the frame 4826 that are configured to receive a portion of the cannula tube 4802. Preferably, the cannula tube 4802 extends downward from the cannula and prong 4805 and can be bent to the side so that it passes through one of the cut-out portions 4871. In some embodiments, the cut-out portions 4871 are configured to hold a portion of the cannula tube 4802 in position within the cut-out portion 4871. Preferably, the cut-out portions 4871 include tab or protrusion 4874 that is configured to retain the tube 4802 in the cut-out portion 4871. The tabs or protrusions 4874 can be configured to flex in order to allow the tube 4802 to enter the cut-out portion 4871. Preferably, the cannula tube 4802 is a small diameter tube and can be bent to exit in either the right hand or left hand direction from the patient. Advantageously, the single prong embodiments generally allow for a smaller manifold and cannula tube diameter. The small cannula tube diameter and/or small manifold can provide a smaller bend radius that can be positioned away from a patient's mouth.

With reference to FIGS. 48R and 48S, some embodiments of the cannula assembly 4800 include a cannula frame 4826 with an opening 4880 on the front or outer side of the cannula. The manifold 4843 is configured to be coupled to the front or outer side of the cannula and can rotate about the axis 4882 that passes through the center of the opening 4880. Preferably, a portion of the manifold 4843 can be coupled to the opening 4880 and the interface between the manifold 4843 and the frame 4826 allows the manifold 4843 to be coupled to the frame 4826, but also rotatable relative to the frame 4826. The manifold 4843 can also include a connector portion 4842 coupled to a cannula tube 4802. As discussed in the previous embodiments, the frame 4826 can extend or bridge outward away from the patient's face in order to provide space under the nose of the patient. The frame 4826 can include recesses 4870 through which a NG/NJ tube 4810 can pass behind the cannula frame 4826 and into the patient's nostril. In other embodiments, the cannula frame 4826 can be configured to provide space for a NG/NJ tube 4810 outside of the frame 4826 and to the side of the prong 4805. Preferably, the portion of the frame 4826 that supports the prong 4805 is narrow so that a NG/NJ tube 4810 can pass on either side of the prong 4805 and into the patient's nostril. The pivoting manifold 4843 can be coupled to the cannula frame 4826 adjacent the prong 4805 and the frame 4826 is configured to provide a space or open area between the frame 4826 and the manifold 4843. In these embodiments, a NG/NJ tube 4810 can extend by the side of the prong 4805 even if the manifold 4843 is rotated to that side. The above embodiments can also include soft pads 4829 that can be configured to provide comfort to the patient and can inhibit or prevent the cannula 4804 from slipping or sliding on the patient's face. The soft pads 4829 can include a soft padding material that provides friction or adhesion between the pads 4829 and the patient's face.

Figure 50A:
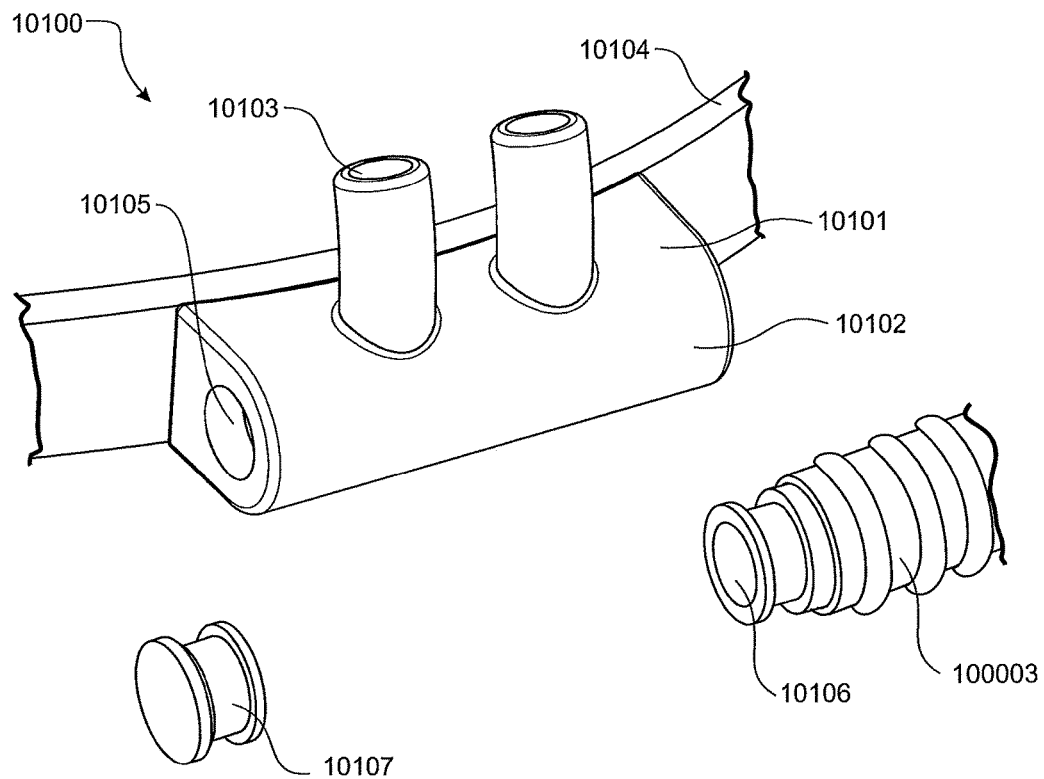
FIGS. 50A and 50B illustrate a nasal cannula assembly comprising a cannula part and a separate plug and conduit connector.
Figure 50B:
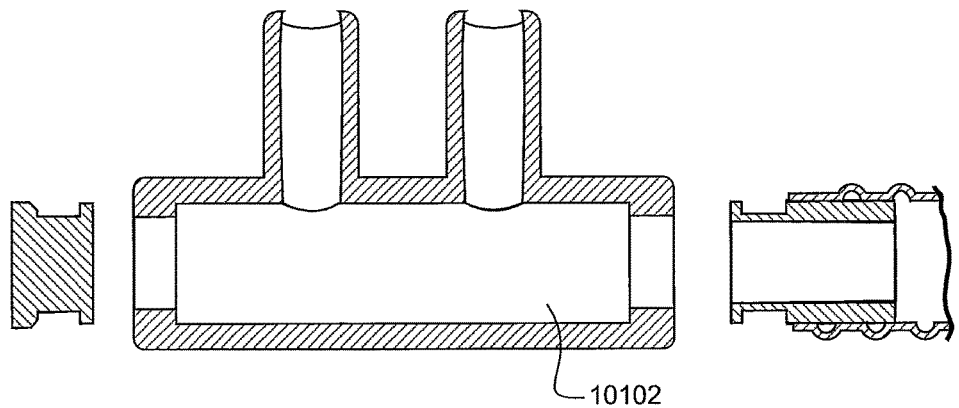

Various cannula assemblies according to some embodiments of the present invention are described with reference to FIGS. 50A to 57. With reference to FIGS. 50A and 50B, in some embodiments a nasal cannula system comprises a cannula assembly 10100, head gear straps (not shown) and a gas supply tube 100003. The cannula assembly 10100 comprises a cannula part or face mount part 10101 for interfacing with a patient's flares. The cannula part may be formed from a thermoplastic, silicone or silicone like material and comprises a manifold 10102, nasal prongs 10103 and side straps or arms 10104 or other connection features for connecting to headgear. In some embodiments the nasal prongs, side arms and manifold may be integrally formed. The manifold is in fluid communication with the nasal prongs and in some embodiments the manifold is open, or has an aperture 10105, at each end. The aperture at each end is adapted to receive the gas tube 100003 or a connector 10106 connected to the gas tube. The cannula assembly also comprises a plug or cap 10107. The cap is configured to be received in the aperture at each end of the manifold. The cannula is therefore configurable to have the tube extend from either the left hand end or the right hand end of the manifold. A user or patient may attach the tube via the connector 10106 to one of the right hand end and the left hand end of the manifold 10102, and the plug 10107 to the other one of the left and right hand ends. The tube and the plug engage in the manifold to seal the apertures 10105 in the ends of the manifold. In the illustrated embodiment the tube connector and plug each comprise a flange to be received in a corresponding groove in the manifold to secure the connector and plug in place and to form a seal with the manifold.

Figure 51:
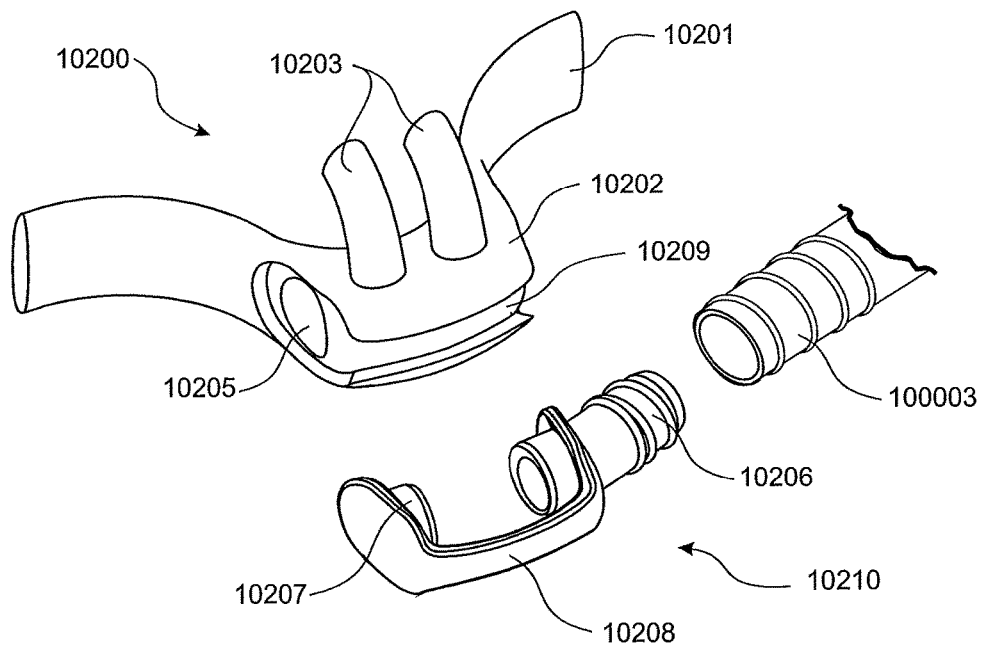
FIG. 51 illustrates a nasal cannula assembly comprising cannula part and a clip comprising a plug and conduit connector for connecting a gas conduit to the cannula part.
Figure 52A:
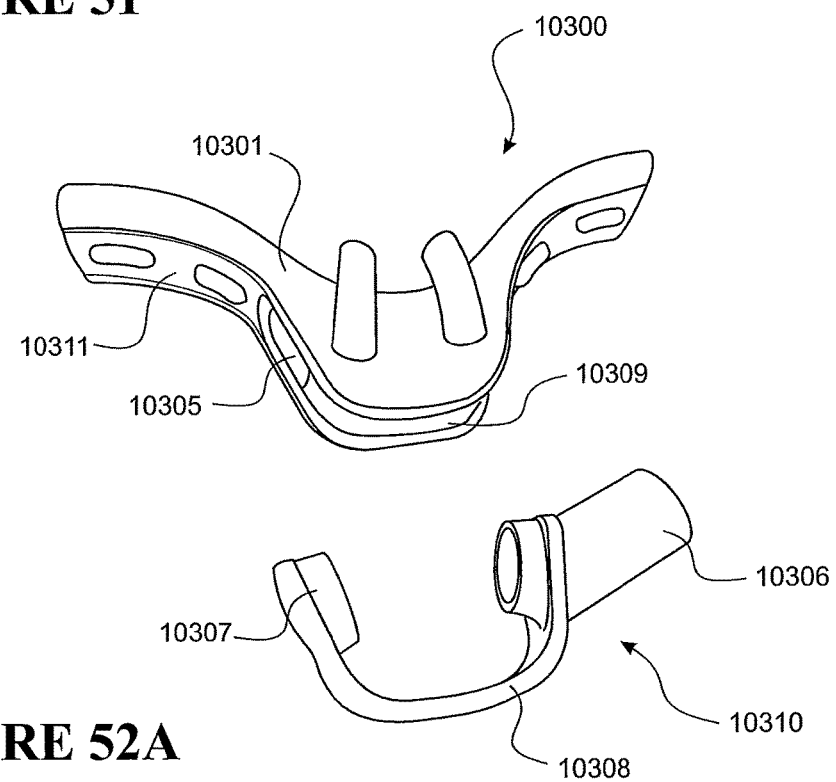
FIGS. 52A and 52B illustrate a nasal cannula assembly comprising cannula part and a clip comprising a plug and conduit connector for connecting a gas conduit to the cannula part. The cannula part comprises a rigid member for interfacing with the clip.
Figure 52B:
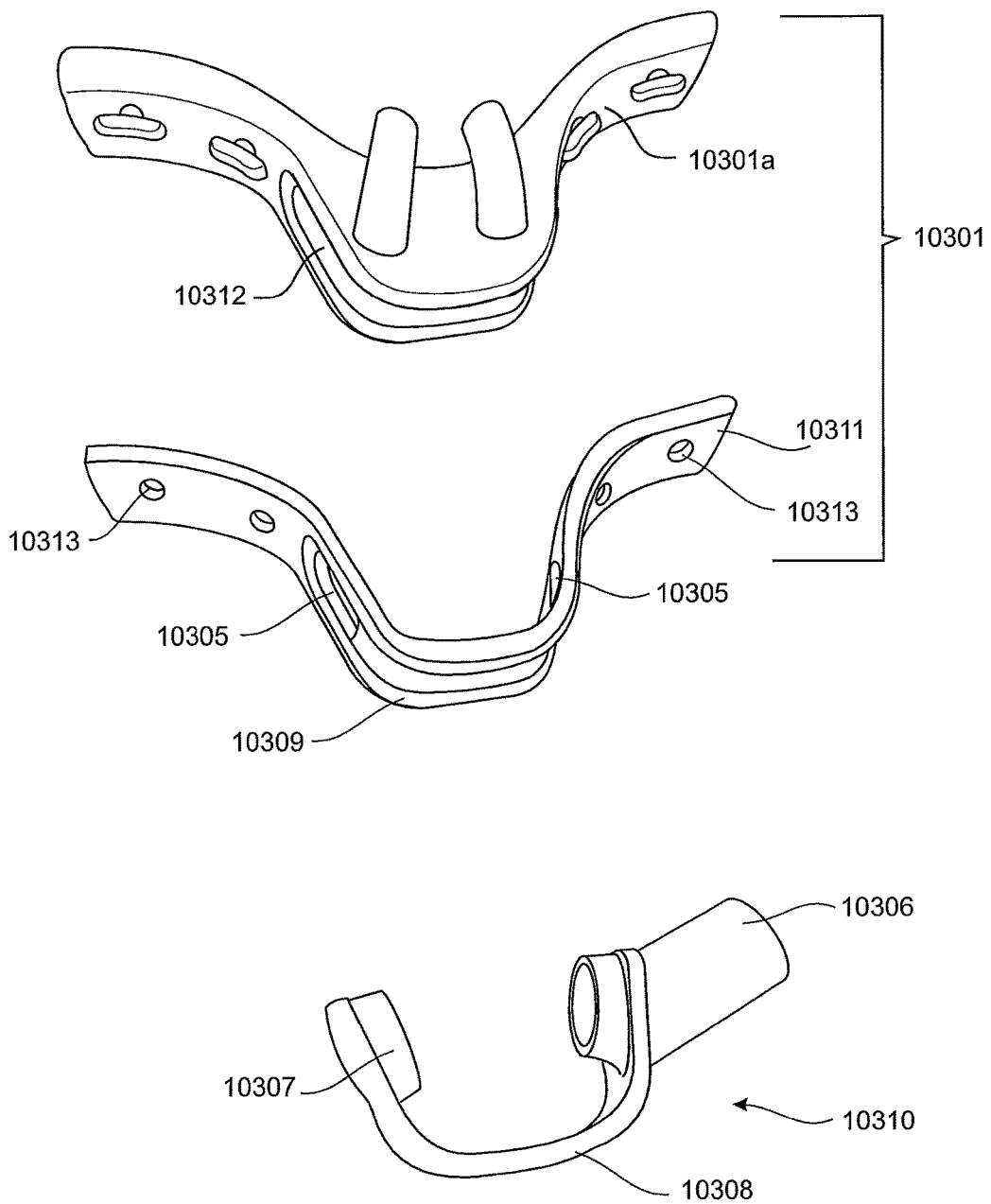
Figure 53A:
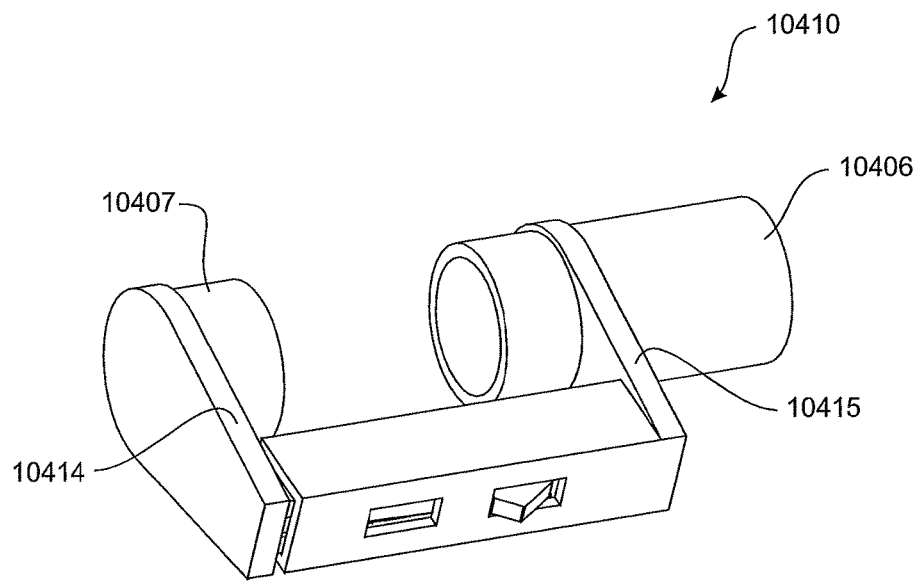
FIGS. 53A and 53B illustrate a clip comprising a conduit connector and a plug, for connecting a gas conduit to a cannula part. A lateral distance between the plug and connector is adjustable.
Figure 53B:
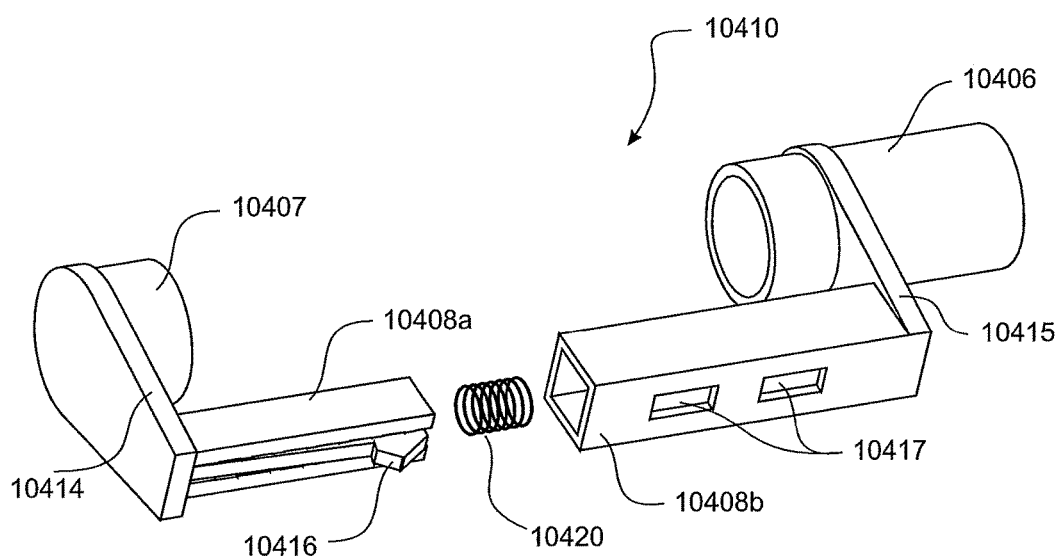

In some embodiments the plug and conduit connector may be coupled or attached together. For example, as illustrated in FIG. 51, the plug 10207 and connector 10206 are connected together by a lateral member 10208. In some embodiments the plug, connector and lateral member are integrally formed to for a clip 10210. The conduit or tube may be provided with the clip 10210 so that the conduit 100003 is a clip on supply tube. In the embodiment of FIG. 51, cannula part 10201 comprises a manifold 10202 in communication with prongs 10203 and two openings 10205, one at each end of the manifold. The clip 10210 may be described as a manifold receiving structure. The manifold receiving structure 10210 can be assembled to the supply tube 100003 at the time of manufacture or can be connectable to the supply tube 100003 prior to use. In certain embodiments, the manifold receiving structure 10210 can be a substantially 'C' or 'U' shaped manifold receiving structure or clip 10210 as illustrated in FIG. 51 or the manifold receiving structure 10210 can have any shape that allows for complimentary coupling to the manifold 10202. In some embodiments, the manifold 10203 has a complimentary shape or matching shape to receive the manifold receiving structure 10210 which can be clipped onto, to the manifold 10202 with the supply tube 100003 positioned facing either way (left or right) as desired. For example, a user may seat the plug 10207 end of the clip in the aperture 10205 at one end of the manifold 10202, and then flex or elastically bend the lateral member 10208 to move the clip 10210 onto the manifold to position the conduit connector 10206 over the aperture 10205 at the other end of the manifold. Once in position the user releases the clip 10210 so that the lateral member 10208 elastically unbends to seat the conduit connector in the aperture at the end of the manifold. In some embodiments the plug and connector each extend into the ends of the manifold to provide a seal and prevent the clip from being simply pulled out of the manifold without deflection of the lateral member of the clip to clear the plug or connector from the corresponding aperture 10205 in the end of the manifold. In some embodiments the clip provides a positive force against the manifold to grip the manifold between the plug and the connector to ensure a seal is formed at each end of the manifold and securely retain the clip to the manifold. In some embodiments the cannula part 10202 may comprise a recessed portion 10209 that is sized and shaped to receive the lateral member 10208. The recessed portion 10209 can be located on the forward and lateral portions of the cannula part and may have a depth suitable to accommodate an entirety of the thickness of the lateral member of the manifold receiving structure 10210, such that an outward-facing surface of the manifold receiving structure 10210 is flush with or recessed within the outer surface of the manifold 10202. Such an arrangement assists in securing the manifold receiving structure 10210 to the manifold 10202 and/or can inform the user how to correctly locate and secure the manifold receiving structure 10210 to the manifold 10209. The recessed portion assists to retain the clip in position on the manifold.

As shown in FIG. 51 the cannula part comprising the manifold, nasal prongs and side arms may be integrally formed, for example from a silicone or silicone like material.

In some embodiments, the cannula part may comprise a relatively rigid part for interfacing with and receiving and/or retaining the clip. For example, illustrated in FIGS. 52A and 52B, the cannula part 10301 may comprise conduit clip receiving or retaining part 10311 for receiving conduit clip 10310. The silicone or silicone like material of the resilient cannula part 10301*a* may be over moulded to the relatively rigid retainer 10311, or attached by other fastening technologies, for example bonding, mechanical snap fitting, ultrasonic welding or any other suitable fastening method known in the art. The resilient part 10301*a* may comprise an open cavity or channel 10312. The manifold apertures 10305 may be provided in the clip receiving part 10311. The clip receiving part and the resilient part 10301*a* are assembled so that the clip receiving part 10311 closes the open channel 10312 except for the apertures 10305. The clip receiving part 10311 and the resilient part combine to form the manifold of the cannula part 10301. The clip receiving part may comprise a recess 10309 for receiving the lateral member 10308 of the clip 10310 as described with reference to the embodiment of FIG. 51. The clip receiving part may comprise through holes 10313 for resilient material of the resilient cannula part to pass to secure the resilient part to the clip receiving part, for example in an over moulding process or an assembly process. The clip receiving part may be formed from the same material as the conduit clip. The relatively rigid (compared to the soft or resilient material of the cannula) material of the clip receiving part provides for positive fitting or engagement between the conduit clip and the cannula part 10301. The clip may be mated with the cannula part by pushing the clip onto the cannula part in a direction on or parallel to the sagittal plane of the cannula assembly, that is a direction perpendicular to a lateral direction of the cannula. By pushing the clip onto the cannula part, interference between the plug and conduit connector with the retainer causes the lateral member of the clip to deflect to allow the plug and connector to move over the apertures at the ends of the manifold. Once the plug and connector are aligned with the manifold apertures the lateral member elastically unbends to snap the clip in place on the cannula part.

In some embodiments the plug and conduit connector may be removably attached together, or the conduit clip may comprise an adjustment feature to adjust the relative position of the plug and conduit connector. For example, with reference to FIGS. 53A and 53B, the conduit clip 10410 comprises two parts, a first part 10414 and a second part 10415. In the illustrated embodiment, the first part comprises the plug 10407 and the second part comprises the conduit connector. The first part comprises a lateral member 10408*a* and the second part comprises a lateral member 10408*b*. In some embodiments the lateral members 10408*a* and 10408*b* assemble together in a telescoping arrangement, and comprise complementary features to set the lateral distance between the plug 10407 and the conduit connector 10406. In the illustrated embodiment the lateral member 10408*a* of the first part 10414 is received in the lateral member 10408*b* of the second part, however the lateral member connected with the conduit connector could be received in a corresponding lateral member connected to the plug. The first and second parts comprise complementary features to set the distance between the plug and conduit connector. For example, as illustrated the one of the first and second parts 10408*a* and 10408*b* may comprise a projection to be received in a corresponding aperture in the other one of the first and second parts. In the illustrated embodiment the first part 10414 comprises a projection 10416 on lateral member 10408*a*, and the second part 10415 comprises an aperture 10417 in the lateral member to receive the projection 10416 to set the lateral distance between the plug and the conduit connector. In some embodiments the clip may be provided with more than one aperture 10417 to provide a range of lateral distances between the plug and conduit connector to accommodate a range of cannula sizes. In use, a user may assemble the conduit clip 10410 to a cannula part (for example cannula part 10201 of FIG. 51 or the cannula part 10301 of FIG. 52A) with the plug and conduit connector initially in an extended position. Once the plug 10407 and conduit connector 10406 are aligned with apertures 10205 of the manifold of the cannula part, the user pushes the plug and conduit connector together in a lateral direction to attach the conduit clip and conduit to the cannula part. In some embodiments the first and second parts are biased apart, for example by a spring 10420 or a resilient member.

In the embodiments of FIGS. 51 to 53B the conduit clip is removable from the cannula part so that the cannula can be assembled with the conduit 100003 extending from either the left hand side or the right hand side of the cannula assembly. In some embodiments, the conduit clip may be movably attached to the cannula assembly. For example, in some embodiments the conduit clip may be rotationally attached to the cannula part so that the conduit connector can be positioned at either the right hand or left hand end of the cannula manifold.

Figure 54A:
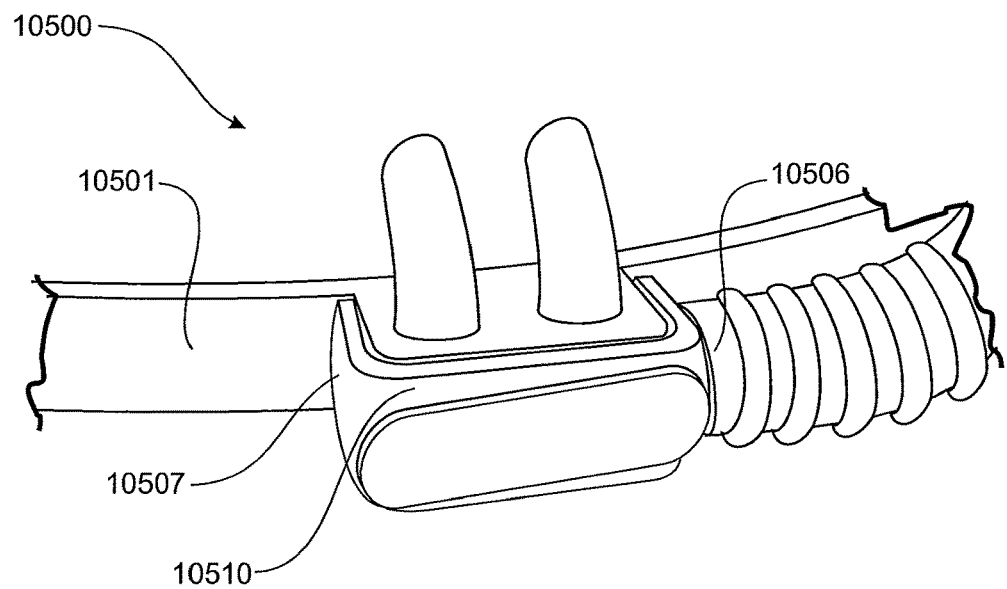
FIG. 54A to 54C illustrate a nasal cannula assembly comprising a cannula part and a clip comprising a plug and conduit connector for connecting a gas conduit to the cannula part. The clip is rotationally mounted to the cannula part.
Figure 54B:
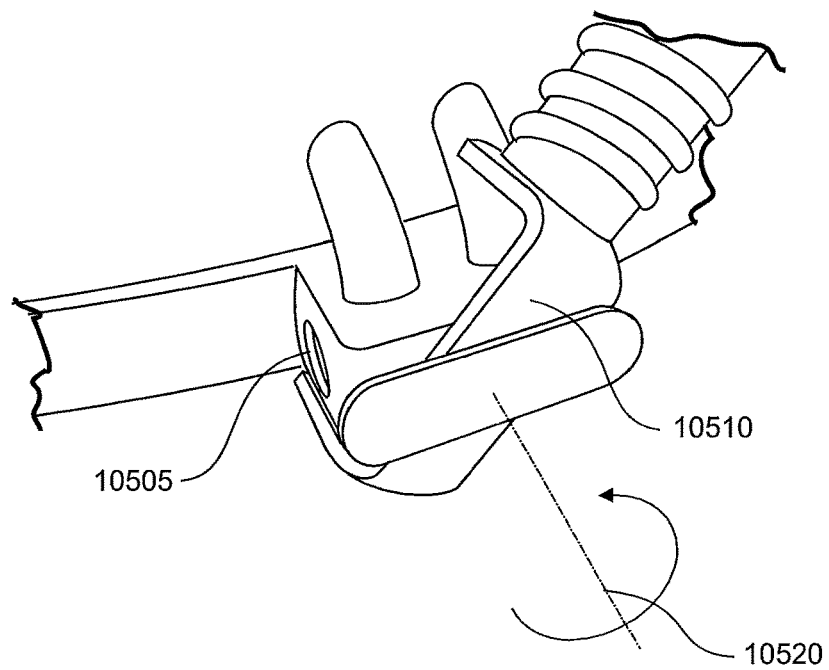
Figure 54C:
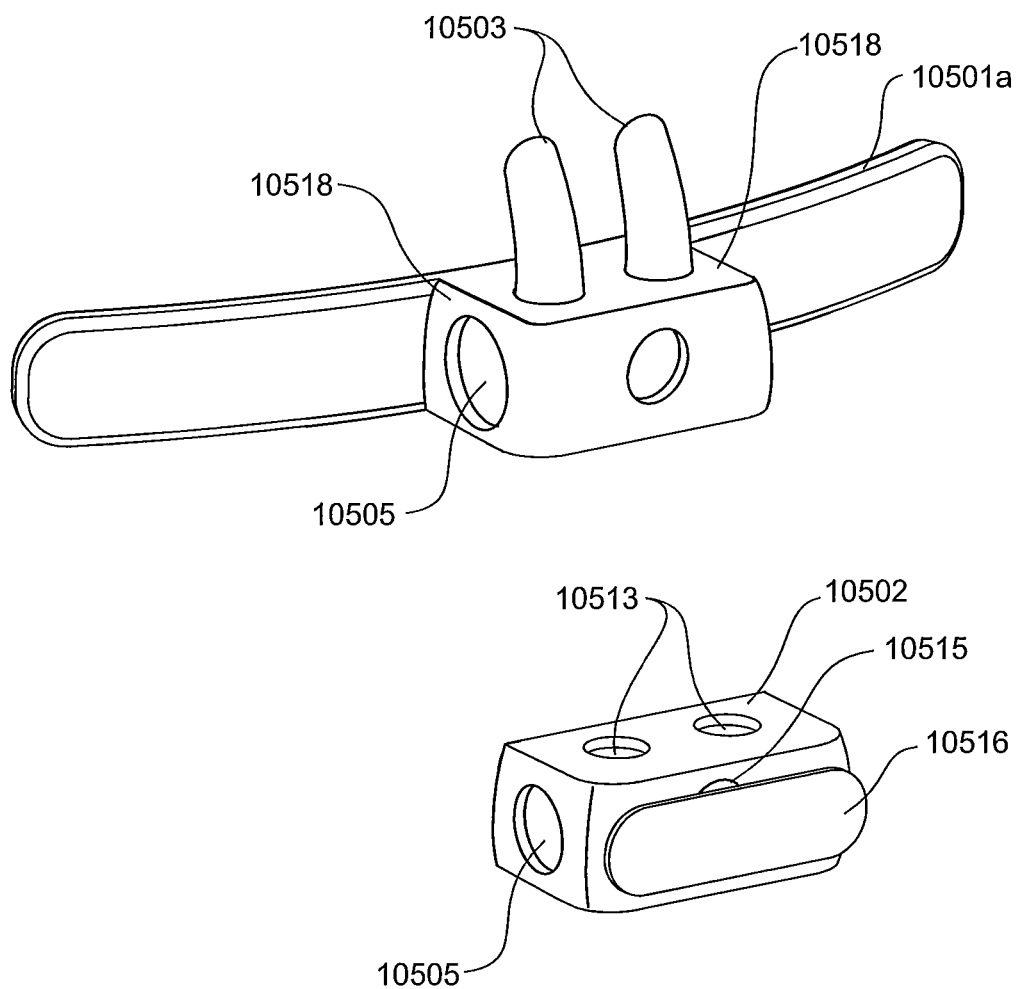

With reference to FIGS. 54A to 54C, in some embodiments the cannula assembly 10500 comprises a conduit clip 10510 rotationally attached to the cannula part 10501 about a rotational axis 10520 that is approximately on or parallel to the sagittal plane of a user (that is, an axis that is approximately horizontal in use with a user in a standing position). To position the conduit to the left or right sides of the cannula assembly the conduit clip is rotated on the axis 10520, as illustrated in FIG. 54B where the clip 10510 is rotated part way between the right and left sides of the assembly. As illustrated in embodiment 546C, in some embodiments the cannula part comprises a resilient material moulded or fitted over a relatively rigid manifold 10502. The manifold 10502 may comprise a hollow member comprising two apertures 10513 to be in communication with nasal prongs 10503, and an aperture 10505 at each end to which the plug 10507 or conduit connector 10506 seals. In some embodiments, the silicone or silicone like material of the resilient cannula part 10501*a* may be over moulded to the relatively rigid manifold 10502, or attached by other fastening technologies, for example bonding, mechanical snap fitting, ultrasonic welding or any other suitable fastening method known in the art. The resilient cannula part is formed with the nasal prongs aligned with or in communication with the apertures 10513 and is formed with an aperture 10505 at each end to communicate with the aperture 10505 of the manifold. In some embodiments, an axle 10515 may be integrally formed with the rigid manifold 10502. The conduit clip 10510 is rotationally received on axle 10515. In some embodiments the clip 10510 may comprise a keyway so that the clip can be removably mounted to the cannula part 10501. In some embodiments the cannula assembly 10500 comprises a flange 10516 at the end of the axle 10515 to retain the conduit clip on the axle. Preferably the ends of the manifold are curved with a centre of curvature on the rotational axis 10520. The plug and the conduit connector have a complementary curvature so that the clip 10510 can rotate on the rotational axis 10520 to position the conduit at either end of the cannula assembly. The resilient material of the cannula part at the ends 10518 of the manifold may provide a seal with the plug and conduit connector. The rigid manifold may be formed from the same material as the conduit clip. The relatively rigid (compared to the soft or resilient material of the cannula) material of the manifold may provide for positive fitting or engagement between the conduit clip 10510 and the cannula part 10501.

Figure 55A:
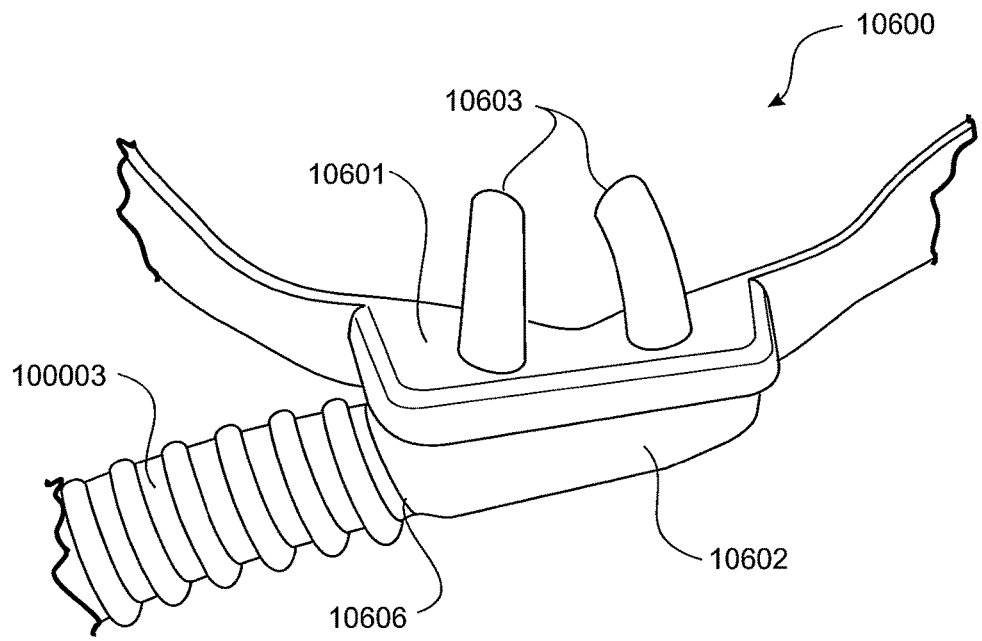
FIGS. 55A and 55B illustrate a nasal cannula assembly comprising a cannula part and a conduit connector comprising a manifold. The cannula part is rotationally mounted to the manifold.
Figure 55B:
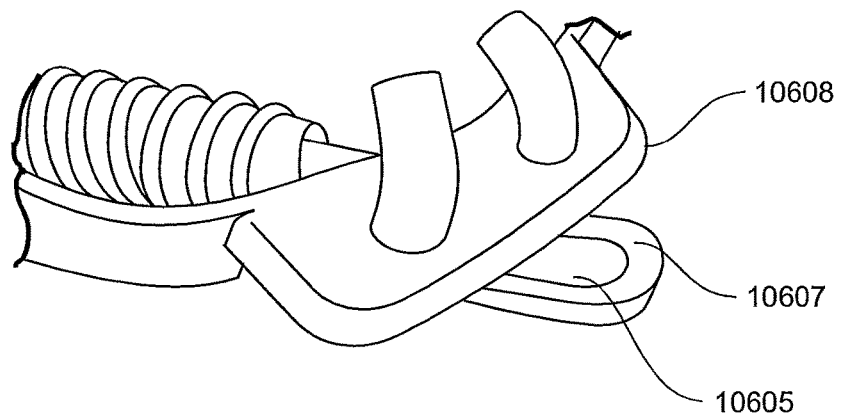

FIGS. 55A and 55B illustrate an embodiment of a nasal cannula assembly 10600. The cannula assembly comprises a cannula part 10601 having a pair of prongs 10603. The conduit 100003 is attached to the cannula assembly 10600 via a connector 10606. The connector comprises a manifold 10602. The manifold comprises an inlet and an outlet. The manifold 10602 is attached to or integrally formed with the conduit connector 10606. The cannula part 10601 is rotatable relative to the manifold 10602. The cannula part 10601 is mounted on and rotatable about a vertical shaft such that the prongs rotate together. In some embodiments, the cannula part 10601 is a separate component from the manifold/tubing assembly and the removable cannula part 10601 can allow for the use of different sizes of prongs for different nose sizes while using the same size manifold 10602 (for example as part of a standard gas conduit). In some embodiments, the manifold 10602 may comprise an open top 10605 that is the manifold outlet. The cannula part 10601 fits over or covers the open top so that the prongs are in communication with the manifold inlet provided by the conduit connector. In some embodiments the manifold comprises a lip 10607 on a surface of the manifold to which the cannula part 10601 connects. In some embodiments the lip may extend about the open top of the manifold. The cannula part 10601 can have a mating section 10608 (for example an annular groove) that is complementary to the lip 10607. In some embodiments that contain a lip 10607 on the manifold 10602, the cannula part 10601 can be lifted from the surface of the manifold and rotated about a vertical shaft so that the prongs 10603 can be repositioned to the appropriate direction. The cannula part 10601 can be rotatable about a vertical, central axis of the manifold 10602 or an axis that is centrally located relative to the prongs such that the conduit 100003 switches between the left hand side or the right hand side of the cannula assembly.

Figure 56A:
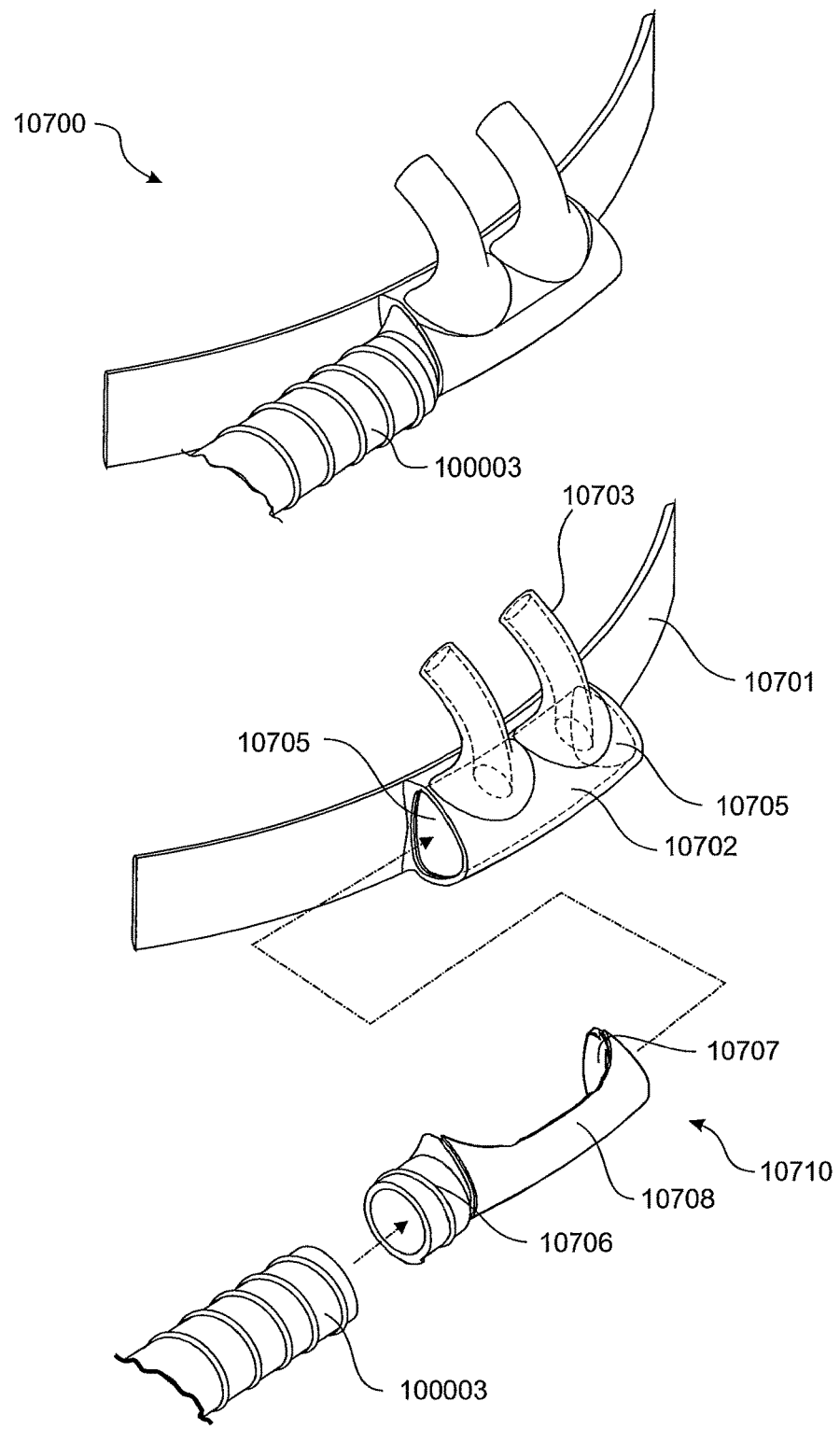

FIG. 56A illustrates an embodiment of a nasal cannula assembly 10700 that is similar to the cannula of FIG. 51. In the cannula assembly of FIG. 56A, the plug 10707 and conduit connector 10706 are connected together by a lateral member 10708. In some embodiments the plug, connector and lateral member are integrally formed to form a clip 10710. The conduit or tube may be provided with the clip 10710 so that the conduit 100003 is a clip on supply tube. In the embodiment of FIG. 56A, cannula part 10701 comprises a manifold 10702 in communication with prongs 10703 and two openings 10705, one at each end of the manifold. The clip 10710 may be described as a manifold receiving structure. The manifold receiving structure 10710 can be assembled to the supply tube 100003 at the time of manufacture or can be connectable to the supply tube 100003 prior to use. In certain embodiments, the manifold receiving structure 10710 can be a substantially 'C' or 'U' shaped manifold receiving structure or clip 10710 as illustrated in FIG. 56A or the manifold receiving structure 10710 can have any shape that allows for complimentary coupling to the manifold 10702.

Unlike the embodiment of FIG. 51 where the clip 10210 is clipped onto the manifold 10202 of the cannula part by mating the plug with the manifold from one end of the manifold and the conduit clip with the manifold from the other end, in the embodiment of FIG. 56A, the clip is pushed into the manifold from one end. That is, the clip is inserted into the manifold from either end of the manifold so that the conduit connector is positioned to the right or the left side of the manifold. The clip is inserted into the manifold via the aperture 10705 at one end until the conduit connector 10706 mates with that aperture and the plug 10707 mates with the aperture 10705 at the opposite end of the manifold 10702. The clip can be pushed into the manifold from either end. The clip is not elastically deformed to mate the clip with the manifold.

In some embodiments, the cannula part 10701 may be provided with a relatively rigid part for interfacing with and receiving and/or retaining the clip 10710. For example, illustrated in FIG. 56B, the cannula part 10701 may comprise conduit clip receiving or retaining part 10711 for receiving conduit clip 10710. The retainer 10711 is illustrated in FIG. 56C. The silicone or silicone like material of the resilient cannula part 10701a may be over moulded to the relatively rigid retainer 10711, or attached by other fastening technologies, for example bonding, mechanical snap fitting, ultrasonic welding or any other suitable fastening method known in the art. The relatively rigid (compared to the soft or resilient material of the cannula) material of the clip receiving part provides for positive fitting or engagement between the conduit clip 10711 and the cannula part 10701. The clip is inserted laterally into the manifold from one end.

Figure 57A:
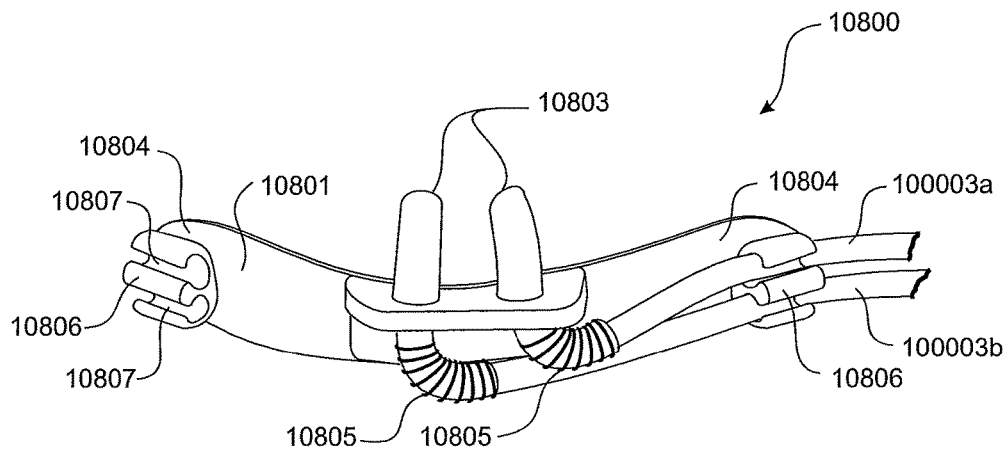
FIG. 57A illustrates a cannula assembly comprising a pair of gas supply conduits, each conduit connected to a nasal prong via a flexible tube section, and a clip at each side of the cannula assembly for configuring the conduits to extend from the left or right side of the cannula.

FIG. 57 illustrates an embodiment of a nasal cannula assembly 10800 that comprises dual gases conduits 100003a, 100003b, one conduit for each nasal prong. The cannula assembly 10800 comprises a cannula part 10801 comprising prongs 10803. The cannula part may be formed from a thermoplastic, silicone or silicone like material and comprises the nasal prongs 10803 and side straps or arms 10804 or other connection features for connecting to headgear. In some embodiments the cannula part is an integrally formed part. Each conduit is connected to a corresponding prong via a joint adapted to allow the conduits to be routed to a left side or a right side of the nasal cannula assembly. In the embodiment of FIG. 57A each conduit is connected to a corresponding prong via a flexible conduit section or tube 10805. For example, the flexible conduit section may be formed from a silicone or silicone like material. The flexible conduit may comprise circumferentially extending ribs so that bending of the flexible conduit section does not cause the flexible conduit section to collapse. Preferably, bending of the flexible conduit section does not cause substantial occlusion of the internal passage of the flexible conduit section. The conduits 100003a, 100003b may be routed to either the right or left side of the cannula by bending each flexible conduit section, for example by 90 degrees to either the left or right sides. To retain the conduits in place, the cannula is preferably provided with a clip 10806 on each side of the cannula assembly 10800. Each clip may comprise two channels or receptacles, each channel for receiving one of the tubes 100003a, 100003b. In some embodiments the clip comprises a channel or receptacle for receiving both conduits 100003a, 100003b. The clip may be formed from silicone or silicone like material, and could be integrally formed with the cannula part, or could be formed from a plastic material that is more rigid than the material of the cannula part. In some embodiments a strap may be provided at the cannula for strapping the conduits to the cannula.

Figure 57B:
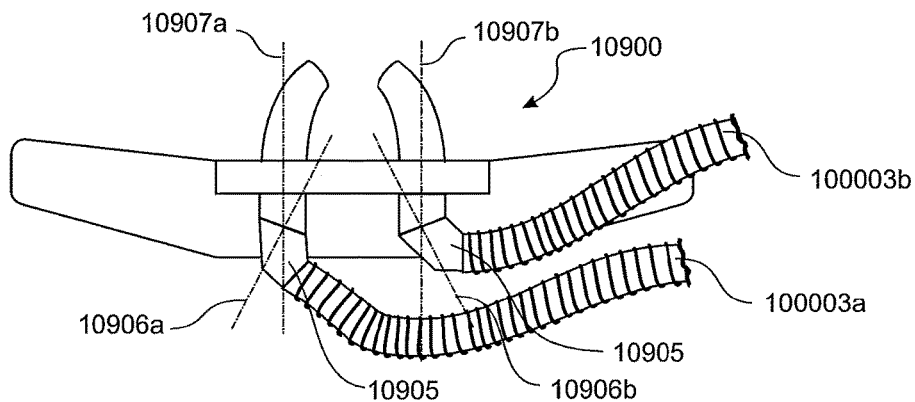
FIGS. 57B and 57C illustrate a nasal cannula assembly comprising a pair of gas supply conduits, each conduit connected to a nasal prong via a swivel elbow.
Figure 57C:
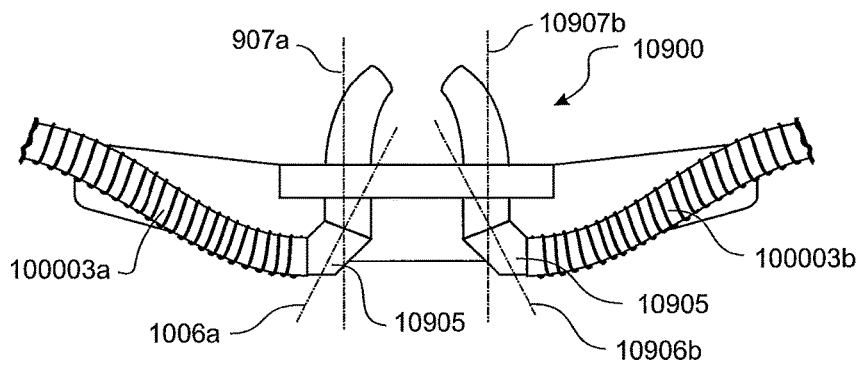

In some embodiments each conduit 100003a, 100003b is connected to a corresponding prong via a swivel joint. The conduits 100003a, 100003b may be routed to either the right or left side of the cannula by rotating each swivel joint at the nasal cannula. An example nasal cannula assembly 10900 is illustrated in FIGS. 57B and 57C. In some embodiments each swivel joint is a swivel elbow. In some embodiments each swivel joint rotates on an axis 10906a, 10906b that is at an angle to an axis 10907a, 10907b of the corresponding prong. Rotation of the swivel joint on an angle as illustrated allows both tubes 100003a, 100003b to be routed to the left side or the right side without overlapping. As illustrated in FIG. 57B, with both tubes routed to the right hand side of the cannula assembly the tube 100003a extending from the left nasal prong extends below the tube 100003b extending from the right nasal prong. In an alternative configuration with both tubes routed to the left hand side of the cannula assembly, the tube 100003b extending from the right nasal prong extends below the tube 100003a extending from the left nasal prong.

Figure 74:
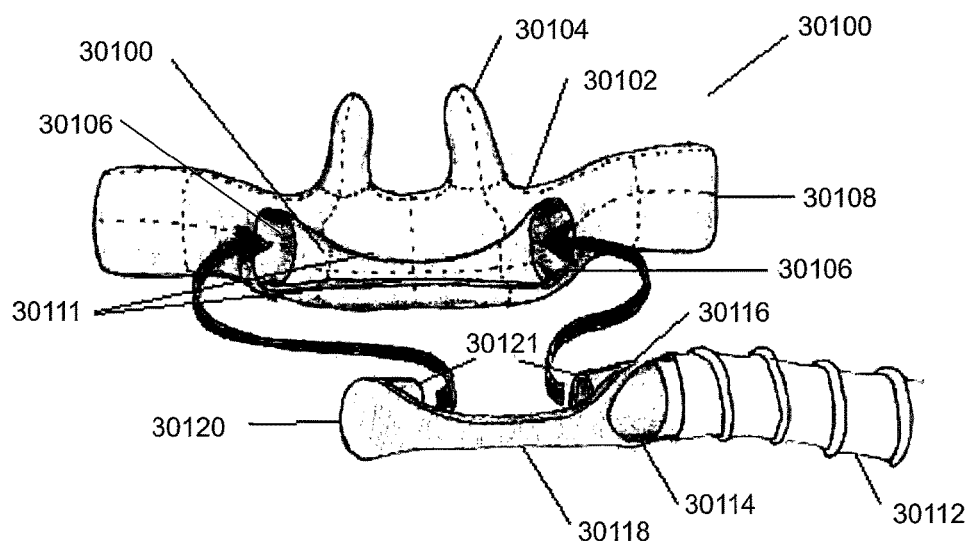
FIG. 74 is a perspective view of an exploded cannula system with a clip-on supply tube attachment.
Figure 75:
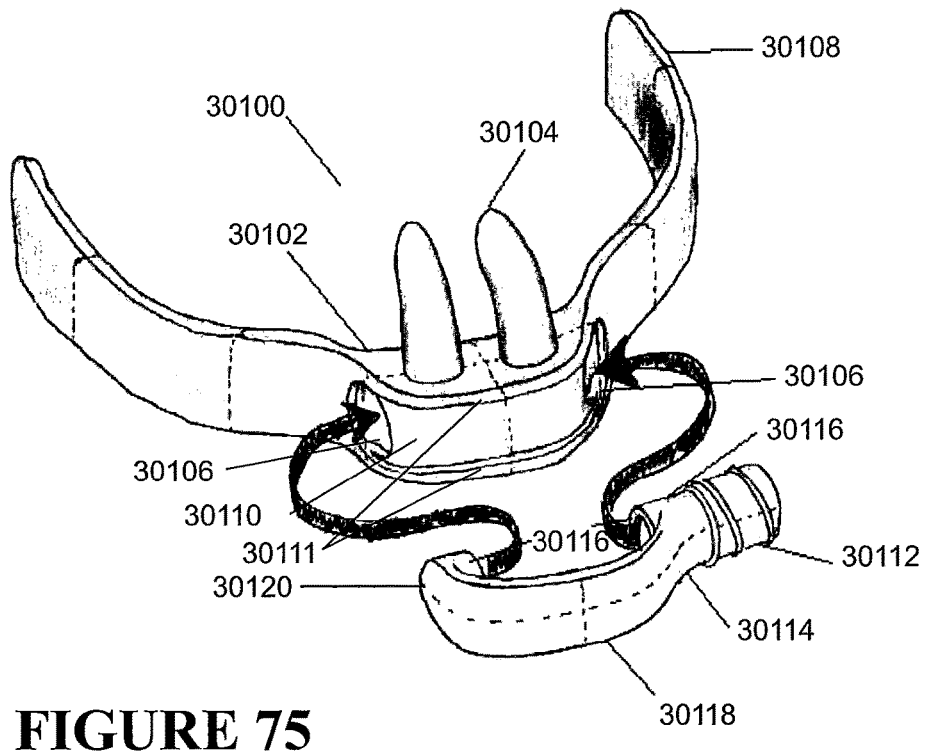
FIG. 75 is a perspective view of an exploded alternative cannula system (relative to FIG. 74) with a clip-on supply tube attachment.

With reference to FIGS. 74 and 75, configurations for similar nasal cannula systems 30100 are shown. In the illustrated configurations, the nasal cannula system 30100 comprises a cannula body 30102 with two prongs 30104 extending from the body 30102 that may be inserted into both nares of a patient. In some configurations, the cannula body may only comprise one prong 30104 that can be placed into a single nare of the patient. The cannula body 30102 also comprises two holes 30106 through which a gas may enter the cannula body 30102, and flaps 30108 which may help to support the cannula body 30102 on the patient's face. Flaps 30108 may be adapted to connect to headgear straps and/or other elements (not shown) that may be placed on and/or around the patient's head in such a way that the main body may be supported on the patient's face such that the prongs 30104 may be placed into one or both of the nares of the patient. For example, flaps 30108 may comprise side release buckles that may interface with similar buckles on headgear straps. In some configurations, the flaps 30108 need not be present, and the straps and/or other elements may interface directly or indirectly with the gases supply tubing 30112, body 30102, prongs 30104 and/or clip-on attachment 30114. In some configurations, the cannula system 30100 can be secured to the face of a patient by using, for example, adhesive pads.

Figure 76:
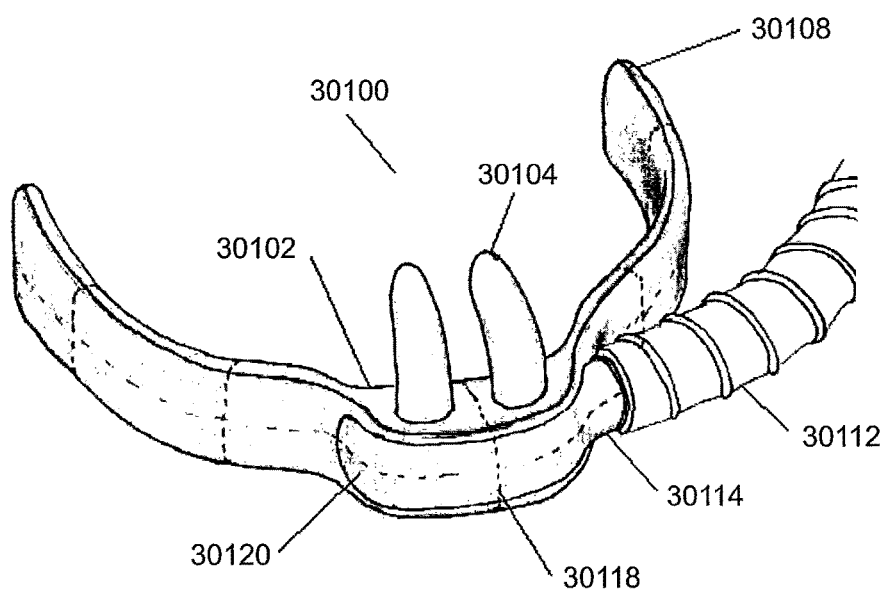
FIG. 76 is a perspective view of the cannula system of FIG. 75, except that the cannula system has been assembled from the exploded components.

In the illustrated configuration, the cannula system 30100 also includes a clip-on supply tube attachment or manifold 30114 that may be integrally molded to or releasably connected with a gases supply tubing 30112. The attachment 30114 may comprise an open end 30116 that may act as an outlet for the gases supply tubing 30112, a bridge 30118, and an end cap 30120 through which gas cannot flow. In use, the supply tube attachment may flex slightly due to the application of force at bridge 30118 so that the open end 30116 and end cap 30120 can fit into the holes 30106 of the cannula body 30102 as shown according to the black arrows shown. Preferably, the open end 30116 and the end cap 30120 will have inner protrusions 30121 that in use can extend into the holes 30106 so that the end 30116 and cap 30120 can securely fit into the cannula body 30102 to ensure a sealed gases pathway between the gases supply tubing 30112 and the prongs 30104. It is also preferred that the body 30106 includes a recess 30110 on the side of the cannula body 30102 that in use faces away from the patient, so that in use the bridge 30118 may securely rest in the recess 30110 and so that the cannula body 30102 may be prevented from rotating away from the patient. Preferably, the upper and lower edges 30111 of the recess 30110 are overhanging or curve inwards so as to help retain the attachment 30114. FIG. 76 illustrates the cannula system 30100 comprising the cannula body 30102 and the attachment 30114, where the body 30102 and the attachment 30114 have been assembled together. Advantageously, as shown in FIGS. 74 and 75, the attachment 30114 may be placed on the cannula body 30102 so that gases flow may enter the cannula body 30102 from the right (from the perspective of one facing the front of the cannula body 30102) or the attachment may be flipped upside down and placed on the cannula body 30102 so that gases flow may enter the cannula body 30102 from the left (from the perspective of one facing the front of the cannula body 102).

Many variations of the configurations of FIGS. 74-76 are possible. Some variations can be seen in the illustrated configuration of FIG. 77. In this configuration, the clip-on supply tube attachment 30114 comprises side wings 30122 through which the open end 30116 and the closed end cap 30120 protrude. The side wings 30122 may include slits 30124 through which headstraps 30126 or other headgear attachment means may be attached. It should be understood, however, that any headgear attachment means may be suitable in place of slits 30124, including buckles, pins, hook-and-loop strips, or other mechanical fastening elements. In some configurations, slits 30124 may not be present and the headgear attachment means may be present on the cannula body 30102. In some configurations, headgear attachment means may be present on both the attachment 30114 and the body 30102. In the illustrated configuration, the cannula recess 30106 substantially extends across the length of the cannula body 30102 to accommodate both the bridge 30118 and the side wings 30122. Advantageously, in such a configuration the forces of the head straps 30126 or other headgear attachment means against the face in use, along with the force of the gases supply tubing 30112 against the face in use, may be distributed over a larger area of the face and cannula body 30102 relative to the configuration as shown in FIGS. 74-76, which may increase comfort and reduce the risk and/or severity of pressure sores on the face.

Figure 77:
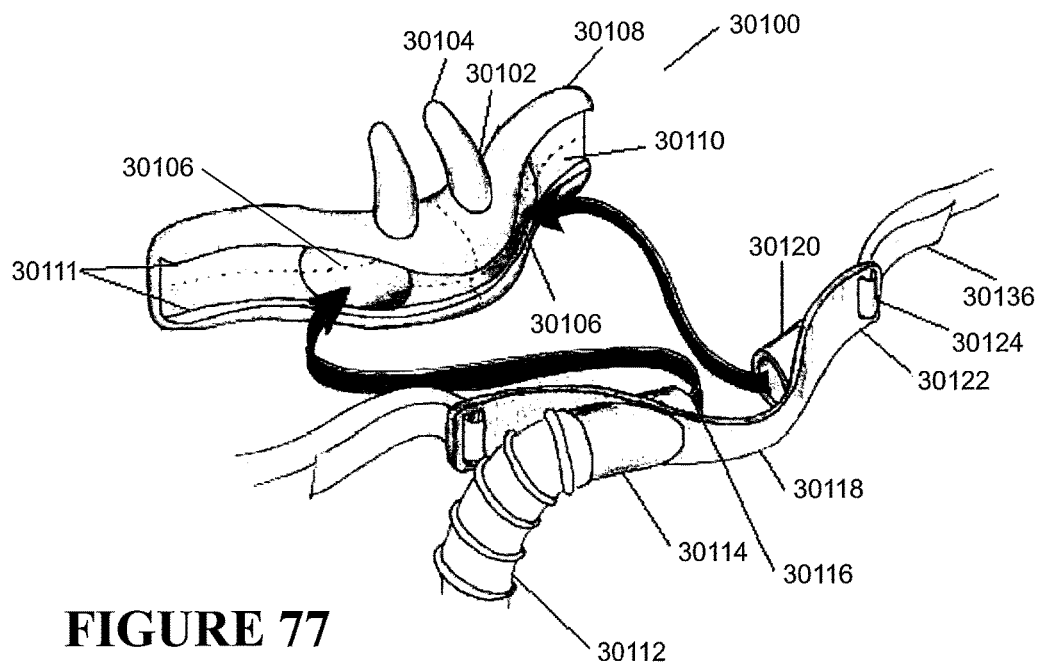
FIG. 77 is a perspective view of an exploded alternative cannula system (relative to FIGS. 74 and 75) with a clip-on supply tube attachment.
Figure 78:
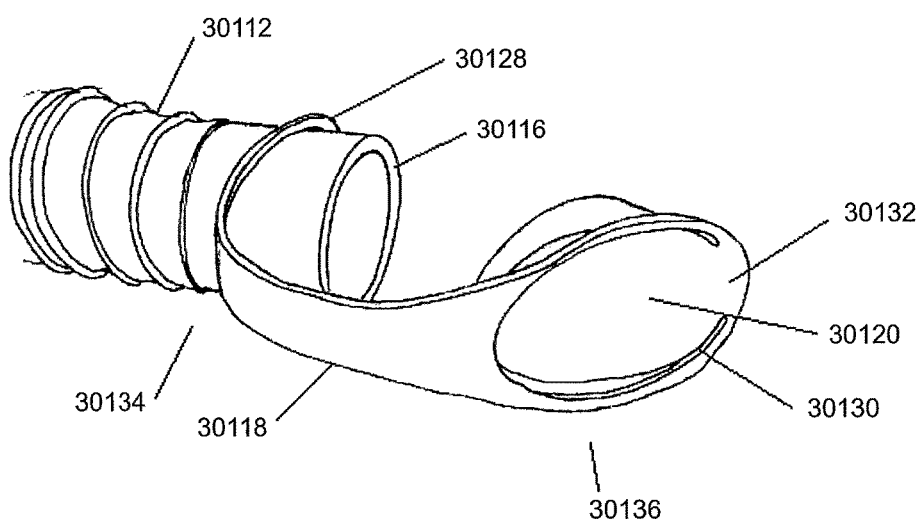
FIG. 78 is a perspective view of a clip-on supply tube attachment with a hinged end cap.
Figure 79:
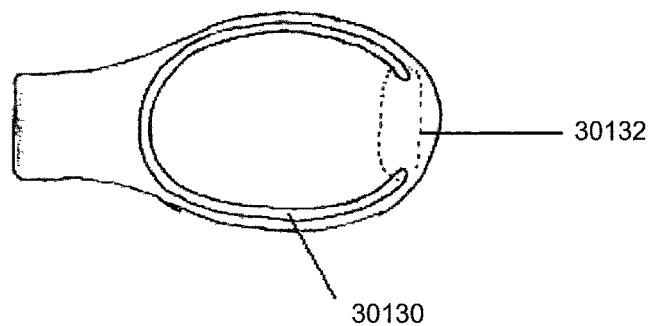
FIG. 79 is a close view of the hinged end cap of FIG. 78.
Figure 80:
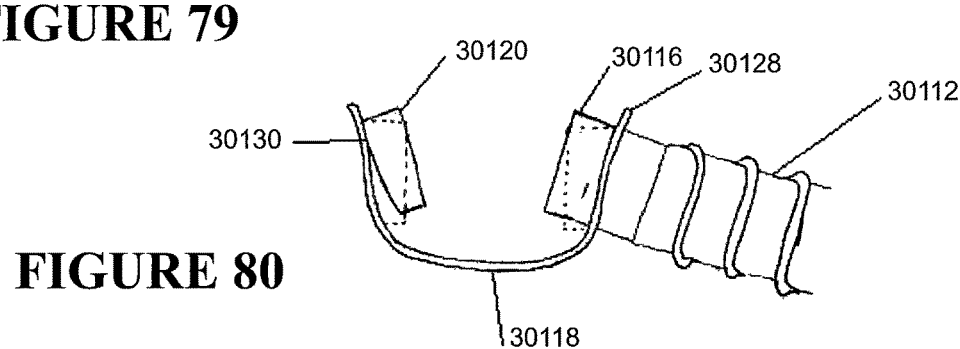
FIG. 80 is a top-down view of the clip-on supply tube of FIG. 78, where the hinged end cap has moved towards the gases supply tubing.
Figure 81:
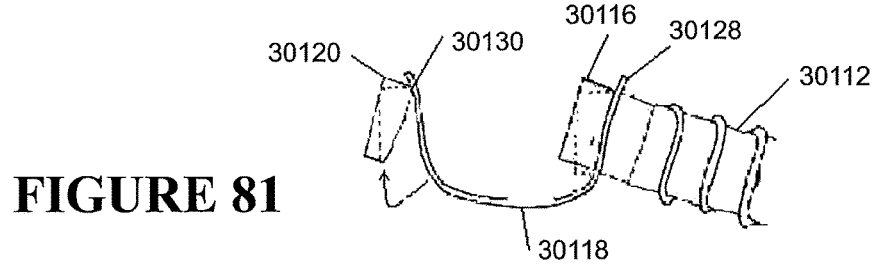
FIG. 81 is a top-down view of the clip-on supply tube of FIG. 78, where the hinged end cap has moved away from the gases supply tubing.
Figure 82:
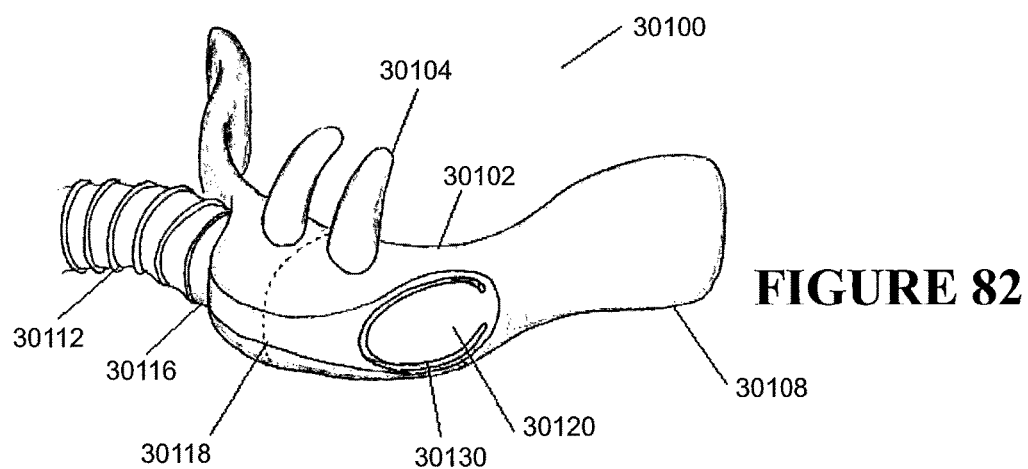
FIG. 82 is a perspective view of an assembled cannula system with the clip-on supply tube attachment of FIG. 78.

Some other variations can be seen in the illustrated configuration of FIG. 78. In this configuration, the clip-on attachment 30114 may comprise multiple sections, including a first section that comprises an open end 30116 that may be integrally formed with the gases supply tubing 30112 or may be removable from the tubing 30112, and a second section 30136 that comprises a ring of plastic 30128 around the open end 30116, the bridge 30118 and the end cap 30120. The end cap also comprises a hinged region 30130, which is shown in detail in FIG. 79. The hinged region comprises a slot 30130 in the end cap 30120 that allows the end cap 30120 to rotate along a line or band 30132. This slot 30130 allows the end cap 30120 to move back and forth as seen in FIGS. 80 and 81. Advantageously relative to the configuration shown in FIGS. 74-77, in use, the hinging action of the end cap 30120 may enable the patient to more easily insert the clip-on attachment 30114 into the holes 30106 of the cannula body 30102 to achieve a complete cannula system 30100 as seen in FIG. 82. It is important to understand that the protrusion 30121 of the end cap 30120 rests within the hinging area 30130 so that flow does not escape from the hinging area 30130 in use.

With further reference to FIGS. 74-82, as well as FIGS. 51-56C, in some embodiments there is provided a nasal cannula including a cannula body defining an open cavity (such as a chamber or void space within the cannula body which is provided to be in fluid communication with for example one or a pair of nasal prongs for delivery of gases supplied to the open cavity to a user), for example such an open cavity may be the void space indicated as item 10102 in FIG. 50B, or may be accessible via the holes indicated as items 30106 in FIGS. 74, 75, 77. The cannula body can comprise at least one (and preferably a pair of) nasal prong(s) extending from the cannula which is/are in fluid communication with the open cavity. A manifold comprising a manifold body, the manifold body for example may be a component such as those indicated by those items 10210 of FIG. 51, 10310 of FIGS. 52A, B, 10410 of FIGS. 53A, B, 10510 of FIGS. 54A, B or 10602 of FIG. 55A, or 10710 of FIG. 56A, the manifold body capable of engaging with the cannula for fluid connection with the open cavity. The manifold body can be oriented or is orientable in either of a first operational position or a second operational position, wherein the first position and second positions are different to each other.

The manifold body is adapted to accept a gases supply conduit at a first end of, or a gases inlet to, the manifold body. The first end of the manifold body is adapted to engage with one end of the open cavity for delivery of gases into the open cavity. A second end of the manifold body is adapted in turn to form a seal or connection with an (or the) other end of the open cavity, such that one in either of the first or second operational positions, the manifold body forms an enclosure to the open cavity, and ensuring a fluid pathway is formed from the inlet to the manifold to the open cavity, such that the delivery mechanism for a user, such as a nasal prong or pair of nasal prongs is receivable of a gas flow.

The cannula body may comprise at least one recess or at least one other form of surface relief or a region of surface relief for retaining the manifold body in an engaged operational position, e.g. either of the first or the second operational positions.

Whilst various forms of a manifold body are described herein, at least some embodiments relate to configurations having the first end and the second end of the manifold body being connected to each other in a manner such that first end provides for a gases inlet to the open cavity and the second end provides for a plug or cap to substantially enclose the open cavity. In enclosing the open cavity using the manifold body, a fluid delivery pathway is achieved for supply gases from the first end of the manifold body into the open cavity and to a terminal end of the at least one nasal prong.

Aside from embodiments where a separate (removable) plug is provided to enclose an end of the open cavity (e.g. such as the embodiment shown by FIGS. 50A,B), other forms of the manifold body as referred to above facilitate the first and second ends of the manifold body being connected to each other by a connecting portion or connecting portions.

The connecting portion can be one or more of at least one arm or at least one finger or at least one frame member, or bridge portion (such a connecting portion may for example be a portion such as that shown by items 30118, 10208, 10308, 10408a-b, 10708).

It will also be appreciated the connecting portion allows for the manifold body to be integrally formed, in this manner the first and second ends are parts of the same component or portion.

Further, the connecting portion or the cannula body defining at least in part the open cavity, or both, may include an alignment feature adapted to enable a predetermined geometric orientation of the manifold body relative to the cannula body for engagement therewith. Such an alignment feature may for example be a recess such as that indicated by item 10209, 10309 which ensures the manifold body is engageable with the cannula body in a predetermined manner. It will also be appreciated such an alignment feature may, for example, be that similar to the arrangement shown by FIG. 56A in which an open cavity is shaped such that manifold body may only be engageable once a user aligns the two components together (i.e. the open cavity may a non-symmetric shape). The alignment feature may also include one or more guides to facilitate the ease of installation or engagement of the manifold body therewith.

The alignment feature may be a region or regions of associated male and female parts or region or regions of associated surface relief.

In other embodiment, the alignment feature may be adapted to provide for an audible response to indicate to a user once a successful engagement of the manifold with the cannula body has been made. Optionally, such an audible response may be made once the first or second operational position of the manifold with the open cavity is made. For example a click or snap-fit of the manifold and open cavity together in forming their operational engagement may provide such feedback to a user. Such an audible response may be achieved by the successful mating respective surfaces of the manifold body and the open cavity.

In further embodiments, such a connecting portion, such as that for connecting the first and second ends to each other, can extend through an internal region of the open cavity. In this respect, in-situ, the first end of such a manifold body is adapted to engage with one end of the open cavity for delivery gases into the open cavity, and the second end of the manifold body is adapted to form a seal or connection with the other end or any remaining portion of the open cavity requiring sealing to enable the delivery of gases to the open cavity.

The connecting portion which can extend through the internal region of the open cavity is shaped or configured to engage with, or be received by, an associated surface or region of the cannula body or an associated surface or region of the cannula body defining the open cavity.

In a further embodiment, a connecting portion of the manifold body connecting the first and second ends to each other can extend about an external surface or exterior region of the cannula body that defines at least in part the open cavity. In this configuration, in-situ, the first end of the manifold body is also adapted to engage with one end of the open cavity for delivery gases into the open cavity, and the second end of the manifold body is also adapted to form a seal or connection with the other end or any remaining portion of the open cavity requiring sealing to enable the delivery of gases to the open cavity.

The connecting portion which can extend about the external surface or exterior region of the cannula body is shaped or configured to engage with, or be received by, an associated surface or region of the cannula body or an associated surface or region of the cannula body defining the open cavity.

A gas supply conduit can be positioned or located substantially about a side or region of the cannula body from which the first end of the manifold body is positioned or projects from the cannula body. To assist with such a configuration, the manifold can be oriented or is orientable with respect to the cannula body, such that a gas supply tube, in-use, is substantially positioned or located to one side of a user (e.g. does not cross the sagittal plane, and is advantageously positioned to extend primarily to one side of the sagittal plane).

The first operational position can allow for the first end of the manifold body to be located to either a left-end or a right-end of the cannula body defining the open cavity, whilst the second operational position can allow for the first end of the manifold body to be located to either a respective right-end or a respective left-end of the cannula body defining the open cavity (e.g. the left-end and right-end being on different sides of the sagittal plane).

The first operational position or the second operational position enable for a connection of a gases supply conduit to the first end of the manifold body from either a left or a right side.

The cannula body can further comprise side arms or side arm portions which extend away from the cannula body defining the open cavity, in-use, each of the side arms or side portions being adapted to extend at least in part along a portion of a user's face.

The nasal cannula as defined above can comprise a first section formed from a first material and a second section formed from a second material, wherein the first section is relatively softer than the second section. Optionally, the embodiments described herein in relation to a first section being formed of a first material and a second section being formed of a second material are reiterated here in relation to construction or configuration of a nasal cannula.

It will be appreciated a terminal end or outer peripheral region of the side arms are adapted to accept connection thereto with a headgear. Optionally the headgear to be associated with such a nasal cannula may be any of the headgear as described herein and are reiterated here.

Figure 69:
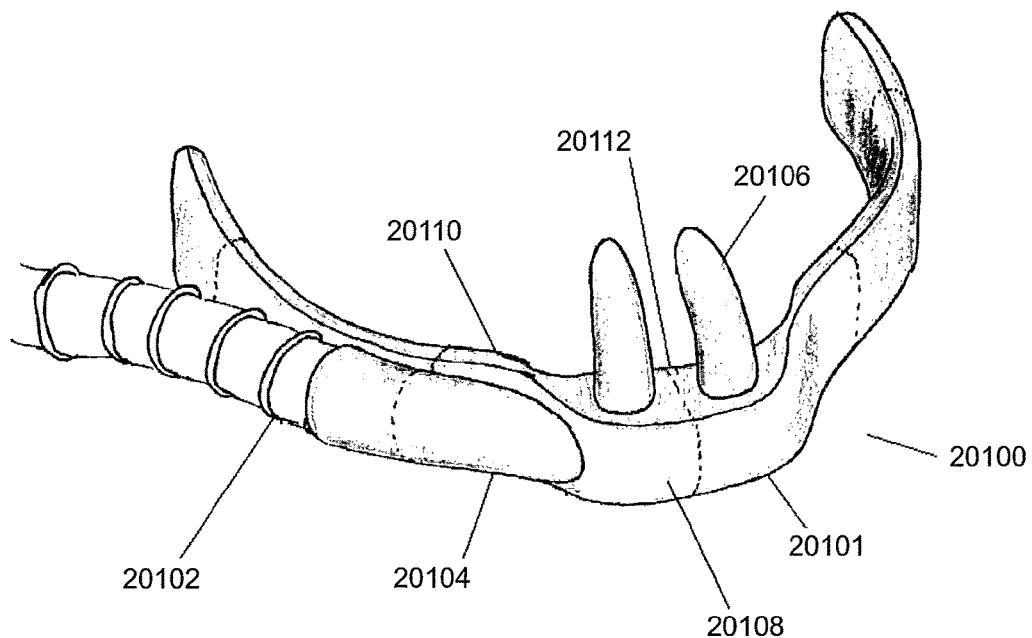
FIG. 69 is a perspective view of a sectioned nasal cannula system that is arranged and configured in accordance with certain features, aspects, and advantages of the present disclosure.

Referring now to FIGS. 69-73, with reference to FIG. 69, a configuration for a nasal cannula system 20100 is shown. In the illustrated configuration, the nasal cannula system 20100 comprises a gases supply tubing 20102 that enters the nasal cannula main body 20101 on one side of the main body 20101 through a connecting sheath 20104 that is connected with the main body 20101. In some configurations, the connecting sheath 20104 may be integrally formed with the main body 20101 or may be removable from the main body 20101. In some configurations, the gases supply tubing 20102 may be integrally formed with the connecting sheath 20104 or may be removable from the connecting sheath 20104. In some configurations, the connecting sheath 20104 is not present, and the gases supply tubing 20102 can interface directly with the main body 20101. The nasal cannula main body 20101 comprises one or more prongs 20106 that may be inserted into one or both nares of a patient. The nasal cannula system 20100 may also have headgear attachment means (not shown) attached to the gases supply tubing 20102, connecting sheath 20104, and/or main body 20101 that may connect to headgear straps and/or other elements that may be placed on and/or around the patient's head in such a way that the main body 20101 may be supported on the patient's face so that the one or more prongs 20106 may be placed into one or both of the nares of the patient. In some configurations, the headgear attachment means need not be present, and the straps and/or other elements may interface directly with the gases supply tubing 20102, connecting sheath 20104, and/or main body 20101. In some configurations, the main body 20101 can be secured to the face of a patient by using, for example, adhesive pads.

In the illustrated configuration, in use, the nasal cannula main body 20101 may rest on or around the upper lip of a patient. Flow generated by a blower or other flow generator means (not shown) may pass through the gases supply tubing 20102 and the connecting sheath 20104 and into the nasal cannula main body 20101, where it moves through the one or more prongs 20106 and into the nares of a patient.

In the illustrated configuration, the nasal cannula main body 20101 comprises a relatively soft section 20110 and a relatively hard section 108. Here, 'relatively soft section 20110' and 'relatively hard section 20108' refer to softness or hardness of a section relative to the other section, e.g.

section 20110 is softer than section 20108. The term 'soft' may be understood to mean 'flexible' and the term 'hard' may be understood to mean 'rigid.' In a preferred configuration, the relatively soft section 20110 is at least soft enough to reduce or eliminate the occurrence of pressure sores on the face of the patient that can happen as a result of cannula use. The relatively soft section 20110 may be on the side of the main body 20101 that contacts the face of the patient in use, while the relatively hard section 20108 may be on the side of the main body 20101 that does not contact the face of the patient in use. Advantageously, the relatively soft section 20110, when pressed against the face, may exert a pressure on the face that is low enough to prevent discomfort and/or pressure sores, while the relatively hard section, when used with the headgear or other head attachment means as described above, may exert force upon the face sufficient to keep the main body 20101 and prongs 20106 properly positioned upon the face. The soft section 20110 may preferably, but not necessarily, be relatively thick on around the middle and around the prongs 20106 to provide a cushion 20112 that may press against the upper lip in use, to provide the patient with additional comfort in what may be an especially sensitive area of the face.

There are no particular limitations to the materials used for the relatively soft section 20110 or the relatively hard section 20108. In some configurations, the soft section 20110 and the hard section 20108 may be made of different grades of the same plastic. In some configurations, the soft section 20110 and the hard section 20108 may be made of the same grade of the same plastic, but may be of different thicknesses. In some configurations, the soft section 20110 and the hard section 20108 may be made of the same plastic, but may be made of different grades of the plastic and have different thicknesses. In some configurations, the soft section 20110 and the hard section 20108 may be made from two different kinds of plastic. In some configurations, the soft section 20110 and the hard section 20108 may be made from different kinds of materials not limited to just plastics, such as metal-plastic composite materials or plastics doped with fillers. In a preferred configuration, the soft section 20110 is made from a silicone polymer or a silicone-based resin, and the hard section 20108 is made from an ABS (Acrylonitrile-butadiene-styrene) polymer or an ABS-based resin.

There are no particular limitations to the method by which the relatively soft section 20110 and the relatively hard section 20108 are assembled together. In some configurations, the sections may be assembled by overmoulding one section onto another. In some configurations, the sections may be assembled by gluing one section to another with an adhesive. In some configurations, the sections may be assembled through the use of ultrasonic welding. In some configurations, the sections may be assembled through use of one or more mechanical fastening elements. The mechanical fastening elements may be integrally formed with the sections of the cannula main body 20101, or may be separate from the sections of the cannula main body 20101.

Figure 70:
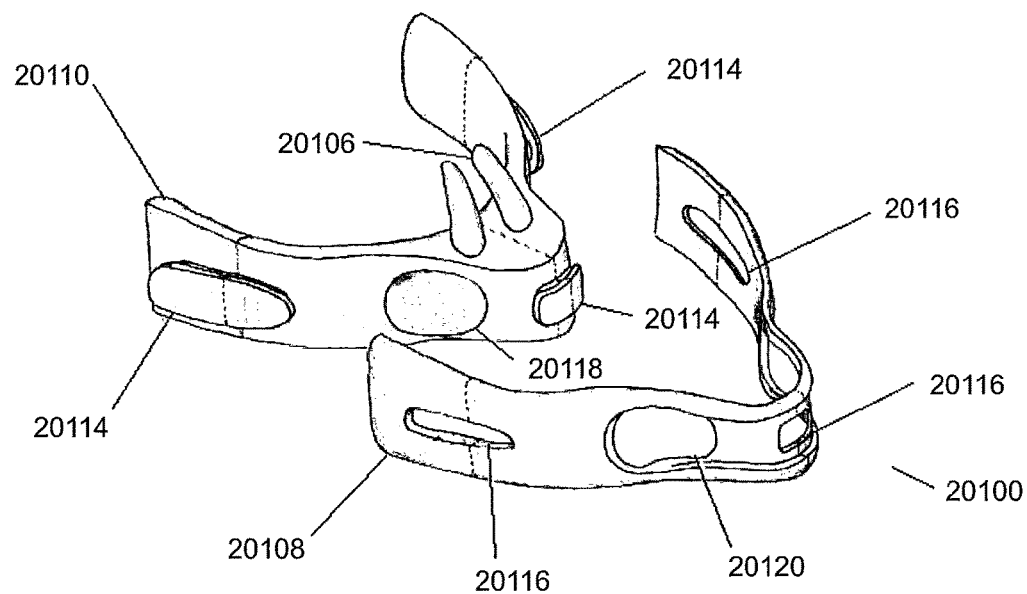
FIG. 70 is an exploded view of a sectioned nasal cannula in which the sections are configured to be mechanically fastened to one another.
Figure 71:
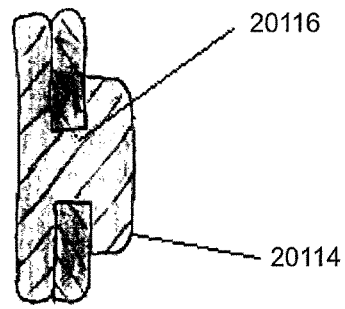
FIG. 71 is a magnified view of the mechanical fastening means of FIG. 70 in use.

A configuration involving a nasal cannula main body 20101 where the sections 20110, 20108 may be assembled through the use of mechanical fastening elements is illustrated in FIG. 70. In the illustrated configuration, relatively soft section 20110 comprises pliable raised tabs or 'mushroom heads' 20114 integrally formed on soft section 20110 and a cavity 20118 extending partially or fully through the body of the soft section 20110 that can accept a gases supply tubing 20102. In use, tabs 20114 can be pushed through orifices (or apertures) 20116 on the hard section 20108 where the tabs 20114 can help to secure a firm fit between sections 20110, 20108. As shown in FIG. 71, in the illustrated configuration, tabs 20114 are at least slightly larger than orifices 20116 so that when forced through the orifices 20116, the tabs 20114 may ensure a secure fit between sections 20110, 20108. Gases supply tubing 20102 may then be placed in cavity 20118 through hole 20120 at one side of the cannula main body 20101 if the cavity extends partially through the body of soft section 20110 or at both sides of the cannula main body 20101 if the cavity extends fully through the body of soft section 20110. In some configurations, the gases supply tubing 20102 manifold may be arranged so that, if the cavity extends fully through the body of soft section 20110, the tubing 20102 may enter the soft section 20110 on one end of the cavity 118 and block the other end of the cavity 20118. Advantageously, the cannula main body 20101 in the illustrated configuration is easy to assemble and the sections may be removable and/or interchangeable, which may, for example, facilitate the use of sectional upgrades and/or replacement of contaminated sections with clean sections.

Figure 72:
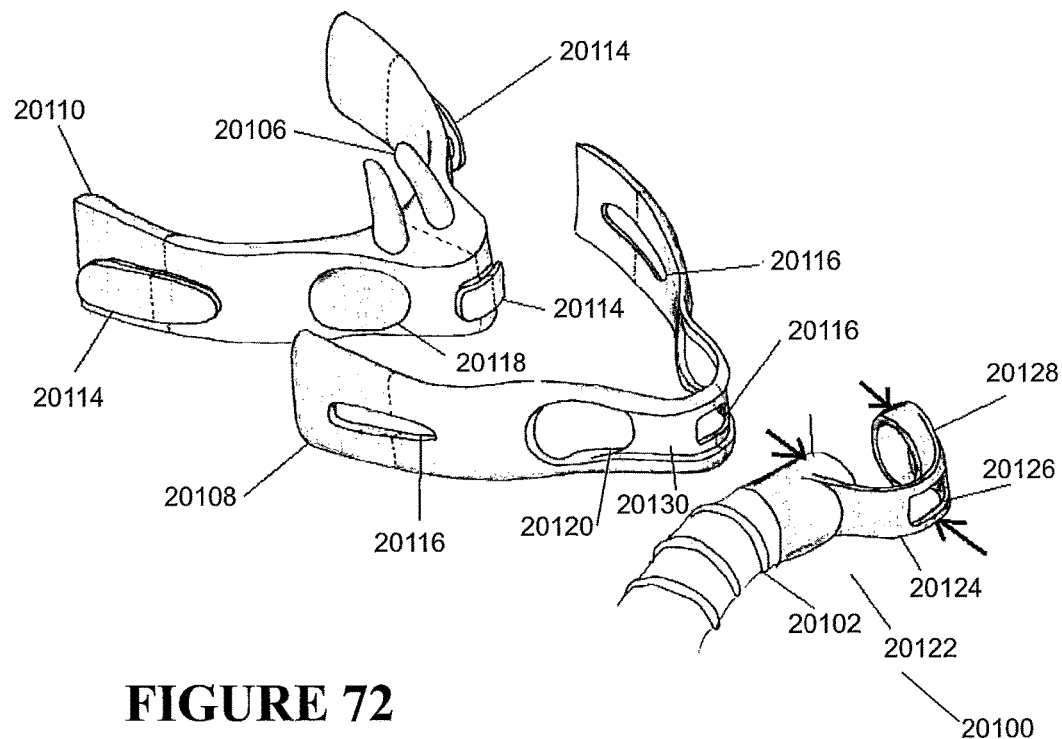
FIG. 72 is similar to the exploded view shown in FIG. 70, but includes a clip-on gases flow supply tube.
Figure 73:
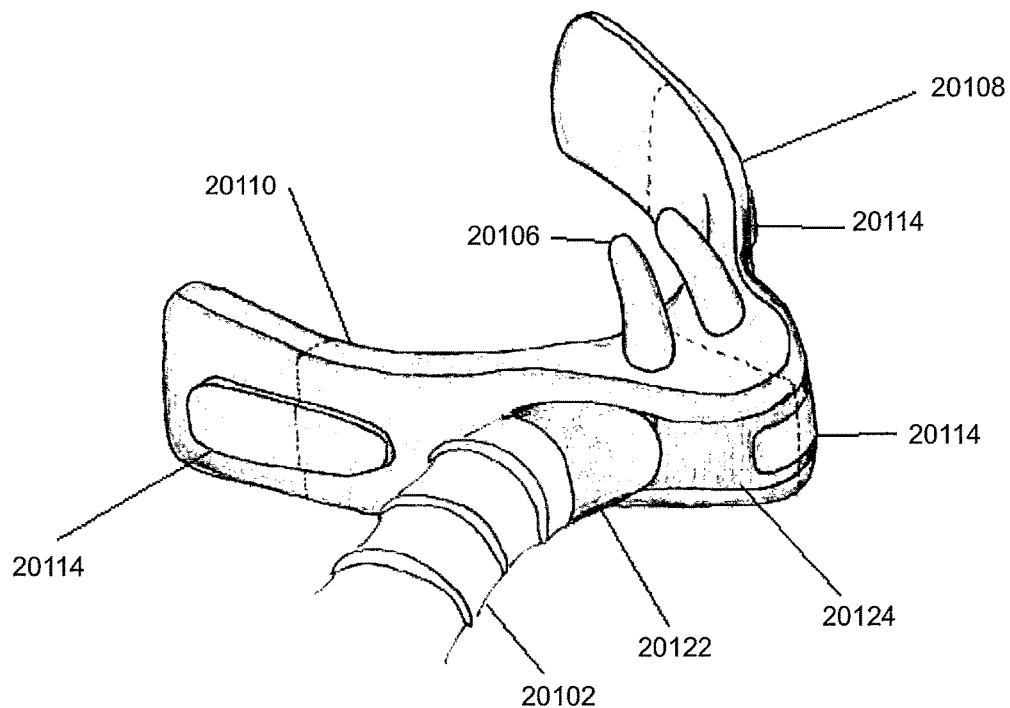
FIG. 73 is a perspective view of a sectioned nasal cannula system similar to that of FIG. 72, except the cannula system has been assembled from the exploded components.

In some configurations, as can be seen in FIG. 72, the gases supply tubing 20102 may be attached to the cannula main body 20101 through use of a clip-on attachment 20122. Preferably in such configurations, the cavity 20118 extends fully through the soft section 20110. The clip-on attachment 20122 preferably comprises a gases exit end 20123, a bridge 20124, a slot 20126 and an end cap 20128 which is not open to gas flow. In a preferred configuration, the hard section 20108 may also comprise a recess 20130. In use, and as can be seen in FIG. 73, similar to the cannula system described above, the soft section 20110 may fit onto the hard section 20108 through the use of tabs 20114 and orifices 20116. The clip-on attachment 20122 of the gases supply tubing 20102 may then be attached to hard section 20108 by flexing at the bridge 20124 by, for example, the application of force on the attachment 20122 at end 20123, bridge 20124 and cap 20128 as indicated by the arrows in FIG. 72, and fitting end 20123 and cap 20128 into both sides of the cavity 20118 through holes 20120, while simultaneously fitting bridge 20124 into recess 20130 and tab 20114 into slot 20126. In such a manner, a firm fit and a sealed gas pathway may be established between the sections of the cannula main body 20101 and the clip-on attachment 20122. Advantageously, in some configurations, the clip-on manifold may be attached in two different ways so that the patient may choose the side from which the cannula may receive gas flow.

In the above configuration, there may be many possible variations in the cannula system 20100 shown. For example, although in the illustrated configuration, there are three tabs or 'mushroom heads' 20114 on soft section 20110 and likewise three orifices 20116 on hard section 20108, any number of tabs 20114 and orifices 20116 may be used. In some configurations, the tabs may be on hard section 20108 and the orifices 20116 may be on soft section 20110. In some configurations, recess 20130 on the hard section 20108 is not present. In some configurations, the slot 20126 on the clip-on attachment 20122 is not present. In some configurations, the bridge 20124 may be a hinge. The illustrated configuration should not be seen as limiting the scope or spirit of the disclosure.

In the illustrated configurations, the nasal cannula main body 20101 comprises 2 sections. However, it should be understand that the cannula main body 20101 may comprise 3 or more sections and still exhibit certain features, aspects and advantages of the present disclosure as long as a relatively soft section has been placed near the face and a relatively hard section has been placed away from the face. Thus, it should be understood that the disclosure may support a nasal cannula main body 20101 that may comprise 2 or more sections.

As noted above, the first section formed of a first material and the second section formed of a second material can be assembled to each other through the use of one or more fasteners or other connection or engaging systems. For example, mechanical fasteners, or for example one or more chemical fastening systems. Further examples include, but are not limited to those such as: adhesive or plastic welding or ultrasonic welding of first and second sections, or portions thereof, together, or overmoulding, or magnetic connections, or sewn connections or snap-fit type arrangements or connections, or there may be sleeved arrangements, for example the second section may be sleeved, partially or wholly, by the first section of first material. combinations of any one or more of these.

As discussed above, the first section is advantageously a user-contacting surface or material and therefore may beneficially be of a user-friendly or comfortable shape or material selection.

The second section may advantageously be provided as a structural or support or shape-defining, component part, of a nasal cannula. In particular embodiments, the second section may be non-contacting of a user.

The configuration or shape of the first section is at least in part defined by parts or portions of the second section. Such a configuration can be enabled by the use of a relatively softer material for the first section, such that joining or attaching or connecting or otherwise assembling the first section with the second section allows for the second section to substantially define the shape taken up by the first section.

In particular embodiments, the first section forms a patient contacting surface, and the second section forms a frame (e.g. a skeleton) upon which the first section is to be assembled or attached The first section may optionally encapsulate at least a part (or an entirety) of the second section. Alternatively, the second section may be, at least in part, over-moulded by the first section.

The first section may define at least an arm or a pair of arms extending outwards from a central body portion. Optionally, the central body portion may comprise at least one (or preferably a pair of) nasal prong(s). The second section may provide for a support or frame to which the first section with the arm or pair of arms is assembled or attached.

It will be appreciated a headgear can be connectable to one or each arm, the headgear extending substantially about a rear part of a user's head. Headgear to be utilised may, for example, be any of the headgear as described in this specification.

The first section is adapted to receive a manifold connection for delivery of a source of gases to the nasal cannula or a body of the nasal cannula in fluid communication with a delivery system for delivery of gases to the user, such as via at least one nasal prong (or preferably a pair of nasal prongs) to, in-use, the nare or nares of the user.

The second section can be adapted to receive a manifold connection, such as for delivery of a source of gases to the nasal cannula or a body of the nasal cannula in fluid communication with a delivery system for delivery of gases to the user. Such a nasal cannula or body may include at least one nasal prong (or preferably a pair of nasal prongs).

A manifold may be a component of a relatively rigid material, relative to the first material, the manifold connectable with an associated region of the nasal cannula or a body of the nasal cannula.

The first section, as described above, may comprise one or more surface relief portions, the surface relief portion(s) of the first section engageable with an associated one or more commensurately or complimentarily shaped or configured surface relief portions of the second section. For example, the first section can include at least one raised region receivable by an associated aperture or detent region of the second section.

As for example shown in FIG. 70, 72, the first section can comprise raised tabs or mushroom-shaped heads 20114 and the second section can comprise associated holes or apertures, such as those of item 20116 receivable of the raised tabs or mushroom-shaped heads.

As shown by at least FIGS. 69-73, the first section can comprise a cannula body portion defining at least in part an open cavity, such as that indicated by item 20118 receivable of a supply of gases directed thereto via a manifold, the open cavity in fluid communication with the nasal prongs, such as items 20106.

The first section and second section can be commensurately or complimentarily shaped or configured to communally receive a manifold connection for delivery of a source of gases to be delivered to a user. For example, FIG. 70 shows the first and second sections which may be assembled together and a respective communally shaped aperture 20118 and 20120 into which the manifold connection can be made.

In certain embodiments, the first section is at least in part a nasal cannula body defining an open cavity, such as that accessible via aperture indicated as item 20118 in FIGS. 70, 72.

It will be appreciated the second section can, at least in part, surround a nasal cannula body defining such an open cavity.

In preferred embodiments, the second section is provided to support the first section in a predetermined configuration. For example, the second section may be shaped so as to be generally indicative of a facial shape upon which the nasal cannula is to be contacting or supported. In this manner, the second section enables for a generally anatomical fit of a nasal cannula for a user. In one further embodiment, the second section may be customised to an individual user's facial shape, such that assembly of the first section to the second section provides for an assembled nasal cannula substantially customised to the individual user.

The second section can extend substantially about the length of a nasal cannula as defined by a first section. Alternatively, the second section can extend to a longer length than the nasal cannula defined by a first section. In a further alternative, the second section extends to a shorter length than the nasal cannula defined by a first section.

A nasal cannula as described herein can include a pair of side arms extending outwardly from a cannula body defining at least in part an open cavity receivable of a source of gases, such as via a manifold connection. In one embodiment, located substantially toward each end of the side arms is a connection system for connecting a headgear, the headgear in-use, to be worn by a user. Such a connection system may be provided or formed by a part of the second section. For example, a part of this second section may project or be exposed for connection thereto.

In a further preferred embodiment, the first section may optionally provide for a seal between a manifold connection or a manifold receivable by at least a part of the first section, such as that defining an open cavity of a cannula body. Such a seal may, for example, be a gasket-type seal (i.e. where the first section provides for a sealing surface extending substantially about the perimeter of a manifold connection being made with the open cavity or a cannula body). In this way, an improved sealing connection may be achieved between a manifold connection part and a first section.

In another embodiment, the second section can provide for a structure to which a manifold connection may be made. In a further alternative, the interection of a manifold connection with the first section may provide for a sealing by the first section about a perimeter portion of the manifold connection being made. It will be further appreciated that in another alternative, a connection, such as a sealed connection, may be made by connection of a manifold with the second section directly.

Where for example the first section is formed of a first material and the second section is formed of a second material, and both materials are the same, it will be appreciated the materials may be the same but may be of a different grade, such as for example the material but where the first material has a different characteristics, such as a Shore Hardness rating compared to that of the second section material.

It will be appreciated in the embodiments above, the nasal cannula can comprise a body defining an open cavity engageable by a manifold, a rear portion of that body being, in-use, substantially adjacent to a user's septum region. Such a rear portion can be substantially compliant or deformable in response to a pressure applied by a user to such a rear portion. In one preferred embodiment, such a rear portion may be a substantially thinned wall section of the body. Alternatively, the rear portion may be defined by a hollow section of the body, with the open cavity being a separate distinct region of the body. In yet a further alternative, the rear portion may define, at least a part, a wall (such as a back wall) of the open cavity. In such an embodiment, the rear portion may be optionally elasticised or be elastically deformable. For example, providing for a comfortable fit or comfortable surface for contacting a user is desirable, as such, soft cushioning or comfortable materials may be selected.

The body defining the open cavity can comprise of a hollowed enclosure substantially adjacent to the user's septum region. Alternatively, the body may comprise of a pillow or pillow-like section substantially adjacent to the user's septum region. For example, the pillow section can be a relatively hollow region, such a hollow region bounded by walls of or which may form the body (or the open cavity), and which can be separate to an open chamber (such as a plenum chamber). Such a pillow section can have a relatively thin wall or elasticised section in the region substantially adjacent to, in use, the user's septum. In this manner, a relatively more comfortable or conformable section of material or of the nasal cannula body can be provided so as to improve comfort or reduce the application of pressure points to a user.

In yet a further alternative, the pillow section may be formed by a rear wall of such an open cavity (or plenum chamber), the rear wall of which may be a relatively thin (or thinner) wall or elasticised section in the region substantially adjacent to, in use, the user's septum.

The pillow section as described above may be formed of suitable materials or other material characteristics which are capable of deforming under application of a pressure by a user during use.

As noted above, in some configurations or embodiments, the nasal cannula interface may comprise a first section and a second section. The first section may comprise a relatively soft material. The second section may comprise a relatively hard material. The first section may, in-use, contact the user's face, and the second section may, in-use, non-contacting of the user's face.

In a further embodiment, the second section, or a portion or portions of the second section, may project so as to provide for connection to a gas supply tube management system, or a tube retainer or clip, or such a management system or retainer or clip may be engageable or connectable to such a second section.

Preferably a nasal cannula as defined above may be utilised in combination with each of the other details described in this specification to provide for a nasal cannula interface.

Various headgear systems or straps according to some embodiments of the present invention are described with reference to FIGS. 58A to 67. A headgear or head strap is attached to a patient interface such as a cannula to hold the patient interface in position on a user's face. Headgear comprises at least one strap that extends about a user's head.

Figure 58A:
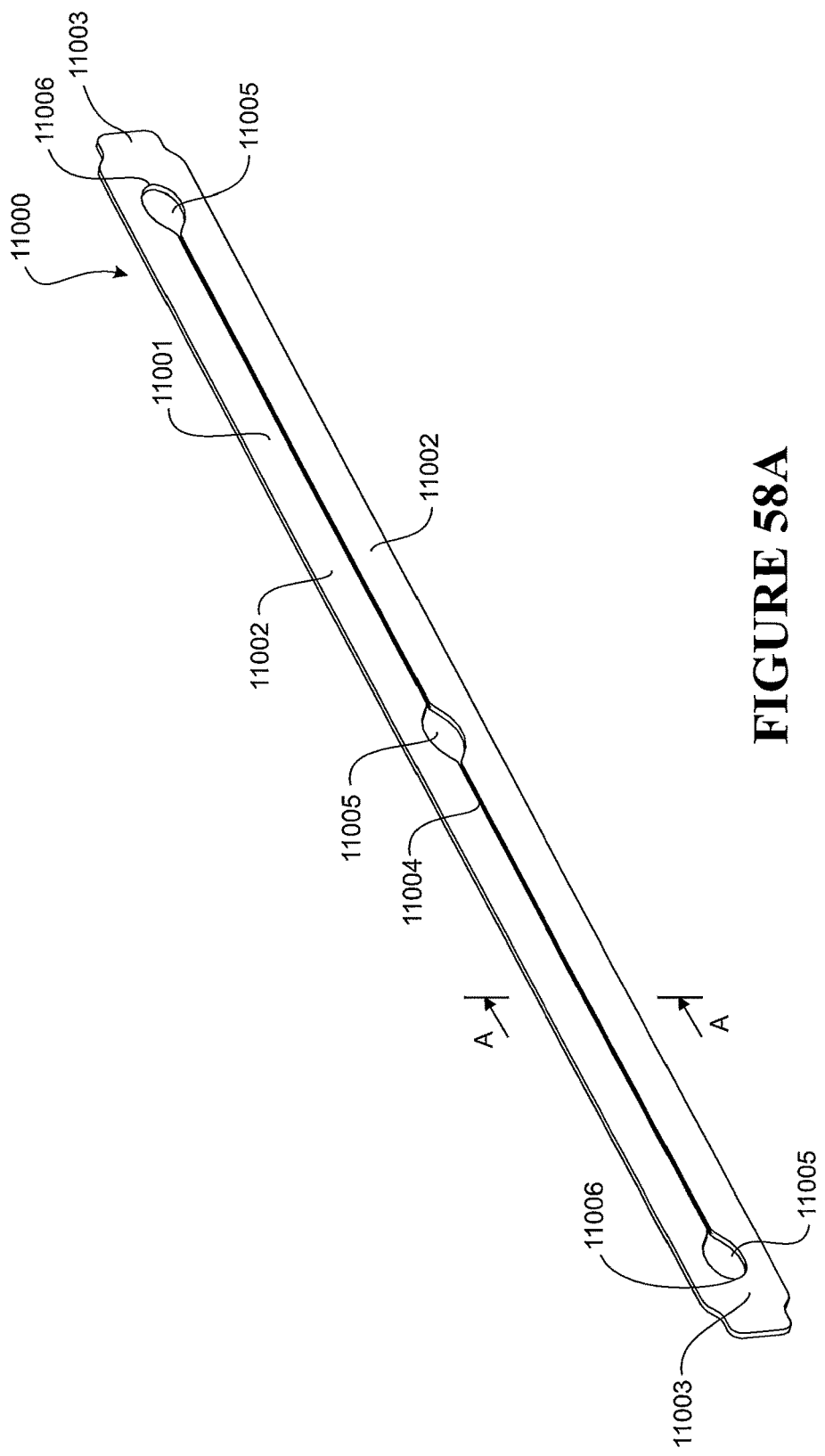
FIG. 58A illustrates a bifurcate-able strap for a headgear comprising a frangible section to bifurcate a portion of the strap into two separate bands.
Figure 58B:
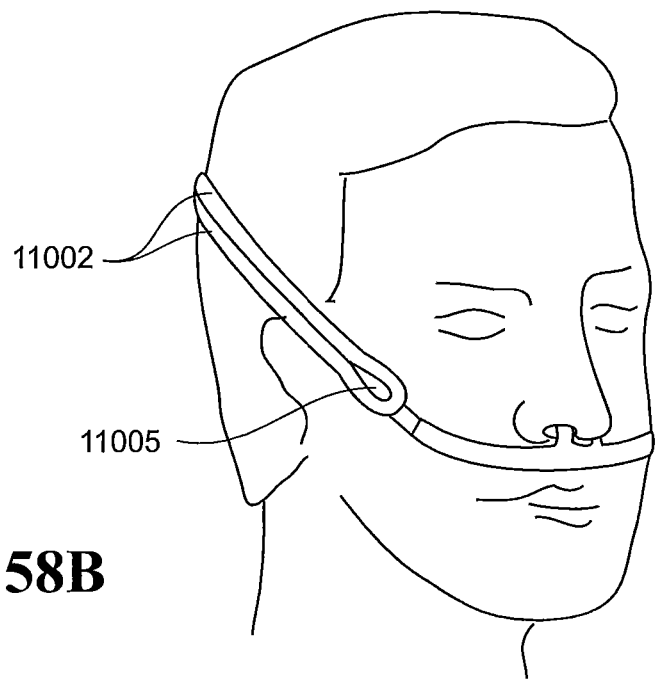
FIG. 58B illustrates a bifurcate-able strap in use in a non-bifurcated configuration.
Figure 58C:
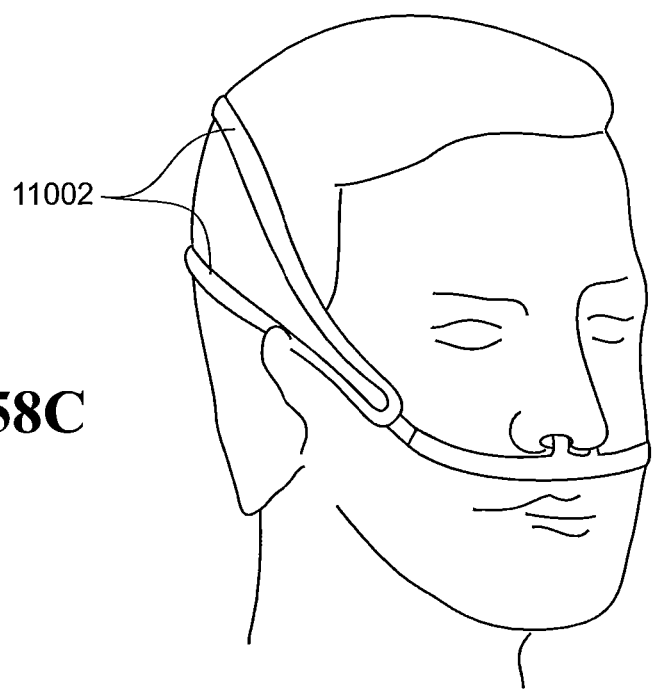
FIG. 58C illustrates a bifurcate-able strap in use in a bifurcated configuration.

With reference to FIGS. 58A to 58F, in some embodiments a head gear strap comprises a portion that is configured to bifurcate into more than one band to extend around the patients head. With reference to FIGS. 58A to 58F, in some embodiments the head gear strap 11000 comprises a portion 11001 that is configured to bifurcate into more than one band 11002. With the strap 11000 in a non-bifurcated or joined configuration the strap is a single band 11000, as illustrated in FIGS. 58A and 58B. Where the bifurcate-able portion 1001 of the strap has been bifurcated into more than one band 11002, the strap provides more than one band to extend about a user's head, as shown in FIG. 58C. When bifurcated, ends of the bands 11002 are joined together at a common or non-bifurcate-able part 11003 of the strap 11000. The non-bifurcate-able parts of the strap are attached to a patient interface in use. For example, ends 11003 of the strap may be attached to a patient interface in use, directly to the interface or via other connecting straps.

In the embodiment illustrated in FIGS. 58A to 58F, the strap 11000 comprises a longitudinal frangible section 11004. In some embodiments the frangible section comprises a relatively thin section 11010 as shown in FIG. 58F to be torn by a user to separate the portion of the strap into more than one band 11002, as shown in FIG. 58D. For example, the strap may be formed from silicone or a silicone like material with a thin portion as shown in FIG. 58F that can be torn by a user. In some embodiments the frangible section may be a perforated section of the strap. The frangible section is a section of the strap that is weaker than the bands 11002 of the strap so that the frangible section may be torn without tearing the bands or other sections of the strap.

Each band extends between the ends of the strap. The bands are separated by the frangible section. In some embodiments, the strap 11000 comprises a finger hole 11005 at the frangible section to assist with separating the bands by tearing the frangible section. For example, in the illustrated embodiment there is a finger hole part way along the frangible section, for example in a centre of the frangible section. In some embodiments there may be a hole at one or both ends of the frangible section. In some embodiments the hole at an end of the frangible section is a tear drop shape with a rounded portion defining an end of the frangible section. The rounded portion 11006 assists with preventing tearing of the strap beyond the frangible section so that only the frangible section tears when separating the bifurcate-able section of the strap into bands. In some embodiments the hole at the end of the frangible section may not be suited for inserting a finger and so may not be used for separating the bands but for preventing tearing of the strap beyond the frangible section. The frangible section may be described as a tear bead.

In some embodiments the frangible strap 11000 is formed from a fabric material and coated on one or both sides with coating layer. In some embodiments the frangible strap 11000 is formed from a foamed fabric material, for example a polyurethane foam, and the coating layer is a polymer, for example a silicone or other flexible polymer, for example Nylon or Spandex or natural alternatives such as latex. With reference to the cross section shown in FIG. 58G, in some embodiments, the frangible section is formed by cutting the fabric 11007 to form the separate bands 11002, and coating the fabric with a coating layer 11008 on at least one side to hold the separate bands together in a single strap with faces of the cut 11009 through the fabric held together or close together. The coating bridging the cut 11009 in the fabric provides the thin section that can be torn by a user to separate the bands apart.

Figure 59:
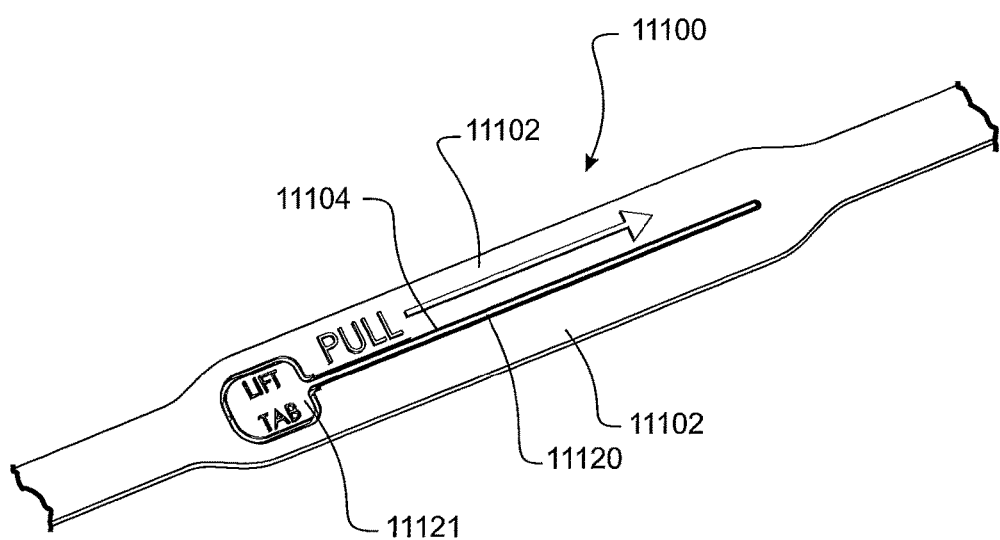
FIG. 59 illustrates a bifurcate-able strap for a headgear comprising a lift out portion defined by a frangible section, for bifurcating a portion of the strap into two separate bands.

In some embodiments, with reference to FIG. 59, the strap 11100 may comprise a lift out or removable portion or tab 11120. The removable section extends the length of the bifurcate-able section and is separated from the bands 11102 of the strap by a frangible section 11104. The frangible section extends around or defines a perimeter of the removable section. The removable section 11120 may comprise a grip tab 11121 at one end for a user to grab to tear the frangible section 11104 to remove the removable section from the strap to separate the bifurcate-able section into separate bands.

In some embodiments the bifurcate-able section of the strap may extend in use to forward of the user's ears. In some embodiments the bifurcate-able section of the strap may extend in use from behind the user's ears.

In the embodiments of FIGS. 58A to 59 the bands 11002 are arranged edge-to-edge when the bands are in a non-bifurcated configuration. In some embodiments, the bands 11002 may be arranged side-by-side when in a non-bifurcated configuration. For example, in the embodiment illustrated in FIG. 62 (described below) the bands 11402 when arranged together in a non-bifurcated configuration are placed one on top of the other (side-by-side).

In an embodiment where the bands are arranged side-by-side when the bands are in a non-bifurcated configuration, the bands may be held together in the non-bifurcated portion by stitching between the bands. The stitching is of a sufficiently low strength so that the stitching may be broken or torn to separate the bands into a bifurcated configuration. In some embodiments the bands are held in a side-by-side configuration by other means, for example a clasp or clasps, buttons, hook and loop fasteners or magnets.

Figure 60A:
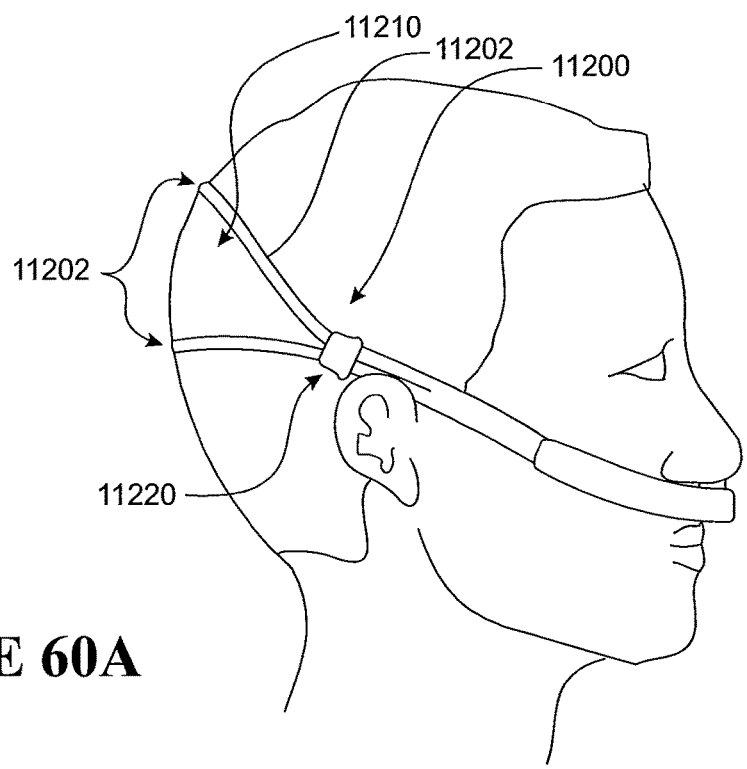
FIGS. 60A and 60B illustrate a bifurcate-able strap for a headgear comprising a clasp slidable along a bifurcate-able section of the strap to configure the bifurcate-able section into a bifurcated or a non-bifurcated configuration.
Figure 60B:
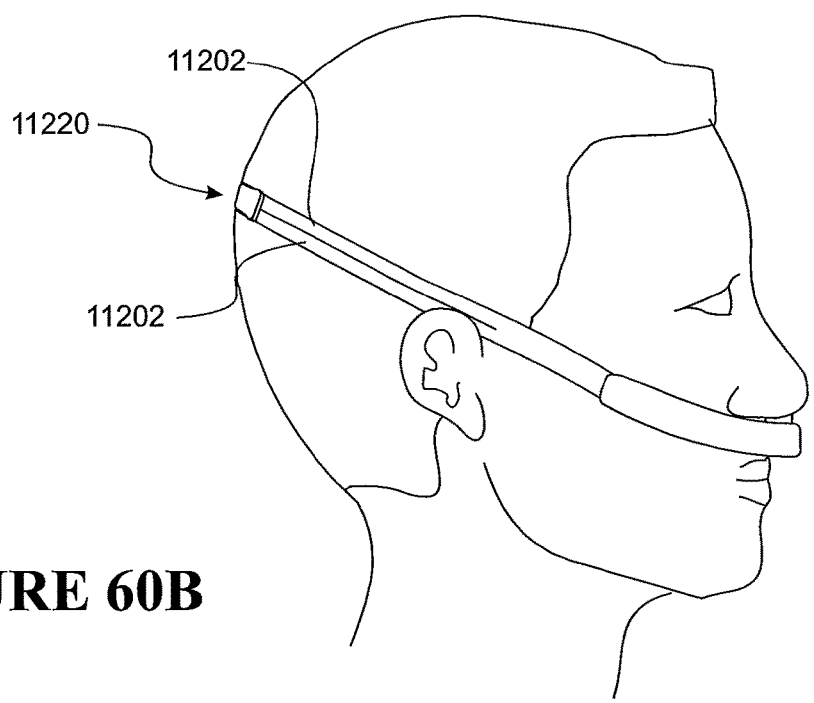

In the embodiments illustrated in FIGS. 58A and 59 the strap is irreversibly bifurcate-able. Once the frangible section is torn, the strap comprises multiple bands. There is no means to rejoin the separate bands into a single strap. In some embodiments, the head gear strap may be reversibly bifurcate-able. For example, as shown in FIGS. 60A and 60B in some embodiments the head gear comprises a strap 11200 and a clasp 11220 that is slidable along at least the bifurcate-able section of the strap. To hold separate bands 11202 together the slidable clasp is moved to or towards a central position of the strap 11200, as shown in FIG. 60B. To allow the separate bands to separate or bifurcate, the slidable clasp is moved towards an end of the bifurcate-able portion of the strap, as illustrated in FIG. 60A. The clasp may be a sleeve that passes around the bands to hold the bands together. In some embodiments the bands may each comprise a feature that interfaces with a corresponding feature on the clasp to bind the bands 11202 together when in a non-bifurcated configuration. For example, the clasp and bands may comprise a zipper where the bands comprises interlocking teeth that are separated or mated by sliding the clasp along the bands from one end of the bifurcate-able section to the other end of the bifurcate-able section. Alternatively one band may comprise a channel extending along the band, the other band comprising a corresponding a projection extending along the band. The clasp is adapted to push the projection into the channel to hold the bands together, or separate the projection from the channel to bifurcate the strap. In some embodiments the head gear comprises a fabric or sheet material or web that extends between the bands. In a non-bifurcated configuration the web is bunched up or folded into a non-expanded configuration. In a bifurcated configuration where the bands 11202 are spaced apart the web 11210 is expanded or unfolded to cover an area between the spaced apart bands, as shown in FIG. 60A.

Figure 61A:
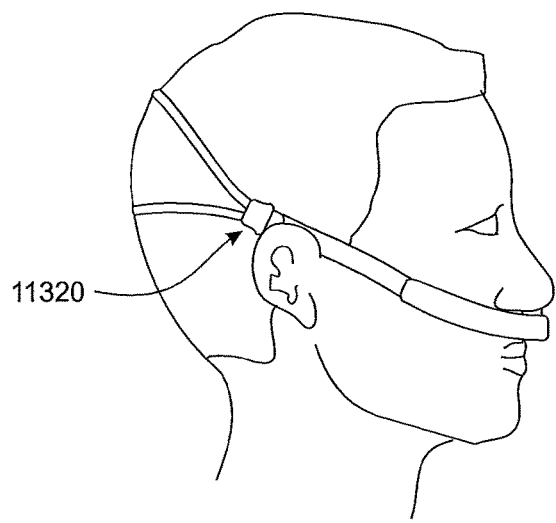
FIGS. 61A to 61C illustrate a bifurcate-able strap for a headgear comprising two clasps slidable along a bifurcate-able section of the strap to configure the bifurcate-able section into a bifurcated or a non-bifurcated configuration.
Figure 61B:
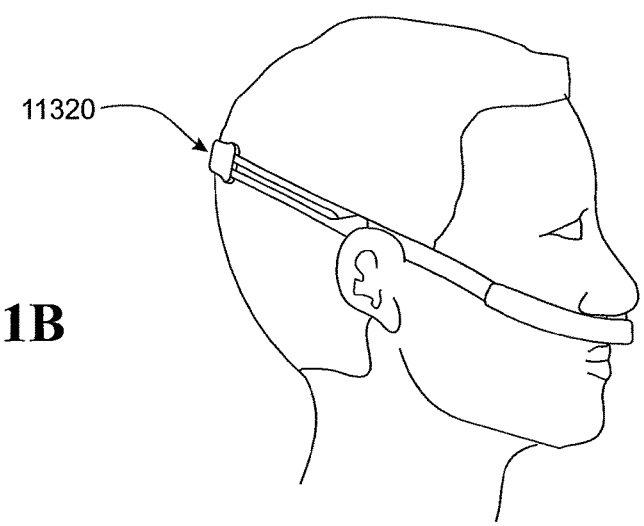
Figure 61C:
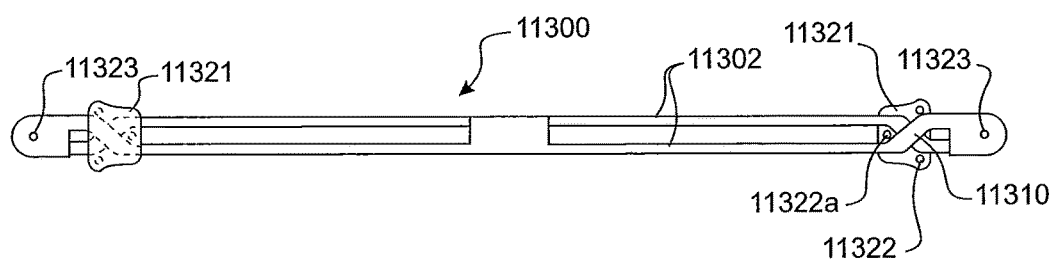

In some embodiments the head gear comprises two clasps as illustrated in FIGS. 61A to 61C. In a non-bifurcated configuration both clasps 11320 are slid towards a central position of the strap to hold the bands together, as illustrated in FIG. 61B. In a bifurcated configuration each clasp is slid to an end of the bands 11302 so that the bands may separate between ends of the bands, as illustrated in FIGS. 61A and 61C.

In some embodiments the clasp comprises two spaced apart flanges 11321 as illustrated in FIG. 61C. In FIG. 61C, the clasp 11320 at the right hand end of the strap is drawn with one flange 11321 omitted to illustrate three posts or pins 11322 extending between the spaced apart flanges 11321. The pins are shown in hidden detail at the clasp at the left hand end of the strap 11300 as drawn. The bands 11302 extend between the flanges 11321. One pin 11322a is positioned between the bands 11302 and the other two pins are positioned on outer edges of the bands. Ends of the bands may be pivotally coupled together at pivot joints 11323. One or each band 11302 may comprise a central tab or stop to limit the amount of travel of the clasps along the bands 11302.

In some embodiments the each clasp and the bands are complementary adapted so that moving each clasp to an end of the bands forces the bands apart to separate the bands into a bifurcated configuration. For example, as shown in FIG. 61C, each clasp comprises two spaced apart flanges and three pins extending between the spaced apart flanges. The bands comprises a cross over portion 11310 near ends of the bands so that when the clasps are moved to the ends of the bands the centre pin pushes the bands apart to separate the bands into the bifurcated configuration.

Figure 62:
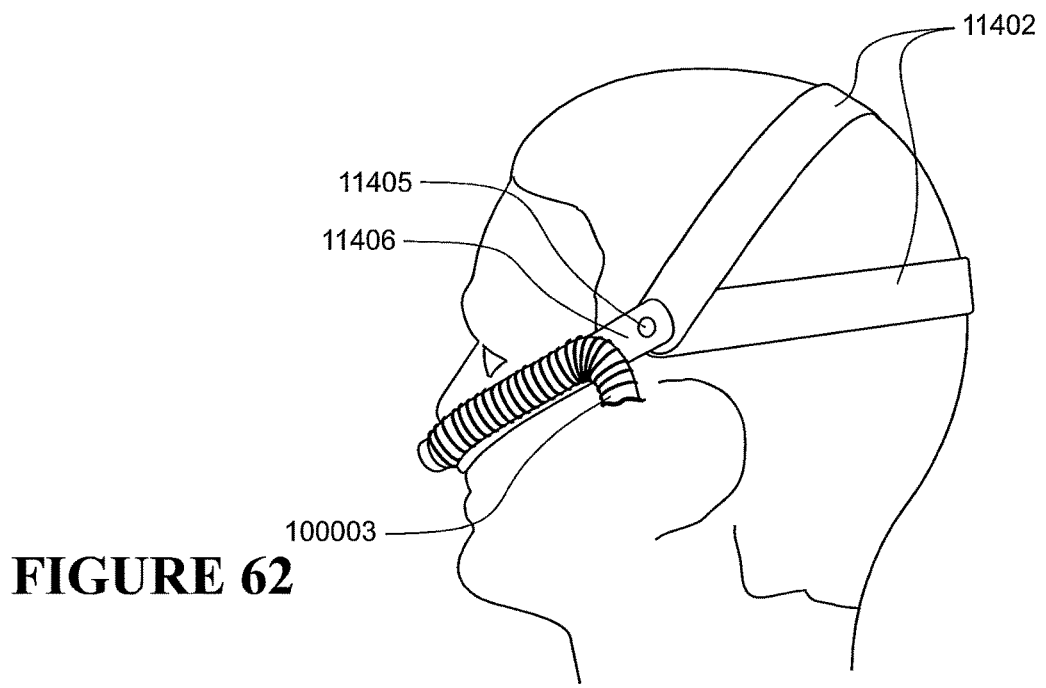
FIG. 62 illustrates a bifurcate-able strap wherein ends of separate bands of the strap are pivotally coupled.

In some embodiments the bifurcate-able strap comprises bands pivotally coupled together at the ends of the bands. For example, as shown in FIG. 62, the headgear comprises bands 11402 pivotally coupled together at the ends of the bands at pivot joint 11405. In a non-bifurcated configuration one band 11402 lies over the top of the other band. Also pivotally coupled to the ends of the bands is a common strap 11406 extending between the ends of the bands 11402 and the patient interface. A gas conduit may be attached or supported by the strap 11406. In some embodiments the pivot points 11406 are forward of a user's ears in use.

Figure 63:
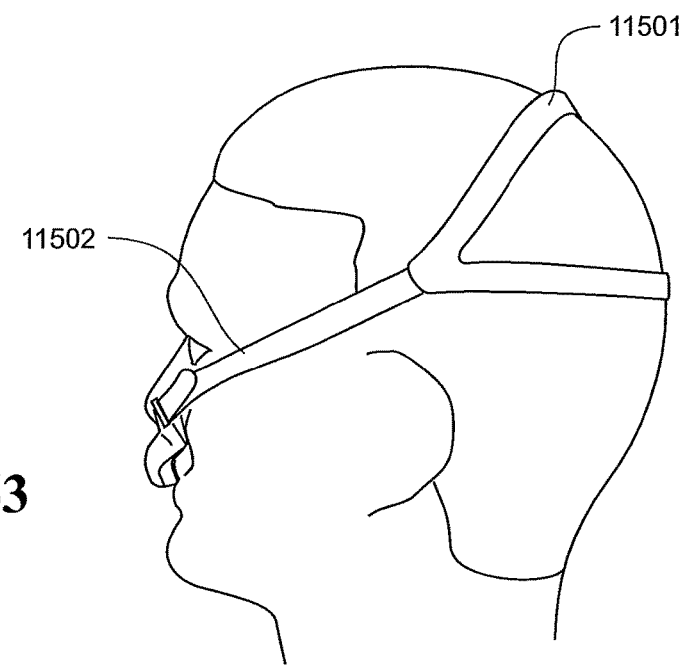
FIG. 63 illustrates a headgear strap comprising a stretchable and a non-stretchable portion. The non-stretchable portion is bifurcated into two separate bands.

In some embodiments a head gear for a patient interface comprises a strap having a non-stretchable section and a stretchable section. The stretchable section may be described as being elasticised or elasticated. The stretchable section may be formed from a rubber or silicone or silicone like material or comprise such a material. In some embodiments, the head gear strap comprises a non-stretchable section to be positioned towards the back of a user's head, and a stretchable section extending between each end of the non-stretchable section and a patient interface. As illustrated in FIG. 63, in some embodiments the non-stretchable section 11501 is bifurcated. Section 11501 may be bifurcate-able from a single non-bifurcated strap as described earlier. A stretchable portion 11502 extends between each end of non-stretch portion 11501 and the patient interface.

Figure 68:
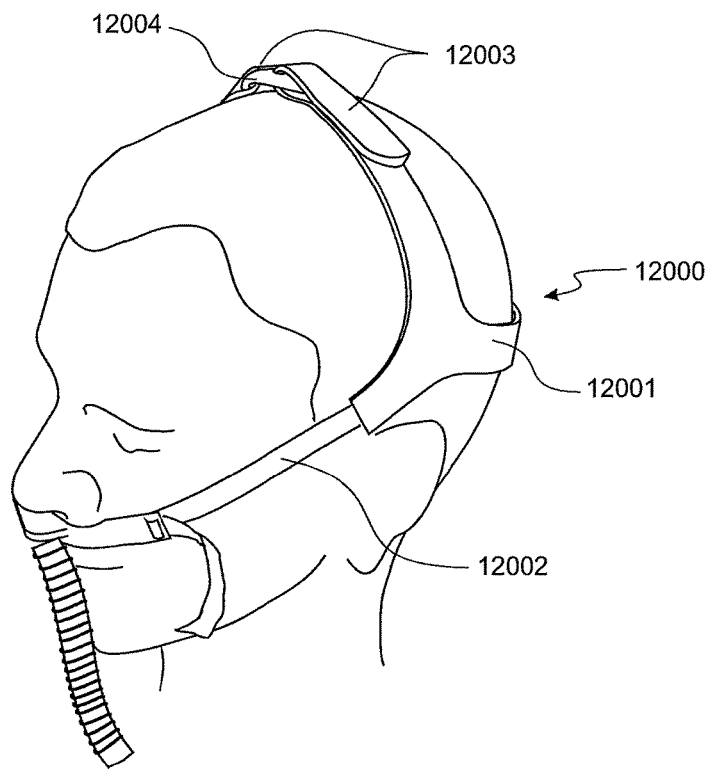
FIG. 68 illustrates a head gear strap comprising a bifurcated portion wherein at least one band of the bifurcated portion is adjustable in length.

In some embodiments, at least one of the bands of the bifurcated section is adjustable in length. For example, as illustrated in FIG. 68, the non-stretchable section is bifurcated comprising two bands 12001 and is intermediate between two stretchable portions 12002. In the example embodiment, the upper one of the two bands 12001 is adjustable in length. For example, the upper band comprises two portions joined by a buckle, for example the two portions 12003 each loop through the buckle and are secured by hook and loop fasteners.

Figure 64:
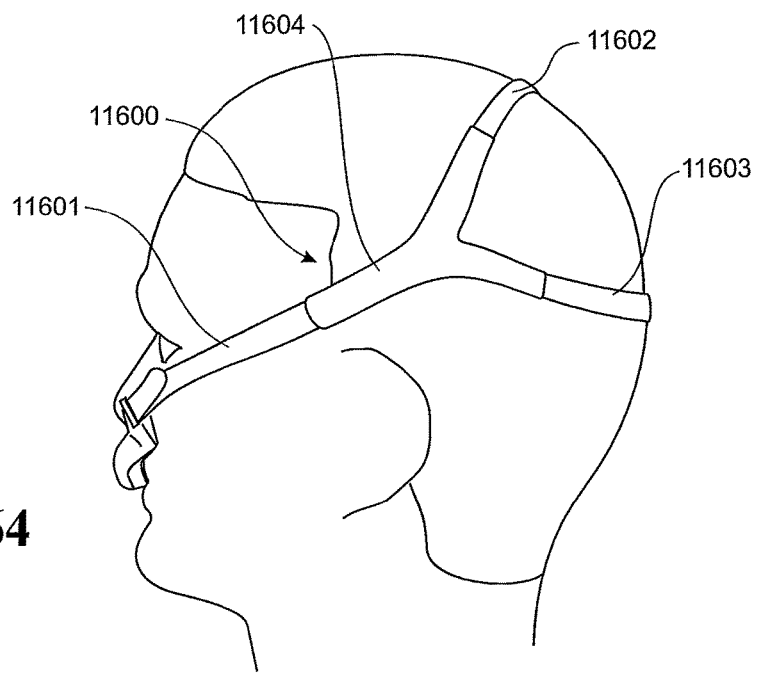
FIG. 64 illustrates a headgear strap comprising a bifurcated portion wherein at least one band of the bifurcated portion is stretchable and ends of the bifurcated bands are joined by a non-stretchable Y connector.

In some embodiments the head gear comprises a bifurcated portion wherein at least one band of the bifurcated portion is stretchable and ends of the bifurcated bands are joined by a non-stretchable Y connector. For example, as illustrated in FIG. 64, in the head gear comprises a bifurcated portion comprising two bands 11602, 11603. Band 11602 is formed of a stretchable material. The bands 11602 and 11603 are joined at both ends by non-stretchable Y connector or Y piece 11604. A portion 11601 of the head gear strap 11600 extending between each Y connector 11604 and the patient interface on each side of the patient interface is stretchable. In some embodiments the bottom band 11603 is non-stretchable. In some embodiments non-stretchable strap 11603 has length adjustment, for example the head gear may comprise a buckle between one end of the band 11603 and a Y connector.

Figure 65:
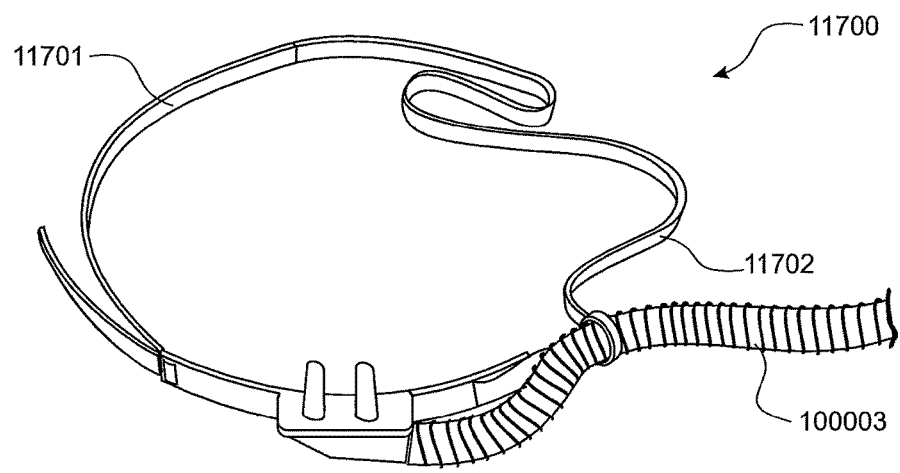
FIG. 65 illustrates a head gear strap comprising a stretchable portion and a non-stretchable portion. The non-stretchable portion supports a gases supply conduit.

In some embodiments the head gear strap comprises a non-stretchable section and a stretchable section, wherein the non-stretchable section is adapted to be attached to the patient interface and support a gases supply conduit coupled to the patient interface. For example, as shown in FIG. 65, the head gear strap 11700 comprises a stretchable portion 11701 and a non-stretchable portion 11702. The stretchable portion 11701 attaches to one side of the patient interface, and the non-stretchable portion attaches to the other side of the patient interface. A gas conduit attached to the patient interface extends from the patient interface on the same side of the interface as the non-stretchable portion of the strap. The non-stretchable portion supports the gases supply conduit 100003. For example the conduit is clipped or coupled to the non-stretchable strap. The weight of the conduit is taken by the strap 11702 so that the weight is not transferred to the patient interface, for example a nasal cannula.

Figure 66:
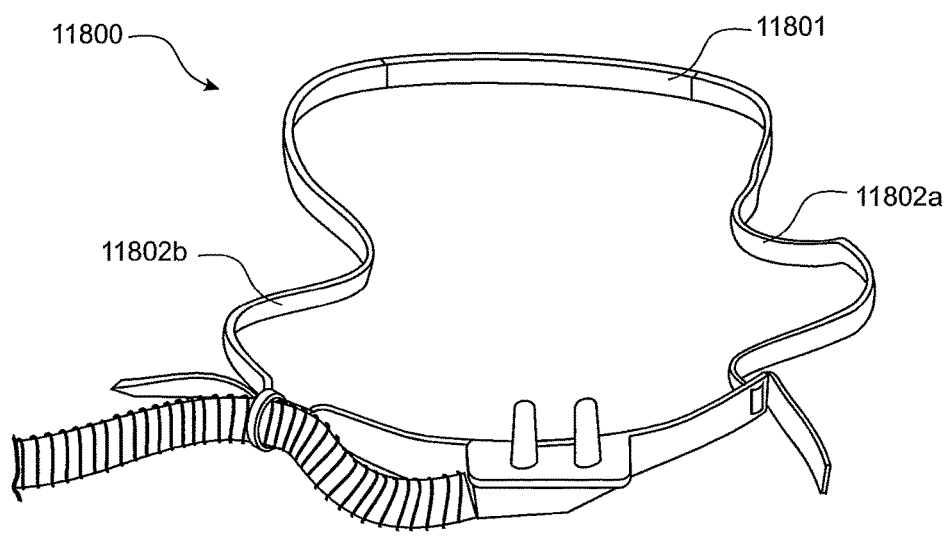
FIG. 66 illustrates a head gear strap comprising a first non-stretchable section attached to one side of a patient interface and a second non-stretchable section attached to an opposite side of the patient interface, and a stretchable intermediate section extending between the first and second non-stretchable sections.

With reference to FIG. 66, in some embodiments the head gear strap 11800 comprises a first non-stretchable section 11802a adapted to be attached to one side of a patient interface and a second non-stretchable section 11802b adapted to be attached to an opposite side of the patient interface, and a stretchable intermediate section 11801 extending between the first and second non-stretchable sections. The conduit 100003 may be routed to extend from either side of the patient interface, and attached or coupled to either the first or second non-stretchable portions of the strap 11800. For example a stretchable or non-stretchable lanyard may hang from the non stretchable strap 11802a or 11802b for supporting the conduit from the non stretchable strap. The non-stretchable portion 11802a or 11802b supports the gases supply conduit 100003. The weight of the conduit is taken by the strap 11802a or 11802b so that the weight is not transferred to the patient interface, for example a nasal cannula. The stretchable strap may be bonded or otherwise fixed to ends of the non-stretchable straps, or releasably attached, for example by a buckle or clip. One or both of the non-stretchable straps may be length adjustable, by for example an adjustable attachment to the patient interface.

Figure 67:
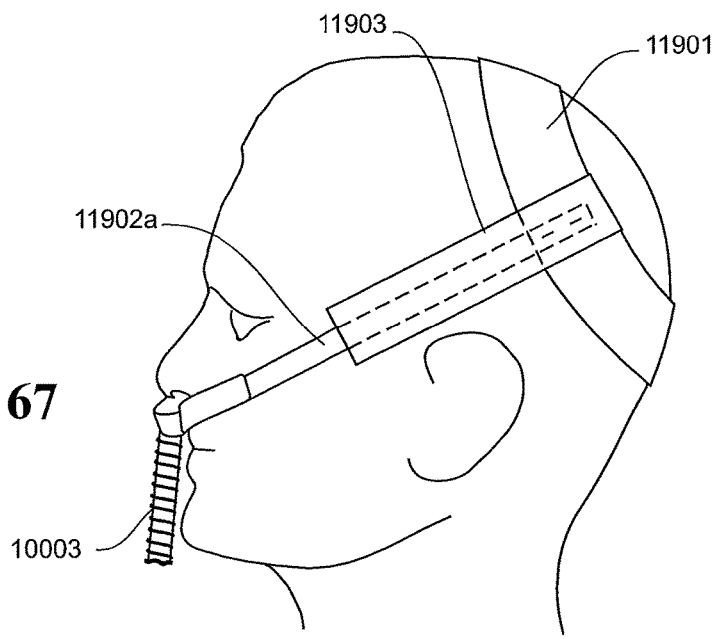
FIG. 67 illustrates a head gear strap comprising a first stretchable section attached to one side of a patient interface and a second non-stretchable section attached to an opposite side of the patient interface, and a non-stretchable annular intermediate section extending between the first and second non-stretchable sections.

With reference to FIG. 66, in some embodiments the first and second sections 11802a and 11802b are stretchable and the intermediate portion 11801 of the strap 11800 is non-stretchable. An alternative embodiment is illustrated in FIG. 67. With reference to FIG. 67, in some embodiments the head gear strap 11900 comprises a first stretchable section 11902a adapted to be attached to one side of a patient interface and a second non-stretchable section 11902b (obscured from view in the Figure) adapted to be attached to an opposite side of the patient interface. A stretchable intermediate section 11901 extends between the first and second non-stretchable sections. In the illustrated embodiment the intermediate portion 11901 is an annular strap or portion that fits on the back of a user's head. Alternatively the intermediate portion may be a skull cap adapted to fit the back of a user's head. The ends of the stretchable sections 11902a and 11902b are fixed to the intermediate portion. In some embodiments, the head gear comprises a non-stretchable sleeve 11903 extending from the intermediate portion towards the patient interface. Preferably the sleeve on each side of the headgear extends from the intermediate portion to forward of the user's ear. The stretchable portion 11902a extends along an inside of the sleeve. The stretchable portion 11902a is not attached to the sleeve along the length of the sleeve from the intermediate portion 11901. The stretchable portion is therefore free to move independently of the sleeve along the length of the sleeve. Both the sleeve and the stretchable portion of the head gear strap are fixed to the intermediate portion of the strap, which in the illustrated embodiment is the annular strap 11901. In some embodiments the conduit 100003 may be attached to the sleeve on either side of the head gear to support the conduit and prevent weight of the conduit being transferred to the patient interface. For example, a stretchable or non-stretchable band may extend from the sleeve 11903 to hang from the sleeve to be connected to the conduit to take the weight of the conduit.

Headgear can be used to keep a patient interface positioned correctly on the face of the patient. A patient interface as herein described may refer to but is not limited to a nasal cannula, nasal prongs, nasal delivery elements or the like. For a nasal cannula, headgear can be used to maintain the position of the nasal cannula at the face of the patient and to maintain the nasal delivery elements in the nostrils of the patient to ensure effective delivery of the therapy. Headgear may be positioned around the head or neck of a patient.

Nasal cannulas can be used to deliver a flow of gases to a patient and may either seal, semi-seal or not provide a seal at the nostrils of a patient. Nasal high flow (NHF) is typically a non-sealing therapy that delivers relatively high-volume flow to the patient through a patient interface such as a nasal cannula.

Headgear is disclosed that uses sections of stretch and non-stretch materials to better stabilize the nasal delivery elements in the nose (FIG. 1) while maintaining comfort. Stretch regions as herein described refer to at least one region that is made from stretch material with but not limited to the capacity to stretch to at least 300%. A stretch region may have multiple discontinuous stretch sections within a region or it may be a continuous stretch section. Non-stretch regions as herein described refer to at least one region that is made from non-stretch material. Stretch regions may be located sufficiently away from any tube loading regions, preferably at a maximum distance from tube loading regions. In one embodiment, the stretch region may be located at the opposite side of the tube loading region which may transfer the force from any tube loading to non-stretch regions and not directly to the stretch regions.

For example, if the tube exits the cannula from the right side, which makes the tube loading region at the right side of the cannula, stretch regions may be located to the left side of the headgear which may prevent the loading from being directly applied to the at least one stretch region. In this way, the stretch regions may move less or may not experience deformation if any loading is applied to the tube and therefore may not influence the position of the nasal delivery elements in the nose of the patient. The stretch regions may allow for easy fitting and application of the interface to the patient, by stretching the headgear over the head of the patient.

The non-stretch regions may have a high-friction surface on the side which contacts the patient, which may prevent the headgear from excessive rotation or movement if a load is applied and may also prevent gradual movement of the headgear over time. By absorbing the force into the friction, the high-friction surface may enable the majority of the force to be distributed over the non-stretch regions of the strap. Due to non-stretch properties, the non-stretch regions may not distort or stretch upon application of a load at the tube. By locating the stretch regions sufficiently away from the tube loading region a much lower force may be applied to the stretch regions of the strap. By having the high friction surface on the non-stretch regions, less load may be applied to the stretch regions which may help to stabilise the cannula and prevent rotation or displacement of the headgear on the patient in use. The non-stretch regions may still be flexible to contour to the head of the patient. A predetermined shape may give the non-stretch regions preloading. The shape may be but is not limited to a hook shape, but could be a different shape, or there may not be any predetermined shape.

Either the stretch or non-stretch regions may be adjustable to increase patient comfort. Adjustable as herein described refers to altering the size of the regions to better fit a patient. There may be one or more than one adjustable region located on the headgear. At least one adjustable region located at the stretch regions may be located above or near to the ear, away from the face of the patient in use, which may increase patient comfort by preventing straps from falling in front of the face of the patient. In some embodiments, at least one adjustable region may be located near the cannula at the cheek of the patient. In the stretch region adjustments may be made using a slide buckle friction adjusting mechanism or by other mechanisms. The non-stretch region adjustments may be located close to the back of the patient's head in use or elsewhere on the headgear, and may use a cable tie or a belt buckle mechanism or other mechanisms for adjustment.

In some embodiments the headgear may have a single size, or may have a range of different sizes. In some embodiments the headgear may not be adjustable.

The tube may be tethered to the headgear or it may be tethered to the interface which may alter the location of the tube loading region in a way that may prevent rotation of the interface on the face of the patient. By absorbing the force into the friction, the high-friction surface may enable the majority of the force to be distributed over the non-stretch regions of the strap. Due to non-stretch properties, the non-stretch regions may not distort or stretch upon application of a load at the tube. By locating the stretch regions sufficiently away from the tube loading region a much lower force may be applied to the stretch regions of the strap. By having the high friction surface on the non-stretch regions, less load may be applied to the stretch regions which may help to stabilise the cannula and prevent rotation or displacement of the headgear on the patient in use. In this way the interface may distort less during loading. The tube may be attached to the headgear or interface using fabric hook and loop fasteners, domes, buttons, hooks, or the like. The tube may attach to one side of the headgear, or it may be able to attach to either side of the headgear to accommodate any side swapping of the cannula.

In some embodiments, the stretch regions of the headgear may be located at the back of the patient's head in use. This may be to maintain a sufficient distance between the stretch regions and the tube loading region if the tube is attached to either side of the interface. Non-stretch regions may be located either side of the stretch regions. In this embodiment the non-stretch adjustments may occur anywhere along the non-stretch regions, which may be located either side of the stretch regions.

Possible materials may include but are not limited to, silicones, foams and fabrics. Different materials may be used for different regions of the headgear or the same materials may be used for the headgear. Combinations of different materials may also be used. The headgear may be made by knitting, weaving, braiding, screen printing over fabric or the like, to achieve the desired result.

Figure 83:
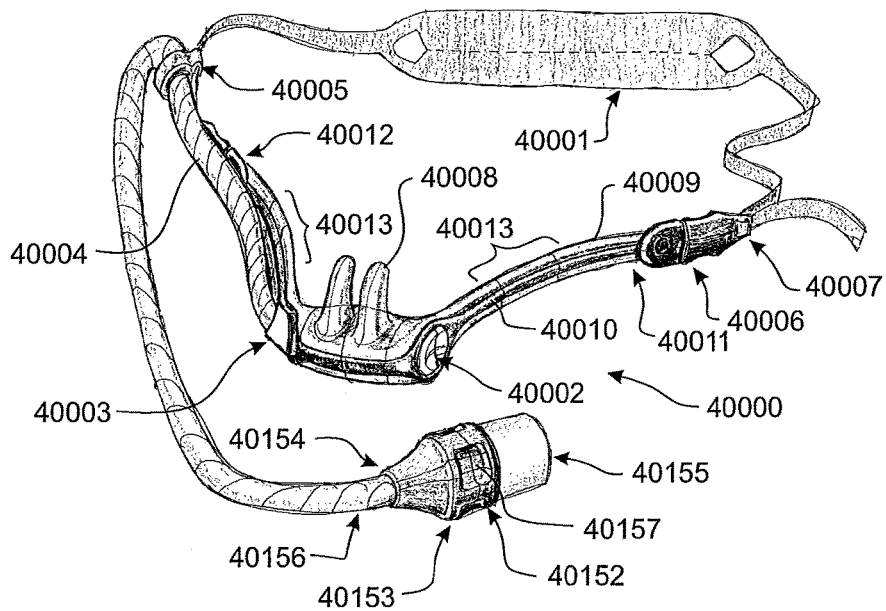
FIG. 83 is one embodiment of a nasal cannula system, including a pair of nasal prongs, a cannula body, a pair of side arms extending from the cannula body, a headgear in connection with the side arms, a gas supply tube for providing a source of gases to be in fluid communication with a pair of nasal prongs, and a connector associated with the gas supply tube.
Figure 84:
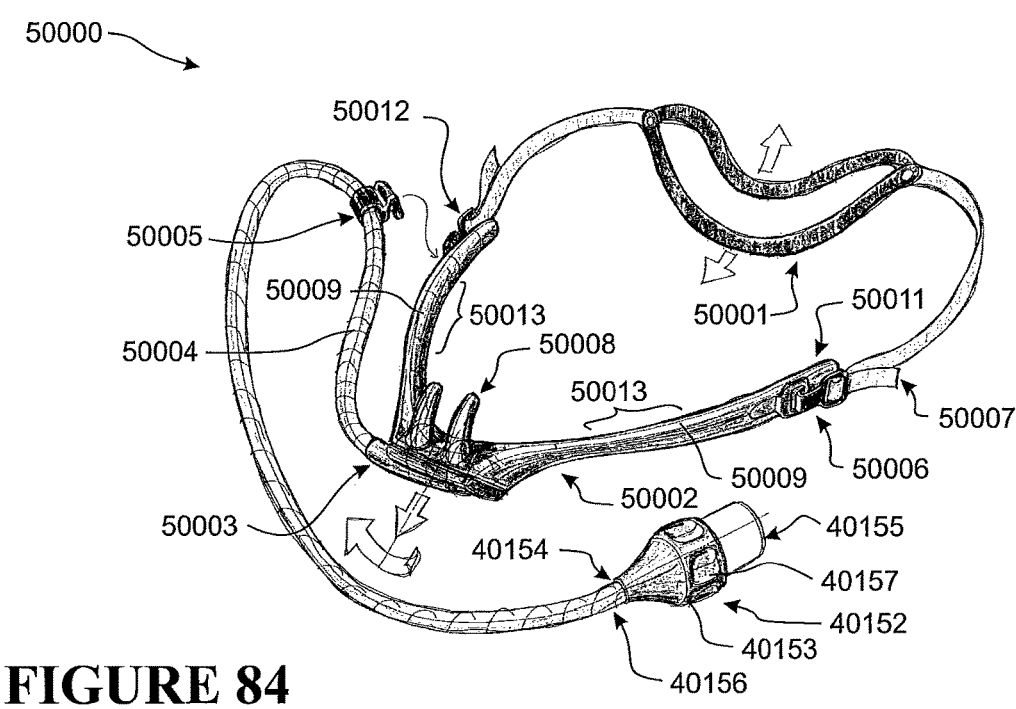
FIG. 84 is another embodiment of a nasal cannula system, including a pair of nasal prongs, a cannula body, a pair of side arms extending from the cannula body, a headgear in connection with the side arms, a gas supply tube for providing a source of gases to be in fluid communication with a pair of nasal prongs, and a connector associated with the gas supply tube.

With reference to FIGS. 83, 84 a connector 40152 is shown. As described above, such connectors may include grips or other surface relief portions to enable a user to better grasp such a connector 40152. A connector 40152 is typically employed for connecting a breathing tube to a device (such as a humidifier or ventilator or other source of gases), or for connecting to at least another breathing tube.

In one embodiment, such a connector 40152 comprises an inner body (not shown) and an outer body 40153. Each of the inner body and outer body 40153 having a first end 40154 and a second end 40155, each of these ends generally indicated by arrows in FIG. 83.

The first end 40154 of the inner and outer bodies 40153 is adapted for receiving a terminal end of a first breathing tube, such as that indicated as 40156. The second end 40155 of the inner and outer bodies 40153 is provided or adapted for connecting to at least one of a further breathable tube (such as an extension for extending the reach of the gas supply tube back to a source of gases or other device), or a device such as may be connected to the gas tube, typically including by not limited to, a humidifier, or a ventilator or a source of gases (e.g. could also be for anaesthetic delivery).

The first end 40154 of the inner body is receivable and fluidly connective with the terminal end of the first breathing tube 40156. Although not shown, the inner body can be provided with a lumen to enable fluid connection between the first end and the second end of said inner body. In this way, once the tube is connected to the inner body, a fluid pathway is defined between the tube, the first end and the second end of the inner body. This allows for delivery of gases to the second end of the inner body and for transport of such gases through the lumen and into the tube for ultimate conveyance to a further system, such as for example through the gas supply tube to a nasal cannula system as for example shown by FIG. 83, 84.

In respect of the connector 40152, the inner body (not shown) is rotatable (or may swivel) relative to the outer body 40153. In this manner, twists or torsion applied to the gas tube or any twists or torsion which is translated to the terminal end if the gas tube 40156 may be alleviated as the tube is free to rotate or swivel with respect to the outer body. Particularly advantageous is the capability to provide for an outer body portion or housing which sleeves the inner body, and where the outer body or housing can be inserted into a further coupling or other connection, and where in doing so, any twist or torsion in aligning such an outer body for coupling or connection is in turn not translated to the gas tube 40156.

It will therefore be appreciated the inner body is adapted to swivel relative to the outer body.

The outer body may comprise one or more surface relief features 40157, for example, finger grips The terminal end of the first breathing tube is in-use to be connected to the first end of the inner body and is allowed to be longitudinally rotatable with respect to the outer body. In one example, the inner body is sleeved with respect to the outer body.

In a preferred embodiment, the second end of the outer body is adapted to connect to the further component, the outer body being non-swiveable (or non-swivelling) relative to a connection being made with the further component, for example at a machine end of a breathing circuit.

It will further be appreciated that the connector 40152 as described herein may be provided as a connector for use with a gas supply tube for a patient interface, such as a nasal cannula, or for use with other breathing tubes of devices to be associated with breathing tubes or as may be described in this specification.

Figure 85:
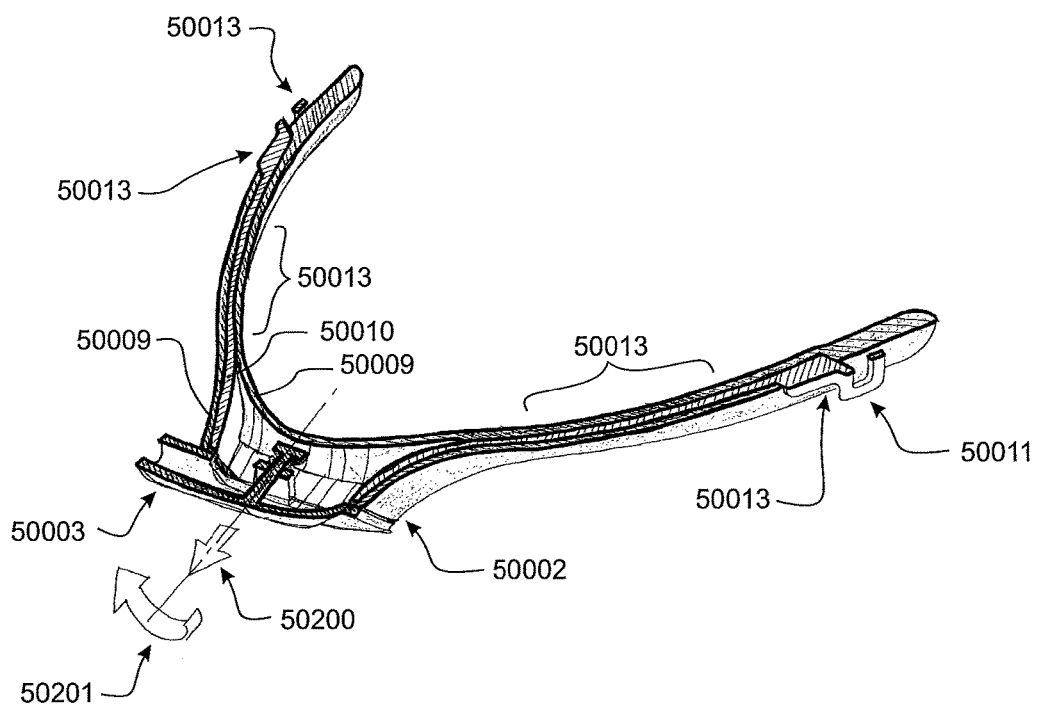
FIG. 85 is a cross-sectional view through the embodiment shown in FIG. 84, the cross-section illustrating one example of how a first section of first material may be provided in combination with a second section of second material, in combination with one example of a pivoting or swivel type manifold.

With reference to FIGS. 83-85, there is shown a patient interface, such as a nasal cannula, that comprises a gases delivery mechanism (such as one or a pair of nasal prongs to engage with the nare or nares of a user's nose). From a body of the nasal cannula with which the gases delivery mechanism is associated, there extends a pair of side arms, such as side arms 40100, 40102, the body and side arms being connected in a manner such that application of a tension to the side arms directs the gases delivery mechanism to move away from a position otherwise imposing upon a user's nasal spine. For example, the side arms 40100, 40102, may be connected by virtue of being a continuous length of material extending from one side arm, through a bridge or central part of a cannula 40101, and continuing to extend onward to the periphery of the second side arm. Such an embodiment may be that as is particularly illustrated by FIGS. 83, 85.

Again, with reference to FIGS. 83-85, there is shown a patient interface, such as a nasal cannula. The nasal cannula may comprise a cannula body, typically indicated in the region of 40101, from which a nasal prong or a pair of nasal prongs can extend therefrom to engage or deliver, in-use, a flow of gases to the nare(s) of a user. As shown, a pair of side arms 40100, 40102, extend outwardly and to which a headgear system is connectable. Although the headgear system shown is that of a bifurcatable strap, it will be appreciated any form of headgear as may be used with a patient interface such as a nasal cannula may be utilised. Although the cannula body in the region indicated by 40101 (or at least a rear portion which may be contactable with a user's face) is substantially conformable to the user, the cannula body is sufficiently rigid so that, in-use, a force or a tension applied to outer-more portions (such as at the portions where a headgear connects to the side arms), the side arms 40100, 40102 direct or encourage the nasal prong or nasal prongs or at least the cannula body 40101 or the portion of the body associated with the prongs to impose less upon a user's nasal spine region.

Advantageously, in this manner, application of a tension to the side arms of the cannula assist to improve the stability of the cannula upon a user's face, whilst working to mitigate an associated increase in pressure upon a user's nasal spine region.

As noted above, one implementation of the above system is provisioned by utilising a continuous section of material to extend along each side arm and connects in a region of the nasal prong or nasal prongs. The continuous section of material is a material capable of translating an applied force or tension from the side arms to the region of the nasal prong or nasal prongs, for example may be a material as described herein as a second section formed of a second material.

In other embodiments, each of the side arms can define a pre-form or shape such that, before application of a force or a tension to the side arms, for example from a headgear, the side arms curve outwardly away from the face of the user, extending more outwardly so as the side arms extend further away from a gas delivery mechanism of the interface or from a nasal prong or a pair of nasal prongs.

Each of the side arms may be, in-use, substantially in contact with a user's face as the arms extend outwardly away from the gas delivery mechanism or nasal prong or pair of nasal prongs, with each of the side arms becoming or being less in contact, and more distant from, a user's face the further the arms extend from the gas delivery mechanism or nasal prong or pair of nasal prongs.

The side arms can define a pre-form or shape such that, in-use, application of a force or a tension to the side arms via the headgear encourages (or directs) the side arms to more into a position of greater facial contact with the user's face or cheeks and the body is encouraged (or directed) to move into a position less engaged with, or imposing upon, or further away from, the user's nasal spine region.

The side arms are configured to, in-use, encourage the translation or location or re-locating or distribution or re-distribution of a force or a tension being applied by a headgear to a nasal cannula, to a user's cheeks and away from the user's nasal spine region or away from the force or tension being applied to the user's nasal spine region.

Each of the side arms are pre-formed or shaped such that, in-use, application of a force or a tension to the side arms, requires the side arms, or at least portions of the side arms, to move closer to a user's face, a hinging or flexing point (or point of flexure), such as may be the region indicated as item 40013 shown in FIG. 83, and a similar region indicated as item 50013 in FIGS. 84, 85, of the side arm upon a user's face being established upon a cheek region, and the nasal prong or nasal prongs or another gases delivery mechanism being encouraged away from imposing upon a user's nasal spine region.

In a preferred embodiment, the hinging or flexing point (or point of flexure) being established in-use, is a region at or about any one or more of the user's left or right (or both):

lower outer maxilla, upper outer maxilla, zygomatic arch, maxilla recess (or below the zygomatic arch).

The foregoing description of the invention includes preferred forms thereof. Modifications may be made thereto without departing from the scope of the invention as defined by the accompanying claims.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". For example, the term "comprising" as used in this specification and claims means "consisting at least in part of". When interpreting each statement in this specification and claims that includes the term "comprising", features other than that or those prefaced by the term may also be present.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features. For example, each of the cannula arrangements or embodiments could be combined with any of the described retention arrangements. Similarly, any of the tube or tubing arrangements or embodiments can be combined with any of the cannula or retentions arrangements. Any of the many parts and features within the embodiments described herein can be combined in any way with any of the other parts and features of the different embodiments.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Preferred Features of the Invention

1. A nasal cannula system, comprising:
a cannula comprising a central body portion, a first side portion and a second side portion, wherein the first and second side portions extend in opposite lateral directions from the central body portion and contact a cheek or other facial features of a user when the system is in use, a first nasal prong and a second nasal prong extending from the central body portion, the central body portion comprising a patient facing side and at least one retention strap that cooperate to define a cavity, wherein the first and second nasal prongs communicate with the cavity;
a manifold that receives a supply of gas from a gas source, the manifold comprising a gas inlet and a gas outlet, wherein the manifold is receivable within the cavity of the cannula such that the gas outlet is aligned with the first and second nasal prongs;
wherein the at least one retention strap defines a first lateral edge and a second lateral edge, and wherein the first and second nasal prongs are located between the first lateral edge and the second lateral edge.

2. The nasal cannula system of claim 1, wherein the at least one retention strap comprises a first retention strap and a second retention strap.

3. The nasal cannula system of claim 1 or 2, wherein the at least one retention strap comprises at least one window through which at least one portion of the manifold is visible.

4. The nasal cannula system of any one of claims 1-3, wherein the cavity has a first end and a second end and the manifold can be inserted through either one of the first and second ends and closes off the other of the first and second ends.

5. The nasal cannula system of any one of claims 1-4, wherein each of the first and second side portions comprises a flex-inducing feature selected from one of a plurality of flex slots and a reduced cross-section portion to facilitate flexing of the first and second side portions relative to the central body portion.

6. The nasal cannula system of any one of claims 1-5, each of the first and second side portions comprises a recessed area on the patient facing side of the first and second portions, the recesses configured to accommodate portions of a headgear strap.

7. The nasal cannula system of any one of claims 1-6, further comprising a supply tube having a first end coupled to the manifold and a second end coupled to a connector, which permits the supply tube to be coupled to a gas delivery conduit, and a lanyard coupled to the supply tube with a lanyard connector, wherein the lanyard connector comprises a breakaway portion and at least one end of the lanyard is coupled to the breakaway portion.

8. The nasal cannula system of any one of claims 1-7, further comprising a lanyard clip proximate the first end of the supply tube, the lanyard clip configured to releasably clip to a lanyard.

9. The nasal cannula system of any one of claims 1-8, wherein the first and second side portions comprise cheek pads configured to be secured to the cheeks of a patient.

10. The nasal cannula system of claim 9, wherein the cheek pads comprise an adhesive layer.

11. The nasal cannula system of claim 9, further comprising a pair of attachment pads having an adhesive layer to allow attachment to the cheeks of a patient, wherein the pair of attachment pads comprise one portion of a hook and loop fastener and the cheek pads comprise the other portion of the hook and loop fastener such that the cheek pads can be secured to the attachment pads.

12. The nasal cannula system of any one of claims 1-12, wherein the patient facing side of the central body portion comprises cushion details configured to space the central body portion away from the patient's face.

13. The nasal cannula system of any one of claims 1-13, further comprising a supply tube having a first end coupled to the manifold and a second end coupled to a connector, which permits the supply tube to be coupled to a gas delivery conduit, and a lanyard coupled to the supply tube with a lanyard connector, wherein a portion of the lanyard coupled to the lanyard connector extends substantially along a longitudinal axis of the lanyard connector.

14. The nasal cannula system of any one of claims 1-14, wherein each of the first and second side portions comprises an undercut on a surface opposite the patient facing side, further comprising a headgear strap comprising a first clip and a second clip that engages the undercut of the respective first and second side portions to couple the headgear strap to the cannula on the surface opposite the patient facing side.

15. The nasal cannula system of any one of claims 1-15, wherein the cannula defines a lateral slot, further comprising a head gear strap extending through the lateral slot.

16. The nasal cannula system of claim 15, wherein the cannula is slidable along the head gear strap.

17. A nasal cannula system, comprising:
a cannula comprising a central body portion, a first side portion and a second side portion, wherein the first and second side portions extend in opposite lateral directions from the central body portion and contact a cheek of a user when the system is in use, a first nasal prong and a second nasal prong extending from the central body portion, the cannula defining a cavity having an inlet at a first end, the cavity having a second end communicating with a first gas path and a second gas path, which communicate with the first and second nasal prongs, respectively, wherein the inlet is located at one of the first and second side portions and the first and second gas paths extend in a lateral direction toward the first and second nasal prongs;
a supply tube having a first end connectable to a supply of gas from a gas source and a second end coupled to the inlet of the cavity of the cannula.

18. The nasal cannula system of claim 17, further comprising a headgear strap and a tube clip coupled to the headgear strap, the tube clip configured to hold the supply tube away from the mouth and face of the user in use.

19. The nasal cannula system of claim 17 or 18, further comprising a lanyard clip proximate the first end of the supply tube, the lanyard clip configured to releasably clip to a lanyard.

20. A nasal cannula system, comprising:
a cannula comprising a central body portion, a first side portion and a second side portion, wherein the first and second side portions extend in opposite lateral directions from the central body portion, a first nasal prong and a second nasal prong extending from the central body portion, the central body portion defining a cavity and a forward-facing inlet to the cavity, wherein the first and second nasal prongs communicate with the cavity;
a manifold that receives a supply of gas from a gas source, the manifold comprising a gas inlet and a gas outlet, wherein the manifold is connectable with the cannula such that the gas outlet is aligned with the forward-facing inlet of the cannula and the gas inlet faces a lateral direction;
a supply tube connected to the gas inlet of the manifold and positioned forward of the forward-facing inlet of the cannula.

21. The nasal cannula system of claim 20, wherein the manifold can be connected to the cannula in either of a first orientation with the gas inlet facing in a first lateral direction and a second orientation with the gas inlet facing in a second lateral direction.

22. The nasal cannula system of claim 20 or 21, further comprising a lanyard clip proximate the first end of the supply tube, the lanyard clip configured to releasably clip to a lanyard.

23. The nasal cannula system of any one of claims 20-22, further comprising a releasable fastener located on each of the first and second side portions of the cannula and corresponding first and second side portions of the manifold.

24. The nasal cannula system of claim 23, further comprising a headgear strap coupled to the first and second side portions of the manifold, wherein the releasable fasteners are located on top of portions of the headgear strap located on the first and second side portions of the manifold.

25. The nasal cannula system of claim 23, wherein the cannula comprises a rigid frame portion surrounding the inlet and extending into the first and second side portions.

26. The nasal cannula system of claim 25, wherein a body portion of the cannula is formed over and at least partially surrounds the rigid frame portion.

27. A nasal cannula patient interface, comprising:
a first nasal prong and a second nasal prong, each of the first and second prongs comprising an inlet end and an outlet end;
at least one support portion configured to rest upon the nose of a patient at a point at or above the tip of the nose;
wherein, in use, no portion of the patient interface contacts an upper lip of the patient to provide any substantial support to the patient interface.

28. The nasal cannula patient interface of claim 27, further comprising a nose strip having an adhesive layer to permit attachment to the nose of a patient, wherein the at least one support portion comprises an attachment pad that couples the at least one support portion to the nose strip.

29. The nasal cannula patient interface of claim 27 or 28, wherein the at least one support portion comprises a first support portion and a second support portion.

30. The nasal cannula patient interface of claim 29, wherein the first support portion is positioned on a first lateral side and the second support portion is positioned on a second lateral side of the patient's nose.

31. The nasal cannula patient interface of claim 29 or 30, wherein the first support portion and first nasal prong are separate from the second support portion and second nasal prong.

32. The nasal cannula patient interface of any one of claims 27-31, further comprising a first supply tube and a second supply tube, the first supply tube connected to the inlet end of the first nasal prong, and the second supply tube connected to the inlet end of the second nasal prong.

33. The nasal cannula patient interface of claim 32, further comprising a cheek pad configured to secure a portion of the first and second supply tubes to one or both of the patient's cheeks.

34. The nasal cannula patient interface of claim 32 or 33, further comprising a lanyard clip proximate the first end of the supply tube, the lanyard clip configured to releasably clip to a lanyard.

35. The nasal cannula patient interface of any one of claims 27-34, wherein each of the first and second nasal prongs has a molded shape having a turn of about 180° between the inlet end and the outlet end.

36. The nasal cannula patient interface of any one of claims 27-35, further comprising a central body portion defining a cavity having an inlet and an outlet, the outlet in communication with the first and second nasal prongs and the inlet configured to receive a manifold coupled to a supply tube.

37. A nasal cannula patient interface, comprising:
a first nasal pillow and a second nasal pillow, each of the first and second nasal pillows comprising an inlet end and an outlet end;
at least one support portion configured to rest upon the nose of a patient at a point at or above the tip of the nose;
wherein, in use, no portion of the patient interface contacts an upper lip of the patient to provide any substantial support to the patient interface.

38. The nasal cannula patient interface of claim 37, wherein the nasal pillows are self-inflating.

39. The nasal cannula patient interface of claim 37 or 38, further comprising at least one supply tube that couples the first and second nasal pillows to a source of gas.

40. The nasal cannula patient interface of claim 39, wherein the at least one supply tube comprises a first supply tube coupled to the first nasal pillow and a second supply tube coupled to the second nasal pillow.

41. A nasal cannula system, comprising:
a cannula comprising a central body portion, a first nasal prong and a second nasal prong extending from the central body portion, the cannula defining a cavity in communication with the first and second nasal prongs, an integrated head strap comprising a first section and a second section, wherein the first and second sections extend in opposite lateral directions from the central body portion, the first section defining a rear portion of the head strap, an adjustable coupling arrangement that permits coupling of the first and section sections in an adjustable manner such that a circumference of the head strap is adjustable;
a supply tube having a first end connectable to a supply of gas from a gas source and a second end coupled to the cavity of the cannula.

42. The nasal cannula system of claim 41, wherein the cannula, first section and second section of the head strap are of a unitary construction.

43. The nasal cannula system of claim 41 or 42, wherein the adjustable coupling arrangement comprises a slot defined by one of the first and second sections and a teeth-defining portion that is adjustably-received within the slot.

44. A nasal cannula system, comprising:
a cannula comprising a central body portion, a first nasal prong and a second nasal prong extending from the central body portion, the cannula defining a cavity in communication with the first and second nasal prongs, wherein the cannula defines a lateral slot;
a head gear strap extending through the lateral slot of the cannula;
a supply tube having a first end connectable to a supply of gas from a gas source and a second end coupled to the cavity of the cannula.

45. The nasal cannula system of claim 44, wherein the cannula is slidable along the head gear strap.

46. A nasal cannula system, comprising:
a cannula comprising a central body portion, a first nasal prong and a second nasal prong extending from the central body portion, the cannula defining a cavity in communication with the first and second nasal prongs, the cannula defining a first opening at a first location of the cavity and a second opening at a second location of the cavity spaced from the first location, a valve body that is movable within the cavity;
a supply tube having a first end connectable to either one of the first opening or the second opening of the cannula and a second end connectable to a supply of gas from a gas source;
wherein, when the first end of the supply tube is connected to the first opening of the cannula, the valve body moves in response to a flow of gas in the cavity from the gas source to block the second opening such that the flow of gas is directed to the first and second nasal prongs and, when the first end of the supply tube is connected to the second opening of the cannula, the valve body moves in response to the flow of gas in the cavity from the gas source to block the first opening such that the flow of gas is directed to the first and second nasal prongs.

47. The nasal cannula system of claim 46, wherein the first location is a first end of the cannula and the second location is a second end of the cannula.

48. The nasal cannula system of claim 46 or 47, wherein the valve body is either a ball or a plate.

49. The nasal cannula system of any one of claims 46-48, wherein the valve body is a ball and the cannula comprises first and second thin wall sections extending radially inward into each of the first and second openings and that create a seal with the ball.

50. The nasal cannula system of any one of claims 46-49, further comprising a connector coupled to the first end of the supply tube, wherein the connector has an interlocking connection with either one of the first and second openings of the cannula.

51. The nasal cannula system of claim 50, further comprising a first insert and a second insert within a respective one of the first opening and the second opening, wherein the connecter engages the first insert when coupled to the first opening and the second insert when coupled to the second opening.

52. A nasal cannula system, comprising:
a cannula comprising a central body portion, a first nasal prong and a second nasal prong extending from the central body portion, the cannula defining a cavity in communication with the first and second nasal prongs, the cannula defining a first opening at a first location of the cavity and a second opening at a second location of the cavity spaced from the first location, the cannula comprising a first valve that selectively closes the first opening and a second valve that selectively closes the second opening;
a supply tube having a first end connectable to either one of the first opening or the second opening of the cannula and a second end connectable to a supply of gas from a gas source;
wherein, when the first end of the supply tube is connected to the first opening of the cannula, the second valve blocks the second opening such that a flow of gas from the gas source is directed to the first and second nasal prongs and, when the first end of the supply tube is connected to the second opening of the cannula, the first valve blocks the first opening such that the flow of gas is directed to the first and second nasal prongs.

53. The nasal cannula system of claim 52, wherein the first location is a first end of the cannula and the second location is a second end of the cannula.

54. The nasal cannula system of claim 52 or 53, wherein the first and second valves comprise one of a flap valve, a slit valve and a pierceable membrane.

55. The nasal cannula system of any one of claims 52-54, further comprising a connector coupled to the first end of the supply tube, wherein the connector has an interlocking connection with either one of the first and second openings of the cannula.

56. The nasal cannula system of claim 55, wherein the first and second valves are pierceable membranes and the connector comprises a piercing point.

57. A nasal cannula system, comprising:
a cannula comprising a central body portion, a first nasal prong and a second nasal prong extending from the central body portion, the cannula defining a cavity in communication with the first and second nasal prongs, the cannula defining a first opening at a first end of the cavity and a second opening at a second end of the cavity;
a supply tube having a first end comprising a first insert and a second end comprising a second insert, wherein each of the first insert and the second insert is positionable within the cavity to seal the first opening and the second opening and deliver a flow of gas from the gas source to the first and second nasal prongs;

wherein, when the first end of the supply tube is connected to the cannula, the second end is connectable to the gas source and, when the second end of the supply tube is connected to the cannula, the first end is connectable to the gas source.

58. The nasal cannula system of claim 57, further comprising a connector that is connectable to a gas supply conduit that is in communication with the gas source, wherein the connector defines a cavity that can accommodate either of the first end and the second end of the supply tube in a substantially sealed manner.

59. The nasal cannula system of claim 57 or 58, wherein the supply tube can pass through the cavity of the cannula when switching from the first end to the second end being connected to the cannula.

60. A nasal cannula system, comprising:
a cannula comprising a central body portion, a first nasal prong and a second nasal prong extending from the central body portion, the cannula defining a cavity in communication with the first and second nasal prongs;
a supply tube having a first end coupled to the cavity of the cannula and a second end connectable to a supply of gas from a gas source, the first end of the supply tube defining a connection axis relative to the cannula, the supply tube comprising a flexible portion at or adjacent the first end that can be bent at least about 90 degrees to either the left or right side without significant occlusion of an internal passage of the supply tube.

61. The nasal cannula system of claim 60, wherein the first end of the supply tube exits the cannula in a forward direction relative to a patient-facing surface of the cannula.

62. A nasal cannula system, comprising:
a cannula comprising a cavity and a first nasal prong and a second nasal prong in communication with the cavity;
a supply tube that receives a flow of gas from a gas source, the supply tube connected to the cannula to supply the flow of gas to the cavity of the cannula;
a clip that removably receives the cannula;
a retention arrangement that secures the clip to the head of a patient;
wherein the cannula is positionable within the clip in a first orientation such that the supply tube extends in a first direction from the clip, and wherein the cannula is positionable within the clip in a second orientation such that the supply tube extends in a second direction from the clip.

63. The nasal cannula system of claim 62, wherein the retention arrangement comprises one of a strap, one or more adhesive pads or a support frame.

64. A nasal cannula system, comprising:
a cannula comprising a first nasal prong and a second nasal prong, the cannula defining a cavity in communication with the first and second nasal prongs, the cannula defining a first opening at a first location of the cavity and a second opening at a second location of the cavity spaced from the first location;
a supply tube assembly comprising a clip that can be releasably coupled to the cannula in either of a first orientation and a second orientation, the supply tube assembly further comprising a supply tube connectable to a supply of gas from a gas source, wherein the clip supports the supply tube and comprises a sealing portion;

wherein, when the clip is connected to the cannula in the first orientation, the supply tube is connected to the first opening of the cannula and extends in a first direction from the cannula and the sealing portion at least substantially seals the second opening and, when the clip is connected to the cannula in the second orientation, the supply tube is connected to the second opening of the cannula and extends in a second direction from the cannula and the sealing portion at least substantially seals the first opening.

65. The nasal cannula system of claim 64, wherein the clip is a generally C-shaped clip.

66. The nasal cannula system of claim 64 or 65, wherein the clip comprises at least one engagement portion that engages a corresponding receiving portion in both the first orientation and the second orientation to lock the clip to the cannula.

67. The nasal cannula system of claim 66, wherein the engagement portion comprises an end portion of the clip.

68. The nasal cannula system of claim 67, wherein the sealing portion comprises a semi-spherical protrusion.

69. The nasal cannula system of any one of claims 64-68, wherein the cannula comprises a recess that accommodates at least a central section of the clip and inhibits movement of the clip relative to the cannula in at least one direction.

70. The nasal cannula system of any one of claims 64-69, wherein an end of the supply tube abuts a surface of the cannula surrounding a respective one of the first and second openings when the clip is connected to the cannula.

71. The nasal cannula system of any one of claims 64-70, wherein an end of the supply tube is positioned within a respective one of the first and second openings when the clip is connected to the cannula.

72. The nasal cannula system of any one of claims 64-71, wherein the first and second prongs are carried by a prong insert that is separate from a main body portion of the cannula that defines the cavity, the first opening and the second opening, wherein the clip secures the prong insert to the main body portion of the cannula.

73. The nasal cannula system of claim 72, wherein the prong insert is selectable from a selection of at least two different sizes of prong inserts comprising at least two different sizes of prongs.

74. The nasal cannula system of any one of claims 64-73, wherein the cannula is rotatable relative to the clip to permit adjustment of an angle of the first and second prongs.

75. A nasal cannula system, comprising:
a cannula clip comprising a first nasal prong and a second nasal prong, the cannula defining a cavity in communication with the first and second nasal prongs;
a supply tube assembly comprising a manifold having at least one manifold opening and a supply tube connectable to a supply of gas from a gas source, wherein the cannula clip is capable of being releasably coupled to the manifold in either of a first orientation and a second orientation in which the manifold is received within the cavity of the cannula clip and the first and second prongs are aligned with the at least one manifold opening such that a flow of gas is provided to the first and second prongs;
wherein, when the cannula clip is connected to the manifold in the first orientation, the supply tube extends in a first direction relative to the first and second prongs and, when the cannula clip is connected to the manifold in the second orientation, the supply tube extends in a second direction relative to the first and second prongs.

76. The nasal cannula system of claim 75, wherein the manifold extends in a lateral direction through the cannula clip.

77. The nasal cannula system of claim 75 or 76, wherein the manifold comprises a rib that is positioned between first and second edges of the cannula clip when the cannula clip is assembled to the manifold in either of the first orientation or the second orientation.

78. A nasal cannula system, comprising:
a cannula comprising a main body defining a cavity and a first nasal prong and a second nasal prong extending from the main body and in communication with the cavity;
a supply tube coupled to the cannula and in communication with the cavity, the supply tube connectable to a supply of gas from a gas source to deliver a flow of gas to the cavity and the first and second nasal prongs;
wherein the first and second nasal prongs are tiltable relative to the main body of the cannula between at least a first position in which the first and second nasal prongs are tilted in a first direction relative to the main body and a second position in which the first and second nasal prongs are tilted in a second direction relative to the main body, wherein a first surface of the main body defines a patient-facing surface of the cannula in the first position and a second surface of the main body defines the patient-facing surface of the cannula in the second position to effectively switch the side from which the supply tube extends from the cannula between the first and second positions.

79. The nasal cannula system of claim 78, wherein the first nasal prong and the second nasal prong are tiltable separately from one another.

80. The nasal cannula system of claim 78 or 79, further comprising one or more ripples surrounding each of the first nasal prong and the second nasal prong, wherein the ripples facilitate tilting of the first and second nasal prongs.

81. The nasal cannula system of claim 80, further comprising a stiffening rib within the ripples that inhibit tilting of the first and second nasal prongs in at least one direction other than the generally first and second directions.

82. The nasal cannula system of any one of Claims 78-81, wherein each of the first and second nasal prongs comprise a collapsible corrugated concertina section that facilitates tilting of the prongs.

83. A nasal cannula system, comprising:
a cannula defining a cavity and comprising a first nasal prong and a second nasal prong extending from the cannula and in communication with the cavity;
a supply tube coupled to the cannula and in communication with the cavity, the supply tube connectable to a supply of gas from a gas source to deliver a flow of gas to the cavity and the first and second nasal prongs;
wherein the first and second nasal prongs are directionally-oriented relative to the cannula and are movable between at least a first position in which the first and second nasal prongs are oriented such that openings of the prongs generally face in a first direction relative to the cannula and a second position in which the first and second nasal prongs are oriented such that the openings of the prongs generally face in a second direction relative to the cannula, wherein a first surface of the cannula defines a patient-facing surface in the first position and a second surface of the cannula defines the patient-facing surface in the second position to effectively switch the side from which the supply tube extends from the cannula between the first and second positions.

84. The nasal cannula system of claim 83, wherein the first nasal prong and the second nasal prong are movable between the first position and the second position separately from one another.

85. The nasal cannula system of claim 83 or 84, wherein the first nasal prong and the second nasal prong are supported by a prong insert that is separate from a main body of the cannula, which defines the cavity, wherein the prong insert is movable relative to the main body to move the prongs together between the first position and the second position.

86. The nasal cannula system of claim 85, wherein the or each prong insert is rotatable on a shaft of the main body of the cannula.

87. The nasal cannula system of claim 86, wherein the shaft is located between the first nasal prong and the second nasal prong.

88. The nasal cannula system of claim 87, wherein the shaft is either aligned with the first and second nasal prongs or offset from the first and second nasal prongs.

89. The nasal cannula system of any one of claims 85-88, wherein the main body defines an opening in communication with the cavity and that removably receives the prong insert.

90. The nasal cannula system of claim 89, wherein the prong insert is selectable from a selection of at least two different sizes of prong inserts comprising at least two different sizes of prongs.

91. A nasal cannula system, comprising:
a cannula defining a patient-facing surface and a cavity and comprising a first nasal prong and a second nasal prong extending from the cannula and in communication with the cavity;
a manifold that supports the cannula for rotation about at least one axis between at least a first position and a second position opposite the first position;
a supply tube coupled to the manifold and in communication with the cavity, the supply tube connectable to a supply of gas from a gas source to deliver a flow of gas to the cavity and the first and second nasal prongs;
wherein, when the cannula is in the first position, the supply tube is positioned on a first side of the first and second nasal prongs and, when the cannula is in the second position, the supply tube is positioned on a second side of the first and second nasal prongs to effectively switch the side from which the supply tube extends from the cannula between the first and second positions.

92. The nasal cannula system of claim 91, wherein the cannula is connected to the manifold by a ball joint arrangement such that the cannula is rotatable relative to the manifold about at least two axes, such that a tilt of the first and second nasal prongs can be adjusted.

93. The nasal cannula system of claim 91 or 92, wherein the cannula is selectable from a selection of at least two different sizes of cannulas comprising at least two different sizes of prongs.

94. The nasal cannula system of any one of claims 91-93, wherein the cannula comprises a prong portion and a connection portion that are separable from one another, wherein the prong portion is selectable from a selection of at least two different sizes of prong portions comprising at least two different sizes of prongs, which can be coupled to the connection portion for use.

95. The nasal cannula system of any one of claims 91-94, wherein the cannula and the manifold comprise interference surface features that assist in securing the cannula in a desired position relative to the manifold.

96. A nasal cannula system, comprising:
a cannula defining a cavity and comprising a first nasal prong and a second nasal prong extending from the cannula and in communication with the cavity;
a supply tube coupled to the cannula and in communication with the cavity, the supply tube connectable to a supply of gas from a gas source to deliver a flow of gas to the cavity and the first and second nasal prongs;
a pressure line in communication with the cavity and configured to be connectable to a control unit of the gas source or a display unit to provide a signal to the control unit or display unit indicative of a pressure within the cavity.

97. The nasal cannula system of claim 96, wherein the pressure line is a tube and the signal is gas pressure within the tube.

98. The nasal cannula system of claim 97, wherein a portion of the pressure line located within the cavity comprises a plurality of openings along a length of the tube.

99. The nasal cannula system of claim 97 or 98, wherein the pressure line is coupled to the gas source, which provides a flow of gas into the pressure line either intermittently or continuously.

100. The nasal cannula system of any one of claims 96-99, wherein the pressure line is an electrical line comprising an electrical pressure sensor and the signal is an electrical signal.

101. The nasal cannula system of any one of claims 96-100, wherein the pressure line is in indirect communication with the cavity.

102. The nasal cannula system of any one of claims 96-101, wherein the pressure line is coupled to a connector that is coupled to the cannula.

103. The nasal cannula system of claim 102, wherein the supply tube is coupled to the cannula by the connector along with the pressure line.

104. The nasal cannula system of any one of claims 96-103, wherein the pressure line extends into the cavity through a one-way self-sealing valve.

105. The nasal cannula system of any one of claims 96-104, wherein the pressure line is integrated with the supply tube.

106. The nasal cannula system of claim 105, wherein the pressure line is integrated with a reinforcing bead of the supply tube.

107. A nasal cannula, comprising:
a cannula body defining a cavity and comprising a first nasal prong and a second nasal prong extending from the cannula and in communication with the cavity, wherein the cannula defines a patient-facing surface having one or more comfort features selected from a plurality of through-holes, a plurality of raised bumps, a plurality of grooves and a gel pad.

108. The nasal cannula of claim 107, wherein the cannula comprises a central portion containing the first and second nasal prongs and first and second side portions extending from each side of the central portion, wherein the comfort features are provided only on the first and second side portions.

109. The nasal cannula of claim 107 or 108, wherein each of the grooves extends from one edge of the cannula to another edge of the cannula such that the grooves are open on each end.

110. The nasal cannula of claim 109, wherein the grooves extend from an upper edge of the cannula to a lower edge of the cannula.

111. A nasal cannula, comprising:
a cannula body defining a cavity and comprising a first nasal prong and a second nasal prong extending from the cannula and in communication with the cavity, the cannula body comprising a central portion containing the first and second nasal prongs and first and second side portions extending from each side of the central portion, wherein the cannula body defines a patient-facing surface;
wherein the central portion is spaced forwardly of adjacent portions of the first and second side portions such that, in use, the patient-facing surface of the central portion is spaced from the upper lip of the patient.

112. The nasal cannula of claim 111, wherein the first and second prongs extend from the patient-facing surface of the central portion.

113. The nasal cannula of claim 111 or 112, wherein the side portions comprise a malleable material portion such that a shape of the side portions can be adjusted.

114. The nasal cannula of claim 113, wherein the malleable material portion is external or is embedded within the side portions.

115. A supply tube for a nasal cannula, comprising:
a tube body having a first end a second end, the tube body comprising a malleable section that permits the section to be shaped by an external force and that substantially retains the shape after the external force is removed.

116. The supply tube of claim 115, wherein the malleable section comprises a malleable member that located in one of the following: an internal passage of the tube body, embedded in a wall of the tube body, embedded in or forming a reinforcement bead of the tube body.

117. The supply tube of claim 115 or 116, wherein the malleable section comprises a plurality of individual members adjustably coupled to one another.

118. the supply tube of claim 117, wherein the individual members are coupled by a ball-and-socket arrangement.

119. the supply tube of any one of claims 115-118, wherein the malleable section comprises a collapsible corrugated concertina tubing.

120. A nasal cannula system, comprising:
a cannula defining a cavity and comprising a first nasal prong and a second nasal prong extending from the cannula and in communication with the cavity;
a supply tube coupled to the cannula and in communication with the cavity, the supply tube connectable to a supply of gas from a gas source to deliver a flow of gas to the cavity and the first and second nasal prongs;
a support arrangement that supports the supply tube at a spaced location from the cannula, wherein the support arrangement comprises a fastener having a first portion coupled to the supply tube and a second portion located at the spaced location.

121. The nasal cannula system of claim 120, wherein the support arrangement comprises an adhesive pad that can be affixed to the patient and the second portion of the fastener is located on the adhesive pad.

122. The nasal cannula system of claim 120 or 121, further comprising a retention arrangement that secures the cannula to the patient, wherein the second portion of the fastener is located on the retention arrangement.

123. The nasal cannula system of any one of claims 120-122, wherein the fastener is one of a hook-and-loop fastener, a button-and-hole, and a snap-fit fastener.

124. A nasal cannula system, comprising:
a cannula defining a cavity and comprising a first nasal prong and a second nasal prong extending from the cannula and in communication with the cavity;

a supply tube coupled to the cannula and in communication with the cavity, the supply tube connectable to a supply of gas from a gas source to deliver a flow of gas to the cavity and the first and second nasal prongs;
a retention arrangement that secures the cannula to the patient;
a support arrangement that supports the supply tube at a spaced location from the cannula, which is located on the retention arrangement.

125. The nasal cannula system of claim 124, wherein the support arrangement comprises a clip that engages the supply tube and is supported by the retention arrangement.

126. The nasal cannula system of claim 124 or 125, wherein the support arrangement comprises a loop that is carried by the retention arrangement.

127. The nasal cannula system of claim 126, wherein the loop is integrated with the retention arrangement.

128. The nasal cannula system of claim 126, wherein the loop is an interrupted loop or an uninterrupted loop.

129. A nasal cannula system, comprising:
a cannula defining a cavity and comprising a first nasal prong and a second nasal prong extending from the cannula and in communication with the cavity;
a supply tube coupled to the cannula and in communication with the cavity, the supply tube connectable to a supply of gas from a gas source to deliver a flow of gas to the cavity and the first and second nasal prongs;
a support arrangement that supports the supply tube at a spaced location from the cannula, wherein the support arrangement comprises a fastener that engages a piece of fabric at the spaced location.

130. The nasal cannula system of claim 129, wherein the fastener is one of a clip, a snap-fit fastener or a clip-and-post fastener in which the piece of fabric is trapped between portions of the fastener, or a button-and-hole fastener in which the button is provided on the piece of fabric.

131. The nasal cannula system of claim 129 or 130, wherein the fastener is integrated with the supply tube.

132. The nasal cannula system of any one of claims 129-131, wherein the fastener comprises an opening configured to receive a lanyard.

133. A nasal cannula system, comprising:
a cannula defining a cavity and comprising a first nasal prong and a second nasal prong extending from the cannula and in communication with the cavity;
a supply tube coupled to the cannula and in communication with the cavity, the supply tube connectable to a supply of gas from a gas source to deliver a flow of gas to the cavity and the first and second nasal prongs;
a support arrangement that supports the supply tube at a spaced location from the cannula, wherein the support arrangement comprises at least one of an armband that engages the supply tube, an adhesive pad comprising a fastener for releasably fastening the supply tube to the adhesive pad, a generally U-shaped support that sits on the patient's shoulder and engages the supply tube, and a headgear strap comprising a strap extending over the top of the patient's head and engages the supply tube.

134. A retention arrangement for a nasal cannula assembly, comprising:
a headgear strap comprising a first ear loop and a second ear loop, each of which at least partially surround an ear of the patient, a connection portion that connects the retention arrangement to the nasal cannula assembly, and a strap portion that extends around the back of the patient's head between the first and second ear loops.

135. The retention arrangement of claim 134, wherein each of the first and second ear loops completely surround the ear of the patient.

136. The retention arrangement of claim 134 or 135, wherein the strap portion is one-piece or separate pieces coupled by an adjustable fastener.

137. The retention arrangement of any one of claims 134-136, wherein the strap portion comprises a mesh section.

138. A retention arrangement for a nasal cannula, comprising:
a headgear strap comprising a strap portion, a first pad and a second pad, which, in use, contact first and second cheeks of the patient, a connection portion that connects the retention arrangement to the nasal cannula, wherein the strap portion extends around the patient's head and extends from the first and second pads at an angle relative to the nasal cannula.

139. The retention arrangement of claim 138, wherein the strap portion is positioned above the ears of the patient.

140. A retention arrangement for a nasal cannula, comprising:
a frame comprising a connection portion that connects the retention arrangement to the nasal cannula, a first ear stem portion and a second ear stem portion extending rearwardly from opposite sides of the connection portion, wherein the ear stem portions are configured to be positioned above the ears of the patient.

141. The retention arrangement of claim 140, further comprising a pad on each of the ear stem portions.

142. A nasal cannula system, comprising:
a cannula having a central portion defining a cavity and comprising a first nasal prong and a second nasal prong extending from the central portion and in communication with the cavity, a first side portion and a second side portion extending in a lateral direction from opposing sides of the central portion;
a supply tube coupled to the cannula and in communication with the cavity, the supply tube connectable to a supply of gas from a gas source to deliver a flow of gas to the cavity and the first and second nasal prongs;
a first adhesive pad and a second adhesive pad configured to be adhesively secured to the face of the patient and connectable to a respective one of the first and second side portions of the cannula through an adjustable fastening arrangement.

143. The nasal cannula system of claim 142, wherein the adjustable fastening arrangement comprises a ratchet assembly between the side portions and the respective adhesive pads, a strip of hook-and-loop fastener between the side portions and the respective adhesive pads, or a post-and-multiple-slot arrangement between the side portions and the respective adhesive pads.

144. A nasal cannula system, comprising:
a cannula defining a cavity and comprising a first nasal prong and a second nasal prong extending from the cannula and in communication with the cavity;
a modular retention arrangement that secures the cannula to the patient, wherein the cannula is configured to be used with any one of the retention arrangements selected from a set of adhesive pads that attach to the patient's face, a headgear strap and a halo-style headgear strap that has a strap portion extending over the top of the patient's head.

145. The nasal cannula system of claim 144, wherein the cannula has multiple connection points with the retention arrangement on each side of the cannula.

146. The nasal cannula system of claim 144 or 145, comprising a kit including the cannula and at least two types of the retention arrangements.

147. A nasal cannula system, comprising:
a cannula defining a cavity and comprising a first nasal prong and a second nasal prong extending from the cannula and in communication with the cavity;
a modular retention arrangement that secures the cannula to the patient, the retention arrangement comprising a nose strip coupled to the cannula and attachable to the nose of a patient and a headgear strap comprising a clip configured to receive the cannula, wherein the cannula can be secured to the patient using either the nose strip or the headgear strap.

148. The nasal cannula system of claim 147, wherein the nose strip can be applied directly to the patients nose via an adhesive layer or is applied via attachment to a separate adhesive strip.

149. The nasal cannula system of claim 147 or 148, wherein the nose strip can be removed from the cannula.

150. A retention arrangement for a nasal cannula, comprising:
a headgear strap that is connectable to a nasal cannula and capable of being tensioned around the head of a patient, the headgear strap comprising a tension indicator that provides a first indication when the tension is at an incorrect value and a second indication when the tension is at a correct value.

151. The retention arrangement of claim 150, wherein the tension indicator is one of a portion that changes color between the first indication and the second indication, a portion that displays a different symbol for the first indication and the second indication, a window that displays a marker in the second indication, a scale, and a gauge.

152. The retention arrangement of claim 151, wherein the tension indicator is a gauge that is positioned on a cheek of the patient and comprises a padded patient-facing surface.

153. The retention arrangement of any one of claims 150-152, wherein the headgear strap comprises a first portion, a second portion and a biasing member that regulates movement between the first portion and the second portion.

154. The retention arrangement of claim 153, wherein the biasing member is one of a spring and an elastic section of the headgear strap.

155. The retention arrangement of any one of claims 150-154, wherein the headgear strap is a single strap comprising multiple strap portions that each extend from one side to the other of the cannula.

156. The retention arrangement of claim 155, wherein the headgear strap can be tightened by adjusting a total length of the strap extending between the sides of the cannula.

157. The retention arrangement of claim 155 or 156, wherein the strap portions are spaced from one another in a top-to-bottom direction of the cannula.

158. A retention arrangement for a nasal cannula, comprising:
a headgear strap that is connectable to a nasal cannula and comprises at least one strap extending around the head of a patient from one side to the other of the cannula;
a tension adjuster that tensions the headgear strap by varying an effective length of the at least one strap by winding up a portion of the at least one strap.

159. The retention arrangement of claim 158, wherein the at least one strap comprises multiple straps.

160. The retention arrangement of claim 158 or 159, wherein the tension adjuster is bidirectional and can wind up or release the portion of the at least one strap to increase or decrease 161. The retention arrangement of any one claims 158-160, wherein the tension adjuster comprises a limiter to limit the tension of the at least one strap.

162. The retention arrangement of claim 161, wherein the limiter is a clutch mechanism.

163. A headgear strap for a nasal cannula, comprising:
a first portion that is connectable to a nasal cannula;
a second, elastic portion that is positioned at a back of a head of a patient in use; and
a pad that extends at least partially along the second, elastic portion.

164. The headgear strap of claim 163, wherein the pad surrounds an entirety of the second, elastic portion.

165. A nasal cannula assembly, comprising:
a cannula defining a cavity and comprising a first nasal prong and a second nasal prong extending from the cannula and in communication with the cavity;
a head strap that is positioned around the head and above the ears of the patient in use; a first arm coupled to a first side of the cannula; and
a second arm coupled to a second side of the cannula, wherein upper end portions of each of the first and second arms are attached to the head strap.

166. The nasal cannula assembly of claim 165, wherein each of the first and second arms is adjustable in height relative to the head strap.

167. The nasal cannula assembly of claim 165 or 166, wherein each of the first and second arms is adjustable in a circumferential direction of the head strap.

168. The nasal cannula assembly of claim 167, wherein each of the first and second arms is adjustable to one of a discrete number of adjustment positions.

169. The nasal cannula assembly of any one of claims 165-168, wherein each of the first and second arms is rotatable relative to the head strap.

170. A nasal cannula system, comprising:
a cannula defining an open cavity and comprising a first nasal prong and a second nasal prong extending from the cannula and in communication with the cavity;
a manifold configured to be removably coupled to the cannula and a portion of the manifold received into the cavity of the cannula, the manifold having first and second holes that align with the first and second nasal prongs when the manifold is coupled to the cannula, the manifold also including a side opening configured to be coupled to a tube;
wherein an inner surface of the cavity of the cannula includes a first attachment portion and an outer surface of the portion of the manifold includes a second attachment portion, the first and second attachment portions being configured to engage one another to secure the manifold to the cannula.

171. The nasal cannula system of claim 170, wherein the first and second attachment portions comprise cooperating portions of a hook and loop material fastener.

172. The nasal cannula system of claim 170 or 171, wherein the cavity and the portion of the manifold have corresponding symmetrical shapes so that the portion of the outer surface of the manifold can be positioned within the cavity in multiple orientations.

173. The nasal cannula system of claim 172, wherein the cavity and the portion of the manifold are circular or oval shaped.

174. The nasal cannula system of any one of claims 170-173, wherein the first and second attachment portions are substantially planar.

175. A nasal cannula assembly, comprising:
a cannula defining a cavity and comprising a first nasal prong and a second nasal prong extending from the cannula and in communication with the cavity, the cannula having a first outer surface and a second outer surface, the first and second outer surfaces being substantially planar and extending along the length of the cannula, the cannula having a first end and a second end;
a retention arrangement coupled to cannula and configured to support the cannula on the face of a patient;
a tube coupled to the cannula adjacent either the first end or the second end of the cannula and configured to be in communication with the cavity;
wherein the cannula has a first position in which the first outer surface contacts the face of the patient and the first and second nasal prongs extend into the nostrils of the patient, and the cannula has a second position in which the second outer surface contacts the face of a patient and the first and second nasal prongs extend into the nostrils of the patient.

176. The nasal cannula assembly of claim 175, wherein the cannula has a substantially triangular cross-sectional shape.

177. The nasal cannula assembly of claim 176, wherein an angle between the first and second nasal prongs and the first outer surface is substantially the same as an angle between the first and second nasal prongs and the second outer surface.

178. The nasal cannula assembly of claim 177, wherein the first and second nasal prongs extend outward from the cannula at a corner of the substantially triangular cross-sectional shape between the first and second outer surfaces.

179. A nasal cannula assembly, comprising:
a cannula body defining a cavity and comprising a first nasal prong and a second nasal prong extending from the cannula and in communication with the cavity, the first and second nasal prongs having a relaxed position in the absence of any substantial external force; and
an outer portion configured to be movably coupled to the cannula body and configured to surround at least a portion of the cannula body, the outer portion defining at least one opening through which the first nasal prong extends, the outer portion including at least one edge defining the at least one opening;
wherein the outer portion can move relative to the cannula body and the first and second nasal prongs, and the at least one edge is configured to engage the first and second prongs and deflect the first and second prongs from their relaxed positions.

180. The nasal cannula assembly of claim 179, wherein the cannula body and the outer portion are substantially cylindrical and the outer portion extends around the circumference of the cannula body, and the outer portion can be rotated about the cannula body.

181. The nasal cannula assembly of claim 179 or 180, wherein each of the first and second nasal prongs includes a flexible base portion configured to allow the angle at which the prong extends from the cannula body to change.

182. The nasal cannula assembly of any one of claims 179-181, wherein the at least one opening comprises a first opening and a second opening and wherein the at least one edge comprises a first edge and a second edge, the first opening defining the first edge and the second opening defining the second edge, wherein the first nasal prong extends through the first opening and the second nasal prong extends through the second opening.

183. The nasal cannula assembly of any one of claims 179-182, wherein the outer portion includes a slot and the cannula body includes a protrusion that extends into the slot, the protrusion being able to move within the slot and the slot having side walls configured to engage the protrusion and limit the amount of movement of the outer portion relative to the cannula body.

184. A nasal cannula system, comprising:
a cannula defining a cavity and comprising at least one nasal prong extending from the cannula and in communication with the cavity;
a frame portion configured to support the cannula; and at least one head strap coupled to the frame portion and positioned around the head of the patient in use;
wherein the cannula is slidably supported by the frame portion and can move relative to the frame portion, the cannula including an opening through which the frame portion extends.

185. The nasal cannula system of claim 184, further comprising a tube support member supported by the frame portion or the head strap, the tube support member being configured to support and selectively release a tube.

186. The nasal cannula system of claim 185, wherein the tube support member is configured to loosely support the tube so that the tube can slide within the support member.

187. The nasal cannula system of claim 185, wherein the tube support member comprises a strap configured to wrap around a tube and a clip configured to couple the strap to the head strap or frame portion.

188. The nasal cannula system of any one of claims 184-187, wherein the frame portion has a circular or rounded cross-section and wherein the cannula can move laterally relative to the frame portion and can rotate relative to the frame portion.

189. The nasal cannula system of any one of claims 184-188, wherein the interface between the cannula and the frame portion is a friction fit that allows the cannula to retain its position relative to the frame portion when not being moved by a user.

190. The nasal cannula system of any one of claims 184-189, wherein the frame portion includes a plurality of notches configured to interact with the cannula and provide discrete locations along the frame portion at which the cannula can be supported.

191. A nasal cannula system, comprising:
a cannula defining a cavity and comprising a first nasal prong and a second nasal prong extending from the cannula and in communication with the cavity, the cannula including an opening extending through a portion of the cannula; and
a head strap that is positioned around the head of the patient in use;
wherein the opening on the cannula is configured to receive the head strap so that the head strap extends through the opening and supports the cannula, the cannula being configured to slide relative to the head strap and change positions along the head strap.

192. The nasal cannula system of claim 191, wherein the cannula further comprises a planar outer surface configured to contact the face of a patient when the first and second prongs are inserted into the nostrils of a patient.

193. The nasal cannula system of claim 191 or 192, wherein the head strap is made of an elastic material and is configured to hold the cannula against the face of a patient.

194. A nasal cannula system, comprising:
a cannula defining a cavity and comprising at least one nasal prong extending from the cannula and in communication with the cavity, the cannula including a first slot and a second slot;
a first frame portion configured to be slidably received by the first slot of the cannula;
a second frame portion configured to be slidably received by the second slot;
at least one head strap coupled to the first and second frame portions and positioned around the head of the patient in use;
wherein the cannula is slidably supported by the first and second frame portions and can be selectively moved relative to the first and second frame portions.

195. The nasal cannula system of claim 194, wherein the cannula includes a side opening configured to receive a supply tube, and the first and second frame portions are configured to allow a tube to pass between them.

196. The nasal cannula system of claim 195, further comprising a tube support member supported by the first and second frame portions and configured to slide relative to the first and second frame portions to position the supply tube relative to the first and second frame portions.

197. The nasal cannula system of any one of claims 194-196, wherein the first and second frame portions have circular cross-sections and the first and second slots are configured to retain the first and second frame portions.

198. The nasal cannula system of any one of claims 194-197, wherein the first frame portion is positioned above the second frame portion and the first and second slots are located on the outer side of the cannula facing away from the patient.

199. The nasal cannula system of any one of claims 194-198, wherein the cannula includes a planar surface facing the face of the patient.

200. A nasal cannula system, comprising:
a cannula defining a cavity and comprising at least one nasal prong extending from the cannula and in communication with the cavity, the cannula including a slot;
a first frame portion configured to be slidably received by the slot of the cannula;
a second frame portion fixedly coupled to the cannula;
a first dial and a second dial, each coupled to both the first frame portion and the second frame portion; and
at least one head strap coupled to the first and second frame portions and positioned around the head of the patient in use;
wherein the cannula is slidably supported by the first frame portion and the dials are configured to rotate to move a section of the second frame portion and the cannula relative to the first frame portion.

201. The nasal cannula system of claim 200, wherein the first and second frame portions are wires coated with a soft material.

202. The nasal cannula system of claim 200 or 201, wherein the second frame portion is located above the first frame portion when the cannula system is worn by a patient.

203. A retention arrangement for a nasal cannula, comprising:
a band configured to extend around the head of a patient;
a first arm pivotally coupled to the band at a first joint;
a second arm pivotally coupled to the first arm at a second joint, the second arm being connectable to a nasal cannula at a third joint;
wherein the first, second and third joints are configured to allow three dimensional movement and are configured to retain the relative position of the band, first arm, second arm, and cannula unless moved by a user.

204. The retention arrangement of claim 203, wherein the band includes a stabilizing portion that is wider than the band and configured to contact the head of a patient.

205. The retention arrangement of claim 203 or 204, wherein the third joint is coupled to the side of a cannula.

206. The retention arrangement of any one of claims 203-205, wherein the first, second and third joints are ball joints.

207. A nasal cannula system, comprising:
a cannula defining a cavity and comprising at least one nasal prong extending from the cannula and in communication with the cavity, the cannula including a slot, the cannula having a clip portion extending from the cannula;
a frame configured to support the cannula and be coupled to a head strap;
wherein the frame includes an opening configured to receive the clip portion of the cannula, the clip portion being movable within the opening so that the cannula can assume different positions relative to the frame while being supported by the frame.

208. The nasal cannula system of claim 207, wherein the cannula is positioned between the frame and the face of a patient when in use.

209. The nasal cannula system of claim 207 or 208, wherein the frame includes at least one pad member arranged to contact the face of a patient when in use.

210. The nasal cannula system of any one of claims 207-209, wherein the interface between the clip portion and the frame opening allows the cannula to be moved laterally and rotated relative to the frame.

211. The nasal cannula system of claim 207, further comprising a head strap coupled to the frame and a tube support member supported by the head strap or frame.

212. A nasal cannula system, comprising:
a cannula defining a cavity and comprising at least one nasal prong extending from the cannula and in communication with the cavity, the cannula having a first end portion and a second end portion;
a first corrugated tube section coupled to the first end portion of the cannula;
a second corrugated tube section coupled to the second end portion of the cannula;
wherein the position of the cannula relative to a patient's face can be adjusted by expanding and compressing the first and second corrugated tube sections.

213. The nasal cannula system of claim 212, further comprising a first non-corrugated tube coupled to the first corrugated tube section and a second non-corrugated tube coupled to the second corrugated tube section.

214. The nasal cannula system of claim 212 or 213, wherein the first and second corrugated tube sections are backed by a head strap.

215. A prong arrangement for a nasal cannula, comprising:
a prong comprising:
a first prong portion comprising a first slot;
a second prong portion comprising a first flange, the second prong portion being coupled to the first prong portion and the first flange extending longitudinally within the first slot;
wherein the first and second prong portions are configured to extend away from a cannula and define a passageway, the first flange being movable within the first slot so that the first prong portion and second prong portion can be moved toward and away from one another to adjust an outer dimension of the prong.

216. The prong arrangement of claim 215, wherein the first and second prong portions each include a sealing member adjacent the cannula and the sealing members overlap each other and are configured to slide relative to one another.

217. The prong arrangement of claim 215 or 216, wherein the prong further comprises a size indicator configured to indicate the relative outer dimensions of the prong.

218. The prong arrangement of any one of claims 215-217, wherein the prong includes a second slot and a second flange, the second flange extending longitudinally within the second slot.

219. The prong arrangement of any one of claims 215-218, wherein the first slot comprises two side walls configured to limit the extent to which the first flange can move within the first slot.

220. A prong arrangement for a nasal cannula, comprising:
a prong comprising:
a first collapsible portion configured to be coupled to a cannula, the first collapsible portion having a first passageway;
a second collapsible portion coupled to the first collapsible portion and having a second passageway; and
a third collapsible portion coupled to the second collapsible portion and having a third passageway;
wherein the first, second and third collapsible portions are configured to collapse and expand telescopically relative to one another so that the height of the prong can be adjusted.

221. The prong arrangement of claim 220, wherein the third collapsible portion includes a top edge that is configured to form a seal with a patient's nostril.

222. The prong arrangement of claim 220 or 221, wherein the outer dimensions of the third collapsible portion are larger than the outer dimensions of the second collapsible portion, and the outer dimensions of the second collapsible portion are larger than the outer dimensions of the first collapsible portion.

223. The prong arrangement of any one of claims 220-222, wherein the first, second and third passageways are coaxial.

224. A prong arrangement for a nasal cannula, comprising:
a cannula defining a cavity, wherein the cannula includes a slot;
a first prong extending from the cannula and fixed relative to the cannula; and
a second prong extending from the cannula through the slot and movable relative to the cannula;
wherein the second prong can be moved within the slot in order to adjust a distance between the first prong and the second prong.

225. The prong arrangement of claim 224, wherein the second prong includes a pin and the slot includes multiple notches, and wherein the notches are configured to receive the pin when the second prong is moved to discrete locations within the slot.

226. The prong arrangement of claim 224 or 225, wherein the second prong includes a rib that extends from the base of the prong and the slot includes multiple grooves configured to receive the rib.

227. The prong arrangement of any one of claims 224-226, wherein the second prong includes a tab having multiple notches that are configured to engage an edge of the slot so that the second prong can be held in multiple discrete positions relative to the slot.

228. A prong for a nasal cannula, comprising:
a film having a substantially cylindrical shape;
a plurality of ribs coupled to the film around the circumference of the film;
wherein the film and ribs expand outward as gas flow increases through the prong, and the outer diameter of the prong increases to form a seal with a patient's nostril.

229. The prong of claim 228, wherein the ribs are substantially fixed and do not bend or move relative to one another.

230. A nasal cannula system, comprising:
a cannula defining a cavity and comprising at least one nasal prong extending from the cannula and in communication with the cavity; and
a support member coupled to the cannula and configured to support the cannula, the support member being configured to extend upward from the cannula and around a patient's nose when in use, wherein the support member contacts a portion above a tip of the patient's nose;
wherein the support member comprises a bendable material that can be shaped to correspond to the shape of the face of a patient.

231. The nasal cannula system of claim 230, further comprising a head strap configured to wrap around the head of a patient, the head strap being removably coupled at one end to the support member and adjustably coupled to the support member at the other end.

232. The nasal cannula system of claim 230 or 231, wherein the bendable material is a metal material and is located at the upper portion of the support member.

233. The nasal cannula system of any one of claims 230-232, wherein the support member includes an attachment portion having multiple notches and the cannula includes an opening configured to receive the attachment portion, and the notches are configured to interact with the opening to couple the support member to the cannula and allow for adjustment of the support member relative to the cannula.

234. The nasal cannula system of any one of claims 230-233, wherein the cannula includes a first tube extending from one side of the cannula and a second tube extending from the other side of the cannula, the support member being coupled to the first and second tubes of the cannula.

235. The nasal cannula system of claim 234, wherein the first tube is supported by a first padded member and the second tube is supported by a second padded member, the first and second padded members being configured to rest against a patient's face.

236. The nasal cannula system of claim 235, further comprising a head strap coupled to the first and second padded members and configured to extend around the head of a patient.

237. The nasal cannula system of any one of claims 234-236, wherein the first tube and the second tube are removable from the cannula so that the cannula can be removed and rotated relative to the rest of the system.

238. A tube arrangement for a nasal cannula system, comprising:
a cannula tube comprising an outer wall and an opening, the tube having a longitudinal axis;
wherein the outer wall comprises a thin material that has been folded or rolled and sealed at an edge.

239. The tube arrangement of claim 238, wherein the outer wall is made of a fabric that provides insulation.

240. The tube arrangement of claim 238 or 239, further comprising a spring extending within the outer wall.

241. The tube arrangement of any one of claims 238-240, wherein the cannula tube is coupled to a connector at its opening and the connector includes a valve.

242. The tube arrangement of any one of claims 238-241, wherein the cannula tube further comprises an extruded tube extending within the outer wall.

243. The tube arrangement of any one of claims 238-242, wherein the outer wall includes a tab having one or more holes configured to be coupled to a head strap.

244. The tube arrangement of any one of claims 238-243, wherein the outer wall is made of an insulating material, a spring extends within the outer wall, and a breathing tube extends within the spring.

245. The tube arrangement of any one of claims 238-244, wherein the outer wall is made of an insulating material and a breathing tube extends within the outer wall, and a spring extends within the breathing tube, and wherein at least a pressure line tube extends within the outer wall in addition to the breathing tube.

246. The tube arrangement of any one of claims 238-245, further comprising a breathing tube within the outer wall, the breathing tube having a cannula portion from which at least one prong extends, the cannula tube being flexible so that it can curve around the face of a patient.

247. The tube arrangement of claim 246, wherein each end of the cannula tube includes a tab with holes configured to receive a pin located on a head strap.

248. The tube arrangement of claim 247, wherein each end of the cannula tube includes a connector configured to receive an inspiratory tube connector, each connector including a valve.

249. The tube arrangement of any one of claims 238-248, wherein the outer wall is made of a breathable material.

250. A tube arrangement for a nasal cannula system, comprising:
a tube comprising an outer wall and an opening, the tube having a longitudinal axis;
wherein the outer wall comprises a thin material that has been folded or rolled, and the outer wall includes one or more cut portions that extend through the material.

251. The tube arrangement of claim 250, wherein the one or more cut portions comprise a tab that can be pulled away from the tube, the tab being configured to engage a support device in order to hang the tube.

252. The tube arrangement of claim 251, wherein the tab includes a hole configured to receive a hook or hanger.

253. The tube arrangement of any one of claims 250-252, wherein the cut portions comprise slots defining a portion of the material that can be pulled away from the tube while remaining connected at two sides, the pulled away material forming a hook portion that can engage a hanger.

254. The tube arrangement of any one of claims 250-253, wherein the cut portions comprise two tabs that can be pulled away from the tube, the ends of the tabs being configured to be coupled together or to another structure.

255. The tube arrangement of claim 250, wherein the tube comprises an inner tube and a spring within the inner tube.

256. A cannula tube arrangement for a nasal cannula system, comprising:
a tube comprising an outer wall, the outer wall comprising a thin film having a first edge and a second edge; the film being folded or rolled and the first and second edges sealed together;
a bead located on the outer wall and configured to provide structural support to the tube.

257. The cannula tube arrangement of claim 256, wherein the bead includes a cannula portion configured to receive a cannula with prongs, the cannula portion including two holes that extend through the film.

258. The cannula tube arrangement of claim 256 or 257, wherein the tube includes a first end and a second end, and the first end and second end are coupled to connectors having valves.

259. The cannula tube arrangement of claim 258, wherein the first and second ends each include a tab having a hole configured to be coupled to a head strap.

260. The cannula tube arrangement of any one of claims 256-259, wherein the first and second edges of the film are heat-sealed to form the tube.

261. The cannula tube arrangement of any one of claims 256-260, wherein the bead is printed onto the outer wall.

262. The cannula tube arrangement of any one of claims 256-260, wherein the bead is extruded onto the outer wall.

263. The cannula tube arrangement of any one of claims 256-262, wherein the bead has a pattern that is configured to create bend areas along the tube length.

264. The cannula tube arrangement of any one of claims 256-260, wherein the bead is on the inside of the tube.

265. The cannula tube arrangement of any one of claims 256-264, wherein the bead comprises thermal and structural elements printed on the film.

266. The cannula tube arrangement of any one of claims 256-265, wherein the first edge overlaps the second edge.

267. The cannula tube arrangement of any one of claims 256-266, wherein the first and second edges extend into the tube.

268. A cannula tube arrangement for a nasal cannula system, comprising:
a tube comprising an outer wall, the outer wall comprising a thin plastic film having a first edge and a second edge;
a substantially planar side wall coupled to the outer wall; and
a bead located on the other wall and configured to provide structural support to the tube;
wherein the first edge is coupled to the side wall and the second edge is also coupled to the side wall so that a cavity exists between the outer wall and the side wall.

269. The cannula tube arrangement of claim 268, wherein the first edge and second edge are heat-sealed to the side wall, and the side wall is made of a fabric material.

270. A cannula tube arrangement, comprising:
a spring having a length and a cross-section having at least one substantially planar side;
a tube surrounding the spring, the tube defining a passageway through which gas can pass; and
at least one nasal prong coupled to the tube and communicating with the passageway.

271. The cannula tube arrangement of claim 270, wherein the spring has a V-shaped or triangular cross-section.

272. The cannula tube arrangement of claim 270 or 271, wherein the spring comprises a thin folded sheet of metal having cut-out portions along the length of the spring.

273. The cannula tube arrangement of any one of claims 270-272, wherein the spring includes a middle section and first and second ends, the cross-section of the middle section being smaller than the cross-section at the first and second ends.

274. The cannula tube arrangement of any one of claims 270-273, wherein the spring is a helical spring having a triangular cross-section.

275. The cannula tube arrangement of claim 274, wherein the spring is a helical wire having bent ends that extend in the direction of a third side.

276. The cannula tube arrangement of any one of claims 270-273, wherein the spring has a substantially triangular cross-section having curved sides.

277. The cannula tube arrangement of any one of claims 270-273, wherein the spring has a cross-section shaped like a half-circle.

278. A cannula breathing tube arrangement, comprising:
a tube made at least in part from a foam material, the tube having a length and a substantially planar side extending along the length of the tube, the tube defining a passageway;
a spring extending through the passageway of the tube and along the length of the tube, the spring being configured to impede kinking of the tube.

279. The cannula breathing tube arrangement of claim 278, wherein the tube includes a cavity extending along the length of the tube and a shapeable rod extending through the cavity.

280. The cannula breathing tube arrangement of claim 278 or 279, wherein the foam material is closed cell foam material.

281. The cannula breathing tube arrangement of any one of claims 278-280, wherein the tube includes a slot extending along the length of the tube, the slot being configured to receive a coupling member.

282. The cannula breathing tube arrangement of claim 281, wherein the coupling member is a mushroom head member configured to slide into the slot.

283. A cannula tube arrangement, comprising:
a tube having a length and a substantially planar side extending along the length of the tube, the tube defining a passageway and having an inner surface;
wherein the tube includes at least one rib located on the inner surface and extending along the length of the tube, the at least one rib being configured to provide structural support and impede kinking of the tube.

284. The cannula tube arrangement of claim 283, wherein the at least one rib comprises multiple ribs on the inner surface.

285. The cannula tube arrangement of claim 283 or 284, wherein the tube comprises a rectangular cross-section and includes a fabric material surrounding the tube.

286. The cannula tube arrangement of claim 283 or 284, wherein the tube has a substantially triangular cross-section.

287. The cannula tube arrangement of claim 283 or 284, wherein the tube has a substantially half-circle cross-section.

288. A cannula tube arrangement, comprising:
a cannula tube defining a passageway and having an end;
a connector coupled to the end of the cannula tube;
a supply tube configured to be coupled to the connector of the cannula tube;
a wire configured to transfer heat extending out of the supply tube;
wherein the cannula tube is configured to receive the wire into the passageway, the wire being configured to transfer heat into the cannula tube.

289. The cannula tube arrangement of claim 288, wherein the wire is insulated and bendable so that it can conform to the shape of the cannula tube.

290. The cannula tube arrangement of claim 288 or 289, wherein the wire is rigid enough to support the cannula tube.

291. A cannula and tube arrangement, comprising:
a cannula tube having a length and defining a passageway;
a heating element extending along the length of the cannula tube and configured to transfer heat to gas passing through the cannula tube;
a cannula comprising at least one nasal prong coupled to the cannula tube.

292. The cannula and tube arrangement of claim 291, wherein the heating element is a coiled wire that extends within the cannula tube.

293. The cannula and tube arrangement of claim 291 or 292, wherein the cannula tube includes an end and an electrical connector is coupled to the end of the cannula tube.

294. The cannula and tube arrangement of claim 293, wherein the electrical connector is also a tube connector configured to attach a second tube to the cannula tube.

295. The cannula and tube arrangement of any one of claims 291-294, wherein the heating element is surrounded by a thin film.

296. The cannula tube arrangement of any one of claims 291-294, wherein the heating element comprises two wires coupled to a conductive polymer, the two wires being configured so that a voltage can be applied through the polymer to generate heat.

297. The cannula tube arrangement of any one of claims 291-296, wherein the heating element is configured to provide structural support to the cannula tube.

298. The cannula tube arrangement of any one of claims 291-297, wherein the heating element is wrapped around the outer surface of the cannula tube.

299. The cannula tube arrangement of any one of claims 291-298, wherein the heating element comprises a film having a conductive strip, the film being wrapped around the cannula tube, and the conductive strip being configured to generate heat when a current is passed therethrough.

300. The cannula tube arrangement of any one of claims 291-299, wherein the heating element is made from positive temperature coefficient material configured so that its resistance increases with temperature so that a constant voltage power supply can be used to power the heating element.

301. The cannula tube arrangement of any one of claims 291-300, wherein the cannula tube is made of a flexible and light material, the cannula tube being coupled to a connector, the connector being coupled to a tube that is less flexible and heavier than the cannula tube, the heating element extending along substantially the entire length of the cannula tube and the tube.

302. The cannula tube arrangement of claim 301, wherein the connector includes an opening configured to receive a temperature sensor.

303. The cannula tube arrangement of claim 302, wherein the cannula tube is configured to removably attach to the cannula.

304. A cannula tube arrangement, comprising:
a cannula tube having a length and defining a first passageway, the cannula tube having an outer surface; and
a spiral tube wrapped around the outer surface of the cannula tube, the spiral tube defining a second passageway and having an inner wall adjacent the cannula tube and an outer wall facing away from the cannula tube;
wherein a first opening extends through the cannula tube and through the inner wall of the spiral tube so that gas flowing inside the cannula tube can enter the spiral tube through the first opening.

305. The cannula tube arrangement of claim 304, wherein the spiral tube includes a second opening extending through the outer wall of the spiral tube so that gas flowing in the spiral tube can escape into the surrounding environment.

306. The cannula tube arrangement of claim 305, wherein the second opening is positioned at an opposite end of the cannula tube from the first opening.

307. A cannula tube arrangement, comprising:
a cannula tube having a length and defining a passageway, the cannula tube having an outer portion;
wherein the outer portion comprises a textile material and a heating element knitted or woven into the textile material, the heating element being configured to transfer heat to a gas passing through the passageway.

308. The cannula tube arrangement of claim 307, wherein the heating element is a wire configured to generate heat when electrical current is passed therethrough.

309. The cannula tube arrangement of claim 307 or 308, wherein the heating element is made of a semi-rigid material that provides structural support to the cannula tube.

310. A manifold for a cannula assembly, comprising:
a manifold body comprising:
a connector portion having an inlet opening and being configured to receive a tube;
a port configured to assist in measuring the pressure of the gas flow; and
an outlet portion configured to be in communication with the port and configured to be coupled to a pressure sensor.

311. The manifold of claim 310, wherein the port is a static pressure port positioned on an inner wall of the manifold that is substantially parallel to the bulk flow direction of the gas within the manifold.

312. The manifold of claim 310 or 311, wherein the port is a total pressure port that is directed towards the bulk flow direction and is configured to measure a combination of the static and dynamic pressure.

313. The manifold of any one of claims 310-312, wherein the port includes a shroud and is directed towards the bulk flow direction.

314. The manifold of any one of claims 310-313, wherein the port includes a static source port or a pitot-static tube.

315. A nasal cannula assembly, comprising:
a cannula defining a cavity and comprising a first nasal prong and a second nasal prong extending from the cannula and in communication with the cavity, the cannula including an opening;
a valve supported within the opening and configured to form a seal when nothing is inserted therethrough;
wherein the cannula and valve are configured so that a tube can extend through the valve, into the cavity, and through the second nasal prong.

316. The nasal cannula assembly of claim 315, wherein the valve is a located substantially below the second prong.

317. The nasal cannula assembly of claim 315 or 316, wherein the valve in configured to form a seal around a tube extending therethrough.

318. The nasal cannula assembly of any one of claims 315-317, wherein the valve is a duck bill valve.

319. The nasal cannula assembly of claim 315, further comprising a removable cover coupled to the outer surface of the cannula and covering the opening.

320. The nasal cannula assembly of claim 315, wherein the cannula includes two openings and two corresponding valves and each of the valves are configured to receive either a cannula tube or a nasogastric tube.

321. The nasal cannula assembly of claim 320, wherein the cannula includes a first side and a second side, and one of the valves is located on each of the first and second sides.

322. The nasal cannula assembly of claim 315, wherein the second prong is removable from the cannula.

323. A nasal cannula assembly, comprising:
a cannula defining a cavity and comprising a first nasal prong extending from the cannula and in communication with the cavity, the cannula including first groove and the first prong including a second groove;
wherein the first groove is aligned with the second groove so that a portion of a tube can extend through the first and second grooves and is directed into a nostril of a patient.

324. The nasal cannula assembly of claim 323, wherein the first and second grooves are configured to accommodate a nasogastric tube.

325. The nasal cannula assembly of claim 323 or 324, wherein the first prong includes an outer surface and the second groove is located on the outer surface of the first prong and extends longitudinally relative to the first prong.

326. The nasal cannula assembly of any one of claims 323-325, wherein the cannula includes a second prong and a third groove, the second prong including a fourth groove, and the third and fourth grooves are aligned so that a portion of a tube can extend through the third and fourth grooves and is directed into a nostril of a patient.

327. A nasal cannula, comprising:
a nasal prong having an outer wall and an end, the outer wall including a cut portion defining a flap that can be pushed into the prong to form an opening in the outer wall of the prong, the opening being configured to receive a tube so that the tube can extend through the opening and out of the end of the prong.

328. The nasal cannula of claim 327, wherein the outer wall defines a passageway, and the flap is configured to block the passageway when a tube is inserted through the opening.

329. The nasal cannula of claim 327 or 328, wherein the flap is configured to align with and form at least a substantial seal with the outer wall when a tube is not inserted through the opening.

330. The nasal cannula of any one of claims 327-329, wherein the prong also includes slit that extends from the cut portion to the end of the prong, the slit being configured to allow a tube to selectively pass through the slit.

331. A nasal cannula assembly, comprising:
a cannula defining a cavity and comprising a first nasal prong extending from the cannula and in communication with the cavity, the cannula including an opening and a valve supported within the opening;
an inner member supported within the cavity and movable relative to the cannula, the inner member including a hole configured to receive a tube;
wherein the opening is positioned substantially below the first nasal prong and the inner member can be moved so that the hole is aligned with the valve so that a tube can extend through the valve and the hole and into the first prong.

332. The nasal cannula assembly of claim 331, wherein the cannula includes a second opening having a second valve positioned substantially below a second nasal prong, and the inner member includes a second hole that can be aligned with the second valve and second prong.

333. The nasal cannula assembly of claim 331 or 332, wherein the inner member is substantially cylindrical and is configured to be coupled to a supply tube.

334. The nasal cannula assembly of any one of claims 331-333, wherein the valve is configured to form a seal when nothing is extended therethrough.

335. A nasal cannula assembly, comprising:
a cannula body having a first slot and a second slot;
a first sliding portion having a first prong coupled to a first tube; and
a second sliding portion having a second prong coupled to a second tube;

wherein a portion of the first sliding portion is configured to slide within the first slot and a portion of the second sliding portion is configured to slide within the second slot, the first and second prongs being movable relative to the cannula body so that each of the first and second prongs can be adjusted relative to the cannula body.

336. The nasal cannula assembly of claim 335, wherein the first slot and the second slot extend substantially horizontally and are positioned side by side on the cannula body.

337. A nasal cannula assembly, comprising:
a cannula defining a cavity and comprising a first nasal prong extending from the cannula and in communication with the cavity; and
a slider member engaging an outer surface of the cannula, the slider member being configured to move relative to the cannula;
wherein the slider member is configured to selectively move along the outer surface of the cannula and over the first nasal prong.

338. The nasal cannula assembly of claim 337, wherein the slider member includes a groove configured to receive a portion of a tube.

339. The nasal cannula assembly of claim 337 or 338, wherein the first nasal prong is flexible and can fold under the slider member when the slider member is moved to cover the first nasal prong.

340. A nasal cannula assembly, comprising:
a cannula defining a cavity and comprising a single nasal prong extending from the cannula and in communication with the cavity; and
a strap configured to support the prong and engage the face of a patient, the strap including an adhesive material configured to selectively couple the strap to a patient's face;
wherein the strap includes an opening through which the prong extends and the strap is configured to extend from under the patient's nose upward along the sides of the patient's nose.

341. The nasal cannula assembly of claim 340, wherein the strap includes at least one slot configured to receive a tube.

342. The nasal cannula assembly of any one of claims 340-341, wherein the strap includes holes positioned to align with a nostril of a patient when the strap is in use.

343. The nasal cannula assembly of any one of claims 340-342, wherein the prong includes corrugations configured to allow the prong to bend and change shape.

344. The nasal cannula assembly of any one of claims 340-343, wherein the prong includes a tapered base portion that is configured to form a seal with a patient's nostril.

345. The nasal cannula assembly of any one of claims 340-344, wherein the cannula is coupled to a tube and the tube includes a support member configured to support the tube and be selectively coupled to the face of a patient.

346. The nasal cannula assembly of claim 345, wherein the support member also includes a support portion configured to receive and support a nasogastric tube.

347. The nasal cannula assembly of claim 345, further comprising a cheek pad configured to adhere to a patient's cheek and be selectively coupled to the support member.

348. The nasal cannula assembly of any one of claims 340-347, wherein the prong includes a tapered base portion that is narrower toward the top and wider toward the bottom, and the prong includes a recess below the tapered portion and the recess is configured to retain the portion of the strap adjacent the opening.

349. A nasal cannula assembly, comprising;
a cannula defining a cavity and comprising a single nasal prong extending from the cannula and in communication with the cavity; and
a frame having a bridge portion that extends away from the face of a patient and creates a space between the bridge portion and the patient's face, the bridge portion being configured to support the cannula, the bridge portion including a slot and a portion of the cannula can move within the slot;
a tube coupled to the cannula and extending from a bottom portion of the cannula;
wherein the tube is configured to extend from under the cannula and bend upward so that it extends over the frame.

350. The nasal cannula assembly of any one of claims claim 349-349, wherein the cannula is supported by the frame and positioned substantially within the space between the bridge portion and the patient's face when the cannula assembly is in use.

351. The nasal cannula assembly of any one of claims 349-350, wherein the bridge portion of the frame includes cut out portions configured to receive a portion of the tube.

352. The nasal cannula assembly of any one of claims 349-351, cannula includes a grip portion that extends through the slot.

353. The nasal cannula assembly of any one of claims 349-352, wherein the frame includes a pad configured to contact the face of a patient when in use.

354. The nasal cannula assembly of any one of claims 349-353, wherein the frame includes one or more openings configured to receive a head strap.

355. The nasal cannula assembly of any one of claims 349-354, wherein the bridge portion includes a tubing arm that at least partially defines a tubing recess through which the tube can extend.

356. A nasal cannula assembly, comprising:
a cannula frame having an upper extension portion, the upper extension portion having a single prong and a prong opening in communication with the prong;
a retainer portion coupled to the extension portion and having a retainer opening aligned with the prong opening; and
a manifold pivotally coupled to the retainer portion, the manifold having a manifold opening aligned with the retainer opening and the prong opening;
wherein the manifold is configured to pivot relative to the cannula frame about the axis of the manifold opening, and gas can pass through the manifold and into the prong.

357. The nasal cannula assembly of claim 356, wherein the cannula frame includes a lower extension portion and the retainer portion includes a lower portion that engages a bottom portion of the manifold.

358. The nasal cannula assembly of claim 357, wherein the bottom portion of the manifold includes a pin and the lower portion of the retainer portion includes a hinge recess, the pin being configured to be received within the hinge recess, and the manifold configured to pivot about the pin.

359. The nasal cannula assembly of claim 356, wherein the manifold is configured to rotate about 180 degrees relative to the cannula frame so that tubing coupled to the manifold can exit in an opposite direction.

360. A nasal cannula assembly, comprising:
a cannula frame having an upper extension portion, the upper extension portion having a single prong and a prong opening in communication with the prong, the upper extension portion having a bottom side;

a tube rotatably coupled to the bottom side of the upper extension portion and in communication with the prong so that gas can pass from the tube through the prong opening and into the prong;

wherein the tube is configured to bend and rotate relative to the cannula frame.

361. A nasal cannula assembly, comprising:

a cannula defining a cavity and comprising a single nasal prong extending from the cannula and in communication with the cavity;

a cable configured to slidably support the cannula, a tube coupled to the cannula and configured to provide gas to the cavity;

wherein the position of the cannula can be adjusted by sliding the cannula along the cable.

362. The nasal cannula assembly of claim 361, wherein the tube is tapered so that its cross-section is narrower closer to the cannula.

363. The nasal cannula assembly of claim 361 or 362, further comprising an attachment portion coupled to the cable and configured to receive a portion of the tube.

364. The nasal cannula assembly of any one of claims 363-363, wherein the tube includes an attachment member that is configured to engage and be coupled to the attachment portion.

365. The nasal cannula assembly of any one of claims 363-364, wherein the tube has a tapered diameter and the attachment portion is configured to couple the tube with a second tube having a constant diameter.

366. The nasal cannula assembly of any one of claims 361-365, wherein the cable includes indent portions configured to retain the cannula in a selected position.

367. A nasal cannula assembly, comprising:

a cannula frame having a bridge portion that extends away from the face of a patient and creates a space between the bridge portion and the patient's face, the bridge portion supporting a single nasal prong;

a first tube coupled to the prong and extending downward from the prong;

wherein the cannula frame defines a recess through which a second tube can extend between the bridge portion and a patient's face when in use.

368. The nasal cannula assembly of claim 367, wherein the bridge portion includes a cut-out portion configured to receive a portion of the first tube, causing the tube to bend and extend away from the assembly to the side of a patient.

369. The nasal cannula assembly of claim 367 or 368, wherein the cannula frame includes a contact portion that is configured to contact the face of a patient and comprises a soft material.

370. A nasal cannula assembly, comprising:

a cannula defining a cavity and comprising a single nasal prong extending from the cannula and in communication with the cavity, the cannula having a cannula opening in communication with the cavity, the opening having an axis;

a manifold pivotally coupled to the cannula and configured to pivot about the axis of the cannula opening;

a tube coupled to the manifold and configured to supply gas to the manifold;

wherein the manifold includes a manifold opening aligned with the cannula opening and in communication with the cavity.

371. The nasal cannula assembly of claim 370, wherein the cannula includes frame portions extending outward from the cannula and the frame portions form one or more recesses between the cannula and the face of a patient when in use, the one or more recesses being configured to receive a second tube.

372. The nasal cannula assembly of claim 370 or 371, wherein the cannula includes a soft material on the side of the cannula facing a patient when in use.

373. The nasal cannula assembly of any one of claims 370-372, wherein the cannula includes a recess on each side of the prong so that a second tube can extend between the manifold and the cannula.

419. A headgear for a patient interface comprising:

a stretch region, a non-stretch region, wherein said stretch region located sufficiently away from a tube loading region.

420. A headgear, interface and tube assembly comprising, at least one stretch region, at least one non-stretch region, said stretch region located sufficiently away from a tube loading region, said stretch-region located at the back a user's head in use, wherein the tube is configured to be attached to either side of the interface.

421. A headgear, interface and tube assembly comprising, at least one stretch region, at least one non-stretch region, said stretch region located sufficiently away from a tube loading region, where the tube loading region is a region that the tube is tethered to the headgear or interface.

422. A nasal cannula system comprising:

a cannula body defining an open cavity and comprising at least one nasal prong extending from the cannula in communication with the cavity; and a manifold comprising a manifold body capable of accepting a gases supply tube, the manifold body capable of being attached to the cannula in a first position and a second position, wherein the second position is different to the first position;

wherein the ends of the manifold body protrude into the open cavity of the cannula body, and the cannula body comprises a recess for retaining the manifold body.

423. The nasal cannula system of claim 422, wherein the manifold comprises a first side portion and a second side portion, where the first and second side portions extend from the manifold body and are adapted to be attached to headgear.

424. The nasal cannula system of claim 422 or 423, wherein the recess of the cannula body retains the first and second side portions of the manifold.

425. The nasal cannula system of any one of claims 422-424, wherein one end of the manifold comprises a cap comprising a hinged area which divides the cap into inner and outer regions connected by a band, and wherein the hinged area permits relative motion between the inner and outer regions at the band.

426. A nasal cannula comprising:

a cannula body defining an open cavity and comprising at least one (and preferably a pair of) nasal prong(s) extending from the cannula in fluid communication with the open cavity; and a manifold comprising a manifold body capable of engaging with the cannula for fluid connection with the open cavity, the manifold body orientable in either of a first operational position or a second operational position, wherein the first operational position and second operational position are different to each other, wherein the manifold body is adapted to accept a gases supply conduit at a first end of, or a gases inlet to, the manifold body, the first end adapted to engage with one end of the open cavity for delivery of gases into the open cavity, and a second end of the manifold body adapted to form a seal or connection with an other end of the open cavity, the manifold body forming an enclosure to the open cavity.

427. The cannula as claimed in claim 426, wherein the cannula body comprises at least one recess or at least one surface relief or region of surface relief for retaining the manifold body in an engaged either of the first operational position or the second operational position.

428. The cannula as claimed in claim 426 or 427, wherein the first end and the second end of the manifold body are connected to each other, the first end providing for a gases inlet to the open cavity and the second end providing for a plug or cap to substantially enclose the open cavity and provide for a fluid delivery pathway of supplied gases from the first end of the manifold body into the open cavity and to a terminal end of the at least one nasal prong.

429. The cannula as claimed in any one of claims 426-428, wherein the first and second ends of the manifold body are integrally formed.

430. The cannula as claimed in any one of claims 426-429, wherein the first and second ends of the manifold body are connected to each other by a connecting portion or connecting portions.

431. The cannula as claimed in claim 430, wherein the connecting portion is one or more of at least one arm or at least one finger or at least one frame member.

432. The cannula as claimed in claim 430 or 431, wherein the connecting portion or the cannula body defining at least in part the open cavity, or both, comprise an alignment feature adapted to enable a predetermined geometric orientation of the manifold body relative to the cannula body.

433. The cannula as claimed in claim 432, wherein the alignment feature may be a region or regions of associated male and female parts or region or regions of associated surface relief.

434. The cannula as claimed in claim 432 or 433, wherein the alignment feature is adapted to provide for an audible response to an engagement of the manifold with the cannula body when in an engaged operational first position or an engaged operational second position.

435. The cannula as claimed in any one of claims 426-434, wherein a connecting portion of the manifold body connecting the first and second ends to each other extends through an internal region of the open cavity, such that, in-situ, the first end of the manifold body is adapted to engage with one end of the open cavity for delivery gases into the open cavity, and the second end of the manifold body is adapted to form a seal or connection with the other end or any remaining portion of the open cavity requiring sealing to enable the delivery of gases to the open cavity.

436. The cannula as claimed in claim 435, wherein the connecting portion extending through the internal region of the open cavity is shaped or configured to engage with, or be received by, an associated surface or region of the cannula body or an associated surface or region of the cannula body defining the open cavity.

437. The cannula as claimed in any one of claims 426-434, wherein a connecting portion of the manifold body connecting the first and second ends to each other extends about an external surface or exterior region of the cannula body defining at least in part the open cavity, such that, in-situ, the first end of the manifold body is adapted to engage with one end of the open cavity for delivery gases into the open cavity, and the second end of the manifold body is adapted to form a seal or connection with the other end or any remaining portion of the open cavity requiring sealing to enable the delivery of gases to the open cavity.

438. The cannula as claimed in claim 437, wherein the connecting portion extending about the external surface or exterior region of the cannula body is shaped or configured to engage with, or be received by, an associated surface or region of the cannula body or an associated surface or region of the cannula body defining the open cavity.

439. The cannula as claimed in any one of claims 426-438, wherein a gas supply conduit is positioned or located substantially about a side or region of the cannula body from which the first end of the manifold body is positioned or projects from the cannula body.

440. The cannula as claimed in any one of claims 426-439, wherein the manifold is orientable with respect to the cannula body, such that a gas supply tube is, in-use, substantially positioned or located to one side of a user.

441. The cannula as claimed in any one of claims 426-440, wherein a first operational position allows for the first end of the manifold body to be located to either a left-end or a right-end of the cannula body defining the open cavity, and wherein a second operational position allows for the first end of the manifold body to be located to either a respective right-end or a respective left-end of the cannula body defining the open cavity.

442. The cannula as claimed any one of claims 426-441, wherein the first operational position or the second operational position enable for connection of a gases supply conduit to the first end of the manifold body from either a left or a right side.

443. The cannula as claimed any one of claims 426-442, wherein the cannula body further comprises side arms or side portions extending away from the cannula body defining the open cavity, in-use, each of the side arms or side portions are adapted to extend at least in part along a portion of a user's face.

444. The cannula as claimed any one of claims 426-443, wherein the nasal cannula as defined above comprises a first section formed from a first material and a second section formed from a second material, wherein the first section is relatively softer than the second section.

445. The cannula as claimed in any one of claims 426-443, wherein the cannula is further defined by any one of claims 374-418.

446. The cannula as claimed in any one of claims 426-445, wherein a terminal end of the side arms adapted to accept connection thereto with a headgear.

447. The cannula as claimed in any one of claims 426-446, wherein the headgear may be that as described in this specification.

448. A connector for connecting a breathing tube to a device (such as a humidifier or ventilator or other source of gases), or for connecting to at least another breathing tube, the connector comprising:
an inner body and an outer body,
each of the inner body and outer body having a first end and a second end,
the first end of the inner and outer bodies for receiving a terminal end of a first breathing tube, and the second end of the inner and outer bodies for connecting to: a further component, such as for example a breathable tube, or a device (e.g. such as a humidifier, or a ventilator or a source of gases),
wherein the first end of the inner body receives and fluidly connects with the terminal end of the first breathing tube, the inner body providing a lumen for fluid connection between the first end and the second end of said inner body, and wherein the inner body is rotatable relative to the outer body.

449. The connector as claimed in claim 448, wherein the inner body is adapted to swivel relative to the outer body.

450. The connector as claimed in claim 448 or 449, wherein the outer body may comprise one or more surface relief features.

451. The connector as claimed in claim 450, wherein the surface relief features are provided, in use, as finger grips for a user.

452. The connector as claimed in any one of claims 448-451, wherein the second ends of the inner body and/or the outer body are adapted to provide a connection system for connecting with another breathing tube or with a device (e.g. such as a humidifier, or a ventilator or a source of gases).

453. The connector as claimed in any one of claims 448-452, wherein the terminal end of the first breathing tube connected to the first end of the inner body may be, in use, longitudinally rotatable with respect to the outer body.

454. The connector as claimed in any one of claims 448-453, wherein the inner body is sleeved with respect to the outer body.

455. The connector as claimed in any one of 448 to 454, wherein the second end of the outer body is adapted to connect to the further component, the outer body being non-swivelable relative to a connection being made with the further component, for example at a machine end of a breathing circuit.

456. The connector as claimed in any one of claims 448-454, wherein the connector as defined above may be provided as a connector for use with a gas supply tube for a nasal cannula or other patient interface as shown or described in this specification.

457. A patient interface, such as a nasal cannula, comprising a gases delivery mechanism (such as one or a pair of nasal prongs to engage with the nare or nares of a user's nose), and a body from which the gases delivery mechanism is associated, and extending from the body is a pair of side arms, the body and side arms being connected in a manner such that application of a tension to the side arms directs the gases delivery mechanism to move away from a position otherwise imposing upon a user's nasal spine.

458. A nasal cannula, comprising a cannula body from which a nasal prong or a pair of nasal prongs extend to engage with the nare(s) of a user, and from which a pair of side arms extends outwardly and to which a headgear system is connectable, the cannula body being substantially conformable to a user's face yet providing sufficient rigidity so that, in-use, a force or a tension applied to outer-more portions of the side arms directs or encourages the nasal prong or nasal prongs to impose less upon a user's nasal spine region.

459. The interface or nasal cannula as claimed in claim 457 or 458, wherein a continuous section of material extends along each side arm and connects, or is mechanically coupled, in a region of the nasal prong or nasal prongs.

460. The interface or cannula as claimed in claim 459, wherein the continuous section of material is a material capable of translating an applied force or tension from the side arms to the region of the nasal prong or nasal prongs.

461. The interface or cannula as claimed in any one of claims 457-460, wherein each of the side arms define a pre-form or shape such that, before application of a force or a tension from a headgear, the side arms curve outwardly away from the face of the user, extending more outwardly so as the side arms extend further away from a gas delivery mechanism of the interface or from a nasal prong or a pair of nasal prongs.

462. The interface or cannula as claimed in any one of claims 457-461, wherein each of the side arms is substantially in contact with a user's face as the arms extend outwardly away from the gas delivery mechanism or nasal prong or pair of nasal prongs, with each of the side arms becoming less in contact or more distant (or both) from a user's face the further the arms extend from the gas delivery mechanism or nasal prong or pair of nasal prongs.

463. The interface or cannula as claimed in any one of claims 457-462, wherein the side arms define a pre-form or shape such that, in-use, application of a force or a tension to the side arms via the headgear encourages (or directs) the side arms to more into a position of greater facial contact with the user's face or cheeks and the body is encouraged (or directed) to move into a position less engaged with, or imposing upon, or further away from, the user's nasal spine region.

464. The interface or cannula as claimed in any one of claims 457-463, wherein the side arms are configured to, in-use, encourage the translation or location or re-locating or distribution or re-distribution of a force or a tension being applied by a headgear to a nasal cannula, to a user's cheeks and away from the user's nasal spine region or away from the force or tension being applied to the user's nasal spine region.

465. The interface or cannula as claimed in any one of claims 457-464, wherein each of the side arms are pre-formed or shaped such that, in-use, application of a force or a tension to the side arms, requires the side arms, or at least portions of the side arms, to move closer to a user's face, a hinging or flexing point (or point of flexure) of the side arm upon a user's face being established upon a cheek region, and the nasal prong or nasal prongs or another gases delivery mechanism being encouraged away from imposing upon a user's nasal spine region.

466. The interface or cannula as claimed in any one of claims 457-165, wherein the hinging or flexing point (or point of flexure) being established in-use, is a region at or about any one or more of the user's left or right (or both): lower outer maxilla, upper outer maxilla, zygomatic arch, maxilla recess (or below the zygomatic arch).

1a. A nasal cannula assembly comprising:
a cannula part comprising a pair of tubular nasal prongs for insertion into the nares of a patient, and a manifold in fluid communication with the nasal prongs, the manifold comprising an aperture at left hand end of the manifold and an aperture at the right hand end of the manifold,
a connector adapted to receive an end of a gases flow conduit and be removably received in the aperture at left hand end of the manifold and the aperture at the right hand end of the manifold, and
a plug adapted to be removably received in the aperture at left hand end of the manifold and the aperture at the right hand end of the manifold,
in use the connector or the plug fitted to one of the apertures at the left and right sides of the manifold, and the plug fitted to the other one of the apertures at the left and right sides of the manifold to configure the conduit to extend from either the left side or right side of the nasal cannula assembly.

2a. A nasal cannula assembly as claimed in claim 1a wherein the plug and connector are separate parts.

3a. A nasal cannula assembly as claimed in claim 1a wherein the plug and connector are coupled or attached together by a lateral member to form a clip.

4a. A nasal cannula assembly as claimed in claim 3a wherein the clip is an integrally formed unitary member.

5a. A nasal cannula assembly as claimed in claim 3a or 4a wherein the clip and cannula part are complimentary adapted so that in use the lateral member is elastically deflected to fit the clip to the cannula part.

6a. A nasal cannula assembly as claimed in claim 3a or 4a wherein the clip is fitted to the cannula part by pushing the clip onto the cannula part in a direction perpendicular to a lateral direction of the cannula.

7a. A nasal cannula assembly as claimed in any one of claims 3a to 6a wherein the cannula part comprises a rigid member for interfacing with the clip and the prongs are formed of a resilient material attached to the rigid member.

8a. A nasal cannula as claimed in claim 7a wherein the rigid member and the lateral member are adapted so that the lateral member is flexed to spread the plug and connector apart when attaching the clip to the cannula part.

9a. A nasal cannula assembly as claimed in claim 4a wherein the clip is substantially 'C' or 'U' shaped.

10a. A nasal cannula assembly as claimed in any one of claims is to 9a wherein the plug and connector each extend into the aperture at the ends of the manifold.

11a. A nasal cannula assembly as claimed in claim 4a wherein the clip provides a positive force against the manifold to grip the manifold between the plug and the connector.

12a. A nasal cannula assembly as claimed in claim 4a wherein the cannula part comprises a recessed portion that is sized and shaped to receive the lateral member.

13a. A nasal cannula assembly as claimed in any one of claims 1a to 12a wherein the cannula part comprising the manifold and nasal prongs is integrally formed.

14a. A nasal cannula assembly as claimed in claim 7a wherein the resilient material is over moulded to the rigid member.

15a. A nasal cannula assembly as claimed in claim 14a wherein the cannula part comprises side arms and the rigid member extends along the side arms.

16a. A nasal cannula assembly as claimed in claim 15a wherein the rigid part comprises through holes in the side arms for the resilient material to extend through by an over moulding process or assembly process.

17a. A nasal cannula assembly as claimed in claim 7a wherein the rigid member comprises a recessed portion that is sized and shaped to receive the lateral member.

18a. A nasal cannula assembly as claimed in claim 7a wherein the apertures at the ends of the manifold are formed in the rigid member.

19a. A nasal cannula assembly as claimed in claim 3a wherein the lateral member is length adjustable.

20a. A nasal cannula assembly as claimed in claim 3a wherein the clip comprises a first part and a second part, the first part comprises one of the plug and the connector and the second part comprises the other one of the plug and the connector, the first part comprises a first lateral member and the second part comprises a second lateral member, and the first and second lateral members coupled together in a telescoping arrangement and comprising complementary features to set the lateral distance between the plug and the connector.

21a. A nasal cannula assembly as claimed in claim 20a wherein the complementary features comprise a projection on one of the first and second parts and a corresponding aperture in the other one of the first and second parts, the projection being received in the aperture to set the lateral distance between the plug and the connector.

22a. A nasal cannula assembly as claimed in claim 21a wherein one of the first and second parts comprises a plurality of corresponding apertures, the projection being received in the one of the plurality of apertures to set the lateral distance between the plug and the connector, the plurality of apertures providing for a range of cannula part sizes.

23a. A nasal cannula assembly as claimed in claim 4a wherein the clip is movably attached to the cannula part.

24a. A nasal cannula assembly as claimed in claim 23a wherein the clip is rotationally coupled to the cannula part.

25a. A nasal cannula assembly as claimed in claim 24a wherein the clip is rotationally coupled to the cannula part on a rotational axis on or parallel to the sagittal plane of the cannula to position the conduit to the left or right side of the nasal cannula assembly.

26a. A nasal cannula assembly as claimed in claim 25a wherein the manifold is formed of a relatively rigid material, and the cannula part comprises a resilient material moulded over the manifold, the nasal prongs integrally formed with the resilient material, and the cannula part comprises an axle extending from the manifold, and the clip rotationally mounted on the axle.

27a. A nasal cannula assembly as claimed in claim 26a wherein the axle is integrally formed with the manifold.

28a. A nasal cannula assembly as claimed in claim 26a wherein the clip comprises a keyway so that the clip can be removably mounted to the cannula part.

29a. A nasal cannula assembly as claimed in any one of claims 26a to 28a wherein cannula part comprises a flange at the end of the axle to retain the clip on the axle in a direction along the rotational axis.

30a. A nasal cannula assembly as claimed in any one of claims 26a to 29a wherein ends of the manifold are curved with a centre of curvature on the rotational axis, and the plug and the connector each have a complementary curvature so that the clip can rotate on the rotational axis to position the connector at either end of the manifold.

31a. A nasal cannula assembly as claimed in claim 30a wherein the over moulded resilient material covers ends of the manifold to provide a seal with the plug and connector.

32a. A nasal cannula assembly as claimed in claim 3 wherein the clip is fitted to the cannula part by pushing the clip laterally into the manifold via one of the aperture at the left hand end and the aperture at the right hand end so that the connector is received in one of the aperture at the left hand end and the aperture at the right hand end and the plug is received in the other one of the aperture at the left hand end and the aperture at the right hand end to configure the conduit to extend from either the left side or right side of the nasal cannula assembly.

33a. A nasal cannula assembly as claimed in claim 32a wherein the cannula part comprises a rigid member for interfacing with the clip and the prongs are formed of a resilient member attached to the rigid member, and the cannula part and the rigid member each comprise side arms extending laterally from the manifold.

1b. A nasal cannula assembly comprising:
a cannula part comprising a pair of tubular nasal prongs for insertion into the nares of a patient,
a connector adapted to receive an end of a gases flow conduit,
a manifold attached to or integrally formed with the connector, the connector providing inlet to the manifold and the manifold having at least one outlet, the cannula part movably attached to the manifold to be attached to the manifold in two orientations to configure the conduit to extend from either the left side or right side of the nasal cannula assembly.

2b. A nasal cannula assembly as claimed in claim 1b wherein the cannula part is rotatable relative to the manifold about a substantially vertical axis.

3b. A nasal cannula assembly as claimed in claim 2b wherein the manifold comprises an open top that is the manifold outlet, and the cannula part fits over the open top so that the prongs are in communication with the connector.

4b. A nasal cannula assembly as claimed in any one of claims 1b to 3b where the manifold comprises a lip on a surface of the manifold to which the cannula part connects.

5b. A nasal cannula assembly as claimed in any one of claims 1b to 4b wherein an axle extends from the manifold or the cannula part and the cannula part rotates relative to the manifold on the axle.

1c. A nasal cannula assembly comprising:
a cannula part comprising a pair of tubular nasal prongs for insertion into the nares of a patient, and a left and a right lateral side arm for attaching headgear,
a first conduit for providing as flow of gas to one said nasal prong and a second conduit for providing a flow of gas to the other said nasal prong,
a first joint connecting the first conduit to one said nasal prong and a second joint connecting the second conduit to the other said nasal prong, the joints adapted to allow the first and second conduits to be routed to a left side or a right side of the nasal cannula assembly, and
a left clip on the left lateral side arm and a right clip on the right lateral side arm,
in use the first conduit being held by the left clip or the right clip to configure the first conduit to extend from either the left side or right side of the nasal cannula assembly, and the second conduit being held by the left clip or the right clip to configure the second conduit to extend from either the left side or right side of the nasal cannula assembly.

2c. A nasal cannula assembly as claimed in claim is wherein the cannula part is an integrally formed part.

3c. Nasal cannula assembly as claimed in claim is or 2c wherein each joint is a flexible tube adapted to bend at least 90 degrees in any direction without substantial occlusion.

4c. A nasal cannula assembly as claimed in claim 3c wherein flexible tubes comprise circumferentially extending ribs so that bending of the flexible conduit section does not cause the flexible conduit section to collapse.

5c. A nasal cannula assembly as claimed in claim 1c or 2c wherein each joint is a swivel joint.

6c. A nasal cannula assembly as claimed in claim 5c wherein each swivel joint rotates on an axis that is at an angle to an axis of the corresponding nasal prong so that rotation of the swivel joint allows both conduits to be routed to the left side or the right side without overlapping.

7c. A nasal cannula assembly as claimed in claim 5c or 6c wherein each swivel joint is a swivel elbow.

8c. A nasal cannula assembly as claimed in any one of claims 1c to 7c wherein each said clip comprises two channels or receptacles each for receiving one of the tubes.

9c. A nasal cannula assembly as claimed in any one of claims 1c to 8c wherein each flexible tube is integrally formed with a nasal prong.

10c. A nasal cannula assembly as claimed in any one of claims 1c to 9c wherein each clip is integrally formed with a said side arm.

11c. A nasal cannula system comprising a nasal cannula assembly as claimed in any one of the preceding claims and a headgear attached to the nasal cannula assembly for attaching the nasal cannula assembly to a patient's head.

12c. A system for providing a flow of respiratory gases to a user or patient comprising a blower, a humidifier, the conduit and a nasal cannula system as claimed in claim 11c.

1d. A headgear comprising:
a strap, each end of the strap adapted to be attached to a patient interface and extend around a patient's head to hold the patient interface in place on a patients face, wherein
at least a portion of the strap is configured to bifurcate into more than one band to extend around the patients head.

2d. A headgear as claimed in claim 1d wherein the strap comprises a longitudinal frangible section extending along a portion of the strap to be torn by a user to separate the portion of the strap into more than one band.

3d. A headgear as claimed in claim 2d wherein the frangible section comprises a relatively thin section.

4d. A headgear as claimed in claim 3d wherein the frangible section is a perforated section.

5d. A headgear as claimed in any one of claims 2d to 4d wherein the bands are separated by the frangible section.

6d. A headgear as claimed in any one of claims 2d to 5d wherein the strap comprises a finger hole at the frangible section to assist with separating the bands by tearing the frangible section.

7d. A headgear as claimed in any one of claims 2d to 6d wherein the strap comprises a hole at an end of the frangible section, the hole comprising a rounded portion defining an end of the frangible section to prevent tearing the strap beyond the frangible section.

8d. A headgear as claimed in claim 6d wherein the hole is a finger hole.

9d. A headgear as claimed in any one of claims 2d to 8d wherein at least the portion of the strap is formed from fabric forming the bands, and the fabric is coated with a polymer with the bands arranged together, the coating providing the frangible section between the bands, the coating adapted to be torn to separate the bands.

10d. A headgear as claimed in claim 9d wherein the bands are formed by a longitudinal cut in the fabric along the portion of the strap, the polymer coating bridging the cut to hold the bands together in a non-bifurcating configuration.

11d. A headgear as claimed in claim 9d or 10d wherein the fabric is a foamed fabric.

12d. A headgear as claimed in any one of claims 2d to 4d wherein the bands are separated by a removable section of the strap comprising a lift tab, the removable section joined to the bands by the frangible section.

13d. A headgear as claimed in claim 1d wherein the headgear comprises a clasp that is slidable along at least the portion of the strap configured to bifurcate.

14d. A headgear as claimed in claim 13d wherein to bifurcate the strap to separate the bands the clasp is slidable to an end of the bands, and the clasp is slidable to a midpoint of the bands to hold the bands together as a single strap.

15d. A headgear as claimed in claim 13d wherein to bifurcate the strap to separate the bands the clasp is slidable to an end of the bands, and the clasp is slidable to an opposite end of the bands to hold the bands together as a single strap.

16d. A headgear as claimed in claim 15d wherein each band comprises a feature that interfaces with a corresponding feature on the clasp to bind the bands together when in a non-bifurcated configuration.

17d. A headgear as claimed in claim 16d wherein the bands comprises interlocking teeth that are separated or mated by sliding the clasp along the bands.

18d. A headgear as claimed in any one of claims 13d to 17d wherein the headgear comprises a web that extends between the bands, in a non-bifurcated configuration the web is bunched up or folded into a non-expanded configuration, and in a bifurcated configuration where the bands are spaced apart the web is expanded or unfolded to cover an area between the spaced apart bands.

19d. A headgear as claimed in claim 13d wherein the headgear comprises two clasps, in a non-bifurcated configuration both clasps are slid towards a central position of the strap to hold the bands together, and in a bifurcated configuration each clasp is slid to an end of the bands so that the bands may separate between ends of the bands.

20d. A headgear as claimed in claim 19d wherein each clasp and the straps are complementary adapted so that moving each clasp to an end of the bands forces the bands apart to separate the bands into a bifurcated configuration.

21d. A headgear as claimed in claim 20d wherein each clasp comprises two spaced apart flanges and three pins extending between the spaced apart flanges, the bands extending between the flanges, one said pin positioned between the bands and the other two pins positioned on outer edges of the bands, and the bands comprises a cross over portion near ends of the bands.

22d. A headgear as claimed in any one of claims 13d to 21d wherein one or each band may comprise a central tab or stop to limit the amount of travel of the clasps along the bands.

23d. A headgear as claimed in any one of claims 1d to 22d wherein the portion of the strap configured to bifurcate extends around the back of the patient's head from behind the patient's ears in use.

24d. A headgear as claimed in claim 1d wherein ends of the bands are pivotally coupled together.

25d. A headgear as claimed in any one of claims 1d to 25d wherein the bands in a non-bifurcated configuration are arranged edge-to-edge.

26d. A headgear as claimed in any one of claims 1d to 25d wherein the bands in a non-bifurcated configuration are arranged side-by-side.

27d. A headgear as claimed in claim 26d wherein the bands in the non-bifurcated configuration are held together by one or more of tearable stitching, a clasp or clasps, buttons, clips, hook and loop fasteners or magnets.

1e. A headgear for securing a patient interface to a user's face comprising:
a strap, each end of the strap adapted to be attached to a patient interface and extend around a patient's head to hold the patient interface in place on a patients face, wherein
the strap comprises a non-stretchable section and a stretchable section, the non-stretchable section adapted to be attached the patient interface and support a gases supply conduit coupled to the patient interface.

2e. A headgear as claimed in claim 1e wherein each end of the strap is a non-stretchable section adapted to be attached to the patient interface and the stretchable section is an intermediate section that extends between the non-stretchable sections around the back of the patient's head.

3e. A headgear as claimed in claim 1e wherein the non-stretchable section is adapted to be attached to one side of the patient interface and the stretchable section is adapted to be attached to an opposite side of the patient interface.

4e. A headgear as claimed in claim 1e or 2e wherein the non-stretchable section comprises a feature for securing the conduit.

1f. A headgear for securing a patient interface to a user's face comprising:
a strap comprising a first stretchable section adapted to be attached to one side of a patient interface and a second stretchable section adapted to be attached to an opposite side of a patient interface, and a non-stretchable intermediate section extending between each end of the stretchable sections.

2f. A headgear as claimed in claim 1f wherein the intermediate portion is an annular portion, ends of the stretchable sections attached to the annular portion.

3f. A headgear as claimed in claim 1f or 2f wherein the headgear comprises a first non-stretchable sleeve and a second non-stretchable sleeve each extending from the non-stretchable intermediate section, and the first stretchable section extends along an inside of the first non-stretchable sleeve and the second stretchable section extends along an inside of the second non-stretchable sleeve.

4f. A headgear as claimed in claim 3f wherein the first and second non-stretchable sleeves extend from the intermediate portion to forward of the patient's ears in use.

5f. A headgear as claimed in 3f wherein the first and second stretchable sections are not attached to the first and second non-stretchable sleeve along the length of the sleeve from the intermediate portion.

6f. A headgear as claimed in any one of claims 3f to 5f wherein one or both sleeves is adapted to support a gas conduit for providing a gas flow to the patient interface.

7f. A headgear as claimed in claim 6f wherein the head gear comprises a lanyard connected to a said sleeve adapted to secure the gas conduit.

8f. A headgear as claimed in claim 7f wherein the lanyard is stretchable.

9f. A headgear as claimed in claim if wherein the non-stretchable intermediate section is bifurcated to comprise two separate bands.

10f. A headgear as claimed in claim if wherein the non-stretchable section is configured to bifurcate into more than one band to extend around the patients head.

11f. A headgear as claimed in claim if wherein the headgear comprises a bifurcated section comprising two bands and one said band is the non-stretchable intermediate section.

12f. A headgear as claimed in claim 11f wherein the headgear comprises a first non-stretchable 'Y' connector connecting between the first stretchable section and one end of the two bands and a second non-stretchable 'Y' connector connecting between the second stretchable section and an opposite end of the two bands.

13f. A headgear as claimed in claim 11f or 12f wherein one of the two bands is a stretchable band.

14f. A headgear as claimed in claim 13f wherein an upper one of the two bands is the stretchable band and a lower one of the two bands is the non-stretchable band.

15f. A headgear as claimed in claim 13f or 14f wherein the non-stretchable band is length adjustable.

16f. A headgear as claimed in claim 9f wherein at least one of the bands is adjustable in length.

17f. A headgear as claimed in claim 16f wherein an upper one of the two bands is adjustable in length.

What is claimed is:
1. A nasal cannula assembly for administering a breathable gas to a user, the nasal cannula assembly comprising:

a nasal cannula comprising:
  a first section comprising a first material, and
  a second section comprising a second material;
a manifold with a manifold connection comprising a rigid material relative to the first material, wherein the manifold connection is substantially C or U shaped;
wherein the first section is relatively softer than the second section,
wherein the first section and second section are commensurately or complimentarily shaped or configured to communally receive the substantially C or U shaped manifold connection for delivery of a gas to the user,
wherein the nasal cannula comprises a body defining an open cavity configured to receive the substantially C or U shaped manifold connection for delivery of the gas to the user, the first section defining at least a portion of the open cavity, wherein the substantially C or U shaped manifold connection has a concave surface forming the C or U shape and an opposite surface, wherein the body covers the concave surface and the opposite surface when the substantially C or U shaped manifold connection is received within the body;
a rear portion of said body being, in-use, substantially adjacent to the user's septum region, the rear portion being substantially compliant or deformable in response to a pressure applied by the user to said rear portion, wherein the rear portion defines at least a part of a rear wall of the open cavity, formed as a pillow section to be substantially adjacent to the user's septum region in-use, the rear portion being one or more of: a substantially thinned wall section of the body, or a substantially elasticised wall section of the body.

2. The nasal cannula assembly as claimed in claim 1, where the second material is different from the first material.

3. The nasal cannula assembly as claimed in claim 1, wherein the first section and the second section are assembled to each other through the use of one or more fastening systems.

4. The nasal cannula assembly as claimed in claim 1, wherein the second section provides for a structural or support or shape-defining, component part, of the nasal cannula.

5. The nasal cannula assembly as claimed in claim 4, wherein the configuration or shape of the first section is at least in part defined by parts or portions of the second section.

6. The nasal cannula assembly as claimed in claim 1, wherein the first section encapsulates at least a part of the second section.

7. The nasal cannula assembly as claimed in claim 1, wherein the second section is at least in part over-moulded by the first section.

8. The nasal cannula assembly as claimed in claim 1, wherein the second section is adapted to receive the substantially C or U shaped manifold connection.

9. The nasal cannula assembly as claimed in claim 1, wherein the first section comprises one or more surface relief portions, the surface relief portion(s) of the first section engageable with an associated one or more commensurately or complimentarily shaped or configured surface relief portions of the second section.

10. The nasal cannula assembly as claimed in claim 1, wherein the second section extends around the first section.

11. The nasal cannula assembly as claimed in claim 1, wherein the nasal cannula includes a pair of side arms extending outwardly from the body.

12. The nasal cannula assembly as claimed in claim 11, wherein located substantially toward each end of the side arms is a connection system for connecting a headgear.

13. The nasal cannula assembly as claimed in claim 1, wherein a concave side of the C or U shape, in use, faces the rear portion of the body, wherein the rear portion of the body is adapted to be substantially adjacent to the user's septum region in use.

14. The nasal cannula assembly as claimed in claim 1, wherein the open cavity is in fluid communication with one or a pair of nasal prongs.

15. The nasal cannula assembly as claimed in claim 1, wherein the manifold is a side-entry manifold.

16. A nasal cannula assembly for administering a breathable gas to a user, the nasal cannula assembly comprising:
  a first section formed from a first material;
  a second section formed from a second material;
  a manifold with a manifold connection comprised of a rigid material relative to the first material;
  wherein the first section is relatively softer than the second section, wherein the first section and the second section comprises a body defining an open cavity engageable by the manifold connection, the first section defining at least in part said open cavity;
  a rear portion of said body being, in-use, substantially adjacent to the user's septum region, the rear portion being substantially compliant or deformable in response to a pressure applied by the user to said rear portion, wherein the rear portion defines at least a part of a rear wall of the open cavity, formed as a pillow section to be substantially adjacent to the user's septum region in-use, the rear portion being one or more of: a substantially thinned wall section of the body, or a substantially elasticised wall section of the body;
  wherein the manifold connection is substantially C or U shaped and a concave rear side of the C or U shape, in use, faces the rear portion, wherein the body covers the concave rear side of the C or U shape and a front side of the manifold connection when the manifold connection is received within the body.

17. A nasal cannula assembly for administering a breathable gas to a user, the nasal cannula assembly comprising:
  a nasal cannula comprising:
    a first section comprising a first material, and
    a second section comprising a second material;
  a manifold with a manifold connection comprising a rigid material relative to the first material, wherein the manifold connection is substantially C or U shaped;
  wherein the nasal cannula comprises a body defining an open cavity configured to receive the manifold connection for delivery of the gas to the user, the first section defining at least a portion of the open cavity, wherein the manifold connection is substantially C or U shaped and a concave rear side of the C or U shape, in use, faces the rear portion, wherein the body covers the manifold connection from the concave rear side to a front side;
  wherein a hollowed region is bound by the substantially C or U shaped manifold connection and a rear portion of the body when the substantially C or U shaped manifold connection is received within the body, the hollowed region substantially adjacent to the user's septum region in-use, the rear portion configured to deform the hollowed region to improve comfort or reduce the application of pressure points by the substantially C or U shaped manifold connection.

\* \* \* \* \*